(12) United States Patent
Ibrahim et al.

(10) Patent No.: US 7,872,018 B2
(45) Date of Patent: Jan. 18, 2011

(54) COMPOUNDS AND METHODS FOR KINASE MODULATION, AND INDICATIONS THEREFOR

(75) Inventors: Prabha N. Ibrahim, Mountain View, CA (US); Ryan Bremer, Oakland, CA (US); Chao Zhang, Moraga, CA (US); Jiazhong Zhang, Foster City, CA (US); Klaus-Peter Hirth, San Francisco, CA (US); Guoxian Wu, Palo Alto, CA (US); Hongyao Zhu, Berkeley, CA (US)

(73) Assignee: Plexxikon, Inc., Berkeley, CA (US)

( * ) Notice: Subject to any disclaimer, the term of this patent is extended or adjusted under 35 U.S.C. 154(b) by 212 days.

(21) Appl. No.: 11/962,044

(22) Filed: Dec. 20, 2007

(65) Prior Publication Data
US 2008/0221148 A1 Sep. 11, 2008

Related U.S. Application Data

(60) Provisional application No. 60/877,052, filed on Dec. 21, 2006.

(51) Int. Cl.
*A61K 31/454* (2006.01)
*A61P 35/00* (2006.01)
*C07D 471/04* (2006.01)

(52) U.S. Cl. ........................ 514/300; 546/113
(58) Field of Classification Search ................ 546/113; 514/300
See application file for complete search history.

(56) References Cited

U.S. PATENT DOCUMENTS

| | | | |
|---|---|---|---|
| 2,234,705 A | 3/1941 | Normington et al. |
| 2,413,258 A | 12/1946 | Soday et al. |
| 4,150,949 A | 4/1979 | Smith |
| 4,568,649 A | 2/1986 | Bertoglio-Matte |
| 4,626,513 A | 12/1986 | Burton et al. |
| 4,727,395 A | 2/1988 | Oda et al. |
| 5,120,782 A | 6/1992 | Hubsch et al. |
| 5,143,854 A | 9/1992 | Pirrung et al. |
| 5,338,849 A | 8/1994 | Festal et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |
| 5,474,935 A | 12/1995 | Chatterjee et al. |
| 5,556,752 A | 9/1996 | Lockhart et al. |
| 5,576,319 A | 11/1996 | Baker et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,712,285 A | 1/1998 | Curtis et al. |
| 5,721,118 A | 2/1998 | Scheffler |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,877,007 A | 3/1999 | Housey |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | During |
| 6,110,458 A | 8/2000 | Freeman et al. |
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossvary |
| 6,235,769 B1 | 5/2001 | Clary |

(Continued)

FOREIGN PATENT DOCUMENTS

DE 24 13 258 A1 10/1975

(Continued)

OTHER PUBLICATIONS

Bloom, A. and Day. A.R., The Preparation of 2-Alkylaminobenzimidazoles, J. Org. Chem. 14, 17 (1939).

Bouzakri, K. and Zierath, J.R., MAP4K4 Gene silencing in Human Skeletal Muscle Prevents Tumor Necrosis Factor-α-induced Insulin Resistance, J. Biol. Chem. 282:7783-7789 (2007).

Chou, T. and Talalay, P., Quantitative analysis of Dose-Effect Relationships: The Combined Effects of Multiple Drugs or Enzyme Inhibitors, Adv. Enzyme Regul. 22:27-55 (1984).

Chou et al., Computerized Quantitation of Synergism and Antagonism of Taxol, Topotecan, and Cisplatin Against Human Teratocarcinoma Cell Growth: a Rational Approach to Clinical Protocol Design, J. Natl. Cancer Inst. 86:1517-24 (1994).

(Continued)

*Primary Examiner*—D. Margaret Seaman
*Assistant Examiner*—Niloofar Rahmani
(74) *Attorney, Agent, or Firm*—Foley & Lardner LLP

(57) ABSTRACT

Compounds active on protein kinases are described, as well as methods of using such compounds to treat diseases and conditions associated with aberrant activity of protein kinases.

12 Claims, No Drawings

U.S. PATENT DOCUMENTS

| | | |
|---|---|---|
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,545,014 B2 | 4/2003 | Verner |
| 6,858,860 B2 | 2/2005 | Hosono et al. |
| 7,259,165 B2 | 8/2007 | Bernotas et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,498,342 B2 | 3/2009 | Ibrahim et al. |
| 7,504,509 B2 | 3/2009 | Ibrahim et al. |
| 7,582,637 B2 | 9/2009 | Arnold et al. |
| 7,601,839 B2 | 10/2009 | Arnold et al. |
| 7,626,021 B2 | 12/2009 | Arnold et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2003/0003004 A1 | 1/2003 | Stones et al. |
| 2004/0002534 A1 | 1/2004 | Lipson et al. |
| 2004/0022534 A1 | 2/2004 | Amano et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0256151 A1 | 11/2005 | Salom et al. |
| 2006/0035898 A1 | 2/2006 | Arnold et al. |
| 2006/0058339 A1 | 3/2006 | Ibrahim et al. |
| 2006/0058340 A1 | 3/2006 | Ibrahim et al. |
| 2007/0032519 A1 | 2/2007 | Zhang et al. |
| 2007/0049615 A1 | 3/2007 | Ibrahim et al. |
| 2007/0287711 A1 | 12/2007 | Arnold et al. |
| 2008/0167338 A1 | 7/2008 | Spevak et al. |
| 2008/0188514 A1 | 8/2008 | Wu et al. |
| 2009/0005356 A1 | 1/2009 | Blaney et al. |
| 2009/0143352 A1 | 6/2009 | Arnold et al. |
| 2009/0306056 A1 | 12/2009 | Arnold et al. |

FOREIGN PATENT DOCUMENTS

| | | |
|---|---|---|
| EP | 0 154 734 | 8/1990 |
| EP | 0 465 970 | 1/1992 |
| EP | 1 057 826 | 12/2000 |
| EP | 0 870 768 | 5/2002 |
| EP | 1 267 111 | 12/2002 |
| EP | 1 749 829 | 2/2007 |
| GB | 2 292 143 | 2/1996 |
| GB | 2 292 145 | 2/1996 |
| GB | 2 298 198 | 8/1996 |
| GB | 2 299 581 | 10/1996 |
| JP | 06-135946 | 5/1994 |
| JP | 10-130269 | 5/1998 |
| JP | 15-073357 | 3/2003 |
| WO | WO-93/13099 | 7/1993 |
| WO | WO-94/14808 | 7/1994 |
| WO | WO-94/20459 | 9/1994 |
| WO | WO-94/20497 | 9/1994 |
| WO | WO-95/04742 | 2/1995 |
| WO | WO-95/07910 | 3/1995 |
| WO | WO-95/28387 | 10/1995 |
| WO | WO-96/00226 | 1/1996 |
| WO | WO-96/11929 | 2/1996 |
| WO | WO-96/05200 | 4/1996 |
| WO | WO-96/17958 | 6/1996 |
| WO | WO-96/18738 | 6/1996 |
| WO | WO-97/46313 | 12/1997 |
| WO | WO-97/46558 | 12/1997 |
| WO | WO-97/49703 | 12/1997 |
| WO | WO-98/06433 | 2/1998 |
| WO | WO-98/22457 | 5/1998 |
| WO | WO-98/47899 | 10/1998 |
| WO | WO-99/00386 | 1/1999 |
| WO | WO-99/09217 | 2/1999 |
| WO | WO-99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO-99/51773 | 10/1999 |
| WO | WO-00/09162 | 2/2000 |
| WO | WO-00/12074 | 3/2000 |
| WO | WO-00/12514 | 3/2000 |
| WO | WO-00/29411 | 5/2000 |
| WO | WO-00/53582 | 9/2000 |
| WO | WO-00/64898 | 11/2000 |
| WO | WO-00/71537 | 11/2000 |
| WO | WO-00/75139 | 12/2000 |
| WO | WO-01/09121 | 2/2001 |
| WO | WO-01/24236 | 4/2001 |
| WO | WO-01/29036 | 4/2001 |
| WO | WO-01/46196 | 6/2001 |
| WO | WO-01/60822 | 8/2001 |
| WO | WO-01/62255 | 8/2001 |
| WO | WO-01/98299 | 12/2001 |
| WO | WO-02/00657 | 1/2002 |
| WO | WO-02/18346 | 3/2002 |
| WO | WO-02/083175 | 10/2002 |
| WO | WO-02/085896 | 10/2002 |
| WO | WO-02/102783 | 12/2002 |
| WO | WO-03/000258 | 1/2003 |
| WO | WO-03/003004 A2 | 1/2003 |
| WO | WO-03/006459 | 1/2003 |
| WO | WO-03/008422 | 1/2003 |
| WO | WO-03/011868 | 2/2003 |
| WO | WO-03/020698 | 3/2003 |
| WO | WO-03/028724 | 4/2003 |
| WO | WO-03/037862 | 5/2003 |
| WO | WO-03/051838 | 6/2003 |
| WO | WO-03/064413 | 8/2003 |
| WO | WO-03/068221 | 8/2003 |
| WO | WO-03/082289 | 10/2003 |
| WO | WO-03/082868 | 10/2003 |
| WO | WO-03/082869 | 10/2003 |
| WO | WO-03/087087 | 10/2003 |
| WO | WO-03/101990 | 12/2003 |
| WO | WO-2004/009600 | 1/2004 |
| WO | WO-2004/009601 | 1/2004 |
| WO | WO-2004/016609 | 2/2004 |
| WO | WO-2004/016610 | 2/2004 |
| WO | WO 2004024895 | 3/2004 |
| WO | WO-2004/065393 | 8/2004 |
| WO | WO-2004/065394 | 8/2004 |
| WO | WO-2004/074286 | 9/2004 |
| WO | WO-2004/078756 | 9/2004 |
| WO | WO 2004078923 | 9/2004 |
| WO | WO-2004/101565 | 11/2004 |
| WO | WO-2005/028475 | 3/2005 |
| WO | WO 2005028624 | 3/2005 |
| WO | WO-2005/044181 | 5/2005 |
| WO | WO-2005/058891 | 6/2005 |
| WO | WO-2005/063746 | 7/2005 |
| WO | WO-2005/063747 | 7/2005 |

| WO | WO 2005062795 | 7/2005 |
| WO | WO-2005/082367 | 9/2005 |
| WO | WO-2005/085244 | 9/2005 |
| WO | WO-2005/095400 | 10/2005 |
| WO | WO-2005/103050 | 11/2005 |
| WO | WO-2005/115363 | 12/2005 |
| WO | WO-2006/004984 | 1/2006 |
| WO | WO-2006/009755 | 1/2006 |
| WO | WO 2006/009797 | 1/2006 |
| WO | WO 2006/015123 | 2/2006 |
| WO | WO-2006/015124 | 2/2006 |
| WO | WO 2006/114180 | 11/2006 |
| WO | WO-2006/127587 | 11/2006 |
| WO | 2007002325 | * 1/2007 |
| WO | 2007002433 | * 1/2007 |
| WO | WO 2007/002325 | 1/2007 |
| WO | WO 2007/002433 | 1/2007 |
| WO | WO 2007/013896 | 2/2007 |
| WO | WO 2007/106236 | 9/2007 |

OTHER PUBLICATIONS

Collins et al., A small interfereing RNA screen for modulators of tumor cell motility identifies MAP4K4 as a prommigratory kinase, Proc. Natl. Acad. Sci. USA, 103:3775-3780 (2006).

Coulie et al, Recombinant Human Neurotropic Factors Accelerate Colonic Transit and Relieve Constipation in Humans, Gastroenterology 119:41-50 (2000).

Crouch et al., The use of ATP bioluminescence as a measure of cell proliferation and cytotoxicity. Journal of Immunological Methods, 160:81-8 (1993).

Crump, M., Inhibition of Raf Kinase in the Treatment of Acute Myeloid Leukemia, Curr. Pharm. Design 8(25):2243-8 (2002).

Douma, S. et al, Suppression of anoikis and induction of metastasis by the neurotropic receptor TrkB, Nature 430:1034-9 (2004).

Chou, T. et al., Chemotherapeutic Synergism, Potentiation and Antagonism, Encyclopedia of Human Biology, Academic Press, 2:371-9 (1991).

Halvorson, K.G. et al., A Blocking Antibody to Nerve Growth Factor Attenuates Skeletal Pain Induced by Prostate Tumor Cells Growing in Bone, Cancer Res. 65:9426-35 (2005).

Hood, J.D. et al., Tumor Regression by Targeted Gene Delivery to the Neovasculature, Science 296, 2404 (2002).

Hudson, P. B. et al., A Simple Method for the Determination of Serum Acid Phosphatase, Journal of Urology 58:89-92 (1947).

Kassel, O. et al., Local increase in the number of mast cells and expression of nerve growth factor in the bronchus of asthmatic patients after repeated inhalation of allergen at low-dose, Clin. Exp. Allergy 31:1432-40 (2001).

Komoyira, S. et. al., Design, synthesis and biological activity of amidinobicyclic compounds (derivatives of DX-9065a) as a factor Xa inhibitors: SAR study of S1 and aryl binding sites, *Bioorg. Med. Chem.* 12, 2099 (2004).

Kunnimalaiyaan, M. and Chen, H. et al., The Raf-1 pathway: a molecular target for treatment of select neuroendocrine tumors? Anticancer Drugs 17(2):139-42 (2006).

Machida, N. et al., Mitogen-activated Protein Kinase Kinase Kinase Kinase 4 as a Putative Effector of Rap2 to Activate the c-Jun N-terminal Kinase, J. Biol. Chem. 279: 15711-15714 (2004).

Mack, K.D. et al., Functional identification of kinases essential for T-cell activation through a genetic suppression screen, Immunol. Lett. 96, 129-145 (2005).

Matayoshi, S. et al, Actions of brain-derived neurotrophic factor on spinal nociceptive transmission during inflammation in the rat, J Physiol. 569:685-95 (2005).

Morgan, C., Pollard, J.W., and Stanley, E.R., Isolation and Characterization of a Cloned Growth Factor Dependent Macrophage Cell Line, BAC1.2F5, Journal of Cellular Physiology, 130:420-427 (1987).

Nakagawara, A. et al., Expression and Function of *TRK-B* an *BDNF* in Human Neuroblastomas, Mol. Cell Biol. 14:759-767 (1994).

Nassentein, C. et al, The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma, J. Exp. Med. 198:455-467 (2003).

Niihori, T. et al., Germline *KRAS* and *BRAF* mutations in cardio-facio-cutaneous syndrome, Nature Genet. 38(3):294-6 (2006).

Ochs, G. et al, A phase I/II trial of recombinant methionyl human brain derived neurotrophic factor administered by intrathecal infusion to patients with amyotrophic lateral sclerosis, Amyotroph Lateral Scler Other Motor Neuron Disord. 1:201-6 (2000).

Sclabas, G.M. et al, Overexpression of Tropomysin-Related Kinase B in Metastatic Human Pancreatic Cancer Cells, Clin. Cancer. Res. V11:440-449 (2005).

Secor, et al., Mast cells are essential for early onset and severe disease in a murine model of multiple sclerosis. J. Exp. Med. 5:813-821 (2000).

Steinman, Multiple sclerosis: A coordinated immunological attack against myelin in the central nervous system. Cell 85:299-302 (1996).

Chou, T.C. and Rideout, D.C., editors: Synergism and Antagonism in Chemotherapy, San Diego, CA: Academic Press, Chapter 2, 61-102 (1991).

Tang, X. et al., An RNA interference-based screen identifies MAP4K4/NIK as a negative regulator of PPARγ, adipogenesis, and insulin-responsive hexose transport, Proc. Natl. Acad. Sci. U. S. A. 103:2087-2092 (2006).

Wild, K.D. et al, Antibodies to Nerve Growth Factor Reverse Established Tactile Allodynia in Rodent Models of Neuropathic Pain without Tolerance, J. Pharmacol. Exp. Ther. 322:282-287 (2007).

Wright, J.H. et al., The STE20 Kinase KGK Is Broadly Expressed in Human tumor Cells and Can Modulate Cellular Transformation, Invasion, and Adhesion, Mol. Cell. Biol. 23:2068-2082 (2003).

Yang, Z.F. et al, Identification of Brain-Derived Neurotrophic Factor as a Novel Functional Protein in Hepatocellular Carcinoma, Cancer Res. 65:219-225 (2005).

Yao, Z. et al., A Novel Human STE20-related Protein Kinase, HGK, That Specifically Activates the c-Jun N-terminal Kinase Signaling Pathway, J. Biol. Chem. 274:2118-2125 (1999).

International Search Report for PCT Patent Application No. PCT/US2007/088443.

Alfthan, K., Surface Plasmon Resonance Biosensors as a Tool in Antibody Engineering, Biosensors & Bioelectronics 13:653-663 (1998).

Allegretti, et al., Palladium-Catalysed Functionalisation at 4- and 6-Position of the 7-Azaindole System, Synlett 5:609-612 (2001).

Al-Obeidi, et al., Peptide and Peptidomimetic Libraries, Mol Biotechnol 9:205-223, 1998.

Alvarez, et al., Synthesis of 3-Aryl- and 3-Heteroaryl-7-Azaindoles, Synthesis 4:615-620 (1999).

Amersdorfer and Marks, Phage Libraries for Generation of Anti-Botulinum scFv Antibodies, Methods in Molecular Biology 145:219-240, 2000.

Anderson, et al., Cooperative Catalyst Effects in Palladium-Mediated Cyanation Reactions of Aryl Halides and Triflates, J. Org. Chem. 63:8224-8228 (1998).

Antonini, et al., Synthesis of 4-Amino-1-β-D-Ribofuranosy1-1H-pyrrolo[2,3-b]pyridine (1-Deazatubercidin) as a Potential Antitumor Agent, J. Med. Chem. 25:1258-1261 (1982).

Ashman et al., The biology of stem cell factor and its receptor C-kit, The International Journal of Biochemistry & Cell Biology, 31:1037-1051, 1999.

Baghestanian, et al., A Case of Malignant Mastocytosis with Circulating Mast Cell Precursors: Biologic and Phenotypic Characterization of the Malignant Clone, Leuk. 10:159-166 (1996).

Bagshawe, Antibody-Directed Enzyme Prodrug Therapy: A Review; 1995, Drug Dev. Res., 34:220-230.

Balak, et. al., Novel D761Y and common secondary T790M mutations in epidermal growth factor receptor-mutant lung adenocarcinomas with acquired resistance to kinase inhibitors. Clin. Cancer Res. 12:6494-501 (2006).

Bancalari, et al., Blood Markers of Early and Late Airway Responses to Allergen in Asthmatic Subjects. Relationship with Functional Findings Allergy 52:32-40, 1997.

Bartlett, et al., CAVEAT: A Program to Facilitate the Structure-Derived Design of Biologically Active Molecules Royal Society of Chemistry 78:180-196, 1989.

Barton et al, The chemistry of pentavalent organobismuth reagants. Part X. Studies on the phenylation and oxidation of phenols, Tetrahedron, vol. 43, No. 2, 1987, pp. 323-332.

Bashford and Harris, Measurement of Ligand Binding to Proteins, Spectrophotometry and Spectrofluorimetry: A Practical Approach 4:91-113 (1987).

Basta et al, High-dose Intravenous Immunoglobulin Exerts Its Beneficial Effect in Patients with Dermatomyositis by Blocking Endomysial Deposition of Activated Complement Fragments; J Clin Invest 1994, 94:1729-1735.

Bedi, et al., BCR-ABL-Mediated Inhibition of Apoptosis With Delay of G2/M Transition After DNA Damage: A Mechanism of Resistance to Multiple Anticancer Agents; Blood 1995, 86:1148-1158.

Bell, (1981) Spectroscopy in Biochemistry, vol. 1, pp. 155-194, CRC Press.

Bellone, et al., Growth Stimulation of Colorectal Carcinoma Cells Via the c-Kit Receptor is Inhibited by TGF-β1, J. Cell Physiol. 172:1-11 (1997).

Berdel, et al., Recombinant Human Stem Cell Factor Stimulates Growth of a Human Glioblastoma Cell Line Expressing c-kit Protooncogene, Canc. Res. 52:3498-3502 (1992).

Bertolini et al., A new Rational Hypothesis for the Pharmacophore of the Active Metabolite of Leflunomide, a Potent Immunosuppressive Drug; 1997, J. Med. Chem., 40:2011-2016.

Bjorntorp, Neuroendocrine Pertuirbations as a Cause of Insulin Resistance; Diabetes Metab. Res. Rev., 1999, 15: 427-441.

Blundell et al., Knowledge-Based Protein Modelling and Design Eur. J. Biochem. 172:513-520 1988.

Böhm, H., On the Use of LUDI to Search the Fine Chemicals Directory for Ligands of Proteins of Known Three-Dimensional Structure, J. Comp. Aided Molec. Design 8:623-632, 1994.

Bokenmeyer, et al., Expression of Stem-Cell Factor and Its Receptor c-kit Protein in Normal Testicular Tissue and Malignant Germ-Cell Tumours, J. Cancer Res. Clin. Oncol. 122:301-306 (1996).

Bolger et al, Computer Modeling of Combining Site Structure of Anti-Hapten Monoclonal Antibodies, Methods Enz., 203:21-45, 1991.

Bongarzone, et al., High Frequency of Activation of Tyrosine Kinase Oncogenes in Human Papillary Thyroid Carcinoma, Oncogene 4(12):1457-1462 (1989).

Bothwell, M., Keeping Track of Neurotroph n. Receptors Cell, 65:915-918 1991.

Bowtell, D., Options Available From Start to Finish For Obtaining Expression Data by Microarray, Nature Genetics Supp. 21:25-32 (1999).

Brenner et al., Encoded Combinatorial Chemistry, Proc. Natl. Acad. Sci. USA 89:5381-5383, 1992.

Broudy, V., Stem Cell Factor and Hematopoiesis, Blood 90:1345-1364 (1997).

Brünger, A., Free R Value: a Novel Statistical Quantity for Assessing the Accuracy of Crystal Structures Nature 355:472-475 (1992).

Buchschacher, Human Immunodeficiency Virus Vectors for Inducible Expression of Foreign Genes; (1992) J. Virol. 66:2731-2739.

Capon, et al., Designing CD4 Immunoadhesins for AIDS Therapy, Nature 337:525-531 (1989).

Carell et al., New Promise in Combinatorial Chemistry: Synthesis, Characterization, and Screening of Small-Molecule Libraries in Solution, Chem. Biol. 2:171-183 (1995).

Carpino, et al., p62dok: A Constitutively Tyrosine-Phosphorylated, GAP-Associated Protein in Chronic Myelogenous Leukemia Progenitor Cells; Cell 1997, 88:197-204.

Castells, et al., The Presence of Membrane-Bound Stem Cell Factor on Highly Immature Nonmetachromatic Mast Cells in the Peripheral Blood of a Patient with Aggressive Systemic Mastocytosis, J. Aller. Clin. Immunol. 98:831-840 (1996).

Chabala, J., Solid-Phase Combinatorial Chemistry and Novel Tagging Methods for Identifying Leads, Curr Opin Biotechnol 6:632-639 (1995).

Chayer, et al., Synthesis of Carboranylpyrroles, Tetrahedron Lett. 42(44):7759-7761 (2001).

Checovich, et al., Fluorescence Polarization—A New Tool for Cell and Molecular Biology, Nature 375:254-256 (1995).

Clark, et al., PRO_LIGAND: An Approach to De Novo Molecular Design. 1. Application to the Design of Organic Molecules, J. Comp. Aided Molec. Design 9:13-32 (1995).

Clohisy et al, Review of Cellular Mechanisms of Tumor Osteolysis; Clin. Orthop. 2000, 373: 104-14.

Coe, et al., Solution-Phase Combinatorial Chemistry, Mol Divers. 4:31-38 (1999).

Cohen, et al., Expression of Stem Cell Factor and C-Kit in Human Neuroblastoma; 1994, Blood 84:3465-3472.

Collioud et al., Oriented and Covalent Immobilization of Target Molecules to Solid Supports: Synthesis and Application of a Light-Activatable and Thiol-Reactive Cross-Linking Reagent; (1993) Bioconjugate Chem. 4:528-536.

Colman, P.M., Structure-Based Drug Design, Current Opinion in Struc. Biol. 4: 868-874 (1994).

Columbo, et al., The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils, J. Immunol 149:599-608 (1992).

Costa, et al., The Cells of the Allergic Response, JAMA 278:1815-1822 (1997).

Coste, et al., Coupling N-Methylated Amino Acids Using PyBroP1 and PyCIoP Halogenophosphonium Salts: Mechanism and Fields of Application, Journal of Organic Chemistry 59:2437-2446 (1994).

Creighton, T., An Empirical Approach to Protein Conformation Stability and Flexibility, Biopolymers 22(1):49-58 (1983).

Curtin et al., Discovery and Evaluation of a Series of 3-Acylindole Imidazopyridine Platelet-Activating Factor Antagonists, J. Med. Chem., vol. 41, 1998, pp. 74-95.

Cwirla et al., Peptides on Phage: A Vast Library of Peptides for Identifying Ligands, Biochemistry 87:6378-6382 (1990).

Dai et al., Targeted disruption of the mouse colony-stimulating factor 1 receptor gene results in osteopetrosis, mononuclear phagocyte deficiency, increased primitive progenitor cell frequencies, and reproductive defects; Blood, 2002, 99: 111-120.

Dandliker, et al., Equilibrium and Kinetic Inhibition Assays Based Upon Fluorescence Polarization, Methods in Enzymology 74:3-28 (1981).

Dastych, et al., Stem Cell Factor Induces Mast Cell Adhesion to Fibronectin; 1994, J. Immunol. 152:213-219.

Demetri, Targeting c-kit mutations in solid tumors: Scientific rationale and novel therapeutic options, Seminars in Oncology, 28(5), Supp. 17, 19-26, 2001.

Dewar et al., Inhibition of c-fms by Imatinib Expanding the Spectrum of Treatment; Cell Cycle 2005, 4(7):851-3.

Dobeli, H., et al., Recombinant Fusion Proteins for the Industrial Production of Disulfide Bridge containing Peptides: Purification, Oxidation without Cancatamer Formation, and Selective Cleavage; (1998) Protein Expr. Puff. 12:404-414.

Dolle et al., Comprehensive Survey of Combinatorial Library Synthesis: 1998, J Comb Chem 1:235-282 (1999).

Donis-Keller, et al., Mutations in the RET Proto-Oncogene are Associated with MEN 2A and FMTC, Hum Mol Genet. 2(7):851-856 (1993).

Doyle and Bryker, Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media; J. Org. Chem. 1979, 44:1572.

Dube and Scholte, Reductive N-Alkylation of Amides, Carbamates and Ureas, Tetrahedron Lett. 40:2295-2298 (1999).

Durbec, et al., GDNF Signalling Through the Ret Receptor Tyrosine Kinase, Nature 381:789-793 (1996).

Dyson, et al., The Human Papilloma Virus 13 16 E7 Oncoprotein is Able to Bind to the Retinoblastoma Gene Product, Science 243:934-937 (1989).

Eklund and Joensuu, Treatment of rheumatoid arthritis with imatinib mesylate: clinical improvements in three refractory cases, Annals of Medicine, 35:362-367, 2003.

Eliseev et al, Dynamic Combinatorial Chemistry: Evolutionary Formation and Screening of Molecular Libraries, Current Topics in Microbiology & Immunology 243:159-172 (1999).

Enjalbal, et al., Mass Spectrometry in Combinatorial Chemistry, Mass Spectrometry Reviews. 19:139-161 (2000).

Escribano, et al., Expression of the c-kit (CD117) Molecule in Normal and Malignant Hematopoiesis, Leuk. Lymph. 30:459-466 (1998).

Feng et al, Tyrosines 559 and 807 in the Cytoplasmic Tail of the Macrophage colony-Stimulating Factor Receptor Play Distinct Roles in Osteoclast Differentiation and Function; Endocrinology 2002, 143: 4868-74.

Feng, et al., Stable in Vivo Gene Transduction Via a Novel Adenoviral/Retroviral Chimeric Vector, Nature Biotechnology 15:866-870 (1997).

Finotto, et al., Glucocorticoids Disease Tissue Mast Cell Number by Reducing the Production of the c-kit Ligand, Stem Cell Factor, by Resident Cells, J. Clin. Invest. 99:1721-1728 (1997).

Fivash et al., BIAcore for macromolecular interaction; (1998) BIAcore for macromolecular interaction, Current Opinion in Biotechnology. 9:97-101.

Flanagan & Lader, Macrophages and the various isoforms of macrophage colony-stimulating factor; Curr Opin Hematol. 1998, 5:181-5.

Franz and Martin, Sulfuranes, X. A Reagent for the Facile Cleavage of Secondary Amides, JACS, 95(6):2017-2019 (1973).

Furitsu, et al., Identification of Mutations in the Coding Sequence of the Proto-oncogene c-kit in a Human Mast Cell Leukemia Cell Line Causing Ligand-independent Activation of the c-kit Product; 1993, J. Clin. Invest. 92:1736-1744.

Furuta, et al., Stem Cell Factor Influences Mast Cell Mediator Release in Response to Eosinophil-Derived Granule Major Basic Protein, Blood 92:1055-1061 (1998).

Gallop et al., Applications of Combinatorial Technologies to Drug Discovery. 1. Background and Peptide Combinatorial Libraries, J. Med. Chem. 37:1233-1251 (1994).

Gassman et al., Journal of the American Chemical Society, 95(13), pp. 4453-4455.

Girgis, N. et.al., The Synthesis of 5-Azaindoles by Substitution-Rearrangement of 7-Azaindoles upon Treatment with Certain Primary Amines; J. Heterocyclic. Chem. 1989, 26:317-325.

Golkar, et al., Mastocytosis, Lancet 349:1379-1385 (1997).

Goodford, P.J., A Computational Procedure for Determining Energetically Favorable Binding Sites on Biologically Important Macromolecules, J. Med. Chem. 28:849-857 (1985).

Goodsell et al, Automated Docking of Substrates to Proteins by Simulated Annealing, Proteins: Structure, Function, and Genetics 8:195-202 (1990).

Gordon et al., Applications of Combinatorial Technologies to Drug Discovery. 2. Combinatorial Organic Synthesis, Library Screening Strategies, and Future Directions, J. Med. Chem. 37:1384-1401 (1994).

Gordon, and Ford, Detection of Peroxides and Their Removal, The Chemist's Companion: A Handbook Of Practical Data, Techniques, And References p. 437 (1972).

Gram H., Phage Display in Proteolysis and Signal Transduction, Combinatorial Chemistry & High Throughput Screening 2:19-28 (1999).

Gravert et al, Synthesis on Soluble Polymers: New Reactions and the Construction of Small Molecules, Curr Opin Chem Biol 1:107-113 (1997).

Greer, J., Model Structure for the Inflammatory Protein C5a, Science 228:1055-1060 (1985).

Grieco, et al., PTC is a Novel Rearranged Form of the ret Proto-Oncogene and is Frequently Detected in Vivo in Human Thyroid Papillary Carcinomas, Cell 60(4):557-563 (1990).

Guida, W., Software for Structure-Based Drug Design, Current Opinion in Struc. Biol. 4:777-781 (1994).

Hafner, et al., Isothermal Amplification and Multimerization of DNA by Bst DNA Polymerase, Biotechniques Apr. 2001;30(4):852-867.

Hallek, et al., Interaction of the Receptor Tyrosine Kinase p145c-kit with the p210bcr/abl Kinase in Myeloid Cells, Brit. J Haem. 94:5-16 (1996).

Hamel, et al., The Road Less Traveled: c-kit and Stem Cell Factor, J. Neuro-Onc. 35:327-333 (1997).

Hands et. al., A convenient Method for the Preparation of 5-, 6- and 7-Azaindoles and Their Derivatives; Synthesis 1996, 877-882.

Hanselman, et al., A cDNA-Dependent Scintillation Proximity Assay for Quantifying Apolipoprotein A-1, J. Lipid Res. 38:2365-2373 (1997).

Hassan and Zander, Stem Cell Factor as a Survival and Growth Factor in Human Normal and Malignant Hematopoiesis, Acta. Hem. 95:257-262 (1996).

Hassan, et al., Expression of Protooncogene c-kit and Its Ligand Stem Cell Factor (SCF) in Gastric Carcinoma Cell Lines; 1998, Digest. Dis. Science 43:8-14.

Hayashi, et al., Dichloro[1,1 19-bis(diphenylophosphino)ferrocene]palladiunn-(II), An Effective Catalyst for Cross-Coupling of Secondary and Primary Alkyl Grignard and Alkylzinc Reagents with Organic Halides, J. Am. Chem. Soc. 106:158-163 1984.

Heacock et al., Orientation and Relative Reaction rate Factors in aromatic Substitution by the Benzensulfonimido Radical, J. Am. Chem. Soc., vol. 82, 1960, pp. 3460-3463.

Heim, et al., Engineering Green Fluorescent Protein for Improved Brightness, Longer Wavelengths and Fluorescence Resonance Energy Transfer, Curr. Biol. 6:178-182 (1996).

Heinrich et al., PDGFRA Activating Mutations in Gastrointestinal Stromal Tumors; (Science 2003, 299:708-10).

Herbst, et al., Differential Effects of W Mutations on p145c-kit Tyrosine Kinase Activity and Substrate Interaction, J. Biol. Chem. 267:13210-13216 (1992).

Hibi, et al., Coexpression of the stem cell factor and the c-kit genes in small-cell lung cancer; 1991, Oncogene 6:2291-2296.

Hirota, et al., Gain-of-function Mutations of c-kit in Human Gastrointestinal Stromal Tumors; 1998, Science 279:577-580.

Hoffmann, m-Trifluoromethylbenzenesulfonyl Chloride, Organic Syntheses, Coll. vol. 60, p. 2 -126, 1981.

Hogaboam, et al., Novel Role of Transmembrane SCF for Mast Cell Activation and Eotaxin Production in Mast Cell-Fibroblast Interactions, J. Immunol. 160:6166-6171 (1998).

Houghten, et al., Generation and Use of Synthetic Peptide Combinatorial Libraries for Basic Research and Drug Discovery, Nature 354:84-86 (1991).

Houghten, R., Parallel Array and Mixture-Based Synthetic Combinatorial Chemistry: Tools for the Next Millennium, Annu Rev Pharmacol Toxicol 40:273-282 (2000).

Houghten, R., Peptide Libraries: Criteria and Trends, Trends Genet. 9:235-239 (1993).

Hughes-Jones, et al., Synthesis of Rh Fv Phage-Antibodies Using VH and VL Germline Genes, British Journal of Haematology 105:811-816 (1999).

Iemura, et al., The c-kit Ligand, Stem Cell Factor, Promotes Mast Cell Survival by Suppressing Apoptosis, Amer. J. Pathol 144:321-328 (1994).

Inoue, et al., Coexpression of the c-kit Receptor and the Stem Cell Factor in Gynecological Tumors, Cancer Res. 54:3049-3053 (1994).

International Search Report and Written Opinion of the ISA dated Oct. 24, 2006 for PCT Application No. PCT/US2006/024524.

International Search Report and Written Opinion of the ISA dated Apr. 4, 2007 for PCT Application No. PCT/US2006/018726.

International Search Report and Written Opinion of the ISA dated Apr. 20, 2006 for PCT Application No. PCT/US2005/021231.

International Search Report and Written Opinion of the ISA dated Jun. 4, 2008 for PCT Application No. PCT/US2007/088231.

International Search Report and Written Opinion of the ISA dated Jun. 4, 2008 for PCT Application No. PCT/US2007/088237.

International Search Report and Written Opinion of the ISA dated Jun. 5, 2008 for PCT Application No. PCT/US2007/083910.

International Search Report and Written Opinion of the ISA dated Jun. 5, 2008 for PCT Application No. PCT/US2007/085289.

International Search Report and Written Opinion of the ISA dated Jun. 5, 2008 for PCT Application No. PCT/US2007/088243.

International Search Report and Written Opinion of the ISA dated Jul. 28, 2008 for PCT Application No. PCT/US2007/085299.

International Search Report and Written Opinion of the ISA dated Oct. 24, 2006 for PCT Application No. PCT/US2006/024361.

International Search Report and Written Opinion of the ISA dated Nov. 17, 2008 for PCT Application No. PCT/US07/088412.

International Search Report and Written Opinion of the ISA dated Nov. 25, 2005 for PCT Application No. PCT/US04/42470.

Isbel et al., Local macrophage proliferation correlates with increased renal M-CSF expression in human glomerulonephritis; Nephrol Dial Transplant 2001, 16: 1638-1647.

Ishizaka, et al., Human ret Proto-Oncogene Mapped to Chromsome 10q11.2, Oncogene 4(12):1519-1521 (1989).

Isozaki, et al., Deficiency of c-kit cells in patients with a myopathic form of chronic idiopathic intestinal pseudo-obstruction; 1997, Amer. J. of Gast. 9 332-334.

Iwane, et al., Myosin Subfragment-1 is Fully Equipped with Factors Essential for Motor Function, Biochem. and Biophys. Res. Comm. 230:76-80 (1997).

Izquierdo, et al., Differential Expression of the c-kit Proto-Oncogene in Germ Cel Tumours, J. Pathol. 177:253-258 (1995).

Jarugula et al., Nonlinear pharmacokinetics of 5-fluorouracil in rats. 1997, J Pharm Sci 86(7):756-757.

Jing, et al., GDNF-Induced Activation of the Ret Protein Tyrosine Kinase is Mediated by GDNFR-a, a Novel Receptor for GDNF, Cell 85:1113-1124 (1996).

Johann, S., et al., GLVR1, a Receptor for gibbon Ape Leukemia Virus, Is Homologous to a Phosphate Permease of Neurospora crassa and is Expressed at High Levels in the Brain and Thymus; (1992) J. Virol. 66:1635-1640.

Johnston, M., Gene Chips: Array of hope for understanding gene regulation; (1998) Curr. Biol. 8:R171-R174.

Jones, R., Biology and Treatment of Chronic Myeloid Leukemia, Curr. Opin. Onc. 9:3-7 (1997).

Jones, T., Interactive Computer Graphics: FRODO, Methods in Enzymology 115:157-171 (1985).

Jose et al., Blockade or Macrophage colony-Stimulating Factor Reduces Macrophage Proliferation and Accumulation in Renal Allograft Rejection; Am J Transplant 2003, 3(3):294-300.

Joseph-McCarthy, D., Computational Approaches to Structure-Based Ligand Design, Pharmacology & Therapeutics 84:179-191 (1999).

Kahl, et al., A Multiple-Approach Scintillation Proximity Assay to Measure the Association Between Ras and Raf, Anal. Biochem. 243:282-283 (1996).

Katritzky, et al., Regiospecific C-Acylation of Pyrroles and Indoles Using N-Acylbenzotriazoles, J. Org. Chem. 68:5720-5723 (2003).

Kay, et al., Eosinophils and Eosinophil-Associated Cytokines in Allergic Inflammation, Int: Arch. Aller. Immunol. 113:196-199 (1997).

Kern and Hampton, Direct Hybridization of Large-Insert Genomic Clones on High-Density Gridded cDNA Filter Arrays, Biotechniques 23:120-124 (1997).

Kim et al, A Merger of Rational Drug Design and Combinatorial Chemistry: Development and Application of Peptide Secondary Structure Mimetics, Combinatorial Chemistry & High Throughput Screening 3:167-183 (2000).

Kim et al, Database CAS on STN (Columbus, OH, USA) No, 138:55974, Preparation of 2-anilino-4-e indolylpyrimidines as tyrosine kinase inhibitors, abstract, 2002) see whole article.

Kinashi and Springer, Steel Factor and c-kit Cell-Matrix Adhesion; Blood 83:1033-1038 (1994).

Kirkpatrick, et al., Structure-Based Drug Design: Combinatorial Chemistry and Molecular Modeling, Combinatorial Chemistry & High Throughput Screening 2:211-221 (1999).

Kitamura, et al., Synthesis of Quinolines and 2H-Dihydropyrroles by Nucleophilic Substitution at the Nitrogen Atom of Oxime Derivatives, Synthesis 15:2415-2426 (2003).

Kline et al., Studies by 1H Nuclear Magnetic Resonance and Distance Geometry of the Solution Conformation of the x-Amylase Inhibitor Tendamistat, J. Mol. Biol. 189:377-382 (1986).

Knighton, et al., Structural Basis of the Intrasteric Regulation of Myosin Light Chain Kinases, Science 258:130-135 (1992).

Kodama et al, Congenital Osteoclast Deficiency in Osteopetrotic (op/op) Mice Is Cured by Injections of Macrophage colony-stimulating Factor; J. Exp,. Med. 1991, 173: 269-72.

Kolaskar et al, A Semi-Empirical Method for Prediction of Antigenic Determinants on Protein Antigens, FEBS Lett. 276:172-174 (1990).

Kondoh, et al., An in vivo model for receptor tyrosine kinase autocrine/paracrine activation: auto-stimulated Kit receptor acts as a tumor promoting factor in papillomavirus-induced tumorigenesis; 1995, Oncogene 10:341-347.

Kondoh, et al., Establishment and Further Characterization of a Line of Transgenic Mice Showing Testicular Tumorigenesis at 100% Incidence, J. Urol. 152:2151-2154 (1994).

Kondoh, et al., Very High Incidence of Germ Cell tumorigenesis (Seminomagenesis) in Human Papillomavirus Type 16 Transgenic Mice; 1991, J. Virol. 65:3335-3339.

Kroll, David J., et al., A Malfunctional Prokaryotic Protein Expression System: Overproduction, Affinity Purification, and Selective Detection; (1993) DNA Cell. Biol. 12:441-53.

Kundu, et al., Combinatorial Chemistry: Polymer Supported Synthesis of Peptide and Non-Peptide Libraries, Progress in Drug Research 53:89-156 (1999).

Kunisada, et al., Murine Cutaneous Mastocytosis and Epidermal Melanocytosis Induced by Keratinocyte Expression of Transgenic Stem Cell Factor; 1998, J. Exp. Med. 187:1565-1573.

Kunkel, T., Rapid and Efficient Site-Specific Mutagenesis Without Phenotypic Selection, Proc. Natl. Acad. Sci. USA 82:488-492 (1985).

Kuntz, et al., A Geometric Approach to Macromolecule-Ligand Interactions, J. Mol. Biol. 161:269-288 (1982).

Kuntz, et al., Structure-Based Molecular Design, Acc. Chem. Res. 27:117-123 (1994).

Lahm, et al., Interleukin 4 Down-Regulates Expressidn of c-kit and Autocrine Stem Cell Factor in Human Colorectal Carcinoma Cells, Cell Growth & Differ 6:1111-1118 (1995).

Lam et al., A new type of synthetic peptide library for identifying ligand-binding activity, Nature, 354: 82-84, 1991.

Langham et al., Metalation of Halogen-Metal Interconversion Reactions of Some Halogenated Phenyl Ethers, J. Am. Chem. Soc., vol. 63, 1941, pp. 545-549.

Lawicki et al., The pretreratment plasma level and disgnostic utility of M-CSF in benign breast tumor and breast cancer patients, Clinica Chimica Acta, 371: 112-116, 2006.

Le Meur et.al., Macrophage accumulation at a site of renal inflammation is dependent on the M-CSF/c-fms pathway; J Leukocyte Biology, 2002, 72: 530-537.

Lebl, et al., One-Bead-One-Structure Combinatorial Libraries, Biopolymers 37:177-198 (1995).

Lee, et al., HLA-DR-Triggered Inhibition of Hemopoiesis Involves Fas/Fas Ligand Interactions and is Prevented by c-kit Ligand, J. Immunol. 159:3211-3219 (1997).

Lee, et al., Mast Cells: A Cellular Link Between Autoantibodies and Inflammatory Arthritis, Science 297:1689-1692 (2002).

Levin, et al., Neoplasms of the Central Nervous System, Cancer Principles & Practice of Oncology 2:2022-2082 (1997).

Li, et al., Abrogation of c-kit/Steel Factor-Dependent Tumorigenesis by Kinase Defective Mutants of the c-kit Receptor: c-kit Kinase Defective Mutants as Candidate Tools for Cancer Gene Therapy, Canc. Res. 56:4343-4346(1996).

Libby, Inflammation in atherosclerosis, Nature, 2002;420:868-874.

Liparoto, et al., Biosensor Analysis of the Interleukin-2 Receptor Complex, Journal of Molecular Recognition 12:316-321 (1999).

Lipinski, et al., Experimental and Computational Approaches to Estimate Solubility and Permeability in Drug Discovery and Development Settings, Advanced Drug Delivery Reviews 23:3-25 (1997).

Lipschultz et al., Experimental design for analysis of complex kinetics using surface plasmon resonance, Methods; (2000) 20(3):310-318.

London, et al., Expression of Stem Cell Factor Receptor (c-kit) by the Malignant Mast Cells from Spontaneous Canine Mast Cell Tumors, 1996, J. Compar. Pathol. 115:399-414.

Longley, et al., Altered Metabolism of Mast-cell Growth Factor (c-kit Ligand) in Cutaneous Mastocytosis, 1993, New Engl. J. Med. 328:1302-1307.

Longley, et al., Chymase Cleavage of Stem Cell Factor Yields a Bioactive Soluble Product, Proc. Natl. Acad. Sci. 94:9017-9021 (1997).

Longley, et al., Somatic c-Kit Activating Mutation in Urticaria Pigmentosa and Aggressive Mastocytosis: Establishment of Clonality in a Human Mast Cell Neoplasm, Nat. Gen. 12:312-314 (1996).

Loveland, et al., Stem Cell Factor and c-kit in the Mammalian Testis: Lessons Originating from Mother Nature 19s Gene Knockouts, J. Endocrinol 153:337-344 (1997).

Lu, et al., Oriented Immobilization of Fab 19 Fragments on Silica Surfaces, Anal. Chem. 67:83-87 (1995).

Lukacs, et al., Stem Cell Factor (c-kit Ligand) Influences Eosinophil Recruitment and Histamine Levels in Allergic Airway Inflammation, J. Immunol. 156:3945-3951 (1996).

Luo, et al., Close Linkage with the RET Proto-Oncogene and Boundaries of Deletion Mutations in Autosomal Dominant Hirschsprung Disease, Hum Mol Genet. 2(11):1803-1808 (1993).

Lyman, et al., c-kit Ligand and Flt3 Ligand: Stem/Progenitor Cell Factors With Overlapping Yet Distinct Activities, Blood 91:1101-1134 (1998).

Ma et al., Indolinone Derivatives Inhibit Constitutively Activated KIT Mutants and Kill Neoplastic Mast Cells, 2000, J Invest Dermatol. 114:392-394.

Ma, et al., The c-KIT Mutation Causing Human Mastocytosis is Resistant to ST1571 and Other KIT Kinase Inhibitors; Kinases with Enzymatic Site Mutations Show Different Inhibitor Sensitivity Profiles Than Wild-type Kinases and Those With Regulatory-Type Mutations, Blood 99:1741-1744 (2002).

Madden, et al., Synthetic Combinatorial Libraries: Views on Techniques and Their Application Perspectives in Drug Discovery and Design 2:269-285 (1994).

Malmborg, et al., BIAcore as a Tool in Antibody Engineering, Journal of Immunological Methods 183:7-13 (1995).

Malmqvist, et al., Biomolecular Interaction Analysis: Affinity Biosensor Technologies for Functional Analysis of Proteins, Current Opinion in Chemical Biology 1:378-383 (1997).

Malmqvist., BIAcore: an affinity biosensor system for characterization of biomolecular interactions, (1999) Biochemical Society Transactions 27:335-40.

Markiewicz, et al., Synthetic Oligonucleotide Combinatorial Libraries and Their Applications, II Farmaco 55:174-177 (2000).

Martin, Y., Computer-Assisted Rational Drug Design, Methods Enz. 203:587-613 (1991).

Mazeas, et. al., Synthesis of new melatoninergic ligands including azaindole moiety. Heterocycles, 50:1065 (1999).

McCall, et al., Characterization of Anti-Mouse FcγRll Single-Chain Fv Fragments Derived from Human Phage Display Libraries, Immunotechnology 4:71-87 (1998).

McPherson, A., Current Approaches to Macromolecule Crystallization, Eur. J. Biochem. 189:1-23 (1990).

Mekori, et al., Transforming Growth Factor-β Prevents Stem Cell Factor-Mediated Rescue of Mast Cells from Apoptosis After IL-3 Deprivation, 1994, J. Immunol 153:2194-2203.

Mekori, et al., The Role of c-Kit and Its Ligand, Stem Cell Factor, in Mast Cell Apoptosis, 1995, Int. Arch. Allergy Immunol. 107:136-138.

Meltzer, The pharmacological basis for the treatment of perennial allergic rhinitis and non-allergic rhinitis with topical corticosteroids, 1997, Aller. 52:33-40.

Meng, et al., Automated Docking with Grid-Based Energy Evaluation, J. Compt. Chem. 13:505-524 (1992).

Merour and Joseph, Synthesis and Reactivity of 7-Azaidoles (1H-Pyrrolo[2,3-b]pyridine), Curr. Org. Chem. 2001, 5:471-506.

Merrit, A., Solution Phase Combinatorial Chemistry, Comb Chem High Throughput Screen 1:57-72 (1998).

Metcalf, D., Lineage Commitment in the Progeny of Murine Hematopoietic Preprogenitor Cells: Influence of Thrombopoietin and Interleukin 5, Proc. Natl. Acad. Sci. USA 95:6408-6412 (1998).

Metcalfe, Classification and Diagnosis of Mastocytosis: Current Status, 1991, J. Invest. Derm 93:2S-4S.

Metcalfe, et al., Mast Cells, Physiol. Rev. 77:1033-1079 (1997).

Miller, et al., FLOG: A System to Select Quasi-Flexible Ligands Complementary to a Receptor of Known Three-Dimensional Structure, J. Comp. Aided Molec. Design 8:153-174 (1994).

Minakata et al., Functionalization of 1H-Pyrrolo[2,3-b]pyridine, Bulletin of the Chemical Society of Japan (1992), 65(11): 2992-2997.

Minakata, et al., Regioselective Funtionalization of 1H-Pyrrolo[2,3-b]pyridine Via its N-Oxide, Synthesis pp. 661-663 (1992).

Miranker et al, Functionality Maps of Binding Sites: A Multiple Copy Simultaneous Search Method, Proteins: Structure, Function, and Genetics 11:29-34 (1991).

Mitra, et al., Fluorescence Resonance Energy Transfer Between Blue-Emitting and Red-Shifted Excitation Derivatives of the Green Fluorescent Protein, Gene 173:13-17 (1996).

Miyaura and Suzuki, Palladium-Catalyzed Cross-Coupling Reactions of Organoboron Compounds, Chem. Rev. 1995, 95:2457.

Mol, et al. Structural Basis for the Autoinhibition and STI-571 Inhibition of c-Kit Tyrosine Kinase, J. Biol. Chem. 279:31655-31663 (2004).

Mol, et al., Structure of a c-Kit Product Complex Reveals the Basis for Kinase Transactivation, J. Biol. Chem. 278:31461-31464 (2003).

Motoyoshi, Biological activities and clinical application of M-CSF, Int J Hematol. 1998, 67:109-22.

Murty, et al., A Genetic Perspective of Male Germ Cell tumors, 1998, Sem. Oncol. 25:133-144.

Naclerio, et al., Rhinitis and Inhalant Allergens, JAMA 278:1842-1848 (1997).

Nagafuji and Cushman, A General Synthesis of Pyrroles and Fused Pyrrole Systems from Ketones and Amino Acids, J. Org. Chem. 61:4999-5003 (1996).

Nagata, et al., Elevated Expression of the Proto-Oncogene c-kit in Patients with Mastocytosis, Leukemia 12:175-181 (1998).

Nahm and Weinreb, N-Methoxy-N-Methylamides as Effective Acylating Agents, Tetrahedron Lett. 22(39):3815-3818 (1981).

Navaza, J., AMoRe: an Automated Package for Molecular Replacement, Acta Cryst. A50:157-163 (1994).

Neidle, et al., Molecular Modeling to Study DNA Intercalation by Anti-Tumor Drugs, Methods Enz. 203:433-458 (1991).

Ng, et al., Engineering Protein-Lipid Interactions: Targeting of Histidine-Tagged Proteins to Metal-Chelating Lipid Monolayers, Langmuir 11:4048-4055 (1995).

Nicholls, et al., Protein Folding and Association: Insights From the Interfacial and Thermodynamic Properties of Hydrocarbons, Proteins 11:281-296 (1991).

Nichols, et al., Development of a Scintillation Proximity Assay for Peroxisome Proliferator-Activated Receptor γ Ligand Binding Domain, Anal. Biochem. 257:112-119 (1998).

Notice of Allowance dated Dec. 26, 2007 for U.S. Appl. No. 11/016,350.

Notice of Allowance dated Jun. 6, 2008 for U.S. Appl. No. 11/154,988.

Okada, et al., Gene Therapy Against an Experimental Glioma Using Adeno-Associated Virus Vectors, Gene Ther. 3:957-964 (1996).

Okayama, et al., Human Lung Mast Cells are Enriched in the Capacity to Produce Granulocyte-Macrophage Colony-Stimulating Factor in Response to IgE-Dependent Stimulation, Eur. J. Immunol. 28:708-715 (1998).

Okayama, et al., Activation of Eosinophils with Cytokines Produced by Lung Mast Cells, Int. Arch. Aller. Immunol. 114(suppl. 1):75-77 (1997).

Olah, et al., Synthetic Methods and Reactions: Part 209. Improved Preparation of Aldehydes and Ketones from N,N-Dimethylamides and Grignard Reagents, Synthesis pp. 228-230 (1984).

O'Shannessy and Winzor, Interpretation of Deviations from Pseudo-First-Order Kinetic Behavior in the Characterization of Ligand Binding by Biosensor Technology, Analytical Biochemistry 236:275-283 (1996).

O'Shannessy, Determination of kinetic rate and equilibrium binding constants for macromolecular interactions: a critique of the surface plasmon resonance literature, (1994) Current Opinions in Biotechnology, 5:65-71.

Ottoni, et al., Efficient and Simple Methods for the Introduction of the Sulfonyl, Acyl and Alkyl Protecting Groups on the Nitrogen of Indole and its Derivatives, Tetrahedron 54:13915-13928 (1998).

Otwinowski, Z., Maximum Likelihood Refinement of Heavy Atom Parameters, Dept. of Molecular Biophysics and Biochemistry pp. 80-86 (1991).

Owicki et al., Application of Fluorescence Polarization Assays in High-Throughput Screening, (1997), Genetic Engineering News, 17:27.

Parker, et al., Development of High Throughput Screening Assays Using Fluorescence Polarization: Nuclear Receptor-Ligand-Binding and Kinase/Phosphatase Assays, J Biomol Screen 5:77-88 (2000).

Perrin, D., Nucleic Acids for Recognition and Catalysis: Landmarks, Limitations, and Looking to the Future, Combinatorial Chemistry & High Throughput Screening 3:243-269 (2000).

Petty et al, The effect of systemically administered recombinant human nerve growth factor in healthy human subjects. Ann Neurol. 36:244-6 (1994).

Pflugrath, et al., Crystal Structure Determination, Refinement and the Molecular Model of the x-Amylase Inhibitor Hoe-467A, J. Mol. Biol. 189:383-386 (1986).

Pierce et al., Local anaesthetics. I. beta-Monoaklylaminoethyl Esters of Alkoxybenzoic Acids, J. Am. Chem. Soc., vol. 64, 1942, pp. 1691-1694.

Pignon, J.M., C-kit mutations and mast cell disorders A model of activating mutations of growth factor receptors, Hermatol Cell Ther 39:114-116 (1997).

Plunkett et al, A Silicon-Based Linker for Traceless Solid-Phase Synthesis, J. Org. Chem. 60:6006-6007 (1995).

Poul, et al., Selection of Tumor-Specific Internalizing Human Antibodies from Phage Libraries, J. Mol. Biol. 301:1149-1161 (2000).

Price et al.; Summary report on the ISOBM TD-4 Workshop: analysis of 56 monoclonal antibodies against the MUC1 mucin, (1998) Tumour Biology 19 Suppl 1:1-20.

Qiao, et. al., Role of Macrophage Colony-Stimulating Factor in Atherosclerosis, Am. J. Path. 1997;150:1687-1699.

Rajavashisth, et. al., Heterozygous Osteopetrotic (op) Mutation Reduces Atherosclerosis in LDL Receptor-deficient Mice, J. Clin. Invest. 1998;101:2702-2710.

Rajpert-de Meyts, et al., Expression of the c-kit Protein Product in Carcinoma-in-situ and Invasive Testicular Germ Cell Tumours, Int. J. Androl. 17:85-92 (1994).

Ricotti, et al., c-kit Is Expressed in Soft Tissue Sarcoma of Neuroectodermic Origin and Its Ligand Prevents Apoptosis of Neoplastic Cells, Blood 91:2397-2405 (1998).

Ridge et al, FMS mutations in myelodysplastic, leukemic, and normal subjects, Proc. Nat. Acad. Sci., 1990, 87:1377-1380.

Roberts, S., et al., Generation of an antibody with enhanced affinity and specificity for its antigen by protein engineering, (1987) Nature 328:731-734.

Robinson et al., Stimulation of Bone Marrow Colony Growth In Vitro by Human Urine; Blood, 1969, 33:396-9.

Robison et al, 7-Azaindole. I. Synthesis and Conversion to 7-Azatryptophan and Other Derivatives, J. Am. Chem. Soc. 77:457-460 (1955).

Rodan, G., et al., Therapeutic Approaches to Bone Diseases, Science. 2000;289:1508.

Rosenfeld, Human artificial chromosomes get real, (1997) Nat. Genet. 15:333-335.

Ryan, et al., Role for the Stem Cell Factor/KIT Complex in Schwann Cell Neoplasia and Mast Cell Proliferation Associated with Neurofibromatosis, 1994, J. Neuro. Res. 37:415-432.

Saify et al, Database CAS on STN (Columbus, OH, USA) No. 124:170379, Synthesis of some 2-azaindole derivatives: their cyctotoxicity and antibacterial activity, abstract, (1996), See RN 271-63-6.

Saify et al., Synthesis of some 7-azaindole derivatives: Their cytotoxicity and antibacterial activity, Pakistan Journal of Scientific and Industrial Research, 37(10): 439-441, 1994.

Saiki, Amplification of Genomic DNA, in PCR Protocols, Innis et al., Eds., Academic Press, San Diego, CA 1990, pp. 13-20.

Sambrook et al, Molecular Cloning: A Laboratory Manual, 1989, Cold Spring Harbor Laboratory Press, Cold Spring Harbor N.Y, pp. 16.30-16.37.

Sandlow, et al., Expression of c-KIT and its Ligand, Stem Cell Factor, in Normal and Subfertile Human Testicular Tissue, 1996, J. Androl. 17:403-408.

Santoro, et al., The ret Proto-Oncogene is Consistently Expressed in Human Pheochromocytomas and Thyroid Medullary Carcinomas, Oncogene, 5(10):1595-1598 (1990).

Sawada et al., 4-(Benzoylindolizinyl)butyric acids; Novel nonsteroidal inhibitors of steroid 5;1-reductase. III, Chemical and Pharmaceutical Bulletin (2001), 49(7): 799-813.

Sawada, et al., Role of Cytokines in Leukemic type Growth of Myelodysplastic CD34+ Cells, 1996, Blood 88:319-327.

Sawai, et al., Aberrant growth of granulocyte-macrophage progenitors in juvenile chronic myelogenous leukemia in serum-free culture, 1996, Exp. Hem. 2:116-122.

Scheffner, et al., The E6 Oncoprotein Encoded by Human Papillomavirus Types 16 and 18 Promotes the Degredation of p53, Cell 63:1129-1136 (1990).

Schiemann and Winkelmüller, p-Fluorobenzoic Acid, Org. Syn. Coll. vol. 2:299, 1943.

Schneider, et al., Functional Purification of a Bacterial ATP-Binding Cassette Transporter Protein (MaIK) from the Cytoplasmic Fraction of an Overproducing Strain, (1995) Protein Expr. Purif. 6435:10.

Schneller et. al., Synthesis of 4-Amino-1 H-pyrrolo[2,3-b]pyridine {1 ,7-Dideazaadenine) and 1H-Pyrrolo[2,3-b]pyridine-4-ol (1,7-Dideazahypoxanthine), J. Org. Chem. 1980, 45:4045.

Schuhmann, et al., Immobilization of Enzymes on Langmuir-Blodgett Films via a Membrane-Bound Receptor. Possible Applications for Amperometric Biosensors, Adv. Mater. 3:388-391 (1991).

Schummer, et al., Inexpensive Handheld Device for the Construction of High-Density Nucleic Acid Arrays, Biotechniques 23:1087-1092 (1997).

Schweizer, et al., Combinatorial Synthesis of Carbohydrates, Curr Opin. Chem. Biol., 3:291-298 (1999).

Selvin, P., Fluorescence Resonance Energy Transfer, Meth. Enzymol. 246:300-345 (1995).

Sheets, et al., Efficient Construction of a Large Nonimmune Phage Antibody Library: The Production of High-Affinity Human Single-Chain Antibodies to Protein Antigens, Proc Natl Acad Sci USA 95:6157-6162 (1998).

Shibata et al, Alveolar macrophage deficiency in osteopetrotic mice deficient in macrophage colony-stimulating factor is spontaneously corrected with age and associated with matrix metalloproteinase expression and emphysema Blood 2001, 98: 2845-2852.

Siegel, et al., Mass Spectral Analysis of a Protein Complex Using Single-Chain Antibodies Selected on a Peptide Target: Applications to Functional Genomics, Journal of Molecular Biology 302:285-293 (2000).

Sigal, et al., A Self-Assembled Monolayer for the Binding and Study of histidine-Tagged Proteins by Surface Plasmon Resonance, (1996) Anal. Chem. 68:490-497.

Smalley et al., c-KIT signaling as the driving oncogenic event in sub-groups of melanomas. Histol Histopathol, 24:643-650, 2009.

Solinas-Toldo, et al., Matrix-Based Comparative Genomic Hybridization Biochips to Screen for Genomic Imbalances, Genes, Chromosomes & Cancer 20:399-407 (1997).

Song et al., Iomerism of Bis(7-azaindolyl)methane, Organic Letters (2002), 4:23, 4049-4052, Table of content p. 1-16 and Supporting information p. 1-15.

Sperling, et al., Expression of the Stem Cell Factor Receptor C-Kit (CD117) in Acute Leukemias, Haemat 82:617-621 (1997).

Stanulla, et al., Coexpression of Stem Cell Factor and Its Receptor c-Kit in Human Malignant Glioma Cell Lines, Act Neuropath 89:158-165 (1995).

Strohmeyer, et al., Expression of the C-kit Proto-Oncogene and its Ligand Stem Cell Factor (SCF) in Normal and Malignant Human Testicular Tissue, 1995, J. Urol. 153:511-515.

Strohmeyer, et al., Expression of the hst-1 and c-kit Protooncogenes in Human Testicular Germ Cell Tumors, Canc. Res. 51:1811-1816 (1991).

Su & Tsou, Synthesis of bromo-substituted Idoxyl Esters for Cytochemical Demonstration of Enzyme Activity, J. Am. Chem. Soc.,82, 1960, 1187.

Sun, C., Recent Advances in Liquid-Phase Combinatorial Chemistry, Comb. Chem. & High Throughput Screening 2:299-318 (1999).

Sun, et al., Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases, J. Med. Chem. 42:5120-5130 (1999).

Supplemental Notice of Allowance dated Jul. 23, 2008 for U.S. Appl. No. 11/154,988.

Supplemental Notice of Allowance dated Sep. 8, 2008 for U.S. Appl. No. 11/154,988.

Supplementary Search Report dated Aug. 4, 2009 for European Application No. 04814626.0.

Tada, et al., Analysis of Cytokine Receptor Messenger RNA Expression in Human Glioblastoma Cells and Normal Astrocytes by Reverse-Transcription Polymerase Chain Reaction, J. Neuro 80:1063-1073 (1994).

Takahashi et al, ret Transforming Gene Encodes a Fusion Protein Homologous to Tyrosine Kinases, Mol Cell Biol. 7:1378-1385 (1987).

Takahashi, et al., Activation of a Novel Human Transforming Gene, ret, by DNA Rearrangement, Cell 42(2):581-588 (1985).

Takahashi, et al., Cloning and Expression of the ret Proto-Oncogene Encoding a Tyrosine Kinase with Two Potential Transmembrane Domains, Oncogene 3(5):571-578 (1988).

Taylor et al. The Rapid Generation of Oligonucleotide-directed Mutations at High Frequency Using Phosphorothloate-Modified DNA; (1985) Nucl. Acids Res. 13:8764-8785.

Teitelbaum, Bone Resorption by Osteoclasts, Science. 2000;289:1504.

Thibault et. al., Concise and Efficient Synthesis of 4-fluoro-1H-pyrrolo[2,3-b] pyridine, Org. Lett. 2003, 5:5023-5025.

Thomas et al, The Eosinophil and its Role in Asthma, Gen. Pharmac 27:593-597 (1996).

Thomas, et. al., Light-Emitting Carbazole Derivatives: Potential Electroluminescent Materials, J. Am. Chem. Soc. 123:9404-9411 (2001).

Toste, et al., A Versatile Procedure for the Preparation of Aryl Thiocyanates Using N-Thiocyanatosuccinimide (NTS), Synth. Comm. 25(8):1277-1286 (1995).

Toyota, et al., Expression of c-kit and kit Ligand in Human Colon Carcinoma Cells, 1993, Turn Biol 14:295-302.

Trupp, et al., Functional Receptor for GDNF Encoded by the c-ret Proto-Oncogene, Nature 381:785-789 (1996).

Tsujimura, et al., Substitution of an Aspartic Acid Results in Constitutive Activation of c-kit Receptor Tyrosine Kinase in a Rat Tumor Mast Cell Line RBL-2H3, 1995, Int. Arch. Aller. Immunol 106:377-385.

Tsujimura, et al.,Ligand-Independent Activation of c-kit Receptor Tyrosine Kinase in a Murine Mastocytoma Cell Line P-815 Generated by a Point Mutation, Blood 9:2619-2626 (1994).

Tsujimura, T., Role of c-kit Receptor Tyrosine Kinase in the Development, Survival and Neoplastic Transformation of Mast Cells, Pathol Int 46:933-938 (1996).

Turner, et al., Nonhematopoeietic Tumor Cell Lines Express Stem Cell Factor and Display c-kit Receptors, 1992, Blood 80:374-381.

Undenfriend, et al., Scintillation Proximity Assay: A Sensitive and Continuous Isotopic Method for Monitoring Ligand/Receptor and Antigen/Antibody Interactions, Anal. Biochem., 161:494-500 (1987).

Uritskaya et al., STN Accession No. 1974-27133; Abstract of Khimiya Geterotsiklicheskikh Soedinenii (1973, (10), 1370-3).

US Notice of Allowance dated May 27, 2010 in related U.S. Appl. No. 11/435,381.

US Office Action dated Jan. 4, 2008 for U.S. Appl. No. 11/154,988.
US Office Action dated Jun. 6, 2007 for U.S. Appl. No. 11/016,350.
US Office Action dated Aug. 22, 2007 for U.S. Appl. No. 11/487,134.
US Office Action dated Sep. 22, 2009 for U.S. Appl. No. 11/986,667.
US Office Action dated Oct. 19, 2007 for U.S. Appl. No. 11/154,988.
US Office Action dated Oct. 26, 2007 for U.S. Appl. No. 11/016,350.
US Office Action dated Aug. 2, 2007 in related U.S. Appl. No. 11/016,350.
US Office Action dated Feb. 19, 2010 for U.S. Appl. No. 11/435,381.
US Office Action dated Feb. 26, 2010 for U.S. Appl. No. 11/986,667.
US Office Action dated Jun. 1, 2009 for U.S. Appl. No. 11/435,381.
US Office Action dated Mar. 4, 2009 for U.S. Appl. No. 11/435,381.
US Office Action dated May 15, 2008 in related U.S. Appl. No. 11/487,134.
US Office Action Dec. 18, 2009 for U.S. Appl. No. 11/473,347.

Valent, P., Biology, Classification and Treatment of Human Mastocytosis, Wein/Klin Wochenschr 108:385-397 (1996).

Van Heyningen,V., One Gene—Four Syndromes, Nature 367:319-320 (1994).

Van Regenmortel, Use of biosensors to characterize recombinant proteins, (1994), Developments in Biological Standardization, 83:143-51.

Vely F. et al., BIAcore® analysis to test phosphopeptide-SH2 domain interactions, (2000), Methods in Molecular Biology, 121:313-21.

Verfaillie, Chronic myelogenous leukemia: too much or too little growth, or both?; Leukemia, 1998, 12:136-138.

Viskochil, D., It Takes Two to Tango: Mast Cell and Schwann Cell Interactions in Neurofibromas, J Clin Invest., 112:1791-1793 (2003).

Vliagoftis, et al., The protooncogene c-kit and c-kit ligand in human disease, Journ. Clin. Immunol, 100:435-440 (1997).

Weber, P., Physical Principles of Protein Crystallization, Adv. Protein Chem., 41:1-36 (1991).

Wendt, et al, Identification of novel binding interactions in the development of potent, selective 2-naphthamidine inhibitors of urokinase, synthesis, structural analysis, and SAR of y-Phenyl amide 6-substitution. J. Med. Chem., 47(2):303 (2004).

Werness, et al., Association of Human Papillomavirus Types 16 and 18 E6 Proteins with p53, Science 248:76-79 (1990).

Wessjohann, L., Synthesis of Natural-Product-Based Compound Libraries, Curr Opin Chem Biol., 4:303-309 (2000).

Wharam, et al., Specific Detection of DNA and RNA Targets Using a Novel Isothermal Nucleic Acid Amplification Assay Based on the Formation of a Three-Way Junction Structure, Nucleic Acids Res., 29:1-8 (2001).

Williams et al., Dissection of the Extracellular Human Interferon y Receptor a-Chain into two Immunoglobulin-like domains. Production in an *Escherichia coli* Thioredoxin Gene Fusion Expression system and Recognition by Neutralizing Antibodies, (1995) Biochemistry 34:1787-1797.

Woon, et al., Construction and Characterization of a 10-Fold Genome Equivalent Rat P1-Derived Artificial Chromosome Library, Genomics, 50:306-316 (1998).

Wuthrich, K., Chapter 10: Three-Dimensional Protein Structures by NMR, NMR of Proteins and Nucleic Acids, 10:176-199 (1986).

Wyckoff et al., Direct visualization of macrophage-assisted tumor cell intravasation in mammary tumors. Cancer Research, 67(6): 2649-2656, 2007.

Xu et al, Modulation of Endothelial Cell function by Normal Polyspecific Human Intraveneous immunoglobulins, Am. J. Path. 1998;153:1257-1266.

Yakhontov et al., Derivatives of 7-azaindole. XV. Electrophilic substitution of 4-methyl-7-azaindole and its derivatives, Zhurnal Obshchei Khimii (1965), 1(11): 2032-2040. (English abstract only).

Yang et al., Nf1-Dependent tumors require a microenvironment containing Nf1+/_-and c-kit-Dependent bone marrow, Cell, 135:437-448, 2008.

Yang et. al., Synthesis of some 5-substituted indoles. Heterocycles, 34:1169 (1992).

Yang, et al., Neurofibromin-Deficient Schwann Cells Secrete a Potent Migratory Stimulus for NF1+/_Mast Cells, J Clin Invest., 112:1851-1861 (2003).

Yee, et al., Role of kit-Ligand in Proliferation and Suppression of Apoptosis in Mast Cells: Basis for Radiosensitivity of White Spotting and Steel Mutant Mice, J. Exp. Med., 179:1777-1787 (1994).

Yeung et al., Friedel-Crafts acylation of indoles in acidic imidazolium chloroaluminate ionic liquid at room temperature, Tetrahedron Letters, (2002), 43(33), 5793-5795.

Yuan, et al., Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1), J. Exp. Med. 186:313-323 (1997).

Zanon, et. al., Copper-Catalyzed Domino Halide Exchange-Cyanation of Aryl Bromides, J. Am. Chem. Soc. 125:2890-2891 (2003).

Zhang et al., An effective procedure for the acylation of azaindoles at C-3, Journal of Organic Chemistry (2002), 67(17): 6226-6227 and p. S1-S30.

* cited by examiner

COMPOUNDS AND METHODS FOR KINASE MODULATION, AND INDICATIONS THEREFOR

RELATED PATENT APPLICATIONS

This application claims priority to U.S. Provisional App. No. 60/877,052, entitled "Compounds and Methods for Kinase Modulation, and Indications Therefor", filed Dec. 1, 2006, and is related to U.S. patent application Ser. No. 11/473,347, entitled "Compounds and Methods for Kinase Modulation, and Indications Therefor", filed Jun. 21, 2006, which claims the benefit of U.S. Provisional App. No. 60/731,528, entitled "Compounds and Methods for Kinase Modulation, and Indications Therefor", filed Oct. 28, 2005, and U.S. Provisional App. No. 60/692,960, entitled "Compounds and Methods for Kinase Modulation, and Indications Therefor", filed Jun. 22, 2005, all of which are incorporated herein by reference in their entireties and for all purposes.

FIELD OF THE INVENTION

The present invention relates to kinases and compounds which modulate kinases, and uses therefor. Particular embodiments contemplate disease indications which are amenable to treatment by modulation of kinase activity by the compounds of the present invention.

BACKGROUND OF THE INVENTION

The information provided herein is intended solely to assist the understanding of the reader. None of the information provided nor references cited is admitted to be prior art to the present invention. Each of the references cited herein is incorporated herein by reference in its entirety.

Receptor protein kinases regulate key signal transduction cascades that control or are involved in the control of a plethora of physiological functions including cellular growth and proliferation, cell differentiation, cellular development, cell division, cell adhesion, stress response, short-range contact-mediated axonal guidance, transcription regulation, aberrant mitogenesis, angiogenesis, abnormal endothelial cell-cell or cell-matrix interactions during vascular development, inflammation, lymphohematopoietic stem cell activity, protective immunity against specific bacteria, allergic asthma, aberrant tissue-specific responses to the activation of the JNK signal transduction pathway, cell transformation, memory, apoptosis, competitive activity-dependent synapse modification at the neuromuscular synapse, immunological mediation of disease, and calcium regulation.

Specific disease states associated with aberrant regulation of protein kinases include, for example without limitation, acrocephalo-syndactyl type I, acute myeloid leukemia, AIDS-induced non-Hodgkin's lymphoma, Alzheimer's disease, amyotrophic lateral sclerosis, arthritis, asthma, atherosclerosis, atopic dermatitis, autoimmune diseases, bacterial infection, bladder cancer, cancer of the breast, cancer of the central nervous system, cancer of the colon, cancer of the endometrium, cancer of the fallopian tube, cancer of the gastrointestinal tract, cancer of the ovary, heart failure, chronic myeloid leukemia, colon carcinoma, colorectal cancer, chronic obstructive pulmonary disease (COPD), Crouzon Syndrome, diabetes, diabetic nephropathy, emphysema, endometriosis, epidermoid cancer, fibrotic disorders, gastrointestinal stromal tumor (GIST), glomerulonephritis, Graves' disease, head injury, hepatocellular carcinoma, Hirschsprung's disease, human gliomas, immunodeficiency diseases, inflammatory disorders, ischemic stroke, Jackson-Weiss syndrome, leiomyosarcoma, leukemias, lupus nephritis, malignant melanoma, malignant nephrosclerosis, mastocytosis, mast cell tumors, melanoma of the colon, MEN2 syndromes, metabolic disorders, migraine, multiple sclerosis, myeloproliferative disorders, nephritis, neurodegenerative diseases, neurotraumatic diseases, non small cell lung cancer, organ transplant rejection, osteoporosis, pain, Parkinson's disease, Pfeiffer Syndrome, polycystic kidney disease, primary lymphoedema, prostate cancer, psoriasis, vascular restenosis, rheumatoid arthritis, dermal and tissue scarring, selective T-cell defect (STD), severe combined immunodeficiency (SCID), small cell lung cancer, spinal cord injury, squamous cell carcinoma, systemic lupus erythematosis, testicular cancer, thrombotic microangiopathy syndromes, Wegener's granulomatosis, X-linked agammaglobulinemia, viral infection, diabetic retinopathy, alopecia, erectile dysfunction, macular degeneration, chronic lymphocytic leukemia (CLL), myelodysplastic syndrome (MDS), neurofibromatosis, and tuberous sclerosis.

This application is related to the following published patent applications: WO 2004024895, US 20040142864, WO 2004078923, US 20050170431, WO 2005028624, US 20050164300, and WO 2005062795, each of which are hereby incorporated by reference herein in their entireties including all specifications, figures, and tables, and for all purposes.

SUMMARY OF THE INVENTION

Compounds are contemplated that are active on protein kinases in general, including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and/or Zap70, including any mutations of these kinases. In some aspects, the compounds are active on protein kinases including, but not limited to, Fms, Kit, MAP4K4, TrkA, and/or TrkB, including any mutations thereof. In some aspects, compounds are of Formula I, Formula II, Formula III, or Formula IV as described below.

Also contemplated in accordance with the present invention are methods for the use of the above-described compounds in treating diseases and conditions associated with regulation of the activity of the above-described kinases. Thus, the use of compounds for therapeutic methods involving modulation of protein kinases is provided, as well as compounds that can be used for therapeutic methods involving modulation of protein kinases.

In some embodiments, compounds have the structure according to the following Formula I:

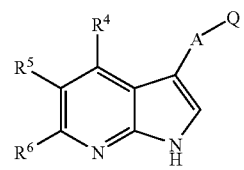

Formula I all salts, prodrugs, tautomers, and isomers thereof, wherein:

Q has a structure selected from the group consisting of

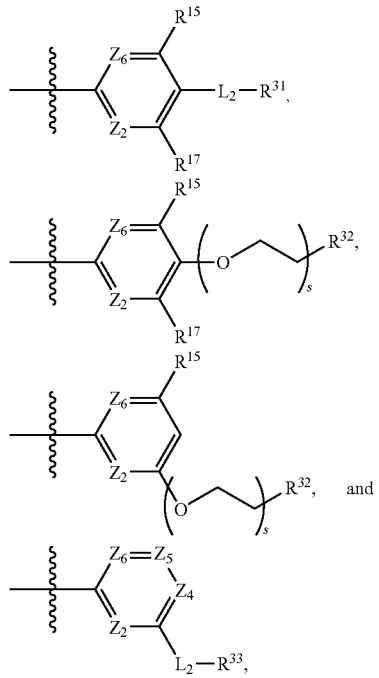

in which ⌇ indicates the attachment point of Q to A of Formula I;

$Z_2$ is N or $CR^{12}$; $Z_4$ is N or $CR^{14}$; $Z_5$ is N or $CR^{15}$; $Z_6$ is N or $CR^{16}$, $L_2$ is selected from the group consisting of —$(CR^{10}R^{11})_p$—$NR^{25}$—$(CR^{10}R^{11})_q$—, —$(CR^{10}R^{11})_p$—X—$(CR^{10}R^{11})_q$—, —$(CR^{10}R^{11})_p$—C(X)—$(CR^{10}R^{11})_q$—, —$(CR^{10}R^{11})_p$—S(O)—$(CR^{10}R^{11})_q$—, —$(CR^{10}R^{11})_p$—S(O)$_2$—$(CR^{10}R^{11})_q$—, —$(CR^{10}R^{11})_p$—C(X)NR^{25}$—$(CR^{10}R^{11})_q$—, —$(CR^{10}R^{11})_p$—S(O)$_2$NR^{25}$—$(CR^{10}R^{11})_q$—, —$(CR^{10}R^{11})_p$—NR^{25}C(X)—$(CR^{10}R^{11})_q$—, and —$(CR^{10}R^{11})_p$—NR^{25}S(O)$_2$—$(CR^{10}R^{11})_q$—;

p and q are independently 0, 1, or 2 provided, however, that at least one of p and q is 0;

s is 1 or 2;

A is selected from the group consisting of —O—, —S—, —$CR^aR^b$—, —$NR^1$—, —C(O)—, —C(S)—, —S(O)—, and —S(O)$_2$—;

$R^a$ and $R^b$ at each occurrence are independently selected from the group consisting of hydrogen, fluoro, —OH, —NH$_2$, lower alkyl, lower alkoxy, lower alkylthio, mono-alkylamino, di-alkylamino, and —$NR^8R^9$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro; or $R^a$ and $R^b$ combine to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^1$ is selected from the group consisting of hydrogen, lower alkyl, cycloalkyl, heterocycloalkyl, aryl, heteroaryl, —C(O)$R^7$, —C(S)$R^7$, —S(O)$_2R^7$, —C(O)NHR$^7$, —C(S)NHR$^7$, and —S(O)$_2$NHR$^7$, wherein lower alkyl is optionally substituted with one or more substituents selected from the group consisting of fluoro, —OH, —NH$_2$, lower alkoxy, lower alkylthio, mono-alkylamino, di-alkylamino, and —$NR^8R^9$, wherein the alkyl chain(s) of lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, further provided that when $R^1$ is lower alkyl, any substitution on the lower alkyl carbon bound to the N of —$NR^1$— is fluoro, and wherein cycloalkyl, heterocycloalkyl, aryl or heteroaryl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^7$ is selected from the group consisting of lower alkyl, cycloalkyl, heterocycloalkyl, aryl, and heteroaryl, wherein lower alkyl is optionally substituted with one or more substituents selected from the group consisting of fluoro, —OH, —NH$_2$, lower alkoxy, lower alkylthio, mono-alkylamino, di-alkylamino, and —$NR^8R^9$, provided, however, that any substitution of the alkyl carbon bound to the N of —C(O)NHR$^7$, —C(S)NHR$^7$ or —S(O)$_2$NHR$^7$ is fluoro, wherein the alkyl chain(s) of lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, and wherein cycloalkyl, heterocycloalkyl, aryl and heteroaryl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

each of $R^4$, $R^5$, $R^6$, $R^{12}$, $R^{14}$, $R^{15}$, and $R^{16}$, are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —CR$^a$R$^b$R$^{26}$, and -LR$^{26}$;

L at each occurrence is independently selected from the group consisting of -(alk)$_a$-X-(alk)$_b$-, -(alk)$_a$-NR$^{25}$-(alk)$_b$-, -(alk)$_a$-C(X)-(alk)$_b$-, -(alk)$_a$-S(O)-(alk)$_b$-, -(alk)$_a$-S(O)$_2$-(alk)$_b$-, -(alk)$_a$-OC(X)-(alk)$_b$-, -(alk)$_a$-C(X)O-(alk)$_b$-, -(alk)$_a$-C(X)NR$^{25}$-(alk)$_b$-, -(alk)$_a$-S(O)$_2$NR$^{25}$-(alk)$_b$-, -(alk)$_a$-NR$^{25}$C(X)-(alk)$_b$-, -(alk)$_a$-NR$^{25}$S(O)$_2$-(alk)$_b$-, -(alk)$_a$-NR$^{25}$C(X)O-(alk)$_b$-, -(alk)$_a$-OC(X)NR$^{25}$-(alk)$_b$-, -(alk)$_a$-NR$^{25}$C(X)NR$^{25}$-(alk)$_b$-, and -(alk)$_a$-NR$^{25}$S(O)$_2$NR$^{25}$-(alk)$_b$-;

a and b are independently 0 or 1;

alk at each occurrence is independently C$_{1-3}$ alkylene or C$_{1-3}$ alkylene substituted with one or more substituents selected from the group consisting of fluoro, —OH, —NH$_2$, lower alkyl, lower alkoxy, lower alkylthio, mono-alkylamino, di-alkylamino, and —NR$^8$R$^9$, wherein lower alkyl or the alkyl chain(s) of lower alkoxy, lower alkylthio, mono-alkylamino or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution of the alkyl chain carbon bound to O of alkoxy, S of thioalkyl or N of mono- or di-alkylamino is fluoro;

X at each occurrence is independently O or S;

R$^{25}$ at each occurrence is independently selected from the group consisting of hydrogen, optionally substituted lower alkyl, optionally substituted cycloalkyl, optionally substituted heterocycloalkyl, optionally substituted aryl, and optionally substituted heteroaryl;

R$^{26}$ at each occurrence is independently selected from the group consisting of hydrogen, provided, however, that hydrogen is not bound to any of S(O), S(O)$_2$, C(O) or C(S) of L, optionally substituted lower alkyl, optionally substituted lower alkenyl, provided, however, that when R$^{26}$ is optionally substituted lower alkenyl, no alkene carbon thereof is bound to N, S, O, S(O), S(O)$_2$, C(O) or C(S) of L, optionally substituted lower alkynyl, provided, however, that when R$^{26}$ is optionally substituted lower alkynyl, no alkyne carbon thereof is bound to N, S, O, S(O), S(O)$_2$, C(O) or C(S) of L, optionally substituted cycloalkyl, optionally substituted heterocycloalkyl, optionally substituted aryl, and optionally substituted heteroaryl;

R$^{10}$ and R$^{11}$ at each occurrence are independently selected from the group consisting of hydrogen, fluoro, lower alkyl, and lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, dialkylamino, and cycloalkylamino; or any two of R$^{10}$ and R$^{11}$ on the same or adjacent carbon atoms combine to form a 3-7 membered monocyclic cycloalkyl or 5-7 membered monocyclic heterocycloalkyl, and any others of R$^{10}$ and R$^{11}$ are independently selected from the group consisting of hydrogen, fluoro, lower alkyl, and lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein the monocyclic cycloalkyl or monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

R$^8$ and R$^9$ combine with the nitrogen to which they are attached to form a 5-7 membered heterocycloalkyl optionally substituted with one or more substituents selected from the group consisting of fluoro, —OH, —NH$_2$, lower alkyl fluoro substituted lower alkyl, lower alkoxy, fluoro substituted lower alkoxy, lower alkylthio, and fluoro substituted lower alkylthio;

R$^{17}$ is selected from the group consisting of hydrogen, halogen, optionally substituted lower alkyl and —OR$^{18}$;

each of R$^{31}$ and R$^{33}$ are independently selected from the group consisting of optionally substituted aryl, optionally substituted heteroaryl, optionally substituted cycloalkyl, and optionally substituted heterocycloalkyl;

R$^{32}$ is selected from the group consisting of hydrogen, optionally substituted lower alkyl, optionally substituted cycloalkyl, optionally substituted heterocycloalkyl, optionally substituted aryl, optionally substituted heteroaryl, and —OR$^{18}$; and R$^{18}$ is hydrogen or optionally substituted lower alkyl;

provided, however, that the compound is not 3-{3-[2-(tetrahydropyran-2-yloxy)-ethoxy]-benzyl}-5-thiophen-3-yl-1H-pyrrolo[2,3-b]pyridine, which has the structure

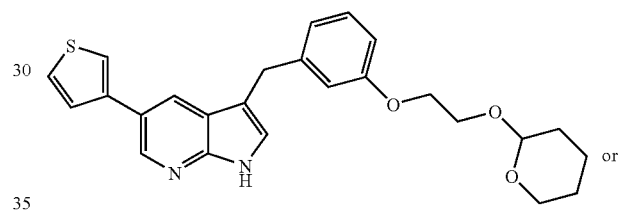

or 4-(4-Methyl-piperazin-1-ylmethyl)-N-[4-(1H-pyrrolo[2,3-b]pyridin-3-ylmethyl)-phenyl]-benzamide, which has the structure

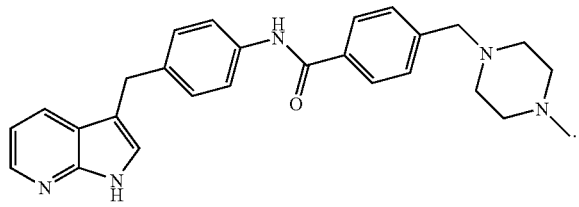

In some embodiments, compounds of Formula I have the structure according to the following sub-generic structure Formula Ia:

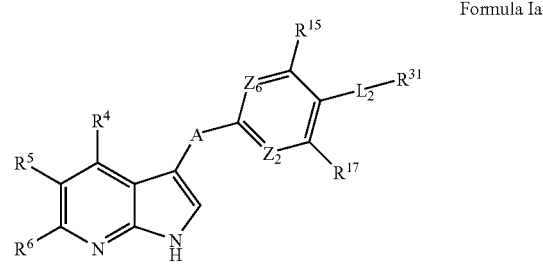

Formula Ia all salts, prodrugs, tautomers and isomers thereof, wherein A, $L_2$, $Z_2$, $Z_6$, $R^4$, $R^5$, $R^6$, $R^{15}$, $R^{17}$ and $R^{31}$ are as defined for Formula I.

In some embodiments of compounds of Formula Ia, $R^4$ and $R^6$ are hydrogen, A is —O—, —$CR^aR^b$—, —$NR^1$—, or —C(O)—, preferably —$CH_2$— or —C(O)—, more preferably —$CH_2$—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^{15}$ is selected from the group consisting of hydrogen, halogen, lower alkyl, fluoro substituted lower alkyl, lower alkoxy, and fluoro substituted lower alkoxy.

In some embodiments of compounds of Formula Ia, $R^4$ and $R^6$ are hydrogen, A is —O—, —$CR^aR^b$—, —$NR^1$—, or —C(O)—, preferably —$CH_2$— or —C(O)—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, $R^{15}$ is selected from the group consisting of hydrogen, halogen, lower alkyl, fluoro substituted lower alkyl, lower alkoxy, and fluoro substituted lower alkoxy, $Z_2$ is N or $CR^2$, $Z_7$ is N or $CR^{16}$, $R^{12}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino.

In some embodiments, compounds of Formula I have the structure according to the following sub-generic structure Formula Ib:

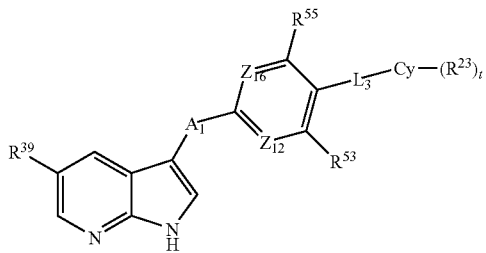

Formula Ib all salts, prodrugs, tautomers, and isomers thereof, wherein:
$A_1$ is —O—, —$CR^{40}R^{41}$—, —C(O)— or —$NR^{48}$—;
$Z_{12}$ is N or $CR^{52}$;
$Z_{16}$ is N or $CR^{56}$;
$R^{40}$ and $R^{41}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or
$R^{40}$ and $R^{41}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;
$L_3$ is selected from the group consisting of —$NR^{48}$—, —S—, —O—, —$NR^{48}CH(R^{49})$—, —$SCH(R^{49})$—, —$OCH(R^{49})$—, —$C(O)NR^{48}$—, —$S(O)_2NR^{48}$—, —$CH(R^{49})NR^{48}$—, —$CH(R^{49})O$—, —$CH(R^{49})S$—, —$NR^{48}C(O)$—, and —$NR^{48}S(O)_2$—;
$R^{53}$ and $R^{55}$ are independently selected from the group consisting of hydrogen, halogen, lower alkyl and lower alkoxy, wherein the alkyl chain of lower alkyl or lower alkoxy is optionally substituted with fluoro, —OH, —$NH_2$, lower alkoxy, fluoro substituted lower alkoxy, lower alkylthio, fluoro substituted lower alkylthio, mono-alkylamino, di-alkylamino or cycloalkylamino, provided, however, that any substitution on the alkyl carbon bound to the —O— of lower alkoxy is fluoro;
$R^{52}$ and $R^{56}$ are independently selected from the group consisting of hydrogen, halogen, lower alkyl, fluoro substituted lower alkyl, lower alkoxy, and fluoro substituted lower alkoxy;
$R^{49}$ is selected from the group consisting of hydrogen, lower alkyl, and fluoro substituted lower alkyl;
Cy is selected from the group consisting of aryl, heteroaryl, cycloalkyl, and heterocycloalkyl;
$R^{39}$ is selected from the group consisting of hydrogen, halogen, lower alkyl, lower alkoxy, aryl, heteroaryl, and $NR^{50}R^{51}$, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, and wherein aryl and heteroaryl are optionally substituted with one or more independent substituents $R^{23}$;
$R^{50}$ is hydrogen or lower alkyl optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkyl amino;
$R^{51}$ is aryl or heteroaryl, wherein aryl and heteroaryl are optionally substituted with one or more independent substituents $R^{23}$;
$R^{23}$ at each occurrence is independently selected from the group consisting of —OH, —$NH_2$, —CN, —$NO_2$, —C(O)OH, —$S(O)_2NH_2$, —$C(O)NH_2$, —$OR^{57}$, —$R^{57}$, —$NR^{48}R^{57}$, —$NR^{48}C(O)R^{57}$, —$N^{48}S(O)_2R^{57}$, —$S(O)_2R^{57}$, —$C(O)R^{57}$, —$C(O)OR^{57}$, —C(O)

NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R$^{23}$, or as substituents of lower alkyl, are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O)$_2$R$^{58}$, —C(O)R$^{58}$, —C(O)OR$^{58}$, —C(O)NR$^{48}$R$^{58}$, —S(O)$_2$NR$^{48}$R$^{58}$, halogen, lower alkyl, fluoro substituted lower alkyl, and cycloalkylamino;

R$^{57}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of —OR$^{57}$, —SR$^{57}$, —NR$^{48}$R$^{57}$, —C(O)OR$^{57}$, —C(O)NR$^{48}$R$^{57}$, or —S(O)$_2$NR$^{48}$R$^{57}$ is fluoro, cycloalkyl, heterocycloalkyl, aryl or heteroaryl, and wherein cycloalkyl, heterocycloalkyl, aryl, and heteroaryl as R$^{57}$ or as substituents of lower alkyl are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, NR$^{48}$R$^{58}$, —NR$^{48}$C(O)R$^{58}$, —NR$^{48}$S(O)$_2$R$^{58}$, —S(O)$_2$R$^{58}$, —C(O)R$^{58}$, —C(O)OR$^{58}$, —C(O)NR$^{48}$R$^{58}$, —S(O)$_2$NR$^{48}$R$^{58}$, halogen, lower alkyl, fluoro substituted lower alkyl, and cycloalkylamino;

R$^{58}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of —OR$^{58}$, —SR$^{58}$, —N$^{48}$R$^{58}$, —C(O)OR$^{58}$, —C(O)NR$^{48}$R$^{58}$, or —S(O)$_2$NR$^{48}$R$^{58}$ is fluoro, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy;

R$^{48}$ at each occurrence is independently hydrogen or lower alkyl; and t is 0, 1, 2, or 3.

In some embodiments of compounds of Formula Ib, A$_1$ is —CR$^{40}$R$^{41}$— or —C(O)—, preferably —CH$_2$— or —C(O)—, more preferably —CH$_2$—. In some embodiments, A$_1$ is —CR$^{40}$R$^{41}$— or —C(O)—, preferably —CH$_2$— or —C(O)—, more preferably —CH$_2$—, and R$^{53}$ and R$^{55}$ are independently selected from the group consisting of hydrogen, halogen, lower alkyl fluoro substituted lower alkyl, lower alkoxy, and fluoro substituted lower alkoxy. In some embodiments, L$_3$ is —NR$^{48}$CH(R$^{49}$)—, —SCH(R$^{49}$)—, or —OCH(R$^{49}$)—, preferably —OCH(R$^{49}$)—. In some embodiments, A$_1$ is —C$^{40}$R$^{41}$— or —C(O)—, preferably —CH— or —C(O)—, more preferably —CH$_2$—, and L$_3$ is —NR$^{48}$CH(R$^{49}$)—, —SCH(R$^{49}$)—, or —OCH(R$^{49}$)—, preferably —OCH(R$^{49}$)—.

In some embodiments, compounds of Formula I have the structure according to the following sub-generic structure Formula Ic:

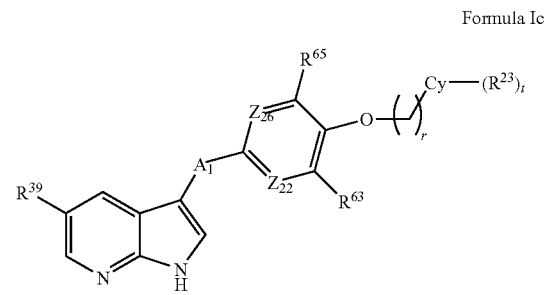

Formula Ic all salts, prodrugs, tautomers, and isomers thereof,
wherein:
A$_1$, R$^{23}$, R$^{39}$, Cy, and t are as defined in Formula Ib;
Z$_{22}$ is N or CR$^{62}$;
Z$_{26}$ is N or CR$^{56}$;
r is 0, 1, or 2; and
R$^{62}$, R$^{63}$, R$^{65}$ and R$^{66}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro.

In some embodiments of compounds of Formula Ic, A$_1$ is —CR$^{40}$R$^{41}$— or —C(O)—, preferably —CH$_2$— or —C(O)—. In some embodiments, A$_1$ is —CR$^{40}$R$^{41}$— or —C(O)—, preferably —CH$_2$— or —C(O)—, and R$^{62}$, R$^{64}$, R$^{65}$ and R$^{66}$ are independently selected horn the group consisting of hydrogen, halogen, lower alkyl, fluoro substituted lower alkyl, lower alkoxy, and fluoro substituted lower alkoxy.

In some embodiments, compounds of Formula I have the structure according to the following sub-generic structure Formula Id:

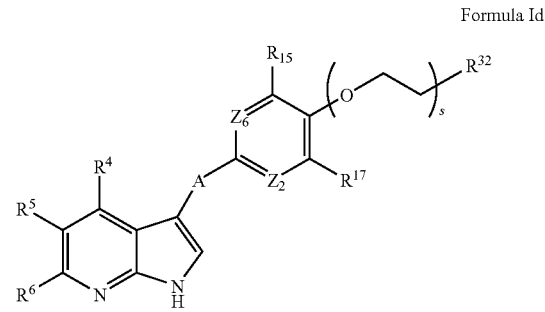

Formula Id all salts, prodrugs, tautomers and isomers thereof, wherein A, s, $Z_2$, $Z_1$, $R^4$, $R^5$, $R^6$, $R^{15}$, $R^{17}$, and $R^{32}$ are as defined for Formula I.

In some embodiments of compounds of Formula Id, $R^4$ and $R^6$ are hydrogen, A is —O—, —$CR^aR^b$—, —$NR^1$—, or —C(O)—, preferably —$CH_2$— or —C(O)—, more preferably —$CH_2$—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^{15}$ is selected from the group consisting of hydrogen, halogen, lower alkyl, fluoro substituted lower alkyl, lower alkoxy, and fluoro substituted lower alkoxy.

In some embodiments of compounds of Formula Id, $R^4$ and $R^6$ are hydrogen, A is —O—, —$CR^aR^b$—, —$NR^1$—, or —C(O)—, preferably —$CH_2$— or —C(O)—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, $R^{15}$ is selected from the group consisting of hydrogen, halogen, lower alkyl, fluoro substituted lower alkyl, lower alkoxy, and fluoro substituted lower alkoxy, $Z_2$ is N or $CR^{12}$, $Z_6$ is N or $CR^{16}$, $R^{12}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, and —$NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, further wherein $R^{32}$ is optionally substituted lower alkyl or —$OR^{18}$, where $R^{18}$ is as defined for Formula I.

In some embodiments, compounds of Formula I have the structure according to the following sub-generic structure Formula Ie:

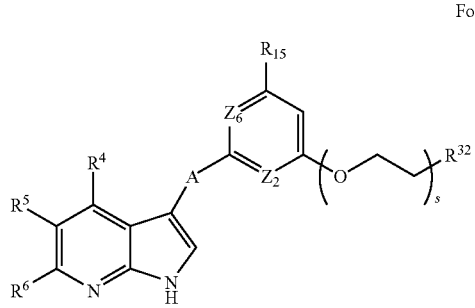

Formula Ie all salts, prodrugs, tautomers and isomers thereof, wherein A, s, $Z_2$, $Z_6$, $R^4$, $R^5$, $R^6$, $R^{15}$, and $R^{32}$ are as defined for Formula I.

In some embodiments of compounds of Formula Ie, $R^4$ and $R^6$ are hydrogen, A is —O—, —$CR^aR^b$—, —$NR^1$—, or —C(O)—, preferably —$CH_2$— or —C(O)—, more preferably —$CH_2$—, and $R^{15}$ is selected from the group consisting of hydrogen, halogen, lower alkyl, fluoro substituted lower alkyl, lower alkoxy, and fluoro substituted lower alkoxy.

In some embodiments of compounds of Formula Ie, $R^4$ and $R^6$ are hydrogen, A is —O—, —$CR^aR^b$—, —$NR^1$—, or —C(O)—, preferably —$CH_2$— or —C(O)—, $R^{15}$ is selected from the group consisting of hydrogen, halogen, lower alkyl, fluoro substituted lower alkyl, lower alkoxy, and fluoro substituted lower alkoxy, $Z_2$ is N or $CR^{12}$, $Z_6$ is N or $CR^{16}$, $R^{12}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, and —$NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, further wherein $R^{32}$ is optionally substituted lower alkyl or —$OR^{18}$, where $R^{15}$ is as defined for Formula I.

In some embodiments, compounds of Formula I have the structure according to the following sub-generic structure Formula If:

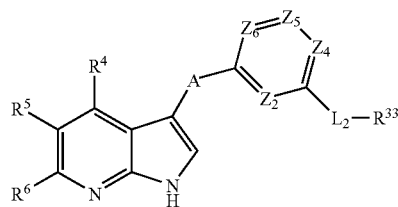

Formula If all salts, prodrugs, tautomers and isomers thereof, wherein A, $L_2$, $Z_2$, $Z_4$, $Z_5$, $Z_6$, $R^4$, $R^5$, $R^6$, and $R^{33}$ are as defined for Formula I.

In some embodiments of compounds of Formula If, $R^4$ and $R^6$ are hydrogen, A is —O—, —$CR^aR^b$—, —$NR^1$—, or —C(O)—, preferably —$CH_2$— or —C(O)—, $Z_2$ is N or $CR^{12}$, $Z_4$ is N or $CR^{14}$, $Z_5$ is N or $CR^{15}$, $Z_6$ is N or $CR^{16}$, and $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro.

In some embodiments of compounds of Formula If, $R^4$ and $R^6$ are hydrogen, A is —O—, —$CR^aR^b$—, —$NR^1$—, or —C(O)—, preferably —$CH_2$— or —C(O)—, $Z_2$ is N or $CR^{12}$, $Z_4$ is N or $CR^{14}$, $Z_5$ is N or $CR^{15}$, $Z_6$ is N or $CR^{16}$, $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^5$ is selected from the group consisting of hydrogen, halogen, lower alkyl, lower alkoxy, optionally substituted aryl, optionally substituted heteroaryl, and $NR^{21}R^{22}$ wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino.

In some embodiments of compounds of Formula If, $R^4$ and $R^6$ are hydrogen, A is —O—, —CR$^a$R$^b$—, —NR$^1$—, or —C(O)—, preferably —CH$_2$— or —C(O)—, $Z_2$ is N or CR$^{12}$, $Z_4$ is N or CR$^{14}$, $Z_5$ is N or CR$^{15}$, $Z_6$ is N or CR$^{16}$, $R^{12}$, $R^{14}$, $R^{15}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino.

In some embodiments, compounds of Formula I have the structure according to the following sub-generic structure Formula Ig:

Formula Ig

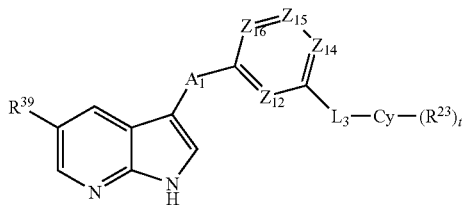

all salts, prodrugs, tautomers, and isomers thereof,
wherein:
$A_1$, $L_3$, $Z_{12}$, $Z_{16}$, $R^{23}$, $R^{39}$, Cy and t are as defined for Formula Ib;
$Z_{14}$ is N or CR$^{54}$;
$Z_{15}$ is N or CR$^{55}$; and
$R^{54}$ and $R^{55}$ are independently selected from the group consisting of hydrogen, halogen, lower alkyl and lower alkoxy, wherein the alkyl chain of lower alkyl or lower alkoxy is optionally substituted with fluoro, —OH, —NH$_2$, lower alkoxy, fluoro substituted lower alkoxy, lower alkylthio, fluoro substituted lower alkylthio, mono-alkylamino, di-alkylamino or cycloalkylamino, provided, however, that any substitution on the alkyl carbon bound to the —O— of lower alkoxy is fluoro.

In some embodiments of compounds of Formula Ig, $A_1$ is —CR$^{40}$R$^{41}$— or —C(O)—, preferably —CH$_2$— or —C(O)—, more preferably —CH$_2$—. In some embodiments, $A_1$ is —CR$^{40}$R$^{41}$— or —C(O)—, preferably —CH$_2$— or —C(O)—, more preferably —CH$_2$—, and $R^{54}$ and $R^{55}$ are independently selected from the group consisting of hydrogen, halogen, lower alkyl, fluoro substituted lower alkyl, lower alkoxy, and fluoro substituted lower alkoxy. In some embodiments, $L_3$ is —NR$^{48}$CH(R$^{49}$)—, —SCH(R$^{49}$)—, or —OCH(R$^{41}$)—, preferably —OCH(R$^{49}$)—. In some embodiments, $A_1$ is —CR$^{40}$R$^{41}$— or —C(O)—, preferably —CH$_2$— or —C(O)—, more preferably —CH$_2$—, and $L_3$ is —NR$^{48}$CH(R$^{49}$)—, —SCH(R$^{49}$)—, or —OCH(R$^{49}$)—, preferably OCH(R$^{49}$)—.

In some embodiments, compounds of Formula I have the structure according to the following sub-generic structure Formula Ih:

Formula Ih

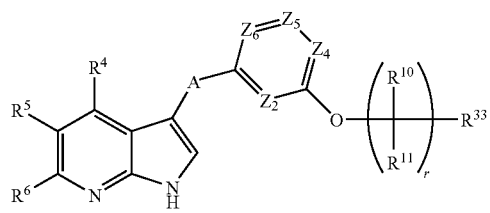

all salts, prodrugs, tautomers and isomers thereof, wherein A, $Z_2$, $Z_4$, $Z_5$, $Z_6$, $R^4$, $R^5$, $R^6$, $R^{10}$, $R^{11}$ and $R^{33}$ are as defined for Formula I, and r is 0, 1, or 2.

In some embodiments of compounds of Formula Ih, $R^4$ and $R^6$ are hydrogen, A is —O—, —CR$^a$R$^b$—, —NR$^1$—, or —C(O)—, preferably —CH$_2$— or —C(O)—, $Z_2$ is N or CR$^{14}$, $Z_4$ is N or CR$^{14}$, $Z_5$ is N or CR$^{15}$, $Z_6$ is N or CR$^{16}$, and $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro.

In some embodiments of compounds of Formula Ih, $R^4$ and $R^6$ are hydrogen, A is —O—, —CR$^a$R$^b$—, —NR$^1$—, or —C(O)—, preferably —CH$_2$— or —C(O)—, $Z_2$ is N or CR$^{12}$, $Z_4$ is N or CR$^{14}$, $Z_5$ is N or CR$^{15}$, $Z_6$ is N or CR$^{16}$, $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, $R^{10}$ and $R^{11}$ are independently selected from the group consisting of hydrogen, fluoro, lower alkyl, and fluoro substituted lower alkyl, and $R^5$ is selected from the group consisting of hydrogen, halogen, lower alkyl, lower alkoxy, optionally substituted aryl, optionally substituted heteroaryl, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino.

In some embodiments of compounds of Formula Ih, $R^4$ and $R^6$ are hydrogen, A is —O—, —$CR^aR^b$—, —$NR^1$—, or —C(O)—, preferably —$CH_2$— or —C(O)—, $Z_2$ is N or $CR^{12}$, $Z_4$ is N or $CR^{14}$, $Z_5$ is N or $CR^{15}$, $Z_6$ is N or $CR^{16}$, $R^{12}$, $R^{14}$, $R^{15}$ and $R^{16}$ are independently selected from the group consisting of hydrogen, halogen, lower alkyl, fluoro substituted lower alkyl, lower alkoxy, and fluoro substituted lower alkoxy, $R^{10}$ and $R^{11}$ are independently selected from the group consisting of hydrogen, fluoro, lower alkyl, and fluoro substituted lower alkyl, and $R^5$ is selected from the group consisting of hydrogen, halogen, lower alkyl, lower alkoxy, optionally substituted aryl, optionally substituted heteroaryl, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino.

In some embodiments, compounds of Formula I have the structure according to the following sub-generic structure Formula Ii:

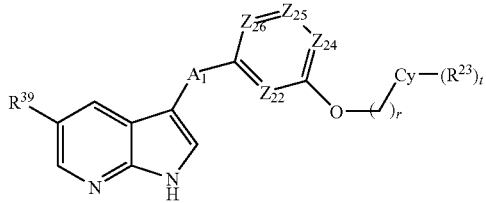

Formula Ii all salts, prodrugs, tautomers, and isomers thereof,
wherein:
$A_1$, $R^{23}$, $R^{39}$, Cy and t are as defined for Formula Ib;
$Z_{22}$, $Z_{26}$, and r are as defined for Formula Ic;
$Z_{24}$ is N or $CR^{64}$;
$Z_{25}$ is N or $CR^{65}$;
$R^{64}$ and $R^{65}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro.

In some embodiments of compounds of Formula Ii, $A_1$ is —$CR^{40}R^{41}$— or —C(O)—, preferably —$CH_2$— or —C(O)—. In some embodiments, $A_1$ is —$CR^{40}R^{41}$— or —C(O)—, preferably —$CH_2$— or —C(O)—, and $R^{62}$, $R^{64}$, $R^{65}$ and $R^{66}$ are independently selected from the group consisting of hydrogen, halogen, lower alkyl, fluoro substituted lower alkyl, lower alkoxy, and fluoro substituted lower alkoxy.

In some embodiments, compounds have the structure according to the following Formula II:

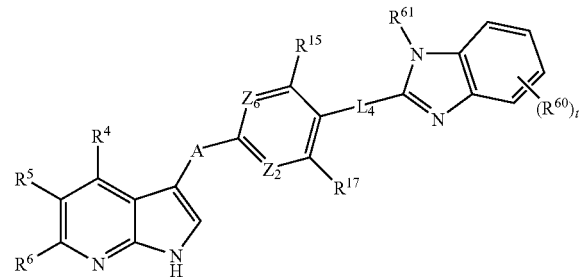

Formula II all salts, prodrugs, tautomers, and isomers thereof,
wherein:
t is 0, 1, 2, or 3;
$L_4$ is selected from the group consisting of —$(CR^{10}R^{11})_p$— $NR^{25}$—$(CR^{10}R^{11})_q$—, —$(CR^{10}R^{11})_p$—X— $(CR^{10}R^{11})_q$—, —$(CR^{10}R^{11})$, —C(X)—$(CR^{10}R^{11})_q$—, —$(CR^{10}R^{11})_p$—S(O)—$(CR^{10}R^{11})_q$—, —$(CR^{10}R^{11})_p$— $S(O)_2$—$(CR^{10}R^{11})_q$, —$(CR^{10}R^{11})_p$—C(X)$NR^{25}$— $(CR^{10}R^{11})_q$—, —$(CR^{10}R^{11})_p$—$S(O)_2NR^{25}$— $(CR^{10}R^{11})_q$—, —$(CR^{10}R^{11})_p$—$NR^{25}C(X)$— $(CR^{10}R^{11})_q$—, —$(CR^{10}R^{11})_p$—$NR^{25}S(O)_2$— $(CR^{10}R^{11})_q$—, —$(CR^{10}R^{11})$, —$NR^{25}C(X)R^{25}$— $(CR^{10}R^{11})_q$, and —$(CR^{10}R^{11})_p$—$NR^{25}S(O)_2NR^{25}$— $(CR^{10}R^{11})$, —

$R^{60}$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —$NO_2$, —$CR^aR^bR^{26}$, and -$LR^{26}$;

$R^{61}$ is hydrogen, lower alkyl, or fluoro substituted lower alkyl; and

A, $Z_2$, $Z_6$, $R^a$, $R^b$, $R^4$, $R^5$, $R^6$, $R^{10}$, $R^{11}$, $R^{15}$, $R^{17}$, $R^{25}$, $R^{26}$, p, q, X and L are as defined for Formula I, provided, however, that the compound is not

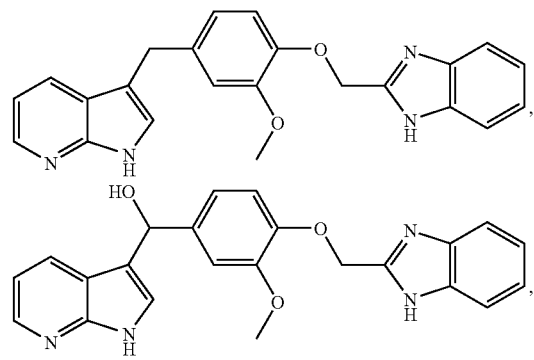

-continued
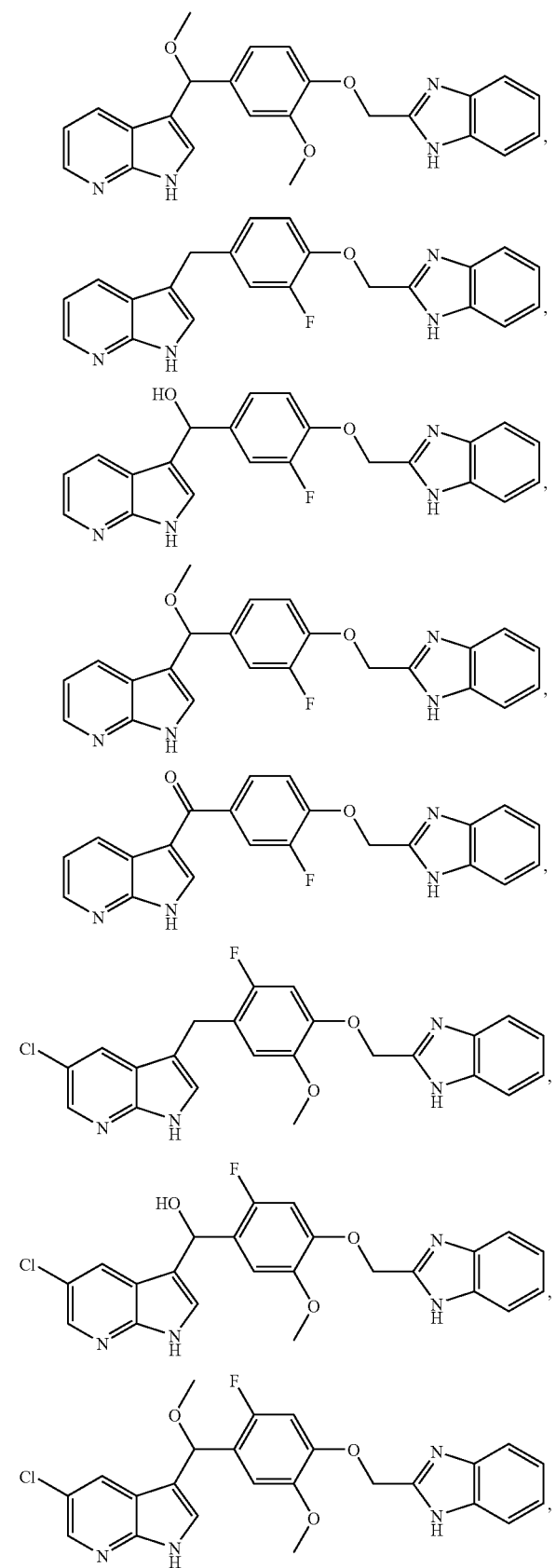
-continued
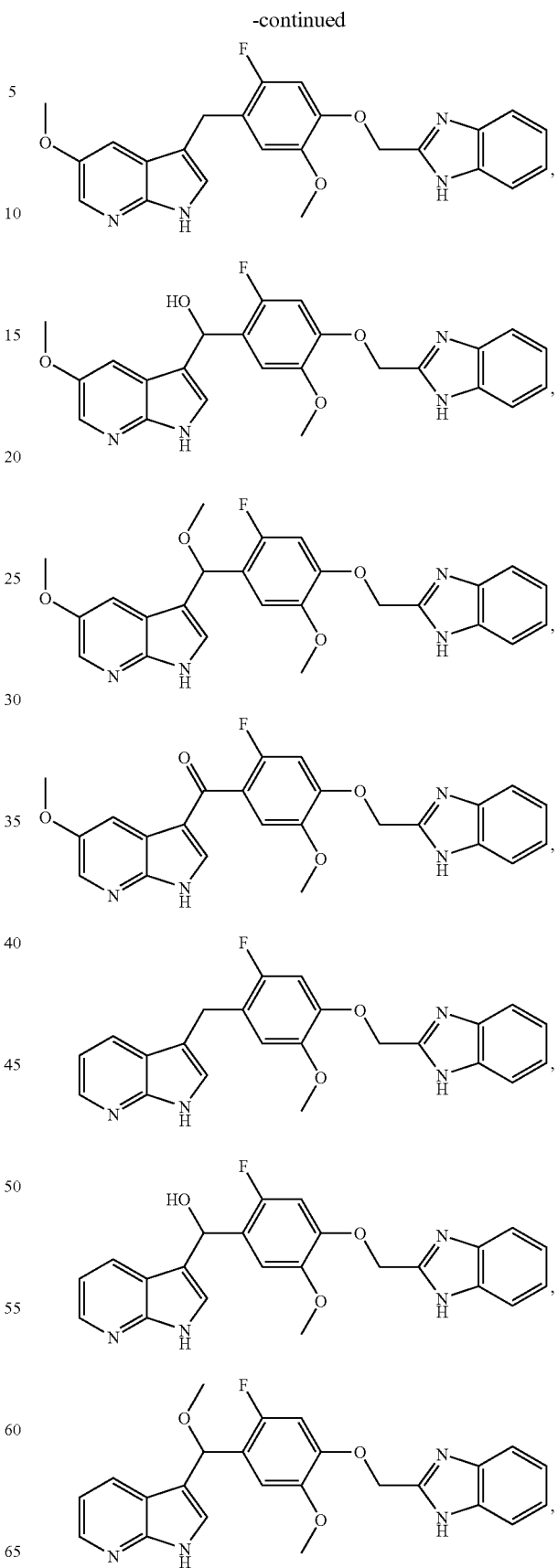

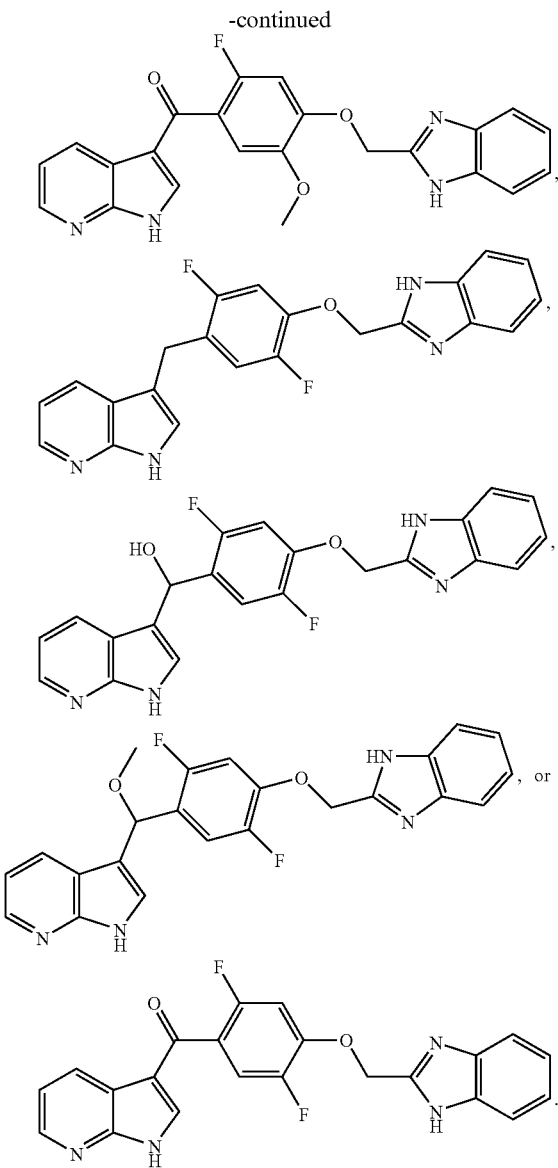

In some embodiments of compounds of Formula II, $R^{61}$ is hydrogen, lower alkyl, or fluoro substituted lower alkyl and t is 0, 1, 2, 3 or 4, provided, however, that when t is 0, $R^{61}$ is lower alkyl or fluoro substituted lower alkyl.

In some embodiments of compounds of Formula II, $R^4$ and $R^6$ are hydrogen and $R^5$ is from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$—, —NR$^{48}$C(O)$_2$R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$—, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, —OH, —NH$_2$, C(O)OH, —C(O)NH$_2$, —OR$^{57}$, —SR$^{57}$, —NR$^{48}$R$^{57}$, —C(O)OR$^{57}$, —C(O)NR$^{48}$R$^{57}$, cycloalkyl, heterocycloalkyl, aryl, and heteroaryl, and wherein cycloalkyl, heterocycloalkyl, aryl, and heteroaryl as $R^5$, or as substituents of lower alkyl, are optionally substituted with one or more substituents selected from the group consisting of —OH, —NH$_2$, —CN, —NO$_2$, —C(O) OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O) R$^{58}$, —S(O)$_2$R$^{58}$, —C(O)R$^{58}$, —C(O)OR$^{58}$, —C(O) NR$^{48}$R$^{58}$, —S(O)$_2$NR$^{48}$R$^{58}$, halogen, lower alkyl, fluoro substituted lower alkyl, and cycloalkylamino, wherein $R^{48}$, $R^{57}$, and $R^{58}$ are as defined for Formula Ib. In some embodiments, $R^4$ and $R^6$ are hydrogen and $R^5$ is optionally substituted aryl or optionally substituted heteroaryl.

In some embodiments of compounds of Formula II, $R^4$ and $R^6$ are hydrogen, A is —O—, —CR$^a$R$^b$—, —NR$^1$—, or —C(O)—, preferably —CH$_2$— or —C(O)—, more preferably —CH$_2$—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^{15}$ is selected from the group consisting of hydrogen, halogen, lower alkyl, fluoro substituted lower alkyl, lower alkoxy, and fluoro substituted lower alkoxy. $R^a$, $R^b$, and $R^1$ are as defined for Formula I.

In some embodiments of compounds of Formula II, $R^{61}$ is hydrogen, lower alkyl, or fluoro substituted lower alkyl and t is 0, 1, 2, 3 or 4, provided, however, that when t is 0, $R^{61}$ is lower alkyl or fluoro substituted lower alkyl, $R^4$ and $R^6$ are hydrogen, A is —O—, —CR$^a$R$^b$—, —NR$^1$—, or —C(O)—, preferably —CH$_2$— or —C(O)—, more preferably —CH$_2$—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^{15}$ is selected from the group consisting of hydrogen, halogen, lower alkyl, fluoro substituted lower alkyl, lower alkoxy, and fluoro substituted lower alkoxy. $R^a$, $R^b$, and $R^1$ are as defined for Formula I.

In some embodiments of compounds of Formula II, $R^4$ and $R^6$ are hydrogen, $R^5$ is selected from the group consisting of hydrogen, —OH, —N$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O) R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, —OH, —NH$_2$, C(O)OH, —C(O)NH$_2$, —OR$^{57}$, —SR$^{57}$, —NR$^{48}$R$^{57}$, —C(O)OR$^{57}$, —C(O)NR$^{48}$R$^{57}$, cycloalkyl, heterocycloalkyl, aryl, and heteroaryl, and wherein cycloalkyl, heterocycloalkyl, aryl, and heteroaryl as $R^5$, or as substituents of lower alkyl, are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$—, —NR$^{48}$S(O)$_2$R$^{58}$, —S(O)R$^{58}$, —S(O)$_2$R$^{58}$, —C(O)R$^{58}$, —C(O)OR$^{58}$, —C(O)NR$^{48}$R$^{58}$, —S(O)$_2$NR$^{48}$R$^{58}$, halogen, lower alkyl, fluoro substituted lower alkyl, and cycloalkylamino, wherein $R^{48}$, $R^{57}$, and $R^{58}$ are as defined for Formula Ib, A is —O—, —CR$^a$R$^b$—, —NR$^1$—, or —C(O)—, preferably —CH$_2$— or —C(O)—, more preferably —CH$_2$—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^{15}$ is selected from the group consisting of hydrogen, halogen, lower alkyl, fluoro substituted lower alkyl, lower alkoxy, and fluoro substituted lower alkoxy. $R^a$, $R^b$, and $R^1$ are as defined for Formula I.

In some embodiments of compounds of Formula II, $R^4$ and $R^5$ are hydrogen, A is —O—, —$CR^aR^b$—, —$NR^1$—, or —C(O)—, preferably —$CH_2$— or —C(O)—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, $R^{15}$ is selected from the group consisting of hydrogen, halogen, lower alkyl, fluoro substituted lower alkyl, lower alkoxy, and fluoro substituted lower alkoxy, $R^{12}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, —CN, —C(O)OH, —C(O)$OR^{22}$, —$OR^{22}$, —S(O)$_2R^{22}$, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino. $R^a$, $R^b$, and $R^1$ are as defined for Formula I.

In some embodiments of compounds of Formula II, $R^{61}$ is hydrogen, lower alkyl, or fluoro substituted lower alkyl and t is 0, 1, 2, 3 or 4, provided, however, that when t is 0, $R^{61}$ is lower alkyl or fluoro substituted lower alkyl, $R^4$ and $R^6$ are hydrogen, A is —O—, —$CR^aR^b$—, —$NR^1$—, or —C(O)—, preferably —$CH_2$— or —C(O)—, $R^{17}$ is selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, $R^{15}$ is selected from the group consisting of hydrogen, halogen, lower alkyl, fluoro substituted lower alkyl, lower alkoxy, and fluoro substituted lower alkoxy, $R^{12}$ and $R^{16}$ are independently selected from the group consisting of hydrogen, halogen, lower alkyl fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, —CN, —C(O)OH, —C(O)$OR^{22}$, —$OR^{22}$, —S(O)$_7R^{22}$, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$ when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino. $R^a$, $R^b$, and $R^1$ are as defined for Formula I.

In some embodiments of any of the above embodiments of compounds of Formula II, both of $Z_2$ and $Z_6$ are N, also one of $Z_2$ or $Z_6$ is N and the other of $Z_2$ or $Z_6$ is $CR^{12}$ or $CR^{16}$, preferably $Z_2$ is $CR^{12}$ and $Z_6$ is $CR^{16}$.

In some embodiments of any of the above embodiments of compounds of Formula II, each $R^{60}$ is independently selected from the group consisting of —OH, —$NH_2$, —CN, —$NO_2$, —C(O)OH, —S(O)$_2NH_2$, —C(O)$NH_2$, —$OR^{57}$, —$SR^{57}$, —$NR^{48}R^{57}$, —$NR^{48}C(O)R^{57}$—$NR^{48}S(O)_2R^{57}$, —S(O)$R^{57}$, —S(O)$_2R^{57}$, —C(O)$R^{57}$, —C(O)$OR^{57}$, —C(O)$NR^{48}R^{57}$, —S(O)$_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, —OH, —$NH_2$, —C(O)OH, —C(O)$NH_2$, —$OR^{57}$, —$SR^{57}$, —$NR^{48}R^{57}$, —C(O)$OR^{57}$, —C(O)$NR^{48}R^{57}$, cycloalkyl, heterocycloalkyl, aryl, and heteroaryl, and wherein cycloalkyl, heterocycloalkyl, aryl, and heteroaryl as $R^{60}$, or as substituents of lower alkyl, are optionally substituted with one or more substituents selected from the group consisting of —OH, —$NH_2$, —CN, —$NO_2$, —C(O)OH, —S(O)$_2NH_2$, —C(O)$NH_2$—$OR^{58}$, —$SR^{58}$, —$NR^{48}R^{58}$, —$NR^{48}C(O)R^{58}$, —$NR^{48}S(O)_2R^{58}$, —S(O)$R^{58}$, —S(O)$_2R^{58}$, —C(O)$R^{58}$, —C(O)$OR^{58}$, —C(O)$NR^{48}R^{58}$, —S(O)$_2NR^{48}R^{58}$, halogen, lower alkyl, fluoro substituted lower alkyl, and cycloalkylamino, wherein $R^{48}$, $R^{57}$ and $R^{58}$ are as defined for Formula Ib, $Z_2$ is $CR^{12}$, $Z_6$ is $CR^{16}$, and $R^{12}$, $R^{15}$, $R^{16}$ and $R^{17}$ are independently selected from the group consisting of hydrogen, halogen, lower alkyl, fluoro substituted lower alkyl, lower alkoxy, and fluoro substituted lower alkoxy.

In one embodiment of compounds of Formula II, the compound is selected from the group consisting of:

2-[5-Chloro-4-(5-chloro-1H-pyrrolo[2,3-b]pyridin-3-ylmethyl)-2-fluoro-phenoxymethyl]-1H-benzoimidazole (P-2099), 2-[4-(5-Chloro-1H-pyrrolo[2,3-b]pyridin-3-ylmethyl)-2,5-difluoro-phenoxymethyl]-1H-benzoimidazole (P-2100), 2-[2,5-Difluoro-4-(5-methoxy-1H-pyrrolo[2,3-b]pyridin-3-ylmethyl)-phenoxymethyl]-1H-benzoimidazole (P-2101), 2-[3,5-Difluoro-4-(1H-pyrrolo[2,3-b]pyridin-3-ylmethyl)-phenoxymethyl]-1H-benzoimidazole (P-2102), 2-[5-Chloro-2-methoxy-4-(1H-pyrrolo[2,3-b]pyridin-3-ylmethyl)-phenoxymethyl]-1H-benzoimidazole (P-2103), 2-[5-Chloro-4-(5-chloro-1H-pyrrolo[2,3-b]pyridin-3-ylmethyl)-2-methoxy-phenoxymethyl]-1H-benzoimidazole (P-2104), 2-[4-(5-Chloro-1H-pyrrolo[2,3-b]pyridin-3-ylmethyl)-3,5-difluoro-phenoxymethyl]-1H-benzoimidazole (P-2105), 2-[4-(5-Chloro-1H-pyrrolo[2,3-b]pyridin-3-ylmethyl)-5-fluoro-2-methoxy-phenoxymethyl]-1-methyl-1H-benzoimidazole (P-2106), 2-[4-(5-Bromo-1H-pyrrolo[2,3-b]pyridin-3-ylmethyl)-2,5-difluoro-phenoxymethyl]-1H-benzoimidazole (P-2107), 2-{2,5-Difluoro-4-[5-(1-methyl-1H-pyrazol-4-yl)-1H-pyrrolo[2,3-b]pyridin-3-ylmethyl]-phenoxymethyl}-1H-benzoimidazole (P-2108), 2-{5-Chloro-2-fluoro-4-[5-(1-methyl-1H-pyrazol-4-yl)-1H-pyrrolo[2,3-b]pyridin-3-ylmethyl]-phenoxymethyl}-1H-benzoimidazole (P-2109),
2-{1-[4-(5-Chloro-1H-pyrrolo[2,3-b]pyridin-3-ylmethyl)-5-fluoro-2-methoxy-phenoxy]-ethyl}-1H-benzoimidazole (P-2110),
6-Chloro-2-[4-(5-chloro-1H-pyrrolo[2,3-b]pyridin-3-ylmethyl)-5-fluoro-2-methoxy-phenoxymethyl]-1H-benzoimidazole (P-2111).
6-Chloro-2-[5-fluoro-2-methoxy-4-(1H-pyrrolo[2,3-b]pyridin-3-ylmethyl)-phenoxymethyl]-1H-benzoimidazole (P-2112),
2-[5-Fluoro-2-methoxy-4-(1H-pyrrolo[2,3-b]pyridin-3-ylmethyl)-phenoxymethyl]-6-methoxy-1H-benzoimidazole (P-2113),
2-[5-Chloro-2-fluoro-4-(5-methoxy-1H-pyrrolo[2,3-b]pyridin-3-ylmethyl)-phenoxymethyl]-1H-benzoimidazole (P-2114),
2-[5-Fluoro-4-(5-fluoro-1H-pyrrolo[2,3-b]pyridin-3-ylmethyl)-2-methoxy-phenoxymethyl]-1H-benzoimidazole (P-2115),
2-[2-Chloro-5-fluoro-4-(5-methoxy-1H-pyrrolo[2,3-b]pyridin-3-ylmethyl)-phenoxymethyl]-1H-benzoimidazole (P-2116),
2-{2-Chloro-5-fluoro-4-[5-(1-methyl-1H-pyrazol-4-yl)-1H-pyrrolo[2,3-b]pyridin-3-ylmethyl]-phenoxymethyl}-1H-benzoimidazole (P-2117),
2-{4-[(5-Chloro-1H-pyrrolo[2,3-b]pyridin-3-yl)-methoxy-methyl]-5-fluoro-2-methoxy-phenoxymethyl}-1H-benzoimidazole (P-2168),
[4-(1H-Benzoimidazol-2-ylmethoxy)-2-fluoro-5-methoxy-phenyl]-(5-chloro-1H-pyrrolo[2,3-b]pyridin-3-yl)-methanone (P-2169),
2-[2,5-Difluoro-4-(5-methanesulfonyl-1H-pyrrolo[2,3-b]pyridin-3-ylmethyl)-phenoxymethyl]-1H-benzoimidazole (P-2170),
3-[4-(1H-Benzoimidazol-2-ylmethoxy)-2-fluoro-5-methoxy-benzyl]-1H-pyrrolo[2,3-b]pyridine-5-carbonitrile (P-2171),
5,6-Dichloro-2-[4-(5-chloro-1H-pyrrolo[2,3-b]pyridin-3-ylmethyl)-5-fluoro-2-methoxy-phenoxymethyl]-1H-benzoimidazole (P-2172),
2-[4-(5-Chloro-1H-pyrrolo[2,3-b]pyridin-3-ylmethyl)-5-fluoro-2-methoxy-phenoxymethyl]-1H-benzoimidazole-5-sulfonic acid dimethylamide (P-2173),
3-[4-(1H-Benzimidazol-2-ylmethoxy)-2-fluoro-5-methoxy-benzyl]-1H-pyrrolo[2,3-b]pyridine-5-carboxylic acid methyl ester (P-2174),
3-[4-(1H-Benzoimidazol-2-ylmethoxy)-2-fluoro-5-methoxy-benzyl]-1H-pyrrolo[2,3-b]pyridine-5-carboxylic acid (P-2175),
2-{2,5-Difluoro-4-[5-(2-methoxy-ethoxy)-1H-pyrrolo[2,3-b]pyridin-3-ylmethyl]-phenoxymethyl}-1H-benzoimidazole (P-2176),
2-[4-(5-Chloro-1H-pyrrolo[2,3-b]pyridin-3-ylmethyl)-5-fluoro-2-methoxy-phenoxymethyl]-1-ethyl-1H-benzoimidazole (P-2177),
2-[4-(5-Chloro-1H-pyrrolo[2,3-b]pyridin-3-ylmethyl)-5-fluoro-2-methoxy-phenoxymethyl]-5-trifluoromethyl-1H-benzoimidazole (P-2178),
2-[4-(5-Chloro-1H-pyrrolo[2,3-b]pyridin-3-ylmethyl)-5-fluoro-2-methoxy-phenoxymethyl]-5-fluoro-1H-benzoimidazole (P-2179),
2-{2-[4-(5-Chloro-1H-pyrrolo[2,3-b]pyridin-3-ylmethyl)-5-fluoro-2-methoxy-phenoxy]-ethyl}-1H-benzoimidazole (P-2180),
2-[4-(5-Bromo-1H-pyrrolo[2,3-b]pyridin-3-ylmethyl)-5-fluoro-2-methoxy-phenoxymethyl]-1H-benzoimidazole (P-2181),
2-[4-(5-Chloro-1H-pyrrolo[2,3-b]pyridin-3-ylmethyl)-5-fluoro-2-methoxy-phenoxymethyl]-5-methoxy-1H-benzoimidazole (P-2182),
5-Chloro-2-[5-fluoro-2-methoxy-4-(5-methyl-1H-pyrrolo[2,3-b]pyridin-3-ylmethyl)-phenoxymethyl]-1H-benzoimidazole (P-2184),
3-[4-(1H-Benzoimidazol-2-ylmethoxy)-2,5-difluoro-benzyl]-1H-pyrrolo[2,3-b]pyridine-5-carbonitrile (P-2185),
2-[5-Fluoro-4-(5-methanesulfonyl-1H-pyrrolo[2,3-b]pyridin-3-ylmethyl)-2-methoxy-phenoxymethyl]-1H-benzoimidazole (P-2186), and all salts, prodrugs, tautomers, and isomers thereof.

In some embodiments, compounds of Formula II have the structure according to the following sub-generic structure Formula IIa:

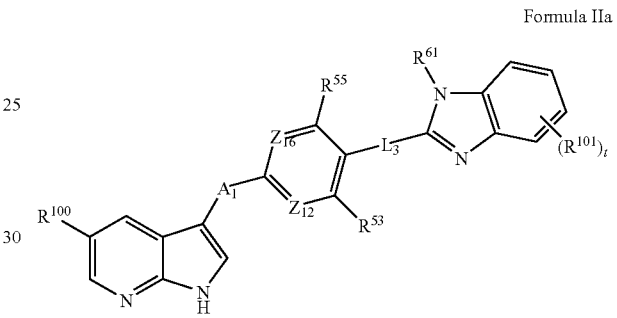

Formula IIa all salts, prodrugs, tautomers, and isomers thereof,
wherein:

$R^{61}$ is hydrogen, lower alkyl, or fluoro substituted lower alkyl;

$R^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, —OH, —NH$_2$, C(O)OH, —C(O)NH$_2$—OR$^{57}$, —SR$^{57}$, —NR$^{48}$R$^{57}$, —C(O)R$^{57}$, —C(O)NR$^{48}$R$^{57}$, cycloalkyl, heterocycloalkyl, aryl, and heteroaryl, and wherein cycloalkyl, heterocycloalkyl, aryl, and heteroaryl as $R^{100}$, or as substituents of lower alkyl, are optionally substituted with one or more independent substituents $R^{101}$;

$R^{101}$ at each occurrence is independently selected from the group consisting of —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, —OH, —NH$_2$, C(O)OH, —C(O)NH$_2$, —OR$^{57}$, —SR$^{57}$, —N$^{48}$R$^{57}$, —C(O)OR$^{57}$—C(O)NR$^{48}$R$^{57}$, cycloalkyl, heterocycloalkyl, aryl, and heteroaryl, and wherein cycloalkyl, heterocycloalkyl, aryl, and heteroaryl as $R^{101}$, or as substituents of lower alkyl, are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O)R$^{58}$, —S(O)$_2$R$^{58}$, —C(O)R$^{58}$, —C(O)OR$^{58}$, —C(O)NR$^{48}$R$^{58}$, —S(O)$_{48}$NR$^{48}$, R$^{58}$, halogen, lower alkyl, fluoro substituted lower alkyl, and cycloalkylamino; and $A_1$, $Z_{12}$, $Z_{16}$, $L_3$, t, $R^{48}$, $R^{53}$, $R^{55}$, $R^{57}$, and $R^{58}$ are as defined for Formula Ib.

In some embodiments of compounds of Formula IIa, $R^{61}$ is hydrogen, lower alkyl, or fluoro substituted lower alkyl and t is 0, 1, 2, 3 or 4, provided, however, that when t is 0, $R^{61}$ is lower alkyl or fluoro substituted lower alkyl.

In some embodiments of compounds of Formula IIa, $R^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —N$^{48}$S(O)$_2$R$^{57}$, —S(O)R$^{57}$, —S(O)$_2$R$^{57}$, —C(O)R$^{57}$, —C(O)OR$^{57}$, —C(O)N$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino.

In some embodiments of compounds of Formula IIa, $A_1$ is —CR$^{40}$R$^{41}$— or —C(O)—, preferably —CH$_2$— or —C(O)—, more preferably —CH$_2$—. In some embodiments, $A_1$ is —CR$^{40}$R$^{41}$— or —C(O)—, preferably —CH$_2$— or —C(O)—, more preferably —CH$_2$—, and $R^{53}$ and $R^{55}$ are independently selected from the group consisting of hydrogen, halogen, lower alkyl, fluoro substituted lower alkyl, lower alkoxy, and fluoro substituted lower alkoxy. In some embodiments, $L_3$ is —NR$^{48}$CH(R$^{49}$)—, —SCH(R$^{49}$)—, or —OCH(R$^{49}$)—, preferably —OCH(R$^{49}$)—. In some embodiments, $A_1$ is —CR$^{40}$R$^{41}$ or —C(O)—, preferably —CH$_2$— or —C(O)—, more preferably —CH$_2$—, and $L_3$ is —NR$^{48}$CH(R$^{49}$)—, —SCH(R$^{49}$)—, or —OCH(R$^{49}$)—, preferably —OCH(R$^{49}$)—. $R^{40}$, $R^{41}$, $R^{48}$ and $R^{49}$ are as defined for Formula Ib.

In some embodiments of compounds of Formula IIa, $R^{61}$ is hydrogen, lower alkyl, or fluoro substituted lower alkyl and t is 0, 1, 2, 3 or 4, provided, however, that when t is 0, $R^{61}$ is lower alkyl or fluoro substituted lower alkyl, $A_1$ is —CR$^{40}$R$^{41}$— or —C(O)—, preferably —CH$_2$— or —C(O)—, more preferably —C$_2$—. In some embodiments, $R^{61}$ is hydrogen, lower alkyl, or fluoro substituted tower alkyl and t is 0, 1, 2, 3 or 4, provided, however, that when t is 0, $R^{61}$ is lower alkyl or fluoro substituted lower alkyl, $A_1$ is —CR$^{40}$R$^{41}$— or —C(O)—, preferably —CH$_2$— or —C(O)—, more preferably —CH$_2$—, and $R^{53}$ and $R^{55}$ are independently selected from the group consisting of hydrogen, halogen, lower alkyl, fluoro substituted lower alkyl, lower alkoxy, and fluoro substituted lower alkoxy. In some embodiments, $R^{61}$ is hydrogen, lower alkyl, or fluoro substituted lower alkyl and t is 0, 1, 2, 3 or 4, provided, however, that when t is 0, $R^{61}$ is lower alkyl or fluoro substituted lower alkyl, $L_3$ is —NR$^{48}$CH(R$^{49}$)—, —SCH(R$^{49}$)—, or —OCH(R$^{49}$)—, preferably —OCH(R$^{49}$)—. In some embodiments, $R^{61}$ is hydrogen, lower alkyl, or fluoro substituted lower alkyl and t is 0, 1, 2, 3 or 4, provided, however, that when t is 0, $R^{61}$ is lower alkyl or fluoro substituted lower alkyl, $A_1$ is —CR$^{40}$R$^{41}$— or —C(O)—, preferably —CH$_2$— or —C(O)—, more preferably —CH$_2$—, and $L_3$ is —NR$^{48}$CH(R$^{49}$)—, —SCH(R$^{49}$)—, or —OCH(R$^{49}$)—, preferably —OCH(R$^{49}$)—, $R^{40}$, $R^{41}$, $R^{48}$ and $R^{49}$ are as defined for Formula Ib.

In some embodiments of compounds of Formula IIa, $R^{100}$ is selected from the group consisting, of hydrogen, —OH, —NH$_2$, —CN, —NO$_2$, —C(O)OH, —S(O)$_2$NH$_2$, —C(O)N$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, NR$^{58}$, —NR$^{48}$R$^{58}$, —NR$^{48}$C(O)R$^{58}$, —R$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino; $A_1$ is —CR$^{40}$R$^{41}$— or —C(O)—, preferably —CH$_2$— or —C(O)—, more preferably —CH$_2$—.

In some embodiments of compounds of Formula IIa, $R^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{57}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino; $A_1$ is —CR$^{40}$R$^{41}$— or —C(O)—, preferably —CH$_2$— or —C(O)—, more preferably —CH$_2$—; and $R^{53}$ and $R^{55}$ are independently selected from the group consisting of hydrogen, halogen, lower alkyl, fluoro substituted lower alkyl, lower alkoxy, and fluoro substituted lower alkoxy.

In some embodiments of compounds of Formula IIa, $R^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino; $L_3$ is —NR$^{48}$CH(R$^{49}$)—, —SCH(R$^{49}$)—, or —OCH(R$^{49}$)—, preferably —OCH(R$^{49}$)—.

In some embodiments of compounds of Formula IIa, $R^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{58}$, NR$^{48}$C(O)R$^{57}$, —NR$^{48}$S(O)$_2$R$^{57}$—, —S(O)R$^{57}$—S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NR$^{58}$, —NR$^{48}$R$^{58}$, —NR$^{48}$C(O)R$^{58}$, —NR$^{48}$S(O)R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino; $A_1$ is —CR$^{40}$R$^{41}$— or —C(O)—, preferably —CH$_2$— or —C(O)—, more preferably —CH$_2$—; and $L_3$ is —NR$^{48}$CH(R$^{49}$)—, —SCH(R$^{49}$)—, or —OCH(R$^{49}$)—, preferably —OCH(R$^{49}$)—, $R^{40}$, $R^{41}$, $R^{48}$ and $R^{49}$ are as defined for Formula Ib.

In some embodiments of compounds of Formula IIa, $R^{100}$ is selected from the group consisting of hydrogen, —CN, —C(O)OH, —C(O)OR$^{57}$, —NR$^{48}$R$^{57}$, —OR$^{57}$, —S(O)$_2$R$^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$. In some embodiments, $R^{100}$ is selected from the group consisting of hydrogen, —CN, —C(O)OH, —C(O)OR$^{57}$, —NR$^{48}$R$^{57}$, —OR$^{57}$, —S(O)$_2$R$^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$; and $R^{101}$ is selected from the group consisting of —OH, —NH$_2$, —CN, —NO$_2$, —C(O)OH, —C(O)NH$_2$, —S(O)$_2$NH$_2$, —C(O)OR$^{57}$, —NR$^{48}$R$^{57}$, —OR$^{57}$, —S(O)$_2$R$^{57}$, —C(O)NR$^{48}$R$^{57}$, —S(O)$_2$NR$^{48}$R$^{57}$, halogen, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$.

In some embodiments of compounds of Formula IIa, $A_1$ is —CH$_2$—; $L_3$ is —OCH(R$^{49}$)—; $R^{100}$ is selected from the group consisting of hydrogen, —CN, —C(O)OH, —C(O)OR$^{57}$, —NR$^{48}$R$^{57}$, —OR$^{57}$, —S(O)$_2$R$^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$; $Z_{12}$ is CR$^{52}$; $Z_{16}$ is CR$^{56}$; $R^{101}$ is selected from the group consisting of —OH, —NH$_2$, —CN, —NO$_2$, —C(O)OH, —C(O)NH$_2$, —S(O)$_2$NH$_2$, C(O)OR$^{57}$, —NR$^{48}$R$^{57}$, —OR$^{57}$, —S(O)$_2$R$^{57}$, —C(O)NR$^{48}$R$^{57}$, —S(O)$_2$NR$^{48}$R$^{57}$, halogen, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$; and $R^{52}$, $R^{53}$, $R^{55}$ and $R^{56}$ are independently selected from the group consisting of hydrogen, halogen, lower alkyl, fluoro substituted lower alkyl, lower alkoxy, and fluoro substituted lower alkoxy.

In some embodiments of any of the above embodiments of compounds of Formula IIa, also one of $Z_{12}$ and $Z_{16}$ are N, also one of $Z_{12}$ or $Z_{16}$ is N and the other of $Z_{12}$ or $Z_{16}$ is CR$^{52}$ or CR$^{56}$, preferably $Z_{12}$ is CR$^{52}$ and $Z_{16}$ is CR$^{56}$. $R^{52}$ and $R^{56}$ are as defined for Formula b.

In some embodiments, compounds of Formula II have the structure according to the following sub-generic structure Formula Ib:

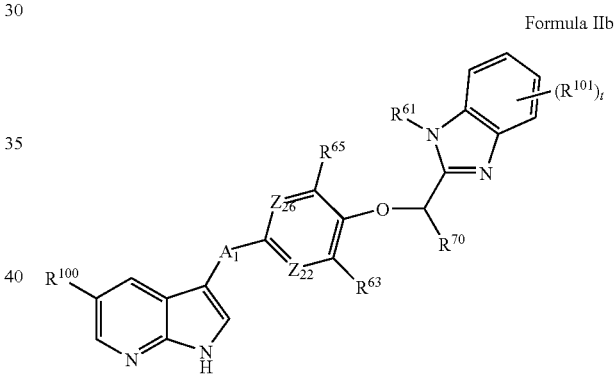

Formula IIb all salts, prodrugs, tautomers, and isomers thereof,
wherein:
$A_1$ and t are as defined for Formula Ib;
$R^{100}$, $R^{101}$ are as defined for Formula Ia;
$R^{63}$, $R^{65}$, $Z_{22}$ and $Z_{26}$ are as defined for Formula Ic; and
$R^{70}$ and $R^{61}$ are independently hydrogen, lower alkyl, or fluoro substituted lower alkyl.

In some embodiments of compounds of Formula IIb, $R^{61}$ is hydrogen, lower alkyl, or fluoro substituted lower alkyl and t is 0, 1, 2, 3 or 4, provided, however, that when t is 0, $R^{61}$ is lower alkyl or fluoro substituted lower alkyl.

In some embodiments of compounds of Formula IIb, $R^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$—C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{100}$ or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{58}$, —$SR^{58}$, —$NHR^{58}$, —$NR^{48}R^{58}$, —$NR^{48}C(O)R^{58}$, —$NR^{48}S(O)_2R^{58}$, —$S(O)_2R^{58}$, —$S(O)_2NR^{48}R^{58}$, —$C(O)R^{58}$, —$C(O)NR^{48}R^{58}$, halogen, lower alkyl, fluoro substituted lower alkyl, and cycloalkylamino. In some embodiments, $R^{100}$ is selected from the group consisting of hydrogen, —CN, —C(O)OH, —$C(O)OR^{57}$, —$NR^{48}R^{57}$, —$OR^{57}$, —$S(O)_2R^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —$NR^{48}R^{58}$, —$OR^{58}$ and —$S(O)R^{58}$.

In some embodiments of compounds of Formula IIb, $A_1$ is —$CR^{40}R^{41}$— or —C(O)—, preferably —$CH_2$— or —C(O)—. In some embodiments, $A_1$ is —$CR^{40}R^{41}$— or —C(O)—, preferably —$CH_2$— or —C(O)—, $Z_{22}$ is $CR^{62}$, and $Z_{26}$ is $CR^{66}$.

In some embodiments of compounds of Formula Ib, $R^{61}$ is hydrogen, lower alkyl, or fluoro substituted lower alkyl and t is 0, 1, 2, 3 or 4, provided, however, that when t is 0, $R^{61}$ is lower alkyl or fluoro substituted lower alkyl, A is —$CR^{40}R^{41}$— or —C(O)—, preferably —$CH_2$— or —C(O)—. In some embodiments, $R^{61}$ is hydrogen, lower alkyl, or fluoro substituted lower alkyl and t is 0, 1, 2, 3 or 4, provided, however, that when t is 0, $R^{61}$ is lower alkyl or fluoro substituted lower alkyl, $A_1$ is —$CR^{40}R^{41}$— or —C(O)—, preferably —$CH_2$— or —C(O)—, $Z_{22}$ is $CR^{62}$, and $Z_{22}$ is $CR^{66}$.

In some embodiments of compounds of Formula IIb, $R^{100}$ is selected from the group consisting of hydrogen, —OH, —$NH_2$, —CN, —$NO_2$, —C(O)OH, —$S(O)_2NH_2$, —$C(O)NH_2$, —$OR^{57}$, —$SR^{57}$, —$NR^{48}R^{51}$, —$NR^{48}C(O)R^{57}$, —$NR^{48}S(O)_2R^{57}$, —$S(O)R^{57}$, —$S(O)_2R^{57}$, —$C(O)R^{57}$, —$C(O)OR^{57}$, —$C(O)NR^{48}R^{57}$, —$S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{100}$ or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{58}$, —$SR^{58}$, —$NHR^{58}$, —$NR^{48}R^{58}$, —$NR^{48}C(O)R^{58}$, —$NR^{48}S(O)_2R^{58}$, —$S(O)_2R^{58}$, —$S(O)_2R^{48}R^{58}$, —$C(O)R^{58}$, —$C(O)NR^{48}R^{58}$, halogen, lower alkyl, fluoro substituted lower alkyl, and cycloalkylamino; $A_1$ is —$CR^{40}R^{41}$— or —C(O)—, preferably —$CH_2$—; and $R^{100}$ is selected from the group consisting of —OH, —$NH_2$, —CN, —$NO_2$, —C(O)OH, —$C(O)NH_2$, —$S(O)_2NH_2$, $C(O)OR^{57}$, —$NR^{48}R^{57}$, —$OR^{57}$, —$S(O)_2R^{57}$, —$C(O)NR^{48}R^{57}$, $S(O)_2NR^{48}R^{57}$, halogen, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —$NR^{48}R^{58}$, —$OR^{58}$ and —$S(O)_2R^{58}$.

In some embodiments of compounds of Formula IIb, $R^{100}$ is selected from the group consisting of hydrogen, —CN, —C(O)OH, —$C(O)OR^{57}$, —$NR^{48}R^{57}$, —$OR^{57}$, —$S(O)_2R^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —$NR^{48}R^{58}$, —$OR^{58}$ and —$S(O)R^{58}$; $A_1$ is —$CR^{40}R^{41}$— or —C(O)—, preferably —$CH_2$—; $R^{101}$ is selected from the group consisting of —OH, —$NH_2$, —CN, —$NO_2$, —C(O)OH, —$C(O)NH_2$, —$S(O)_2NH_2$, $C(O)OR^{57}$, —$NR^{48}R^{57}$, —$OR^{57}$, —$S(O)_2R^{57}$, —$C(O)NR^{48}R^{57}$, —$S(O)_2NR^{48}R^{57}$, halogen, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —$NR^{48}R^{58}$, —$OR^{58}$ and —$S(O)_2R^{58}$; $Z_{22}$ is $CR^{62}$; and $Z_{26}$ is $CR^{66}$.

In some embodiments of any of the above embodiments of compounds of Formula IIb, both of $Z_{22}$ and $Z_{26}$ are N, also one of $Z_{22}$ or $Z_{26}$ is N and the other of $Z_{22}$ or $Z_{26}$ is $CR^{62}$ or $CR^{66}$, preferably $Z_{22}$ is $CR^{26}$ and $Z_{26}$ is $CR^{66}$.

In some embodiments, compounds have the structure according to the following Formula III:

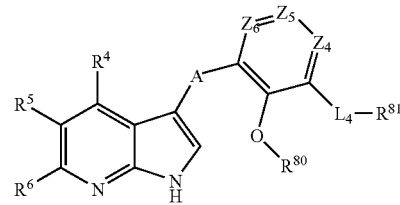

Formula III all salts, prodrugs, tautomers, and isomers thereof,
wherein:

A, $Z_4$, $Z_5$, $Z_6$, $R^4$, $R^5$, and $R^6$, are as defined for Formula I;

$L_4$ is as defined for Formula II;

$R^{80}$ is $C_{1-3}$ alkyl or $C_{3-5}$ cycloalkyl, wherein $C_{1-3}$ alkyl is optionally substituted with one or more substituents selected from the group consisting of fluoro and $C_{3-5}$ cycloalkyl; and $R^{81}$ is selected from the group consisting of optionally substituted aryl, optionally substituted heteroaryl, optionally substituted cycloalkyl, optionally substituted heterocycloalkyl, $C_{2-4}$ alkyl fluoro substituted $C_{2-4}$ alkyl, and —$(CH_2CH_2O)_mR^{71}$;

m is 1, 2, or 3; and $R^{71}$ is $C_{1-3}$ alkyl or fluoro substituted $C_{1-3}$ alkyl, provided, however, that the compound is not

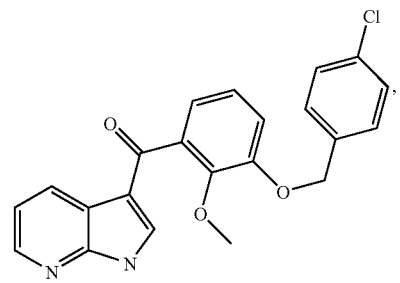

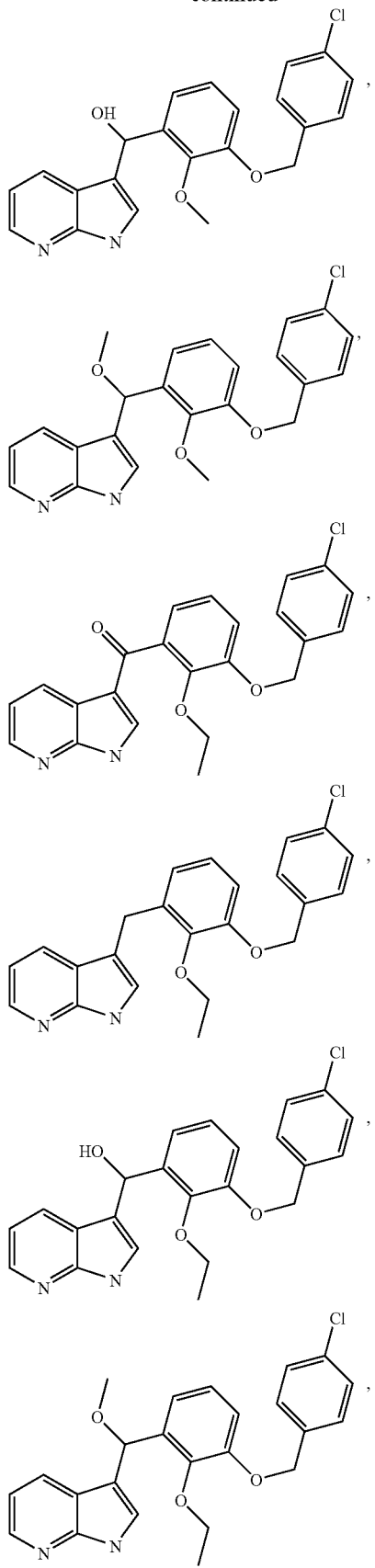
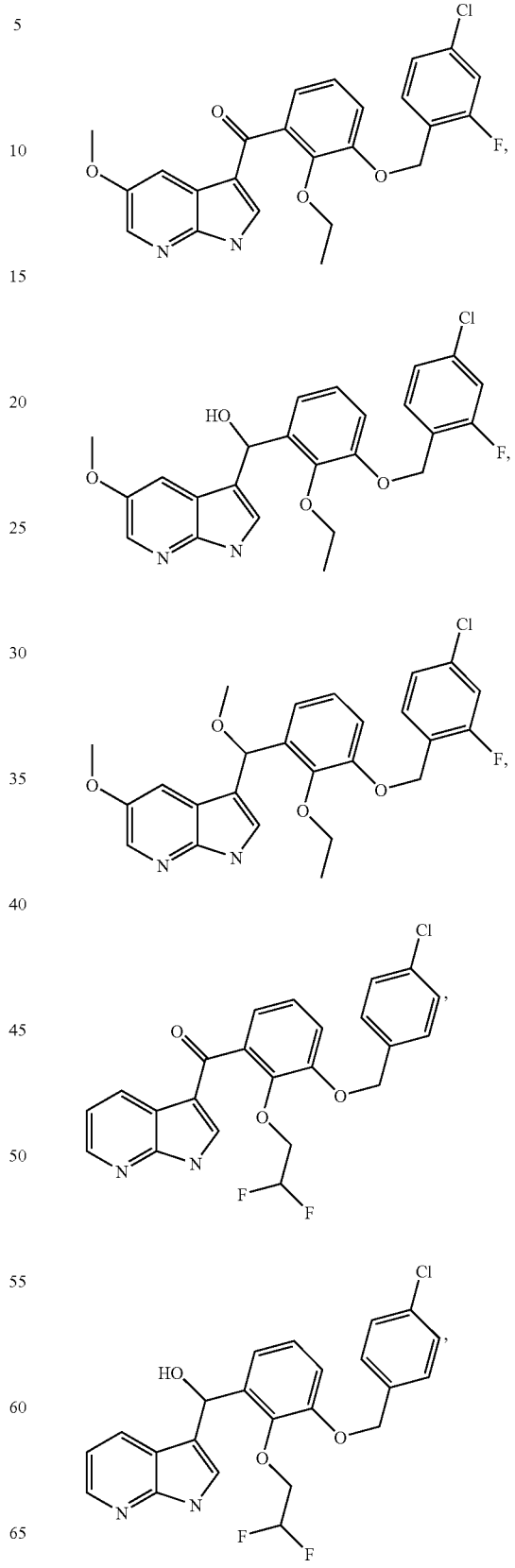

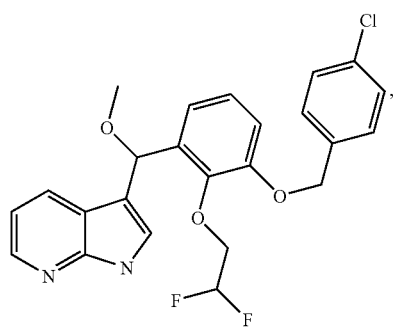
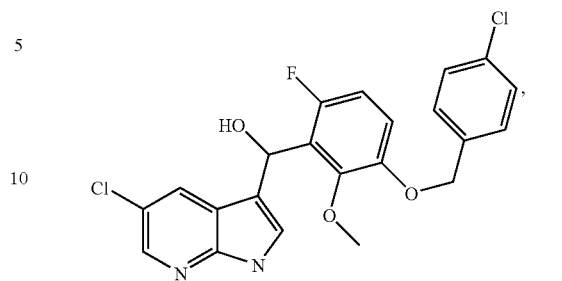
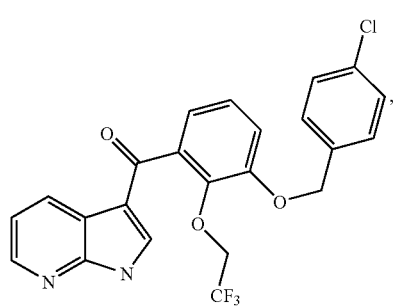
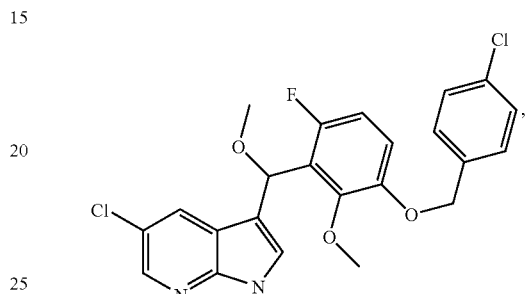
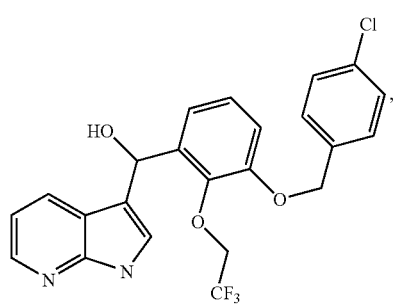
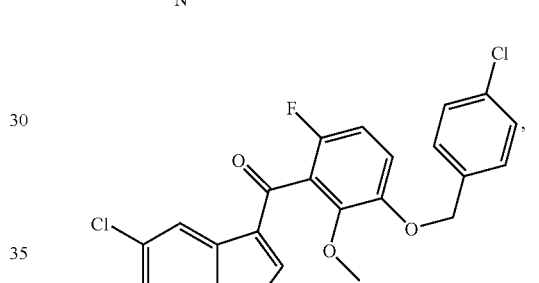
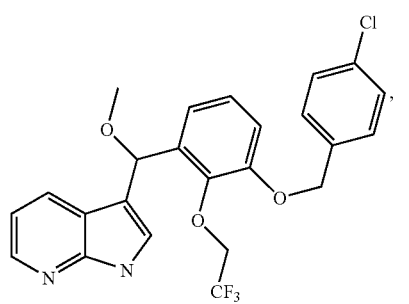
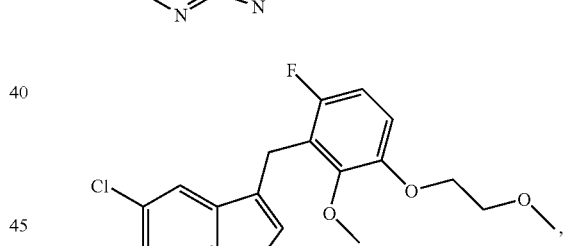
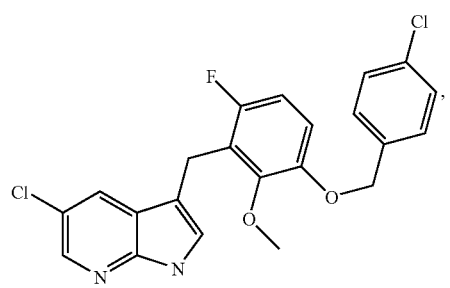
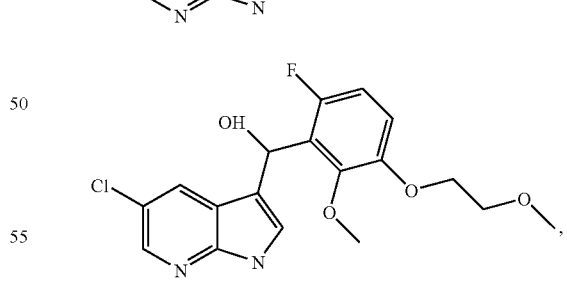
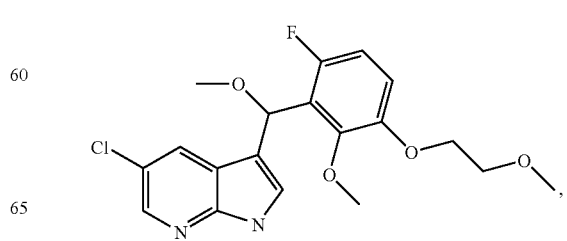

-continued

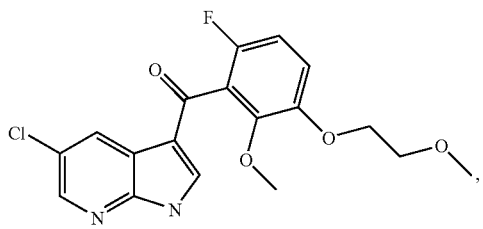
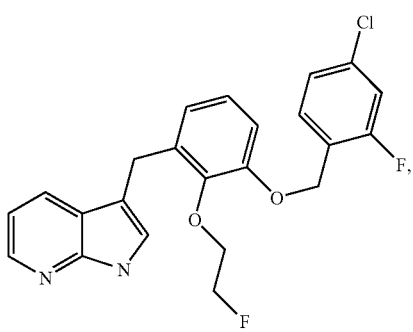
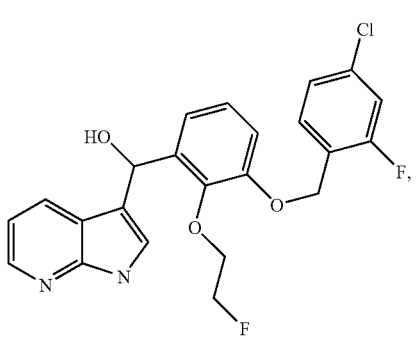
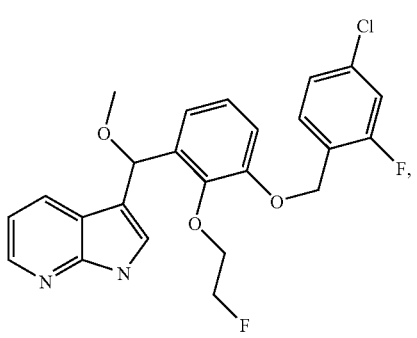
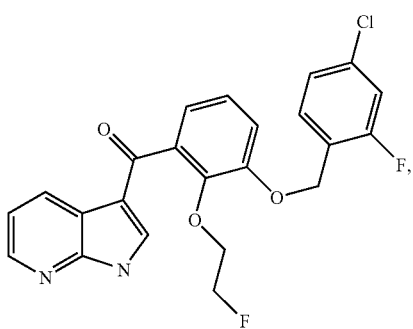

-continued

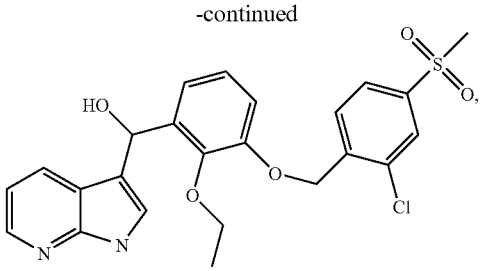
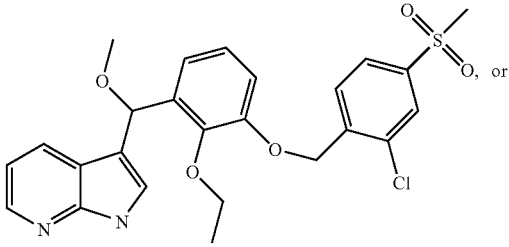
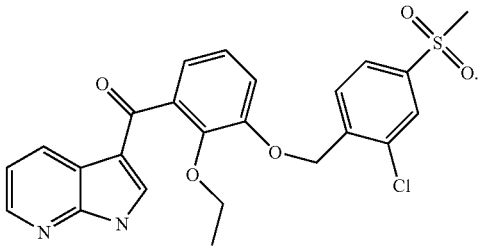

In some embodiments of compounds of Formula III, $R^{81}$ is optionally substituted heteroaryl.

In some embodiments of compounds of Formula III, $R^4$ and $R^6$ are hydrogen and $R^5$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, —OH, —NH$_2$, —C(O)OH, —C(O)NH$_2$, —OR$^{57}$, —SR$^{57}$, —NR$^{48}$R$^{57}$, —C(O)OR$^{57}$, —C(O)NR$^{48}$R$^{57}$, cycloalkyl, heterocycloalkyl, aryl, and heteroaryl, and wherein cycloalkyl, heterocycloalkyl, aryl, and heteroaryl as $R^5$, or as substituents of lower alkyl, are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O)R$^{58}$, —S(O)$_2$R$^{58}$, —C(O)R$^{58}$, —C(O)OR$^{58}$, —C(O)NR$^{48}$R$^{58}$, —S(O)$_2$NR$^{48}$R$^{58}$, halogen, lower alkyl, fluoro substituted lower alkyl, and cycloalkylamino, wherein $R^{48}$, $R^{57}$, and $R^{58}$ are as defined for Formula Ib. In some embodiments, $R^4$ and $R^6$ are hydrogen and $R^5$ is optionally substituted aryl or optionally substituted heteroaryl.

In some embodiments of compounds of Formula III, $R^4$ and $R^6$ are hydrogen, A is —O—, —CR$^a$R$^b$—, —NR$^1$—, or —C(O)—, preferably —CH$_2$— or —C(O)—, and $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro. $R^a$, $R^b$, and $R^1$ are as defined for Formula I.

In some embodiments of compounds of Formula III, $R^4$ and $R^6$ are hydrogen, A is —O—, —$CR^aR^b$—, —$NR^1$—, or —C(O)—, preferably —$CH_2$— or —C(O)—, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^{81}$ is optionally substituted heteroaryl. $R^a$, $R^b$, and $R^1$ are as defined for Formula I.

In some embodiments of compounds of Formula III, $R^4$ and $R^6$ are hydrogen, $R^5$ is selected from the group consisting of hydrogen, —OH, —$NH_2$, —CN, —$NO_2$, —C(O)OH, —$S(O)_2N_2$, —C(O)$NH_2$, —$OR^{57}$, —$SR^{57}$, —$NR^{48}R^{57}$, —$NR^{48}C(O)R^{57}$, —$NR^{48}S(O)_2R^{57}$, —$S(O)R^{57}$, —$S(O)_2R^{57}$, —C(O)$R^{57}$, —C(O)$OR^{57}$, —C(O)$NR^{48}R^{57}$, —$S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, —OH, —$NH_2$, —C(O)OH, —C(O)$NH_2$, —$OR^{57}$, —$SR^{57}$, —$NR^{48}R^{57}$, —C(O)$OR^{57}$, —C(O)$NR^{48}R^{57}$, cycloalkyl, heterocycloalkyl, aryl, and heteroaryl, and wherein cycloalkyl, heterocycloalkyl, aryl, and heteroaryl as $R^5$, or as substituents of lower alkyl, are optionally substituted with one or more substituents selected from the group consisting of —OH, —$NH_2$, —CN, —$NO_2$, —C(O)OH, —$S(O)_2NH_2$, —C(O)$NH_2$, —$OR^{58}$, —$SR^{58}$, —$NR^{48}R^{58}$, —$NR^{48}C(O)R^{58}$, —$NR^{48}S(O)R^{58}$, —$S(O)R^{58}$, —$S(O)_2R^{58}$, —C(O)$R^{58}$, —C(O)$OR^{58}$, —C(O)$NR^{48}R^{58}$, —$S(O)_2NR^{48}R^{58}$, halogen, lower alkyl, fluoro substituted lower alkyl, and cycloalkylamino, wherein $R^{48}$, $R^{57}$, and $R^{58}$, A is —O—, —$CR^aR^b$—, —$NR^1$—, or —C(O)—, preferably —$CH_2$— or —C(O)—, and $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro. $R^a$, $R^b$, and $R^1$ are as defined for Formula I.

In some embodiments of compounds of Formula III, $R^4$ and $R^6$ are hydrogen, A is —O—, —$CR^aR^b$—, —$NR^1$—, or —C(O)—, preferably —$CH_2$— or —C(O)—, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^5$ is selected from the group consisting of hydrogen, halogen, lower alkyl, lower alkoxy, optionally substituted aryl, optionally substituted heteroaryl, —CN, —C(O)OH, —C(O)$OR^{22}$, —$OR^{22}$, —$S(O)_2R^{22}$, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^2$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino. $R^a$, $R^b$, and $R^1$ are as defined for Formula I.

In some embodiments of compounds of Formula III, $R^4$ and $R^6$ are hydrogen, A is —O—, —$CR^aR^b$—, —$NR^1$—, or —C(O)—, preferably —$CH_2$— or —C(O)—, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, $R^5$ is selected from the group consisting of hydrogen, halogen, lower alkyl, lower alkoxy, optionally substituted aryl, optionally substituted heteroaryl, —CN, —C(O)OH, —C(O)$OR^{22}$, —$OR^{22}$, —$S(O)_2R^{22}$, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, and $R^{81}$ is optionally substituted heteroaryl. $R^a$, $R^b$, and $R^1$ are as defined for Formula I.

In some embodiments of compounds of Formula III, $R^4$ and $R^6$ are hydrogen, A is —O—, —$CR^aR^b$—, —$NR^1$—, or —C(O)—, preferably —$CH_2$— or —C(O)—, $R^{14}$, $R^{15}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, —CN, —C(O)OH, —C(O)$OR^{22}$, —$OR^{22}$, —$S(O)_2R^{22}$, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino. $R^a$, $R^b$, and $R^1$ are as defined for Formula I.

In some embodiments of compounds of Formula III, $R^4$ and $R^6$ are hydrogen, A is —O—, —$CR^aR^b$—, —$NR^1$—, or —C(O)—, preferably —$CH_2$— or —C(O)—, $R^{14}$, $R^{15}$ and $R^{16}$ are independently selected from the group consisting of hydrogen, halogen, lower alkyl, fluoro substituted lower alkyl, lower alkoxy, and fluoro substituted lower alkoxy, and $R^5$ is selected from the group consisting of hydrogen, halogen, lower alkyl, lower alkoxy, optionally substituted aryl, optionally substituted heteroaryl, —CN, —C(O)OH, —C(O)$OR^{22}$, —$OR^{22}$, —$S(O)_2R^{12}$, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, and $R^{81}$ is optionally substituted heteroaryl. $R^a$, $R^b$, and $R^1$ are as defined for Formula I.

In some embodiments of any of the above embodiments of compounds of Formula III, at most two of $Z_4$, $Z_5$, or $Z_6$ are N, also at most one of $Z_4$, $Z_5$, or $Z_6$ is N, preferably $Z_4$ is $CR^{14}$, $Z_5$ is $CR^{15}$ and $Z_6$ is $CR^{16}$.

In some embodiments of any of the above embodiments of compounds of Formula III, $R^{81}$ is selected from the group consisting of aryl, heteroaryl, cycloalkyl, heterocycloalkyl, $C_{2-4}$ alkyl, fluoro substituted $C_{2-4}$ alkyl, and —(CH$_2$CH$_2$O)$_m$R$^{71}$, wherein aryl, heteroaryl, cycloalkyl, or heterocycloalkyl are optionally substituted with one or more substituents selected from the group consisting of —OH, —NH$_2$, —CN, —NO$_2$, —C(O)OH, —S(O)$_2$N$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, —OH, —NH$_2$, —C(O)OH, —C(O)NH$_2$, —OR$^{57}$, —SR$^{57}$, —NR$^{48}$R$^{57}$, —C(O)OR$^{57}$, —C(O)NR$^{48}$R$^{57}$, cycloalkyl, heterocycloalkyl, aryl, and heteroaryl, and wherein cycloalkyl, heterocycloalkyl, aryl, and heteroaryl as a substituent of $R^{81}$, or as substituents of lower alkyl, are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O)R$^{58}$, —S(O)$_2$R$^{58}$, —C(O)R$^{58}$, —C(O)OR$^{58}$, —C(O)NR$^{48}$R$^{58}$, —S(O)$_2$NR$^{48}$R$^{58}$, halogen, lower alkyl, fluoro substituted lower alkyl, and cycloalkylamino, wherein $R^{48}$, $R^{57}$ and $R^{58}$ are as defined for Formula Ib, $Z_4$ is $CR^{14}$, $Z_5$ is $CR^{15}$, $Z_6$ is $CR^{16}$, and $R^{14}$, $R^{15}$ and $R^{16}$ are independently selected from the group consisting of hydrogen, halogen, lower alkyl, fluoro substituted lower alkyl, lower alkoxy, and fluoro substituted lower alkoxy.

In one embodiment of compounds of Formula III, the compound is selected from the group consisting of:
[3-(4-Chloro-benzyloxy)-2-(2-fluoro-ethoxy)-phenyl]-(1H-pyrrolo[2,3-b]pyridin-3-yl)-methanone (P-2118),
[3-(4-Chloro-2-fluoro-benzyloxy)-2-(2,2-difluoro-ethoxy)-phenyl]-(1H-pyrrolo[2,3-b]pyridin-3-yl)-methanone (P-2119),
[3-(4-Chloro-2-fluoro-benzyloxy)-2-cyclopropyl ethoxy-phenyl]-(1H-pyrrolo[2,3-b]pyridin-3-yl)-methanone (P-2120),
[2-Ethoxy-3-(2-pyrrolidin-1-yl-ethoxy)-phenyl]-(1H-pyrrolo[2,3-b]pyridin-3-yl)-methanone (P-2121),
[2-Ethoxy-3-(6-methyl-pyridin-2-ylmethoxy)-phenyl]-(1H-pyrrolo[2,3-b]pyridin-3-yl)-methanone (P-2122),
[3-(4-Chloro-2-fluoro-benzyloxy)-2-ethoxy-phenyl]-(1H-pyrrolo[2,3-b]pyridin-3-yl)-methanone (P-2123),
[3-(2,4-Dimethyl-thiazol-5-ylmethoxy)-2-ethoxy-phenyl]-(1H-pyrrolo[2,3-b]pyridin-3-yl)-methanone (P-2124),
[3-(2,5-Dimethyl-2H-pyrazol-3-ylmethoxy)-2-ethoxy-phenyl]-(1H-pyrrolo[2,3-b]pyridin-3-yl)-methanone (P-2125),
[2-Ethoxy-3-(2-fluoro-benzyloxy)-phenyl]-(1H-pyrrolo[2,3-b]pyridin-3-yl)-methanone (P-2127),
[2-Ethoxy-3-(6-morpholin-4-yl-pyridin-3-ylmethoxy)-phenyl]-(1H-pyrrolo[2,3-b]pyridin-3-yl)-methanone (P-2128),
[2-Ethoxy-3-(6-trifluoromethyl-pyridin-3-ylmethoxy)-phenyl]-(1H-pyrrolo[2,3-b]pyridin-3-yl)-methanone (P-2129),
[3-(2,4-Dichloro-benzyloxy)-2-ethoxy-phenyl]-(1-pyrrolo[2,3-b]pyridin-3-yl)-methanone (P-2130),
[2-Ethoxy-3-(4-imidazol-1-yl-benzyloxy)-phenyl]-(1H-pyrrolo[2,3-b]pyridin-3-yl)-methanone (P-2131),
[3-(2,4-Difluoro-benzyloxy)-2-ethoxy-phenyl]-(1H-pyrrolo[2,3-b]pyridin-3-yl)-methanone (P-2132),
{2-Ethoxy-3-[1-(2-fluoro-phenyl)-ethoxy]-phenyl}-(1H-pyrrolo[2,3-b]pyridin-3-yl)-methanone (P-2133),
[3-(1,5-Dimethyl-1H-pyrazol-3-ylmethoxy)-2-ethoxy-phenyl]-(1H-pyrrolo[2,3-b]pyridin-3-yl)-methanone (P-2134),
[2-Ethoxy-3-(1-pyridin-4-yl-ethoxy)-phenyl]-(1H-pyrrolo[2,3-b]pyridin-3-yl)-methanone (P-2135),
[2-Ethoxy-3-((R)-1-pyridin-4-yl-ethoxy)-phenyl]-(1H-pyrrolo[2,3-b]pyridin-3-yl)-methanone (P-2136),
[2-Ethoxy-3-(2,4,6-trifluoro-benzyloxy)-phenyl]-(1H-pyrrolo[2,3-b]pyridin-3-yl)-methanone (P-2137),
{3-[1-(2,4-Dichloro-phenyl)-ethoxy]-2-ethoxy-phenyl}-(1H-pyrrolo[2,3-b]pyridin-3-yl)-methanone (P-2138),
[3-(4-Chloro-2-fluoro-benzyloxy)-2-(2,2,2-trifluoro-ethoxy)-phenyl]-(1H-pyrrolo[2,3-b]pyridin-3-yl)-methanone (P-2139),
(5-Chloro-1H-pyrrolo[2,3-b]pyridin-3-yl)-[2-cyclopropylmethoxy-3-(2,4-dimethyl-thiazol-5-ylmethoxy)-phenyl]-methanone (P-2140),
(5-Chloro-1H-pyrrolo[2,3-b]pyridin-3-yl)-[2-cyclopropylmethoxy-3-(2,4,6-trifluoro-benzyloxy)-phenyl]-methanone (P-2141),
(5-Chloro-1H-pyrrolo[2,3-b]pyridin-3-yl)-[2-cyclopropylmethoxy-3-(6-trifluoromethyl-pyridin-3-ylmethoxy)-phenyl]-methanone (P-2142),
[3-(6-Diethylamino-pyridin-3-ylmethoxy)-2-ethoxy-phenyl]-(1H-pyrrolo[2,3-b]pyridin-3-yl)-methanone (P-2143),
[2-Ethoxy-3-(6-pyrrolidin-1-yl-pyridin-3-ylmethoxy)-phenyl]-(1H-pyrrolo[2,3-b]pyridin-3-yl)-methanone (P-2144), and all salts, prodrugs, tautomers, and isomers thereof.

In some embodiments, compounds of Formula III have the structure according to the following sub-generic structure Formula IIa:

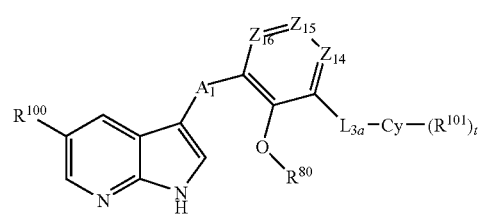

Formula IIIa all salts, prodrugs, tautomers, and isomers thereof,
wherein:
$R^{100}$ and $R^{101}$ are as defined for Formula IIa;
$Z_{14}$ and $Z_{15}$ are as defined for Formula Ig;
Cy is selected from the group consisting of aryl, heteroaryl, cycloalkyl, and heterocycloalkyl;

$L_{3a}$ is selected from the group consisting of —NR$^{48}$—, —S—, —O—, —NR$^{48}$CH(R$^{49}$)—, —SCH(R$^{49}$)—, —OCH(R$^{49}$)—, —C(O)NR$^{48}$—, —S(O)$_2$NR$^{48}$—, —CH(R$^{49}$)NR$^{48}$—, —CH(R$^{49}$)O—, —CH(R$^{49}$)S—, —NR$^{48}$C(O)—, and —NR$^{48}$S(O)$_2$—;

R$^{80}$ is C$_{1-3}$ alkyl or C$_{3-5}$ cycloalkyl, wherein C$_{1-3}$ alkyl is optionally substituted with one or more substituents selected from the group consisting of fluoro and C$_{3-5}$ cycloalkyl; and A$_1$, Z$_{16}$, R$^{48}$, R$^{49}$, and t are as defined for Formula Ib.

In some embodiments of compounds of Formula IIIa, Cy is heteroaryl.

In some embodiments of compounds of Formula IIIa, R$^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as R$^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino. In some embodiments, R$^{100}$ is selected from the group consisting of hydrogen, —CN, —C(O)OH, —C(O)OR$^{57}$, —NR$^{48}$R$^{57}$, —OR$^{57}$, —S(O)$_2$R$^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$.

In some embodiments of compounds of Formula IIIa, A$_1$ is —CR$^{40}$R$^{41}$— or —C(O)—, preferably —C(O)—. In some embodiments, A$_1$ is —CR$^{40}$R$^{41}$— or —C(O)—, preferably —C(O)—, and R$^{58}$ and R$^{55}$ are independently selected from the group consisting of hydrogen, halogen, lower alkyl, fluoro substituted lower alkyl, lower alkoxy, and fluoro substituted lower alkoxy. In some embodiments, L$_3$ is —NR$^{48}$CH(R$^{49}$)—, —SCH(R$^{49}$)—, or —OCH(R$^{49}$)—, preferably —OCH(R$^{49}$)—. In some embodiments, A$_1$ is —CR$^{40}$R$^{41}$— or —C(O)—, preferably —C(O)—, and L$_3$ is —NR$^{48}$CH(R$^{49}$)—, —SCH(R$^{49}$)—, or —OCH(R$^{49}$)—.

In some embodiments of compounds of Formula IIIa, Cy is heteroaryl, A$_1$ is —CR$^{40}$R$^{41}$— or —C(O)—, preferably —C(O)—. In some embodiments, Cy is heteroaryl, A$_1$ is —CR$^{40}$R$^{41}$— or —C(O)—, preferably —C(O)—, and R$^{54}$ and R$^{55}$ are independently selected from the group consisting of hydrogen, halogen, lower alkyl, fluoro substituted lower alkyl, lower alkoxy, and fluoro substituted lower alkoxy. In some embodiments, Cy is heteroaryl, L$_3$ is —NR$^{48}$CH(R$^{49}$)—, —SCH(R$^{49}$)—, or —OCH(R$^{49}$)—, preferably —OCH(R$^{49}$)—. In some embodiments, Cy is heteroaryl, A$_1$ is —CR$^{40}$R$^{41}$— or —C(O)—, preferably —C(O)—, and L$_3$ is —NR$^{48}$CH(R$^{49}$)—, —SCH(R$^{49}$)—, or —OCH(R$^{49}$)—, preferably —OCH(R$^{49}$)—.

In some embodiments of compounds of Formula IIa, R$^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as R$^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino; A$_1$ is —CR$^{40}$R$^{41}$— or —C(O)—, preferably —C(O)—.

In some embodiments of compounds of Formula IIIa, R$^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$SR$^{57}$, —S(O)$_2$NR$^{41}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as R$^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino; A$_1$ is —CR$^{40}$R$^{41}$— or —C(O)—, preferably —C(O)—; and R$^{54}$ and R$^{55}$ are independently selected from the group consisting of hydrogen, halogen, lower alkyl, fluoro substituted lower alkyl, lower alkoxy, and fluoro substituted lower alkoxy.

In some embodiments of compounds of Formula IIIa, R$^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as R$^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino; L$_3$ is —NR$^{48}$CH(R$^{49}$)—, —SCH(R$^{49}$)—, or —OCH(R$^{49}$)—, preferably —OCH(R$^{49}$)—.

In some embodiments of compounds of Formula IIIa, $R^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as $R^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino; $A_1$ is —CR$^{40}$R$^{41}$— or —C(O)—, preferably —C(O)—; and $L_3$ is —NR$^{48}$CH(R$^{49}$)—, —SCH(R$^{49}$)—, or —OCH(R$^{49}$)—, preferably —OCH(R$^{49}$)—.

In some embodiments of compounds of Formula IIIa, $R^{100}$ is selected from the group consisting of hydrogen, —CN, —C(O)OH, —C(O)OR$^{57}$, —NR$^{48}$R$^{57}$, —OR$^{57}$, —S(O)$_2$R$^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$. In some embodiments, $R^{100}$ is selected from the group consisting of hydrogen, —CN, —C(O)OH, —C(O)OR$^{57}$, —NR$^{48}$R$^{57}$, —OR$^{57}$, —S(O)$_2$R$^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$; and $R^{101}$ is selected from the group consisting of —OH, —NH$_2$, —CN, —NO$_2$, —C(O)OH, —C(O)NH$_2$, —C(O)OR$^{57}$, —S(O)$_2$NH—, C(O)OR$^{57}$, —NR$^{48}$R$^{57}$, —OR$^{57}$, —S(O)$_2$R$^{57}$, —C(O)NR$^{48}$R$^{57}$, —S(O)$_2$NR$^{48}$R$^{57}$, halogen, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$.

In some embodiments of compounds of Formula IIIa, $A_1$ is —C(O)—; $L_3$ is —OCH(R$^{49}$)—; $R^{100}$ is selected from the group consisting of hydrogen, —CN, —C(O)OR$^{57}$, —NR$^{48}$R$^{57}$, —OR$^{57}$, —S(O)$_2$R$^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$; $Z_{14}$ is CR$^{54}$; $Z_{15}$ is CR$^{55}$; $Z_{16}$ is CR$^{56}$; $R^{10l}$ is selected from the group consisting of —OH, —NH$_2$, —CN, —NO$_2$, —C(O)OH, —C(O)NH$_2$, —S(O)$_2$NH$_2$, C(O)OR$^{57}$, —NR$^{48}$R$^{57}$, —OR$^{57}$, —S(O)$_2$R$^{57}$, —C(O)NR$^{48}$R$^{57}$, —S(O)$_2$NR$^{48}$R$^{57}$, halogen, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$; and $R^{54}$, $R^{55}$ and $R^{56}$ are independently selected from the group consisting of hydrogen, halogen, lower alkyl, fluoro substituted lower alkyl, lower alkoxy, and fluoro substituted lower alkoxy.

In some embodiments of any of the above embodiments of compounds of Formula IIIa, two of $Z_{14}$, $Z_{15}$, or $Z_{16}$ are N and the other of $Z_{14}$, $Z_{15}$, or $Z_{16}$ is CR$^{54}$, CR$^{55}$ or CR$^{56}$, also one of $Z_{14}$, $Z_{15}$, or $Z_{16}$ is N and the others of $Z_{14}$, $Z_{15}$, or $Z_{16}$ are CR$^{54}$, CR$^{55}$ or CR$^{56}$, preferably $Z_{14}$ is CR$^{54}$, $Z_{15}$ is CR$^{55}$ and $Z_{16}$ is CR$^{56}$.

In some embodiments, compounds of Formula III have the structure according to the following sub-generic structure Formula IIIb:

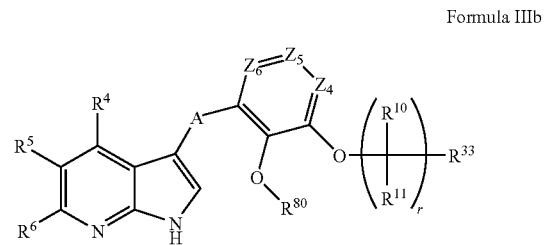

Formula IIIb all salts, prodrugs, tautomers, and isomers thereof,
wherein:

A, $Z_4$, $Z_5$, $Z_6$, $R^4$, $R^5$, $R^6$, $R^{10}$, $R^{11}$ and $R^{33}$ are as defined for Formula I;

$R^{80}$ is as defined for Formula III; and r is 0, 1, or 2.

In some embodiments of compounds of Formula IIIb, $R^{33}$ is optionally substituted heteroaryl.

In some embodiments of compounds of Formula IIIb, $R^4$ and $R^6$ are hydrogen and $R^5$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)N$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as $R^5$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino. In some embodiments, $R^4$ and $R^6$ are hydrogen and $R^5$ is optionally substituted aryl or optionally substituted heteroaryl.

In some embodiments of compounds of Formula IIIb, $R^4$ and $R^6$ are hydrogen, A is —O—, —CR$^a$R$^b$—, —NR$^1$—, or —C(O)—, preferably —CH$_2$— or —C(O)—, and $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro. R$^a$, R$^b$, and R$^1$ are as defined for Formula I.

In some embodiments of compounds of Formula IIIb, R$^4$ and R$^6$ are hydrogen, A is —O—, —CR$^a$R$^b$—, —NR$^1$—, or —C(O)—, preferably —CH$_2$— or —C(O)—, R$^{14}$, R$^{15}$ and R$^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and R$^{33}$ is optionally substituted heteroaryl. R$^a$, R$^b$, and R$^1$ are as defined for Formula I.

In some embodiments of compounds of Formula IIIb, R$^4$ and R$^6$ are hydrogen, R$^5$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{45}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as R$^5$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino, A is —O—, —CR$^a$R$^b$—, —NR$^1$—, or —C(O)—, preferably —CH$_2$— or —C(O)—, and R$^{14}$, R$^{15}$ and R$^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro. R$^a$, R$^b$, and R$^1$ are as defined for Formula I.

In some embodiments of compounds of Formula IIIb, R$^4$ and R$^6$ are hydrogen, A is —O—, —CR$^a$R$^b$—, —NR$^1$—, or —C(O)—, preferably —CH$_2$— or —C(O)—, R$^{14}$, R$^{15}$ and R$^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, R$^{10}$ and R$^{11}$ are independently selected from the group consisting of hydrogen, fluoro, lower alkyl, and fluoro substituted lower alkyl, and R$^5$ is selected from the group consisting of hydrogen, halogen, lower alkyl, lower alkoxy, optionally substituted aryl, optionally substituted heteroaryl, —CN, —C(O)OH, —C(O)OR$^{22}$, —OR$^{22}$, —S(O)$_2$R$^{22}$, and NR$^{21}$R$^{22}$, wherein R$^{21}$ is hydrogen or lower alkyl, and R$^{22}$ is hydrogen, lower alkyl, optionally substituted aryl or optionally substituted heteroaryl, and wherein the alkyl chain of R$^5$, R$^{21}$ or R$^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino. R$^a$, R$^b$, and R$^1$ are as defined for Formula I.

In some embodiments of compounds of Formula IIIb, R$^4$ and R$^6$ are hydrogen, A is —O—, —CR$^a$R$^b$—, —NR$^1$—, or —C(O)—, preferably —CH$_2$— or —C(O)—, R$^{14}$, R$^{15}$ and R$^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, R$^{10}$ and R$^{11}$ are independently selected from the group consisting of hydrogen, fluoro, lower alkyl, and fluoro substituted lower alkyl, R$^5$ is selected from the group consisting of hydrogen, halogen, lower alkyl, lower alkoxy, optionally substituted aryl, optionally substituted heteroaryl, —CN, —C(O)OH, —C(O)OR$^{22}$, —OR$^{22}$, —S(O)$_2$R$^{22}$, and NR$^{21}$R$^{22}$, wherein R$^{21}$ is hydrogen or lower alkyl, and R$^{22}$ is hydrogen, lower alkyl, optionally substituted aryl or optionally substituted heteroaryl, and wherein the alkyl chain of R$^5$, R$^{21}$ or R$^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, and R$^{33}$ is optionally substituted heteroaryl. R$^a$, R$^b$, and R$^1$ are as defined for Formula I.

In some embodiments of compounds of Formula IIIb, R$^4$ and R$^6$ are hydrogen, A is —O—, —CR$^a$R$^b$—, —NR$^1$—, or —C(O)—, preferably —CH$_2$— or —C(O)—, R$^{14}$, R$^{15}$ and R$^{16}$ are independently selected from the group consisting of hydrogen, halogen, lower alkyl, fluoro substituted lower alkyl, lower alkoxy, and fluoro substituted lower alkoxy, R$^{10}$ and R$^{11}$ are independently selected from the group consisting of hydrogen, fluoro, lower alkyl, and fluoro substituted lower alkyl, and R$^5$ is selected from the group consisting of hydrogen, halogen, lower alkyl, lower alkoxy, optionally substituted aryl, optionally substituted heteroaryl, —CN, —C(O)OH, —C(O)OR$^{22}$, —OR$^{22}$, —S(O)$_2$R$^{22}$, and NR$^{21}$R$^{22}$, wherein R$^{21}$ is hydrogen or lower alkyl, and R$^{22}$ is hydrogen, lower alkyl, optionally substituted aryl or optionally substituted heteroaryl, and wherein the alkyl chain of R$^5$, R$^{21}$ or R$^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino. R$^a$, R$^b$, and R$^1$ are as defined for Formula I.

In some embodiments of compounds of Formula IIb, R$^4$ and R$^6$ are hydrogen, A is —O—, —CR$^a$R$^b$—, —NR$^1$—, or —C(O)—, preferably —C$_2$— or —C(O)—, R$^{14}$, R$^{15}$ and R$^{16}$ are independently selected from the group consisting of hydrogen, halogen, lower alkyl, fluoro substituted lower alkyl, lower alkoxy, and fluoro substituted lower alkoxy, R$^{10}$ and $R^{11}$ are independently selected from the group consisting of hydrogen, fluoro, lower alkyl, and fluoro substituted lower alkyl, $R^5$ is selected from the group consisting of hydrogen, halogen, lower alkyl, lower alkoxy, optionally substituted aryl, optionally substituted heteroaryl, —CN, —C(O)OH, —C(O)OR$^{22}$, —OR$^{22}$, —S(O)$_2$R$^{22}$, and NR$^{21}$R$^{22}$, wherein $R^{21}$ is hydrogen or lower alkyl, and $R^{22}$ is hydrogen, lower alkyl optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, and $R^{33}$ is optionally substituted heteroaryl. $R^a$, $R^b$, and $R^1$ are as defined for Formula I.

In some embodiments of any of the above embodiments of compounds of Formula IIIb, two of $Z_4$, $Z_5$, or $Z_6$ are N and the other of $Z_4$, $Z_5$, or $Z_6$ is CR$^{14}$, CR$^{15}$ or CR$^6$, also one of $Z_4$, $Z_5$, or $Z_6$ is N and the others of $Z_4$, $Z_5$, or $Z_6$ are CR$^{14}$, CR$^{15}$ or CR$^{16}$, preferably $Z_4$ is CR$^{14}$, $Z_5$ is CR$^{15}$ and $Z_6$ is CR$^{16}$.

In some embodiments of any of the above embodiments of compounds of Formula IIIb, $R^{33}$ is aryl, heteroaryl, cycloalkyl or heterocycloalkyl, wherein aryl, heteroaryl, cycloalkyl, or heterocycloalkyl are optionally substituted with one or more substituents selected from the group consisting of —OH, —NH$_2$, —CN, —NO, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, —OH, —NH$_2$, C(O)OH, —C(O)N$_2$, —OR$^{57}$, —SR$^{57}$, —NR$^{48}$R$^{57}$, —C(O)OR$^{57}$, —C(O)NR$^{48}$R$^{57}$, cycloalkyl, heterocycloalkyl, aryl, and heteroaryl, wherein cycloalkyl, heterocycloalkyl, aryl, and heteroaryl as a substituent of $R^{33}$, or as substituents of lower alkyl, are optionally substituted with one or more substituents selected from the group consisting of —OH, —NH$_2$, —CN, —NO$_2$, —C(O)OH, —S(O)$_2$NH$_2$, —C(O)NH$_2$, —OR$^{58}$, —SR$^{58}$, —NR$^{48}$R$^{58}$, —NR$^{48}$C(O)R$^{58}$, —NR$^{48}$S(O)$_2$R$^{58}$, —S(O)R$^{58}$, —S(O)$_2$R$^{58}$, —C(O)R$^{58}$, —C(O)OR$^{58}$, —C(O)NR$^{48}$R$^{58}$, —S(O)$_2$NR$^{48}$R$^{58}$, halogen, lower alkyl, fluoro substituted lower alkyl, and cycloalkylamino, wherein $R^{48}$, $R^{57}$ and $R^{58}$ are as defined for Formula Ib, $Z_4$ is CR$^{14}$, $Z_5$ is CR$^{15}$, $Z_6$ is CR$^{16}$, and $R^{14}$, $R^{15}$ and $R^{16}$ are independently selected from the group consisting of hydrogen, halogen, lower alkyl, fluoro substituted lower alkyl, lower alkoxy, and fluoro substituted lower alkoxy.

In some embodiments, compounds of Formula III have the structure according to the following sub-generic structure Formula IIIc:

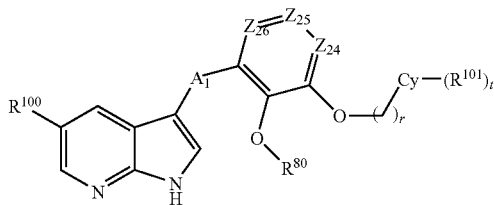

Formula IIIc all salts, prodrugs, tautomers, and isomers thereof,
wherein:
$A_1$, Cy and t are as defined for Formula Ib;

$R^{100}$ and $R^{101}$ are as defined for Formula Ia;
$R^{80}$ is as defined for Formula IIIa;
$Z_{26}$ and r are as defined for Formula Ic; and
$Z_{24}$ and $Z_{25}$ are as defined for Formula Ii.

In some embodiments of compounds of Formula IIIc, Cy is heteroaryl.

In some embodiments of compounds of Formula IIIc, $R^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, —NR$^{48}$C(O)R$^{57}$, —NR$^{48}$S(O)$_2$R$^{57}$, —S(O)R$^{57}$, S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as $R^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino. In some embodiments, $R^{10}$ is selected from the group consisting of hydrogen, —CN, —C(O)OH, —C(O)OR$^{57}$, —NR$^{48}$R$^{57}$, —OR$^{57}$, —S(O)$_2$R$^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NR$^{48}$R$^{58}$, —OR$^{58}$ and —S(O)$_2$R$^{58}$.

In some embodiments of compounds of Formula IIIc, $A_1$ is —CR$^{40}$R$^{41}$— or —C(O)—, preferably —CH$_2$— or —C(O)—. In some embodiments, $A_1$ is —CR$^{40}$R$^{41}$— or —C(O)—, preferably —CH$_2$— or —C(O)—, and $R^{64}$, $R^{65}$ and $R^{66}$ are independently selected from the group consisting of hydrogen, halogen, lower alkyl fluoro substituted lower alkyl, lower alkoxy, and fluoro substituted lower alkoxy.

In some embodiments of compounds of Formula IIIc, Cy is heteroaryl, $A_1$ is —CR$^{40}$R$^{41}$— or —C(O)—, preferably —CH$_2$— or —C(O)—. In some embodiments, Cy is heteroaryl, A, is —CR$^{40}$R$^{41}$— or —C(O)—, preferably —CH$_2$— or —C(O)—, and $R^{64}$, $R^{65}$ and $R^{66}$ are independently selected from the group consisting of hydrogen, halogen, lower alkyl, fluoro substituted lower alkyl, lower alkoxy, and fluoro substituted lower alkoxy.

In some embodiments of compounds of Formula IIIc, $R^{100}$ is selected from the group consisting of hydrogen, —OH, —NH$_2$, —CN, —NO$_2$, —C(O)OH, —S(O)$_2$NH$_2$, —C(O)NH$_2$, —OR$^{57}$, —SR$^{57}$, —NR$^{48}$R$^{57}$, NR$^{48}$C(O)R$^{57}$, —NR$^{48}$S(O)$_2$R$^{57}$, —S(O)R$^{57}$, —S(O)$_2$R$^{57}$, —C(O)R$^{57}$, —C(O)OR$^{57}$, —C(O)NR$^{48}$R$^{57}$, —S(O)$_2$NR$^{48}$R$^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as $R^{100}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{58}$, —SR$^{58}$, —NHR$^{58}$, —NR$^{48}$R$^{58}$, —NR$^{48}$C(O)R$^{58}$, —NR$^{48}$S(O)$_2$R$^{58}$, —S(O)$_2$R$^{58}$, —S(O)$_2$NR$^{48}$R$^{58}$, —C(O)R$^{58}$, —C(O)NR$^{48}$R$^{58}$, halogen, lower alkyl, fluoro substituted lower alkyl, and cycloalkylamino; $A_1$ is —$CR^{40}R^{41}$— or —C(O)—, preferably —$CH_2$— or —C(O)—.

In some embodiments of compounds of Formula IIIc, $R^{100}$ is selected from the group consisting of hydrogen, —OH, —$NH_2$, —CN, —$NO_2$, —C(O)OH, —$S(O)_2NH_2$, —C(O)$NH_2$, —$OR^{57}$, —$SR^{57}$, —$NR^{48}R^{57}$, —$NR^{48}C(O)R^{57}$, —$NR^{48}S(O)_2R^{57}$, —$S(O)R^{57}$, —$S(O)_2R^{57}$, —$C(O)R^{57}$, —$C(O)OR^{57}$, —$C(O)NR^{48}R^{57}$, —$S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as $R^{100}$ or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{58}$, —$SR^{58}$, —$NHR^{58}$, —$N^{48}R^{58}$, —$NR^{48}C(O)R^{58}$, —$NR^{48}S(O)_2R^{58}$, —$S(O)_2R^{58}$, —$S(O)_2NR^{48}R^{58}$, —$C(O)R^{58}$, —$C(O)NR^{48}R^{58}$, halogen, lower alkyl, fluoro substituted lower alkyl, and cycloalkylamino; $A_1$ is —$CR^{40}R^{41}$— or —C(O)—, preferably —$CH_2$— or —C(O)—; and $R^{64}$, $R^{65}$ and $R^{66}$ are independently selected from the group consisting of hydrogen, halogen, lower alkyl, fluoro substituted lower alkyl, lower alkoxy, and fluoro substituted lower alkoxy.

In some embodiments of compounds of Formula IIIc, $R^{100}$ is selected from the group consisting of hydrogen, —CN, —C(O)OH, —$C(O)OR^{57}$, —$NR^{48}R^{57}$, —$OR^{57}$, —$S(O)_2R^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —$NR^{48}R^{58}$, —$OR^{58}$ and —$S(O)_2R^{58}$. In some embodiments, $A_1$ is —$CH_2$— or —C(O)—; $R^{100}$ is selected from the group consisting of hydrogen, —CN, —C(O)OH, —$C(O)OR^{57}$—, —$NR^{48}R^{57}$, —$OR^{57}$, —$S(O)_2R^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —$NR^{48}R^{58}$, —$OR^{58}$ and —$S(O)_2R^{58}$; and $R^{64}$, $R^{65}$ and $R^{66}$ are independently selected from the group consisting of hydrogen, halogen, lower alkyl, fluoro substituted lower alkyl, lower alkoxy, and fluoro substituted lower alkoxy.

In some embodiments of compounds of Formula IIIc, $A_1$ is —$CH_2$— or —C(O)—; $R^{100}$ is selected from the group consisting of hydrogen, —CN, —C(O)OH, —$C(O)OR^{57}$, —$NR^{46}R^{57}$, —$OR^{57}$, —$S(O)_2R^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —$NR^{48}R^{58}$, —$OR^{58}$ and —$S(O)_2R^{58}$; $Z_{24}$ is $CR^{64}$; $Z_{25}$ is $CR^{65}$; $Z_{26}$ $CR^{66}$; and $R^{64}$, $R^{65}$ and $R^{66}$ are independently selected from the group consisting of hydrogen, halogen, lower alkyl, fluoro substituted lower alkyl, lower alkoxy, and fluoro substituted lower alkoxy.

In some embodiments of any of the above embodiments of compounds of Formula IIIc, two of $Z_{24}$, $Z_{25}$, or $Z_{26}$ are N and the other of $Z_{24}$, $Z_{25}$, or $Z_{26}$ is $CR^{64}$, $CR^{65}$ or $CR^{66}$, one of $Z_{24}$, $Z_{25}$, or $Z_{26}$ is N and the others of $Z_{24}$, $Z_{25}$, or $Z_{26}$ are $CR^{64}$, $CR^{65}$ or $CR^{66}$, preferably $Z_{24}$ is $CR^{64}$, $Z_{25}$ is $CR^{65}$ and $Z_{26}$ is $CR^{66}$.

In some embodiments, compounds have the structure according to the following Formula IV:

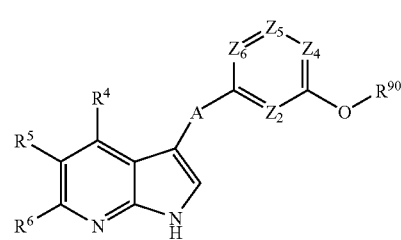

Formula IV all salts, prodrugs, tautomers, and isomers thereof.

wherein:

A, $R^4$, $R^5$, $R^6$, $Z_2$, $Z_4$, $Z_5$, and $Z_6$ are as defined for Formula I; and $R^{90}$ is $C_{2-4}$ alkyl, fluoro substituted $C_{2-4}$ aryl, or —$(CH_2CH_2O)_mR^{91}$;

m is 1, 2, or 3; and $R^{91}$ is $C_{1-3}$ alkyl or fluoro substituted $C_{1-3}$ alkyl, provided, however, the compound is not

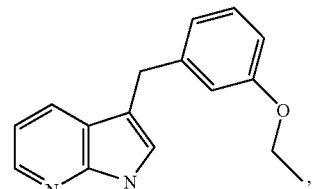

,

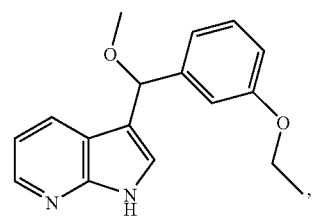

,

,

,

-continued
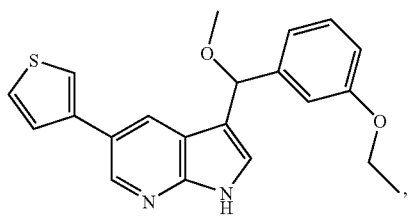
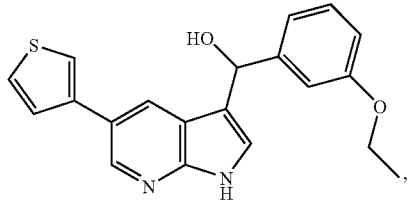
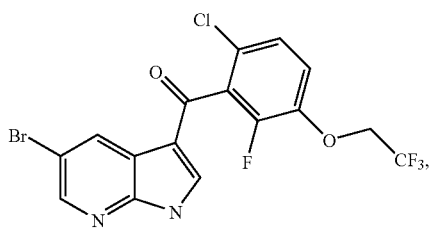
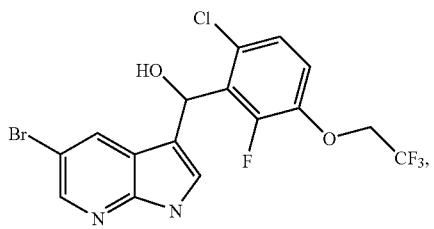
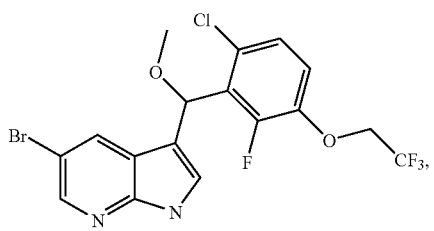
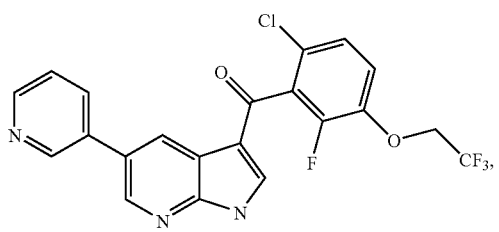
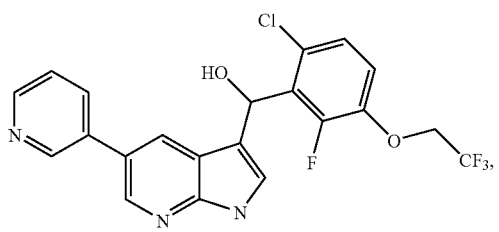
-continued
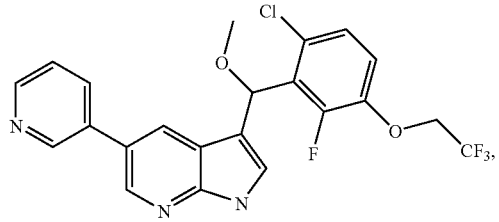
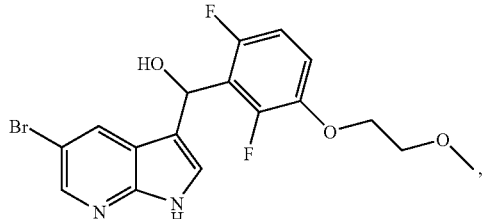
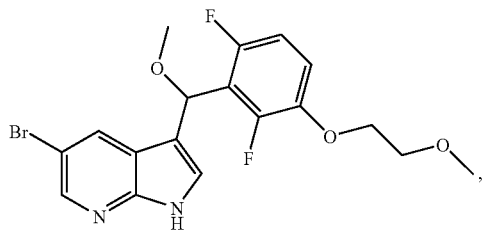
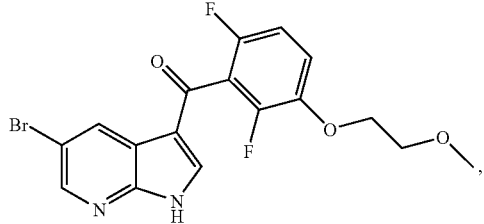
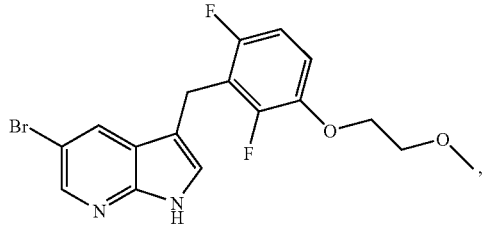
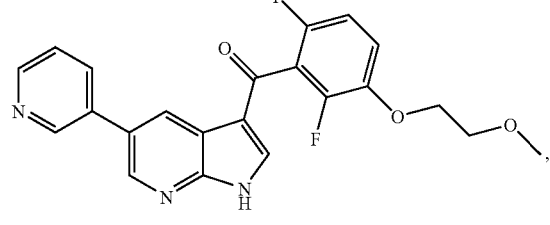
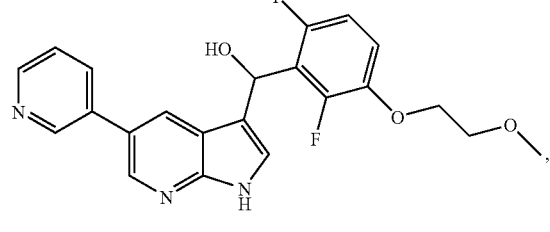

-continued
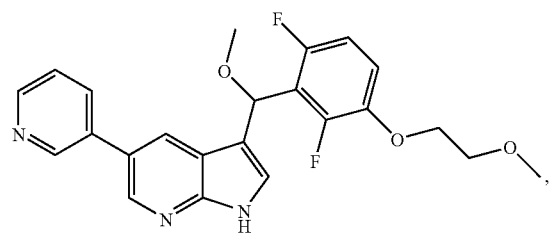
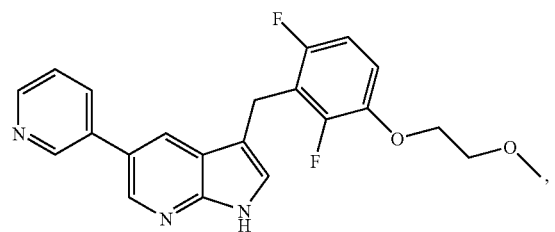
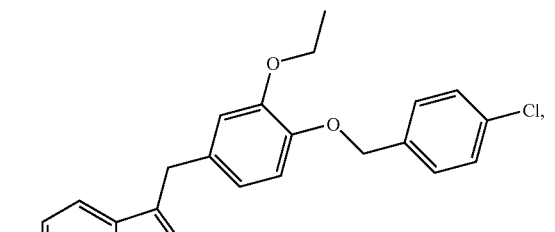
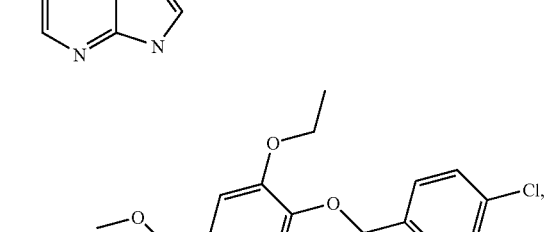
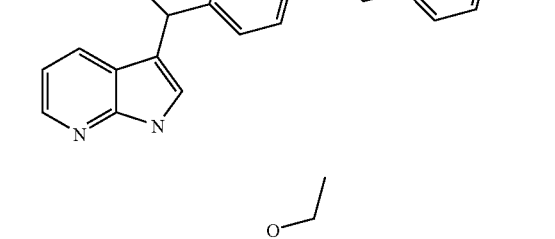
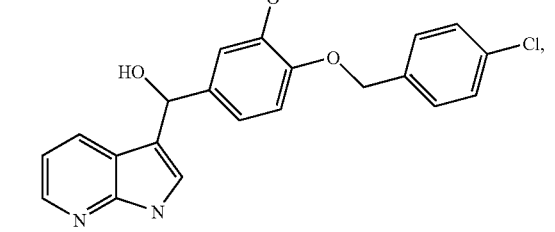
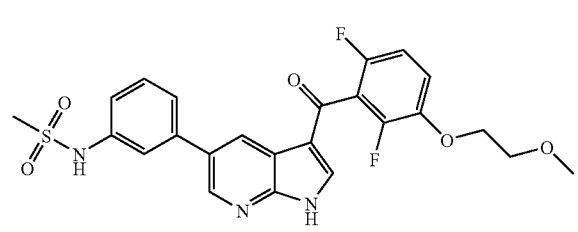
-continued
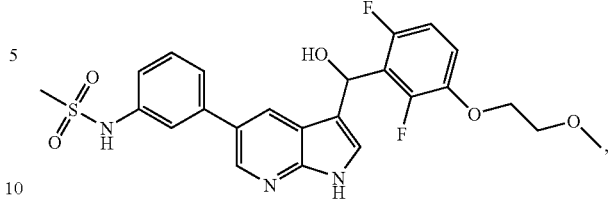
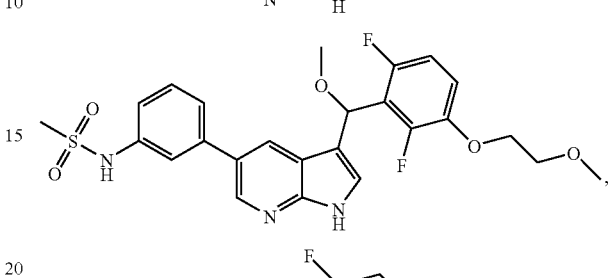
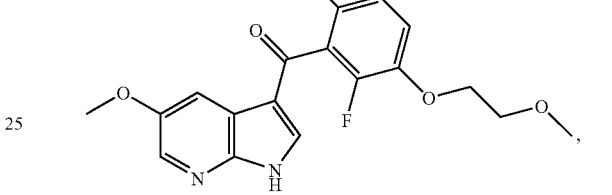
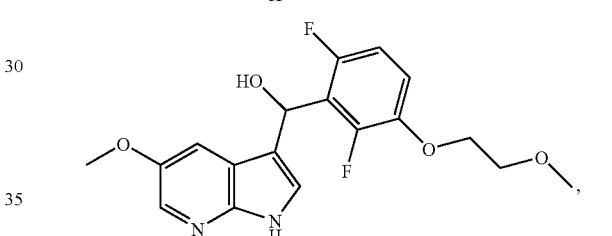
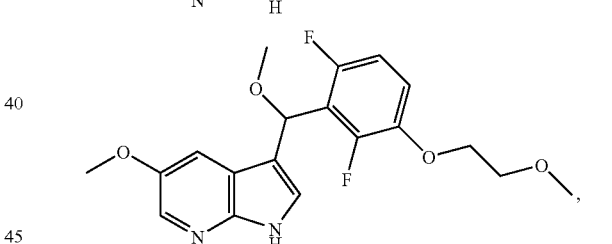
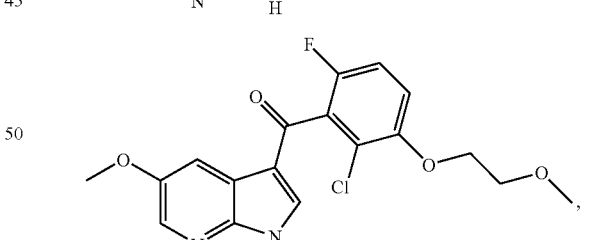
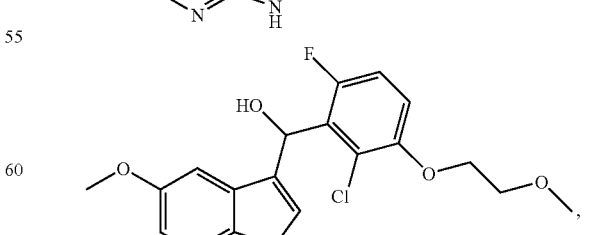

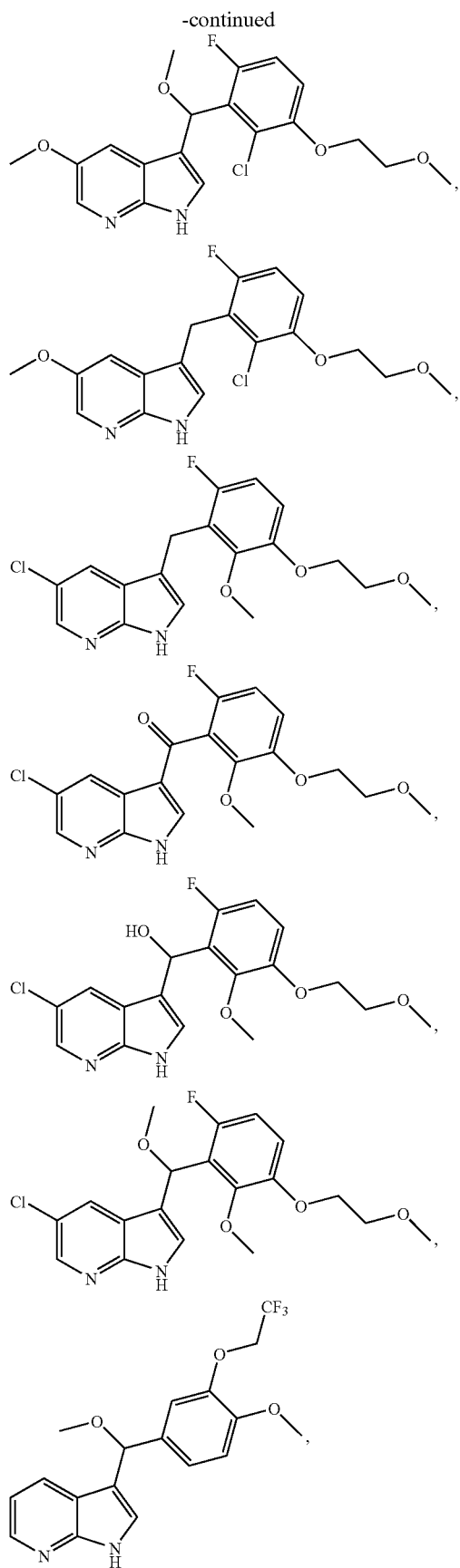

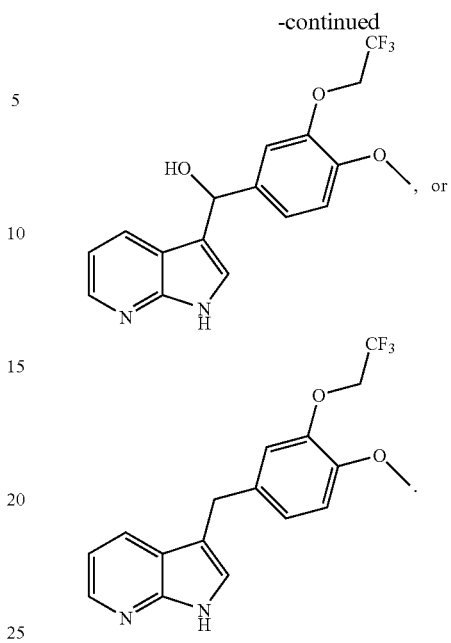

In some embodiments of compounds of Formula IV, $R^4$ and $R^6$ are hydrogen, A is —O—, —$CR^aR^b$—, —$NR^1$—, or —C(O)—, preferably —$CH_2$— or —C(O)—, and $R^{12}$, $R^{14}$, $R^{15}$ and $R^{26}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro $R^a$, $R^b$, and $R^1$ are as defined for Formula I.

In some embodiments of compounds of Formula IV, $R^4$ and $R^6$ are hydrogen, A is —O—, —$CR^aR^b$—, —$NR^1$—, or —C(O)—, preferably —$CH_2$— or —C(O)—, $R^{12}$, $R^{14}$, $R^{15}$ and $R^{16}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro, and $R^5$ is selected from the group consisting of hydrogen, halogen, lower alkyl, lower alkoxy, optionally substituted aryl, optionally substituted heteroaryl, —CN, —C(O)OH, —C(O)$OR^{22}$, —$OR^{22}$, —S(O)$_2R^{22}$, and $NR^{21}R^{22}$, wherein $R^{21}$ is hydrogen or lower alkyl, and $R^{22}$ is hydrogen, lower alkyl, optionally substituted aryl or optionally substituted heteroaryl, and wherein the alkyl chain of $R^5$, $R^{21}$ or $R^{22}$, when lower alkyl, or the alkyl chain of lower alkoxy is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino and cycloalkylamino. $R^a$, $R^b$, and $R^1$ are as defined for Formula I.

In some embodiments of compounds of Formula IV, $R^4$ and $R^6$ are hydrogen, A is —O—, —$CR^aR^b$—, —$NR^1$—, or —C(O)—, preferably —CH$_2$— or —C(O)—, R$^{12}$, R$^{14}$, R$^{15}$ and R$^{16}$ are independently selected from the group consisting of hydrogen, halogen, lower alkyl, fluoro substituted lower alkyl, lower alkoxy, and fluoro substituted lower alkoxy, and R$^5$ is selected from the group consisting of hydrogen, halogen, lower alkyl, lower alkoxy, optionally substituted aryl, optionally substituted heteroaryl, —CN, —C(O)OH, —C(O)OR$^{22}$, —OR$^{22}$, —S(O)$_2$R$^{22}$, and NR$^{21}$R$^{22}$, wherein R$^{21}$ is hydrogen or lower alkyl, and R$^{22}$ is hydrogen, lower alkyl, optionally substituted aryl or optionally substituted heteroaryl, and wherein the alkyl chain of R$^5$, R$^{21}$ or R$^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino. R$^a$, R$^b$, and R$^1$ are as defined for Formula I.

In some embodiments of any of the above embodiments of compounds of Formula IV, two of Z$_2$, Z$_4$, Z$_5$, or Z$_6$ are N and the others of Z$_2$, Z$_4$, Z$_5$, or Z$_6$ are CR$^{12}$, CR$^{14}$, CR$^{15}$ or CR$^{16}$, also one of Z$_2$, Z$_4$, Z$_5$, or Z$_6$ is N and the others of Z$_7$, Z$_4$, Z$_5$, or Z$_6$ are CR$^{12}$, CR$^{14}$, CR$^{15}$ or CR$^{16}$, preferably Z$_2$ is CR$^{12}$, Z$_4$ is CR$^{14}$, Z$_5$ is CR$^{15}$ and Z$_7$ is CR$^{16}$.

In one embodiment of compounds of Formula IV, the compound is selected from the group consisting of:
3-[2-Chloro-6-fluoro-3-(2,2,2-trifluoro-ethoxy)-benzyl]-1H-pyrrolo[2,3-b]pyridine (P-2148),
[2-Chloro-6-fluoro-3-(2,2,2-trifluoro-ethoxy)-phenyl]-(5-methoxy-1H-pyrrolo[2,3-b]pyridin-3-yl)-methanone (P-2149),
[2-Chloro-6-fluoro-3-(2,2,2-trifluoro-ethoxy)-phenyl]-(1H-pyrrolo[2,3-b]pyridin-3-yl)-methanone (P-2150),
[2,6-Dichloro-3-(2,2,2-trifluoro-ethoxy)-phenyl]-[5-(1-methyl-1H-pyrazol-4-yl)-1H-pyrrolo[2,3-b]pyridin-3-yl]-methanone (P-2151),
3-[2,6-Dichloro-3-(2,2,2-trifluoro-ethoxy)-benzyl]-5-methoxy-1H-pyrrolo[2,3-b]pyridine (P-2153),
[2,6-Dichloro-3-(2,2,2-trifluoro-ethoxy)-phenyl]-(5-methoxy-1H-pyrrolo[2,3-b]pyridin-3-yl)-methanone (P-2154),
5-Chloro-3-[2-chloro-6-fluoro-3-(2-methoxy-ethoxy)-benzyl]-1H-pyrrolo[2,3-b]pyridine (P-2157),
3-[2-Chloro-6-fluoro-3-(2-methoxy-ethoxy)-benzyl]-1H-pyrrolo[2,3-b]pyridine (P-2158),
[2-Chloro-6-fluoro-3-(2-methoxy-ethoxy)-phenyl]-(5-chloro-1H-pyrrolo[2,3-b]pyridin-3-yl)-methanone (P-2159),
[2-Chloro-6-fluoro-3-(2-methoxy-ethoxy)-phenyl]-(1H-pyrrolo[2,3-b]pyridin-3-yl)-methanone (P-2160), and all salts, prodrugs, tautomers, and isomers thereof.

In some embodiments, compounds of Formula IV have the structure according to the following sub-generic structure Formula IVa:

Formula IVa

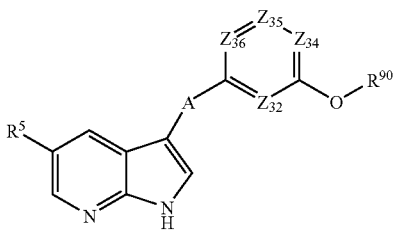

all salts, prodrugs, tautomers, and isomers thereof, wherein:
A and R$^5$ are as defined for Formula I;
R$^{90}$ is as defined for Formula IV;
Z$_{32}$ is N or CR$^{72}$;
Z$_{34}$ is N or CR$^{74}$;
Z$_{35}$ is N or CR$^{75}$;
Z$_{36}$ is N or CR$^{76}$; and
R$^{72}$, R$^{74}$, R$^{75}$, and R$^{76}$ are independently selected from the group consisting of hydrogen, halogen, lower alkyl and lower alkoxy, wherein the alkyl chain of lower alkyl or lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution on the alkyl carbon bound to the —O— of lower alkoxy is fluoro.

In some embodiments of compounds of Formula IVa, A is —O—, —CR$^a$R$^b$—, —NR$^1$—, or —C(O)—, preferably —CH$_2$— or —C(O)—. In some embodiments, A is —O—, —CR$^a$R$^b$—, —NR$^1$—, or —C(O)—, preferably —CH$_2$— or —C(O)—, and R$^{72}$, R$^{74}$, R$^{75}$ and R$^{76}$ are independently selected from the group consisting of hydrogen, halogen, lower alkyl, fluoro substituted lower alkyl, lower alkoxy and fluoro substituted lower alkoxy. R$^a$, R$^b$, and R$^1$ are as defined for Formula I.

In some embodiments of compounds of Formula IVa, A is —O—, —CR$^a$R$^b$—, —NR$^1$—, or —C(O)—, preferably —CH$_2$— or —C(O)—, and R$^5$ is selected from the group consisting of hydrogen, halogen, lower alkyl, lower alkoxy, optionally substituted aryl, optionally substituted heteroaryl, —CN, —C(O)OH, —C(O)OR$^{22}$, —OR$^{22}$, —S(O)$_2$R$^{22}$, and NR$^{21}$R$^{22}$, wherein R$^{21}$ is hydrogen or lower alkyl and R$^{22}$ is hydrogen, lower alkyl, optionally substituted aryl or optionally substituted heteroaryl, and wherein the alkyl chain of R$^5$, R$^{21}$ or R$^{22}$, when lower alkyl or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino. R$^a$, R$^b$, and R$^1$ are as defined for Formula I.

In some embodiments of compounds of Formula IVa, A is —O—, —CR$^a$R$^b$—, —NR$^1$—, or —C(O)—, preferably —CH$_2$— or —C(O)—, R$^{72}$, R$^{74}$, R$^{75}$ and R$^{76}$ are independently selected from the group consisting of hydrogen, halogen, lower alkyl, fluoro substituted lower alkyl, lower alkoxy, and fluoro substituted lower alkoxy, and R$^5$ is selected from the group consisting of hydrogen, halogen, lower alkyl, lower alkoxy, optionally substituted aryl, optionally substituted heteroaryl, —CN, —C(O)O, —C(O)OR$^{22}$, —OR$^{22}$, —S(O)$_2$R$^{22}$, and NR$^{21}$R$^{22}$, wherein R$^{21}$ is hydrogen or lower alkyl, and R$^{22}$ is hydrogen, lower alkyl, optionally substituted aryl or optionally substituted heteroaryl, and wherein the alkyl chain of R$^5$, R$^{21}$ or R$^{22}$, when lower alkyl, or the alkyl chain of lower alkoxy is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino. R$^a$, R$^b$, and R$^1$ are as defined for Formula I.

In some embodiments of any of the above embodiments of compounds of Formula IVa, two of Z$_{32}$, Z$_{34}$, Z$_{35}$, or Z$_{36}$ are N and the others of Z$_{32}$, Z$_{34}$, Z$_{35}$, or Z$_{36}$ are CR$^{72}$, CR$^{74}$, CR$^{75}$ or CR$^{76}$, also one of Z$_{32}$, Z$_{34}$, Z$_{35}$, or Z$_{35}$ is N and the others of $Z_{32}$, $Z_{34}$, $Z_{35}$, or $Z_{36}$ are $CR^{72}$, $CR^{74}$, $CR^{75}$ or $CR^{76}$, preferably $Z_2$ is $CR^{72}$, $Z_4$ is $CR^{74}$, $Z_5$ is $CR^{75}$ and $Z_6$ is $CR^{76}$.

In some embodiments, compounds have the structure according to the following Formula IVb:

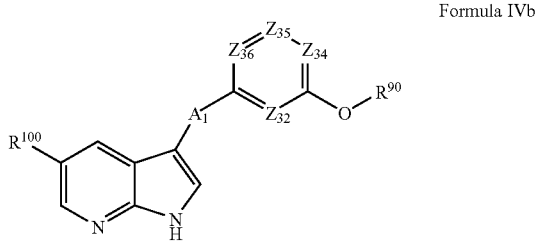

Formula IVb all salts, prodrugs, tautomers, and isomers thereof,
wherein:
$A_1$ is as defined for Formula Ib;
$R^{100}$ is as defined for Formula IIa;
$Z_{32}$, $Z_{34}$, $Z_{35}$, and $Z_{36}$ are as defined for Formula IVa; and
$R^{90}$ is as defined for Formula IV.

In some embodiments of compounds of Formula Ib, $A_1$ is $-CR^{40}R^{41}-$ or $-C(O)-$, preferably $-CH_2-$ or $-C(O)-$. In some embodiments, $A_1$ is $-CR^{40}R^{41}-$ or $-C(O)-$, preferably $-CH_2-$ or $-C(O)-$, and $R^{72}$, $R^{74}$, $R^{75}$ and $R^{76}$ are independently selected from the group consisting of hydrogen, halogen, lower alkyl, fluoro substituted lower alkyl, lower alkoxy, and fluoro substituted lower alkoxy.

In some embodiments of compounds of Formula IVb, $R^{100}$ is selected from the group consisting of hydrogen, $-OH$, $-NH_2$, $-CN$, $-NO_2$, $-C(O)OH$, $-S(O)_2NH_2$, $-C(O)$ $NH_2$, $-OR^{57}$, $-SR^{57}$, $-NR^{48}R^{57}$, $-NR^{48}C(O)R^{57}$, $-NR^{48}S(O)_2R^{57}$, $-S(O)R^{57}$, $-S(O)_2R^{57}$, $-C(O)R^{57}$, $OC(O)OR^{57}$, $-C(O)NR^{48}R^{57}$, $-S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as $R^{100}$ or as substituents of lower alkyl are optionally substituted with one or more substituents selected from the group consisting of $-OH$, $-NH_2$, $-CN$, $-NO_2$, $-S(O)_2NH_2$, $-C(O)NH_2$, $-OR^{58}$, $-SR^{58}$, $-NHR^{58}$, $-NR^{48}R^{58}$, $-NR^{48}C(O)R^{58}$, $-NR^{48}S(O)_2R^{58}$, $-S(O)_2$ $R^{58}$, $-S(O)_2NR^{48}R^{58}$, $-C(O)R^{58}$, $-C(O)NR^{48}R^{58}$, halogen, lower alkyl, fluoro substituted lower alkyl, and cycloalkylamino. In some embodiments, $A_1$ is $-CH_2-$ or $-C(O)-$; $R^{100}$ is selected from the group consisting of hydrogen, $-OH$, $-NH_2$, $-CN$, $-NO_2$, $-C(O)OH$, $-S(O)_2NH_2$, $-C(O)NH_2$, $-OR^{57}$, $-SR^{57}$, $-NR^{48}R^{57}$, $-NR^{48}C(O)R^{57}$, $NR^{48}S(O)_2R^{57}$, $-S(O)R^{57}$, $-S(O)_2R^{57}$, $-C(O)R^{57}$, $-C(O)OR^{57}$, $-C(O)NR^{48}R^{57}$, $-S(O)_2$ $NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as $R^{100}$ or as substituents of lower alkyl are optionally substituted with one or more substituents selected from the group consisting of $-OH$, $-NH_2$, $-CN$, $-NO_2$, $-S(O)_2NH_2$, $-C(O)NH_2$, $-OR^{58}$, $-SR^{58}$, $-NHR^{58}$, $-NR^{48}R^{58}$, $-NR^{48}C(O)R^{58}$, $-NR^{48}S(O)_2R^{58}$, $-S(O)_2R^{58}$, $-S(O)_2NR^{48}R^{58}$, $-C(O)R^{58}$, $-C(O)$ $NR^{48}R^{58}$, halogen, lower alkyl, fluoro substituted lower alkyl, and cycloalkylamino; and $R^{72}$, $R^{74}$, $R^{75}$ and $R^{76}$ are independently selected from the group consisting of hydrogen, halogen, lower alkyl, fluoro substituted lower alkyl, lower alkoxy, and fluoro substituted lower alkoxy.

In some embodiments of compounds of Formula IVb, $R^{100}$ is selected from the group consisting of hydrogen, $-CN$, $-C(O)OH$, $-C(O)OR^{57}$, $-NR^{48}R^{57}$, $-OR^{57}$, $-S(O)_2$ $R^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, $-NR^{48}R^{58}$, $OR^{58}$ and $-S(O)_2R^{58}$.

In some embodiments, $A_1$ is $-CH_2-$ or $-C(O)-$; $R^{100}$ is selected from the group consisting of hydrogen, $-CN$, $-C(O)OH$, $-C(O)OR^{57}$, $-NR^{48}R^{57}$, $-OR^{57}$, $-S(O)_2$ $R^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, $-NR^{48}R^{58}$, $-OR^{58}$ and $-S(O)_2R^{58}$; and $R^{72}$, $R^{74}$, $R^{75}$ and $R^{76}$ are independently selected from the group consisting of hydrogen, halogen, lower alkyl, fluoro substituted lower alkyl, lower alkoxy, and fluoro substituted lower alkoxy.

In some embodiments of compounds of Formula IVb, $A_1$ is $-CH_2-$ or $-C(O)-$; $R^{100}$ is selected from the group consisting of hydrogen, $-OH$, $-NH_2$, $-CN$, $-NO_2$, $-C(O)$ $OH$, $-S(O)_2NH_2$, $-C(O)NH_2$, $-OR^{57}$, $-SR^{57}$, $-NR^{48}R^{57}$, $NR^{48}C(O)R^{57}$, $-NR^{48}S(O)_2R^{57}$, $-S(O)R^{57}$, $-S(O)_2R^{57}$, $-C(O)R^{57}$, $-C(O)OR^{57}$, $-C(O)NR^{48}R^{57}$, $-S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, or heteroaryl as $R^{100}$ or as substituents of lower alkyl are optionally substituted with one or more substituents selected from the group consisting of $-OH$, $-NH_2$, $-CN$, $-NO_2$, $-S(O)_2N_2$—$C(O)NH_2$, $-OR^{58}$, $-SR^{58}$, $-NHR^{58}$, $-NR^{48}R^{58}$, $-NR^{48}C(O)R^{58}$, $-NR^{48}S$ $(O)_2R^{58}$, $-S(O)_2R^{58}$, $-S(O)_2NR^{48}R^{58}$, $-C(O)R^{58}$, $-C(O)NR^{48}R^{58}$, halogen, lower alkyl, fluoro substituted lower alkyl, and cycloalkylamino; $Z_{32}$ is $CR^{72}$; $Z_{34}$ is $CR^{74}$; $Z_{35}$ is $CR^{75}$; $Z_{36}$ is $CR^{76}$; and $R^{72}$, $R^{74}$, $R^{75}$ and $R^{76}$ are independently selected from the group consisting of hydrogen, halogen, lower alkyl, fluoro substituted lower alkyl, lower alkoxy, and fluoro substituted lower alkoxy.

In some embodiments of compounds of Formula IVb, $A_1$ is $-CH_2-$ or $-C(O)-$; $R^{100}$ is selected from the group consisting of hydrogen, $-CN$, $-C(O)OH$, $-C(O)OR^{57}$, $-NR^{45}R^{57}$, $-OR^{57}$, $-S(O)_2R^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, $-NR^{48}R^{58}$, $-OR^{58}$ and $-S(O)_2R^{58}$; $Z_{32}$ is $CR^{72}$; $Z_{34}$ is $CR^{74}$; $Z_{35}$ is $CR^{75}$; $Z_{36}$ is $CR^{76}$; and $R^{72}$, $R^{74}$, $R^{75}$ and $R^{76}$ are independently selected from the group consisting of hydrogen, halogen, lower alkyl fluoro substituted lower alkyl, lower alkoxy, and fluoro substituted lower alkoxy.

In some embodiments of any of the above embodiments of compounds of Formula IVb, two of $Z_{32}$, $Z_{34}$, $Z_{35}$, or $Z_{36}$ are N and the others of $Z_{32}$, $Z_{34}$, $Z_{35}$, or $Z_{35}$ are $CR^{72}$, $CR^{74}$, $CR^{75}$ or $CR^{76}$, also one of $Z_{32}$, $Z_{34}$, $Z_{35}$, or $Z_{36}$ is N and the others of $Z_{32}$, $Z_{34}$, $Z_{35}$, or $Z_{36}$ are $CR^{72}$, $CR^{74}$, $CR^{75}$ or $CR^{76}$, preferably $Z_2$ is $CR^{72}$, $Z_4$ is $CR^{74}$, $Z_5$ is $CR^{75}$ and $Z_6$ is $CR^{76}$.

In some embodiments of the above compounds, compounds are excluded where N (except where N is a heteroaryl ring atom), O, or S is bound to a carbon that is also bound to N (except where N is a heteroaryl ring atom), O, or S except where the carbon forms a double bond with one of the heteroatoms, such as in an amide, carboxylic acid, and the like; or where N (except where N is a heteroaryl ring atom), O, C(S), C(O), or $S(O)_n$ (n is 0-2) is bound to an alkene carbon of an alkenyl group or bound to an alkyne carbon of an alkynyl group; accordingly, in some embodiments compounds which include linkages such as the following are excluded from the compounds provided: —NR—$CH_2$—NR—, —O—$CH_2$—NR—, —S—$CH_2$—NR—, —NR—$CH_2$—O—, —O—CH, —O—, —S—CH, —O—, —NR—$CH_2$—S—, —O—$CH_2$—S—, —S—$CH_2$—S—, —NR—CH=CH—, —CH=CH—NR—, —NR—C≡C—, —C≡C—NR—, —O—CH=CH—, —CH=CH—O—, —O—C≡C—, —C≡O—O—, —$S(O)_{0-2}$—CH=CH—, —CH=CH—S $(O)_{0-2}$—, —$S(O)_{0-2}$—C≡O—, —C≡C—$S(O)_{0-2}$—, —C(O)—CH=CH—, —CH=CH—C(O)—, —C≡C—C (O)—, or —C(O)—C≡C—, —C(S)—CH=CH—, —CH=CH—C(S)—, —C≡C—C(S)—, or —C(S)—C≡C—.

In reference to compounds herein, unless clearly indicated to the contrary, specification of a compound or group of compounds includes pharmaceutically acceptable salts of such compound(s), prodrug(s), and all stereoisomers thereof. In reference to compositions, kits, methods of use, etc. of compounds of Formula I, II, III, or IV described herein, it is understood that a compound of Formula I includes compounds of Formulae Ia-Ii, and all sub-embodiments thereof. Formula II includes compounds of Formulae IIa-Ib, and all sub-embodiments thereof, Formula III includes compounds of Formulae IIIa-IIIc, and all sub-embodiments thereof, Formula IV includes compounds of Formulae IVa-IVb, and all sub-embodiments thereof, unless indicated otherwise.

In one aspect, methods are provided for treating a protein kinase mediated disease or condition in an animal subject, wherein the method involves administering to the subject an effective amount of one or more compounds of Formula II, Formula III, or Formula IV. The terms "treat," "therapy," and like terms refer to the administration of material, e.g., one or more compounds of Formula II, Formula III or Formula IV, in an amount effective to prevent, alleviate, or ameliorate one or more symptoms of a disease or condition, i.e., indication, and/or to prolong the survival of the subject being treated. The term "protein kinase mediated disease or condition" refers to a disease or condition in which the biological function of a protein kinase affects the development, course and/or symptoms of the disease or condition, and or in which modulation of the protein kinase alters the development, course, and/or symptoms of the disease or condition. A protein kinase mediated disease or condition includes a disease or condition for which modulation provides a therapeutic benefit, e.g. wherein treatment with protein kinase inhibitors, including compounds described herein, provides a therapeutic benefit to the subject suffering from or at risk of the disease or condition. In one aspect, the method involves administering to the subject an effective amount of one or more compounds of Formula IT, Formula III or Formula IV in combination with one or more other therapies for the disease or condition.

In one aspect, methods are provided for treating a protein kinase mediated disease or condition in an animal subject, wherein the method involves administering to the subject an effective amount of a compound of any one or more of Formula II, Formula III or Formula IV.

In one aspect, methods are provided for treating a Fms protein kinase mediated disease or condition in an animal subject, wherein the method involves administering to the subject an effective amount of one or more compounds of Formula II, Formula III or Formula IV. The terms "Fms protein kinase mediated disease or condition," "Fms mediated disease or condition," and the like refer to a disease or condition in which the biological function of a Fms protein kinase, including any mutations thereof, affects the development, course and/or symptoms of the disease or condition, and/or in which modulation of Fms alters the development, course, and/or symptoms of the disease or condition. A Fms mediated disease or condition includes a disease or condition for which Fms inhibition provides a therapeutic benefit, e.g. wherein treatment with Fms inhibitors, including compounds described herein, provides a therapeutic benefit to the subject suffering from or at risk of the disease or condition. In one aspect, the method involves administering to the subject an effective amount of one or more compounds of Formula II, Formula III or Formula IV in combination with one or more other therapies for the disease or condition.

In one aspect, methods are provided for treating a Kit protein kinase mediated disease or condition in an animal subject, wherein the method involves administering to the subject an effective amount of one or more compounds of Formula II, Formula III or Formula IV. The terms "Kit mediated disease or condition," "Kit protein kinase mediated disease or condition," and the like refer to a disease or condition in which the biological function of a Kit protein kinase, including any mutation thereof, affects the development, course and/or symptoms of the disease or condition, and/or in which modulation of Kit alters the development, course, and/ or symptoms of the disease or condition. A Kit mediated disease or condition includes a disease or condition for which Kit inhibition provides a therapeutic benefit, e.g. wherein treatment with Kit inhibitors, including compounds described herein, provides a therapeutic benefit to the subject suffering from or at risk of the disease or condition. In one aspect, the method involves administering to the subject an effective amount of one or more compounds of Formula II, Formula III or Formula I in combination with one or more other therapies for the disease or condition.

In one aspect, methods are provided for treating a TrkA protein kinase mediated disease or condition in an animal subject, wherein the method involves administering to the subject an effective amount of one or more compounds of Formula II, Formula III or Formula IV. The terms "TrkA mediated disease or condition," "TrkA protein kinase mediated disease or condition," and the like refer to a disease or condition in which the biological function of a TrkA protein kinase, including any mutation thereof, affects the development, course, and/or symptoms of the disease or condition, and/or in which modulation of TrkA alters the development, course, and/or symptoms of the disease or condition. A TrkA mediated disease or condition includes a disease or condition for which TrkA inhibition provides a therapeutic benefit, e.g. wherein treatment with TrkA inhibitors, including compounds described herein, provides a therapeutic benefit to the subject suffering from or at risk of the disease or condition. In one aspect, the method involves administering to the subject an effective amount of one or more compounds of Formula II, Formula III or Formula IV in combination with one or more other therapies for the disease or condition.

In one aspect, methods are provided for treating a TrkB protein kinase mediated disease or condition in an animal subject, wherein the method involves administering to the subject an effective amount of one or more compounds of Formula II, Formula III or Formula I. The terms "TrkB mediated disease or condition," "TrkB protein kinase mediated disease or condition," and the like refer to a disease or condition in which the biological function of a TrkB protein kinase, including any mutation thereof, affects the development, course and/or symptoms of the disease or condition, and/or in which modulation of TrkB alters the development, course, and or symptoms of the disease or condition. A TrkB mediated disease or condition includes a disease or condition for which TrkB inhibition provides a therapeutic benefit, e.g. wherein treatment with TrkB inhibitors, including compounds described herein, provides a therapeutic benefit to the subject suffering from or at risk of the disease or condition. In one aspect, the method involves administering to the subject an effective amount of one or more compounds of Formula II, Formula III or Formula IV in combination with one or more other therapies for the disease or condition.

In some embodiments, a compound of Formula I, Formula II, Formula III or Formula IV will have an $IC_{50}$ of less than 500 nm, less than 100 nM, less than 50 nM, less than 20 nM, less than 10 nM, less than 5 mM, or less than 1 nM as determined in a generally accepted kinase activity assay. In some embodiments, a compound of any of Formula I, Formula II, Formula III or Formula IV will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutations thereof.

In some embodiments, a compound of Formula I, Formula II, Formula III or Formula IV will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, Akt 1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kit, LCK, MAP2K1, MAP2K2, MAP4K4, MAPKAPK2, Met, Mnk1, MLK1, p38, PDPK1, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70, including any mutations thereof.

In some embodiments, a compound of Formula I, Formula II, Formula III or Formula IV will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, MAP2K1, MAP4K4, MAPKAP kinase 2, Met, p38, PDGFRB, Pim1, PKC theta, Pyk2, Ret, Src, Stk6, TrkA, TrkB, Yes, and Zap70, including any mutations thereof.

In some embodiments, a compound of Formula I, Formula II, Formula III or Formula IV will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, A-Raf, B-Raf, Btk, c-Raf-1, EGFR, EphB2, Erk2, Fak, Fms, Irak4, Jnk1, Jnk2, Jnk3, Kit, MAP2K1, MAP4K4, MAPKAP kinase 2, Met, p38, Pim1, PKC theta, Pyk2, Src, Stk6, TrkA, TrkB, Yes, and Zap70, including any mutations thereof.

In some embodiments, a compound of Formula I, Formula II, Formula III or Formula IV will have an $IC_{50}$ of less than 500 nm, less than 100 nM, less than 50 mM, less than 20 nM, less than 10 nM, less than 5 nM, or less than 1 nM with respect to at least one kinase selected from the group consisting of Fms, Kit, MAP4K4, TrkA, and TrkB, and any mutations thereof. In some embodiments, a compound of any of Formula I, Formula II, Formula III or Formula IV will have an $IC_{50}$ of less than 500 nm, less than 100 nM, less than 50 mM, less than 20 nM, less than 10 nM, less than 5 nM, or less than 1 nM with respect to Fms, MAP4K4, TrkA, and/or TrkB.

In some embodiments, a compound of Formula I, Formula II, Formula III or Formula IV is an inhibitor of a Fms kinase and has an $IC_{50}$ of less than 500 nM, less than 100 nM, less than 50 nM, less than 20 nM, less than 10 nM, less than 5 nM, or less than 1 nM as determined in a generally accepted Fms kinase activity assay. In some embodiments, a compound of Formula I, Formula II, Formula III or Formula IV will selectively inhibit Fms kinase relative to Kit kinase.

In some embodiments, a compound of Formula I, Formula II, Formula III or Formula IV is an inhibitor of a Fms kinase, a MAP4K4 kinase, a TrkA kinase, and/or a TrkB kinase and has an $IC_{50}$ of less than 500 nm, less than 100 nM, less than 50 nM, less than 20 in M, less than 10 nM, less than 5 nM, or less than 1 nM as determined in a generally accepted Fms kinase activity assay, MAP4K4 kinase activity assay, TrkA kinase activity assay, and/or TrkB kinase activity assay. In some embodiments, a compound of Formula I, Formula II, Formula III or Formula IV will selectively inhibit Fms kinase, MAP4K4 kinase, TrkA kinase, and/or TrkB kinase relative to Kit kinase.

In some embodiments, a compound of Formula I, Formula II, Formula III or Formula IV is an inhibitor of a Kit kinase and has an $IC_{50}$ of less than 500 nm, less than 100 nM, less than 50 nM, less than 20 nM, less than 10 nM, less than 5 nM, or less than 1 mM as determined in a generally accepted Kit kinase activity assay.

Further to any of the above embodiments, a compound may selectively inhibit one kinase relative to one or more other kinases, where preferably inhibition is selective with respect to any of the other kinases, whether a kinase discussed herein, or other kinases. In some embodiments, the compound may selectively inhibit the effects of a mutation of the kinase relative to the wild type kinase, for example B-Raf V600E relative to wild type B-Raf. In some embodiments, the compound may selectively inhibit Fms relative to Kit. Selective inhibition of one kinase relative to another is such that the $IC_{50}$ for the one kinase may be at least about 2-fold, also 5-fold, also 10-fold, also 20-fold, also 50-fold, or at least about 100-fold less than the $IC_{50}$ for any of the other kinases as determined in a generally accepted kinase activity assay.

Further to any of the above embodiments, a compound may selectively inhibit one or more kinases relative to one or more other kinases, where preferably inhibition is selective with respect to any of the other kinases, whether a kinase discussed herein, or other kinases. In some embodiments, the compound may selectively inhibit Fms and one or more kinases relative to Kit, such as Fms and/or TrkA relative to Kit. Selective inhibition of one kinase relative to another is such that the $IC_{50}$ for the one kinase may be at least about 2-fold, also 5-fold, also 10-fold, also 20-fold, also 50-fold, or at least about 100-fold less than the $IC_{50}$ for any of the other kinases as determined in a generally accepted kinase activity assay.

In another aspect, compositions are provided that include a therapeutically effective amount of one or more compounds of Formula II, Formula III or Formula IV and at least one pharmaceutically acceptable carrier, excipient, and/or diluent, including combinations of any two or more compounds of Formula II, Formula III or Formula IV. The composition can further include a plurality of different pharmacologically active compounds, which can include one or more compounds of Formula I, Formula II, Formula III or Formula IV. In another aspect, the composition can include one or more compounds of Formula II, Formula III or Formula IV along with one or more compounds that are therapeutically effective for the same disease indication. In one aspect, the composition includes one or more compounds of Formula II, Formula III or Formula IV along with one or more compounds that are therapeutically effective for the same disease indication, wherein the compounds have a synergistic effect on the disease indication.

In another aspect, methods are provided for modulating the activity of a protein kinase selected from the group consisting of Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk1, ROCK1, ROCK2, Ron, Src, Stk6, Syk, TEC, Tie2, TrkA, TrkB, Yes, or Zap70 by contacting the protein kinase with an effective amount of one or more compounds of Formula II, Formula III or Formula IV.

In another aspect, methods are provided for treating a protein kinase mediated disease or condition in an animal subject, wherein the method involves administering to the subject an effective amount of a composition including one or more compounds of Formula II, Formula III or Formula IV.

In one aspect, methods are provided for treating a disease or condition mediated by a protein kinase selected from the group consisting of Ab1, Akt 1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Fyn, Gsk3α, Gsk3β, HCK, Her21Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70 by administering to the subject an effective amount of a composition including one or more compounds of Formula II, Formula III or Formula IV.

In one aspect, the invention provides methods for treating a disease or condition mediated by a protein kinase selected from the group consisting of Ab1, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB2, EphB4, Erk2, Fak, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kit, LCK, MAP2K1, MAP2K2, MAP4K4, MAPKAPK2, Met, Mnk1, MLK1, p38, PDPK1, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70 by administering to the subject an effective amount of a composition including one or more compounds of Formula II, Formula III or Formula IV.

In one aspect, the invention provides methods for treating a disease or condition mediated by a protein kinase selected from the group consisting of Abl, A-Raf, B-Raf, Btk, c-Raf-1, EGFR, EphB2, Erk2, Fak, FGR1, Flt1, Flt3, Flt4, Fms, Irak4, Jnk1, Jnk2, Jnk3, Kdr, Kit, MAP2K1, MAP4K4, MAPKAPK2, Met, p38, PDGFRB, Pim1, PKC theta, Pyk2, Ret, Src, Stk6TrkA, TrkB, Yes, and Zap70 by administering to the subject an effective amount of a composition including one or more compounds of Formula II, Formula III or Formula IV.

In one aspect, the invention provides methods for treating a disease or condition mediated by a protein kinase selected from the group consisting of Abl, A-Raf, B-Raf, Btk, c-Raf-1, EGFR, EphB2, Erk2, Fak, Fms, Irak4, Jnk1, Jnk2, Jnk3, Kit, MAP2K1, MAP4K2, Met, p38, Pim1, PKC theta, Pyk2, Src, Stk6, TrkA, TrkB, Yes, and Zap70 by administering to the subject an effective amount of a composition including one or more compounds of Formula II, Formula III or Formula IV.

In one aspect, the invention provides methods for treating a disease or condition mediated by a protein kinase selected from the group consisting of Fms, Kit, MAP4K4, TrkA, and TrkB, and any mutations thereof, by administering to the subject an effective amount of a composition including one or more compounds of Formula II, Formula III or Formula IV.

In one aspect, the invention provides a method of treating a cancer by administering to the subject an effective amount of a composition including one or more compounds of Formula II, Formula III or Formula IV, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one aspect, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or α particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, and bone marrow and stem cell transplantation.

In one aspect, the invention provides a method of treating a cancer by administering to the subject an effective amount of a composition including one or more compounds of Formula II, Formula III or Formula IV, in combination with one or more suitable chemotherapeutic agents. In one aspect, the one or more suitable chemotherapeutic agents is selected from an alkylating agent, including, but not limited to, adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibiotic, including, but not limited to, bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguaninie, and trimetrexate; an immunotherapy, including, but not limited to, alemtuzumab, bevacizumab, cetuximab, galiximab, gemtuzumab, panitumumab, pertuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, paclitaxel and DHA-paclitaxel; a retinoid, including, but not limited to, alitretinoin, bexarotene, fenretinide, isotretinoin, and tretinoin; an alkaloid, including, but not limited to, etoposide, homoharringtonine, teniposide, vinblastine, vincristine, vindesine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, edotecarin, exatecan, irinotecan (also active metabolite SN-38 (7-ethyl-10-hydroxy-camptothecin)), rubitecan, topotecan, and 9-aminocamptothecin; a kinase inhibitor, including, but not limited to, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to, 3-AP (3-amino-2-carboxyaldehyde thiosemicarbazone), aminoglutethimide, asparaginase, bryostatin-1, cilengitide, E7389, ixabepilone, procarbazine, sulindac, temsirolimus, tipifamib. Preferably, the method of treating a cancer involves administering to the subject an effective amount of a composition of Formula II, Formula III or Formula IV in combination with a chemotherapeutic agent selected from 5-fluorouracil, carboplatin, dacarbazine, gefitinib, oxaliplatin, paclitaxel, SN-38, temozolomide, vinblastine, bevacizumab, cetuximab, or erlotinib.

In another aspect, the invention provides a method of treating or prophylaxis of a disease or condition in a mammal, by administering to the mammal a therapeutically effective amount of one or more compounds of Formula II, Formula III or Formula IV, a prodrug of such compound, or a pharmaceutically acceptable salt of such compound or prodrug. The compound can be alone or can be part of a composition.

In a related aspect, the invention provides kits that include a composition as described herein. In some embodiments, the composition is packaged, e.g., in a vial, bottle, flask, which may be further packaged, e.g., within a box, envelope, or bag; the composition is approved by the U.S. Food and Drug Administration or similar regulatory agency for administration to a mammal, e.g., a human; the composition is approved for administration to a mammal, e.g., a human, for a protein kinase mediated disease or condition; the invention kit includes written instructions for use and/or other indication that the composition is suitable or approved for administration to a mammal, e.g., a human, for a protein kinase-mediated disease or condition; and the composition is packaged in unit dose or single dose form, e.g., single dose pills, capsules, or the like.

In aspects involving treatment or prophylaxis of a disease or condition with the compounds of Formula II, Formula III or Formula IV, the disease or condition is, for example without limitation, neurologic diseases, including, but not limited to, cerebrovascular ischemia, multi-infarct dementia, head injury, spinal cord injury, Alzheimer's disease (AD), Parkinson's disease, amyotrophic lateral sclerosis, dementia, senile chorea, and Huntington's disease; neoplastic diseases and associated complications, including, but not limited to, chemotherapy-induced hypoxia, gastrointestinal stromal tumors (GISTs), prostate tumors, mast cell tumors (including, but not limited to, canine mast cell tumors), acute myeloid leukemia, acute lymphocytic leukemia, chronic myeloid leukemia, chronic lymphocytic leukemia, multiple myeloma, melanoma, mastocytosis, gliomas, glioblastoma, astrocytoma, neuroblastoma, sarcomas (e.g. sarcomas of neuroectodermal origin, leiomyosarcoma), carcinomas (e.g. lung, breast, pancreatic, colon, hepatocellular, renal, female genital tract, squamous cell, carcinoma in situ), lymphoma (e.g. histiocytic lymphoma, non-Hodgkin's lymphoma), MEN2 syndromes, neurofibromatosis (including, but not limited to, Schwann cell neoplasia), myelodysplastic syndrome, leukemia, tumor angiogenesis, cancers of the thyroid, liver, bone, skin, brain, central nervous system, pancreas, lung (e.g. small cell lung cancer, non small cell lung cancer), breast, colon, bladder, prostate, gastrointestinal tract, endometrium, fallopian tube, testes and ovary, and metastasis of tumors to other tissues; pain of neuropathic or inflammatory origin, including, but not limited to, acute pain, chronic pain, bone pain, cancer-related pain and migraine; cardiovascular diseases, including, but not limited to, heart failure, ischemic stroke, cardiac hypertrophy, thrombosis (e.g. thrombotic microangiopathy syndromes), atherosclerosis, reperfusion injury and ischemia (e.g. cerebrovascular ischemia, liver ischemia); inflammation including, but not limited to, age-related macular degeneration, rheumatoid arthritis, allergic rhinitis, inflammatory bowel disease (TED), ulcerative colitis, Crohn's disease, systemic lupus erythematosis, Sjogren's Syndrome, Wegener's granulomatosis, psoriasis, scleroderma, chronic thyroiditis, Grave's disease, myasthenia gravis, multiple sclerosis, osteoarthritis, endometriosis, scarring (e.g. dermal, tissue), vascular restenosis, fibrotic disorders, hypereosinophilia, CNS inflammation, pancreatitis, nephritis, atopic dermatitis, and hepatitis; immunodeficiency diseases, including, but not limited to, severe combined immunodeficiency (SCID), organ transplant rejection, and graft versus host disease; renal or prostatic diseases, including, but not limited to, diabetic nephropathy, polycystic kidney disease, nephrosclerosis, glomerulonephritis, interstitial nephritis, Lupus nephritis, prostate hyperplasia, chronic renal failure, tubular necrosis, diabetes-associated renal complications, and hypertrophy; metabolic diseases, including, but not limited to, type 1 diabetes, type 2 diabetes, metabolic syndrome, obesity, hepatic steatosis, insulin resistance, hyperglycemia, lipolysis and obesity; infection, including, but not limited to, *Helicobacter pylori*, Hepatitis and Influenza viruses, fever, and sepsis; pulmonary diseases, including, but not limited to, chronic obstructive pulmonary disease (COPD), acute respiratory distress syndrome (ARDS), asthma, allergy, bronchitis, emphysema, and pulmonary fibrosis; genetic developmental diseases, including, but not limited to, Noonan's syndrome, Crouzon syndrome, acrocephalo-syndactyl type I, Pfeiffer's syndrome, Jackson-Weiss syndrome, Costello syndrome, (faciocutaneoskeletal syndrome), LEOPARD syndrome, cardio-faciocutaneous syndrome (CFC) and neural crest syndrome abnormalities causing cardiovascular, skeletal, intestinal, skin, hair and endocrine diseases; disorders of bone structure, mineralization and bone reformation and resorption, including, but not limited to, osteoporosis, increased risk of fracture, Paget's disease, hypercalcemia, and metastatis of cancer to bone; Grave's disease; Hirschsprung's disease; lymphoedema; selective T-cell defect (STD); X-linked agammaglobulinemia; diabetic retinopathy; alopecia; erectile dysfunction; tuberous sclerosis, and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophics), motor neuron diseases (including, but not limited to, atyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenital central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

In a further aspect, the invention provides methods for treating a c-fms-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal c-fms activity (e.g. kinase activity). Invention methods involve administering to the subject suffering from or at risk of a c-fms-mediated disease or condition an effective amount of compound of Formula II, Formula III or Formula IV. In one embodiment, the c-fms mediated disease is selected from the group consisting of immune disorders, including, but not limited to, rheumatoid arthritis, systemic lupus erythematosis (SLE), and transplant rejection; inflammatory diseases including, hut not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), prostate cancer, breast cancer, ovarian cancer, melanoma, glioblastoma multiforme, metastasis of tumors to other tissues, and other chronic mycloproliferative diseases such as myelofibrosis. In one embodiment, the c-fms mediated disease is selected from the group consisting of inflammatory bowel syndrome, ulcerative colitis, Crohn's disease, Type I diabetes, Type II diabetes, Paget's disease, diabetic nephropathy, multiple sclerosis, stroke, Alzheimer's disease and Parkinson's disease, inflammatory pain, chronic pain, bone pain, prostate cancer, and metastasis of tumors to tissues other than bone. In one embodiment, the c-fms mediated disease is selected from the group consisting of multiple sclerosis, stroke, Alzheimer's disease, Parkinson's disease, inflammatory pain, chronic pain, and bone pain. In one embodiment, the c-fms mediated disease is selected from the group consisting of multiple sclerosis, stroke, Alzheimer's disease, and Parkinson's disease. In one embodiment, the c-fms mediated disease is selected from the group consisting of inflammatory pain, chronic pain, and bone pain.

In a further aspect, the invention provides methods for treating a c-fms-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal c-fms activity (e.g. kinase activity). Invention methods involve administering to the subject suffering from or at risk of a c-fms-mediated disease or condition an effective amount of compound of Formula I. In one embodiment, the c-fms mediated disease is selected from the group consisting of inflammatory bowel syndrome, ulcerative colitis, Crohn's disease, Type I diabetes, Type II diabetes, Paget's disease, diabetic nephropathy, multiple sclerosis, stroke, Alzheimer's disease and Parkinson's disease, inflammatory pain, chronic pain, bone pain, prostate cancer, and metastasis of tumors to tissues other than bone. In one embodiment, the c-fms mediated disease is selected from the group consisting of multiple sclerosis, stroke, Alzheimer's disease, Parkinson's disease, inflammatory pain, chronic pain, and bone pain. In one embodiment, the c-fms mediated disease is selected from the group consisting of multiple sclerosis, stroke, Alzheimer's disease, and Parkinson's disease. In one embodiment, the c-fms mediated disease is selected from the group consisting of inflammatory pain, chronic pain, and bone pain.

In a related aspect, invention methods involve administering to the subject suffering from or at risk of a c-fms-mediated disease or condition an effective amount of compound of Formula I, Formula II, Formula III or Formula IV, wherein the Fms-mediated disease or condition is selected from the group consisting of inflammatory bowel syndrome, ulcerative colitis, Crohn's disease, Type I diabetes, Type II diabetes, Paget's disease, diabetic nephropathy, multiple sclerosis, stroke, Alzheimer's disease, Parkinson's disease, inflammatory pain, chronic pain, bone pain, prostate cancer, and metastasis of tumors to other tissues.

In a related aspect, invention methods involve administering to the subject suffering from or at risk of a c-fms-mediated disease or condition an effective amount of compound of Formula I, Formula II, Formula III or Formula IV, wherein the Fms-mediated disease or condition is selected from the group consisting of multiple sclerosis, stroke, Alzheimer's disease, Parkinson's disease, inflammatory pain, chronic pain, and bone pain.

In a related aspect, invention methods involve administering to the subject suffering from or at risk of a c-fms-mediated disease or condition an effective amount of compound of Formula I, Formula II, Formula III or Formula IV, wherein the Fms-mediated disease or condition is selected from the group consisting of multiple sclerosis, stroke, Alzheimer's disease, and Parkinson's disease.

In a related aspect, invention methods involve administering to the subject suffering from or at risk of a c-fms-mediated disease or condition an effective amount of compound of Formula I, Formula II, Formula III or Formula IV, wherein the Fms-mediated disease or condition is selected from the group consisting of inflammatory pain, chronic pain, and bone pain.

In a related aspect, compounds of Formula II, Formula III or Formula IV, can be used in the preparation of a medicament for the treatment of a Fms-mediated disease or condition selected from the group consisting of immune disorders, including, but not limited to, rheumatoid arthritis, systemic lupus erythematosis (SLE), and transplant rejection; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), prostate cancer, breast cancer, ovarian cancer, melanoma, glioblastoma multiforme, metastasis of tumors to other tissues, and other chronic myeloproliferative diseases such as myelofibrosis.

In a related aspect, compounds of Formula II, Formula III or Formula IV, can be used in the preparation of a medicament for the treatment of a Fms-mediated disease or condition selected from the group consisting of inflammatory bowel syndrome, ulcerative colitis, Crohn's disease, Type I diabetes, Type II diabetes, Paget's disease, diabetic nephropathy), multiple sclerosis, stroke, Alzheimer's disease, Parkinson's disease, inflammatory pain, chronic pain, bone pain, prostate cancer, and metastasis of tumors to other tissues.

In a related aspect, compounds of Formula II, Formula III or Formula IV, can be used in the preparation of a medicament for the treatment of a Fms-mediated disease or condition selected from the group consisting of multiple sclerosis, stroke, Alzheimer's disease, Parkinson's disease, inflammatory pain, chronic pain, and bone pain.

In a related aspect, compounds of Formula II, Formula III or Formula IV, can be used in the preparation of a medicament for the treatment of a Fins-mediated disease or condition selected from the group consisting of multiple sclerosis, stroke, Alzheimer's disease, and Parkinson's disease.

In a related aspect, compounds of Formula II, Formula III or Formula IV, can be used in the preparation of a medicament for the treatment of a Fms-mediated disease or condition selected from the group consisting of inflammatory pain, chronic pain, and bone pain.

In a related aspect, compounds of Formula II, Formula III or Formula IV, can be used in the preparation of a medicament for the treatment of a Kit-mediated disease or condition selected from the group consisting of malignancies, including, but not limited to, mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including, but not limited to, asthma, rheumatoid arthritis, allergic rhinitis, multiple sclerosis, inflammatory bowel syndrome, transplant rejection, and hypereosiniophilia.

The compounds of Formula I, Formula II, Formula III or Formula IV with kinase activity $IC_{50}$ less than 10 μM as determined in a standard assay described herein can be used to treat protein kinase mediated diseases and conditions related to the following protein kinases, for example without limitation:

Ab1, related to chronic myeloid leukemia (CML), acute lymphoblastic leukemia (ALL) and acute myelogenous leukemia (AML);

Akt1, related to gastric, prostate, colorectal, ovarian, pancreatic and breast cancer, glioblastoma and leukemia, as well as schizophrenia and bipolar disorders, and also use in combination with other chemotherapeutic drugs;

Akt2, related to hyperglycemia due to peripheral insulin resistance and nonsuppressible hepatic glucose production accompanied by inadequate compensatory hyperinsulinemia, also related to pancreatic, ovarian and breast cancer;

Akt3, related to melanoma, prostate and breast cancer;

ALK, related to non-Hodgkin lymphomas such as diffuse large B-cell lymphoma and anaplastic large cell lymphoma;

Alk5, related to pancreatic and biliary cancers, and cutaneous T-cell lymphoma;

A-Raf, related to neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including, but not limited to, acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenital central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf or c-Raf-1, related to neurologic diseases, including, but not limited to, as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, Hepatitis and Influenza viruses, fever, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases, Brk, related to breast and colon cancer, and head and neck squamous cell carcinoma;

Btk, related to X-linked agammaglobulinemia, acute lymphocytic leukemia, autoimmune diseases such as multiple sclerosis, systemic lupus erythematosis, rheumatoid arthritis, and Graves' disease, immune suppression in organ transplant, and drug sensitivity of B-lineage cells;

Cdk2, related to prostate, breast, colorectal and ovarian cancer;

Cdk4, related to glioblastoma (e.g. glioblastoma multiforme), anaplastic astrocytoma, and breast cancer;

Cdk5, related to Alzheimer's disease, amyotrophic lateral sclerosis and Lewy body disease;

Cdk6, related to glioblastoma multiforme, non-Hodgkin's lymphoma, splenic marginal zone lymphoma, 1-cell lymphoblastic lymphoma (T-LBL) and T-cell acute lymphoblastic leukemia (T-ALL);

CHK1, related to DNA damage repair, sensitizes cells to chemotherapeutic agents;

Csk, related to colon and pancreatic carcinomas and autoimmune pathology such as type 1 diabetes, rheumatoid arthritis and systemic lupus erythematosus;

EGFR, related to breast, colorectal, bladder, prostate and non small cell lung cancer, squamous cell carcinomas of the head and neck cancer, oral cavity, and esophagus, and glioblastoma multiforme;

EphA1, related to head and neck squamous cell carcinoma, hepatoma and lung cancer;

EphA2, related to aberrant short-range contact-mediated axonal guidance, bladder, breast, prostate, colon, skin, cervical, ovarian, pancreatic and lung cancers, and metastatic melanoma;

EphB2, related to angiogenesis disorder (e.g. ocular angiogenesis disease such as retinopathy), and cancer (e.g. glioblastoma, breast and liver cancer);

EphB4, related to colorectal cancer (CRC), head and neck squamous cell carcinoma, and tumours of the prostate, breast, endometrium, and bladder;

Erk2, related to aberrant proliferation, differentiation, transcription regulation and development, and may be useful in treating inflammation, for example inflammation associated with Lyme neuroborreliosis, and in treating cancers, such as gastric cancer;

Fak, related to colon and breast tumors, and is also related to esophageal squamous cell carcinoma, melanoma, anaplastic astrocytoma, glioblastoma, ductal carcinoma in situ, prostate and hepatocellular carcinoma, and tumor metastases, and may also provide synergistic effects when used with other chemotherapeutic drugs;

FGFR1, related to 8p11 myeloproliferative syndrome;

FGFR2, related to Crouzon Syndrome, Jackson-Weiss Syndrome, Apert Syndrome, craniosynostosis, Pfeiffer Syndrome, acrocephalo syndactyly type V, and Beare-Stevenson Cutis Gyrata Syndrome;

FGFR3, related to angiogenesis, wound healing, achondroplasia, Muenke craniosynostosis, Crouzon syndrome, acanthosis nigricans, thanatophoric dysplasia, bladder carcinomas, and multiple myeloma;

FGFR4, related to cancer of the breast, lung, colon, medullary thyroid, pancreas, ovary, prostate, endometrium, and fallopian tube, head and neck squamous cell carcinomas and leiomyosarcoma;

Flt1, related to non-small cell lung carcinoma, prostate carcinoma, and colorectal cancer;

Flt3, related to acute myeloid leukemia, myelodysplastic syndrome, acute lymphoblastic leukemia;

Flt4, related to primary lymphoedema;

Fms, related to immune disorders, including, but not limited to, rheumatoid arthritis, systemic lupus erythematosis (SLE), and transplant rejection; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), prostate cancer, breast cancer, ovarian cancer, melanoma, glioblastoma multiforme, metastasis of tumors to other tissues, and other chronic myeloproliferative diseases such as myelofibrosis;

Frk, related to acute myeloid leukemia and type I diabetes;

Fyn, related to Alzheimer's disease, schizophrenia and prevention of metastases, e.g. in melanoma and squamous cell carcinoma;

GSK3 (Gsk3α and/or Gsk3β), related to CNS disorders such as Alzheimer's disease, Parkinson's disease, amyotrophic lateral sclerosis, diabetes type IT, bipolar disorders, stroke, cancer, chronic inflammatory disease, leucopenia, schizophrenia, chronic pain, neuropathic pain, and traumatic head injury;

HCK, related to chronic myelogenous leukemia and acute lymphocytic leukemia;

Her2/Erbb2, related to prostate and breast cancer;

Her4/Erbb4, related to childhood medulloblastoma;

IGF1R, related to prostate cancer, hepatocellular carcinoma;

IKK beta, related to leukemia of T-cells, necrosis, insulin resistance, and malignant neoplasms;

Irak4, related to bacterial infections, immunodeficiency syndrome, Crohn's disease, ulcerative colitis, asthma, chronic bronchitis, cardio hypertrophy, and kidney hypertension;

Itk, related to allergic asthma;

Jak1, related to Hepatitis C virus infection;

Jak2, related to myeloproliferative disorders such as polyeythaemia vera, myelofibrosis, essential thrombocythemia, myeloid metaplasia and leukemias, including, but not limited to, acute lymphoblastic leukemia, chronic neutrophilic leukemia, juvenile myelomonocytic leukemia, CMML, Philadelphia chromosome-negative CML, megakaryocytic leukemia, and acute erythroid leukemia;

Jak3, related to X-linked severe combined immunodeficiency, myeloproliferative disorders, transplant rejection and autoimmune diseases such as rheumatoid arthritis, inflammatory bowel syndrome, Crohn's disease, systemic lupus erythematosis, ulcerative colitis, psoriasis and multiple sclerosis;

Jnk (Jnk1, Jnk2, Jnk3), related to metabolic diseases including, but not limited to, type 1 diabetes, type 2 diabetes, metabolic syndrome, obesity, and hepatic steatosis; cardiovascular diseases such as atherosclerosis, ischemia (e.g. cerebrovascular ischemia, liver ischemia), reperfusion injury, cardiac hype trophy; renal diseases such as chronic renal failure; neoplastic diseases and associated complications, including, but not limited to, chemotherapy-induced hypoxia, prostate tumors, myeloid leukemia and cancers of the liver, bone, skin, brain, pancreas, lung breast, colon, prostate and ovary; transplant rejection; pain of neuropathic or inflammatory origin including, but not limited to, acute and chronic pain; inflammatory and autoimmune diseases including, but not limited to, age-related macular degeneration, rheumatoid arthritis, inflammatory bowel disease, ulcerative colitis, Crohn's disease, systemic lupus erythematosis, Sjogren's Syndrome, psoriasis, scleroderma, chronic thyroiditis, Grave's disease, myasthenia gravis, and multiple sclerosis, and inflammation in other organs including, but not limited to, CNS inflammation, pancreatitis, nephritis, atopic dermatitis, and hepatitis; airway inflammatory diseases such as asthma, allergy, bronchitis, pulmonary fibrosis, chronic obstructive pulmonary disease; neurologic diseases such as stroke, cerebrovascular ischemia, neurodegenerative diseases such as Parkinson's disease, Alzheimer's disease, amyotrophic lateral sclerosis, dementia, senile chorea, head and spinal cord trauma, and Huntington's disease. More particularly, Jnk1 is related to type I diabetes, type 2 diabetes, metabolic syndrome, obesity and hepatic steatosis, Jnk is related to atherosclerosis, and Jnk3 is related to inflammatory diseases including, but not limited to, autoimmune diseases such as rheumatoid arthritis, inflammatory bowel syndrome, Crohn's disease, systemic lupus erythematosis, Sjogren's Syndrome, psoriasis and multiple sclerosis, airway inflammatory diseases such as asthma, allergy, pulmonary fibrosis, and chronic obstructive pulmonary disease, and inflammation in other organs, such as CNS inflammation, pancreatitis, nephritis, and hepatitis; neurologic diseases such as stroke, cerebrovascular ischemia, and neurodegenerative diseases such as Parkinson's disease, Alzheimer's disease, and Huntington's disease; and neoplastic diseases such as prostate tumors and myeloid leukemia;

Kdr, related to anti-angiogenesis for treating solid tumor growth (e.g. ovarian, lung, breast, pancreatic, prostate, colon, gastrointestinal stromal tumor, non small cell lung cancer, and epidermoid cancer), metastasis, psoriasis, rheumatoid arthritis, diabetic retinopathy and age related macular degeneration;

Kit, related to malignancies, including, but not limited to, mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including, but not limited to, asthma, rheumatoid arthritis, allergic rhinitis, multiple sclerosis, inflammatory bowel syndrome, transplant rejection, and hypereosinophilia;

LCK, related to acute lymphoblastic leukemia, T-cell lymphoma, lymphopenia, renal carcinoma, colon carcinoma, severe combined immunodeficiency, multiple sclerosis, inflammatory bowel and type I diabetes;

MAP2K1, related to acute myeloid leukemia, breast, ovarian and liver cancer;

MAP2K2, related to cancer and inflammation;

MAP4K4, related to metabolic indications, including, but not limited to, re-sensitizing fat and muscle cells to insulin, ameliorating the pathology in adipocytes, ameliorating the pathology in muscle cells, metabolic syndrome, and type II diabetes; a broad range of oncology indications, including, but not limited to, blocking the migration, invasion and metastasis in many different tumor types; and T-cell mediated autoimmune diseases;

MAPKAPK2, cancer (e.g. prostate, breast), stroke, meningitis, and inflammatory disorders;

Met, related to kidney, breast, bladder, non-small-cell lung, colorectal, and bladder cancers, and hepatocellular carcinoma;

Mnk1, related to conditions associated with heat shock, nutrient deprivation, oxidative or osmotic stress, and infection of mammalian cells (e.g. with viruses such as adenovirus (Ad) or influenza virus), and autoimmune diseases;

MLK1, related to neurodegenerative diseases such as Alzheimer's disease and Parkinson's disease, and inflammatory disorders;

p38, related to acute coronary syndrome, stroke, atherosclerosis, and inflammatory autoimmune diseases such as rheumatoid arthritis, inflammatory bowel disease, and Crohn's disease;

PDGFR (PDGFRA, PDGFRB), related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis. More particularly, PDGFRA related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis, and PDGFRB related to idiopathic hypereosinophilic syndrome, chronic eosinophilic leukemia, juvenile myelomonocytic leukemia, and metastatic medulloblastoma;

PDPK1, related to cancer and diabetes;

Pim1, related to cancers such as hematopoietic (e.g. acute myeloid and acute lymphoid leukemias) and prostate cancers, and non-Hodgkin's lymphomas;

Pim2, related to lymphomas;

Pim3, related to hepatocellular carcinoma;

PKC alpha, related to pituitary tumors and prefrontal cortical dysfunction such as distractibility, impaired judgment, impulsivity, and thought disorder, also may be used to sensitize chemotherapy in breast, colon, and non small cell lung cancers;

PKC beta, related to diabetic retinopathy;

PKC-theta, related to insulin resistance, T-cell lymphoma;

Plk1, related to cancers (e.g. lymphoma of the thyroid, non-Hodgkin's lymphomas, colorectal cancers, leukemias and melanoma), also useful as sensitizer in chemotherapy;

Pyk2, related to inflammation (e.g. osteoporosis, polycystic kidney disease, rheumatoid arthritis and inflammatory bowel disease), CNS disease (e.g. Parkinson's disease and Alzheimer's disease), stroke and cancers (e.g. gliomas, breast cancer, and pancreatic cancer);

Ret, related to cancer of the thyroid, neuroblastoma, familial medullary thyroid carcinoma (FMTC), multiple endocrine neoplasia type IA and IIB (MEN2A, MEN2B), and neurodegenerative disorders (e.g. Hirschsprung's disease, Parkinson's disease, Alzheimer's disease, and amyotrophic lateral sclerosis);

ROCK (ROCK-1, ROCK-2), related to cancers (e.g. ovarian cancer, hepatocellular carcinoma, pancreatic cancer), ocular disease (e.g. glaucoma), cardiac hypertrophy, improved renal perfusion, transplant rejection, and acute respiratory distress syndrome;

Ron, related to cancer and inflammation;

Src, related to cancer and osteoporosis;

Stk6, related to gastric, bladder, breast, lung, CNS, ovarian, kidney, colon, prostate, pancreas, and cervical cancers, melanoma, leukemia, and neuroblastoma;

Syk, related to lymphomas (e.g. mantle cell lymphoma);

TEC, related to sepsis, septic shock, inflammation, rheumatoid arthritis, Crohn's disease, irritable bowel disease (IBD), and ulcerative colitis;

Tie2 (TEK), related to cancer, arthritis (e.g. rheumatoid arthritis), and atherosclerosis;

TrkA, related to pain (e.g. chronic pain, neuropathic pain), cancer (e.g. prostate cancer, lung cancer, pancreatic cancer), allergic disorders (e.g. asthma), arthritis, diabetic retinopathy, macular degeneration and psoriasis;

TrkB, related to obesity, hyperphagia, developmental delays, cancer (e.g. prostate cancer, lung cancer, Wilms tumors, neuroblastoma, pancreatic cancer), various neuropathies (e.g. stroke, multiple sclerosis, transverse myelitis, and encephalitis), and diabetes.

Yes, related to various cancers including, but not limited to, esophageal squamous cell carcinoma; and Zap70, related to AIDS, systemic lupus erythematosus, myasthenia gravis, atherosclerosis, rejection of transplanted organs or tissues, allograft rejection including, but not limited to, acute and chronic allograft rejection, graft versus host disease, rheumatoid arthritis, psoriasis, systemic sclerosis, atopic dermatitis, eczematous dermatitis, alopecia, and inflammation of the nasal mucus membrane, including all forms of rhinitis.

Additional aspects and embodiments will be apparent from the following Detailed Description and from the claims.

DETAILED DESCRIPTION OF THE PREFERRED EMBODIMENTS

As used herein the following definitions apply unless clearly indicated otherwise:

"Halogen" refer to all halogens, that is, chloro (Cl), fluoro (F), bromo (Br), or iodo (I).

"Hydroxyl" or "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched alkyl group is attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. A "substituted lower alkyl" denotes lower alkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)N$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^e$, —R$^f$, and —R$^g$. Furthermore, possible substitutions include subsets of these substitutions, such as are indicated herein, for example, in the description of compounds of Formula I, Formula II, Formula III or Formula IV, attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety. "C$_{2-6}$ alkyl" denotes lower alkyl containing 2-6 carbon atoms. A "substituted C$_{2-6}$ alkyl" denotes optionally substituted lower alkyl containing 2-6 carbon atoms, A "substituted methyl" denotes methyl that is independently substituted, unless indicated otherwise, with 1, 2, or 3 substituents, wherein the substituents are selected as per optionally substituted lower alkyl.

"C$_{1-3}$ alkylene" refers to a divalent alkane-derived radical containing 1-3 carbon atoms, straight chain or branched, from which two hydrogen atoms are taken from the same carbon atom or from different carbon atoms. C$_{1-3}$ alkylene includes methylene —CH$_2$—, ethylene —CH$_2$CH$_2$—, propylene —CH$_2$CH$_2$CH$_2$—, and isopropylene —CH(CH$_3$)CH$_2$— or —CH$_2$CH(CH$_3$)—. C$_{1-3}$ alkylene substituted with one or more substituents indicates C$_{1-3}$ alkylene that is independently substituted, with one or more, preferably 1, 2, 3, 4 or 5, also 1, 2, or 3 substituents as indicated, attached at any available atom to produce a stable compound.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. Examples of lower alkenyl groups include ethenyl, propenyl, isopropenyl, butenyl, and the like. A "substituted lower alkenyl" denotes lower alkenyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)R$^o$, —C(O)NR$^o$, —C(S)NR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^d$, —R$^f$, and —R$^g$. Further, possible substitutions include subsets of these substitutions, such as are indicated herein, for example, in the description of compounds of Formula I, Formula II, Formula III or Formula IV, attached at any available atom to produce a stable compound. For example "fluoro substituted lower alkenyl" denotes a lower alkenyl group substituted with one or more fluoro atoms, where preferably the lower alkenyl is substituted with 1, 2, 3, 4 or 5 fluoro atoms, also 1, 2, or 3 fluoro atoms. While it is understood that substitutions are attached at any available atom to produce a stable compound, substitution of alkenyl groups are such that —F, —C(O)—, —C(S)—, —C(NH)—, —S(O)—, —S(O)$_2$—, —O—, —S—, or N (except where N is a heteroaryl ring atom), are not bound to an alkene carbon thereof. Further, where alkenyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or N thereof (except where N is a heteroaryl ring atom) are not bound to an alkene carbon of the alkenyl substituent or R group. Further, where alkenyl is a substituent of another moiety or an R group of a moiety such as —OR, —NHR, —C(O)NHR, and the like, substitution of the alkenyl R group is such that substitution of the alkenyl carbon bound to any O, S, or N of the moiety (except where N is a heteroaryl ring atom) excludes substituents that would result in any O, S, or N of the substituent (except where N is a heteroaryl ring atom) being bound to the alkenyl carbon bound to any O, S, or N of the moiety. An "alkenyl carbon" refers to any carbon within an alkenyl group, whether saturated or part of the carbon to carbon double bond. An "alkene carbon" refers to a carbon within an alkenyl group that is part of a carbon to carbon double bond.

"Lower alkynyl" alone or in combination means a straight or branched hydrocarbon containing 2-6 carbon atoms (unless specifically defined) containing at least one, preferably one, carbon to carbon triple bond. Examples of alkynyl groups include ethynyl, propynyl, butynyl, and the like. A "substituted lower alkynyl" denotes lower alkynyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR°C(O)NHR°, —NR°C(S)NHR°, —NC(O)NR°R°, —NHC(S)NR°R°, —NR°C(O)NR°R°, —NR°C(S)NR°R°, —NHS(O)$_2$NHR°, —NR°S(O)$_2$NH$_2$, —NR°S(O)$_2$NHR°, —NHS(O)$_2$NR°R°, —NR°S(O)$_2$NR°R°, —NHR°, —NR°R°, —R$^d$, —R$^e$, and —R$^g$. Further, possible substitutions include subsets of these substitutions, such as are indicated herein, for example, in the description of compounds of Formula I, Formula II, Formula III or Formula IV, attached at any available atom to produce a stable compound. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. While it is understood that substitutions are attached at any available atom to produce a stable compound, substitution of alkynyl groups are such that —F, —C(O)—, —C(S)—, —C(NH)—, —S(O)—, —S(O)$_2$—, —O—, —S—, or N (except where N is a heteroaryl ring atom) are not bound to an alkyne carbon thereof. Further, where alkynyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or N thereof (except where N is a heteroaryl ring atom) are not bound to an alkyne carbon of the alkynyl substituent or R group. Further, where alkynyl is a substituent of another moiety or an R group of a moiety such as —OR, —NHR, —C(O)NHR, and the like, substitution of the alkynyl R group is such that substitution of the alkynyl carbon bound to any O, S, or N of the moiety (except where N is a heteroaryl ring atom) excludes substituents that would result in any O, S, or N of the substituent (except where N is a heteroaryl ring atom) being bound to the alkynyl carbon bound to any O, S, or N of the moiety. An "alkynyl carbon" refers to any carbon within an alkynyl group, whether saturated or part of the carbon to carbon triple bond. An "alkyne carbon" refers to a carbon within an alkynyl group that is part of a carbon to carbon triple bond.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like. A "substituted cycloalkyl" is a cycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR°, —SR°, —OC(O)R°, —OC(S)R°, —C(O)R°, —C(S)R°, —C(O)OR°, —C(S)OR°, —S(O)R°, —S(O)$_2$R°, —C(O)NHR°, —C(S)NHR°, —C(O)NR°R°, —C(S)NR°R°, —S(O)$_2$NHR°, —S(O)$_2$NR°R°, —C(NH)NHR°, —C(NH)NR$^p$R$^c$, —NHC(O)R°, —NHC(S)R°, —NR°C(O)R°, —NR°C(S)R°, —NHS(O)$_2$R°, —NR°S(O)$_2$R°, —NHC(O)NHR°, —NHC(S)NHR°, —NR°C(O)NH$_2$, —NR°C(S)NH$_2$, —NR°C(O)NHR°, —NR°C(S)NHR°, —NHC(O)NR°R°, —NHC(S)NR°R°, —NR°C(O)NR°R°, —NR°C(S)NR°R°, —NHS(O)$_2$NHR°, —NR°S(O)$_2$NH$_2$, —NR°S(O)$_2$NHR°, —NHS(O)$_2$NR°R°, —NR°S(O)$_2$NR°R°, —NHR°, —NR°R°, —R$^d$, R$^e$, —R$^f$ and —R$^g$.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. A "substituted heterocycloalkyl" is a heterocycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR°, —SR°, —OC(O)R°, —OC(S)R°, —C(O)R°, —C(S)R°, —C(O)OR°, —C(S)OR°, —S(O)R°, —S(O)$_2$R°, —C(O)NHR°, —C(S)NHR°, —C(O)NR°R°, —C(S)NR°R°, —S(O)$_2$NHR°, —S(O)$_2$NR°R°, —C(NH)NHR°, —C(NH)NR$^p$R$^c$, —NHC(O)R°, —NHC(S)R°, —NR°C(O)R°, —NR°C(S)R°, —NHS(O)$_2$R°, —NR°S(O)$_2$R°, —NHC(O)NHR°, —NHC(S)NHR°, —NR°C(O)NH$_2$, —NR°C(S)NH$_2$, —NR°C(O)NHR°, —NR°C(S)NHR°, —NHC(O)NR°R°, —NHC(S)NR°R°, —NR°C(O)NR°R°, —NR°C(S)NR°R°, —NHS(O)$_2$NHR°, —NR°S(O)$_2$NH$_2$, —NR°S(O)$_2$NHR°, —NHS(O)$_2$NR°R°, —NR°S(O)$_2$NR°R°, —NHR°, —NR°R°, —R$^d$, —R$^e$, —R$^f$, and —R$^g$.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. "Arylene" is a divalent aryl. A "substituted aryl" is an aryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR°, —SR°, —OC(O)R°, —OC(S)R°, —C(O)R°, —C(S)R°, —C(O)OR°, —C(S)OR°, —S(O)R°, —S(O)$_2$R°, —C(O)NHR°, —C(S)NHR°, —C(O)NR°R°, —C(S)NR°R°, —S(O)$_2$NHR°, —S(O)$_2$NR°R°, —C(NH)NHR°, —C(NH)NR$^p$R$^c$, —NHC(O)R°, —NHC(S)R°, —NR°C(O)R°, —NR°C(S)R°, —NHS(O)$_2$R°, —NR°S(O)$_2$R°, —NHC(O)NHR°, —NHC(S)NHR°, —NR°C(O)NH$_2$, —NR°C(S)NH$_2$, —NR°C(O)NHR°, —NR°C(S)NHR°, —NHC(O)NR°R°, —NHC(S)NR°R°, —NR°C(O)NR°R°, —NR°C(S)NR°R°, —NHS(O)$_2$NHR°, —NR°S(O)$_2$NH$_2$, —NR°S(O)$_2$NHR°, —NHS(O)$_2$NR°R°, —NR°S(O)$_2$NR°R°, —NHR°, —NR°R°, —R$^d$, —R$^e$, —R$^f$, and —R$^g$. A "substituted arylene" is a divalent substituted aryl.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Nitrogen containing heteroaryl" refers to heteroaryl wherein any heteroatoms are N. "Heteroarylene" is a divalent heteroaryl. A "substituted heteroaryl" is a heteroaryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NH(C(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^d$, —R$^e$, —R$^f$, and —R$^g$. "Substituted heteroarylene" is a divalent substituted heteroaryl.

The variables R$^o$, R$^p$, R$^c$, R$^d$, R$^e$, R$^f$ and R$^g$ as used in the description of optional substituents for alkyl, alkenyl, alkynyl, cycloalkyl, heterocycloalkyl, aryl and heteroaryl are defined as follows:

each R$^o$, R$^p$, and R$^c$ are independently selected from the group consisting of R$^d$, R$^e$, R$^f$, and R$^g$, or R$^p$ and R$^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, —OR$^u$, —SR$^u$, —NHR$^u$, —NR$^u$R$^u$, —R$^x$, and —R$^y$;

each R$^d$ is independently lower alkyl, wherein lower alkyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$R$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^i$, and —R$^j$;

each R$^e$ is independently lower alkenyl, wherein lower alkenyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(N)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, S(O)$_2$R$^k$, —C(O)NHR$^k$, C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;

each R$^f$ is independently lower alkynyl, wherein lower alkynyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;

each R$^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, R$^h$, —R$^i$, and —R$^j$;

wherein R$^k$, R$^m$, and R$^n$ at each occurrence are independently selected from the group consisting of R$^h$, R$^i$, and R$^j$, or R$^m$ and R$^n$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each R$^h$ is independently lower alkyl optionally substituted with one or more, preferably 1, 2, 3, 4 or 5, also 1, 2, or 3 substituents selected from the group consisting of fluoro, —OH, —NH$_2$, —NO$_2$, —CN, —C(O)OH, —C(S)OH, C(O)NH$_2$, —C(S)NH$_2$, —S(O)$_2$NH$_2$, —NHC(O)NH$_2$, —HC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$R$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, —NR$^r$R$^r$, —R$^i$, and —R$^j$;

wherein each R$^i$ is independently selected from the group consisting of lower alkenyl and lower alkynyl, wherein lower alkenyl or lower alkynyl are optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NHR$^r$, —NHR$^r$, —NR$^r$R$^r$, and —R$^j$;

wherein each R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(N—H)NH$_2$, —OR$^r$, —SR$^r$, —OC(O)R$^r$, —OC(s)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, —NR$^r$R$^r$, cycloalkylamino, and —R$^x$;

wherein each R$^r$, R$^s$, and R$^t$ at each occurrence are independently selected from the group consisting of lower alkyl, C$_{3-6}$ alkenyl, C$_{3-6}$ alkynyl, cycloalkyl, heterocycloalkyl, aryl and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the lower alkyl carbon bound to any O, S, or N, of —OR$^r$, —SR$^r$, —C(O)OR$^r$, —C(S)OR$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —NR$^r$C(O)R$^r$, —NR$^r$C(S)R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, or —NR$^r$R$^r$ is selected from the group consisting of fluoro and —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided, however, that any substitution of the C$_{3-6}$ alkenyl or C$_{3-6}$ alkynyl carbon bound to any O, S, or N, of —OR$^r$, —SR$^r$, —C(O)OR$^r$, —C(S)OR$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —NR$^r$C(O)R$^r$, —NR$^r$C(S)R$^r$, —NR$^r$S(O)$_2$R$^r$, —NHC(O)NHR$^r$, —NHC(S)NHR$^r$, —NR$^r$C(O)NR$^r$R$^r$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^o$C(S)NR$^r$R$^r$, —NHS(O)$_2$NHR$^r$, —NR$^r$S(O)$_2$NH$_{12}$, —NR$^r$S(O)$_2$NHR$^r$, —NHS(O)$_2$NR$^r$R$^r$, —NR$^r$S(O)$_2$NR$^r$R$^r$, —NHR$^r$, or —NR$^r$R$^r$ is selected from the group consisting of fluoro, lower alkyl, fluoro substituted lower alkyl, and —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or R$^s$ and R$^t$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO, —CN, —OH, —NH$_2$, OR$^u$, —SR$^u$, —NHR$^u$, —NR$^u$R$^u$, —R$^x$, and —R$^y$;

wherein each R$^u$ is independently selected from the group consisting of lower alkyl, C$_{3-6}$ alkenyl, C$_{3-6}$ alkynyl, cycloalkyl, heterocycloalkyl, aryl, and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the lower alkyl carbon bound to the O of —OR$^u$, S of —SR$^u$, or N of —NHR$^u$ is fluoro or —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided, however, that any substitution of the $C_{3-6}$ alkenyl or $C_{3-6}$ alkynyl carbon bound to the O of —$OR^u$, S of —$SR^u$, or N of —$NHR^u$ is fluoro, lower alkyl, fluoro substituted lower alkyl, or —$R^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —$NH_2$, —$NO_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each $R^x$ is selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of —$R^y$, fluoro, —OH, —$NH_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, preferably 1, 2, 3, 4 or 5, also 1, 2, or 3 substituents selected from the group consisting of —$R^y$, fluoro, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each $R^y$ is selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —$NH_2$, —$NO_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted $C_{2-6}$ alkyl, optionally substituted lower alkenyl, or optionally substituted lower alkynyl are optionally substituted with one or more, also 1, 2 or 3 groups or substituents selected from the group consisting of fluoro, —$NO_2$, —CN, —$OR^{1a}$, —$SR^{1a}$, —$NR^{1a}R^{1a}$, —$OC(O)R^{1a}$, —$OC(S)R^{1a}$, —$C(O)R^{1a}$, —$C(S)R^{1a}$, —$C(O)OR^{1a}$, —$C(S)OR^{1a}$, —$C(O)NR^{1a}R^{1a}$, —$C(S)NR^{1a}R^{1a}$, —$S(O)_2NR^{1a}R^{1a}$, —$C(NH)NR^{1a}R^{1a}$, —$NR^{1a}C(O)R^{1a}$, —$NR^{1a}C(S)R^{1a}$, —$NR^{1a}S(O)_2R^{1a}$, —$NR^{1a}C(O)NR^{1a}R^{1a}$, —$NR^{1a}C(S)NR^{1a}R^{1a}$, —$NR^{1a}S(O)_2NR^{1a}R^{1a}$, —$S(O)R^{1a}$, —$S(O)_2R^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —$NO_2$, —CN, —$OR^{1a}$, —$SR^{1a}$, —$NR^{1a}R^{1a}$, —$OC(O)R^{1a}$, —$OC(S)R^{1a}$, —$C(O)R^{1a}$, —$C(S)R^{1a}$, —$C(O)OR^{1a}$, —$C(S)OR^{1a}$, —$C(O)NR^{1a}R^{1a}$, —$C(S)NR^{1a}R^{1a}$, —$S(O)_2NR^{1a}R^{1a}$, —$C(NH)NR^{1a}R^{1a}$, —$NR^{1a}C(O)R^{1a}$, —$NR^{1a}C(S)R^{1a}$, —$NR^{1a}S(O)_2R^{1a}$, —$NR^{1a}C(O)NR^{1a}R^{1a}$, —$NR^{1a}C(S)NR^{1a}R^{1a}$, —$NR^{1a}S(O)_2NR^{1a}R^{1a}$, —$S(O)R^{1a}$, —$S(O)_2R^{1a}$, —$R^{1b}$, and lower alkyl optionally substituted with one or more, also 1, 2 or 3 groups or substituents selected from the group consisting of fluoro, —CH, —$NH_2$, lower alkoxy, fluoro substituted lower alkoxy, lower alkylthio, fluoro substituted lower alkylthio, mono-alkylamino, di-alkylamino, and —$R^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 groups or substituents selected from the group consisting of halogen, —$NO_2$, —CN, —$OR^{1a}$, —$SR^{1a}$, —$NR^{1a}R^{1a}$, —$OC(O)R^{1a}$, —$OC(S)R^a$, —$C(O)R^{1a}$, —$C(S)R^{1a}$, —$C(O)OR^{1a}$, —$C(S)OR^{1a}$, —$C(O)NR^{1a}R^{1a}$, —$C(S)NR^{1a}R^{1a}$, —$S(O)_2NR^{1a}R^{1a}$, —$C(NH)NR^{1a}R^{1a}$, —$NR^{1a}C(O)R^{1a}$, —$NR^{1a}C(S)R^{1a}$, —$NR^{1a}S(O)_2R^{1a}$, —$NR^{1a}C(O)NR^{1a}R^{1a}$, —$NR^{1a}C(S)NR^{1a}R^{1a}$, —$NR^{13}S(O)_2NR^{1a}R^{1a}$, —$S(O)R^{1a}$, —$S(O)_2R^{1a}$, —$R^{1b}$, and lower alkyl optionally substituted with one or more, also 1, 2 or 3 groups or substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino, and —$R^{1b}$, wherein $R^{1a}$ is selected from the group consisting of hydrogen, provided, however, that hydrogen is not bound to any of C(S), C(O), S(O), or $S(O)_2$ of —$OC(O)R^{1a}$, —$OC(S)R^{1a}$, —$C(O)R^{1a}$, —$C(S)R^{1a}$, —$NR^{1a}C(O)R^{1a}$, —$NR^{1a}C(S)R^{1a}$, —$NR^{1a}S(O)_2R^{1a}$, —$S(O)R^{1a}$, or —$S(O)_2R^{1a}$, —$R^{1b}$, and lower alkyl optionally substituted with one or more, also 1, 2 or 3 groups or substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino, and —$R^{1b}$, provided, however, that any substitution of the alkyl carbon bound to O, S, or N of —$OR^{1a}$, —$SR^{1a}$, —$NR^{1a}R^{1a}$, —$C(O)OR^{1a}$, —$C(S)OR^{1a}$, —$C(O)NR^{1a}R^{1a}$, —$C(S)NR^{1a}R^{1a}$, $S(O)_2NR^{1a}R^{1a}$, —$C(NH)NR^{1a}R^{1a}$, —$NR^{1a}C(O)R^{1a}$, —$NR^{1a}C(S)R^{1a}$, —$NR^{1a}S(O)_2R^{1a}$, —$NR^{1a}C(O)NR^{1a}R^{1a}$, —$NR^{1a}C(S)NR^{1a}R^{1a}$, or —$NR^{1a}S(O)_2NR^{1a}R^{1a}$, is fluoro or —$R^{1b}$ and wherein —$R^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —$NH_2$, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted $C_{2-6}$ alkyl, optionally substituted lower alkenyl, or optionally substituted lower alkynyl are optionally substituted with one or more, also 1, 2 or 3 groups or substituents selected from the group consisting of fluoro, —CN, —$OR^{1a}$, —$SR^{1a}$, —$NR^{1a}R^{1a}$, —$C(O)R^{1a}$, —$C(S)R^{1a}$, —$C(O)OR^{1a}$, —$C(O)NR^{1a}R^{1a}$, —$C(S)NR^{1a}R^{1a}$, —$S(O)_2NR^{1a}R^{1a}$, —$NR^{1a}(O)R^{1a}$, —$NR^{1a}C(S)R^{1a}$, —$NR^{1a}S(O)_2R^{1a}$, —$S(O)R^{1a}$, —$S(O)_2R^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —$OR^{1a}$, —$SR^{1a}$, —$NR^{1a}R^{1a}$, —$C(O)R^{1a}$, —$C(S)R^{1a}$, —$C(O)OR^{1a}$, —$C(O)NR^{1a}R^{1a}$, —$C(S)NR^{1a}R^{1a}$, —$S(O)_2NR^{1a}R^{1a}$, —$NR^{1a}C(O)R^{1a}$, —$NR^{1a}C(S)R^{1a}$, —$NR^{1a}S(O)_2R^{1a}$, —$S(O)R^{1a}$, —$S(O)_2R^{1a}$, —$R^{1b}$, and lower alkyl optionally substituted with one or more, also 1, 2 or 3 groups or substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino, and —$R^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 groups or substituents selected from the group consisting of halogen, —CN, —OR$^{1a}$, —SR$^{1a}$, —NR$^{1a}$R$^{1a}$, —C(O)R$^{1d}$, —C(S)R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, wherein R$^{1a}$ is selected from the group consisting of hydrogen, provided, however, that hydrogen is not bound to any of C(S), C(O), S(O), or S(O)$_2$ of —C(O)R$^{1a}$, —C(S)R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, or —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, provided, however, that any substitution of the alkyl carbon bound to O, S, or N of —OR$^{1a}$, —SR$^{1a}$, —NR$^{1a}$R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, or —NR$^{1a}$S(O)$_2$R$^{1a}$, is fluoro or —R$^{1b}$, and wherein —R$^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

"Lower alkoxy" denotes the group —OR$^z$, where R$^z$ is lower alkyl. "Substituted lower alkoxy" denotes lower alkoxy in which R$^z$ is lower alkyl substituted with one or more substituents as indicated herein, for example, in the description of compounds of Formula I, Formula II, Formula III or Formula IV, including descriptions of substituted cycloalkyl, cycloheteroalkyl, aryl and heteroaryl, attached at any available atom to produce a stable compound. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Lower alkylthio" denotes the group —SR$^{aa}$, where R$^{aa}$ is lower alkyl. "Substituted lower alkylthio" denotes lower alkylthio in which R$^{aa}$ is lower alkyl substituted with one or more substituents as indicated herein, for example, in the description of compounds of Formula I, Formula II, Formula III or Formula IV, including descriptions of substituted cycloalkyl, cycloheteroalkyl, aryl and heteroaryl, attached at any available atom to produce a stable compound. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. While it is understood that substitutions on alkylthio are attached at any available atom to produce a stable compound, substitution of alkylthio is such that O, S, or N (except where N is a heteroaryl ring atom), are not bound to the alkyl carbon bound to the alkylthio S. Further, where alkylthio is described as a substituent of another moiety, the alkylthio sulfur is not bound to a carbon atom that is bound to an O, S, or N of the other moiety (except where N is a heteroaryl ring atom), or to an alkene or alkyne carbon of the other moiety.

"Amino" or "amine" denotes the group —NH$_2$. "Mono-alkylamino" denotes the group —NHR$^{bb}$ where R$^{bb}$ is lower alkyl. "Di-alkylamino" denotes the group —NR$^{bb}$R$^{cc}$, where R$^{bb}$ and R$^{cc}$ are independently lower alkyl. "Cycloalkylamino" denotes the group —NR$^{dd}$R$^{ee}$, where R$^{dd}$ and R$^{ee}$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. While it is understood that when mono-alkylamino, di-alkylamino, or cycloalkylamino are substituents on other moieties that are attached at any available atom to produce a stable compound, the nitrogen of mono-alkylamino, di-alkylamino, or cycloalkylamino as substituents is not bound to a carbon atom that is bound to an O, S, or N of the other moiety.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

As used herein, the terms "ligand" and "modulator" are used equivalently to refer to a compound that changes (i.e., increases or decreases) the activity of a target biomolecule, e.g., an enzyme such as a kinase. Generally a ligand or modulator will be a small molecule, where "small molecule refers to a compound with a molecular weight of 1500 daltons or less, or preferably 1000 daltons or less, 800 daltons or less, or 600 daltons or less. Thus, an "improved ligand" is one that possesses better pharmacological and/or pharmacokinetic properties than a reference compound, where "better" can be defined by one skilled in the relevant art for a particular biological system or therapeutic use.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

As used herein in connection with compounds of the invention, the term "synthesizing" and like terms means chemical synthesis from one or more precursor materials.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

The present invention concerns compounds of Formula I, and all sub-generic formulae, compounds of Formula II and all sub-generic formulae, compounds of Formula III and all sub-generic formulae, and compounds of Formula IV and all sub-generic formulae that are modulators of protein kinases, for example without limitation, the compounds are modulators of at least one of the kinases selected from the group consisting of Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, and the use of such compounds in the treatment of diseases or conditions, II. Kinase Targets and Indications of the Invention Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Description of specific target protein kinases contemplated by the present invention may be found, for example, in U.S. patent application Ser. No. 11/473,347 (PCT publication WO2007002433), the disclosure of which is hereby incorporated by reference in its entirety, in addition to the following:

Exemplary Diseases Associated with Raf Kinases.

A-Raf: Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including, but not limited to, acute pain, chronic pain, cancer-related pain and migraine, and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenital central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf: Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS->Raf->MEK->ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAS inhibitors, and this can be envisioned as a transition in codon 529 from ACC to ATC.

Niihori et al., report that in 43 individuals with cardio-facio-cutaneous (CFC) syndrome, they identified two heterozygous KISS mutations in three individuals and eight BRAF mutations in 16 individuals, suggesting that dysregulation of the RAS-RAF-ERK pathway is a common molecular basis for the three related disorders (Niihori et al., Nat. Genet. 2006, 38(3):294-6).

c-Raf-1: Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including, but not limited to, colorectal, ovarian, lung and renal cell carcinoma. C-Raf-1 is also implicated as an important mediator of tumor angiogenesis (Hood, J. D. et al., 2002, Science 296, 2404). C-Raf-1 inhibitors may also be useful for the treatment of acute myeloid leukemia and myelodysplastic syndromes (Crump, Curr Pharm Des 2002, 8(25):2243-8). Raf-1 activators may be useful as treatment for neuroendocrine tumors, such as medullary thyroid cancer, carcinoid, small cell lung cancer and pheochromocytoma (Kunnimalaiyaan et al., Anti-cancer Drugs 2006, 17(2):139-42).

B-Raf and/or C-Raf inhibitors may be useful in treating A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases, including, but not limited to, heart failure, ischemic stroke, cardiac hypertrophy, thrombosis (e.g. thrombotic microangiopathy syndromes), atherosclerosis, and reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, Hepatitis and Influenza viruses, fever, and sepsis; pulmonary diseases, including, but not limited to, chronic obstructive pulmonary disease (COPD) and acute respiratory distress syndrome (ARDS); genetic developmental diseases, including, but not limited to, Noonan's syndrome, Costello syndrome, (facio-cutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases.

Exemplary Diseases Associated with c-Kit.

The compounds described herein are useful for treating disorders related to c-kit e.g., diseases related to unregulated kinase signal transduction, including, but not limited to, cell proliferative disorders, fibrotic disorders and metabolic disorders, among others. As described in more detail below and in Lipson et al., U.S. 20040002534 (U.S. application 101600, 868, filed Jun. 23, 2003) which is incorporated herein by reference in its entirety, cell proliferative disorders which can be treated by the present invention include cancers, and mast cell proliferative disorders.

The presence of c-kit has also been associated with a number of different types of cancers. In addition, the association between abnormalities in c-kit and disease are not restricted to cancer. As such, c-kit has been associated with malignancies, including, but not limited to, mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including, but not limited to, asthma, rheumatoid arthritis, allergic rhinitis, multiple sclerosis, inflammatory bowel syndrome, transplant rejection, and hypereosinophilia.

Exemplary Diseases Associated with c-fms

The presence of c-fms has been associated with a number of different types of diseases. As such, c-fms has been associated with immune disorders, including, but not limited to, rheumatoid arthritis, systemic lupus erythematosis (SLE), and transplant rejection; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), prostate cancer, breast cancer, ovarian cancer, melanoma, glioblastoma multiforme, metastasis of tumors to other tissues, and other chronic myeloproliferative diseases such as myelofibrosis.

Exemplary Diseases Associated with TrkA and TrkB

TrkA: Target kinase TrkA (i.e., neurotrophic tyrosine kinase, receptor, type 1) is a 140 kDa tyrosine kinase encoded by chromosome 1q21-q22 (symbol: NTRK1). TrkA inhibitors may be useful in treating pain (e.g. chronic pain, neuropathic pain), cancer (e.g. prostate cancer, lung cancer, myeloid leukemia, pancreatic cancer), allergic disorders (e.g. asthma), arthritis, diabetic retinopathy, macular degeneration and psoriasis.

TrkA is a plasma member receptor composed of an extracellular domain (responsible for high affinity binding to nerve growth factor, NGF), a transmembrane segment and an intracellular protein tyrosine kinase domain (responsible to transmit the NGF signal to initiate and coordinate neuronal responses). NGF binding induces TrkA clustering on the membrane and activates the kinase. The kinase initiates a cascade of protein phosphorylation events through multiple pathways including SHC/Ras/MAPK, PI3K and PLCg1. A TrkA kinase inhibitor would not prevent NGF/TrkA binding, but could prevent down-stream signal transduction.

Nerve Growth Factor (NGF) is produced by a number of tissues and inflammatory cells during tissue injury and host immune response. It initiates and maintains hypersensitivity to incoming stimulus (hyperalgesia) and the perception of non-noxious stimuli (allodynia). Through its high-affinity receptor TrkA, NGF increases the excitation state of sensory neurons leading to the central nervous system (peripheral sensitization), and increases transmitter release from the dorsal spinal cord (central sensitization). In clinical trials, a single NGF subcutaneous injection generated local hyperalgesia persisting up to 7 weeks. At doses above 0.1 microgram/kg, NGF caused muscle pain that varied from mild to moderate, primarily in the bulbar and truncal musculature. Intravenous NGF produced earlier and more pronounced systemic effects (Petty et al, 1994, Ann Neurol. 36: 244-6). Conversely, TrkA kinase inhibitors could be used to treat diseases of enhanced states of nociception.

In Complete Freund's Adjuvant (CFA)-induced hind-paw inflammation, spinal nerve ligation and streptozoticin-induced neuropathic pain models, a single intraperitoneal injection of anti-NOF reversed established tactile allodynia from day 3 to day 7 following treatment. In the mouse CCI model, anti-NGF reversed tactile allodynia when administered 2 weeks after surgery Repeated administration of this antibody to CCI mice for 3 weeks produced a sustained reversal of tactile allodynia (Wild et al. 2007, J. Pharmacol. Exp. Ther. 322:282-287).

Prostate tumors that have metastasized to bone frequently induce bone pain which can be difficult to fully control as it seems to be driven simultaneously by inflammatory, neuropathic, and tumorigenic mechanisms. Anti-NGF produced a significant reduction in both early and late stage bone cancer pain-related behaviors. This therapy did not influence tumor-induced bone remodeling, osteoblast proliferation, osteoclastogenesis, tumor growth, or markers of sensory or sympathetic innervation in the skin or bone. All nerve fibers that innervate the bone express TrkA and p75, and these are the receptors through which NGF sensitizes and/or activates nociceptors (Halvorson et al, 2005, Cancer Res. 65:9426-35).

In patients with mild asthma due to exposure to cat allergen, NGF expression was strongly induced in epithelial cells, fibroblasts, blood vessels, and a few infiltrating cells. TrkA mRNA and protein levels in bronchial biopsies were increased significantly after allergen exposure in infiltrating mast cells before the onset of symptoms (Kassel et al, 2001, Clin Exp Allergy 31:1432-40).

The late phase reaction in asthma following allergen provocation is dominated by an influx of activated eosinophils into the bronchial lumen, which correlates with the release of eosinophilic products into the airways to increase disease severity. The viability and activation of eosinophils from patients with mild asthma were significantly enhanced after NGF stimulation. Addition of neutralizing anti-NGF antibodies ex vivo abrogated the effects (Nassentein et al, 2003, J Exp Med 198:455-467). TrkA kinase inhibitors could decrease this paracrine loop between the respiratory tract and infiltrating mast cells as well as endobronchial eosinophils, and thus be useful for the treatment of asthma and other allergic disorders.

TrkB: Target kinase TrkB (i.e., neurotrophic tyrosine kinase, receptor, type 2) is a 145 kDa tyrosine kinase encoded by chromosome 9q22.1 (symbol: NTRK2). TrkB inhibitors may be useful in treating various cancers and their metastases (e.g. prostate cancer, lung cancer, Wilms tumors, neuroblastoma, and pancreatic cancer), and various neuropathies (e.g. stroke, multiple sclerosis, transverse myelitis, and encephalitis).

In clinical trials with recombinant BDNF, paresthesia was developed at the site of subcutaneous injection (Coulie et al, 2000, Gastroenterology 119:41-50). Intrathecal infusion of BDNF in humans also induced paresthesia and warmth as side effects (Ochs et al, 2000, Amyotroph Lateral Seler Other Motor Neuron Disord. 1:201-6). Chronic paresthesia is often a symptom of an underlying neurological disease or traumatic nerve damage. Paresthesia can be caused by disorders affecting the central nervous system, such as stroke and transient ischemic attacks (mini-strokes), multiple sclerosis, transverse myelitis, and encephalitis. Since BDNF binds to TrkB specifically with high affinity these neuropath effects are mediated though TrkB signaling. Thus Trkb kinase inhibitors could be used to treat certain patients with neuropathy.

BDNF is known to act at the synapses between primary sensory and spinal dorsal horn neurons to affect pain transmission during inflammation. The primary afferent is the only source of BDNF in the spinal cord, and it is up-regulated in the dorsal root ganglion (DRG) by peripheral NGF a few days after inflammation, and is transported and released into the superficial dorsal horn in an activity-dependent manner. TrkB expression in the dorsal horn also increases for a few days after inflammation. These findings suggest that BDNF may act during the restricted period in the early phase of inflammation. Through TrkB, BDNF activates two distinct channels: (1) transient receptor potential canonicals (TRPC3), which produces a slow response by opening of a non-selective cation channel; and (2) Na+ channel, which mediates a rapid depolarization in the hippocampus. These channels have been strongly associated with inflammatory pain. Anti-BDNF significantly increased the withdrawal threshold in CFA-treated rats, a model of inflammatory pain. Since the swelling at the site of CFA injection was not affected by antiserum, the residual component might be due to peripheral sensitization (Matayoshi et al, 2005, J. Physiol. 569:685-95).

In patients with neuroblastomas, co-expression of TrkB and BDNF, co-expression of TrkB with N-Myc amplification, and expression of truncated TrkB are found to be associated with poorer clinical outcome (Nakagawara et al, 1994, Mol Cell Biol. 14:759-767). Co-expression of TrkB with its ligand BDNF could generate a positive feedback loop through autocrine and paracrine loops. Also TrkB truncations found in these tumors generate activated forms of the intracellular protein tyrosine kinase. The constitutively active TrkB signals through multiple pathways to promote cancer initiation, progression and metastasis. These truncated TrkB kinases were also found in hepatocellular carcinoma (Yang et al, 2005, Cancer. Res 65:219-225). Thus TrkB inhibitors could be used to treat a sub-population of cancer patients with an activated TrkB pathway.

In patients with pancreatic cancer, TrkB expression is correlated with perineural invasion, positive retroperitoneal margin, and shorter latency to development of liver metastasis (Sclabas et al, 2005, Clin. Cancer. Res V11:440-449). Mechanistically, TrkB activates the PI3K pathway to suppress anoikis (apoptosis resulting from loss of cell-matrix interactions) which is one of the physiological barriers to metastasis. TrkB kinase inhibition could break down resistance to anoikis of metastasizing tumors (Douma et al, 2004, Nature 430: 1034-9). Therefore, TrkB inhibitors could have utility in a broad range of tumor types.

Exemplary Diseases Associated with MAPK4K

MAP4K4: Target kinase MAP4K4 (i.e., Mitogen-activated protein kinase kinase 4, aka Hematopoietic progenitor kinase/Germinal center kinase-like Kinase) is a 130 kDa serine/threonine kinase encoded by chromosome 2q11.2-q12 (symbol: MAP4K4) and is also known as HGK. It is a member of the human STE20/mitogen-activated protein kinase kinase kinase kinase (MAP4K) family of serine/threonine kinases and is the human ortholog of mouse NIK (Nck-interacting kinase). The N-terminus of the mature HGK protein has a catalytic kinase domain that shares 47% and 48% amino acid sequence identity to the catalytic domain of Hematopoietic progenitor kinase 1 (HPK1) and Germinal center kinase (GCK), respectively. Yao et al. (J. Biol. Chem. 274: 2118-2125, 1999) identified 2 HGK isoforms, one of which has no proline-rich domains, and another, longer variant that contains such domains and appears to be expressed in brain only. Northern blot analysis revealed expression of 3 HGK transcripts of approximately 4.6, 6.5, and 8.5 kb in hear, brain, skeletal muscle, pancreas, placenta, liver, lung, and kidney. By Western blot analysis with a polyclonal antibody, Yao et al., J. Biol. Chem. 274: 2118-2125, 1999) found that the 130-kD protein is expressed in multiple cell lines.

Expression of HGK in transfected cell lines resulted in strong JNK activation and, in turn, c-jun transcriptional activity (Yao et al. J. Biol. Chem. 274: 2118-2125, 1999). HGK-induced JNK activation was inhibited by dominant-negative MAP2K4, MAP2K7, and TAK1 mutants. TNF-alpha also stimulated HGK kinase activity. HGK was identified as a putative effect of Rap2 to activate JNK (Machida et al. J. Biol. Chem. 279: 15711-15714, 2004). This link establishes HGK as a potential target for a range of metabolic indications, since the JNK pathway clearly antagonizes insulin signaling. An HGK inhibitor could re-sensitize fat and muscle cells to insulin.

HGK is found to be broadly expressed in human tumor cells and can modulate cellular transformation, invasion, and adhesion (Wright et al. Mol. Cell. Biol. 23: 2068-2082, 2003). Wright et al showed HGK to be highly expressed in most tumor cell lines relative to normal tissue. An active role for this kinase in transformation was suggested by an inhibition of H-Ras(V12)-induced focus formation by expression of inactive, dominant-negative mutants of HGK in both fibroblast and epithelial cell lines. Expression of an inactive mutant of HGK also inhibited the anchorage-independent growth of cells yet had no effect on proliferation in monolayer culture. Expression of HGK mutants modulated integrin receptor expression and had a striking effect on hepatocyte growth factor-stimulated epithelial cell invasion. Together, these results suggest an important role for HGK in cell transformation and invasiveness. More recently, a small interfering RNA screen for modulators of tumor cell motility identifies MAP4K4 as a promigratory kinase (Collins et al. Proc. Natl. Acad. Sci. USA, 103: 3775-3780, 2006). Collins et al. showed that the knockdown of the HGK transcript inhibited the migration of multiple carcinoma cell lines, indicating a broad role in cell motility, and potently suppressed the invasion of SKOV-3 cells in vitro. The effect of HGK on cellular migration was found to be mediated through JNK kinase, independent of AP1 activation and downstream transcription. Accordingly, small molecule inhibition of c-Jun N-terminal kinase suppressed SKOV-3 cell migration, underscoring the potential therapeutic utility of mitogen-activated protein kinase pathway inhibition in cancer progression (Collins et al. Proc. Natl. Acad. Sci. USA, 103: 3775-3780, 2006). These studies strongly support HGK as a target in a broad range of oncology indications. In particular, an HGK inhibitor could have utility in blocking the migration, invasion and metastasis in many different tumor types.

Activation of T-cells by antigens initiates a complex series of signal-transduction events that are critical for immune responses. Mack et al. (Immunol. Lett. 96, 129-145, 2005) developed a genetic screen to survey the functional roles of kinases in antigen mediated T-cell activation and identified 19 protein kinases that were previously implicated in T-cell signaling processes and 12 kinases that were not previously linked to 1-cell activation, including HGK. siRNA studies showed a role for HGK in antigen mediated T-cell responses in Jurkat and primary T-cells. In addition, by analyzing multiple promoter elements using reporter assays, Mack et al. have shown that MAP4K4 is implicated in the activation of the TNF-alpha promoter. Therefore, inhibition of HGK could have broad therapeutic utility for T-cell-mediated autoimmune diseases.

Insulin-regulated glucose transporter GLUT4 is a key modulator of whole body glucose homeostasis, and its selective loss in adipose tissue or skeletal muscle causes insulin resistance and diabetes. Using an RNA interference-based screen, Tang et al. (Proc Natl Acad Sci USA. 103:2087-2092, 2006) found 4 negative regulators of insulin-responsive glucose transport in mouse adipocytes: Pctk1, Pftk1, Ikbka (CHUK), and HGK. HGK suppressed expression of adipogenic transcription factors, C/EBPA, C/EBPB, and PPARG, and it suppressed surface expression of GLUT4 (SLC2A4), resulting in attenuated membrane hexose transport activity. RNA interference-mediated depletion of HGK early in differentiation enhanced adipogenesis and triglyceride deposition; in fully differentiated adipocytes, loss of HGK upregulated GLUT4 expression. Conversely, conditions that inhibited adipogenesis, such as TNF-alpha treatment or PPARG depletion, markedly upregulated HGK. Tang et al. (Proc Natl Acad Sci USA. 103:2087-2092, 2006) concluded that MAP4K4-dependent signaling inhibited PPARG-responsive gene expression, adipogenesis, and insulin-stimulated glucose transport. Furthermore, TNF-alpha signaling to down-regulate GLUT4 is impaired in the absence of HGK, indicating that HGK expression is required for optimal TNF-alpha action. This study further supports HGK as a target in metabolic disease, and suggests a role for HGK inhibition in ameliorating the pathology in adipocytes.

In a separate study (Bouzakri and Zierath J. Biol. Chem. 282:7783-7789, 2007), using small interfering RNA (siRNA) to suppress the expression of HGK protein 85% in primary human skeletal muscle cells, TNF-alpha-induced insulin resistance on glucose uptake was completely prevented. HGK silencing inhibited TNT-alpha-induced negative signaling inputs by preventing excessive JNK and ERK-1/2 phosphorylation, as well as IRS-1 serine phosphorylation. These results highlight the HGK/JNK/ERK/IRS module in the negative regulation of insulin signaling to glucose transport in response to TNF-alpha. Depletion of HGK also prevented TNF-alpha-induced insulin resistance on AKT and the AKT substrate 160 (AS160), providing evidence that appropriate insulin signaling inputs for glucose metabolism were rescued. The authors suggested that strategies to inhibit HGK may be efficacious in the prevention of TNF-alpha-induced inhibitory signals that cause skeletal muscle insulin resistance on glucose metabolism in humans. Moreover, in myotubes from insulin-resistant type II diabetic patients, siRNA against HGK restored insulin action on glucose uptake to levels observed in healthy subjects. This study further supports HGK as a target in metabolic diseases such as type II diabetes, and suggests a role for HGK inhibition in ameliorating the pathology in muscle cells.

HGK inhibitors may be useful in treating metabolic indications, including, but not limited to, re-sensitizing fat and muscle cells to insulin, ameliorating the pathology in adipocytes, ameliorating the pathology in muscle cells, metabolic syndrome and type II diabetes; a broad range of oncology indications, including, but not limited to, blocking the migration, invasion and metastasis in many different tumor types; and T-cell mediated autoimmune diseases.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

The versatility of computer-based modulator design and identification lies in the diversity of structures screened by the computer programs. The computer programs can search databases that contain very large numbers of molecules and can modify modulators already complexed with the enzyme with a wide variety of chemical functional groups. A consequence of this chemical diversity is that a potential modulator of kinase function may take a chemical form that is not predictable. A wide array of organic synthetic techniques exist in the art to facilitate constructing these potential modulators. Many of these organic synthetic methods are described in detail in standard reference sources utilized by those skilled in the art. One example of such a reference is March, 1994, *Advanced Organic Chemistry; Reactions, Mechanisms and Structure*, N.Y., McGraw Hill. Thus, the techniques useful to synthesize a potential modulator of kinase function identified by computer-based methods are readily available to those skilled in the art of organic chemical synthesis.

Regarding the synthetic examples described herein, solvents include polar and non-polar solvents known to those of skill in the art, including polar aprotic and polar protic solvents. Polar solvents include, without limitation, protic solvents such as methanol, ethanol, isopropyl alcohol, t-butanol, n-butanol, acetic acid, formic acid or water, or aprotic solvents such as tetrahydrofuran (THF), acetonitrile, dioxane, methylene chloride, dimethylsulfoxide (DMSO), acetone, N,N-dimethylformamide (DMF), N,N-dimethylacetamide (DMA), ethyl acetate, 1,2-dimethoxyethane, 1,2-dichloroethane, chloroform, 1,2-dichloroethane, or pyridine. Polar solvents include a mixture of water with any of the above, or a mixture of any two or more of the above. Apolar solvents include, without limitation, toluene, benzene, chlorobenzene, xylenes and hexanes.

Regarding the synthetic examples described herein, reducing agent includes, without limitation, a reducing agent such as catalytic reducing agents using hydrogen and transition metal catalysts such as palladium, platinum, rhodium, etc. (e.g. Pt/acetic acid/$H_2$); a mixture of trifluoroacetic acid and triethylsilane, borane tetrahydrofuran complex, diborane, borane dimethylsulfide complex, and a combination of sodium borohydride and boron trifluoride; metals such as reduced iron, zinc powder, magnesium etc.; metal hydrogen complex compounds such as alkali metal borohydrides (for example, potassium borohydride, sodium borohydride, lithium borohydride, zinc borohydride, sodium triacetoxyborohydride, etc.), aluminum lithium hydride, etc.; metal hydrides such as sodium hydride, etc.; organic tin compounds (triphenyltin hydride, etc.); and metal salts such as nickel compounds, zinc compounds, tin compounds (for example tin(II) chloride), and samarium iodide/pivalic acid/hexamethylphorphoric triamide.

Regarding the synthetic examples described herein, oxidizing agent includes, without limitation, an oxidizing agent such as Dess-Martin reagent, TEMPO (2,2,6,6-tetramethylpiperidine-N oxide), DDQ (2,3-Dichloro-5,6-dicyano-1,4-benzoquinone), PDC (pyridinium dichromate), PCC (pyridinium chlorochromate), Pyridine.SO3, Chromium trioxide, p-nitroperbenzoic acid, magnesium monoperoxyphthalate, sodium periodate, potassium periodate, hydrogen peroxide, urea peroxide, alkali metal bromates, cumene hydroperoxide, tert-butyl peroxide, peracids such as performic acid, peracetic acid, pertrifluoroacetic acid, perbenzoic acid, m-chloroperbenzoic acid, o-carboxyperbenzoic acid and the like; sodium metaperiodate, bichromic acid; bichromates such as sodium bichromate, potassium bichromate; permanganic acid; permanganates such as potassium permanganate, sodium permanganate; and lead salts such as lead tetraacetate.

Regarding the synthetic examples described herein, a nitrogen protecting group is a chemical group covalently bound to a nitrogen atom of a compound that is used to protect the nitrogen from reaction during a synthetic step. The nitrogen protecting group may be added to a compound and removed in a subsequent step by methods known to those of skill in the art. Nitrogen protecting groups include, without limitation, carbamates, amides, N-sulfonyl derivatives, groups of formula —C(O)OR, wherein R is, for example, methyl, ethyl, t-butyl, benzyl, phenylethyl, CH$_2$=CHCH$_2$—, and the like, groups of the formula —C(O)R', wherein R' is, for example, methyl, phenyl, trifluoromethyl, and the like, groups of the formula —SO$_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like. Other suitable nitrogen protecting groups may be found in texts such as T. W. Greene & P. G. M. Wuts, *Protective Groups in Organic Synthesis*, John Wiley & Sons, 1991.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, such as (a) Isomers, Prodrugs, and Active Metabolites (b) Tautomers, Stereoisomers, Regioisomers, and Solvated Forms (c) Prodrugs and Metabolites (d) Pharmaceutically acceptable salts and (e) Polymorphic forms, are described, for example, in U.S. patent application Ser. No. 11/473,347 (see also, PCT publication WO2007002433), the disclosure of which is hereby incorporated by reference in its entirety.

Administration

The methods and compounds will typically be used in therapy for human subjects. However, they may also be used to treat similar or identical indications in other animal subjects. In this context, the terms "subject," "animal subject," and the like refer to human and non-human vertebrates, e.g. mammals, such as non-human primates, sports and commercial animals, e.g., equines, bovines, porcines, ovines, rodents, and pets, e.g., canines and felines. A description of possible methods and routes of administration may be found, for example, in U.S. patent application Ser. No. 11/473,347 (see also, PCT publication WO2007002433), the disclosure of which is hereby incorporated by reference in its entirety.

EXAMPLES

Examples related to the present invention are described below. In most cases, alternative techniques can be used. The examples are intended to be illustrative and are not limiting or restrictive to the scope of the invention. In some examples, the mass spectrometry result indicated for a compound may have more than one value due to the isotope distribution of an atom in the molecule, such as a compound having a bromo or chloro substituent.

Unless specifically indicated otherwise, the Formula enumerations and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods. In addition to the following Examples, exemplary methods which may be employed for synthesis of compounds of the present invention may be found in U.S. patent application Ser. No. 11/473,347 (see also, PCT publication WO2007002433), the disclosure of which is hereby incorporated by reference in its entirety. The 1H-pyrrolo[2,3-b]pyridine core of compounds described in the examples may also be referred to as 7-azaindole in the examples.

Example 1

Synthesis of Compounds of Formula X

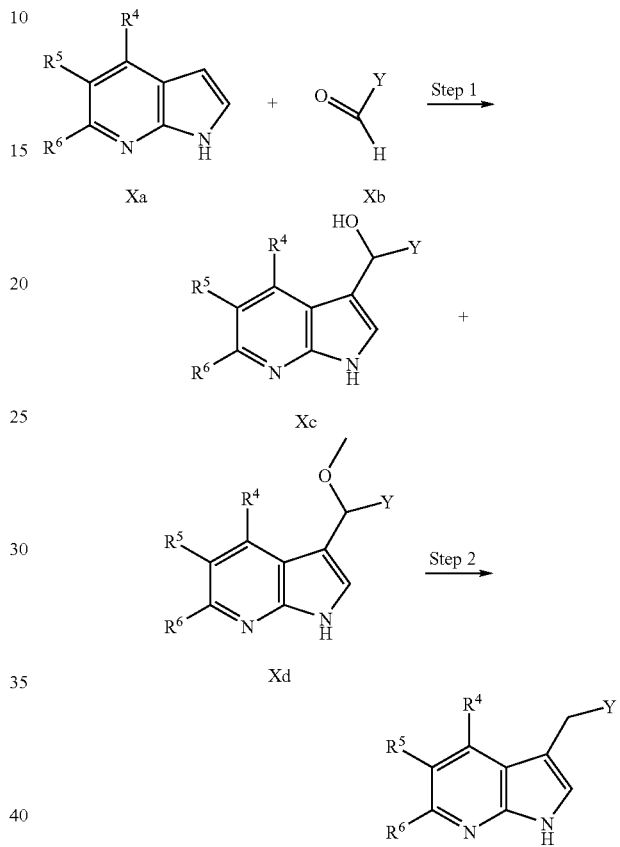

Step 1—Preparation of Compounds of Formula Xc and Xd

To a compound of Formula Xa (R$^4$, R$^5$, and R$^6$ are as defined with respect to Formula I) and a compound of Formula Xb (Y is consistent with compounds of Formula II, Formula III, or Formula IV, e.g. Y is:

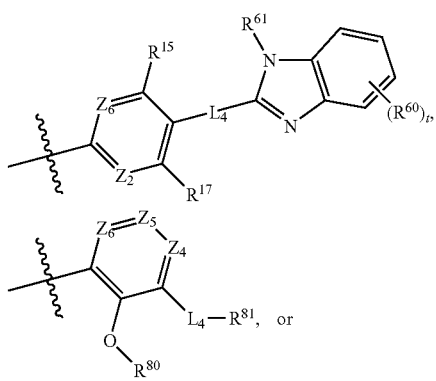

-continued

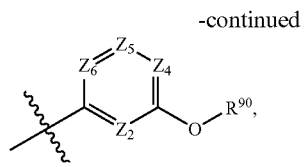

where $Z_2$, $Z_4$, $Z_5$, $Z_6$, $R^{15}$ and $R^{17}$ are as defined with respect to Formula I, $L_4$, $R^{60}$ and $R^{61}$ are as defined with respect to Formula II, $R^{80}$ and $R^{81}$ are as defined with respect to Formula III, and $R^{90}$ is as defined with respect to Formula IV, where ⸺ indicates the attachment point to the carbonyl carbon) is added an appropriate solvent (e.g. methanol) followed by an appropriate base (e.g. potassium hydroxide, sodium methoxide). The reaction is typically allowed to stir at room temperature overnight. Isolation by conventional means (e.g. extraction, washing and filtering) affords a mixture of compounds of Formula Xc and Xd, which may be separated by silica gel chromatography if desired.

Step 2—Preparation of Compounds of Formula X

To a compound of Formula Xc or Xd in an appropriate solvent (e.g. acetonitrile) is added a reducing agent (e.g. trifluoroacetic acid and triethylsilane). Typically, the reaction is allowed to stir at room temperature overnight. Isolation by conventional means (e.g. extraction and silica gel column chromatography) affords compounds of Formula X.

Example 2

Synthesis of Compounds of Formula XI

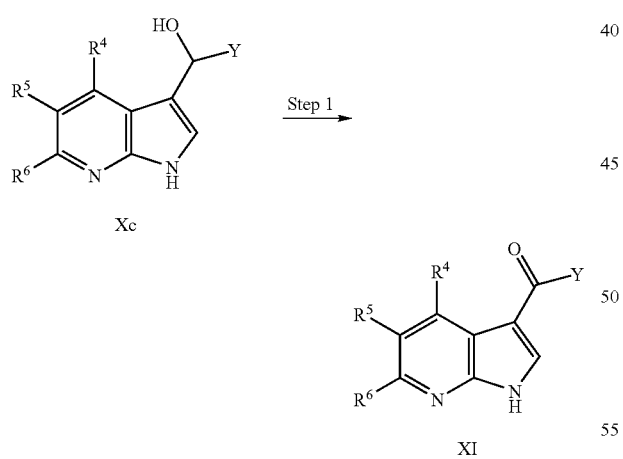

Step 1—Preparation of Compounds of Formula X

To a compound of Formula Xc (See Example 1) in an appropriate solvent (e.g. tetrahydrofuran) is added an oxidizing agent (e.g. Dess-Martin periodane, TEMPO, DDQ). Typically, the reaction is allowed to stir at room temperature for 20 minutes. Isolation by conventional means (e.g. extraction and silica gel column chromatography) affords compounds of Formula XI.

Example 3

Synthesis of Compounds of Formula XI

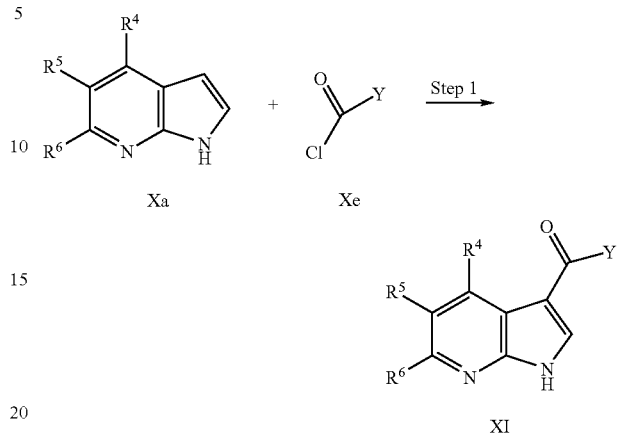

Step-1—Synthesis of Compound of Formula XI

Compound of Formula XI is synthesized by reacting a compound of Formula Xa (see Example 1) with a compound of Formula Xe (Y is as defined in Example 1), e.g. benzoyl chloride, in the presence of a Lewis acid (e.g. aluminum trichloride) in an inert solvent (e.g. dichloromethane) under an inert atmosphere (e.g. argon) at room temperature or with heating up to reflux for 1-18 hours. The desired compound XI is isolated by extraction and silica gel column chromatography.

Example 4

Synthesis of 5-chloro-1H-pyrrolo[2,3-b]pyridine 4

Compound 4 was synthesized in three steps from 5-bromo-7-azaindole 1 as shown in Scheme 1.

Scheme 1

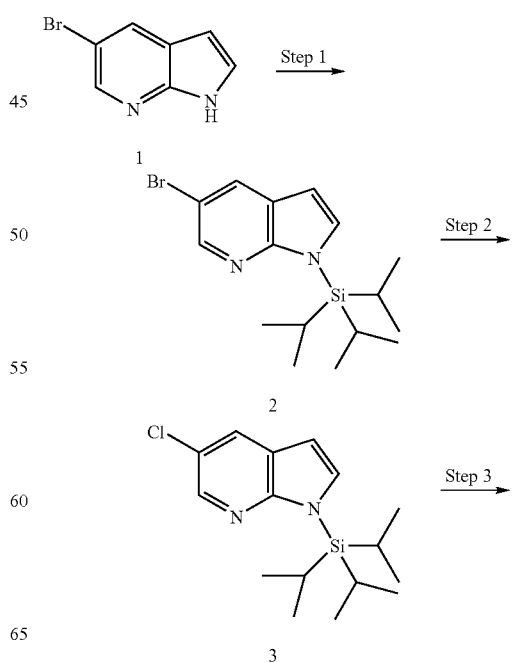

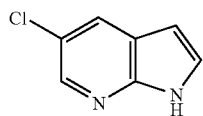

4

Step 1—Preparation of 5-bromo-1-triisopropylsilanyl-1H-pyrrolo[2,3-b]pyridine (2)

To 5-bromo-7-azaindole (1, 1.5 g, 7.6 mmol) in N,N-dimethylformamide (20 mL) were added sodium hydride (60% in mineral oil, 0.27 g, 11.0 mmol) and triisopropylsilyl chloride (2.6 mL, 12.0 mmol), under an atmosphere of nitrogen. The reaction was stirred for 2 hours at room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give the compound (2, 1.6 g, 59%). MS (ESI) [M+H$^+$]$^+$=352.3.

Step 2—Preparation 5-chloro-1-triisopropylsilanyl-1H-pyrrolo[2,3-b]pyridine (3)

To 5-bromo-1-triisopropylsilyl-7-azaindole (2, 1.60 g, 4.53 mmol) in tetrahydrofuran (50.0 mL), under an atmosphere of nitrogen at −78° C., was added tert-butyllithium (1.70 M in hexane, 6.12 mL). The reaction was stirred for 1 hour, followed by addition of hexachloroethane (1.29 g, 5.43 mmol). The reaction was stirred for 3 hours, poured into water, and extracted with ethyl acetate. The organic layer was dried over anhydrous sodium sulfate and filtered. The filtrate was concentrated to give the crude compound (3, 1.60 g). MS (ESI) [M+H$^+$]$^+$=309.3.

Step 3—Preparation 5-chloro-1H-pyrrolo[2,3-b]pyridine (4)

To 5-chloro-1-triisopropylsilanyl-1H-pyrrolo[2,3-b]pyridine (3, 1.40 g, 4.53 mmol) in tetrahydrofuran (15 mL) was added tetra-n-butylammonium fluoride (1.42 g, 5.43 mmol). The reaction mixture was stirred at room temperature for 10 minutes. The reaction mixture was concentrated and isolated by silica gel column chromatography eluting with 30% ethyl acetate in hexane to give the compound (4, 0.40 g, 58% over 2 steps). MS (ESI) [M−H$^+$]$^−$=153.1.

5-Fluoro-1H-pyrrolo[2,3-b]pyridine 5

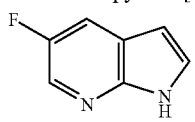

was prepared using the protocol of Scheme 1, substituting hexachloroethane with N-fluoro-N-(phenylsulfonyl)benzenesulfonamide in Step 2. MS (ESI) [M+H$^+$]$^+$=137.1.

Example 5

Synthesis of 1-triisopropylsilanyl-1H-pyrrolo[2,3-b]pyridine-3-carbaldehyde 8

Compound 8 was synthesized in two steps from 7-azaindole 6 as described in Scheme 2.

Scheme 2

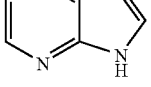

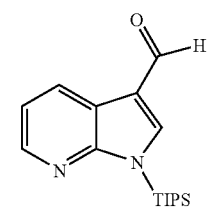

Step 1—Preparation of 1H-pyrrolo[2,3-b]pyridine-3-carbaldehyde (7)

To 1H-Pyrrolo[2,3-b]pyridine (6, 16.0 g, 135 mmol) in water (110 mL), were added hexamethylenetetramine (26.0 g, 185 mmol), and acetic acid (55.0 mL, 967 mmol). The reaction was refluxed for 12 hours. Water (329 mL) was added and the reaction was cooled to room temperature. The reaction was filtrated and washed with water to give the compound (7, 15.0 g, 76%). MS (ESI) [M+H$^+$]$^+$=147.

Step 2—Preparation of 1-triisopropylsilanyl-1H-pyrrolo[2,3-b]pyridine-3-carbaldehyde (8)

To 1H-Pyrrolo[2,3-b]pyridine-3-carbaldehyde (7, 4.05 g, 27.71 mmol) in tetrahydrofuran (30.0 mL) were added sodium hydride (60% in mineral oil, 1.5 g, 38 mmol) and triisopropylsilyl chloride (8.0 mL, 38 mmol) under an atmosphere of nitrogen. The reaction was stirred for 2 hours at room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give the compound (8, 3.0 g, 36%). MS (ESI) [M+H$^+$]$^+$=303.

Example 6

Synthesis of 5-isopropyl-1H-pyrrolo[2,3-b]pyridine 11

Compound 11 was synthesized in three steps from 5-bromo-1-triisopropylsilanyl-1H-pyrrolo[2,3-b]pyridine 2 described in Scheme 3.

Scheme 3

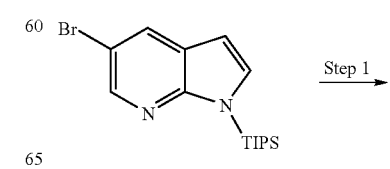

2

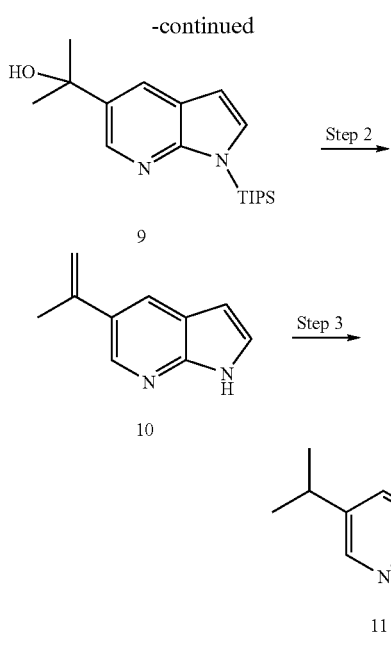

Step 1—Preparation of 2-(1-triisopropylsilanyl-1H-pyrrolo[2,3-b]pyridin-5-yl)-propan-2-ol (9)

To 5-bromo-1-triisopropylsilanyl-1H-pyrrolo[2,3-b]pyridine (2, 2.0 g, 5.66 mmol, prepared as described in Example 4) in tetrahydrofuran (20.0 mL), cooled in a −78° C. acetone/dry ice bath, under an atmosphere of nitrogen, was added tert-butyllithium (1.7 M in tetrahydrofuran, 7.3 mL, 12 mmol) dropwise. After 20 minutes, acetone (0.830 mL, 11 mmol) was added dropwise to the reaction. The reaction was stirred for 30 minutes at −78° C. and then allowed to reach room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give the compound (9, 1.30 g, 69%). MS (ESI) [M+H$^+$]$^+$=333.

Step 2—Preparation of 5-isopropenyl-1H-pyrrolo[2,3-b]pyridine (10)

To 2-(1-triisopropylsilanyl-1H-pyrrolo[2,3-b]pyridin-5-yl)-propan-2-ol (9, 0.500 g, 1.5 mmol) in acetonitrile (10.0 mL) were added triethylsilane (1.00 mL, 6.3 mmol) and trifluoroacetic acid (0.50 mL, 6.5 mmol) under an atmosphere of nitrogen. The reaction was refluxed for 3 hours, then cooled down to room temperature. The reaction was poured into water and extracted with ethyl acetate. The organic layer was washed with brine, dried over anhydrous sodium sulfate and filtered. The filtrate was concentrated and purified by silica gel column chromatography eluting with 50% ethyl acetate in hexane to give the compound (10, 0.200 g, 84%). MS (ESI) [M+H$^+$]$^+$=159.

Step 3—Preparation of 5-isopropyl-1H-pyrrolo[2,3-b]pyridine (11)

To 5-isopropenyl-1H-pyrrolo[2,3-b]pyridine (10, 0.080 g, 0.501 mmol) in tetrahydrofuran (5.0 mL) was added 20% palladium hydroxide on carbon (5.0 mg). The reaction was stirred under hydrogen at 40 psi for 30 minutes. The reaction mixture was filtered and concentrated to give the compound (11, 0.078 g, 96%). MS (ESI) [M+H$^+$]$^+$=161.

Example 7

Synthesis of 5-Methyl-1H-pyrrolo[2,3-b]pyridine 13

Compound 13 was synthesized in two steps from 5-bromo-1-triisopropylsilanyl-1H-pyrrolo[2,3-b]pyridine 2 described in Scheme 4.

Scheme 4

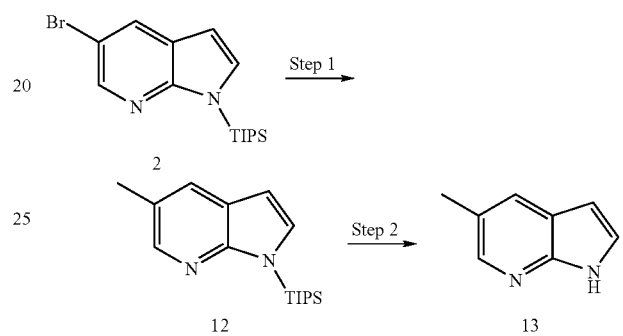

Step 1—Preparation of 5-Methyl-1-triisopropylsilanyl-1H-pyrrolo[2,3-b]pyridine (12)

To PdCl$_2$(dppf) (0.04 g, 0.05 mmol) in toluene (10.0 mL) under an atmosphere of nitrogen were added 5-bromo-1-triisopropylsilanyl-1H-pyrrolo[2,3-b]pyridine (2, 0.3 g, 0.8 mmol, prepared as described in Example 4, 1.0 mL in toluene) and methylmagnesium bromide (1.0 M in tetrahydrofuran, 3.0 mL, 3.0 mmol). The reaction was stirred 90° C. for 2 hours and then allowed to reach to room temperature. The reaction was poured into citric acid (0.1 M in water) and extracted with ethyl acetate. The organic layer was washed with brine, dried over anhydrous sodium sulfate and filtered. The filtrate was concentrated and purified by silica gel column chromatography eluting with 50% ethyl acetate in hexane to give the compound (12, 0.16 g 60.0%). MS (ESI) [M+H$^+$]$^+$=289.4.

Step 2—Preparation of 5-Methyl-1H-pyrrolo[2,3-b]pyridine (13)

To 5-Methyl-1-triisopropylsilanyl-1H-pyrrolo[2,3-b]pyridine (12, 0.160 g, 0.55 mmol) in tetrahydrofuran (3.0 mL) was added tetra-n-butylammonium fluoride (0.145 g, 0.55 mmol). The reaction was stirred for 1 hour at room temperature. The reaction was poured into water and extracted with ethyl acetate. The organic layer was washed with brine, dried over anhydrous sodium sulfate and filtered. The filtrate was concentrated and purified by silica gel column chromatography eluting with 3% methanol in dichloromethane to provide light yellow solid (13, 0.07 g, 95%).

MS (ESI) [M+H$^+$]$^+$=133.2.

5-Methyl-1H-pyrrolo[2,3-b]pyridine 14

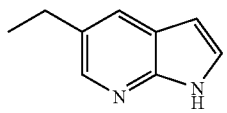

was prepared following the protocol of Scheme 4, substituting methylmagnesium bromide with ethylmagnesium bromide in Step 1.

Example 8

Synthesis of 5-Methoxy-1H-pyrrolo[2,3-b]pyridine 15 and related compounds

Compound 15 was synthesized in one step from 5-bromo-1H-pyrrolo[2,3-b]pyridine 1 as described in Scheme 5.

Scheme 5

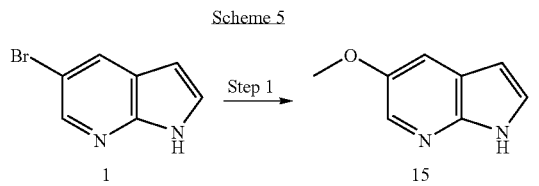

Step 1—Preparation of 5-Methoxy-1H-pyrrolo[2,3-b]pyridin (15)

To 5-bromo-7-azaindole (1, 500.0 mg, 2.53 mmol) in N,N-dimethylformamide (8 mL) were added copper(I) iodide (966 mg, 5.08 mmol) and sodium methoxide in methanol (3 M, 5 mL). The reaction was stirred overnight at 120° C. under an atmosphere of Argon. The reaction was poured into water, and extracted with ethyl acetate. The organic layer was dried over anhydrous sodium sulfate, filtered. The filtrate was concentrated and purified with silica gel column chromatograph eluting with 20% ethyl acetate in hexane to give white solid (15, 140 mg, 28%). MS (ESI) [M+H$^+$]$^+$=149.1. In an alternative method, 2.3 g (11.7 mmol) 5-bromo-7-azaindole (1, 2.3 g, 11.7 mmol) was dissolved in 75 mL N,N-dimethylformamide and 50 mL methanol (50 mL), adding sodium methoxide (32 g, 0.6 mol) and copper-(I) bromide (3.2 g, 22.4 mmol) at room temperature. The reaction was stirred for three hours at 100° C. under an atmosphere of argon. The mixture was diluted with ethyl acetate and poured into a solution of ammonium chloride:ammonium hydroxide (4:1). The organic layer was extracted with ammonium chloride:ammonium hydroxide (4:1), washed with brine, dried over anhydrous sodium sulfate, filtered and concentrated. The desired compound was isolated by silica gel column chromatography eluting with 30% to 70% ethyl acetate in hexanes to give a yellow solid (15, 0.27 g, 15.6%). MS (ESI) [M+H$^+$]$^+$=149.2.

5-Ethoxy-1H-pyrrolo[2,3-b]pyridine 16

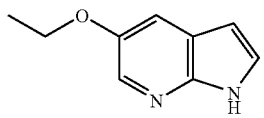

was prepared using the protocol of Scheme 5, substituting methanol with ethanol and sodium methoxide with sodium ethoxide.

5-(2-Methoxy-ethoxy)-1H-pyrrolo[2,3-b]pyridine 17

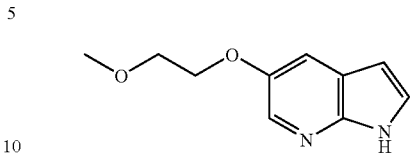

was prepared using the protocol of Scheme 5, substituting methanol with 2-methoxy-ethanol and sodium methoxide with sodium 2-methoxy-ethoxide (prepared from 2-methoxy-ethanol and sodium hydride). MS (ESI) [M+H$^+$]$^+$=193.3.

Diethyl-[2-(1H-pyrrolo[2,3-b]pyridin-5-yloxy)-ethyl]-amine 18

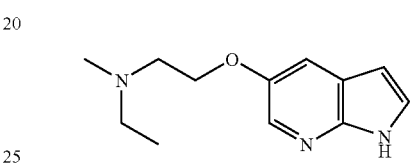

was prepared using the protocol of Scheme 5, substituting methanol with 2-diethylamino-ethanol and sodium methoxide with sodium 2-diethylamino-ethoxide (prepared from 2 2-diethylamino-ethanol and sodium hydride). MS (ESI) [M+H$^+$]$^+$=234.5.

Example 9

Synthesis of 5-Pyridin-3-yl-1H-pyrrolo[2,3-b]pyridine 20 and Related Compounds 5-Pyridin-3-yl-1H-pyrrolo[2,3-b]pyridine 20 was synthesized in one step from 5-bromo-1H-pyrrolo[2,3-b]pyridine 1 as described in Scheme 6.

Scheme 6

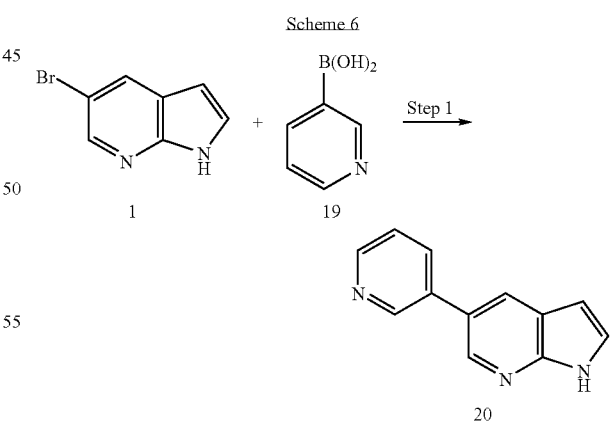

Step 1—Preparation of 5-Pyridin-3-yl-1H-pyrrolo[2,3-b]pyridine (20)

To 5-bromo-7-azaindole (1, 1.00 g, 5.08 mmol) in water (13.0 mL) and acetonitrile (36 mL) were added pyridine-3-boronic acid (19, 1.0 g, 8.1 mmol), potassium carbonate (1.79 g, 0.0130 mol) and Tetrakis(triphenylphosphine)palladium (0) (50.0 mg, 0.043 mmol) under an atmosphere of nitrogen. The reaction mixture was heated to 170° C. overnight. The reaction mixture was poured into water and extracted with ethyl acetate. The organic layer was washed with brine, dried over sodium sulfate, and concentrated. The residue was purified with silica gel column chromatography eluting with 25% ethyl acetate in hexane to provide a light yellow solid (20, 820 mg, 82%).

MS (ESI) $[M+H^+]^+$=196.1.

Additional compounds were prepared following the protocol of Scheme 6, either by substituting pyridine-3-boronic acid with an appropriate boronic acid or by substituting the 5-bromo-7-azaindole with 5-(4,4,5,5-Tetramethyl-[1,3,2]dioxaborolan-2-yl)-1H-pyrrolo[2,3-b]pyridine and reacting with a suitable aryl or heteroaryl halide (i.e. coupling with the boronic acid ester on the azaindole, and the halide on the group to be coupled to the 5-position of the azaindole). The following compounds were prepared by this procedure:
5-(4-Chloro-phenyl)-1H-pyrrolo[2,3-b]pyridine,
5-(4-Fluoro-phenyl)-1H-pyrrolo[2,3-b]pyridine,
5-Phenyl-1H-pyrrolo[2,3-b]pyridine,
5-(6-Methoxy-pyridin-3-yl)-1H-pyrrolo[2,3-b]pyridine,
5-(2-Methoxy-pyrimidin-5-yl)-1H-pyrrolo[2,3-b]pyridine,
5-Pyridin-4-yl-1H-pyrrolo[2,3-b]pyridine,
4-(1H-Pyrrolo[2,3-b]pyridin-5-yl)-benzenesulfonamide,
3-(1H-Pyrrolo[2,3-b]pyridin-5-yl)-benzenesulfonamide,
5-Pyrimidin-5-yl-1H-pyrrolo[2,3-b]pyridine,
5-(3-Methanesulfonyl-phenyl)-1H-pyrrolo[2,3-b]pyridine,
3-(1H-Pyrrolo[2,3-b]pyridin-5-yl)-benzamide,
5-(5-Methyl-1H-imidazol-2-yl)-1H-pyrrolo[2,3-b]pyridine,
5-(1-Methyl-1H-imidazol-2-yl)-1H-pyrrolo[2,3-b]pyridine and
5-(1,5-Dimethyl-1H-imidazol-2-yl)-1H-pyrrolo[2,3-b]pyridine.

The following table indicates either 5-bromo-7-azaindole or 5-(4,4,5,5-Tetramethyl-[1,3,2]dioxaborolan-2-yl)-1-pyrrolo[2,3-b]pyridine starting material (column 1) and the appropriate reagent to be coupled to the 5 position of the azaindole (column 2) to afford the resulting compound (column 3), with the observed mass given in column 4.

| Starting azaindole | Reagent coupled to 5 position | Compound | MS(ESI) $[M + H^+]^+$ observed |
|---|---|---|---|
| 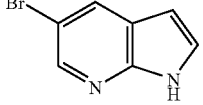 | 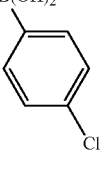 | 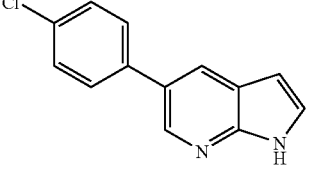 | 229.1 |
| 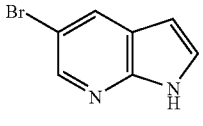 | 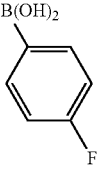 |  | 213.1 |
| 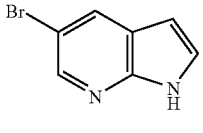 | 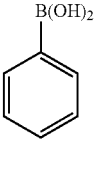 | 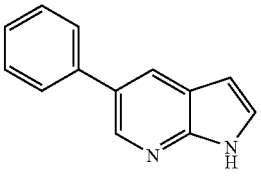 | 195.2 |
| 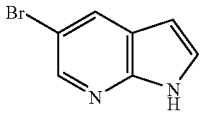 | 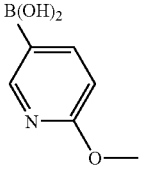 | 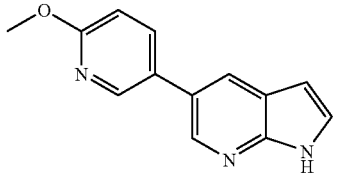 | 226.2 |
| 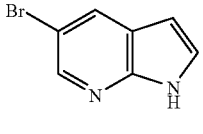 | 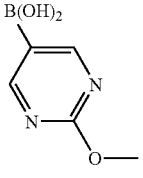 | 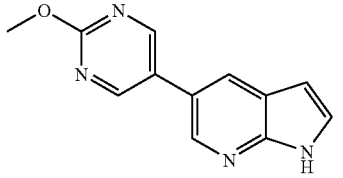 | 227.2 |

-continued

| Starting azaindole | Reagent coupled to 5 position | Compound | MS(ESI) [M + H⁺]⁺ observed |
|---|---|---|---|
| | | | 196.2 |
| | | | 274.1 |
| | | | 274.1 |
| | | | 197.2 |
| | | | 273.1 |
| | | | 238.2 |
| | | | 199.2 |
| | | | 199.2 |

| Starting azaindole | Reagent coupled to 5 position | Compound | MS(ESI) [M + H⁺]⁺ observed |
|---|---|---|---|
| 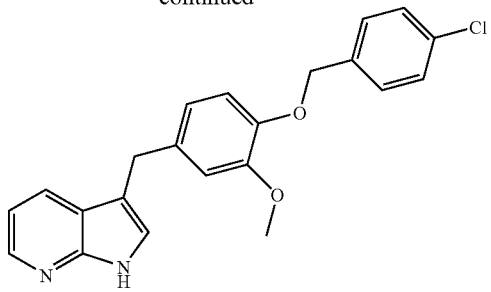 | | | 213.2 |

Example 10

Synthesis of 3-(4-(4-chlorobenzyloxy)-3-methoxy-benzyl)-1H-pyrrolo[2,3-b]pyridine P-1247

Compound P-1247 was synthesized in three steps from 4-hydroxy-3-methoxybenzaldehyde 21 as shown in Scheme 7.

Scheme 7

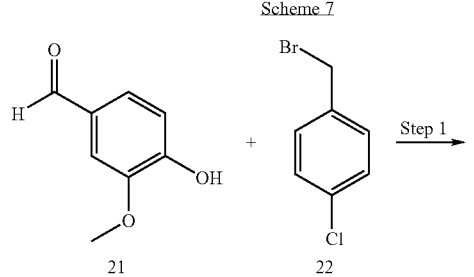

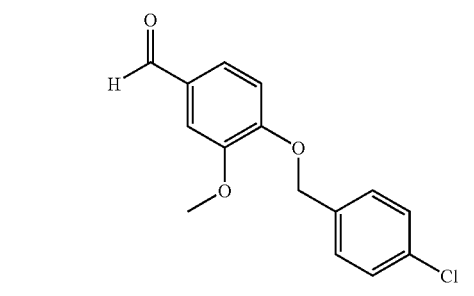

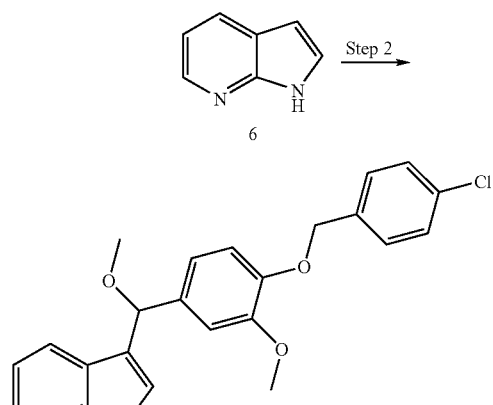

Step 1—Preparation of 4-(4-chlorobenzyloxy)-3-methoxybenzaldehyde (23)

To 4-hydroxy-3-methoxybenzaldehyde (21, 600.0 mg, 3.94 mmol) and 4-chlorobenzyl bromide (22, 1.20 g, 5.84 mmol) in acetonitrile (6 mL) was added potassium carbonate (0.390 g, 2.82 mmol). The reaction was microwaved on 300 watts, 120° C. for 10 minutes. The reaction was extracted with ethyl acetate and water. The organic layer was washed with brine, dried over magnesium sulfate, filtered and the volatiles removed by evaporation. The desired compound was purified by recrystallization from hexanes to provide 23 (1.01 g, 93%). MS (ESI) [M–H⁺]⁻=275.1.

Step 2—Preparation of 3-((4-(4-chlorobenzyloxy)-3-methoxyphenyl)(methoxy)methyl)-1H-pyrrolo[2,3-b]pyridine (24)

To 1H-Pyrrolo[2,3-b]pyridine (6, 0.235 g, 1.99 mmol) and 4-(4-chlorobenzyloxy)-3-methoxybenzaldehyde (23, 0.500 g, 1.81 mmol) was added 5 mL of methanol followed by the addition of solid potassium hydroxide (0.203 g, 3.61 mmol). The reaction was allowed to stir at ambient temperature for 18 days. The reaction mixture was poured into water and extracted with ethyl acetate. The organic layer was separated and volatiles removed to give a solid which was suspended in hot ethyl acetate. The suspension was allowed to cool and the solid collected by vacuum filtration to provide 24 (548 mg, 74%). MS (ESI) [M+H⁺]⁺=409.4.

Step 3—Preparation of 3-(4-(4-chlorobenzyloxy)-3-methoxybenzyl)-1H-pyrrolo[2,3-b]pyridine (P-1247)

To 3-((4-(4-chlorobenzyloxy)-3-methoxyphenyl)(methoxy)methyl)-1H-pyrrolo[2,3-b]pyridine (24, 0.548 g, 1.34 mmol) in acetonitrile (20 mL) was added trifluoroacetic acid (1.7 mL, 2.21 mmol) and triethylsilane (3.47 mL, 2.17 mmol). The reaction was stirred at 60° C. for 15 hours. The volatiles were removed and the desired compound was purified by silica gel chromatography, eluting with a gradient from 0% to 60% ethyl acetate in hexanes to provide a white solid (P-1247, 505 mg, 99%). MS (ESI) [M+H$^+$]$^+$=379.4.

Additional compounds were prepared using the protocol of Scheme 7, Steps 2 and 3, replacing 4-(4-chlorobenzyloxy)-3-methoxybenzaldehyde 23 with a suitable aldehyde (prepared as described in Example 15 or 33), and optionally replacing 1H-Pyrrolo[2,3-b]pyridine 6 with an appropriate substituted 7-azaindole (5-chloro-7-azaindole per Example 4 or 5-methoxy-7-azaindole per Example 8) in Step 2. The following compounds were made following this procedure:

3-[3-Methoxy-4-(4-trifluoromethyl-benzyloxy)-benzyl]-1H-pyrrolo[2,3-b]pyridine (P-1721),
3-[3-Trifluoromethyl-4-(4-trifluoromethyl-benzyloxy)-benzyl]-1H-pyrrolo[2,3-b]pyridine (P-1797),
3-{3-Methoxy-4-[4-(4-methyl-piperazin-1-ylmethyl)-benzyloxy]-benzyl}-1H-pyrrolo[2,3-b]pyridine (P-1821),
3-[4-(4-Chloro-benzyloxy)-2-fluoro-5-methoxy-benzyl]-1H-pyrrolo[2,3-b]pyridine (P-1844),
3-[4-(3-Fluoro-4-trifluoromethyl-benzyloxy)-3-methoxy-benzyl]-1H-pyrrolo[2,3-b]pyridine (P-1849),
3-[4-(4-Chloro-3-trifluoromethyl-benzyloxy)-3-methoxy-benzyl]-1H-pyrrolo[2,3-b]pyridine (P-1851),
2-[2-Methoxy-4-(1H-pyrrolo[2,3-b]pyridin-3-ylmethyl)-phenoxymethyl]-1H-benzoimidazole (P-1870),
3-[4-(4-Chloro-2-fluoro-benzyloxy)-2-fluoro-5-methoxy-benzyl]-5-methoxy-1H-pyrrolo[2,3-b]pyridine (P-1885),
3-[4-(3,4-Dichloro-benzyloxy)-3-methoxy-benzyl]-1H-pyrrolo[2,3-b]pyridine (P-1886),
3-[4-(4-Chloro-benzyloxy)-3-fluoro-benzyl]-1H-pyrrolo[2,3-b]pyridine (P-1896),
2-[2-Fluoro-4-(1H-pyrrolo[2,3-b]pyridin-3-ylmethyl)-phenoxymethyl]-1H-benzoimidazole (P-1899),
3-(4-Benzyloxy-2,5-difluoro-benzyl)-1H-pyrrolo[2,3-b]pyridine (P-1901),
5-Chloro-3-[4-(4-chloro-benzyloxy)-2-fluoro-5-methoxy-benzyl]-1H-pyrrolo[2,3-b]pyridine (P-1970),
5-Chloro-3-[4-(4-chloro-2-fluoro-benzyloxy)-2-fluoro-5-methoxy-benzyl]-1H-pyrrolo[2,3-b]pyridine (P-1972),
3-[4-(4-Chloro-2-fluoro-benzyloxy)-2-fluoro-5-methoxy-benzyl]-1H-pyrrolo[2,3-b]pyridine (P-1973),
2-[4-(5-Chloro-1H-pyrrolo[2,3-b]pyridin-3-ylmethyl)-5-fluoro-2-methoxy-phenoxymethyl]-1H-benzoimidazole (P-1976),
2-[5-Fluoro-2-methoxy-4-(5-methoxy-1H-pyrrolo[2,3-b]pyridin-3-ylmethyl)-phenoxymethyl]-1-benzoimidazole (P-1977),
2-[5-Fluoro-2-methoxy-4-(1H-pyrrolo[2,3-b]pyridin-3-ylmethyl)-phenoxymethyl]-1H-benzoimidazole (P-1978),
3-{4-[2-(2-Bromo-ethoxy)-ethoxy]-2-fluoro-5-methoxy-benzyl}-5-chloro-1H-pyrrolo[2,3-b]pyridine (P-1984),
5-Chloro-3-[2,5-difluoro-4-(2-methoxy-ethoxy)-benzyl]-1H-pyrrolo[2,3-b]pyridine (P-1986),
5-Chloro-3-[2-fluoro-5-methoxy-4-(2-methoxy-ethoxy)-benzyl]-1H-pyrrolo[2,3-b]pyridine (P-1990),
{3-[4-(5-Chloro-1H-pyrrolo[2,3-b]pyridin-3-ylmethyl)-5-fluoro-2-methoxy-phenoxy]-propyl}-diethyl-amine (P-2004),
5-Chloro-3-{2-fluoro-5-methoxy-4-[2-(2-methoxy-ethoxy)-ethoxy]-benzyl}-1H-pyrrolo[2,3-b]pyridine (P-2002),
3-(4-Benzyloxy-2,6-difluoro-benzyl)-1H-pyrrolo[2,3-b]pyridine (P-2022),
3-{2-Fluoro-5-methoxy-4-[2-(2-methoxy-ethoxy)-ethoxy]-benzyl}-5-methoxy-1H-pyrrolo[2,3-b]pyridine (P-2025), and
3-{2-Fluoro-5-methoxy-4-[2-(2-methoxy-ethoxy)-ethoxy]-benzyl}-1H-pyrrolo[2,3-b]pyridine (P-2026).

The following table indicates the aldehyde (column 2) and the azaindole (column 3) used to afford the target compound (column 4). Column 1 indicates the compound number and column 5 the observed mass.

| | Aldehyde | Azaindole | Compound | MS(ESI) [M + H$^+$]$^+$ observed |
|---|---|---|---|---|
| P-1721 | | | | 413.2 |
| P-1797 | | | | 451.3 |

|  | Aldehyde | Azaindole | Compound | MS(ESI) [M + H⁺]⁺ observed |
|---|---|---|---|---|
| P-1821 | | | | 457.4 |
| P-1844 | | | | 397.2 |
| P-1849 | | | | 432.4 |
| P-1851 | | | | |
| P-1870 | | | | 385.4 |
| P-1885 | | | | 445.3 |

-continued

| | Aldehyde | Azaindole | Compound | MS(ESI) [M + H+]+ observed |
|---|---|---|---|---|
| P-1886 | | | | 413.3 |
| P-1896 | | | | 367.3 |
| P-1899 | | | | 373.4 |
| P-1901 | | | | 351.4 |
| P-1970 | | | | 431.2 |
| P-1972 | | | | 449.2 |
| P-1973 | | | | 415.3 |

-continued
| | Aldehyde | Azaindole | Compound | MS(ESI) [M + H⁺]⁺ observed |
|---|---|---|---|---|
| P-1976 | 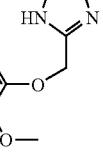 | 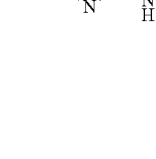 | 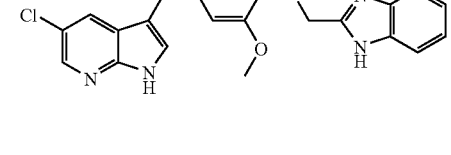 | 437.3 |
| P-1977 | 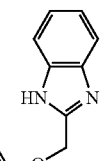 | 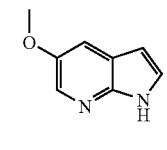 | 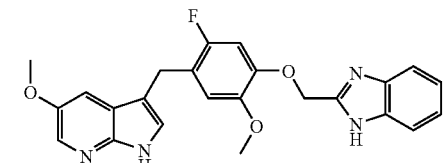 | 433.4 |
| P-1978 | 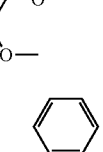 | 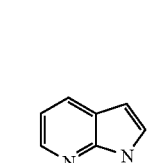 | 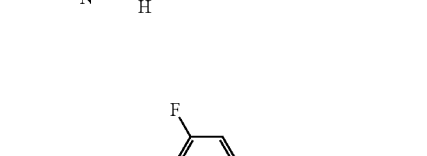 | 403.4 |
| P-1984 | 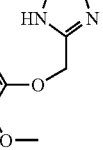 | 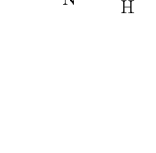 | 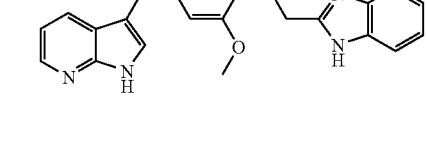 | 457.4<br>459.4 |
| P-1986 | 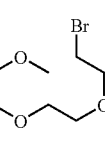 |  | 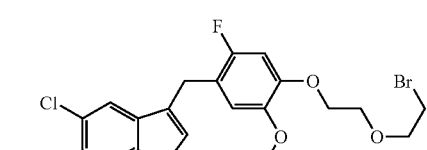 | 353.4 |
| P-1990 | 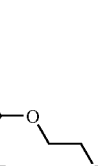 | 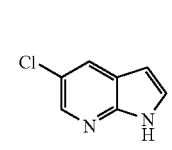 | 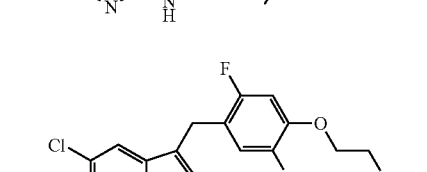 | 365.3 |
| P-2004 | 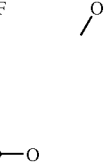 | 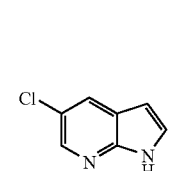 | 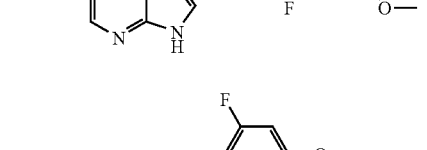 | 420.4 |

-continued

| | Aldehyde | Azaindole | Compound | MS(ESI) [M + H+]+ observed |
|---|---|---|---|---|
| P-2002 | | | | 409.3 |
| P-2022 | | | | 438.1 |
| P-2025 | | | | 405.2 |
| P-2026 | | | | 373.2 |

Example 11

Synthesis of (3-Benzyloxy-2,6-difluorophenyl)-(5-pyridin-3-yl-1H-pyrrolo[2,3-b]pyridin-3-yl)-methanone P-1467 and related compounds Compound P-1467 was synthesized in four steps from 2,4-difluorophenol 25 as shown in Scheme 8.

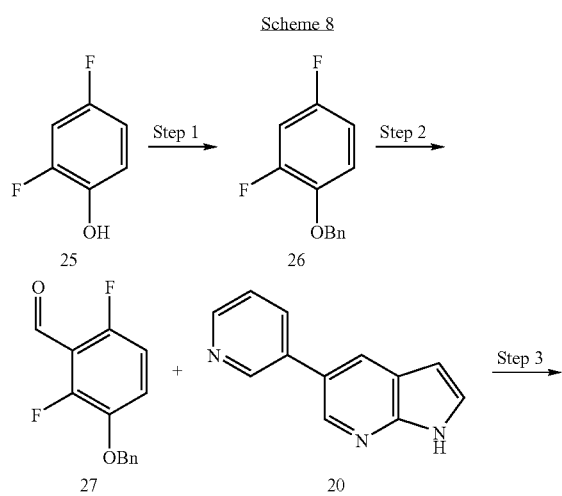

Scheme 8

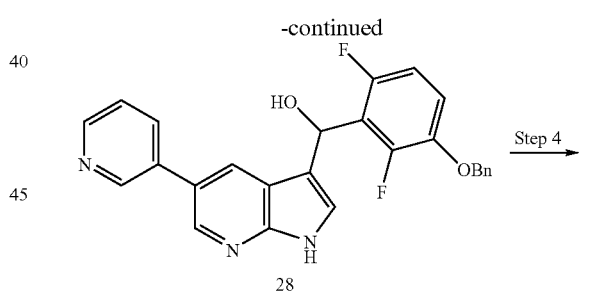

Step 1—Preparation of 1-Benzyloxy-2,4-difluoro-benzene (26)

To 2,4-difluoro-phenol (25, 7.60 g, 0.0584 mol) in N,N-dimethylformamide (50.0 mL) were added benzyl bromide (8.0 mL, 0.067 mol) and potassium carbonate (9.00 g, 0.0651 mol) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the compound as white solid (26, 3.20 g, 25%).

Step 2—Preparation of 3-Benzyloxy-2,6-difluoro-benzaldehyde (27)

To 1-Benzyloxy-2,4-difluoro-benzene (26, 3.00 g, 13.6 mmol) in tetrahydrofuran (48 mL) under an atmosphere of nitrogen and cooled with dry ice/acetone was added n-butyl-lithium (1.60 M in hexane, 8.94 mL). After 20 minutes, N,N-dimethylformamide (1.46 mL, 0.0189 mol) was added to the reaction. After another 20 minutes, the flask was stirred at room temperature for 30 minutes. The reaction mixture was poured into water, acidified to pH=1, and extracted with ethyl acetate. The organic layer was washed with brine, dried over sodium sulfate, concentrated and purified with silica gel column chromatography eluting with 30% ethyl acetate in hexane to give the compound as a yellow solid (27, 2.5 g, 74%).

Step 3—Preparation of (3-Benzyloxy-2,6-difluoro-phenyl)-(5-pyridin-3-yl-1H-pyrrolo[2,3-b]pyridin-3-yl)-methanol (28)

To 5-pyridin-3-yl-1H-pyrrolo[2,3-b]pyridine (20, 750.0 mg, 0.003842 mol, prepared as in Example 9) in methanol (20.0 mL) were added 3-benzyloxy-2,6-difluoro-benzaldehyde (27, 1.12 g, 4.5 mmol) and potassium hydroxide (1.50 g, 0.0267 mol) under an atmosphere of nitrogen. The reaction was stirred at room temperature overnight and then poured into water, acidified with 1N HCl to pH around 2 and extracted with ethyl acetate. The organic layer was dried over anhydrous sodium sulfate and filtered. The filtrate was concentrated and purified by silica gel column chromatography eluting with 20% ethyl acetate in hexane to give the compound (28, 700 mg, 35%).

Step 4—Preparation of (3-Benzyloxy-2,6-difluoro-phenyl)-(5-pyridin-3-yl-1H-pyrrolo[2,3-b]pyridin-3-yl)-methanone (P-1467)

To (3-Benzyloxy-2,6-difluoro-phenyl)-(5-pyridin-3-yl-1H-pyrrolo[2,3-b]pyridin-3-yl)-methanol (28, 300.0 mg, 0.68 mmol) in tetrahydrofuran (10.0 mL) was added Dess-Martin periodinane (344 mg, 0.81 mmol). The reaction was stirred at room temperature for 10 minutes. The reaction mixture was concentrated with silica and purified with silica gel column chromatography eluting with 10% methanol in dichloromethane to give the compound (P-1467, 240 mg, 80%). MS (ESI) [M+H$^+$]$^+$=442.2.

(5-Bromo-1H-pyrrolo[2,3-b]pyridin-3-yl)-[2,6-difluoro-3-(2-methoxy-ethoxy)-phenyl]-methanone P-1453

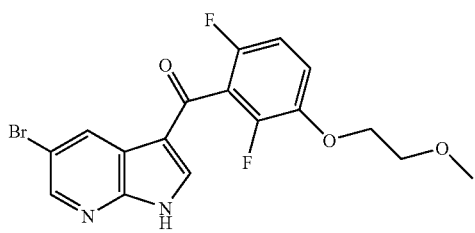

was prepared following the protocol of Scheme 8, substituting benzyl bromide with 1-Bromo-2-methoxy-ethane in Step 1 and 5-Pyridin-3-yl-1H-pyrrolo[2,3-b]pyridine 20 with 5-Bromo-1H-pyrrolo[2,3-b]pyridine 1 in Step 3. MS (ESI) [M+H$^+$]$^+$=410.1, 412.1.

[2,6-Difluoro-3-(2-methoxy-ethoxy)-phenyl]-(5-methoxy-1H-pyrrolo[2,3-b]pyridin-3-yl)-methanone P-1584

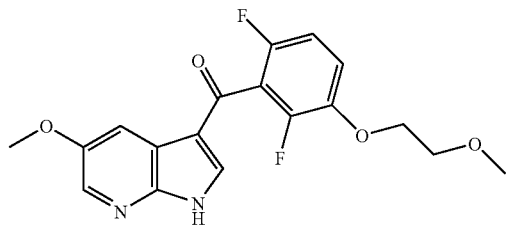

was prepared following the protocol of Scheme 8, substituting benzyl bromide with 1-Bromo-2-methoxy-ethane in Step 1 and 5-Pyridin-3-yl-1H-pyrrolo[2,3-b]pyridine 20 with 5-methoxy-1H-pyrrolo[2,3-b]pyridine (15, prepared as in Example 8) in Step 3. MS (ESI) [M+H$^+$]$^+$=363.2.

(3-Benzyloxy-2,6-difluoro-phenyl)-(5-methoxy-1H-pyrrolo[2,3-b]pyridin-3-yl)-methanone P-1597

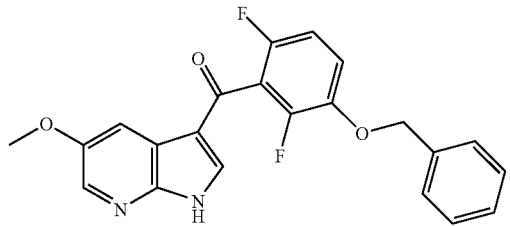

was prepared following the protocol of Scheme 8, substituting 5-pyridin-3-yl-1H-pyrrolo[2,3-b]pyridine 20 with 5-methoxy-1H-pyrrolo[2,3-b]pyridine (15, prepared as in Example 8) in Step 3. MS (ESI) [M+H$^+$]$^+$=395.2.

(5-Bromo-1H-pyrrolo[2,3-b]pyridin-3-yl)-(2,6-difluoro-3-methoxy-phenyl)-methanone P-1386

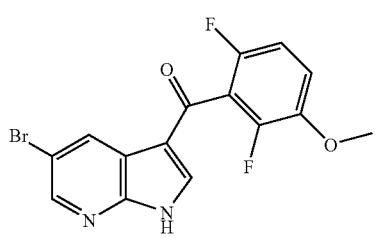

was prepared following the protocol of Steps 2, 3 and 4 of Scheme 8, substituting 1-benzyloxy-2,4-difluoro-benzene 26 with 2,4-difluoro-1-methoxy-benzene in Step 2 and 5-Pyridin-3-yl-1H-pyrrolo[2,3-b]pyridine 20 with 5-bromo-1H-pyrrolo[2,3-b]pyridine 1 in Step 3. MS (ESI) [M+H$^+$]$^+$=367.0, 369.0.

(3-Benzyloxy-2,6-difluoro-phenyl)-(1H-pyrrolo[2,3-b]pyridin-3-yl)-methanone P-1802

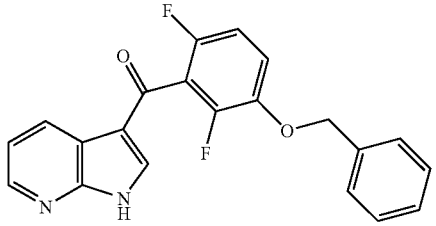

was prepared following the protocol of Scheme 8, substituting 5-pyridin-3-yl-1H-pyrrolo[2,3-b]pyridine 20 with 7-azaindole 6 in Step 3. To a solution of (3-benzyloxy-2,6-difluoro-phenyl)-(1H-pyrrolo[2,3-b]pyridin-3-yl)-methanone (P-1802, 0.5 g, 1.37 mol) in methanol (70 mL) and tetrahydrofuran (30 mL) was added palladium on carbon (120 mg, 10% wt., 0.58 mol). The mixture was stirred under hydrogenation (60 psi) for six hours. After removal of solvent, the residue was dried under vacuum, which provided (2,6-Difluoro-3-hydroxy-phenyl)-(1H-pyrrolo[2,3-b]pyridine-3-yl)-methanone 89

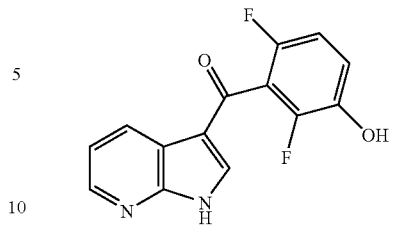

as a white solid (363 mg, 96%). MS (ESI) [M+H$^+$]$^+$=275.36.

Additional compounds were prepared following steps 3 and 4 of Scheme 8, replacing 3-benzyloxy-2,6-difluoro-benzaldehyde 27 with an appropriate aldehyde and/or pyridin-3-yl-1H-pyrrolo[2,3-b]pyridine 20 with an appropriate azaindole in Step 3. The 5-chloro-7-azaindole was synthesized as described in Example 4. The 4-(4-Chloro-benzyloxy)-3-methoxy benzaldehyde and 2-fluoro-5-methoxy-4-[2-(2-methoxy-ethoxy)-ethoxy]-benzaldehyde used were synthesized as described in Example 15. The following compounds were made following this procedure:
(5-Chloro-1H-pyrrolo[2,3-b]pyridin-3-yl)-{2-fluoro-5-methoxy-4-[2-(2-methoxy-ethoxy)-ethoxy]-phenyl}-methanone (P-2003),
(4-Benzyloxy-2,6-difluoro-phenyl)-(1H-pyrrolo[2,3-b]pyridin-3-yl)-methanone (P-2020), and
[4-(4-Chloro-benzyloxy)-3-methoxy-phenyl]-(1H-pyrrolo[2,3-b]pyridin-3-yl)-methanone (P-1698).

The following table indicates the aldehyde (column 2) and the azaindole (column 3) used to afford the target compound (column 4). Column 1 provides the compound number and column 5 the observed mass.

| | Aldehyde | Azaindole | Compound | MS(ESI) [M + H$^+$]$^+$ observed |
|---|---|---|---|---|
| P-2003 | [structure] | [structure] | [structure] | 423.3 |
| P-2020 | [structure] | [structure] | [structure] | 363.1 |
| P-1698 | [structure] | [structure] | [structure] | 393.2 |

Example 12

Synthesis of 3-(3-Benzyloxy-2,6-difluoro-benzyl)-5-pyridin-3-yl-1H-pyrrolo[2,3-b]pyridine P-1455

Compound P-1455 was synthesized in four steps from 2,4-difluorophenol 25 as shown in Scheme 8a.

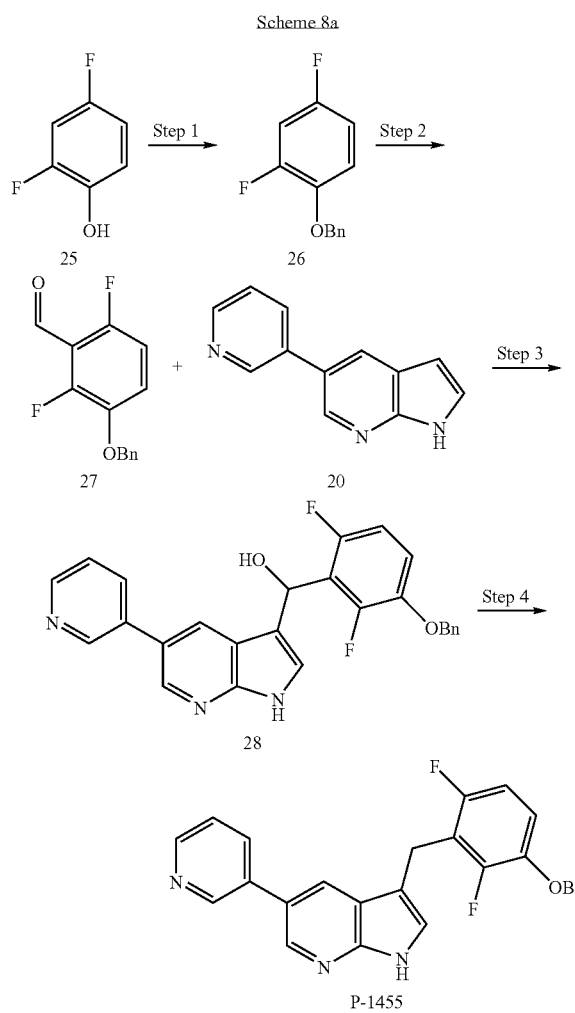

Steps 1-3 are identical to Steps 1-3 of Scheme 8.

Step 4—Preparation of 3-(3-Benzyloxy-2,6-difluoro-benzyl)-5-pyridin-3-yl-1H-pyrrolo[2,3-b]pyridine (P-1455)

To (3-benzyloxy-2,6-difluoro-phenyl)-(5-pyridin-3-yl-1H-pyrrolo[2,3-b]pyridin-3-yl)-methanol (28, 580.0 mg, 1.3 mmol) in acetonitrile (29.0 mL) were added trifluoroacetic acid (1.9 mL, 0.025 mol) and triethylsilane (3.9 mL, 0.024 mol). The reaction was stirred at 80° C. for 1 hour. The reaction was poured into water, basified with 1 M potassium carbonate to pH=4, and extracted with ethyl acetate. The organic layer was dried over anhydrous sodium sulfate and filtered. The filtrate was concentrated and purified by silica gel column chromatography eluting with 50% ethyl acetate in hexane to give as a yellow solid (P-1455, 530 mg). MS (ESI) [M+H$^+$]$^+$=428.3.

5-Bromo-3-[2,6-difluoro-3-(2-methoxy-ethoxy)-benzyl] 1H-pyrrolo[2,3-b]pyridine P-1454

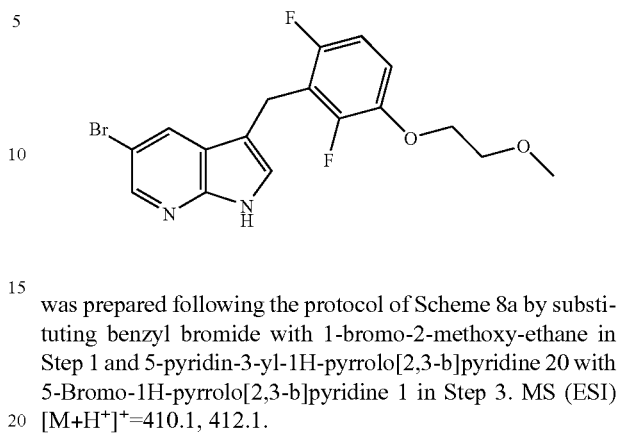

was prepared following the protocol of Scheme 8a by substituting benzyl bromide with 1-bromo-2-methoxy-ethane in Step 1 and 5-pyridin-3-yl-1H-pyrrolo[2,3-b]pyridine 20 with 5-Bromo-1H-pyrrolo[2,3-b]pyridine 1 in Step 3. MS (ESI) [M+H$^+$]$^+$=410.1, 412.1.

Example 13

Synthesis of 3-[3-chloro-4-(4-chloro-benzyloxy)-benzyl]-1H-pyrrolo[2,3-b]pyridine P-1449

Compound P-1449 was synthesized in three steps from 3-chloro-4-hydroxy-benzaldehyde 29 as shown in Scheme 9.

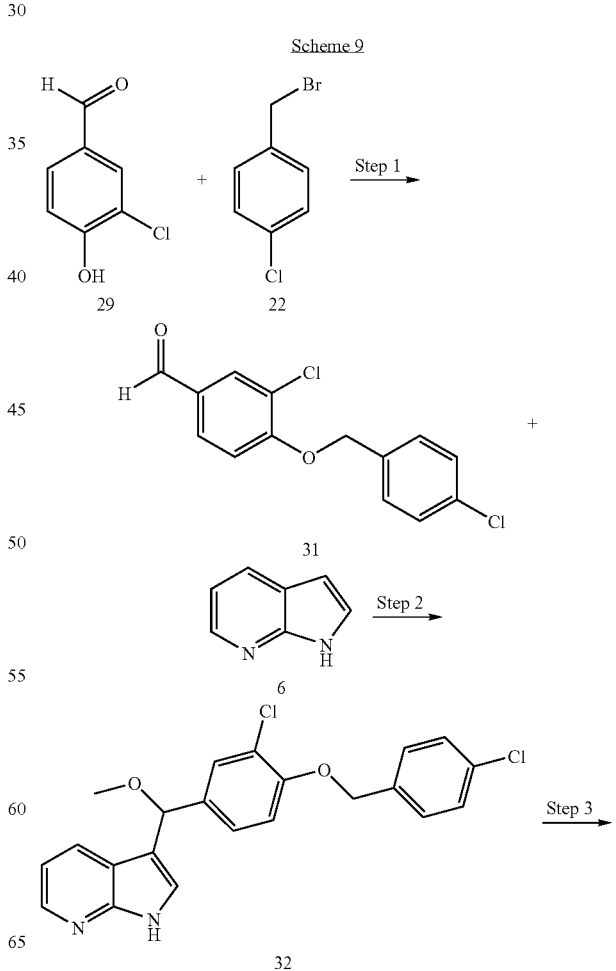

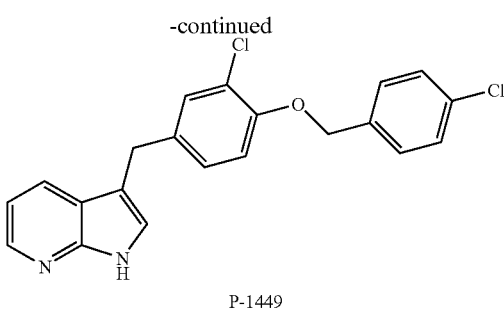

P-1449

Step 1—Preparation of 3-chloro-4-(4-chloro-benzyloxy)-benzaldehyde (31)

To acetonitrile (15.0 mL) were added 3-chloro-4-hydroxy-benzaldehyde (29, 0.6 g, 4 mmol), 4-chlorobenzyl bromide (22, 1.2 g, 6 mmol), and potassium carbonate (0.9 g, 7 mmol). The reaction was heated to 150° C. for 10 minutes in a CEM Discover microwave instrument. The reaction was poured into water, extracted with ethyl acetate, and washed with brine. The organic layer was dried over anhydrous sodium sulfate, filtered and concentrated. The desired compound was isolated by silica gel column chromatography (ethyl acetate: hexanes) (31, 0.85 g, 76%).

Step 2—Preparation of 3-[3-chloro-4-(4-chloro-benzyloxy)-phenyl]-methoxy-methyl-1H-pyrrolo[2,3-b]pyridine (32)

1H-Pyrrolo[2,3-b]pyridine (6, 0.3 g, 2.8 mmol) was mixed with 3-chloro-4-(4-chloro-benzyloxy)-benzaldehyde (31, 0.8 g, 3 mmol), potassium hydroxide (0.9 g, 17 mmol) and methanol (90.0 mL). The reaction was heated to 50° C. under an atmosphere of nitrogen for six days. After neutralization with 6N hydrochloric acid the reaction was poured into water, extracted with ethyl acetate, and washed with brine. The organic layer was dried over anhydrous sodium sulfate, filtered and concentrated. The desired compound was isolated by silica gel column chromatography (ethyl acetate:hexanes) to give a yellow solid (32, 0.6 g, 41%). MS (ESI) [M+H$^+$]$^+$= 413.2, 415.2 [M−H$^+$]$^-$=411.1, 413.1.

Step 3—Preparation of 3-[3-chloro-4-(4-chloro-benzyloxy)-benzyl]-1H-pyrrolo[2,3-b]pyridine (P-1449)

3-[3-Chloro-4-(4-chloro-benzyloxy)-phenyl]-methoxy-methyl-1H-pyrrolo[2,3-b]pyridine (32, 0.2 g, 0.6 mmol) was mixed with trifluoroacetic acid (0.226 mL, 3 mmol), triethylsilane (0.4 mL, 3 mmol) and acetonitrile (5 mL). The reaction was heated at 50° C. and stirred for two days. The reaction was concentrated. The residue was diluted with ethyl acetate and neutralized with 2M aqueous sodium hydroxide. The reaction was poured into water, extracted with ethyl acetate, and washed with brine. The organic layer was dried over anhydrous sodium sulfate, filtered and concentrated. The desired compound was isolated by silica gel column chromatography (ethyl acetate:hexanes) to give a yellow solid (P-1449, 0.0744 g, 33%). MS (ESI) [M+H$^+$]$^+$=383.2, 385.2.

Additional compounds were prepared following the protocol of Scheme 9, replacing 3-chloro-4-hydroxy-benzaldehyde 29 with an appropriate aldehyde and optionally replacing 4-chlorobenzyl bromide 22 with an appropriate benzyl halide in Step 1, and optionally replacing 1H-pyrrolo[2,3-b]pyridine 6 with an appropriate azaindole (7-azaindole (5-chloro-7-azaindole per Example 4 or 5-methoxy-7-azaindole per Example 8) in Step 2. The following compounds were made following this procedure:

3-[4-(4-chloro-benzyloxy)-2-methoxy-benzyl]-1H-pyrrolo[2,3-b]pyridine (P-1450),

3-[4-(4-Chloro-benzyloxy)-benzyl]-1H-pyrrolo[2,3-b]pyridine (P-1462),

3-[4-(4-Chloro-benzyloxy)-3-fluoro-5-methoxy-benzyl]-1H-pyrrolo[2,3-b]pyridine (P-1466), 3-[4-(4-Chloro-benzyloxy)-3-ethoxy-benzyl]-1H-pyrrolo[2,3-b]pyridine (P-1470), 3-[2-Chloro-4-(4-chloro-benzyloxy)-benzyl]-1H-pyrrolo[2,3-b]pyridine (P-1471), 3-[4-(4-Chloro-benzyloxy)-3-trifluoromethoxy-benzyl]-1H-pyrrolo[2,3-b]pyridine (P-1487), 3-[4-(4-Chloro-benzyloxy)-3-methoxy-benzyl]-5-methoxy-1H-pyrrolo[2,3-b]pyridine (P-1531), 5-Chloro-3-[4-(4-chloro-benzyloxy)-3-methoxy-benzyl]-1H-pyrrolo[2,3-b]pyridine (P-1532), 3-[4-(4-Chloro-2-fluoro-benzyloxy)-3-methoxy-benzyl]-1H-pyrrolo[2,3-b]pyridine (P-1544), 3-[4-(2,4-Dichloro-benzyloxy)-3-methoxy-benzyl]-1H-pyrrolo[2,3-b]pyridine (P-1568), 3-[3-Methoxy-4-(4-methoxy-benzyloxy)-benzyl]-1H-pyrrolo[2,3-b]pyridine (P-1569), 3-[3-Methoxy-4-(2,4,6-trifluoro-benzyloxy)-benzyl]-1H-pyrrolo[2,3-b]pyridine (P-1578), 3-[4-(2,6-Dichloro-benzyloxy)-3-methoxy-benzyl]-1H-pyrrolo[2,3-b]pyridine (P-1579), and 3-[3-Chloro-4-(4-chloro-benzyloxy)-5-methoxy-benzyl]-1H-pyrrolo[2,3-b]pyridine (P-1616).

The following table indicates the aldehyde (Column 2), the benzyl halide (Column 3), and the azaindole (Column 4) used to afford the target compound (Column 5). Column 1 indicates the compound number and column 6 the observed mass.

| | Aldehyde | Benzyl halide | Azaindole | Compound | MS(ESI) [M + H$^+$]$^+$ observed |
|---|---|---|---|---|---|
| P-1450 | | | | | 379.2 381.2 |

-continued
| | Aldehyde | Benzyl halide | Azaindole | Compound | MS(ESI) [M + H⁺]⁺ observed |
|---|---|---|---|---|---|
| P-1462 | 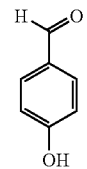 | 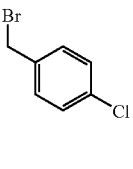 | 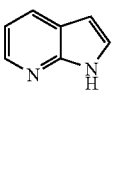 | 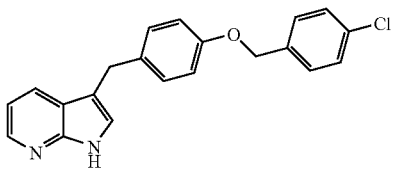 | 349.1 351.2 |
| P-1466 | 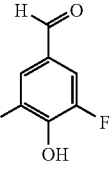 | 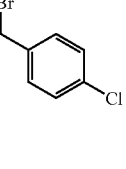 | 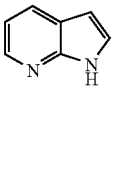 | 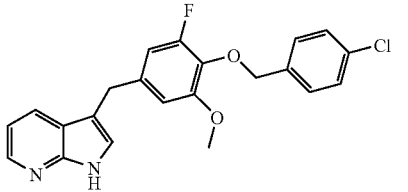 | 397.2 399.2 |
| P-1470 | 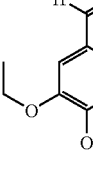 | 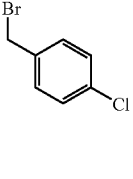 | 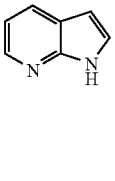 | 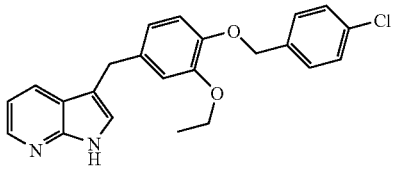 | 393.2 395.2 |
| P-1471 | 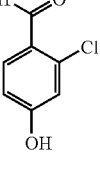 | 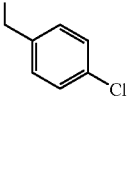 | 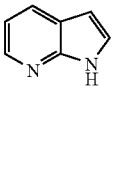 | 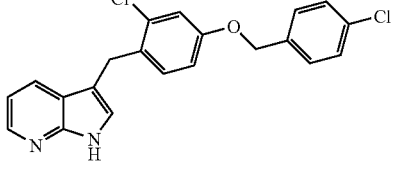 | 383.1 385.1 |
| P-1487 | 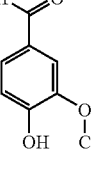 | 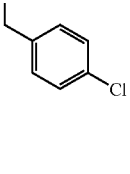 | 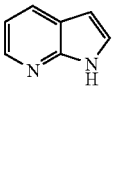 | 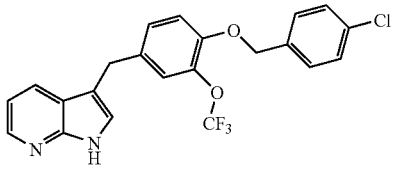 | 433.2 435.2 |
| P-1531 | 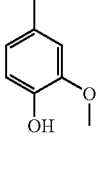 | 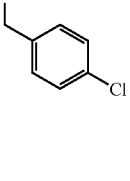 | 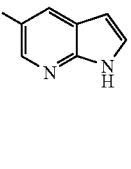 | 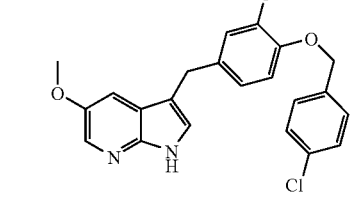 | 409.2 |
| P-1532 | 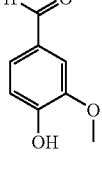 | 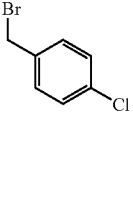 | 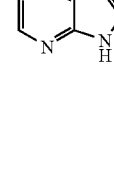 |  | 413.1 |

-continued
| | Aldehyde | Benzyl halide | Azaindole | Compound | MS(ESI) [M + H+]+ observed |
|---|---|---|---|---|---|
| P-1544 | | | | | 397.2 |
| P-1568 | | | | | 413.1 415.1 416.2 |
| P-1569 | | | | | 375.2 |
| P-1578 | | | | | 399.2 397.1 ([M − H+]−) |
| P-1579 | | | | | 413.2 415.2 416.2 ([M − H+]−) |
| P-1616 | | | | | 413.1 |
Example 14
Synthesis of 3-(4-benzyloxy-3-methoxy-benzyl)-1H-pyrrolo[2,3-b]pyridine P-1613
Compound P-1613 was synthesized in two steps from 4-benzyloxy-3-methoxy-benzaldehyde 33 as shown in Scheme 10.
Scheme 10
-continued

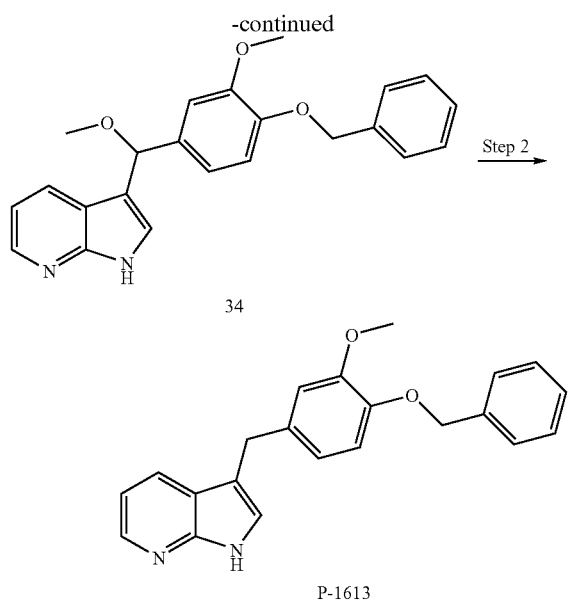

34

P-1613

Step 1—Preparation of 3-[(4-benzyloxy-3-methoxy-phenyl)-methoxy-methyl]-1H-pyrrolo[2,3-b]pyridine (34)

Methanol (125 mL) and potassium hydroxide (4.4 g, 79 mmol) were mixed with 1H-pyrrolo[2,3-b]pyridine (6, 3.1 g, 26.6 mmol) and 4-benzyloxy-3-methoxy-benzaldehyde (33, 12.9 g, 53.2 mmol). The reaction was stirred at room temperature for 2 days. The resulting white solid was filtered and washed with water, Crude material was carried forward without further purification.

Step 2—Preparation of 3-(4-benzyloxy-3-methoxy-benzyl)-1H-pyrrolo[2,3-b]pyridine (P-1613)

The crude 3-[(4-benzyloxy-3-methoxy-phenyl)-methoxy-methyl]-1H-pyrrolo[2,3-b]pyridine (34, 0.9 g, 2.4 mmol) from step 1 and acetonitrile (50 mL) were mixed with trifluoroacetic acid (0.360 mL, 4.7 mmol) and triethylsilane (0.746 mL, 4.7 mmol). The reaction was heated at 80° C. and stirred overnight. The reaction was concentrated. The mixture was extracted with ethyl acetate and saturated sodium bicarbonate. The organic layer was dried over anhydrous sodium sulfate, filtered and concentrated. The desired compound was isolated by silica gel column chromatography to give the compound (P-1613, 0.454 g 54.8%). MS (ESI) [M+H$^+$]$^+$= 345.3.

Example 15

Synthesis of Aldehyde Reagents for Coupling to 7-azaindoles

Aldehyde compounds for coupling to the 3-position of a 7-azaindole are shown in the following Schemes. 3-Methoxy-4-[4-(4-methyl-piperazin-1-ylmethyl)-benzyloxy]-benzaldehyde 37 was prepared in one Step as shown in Scheme 11.

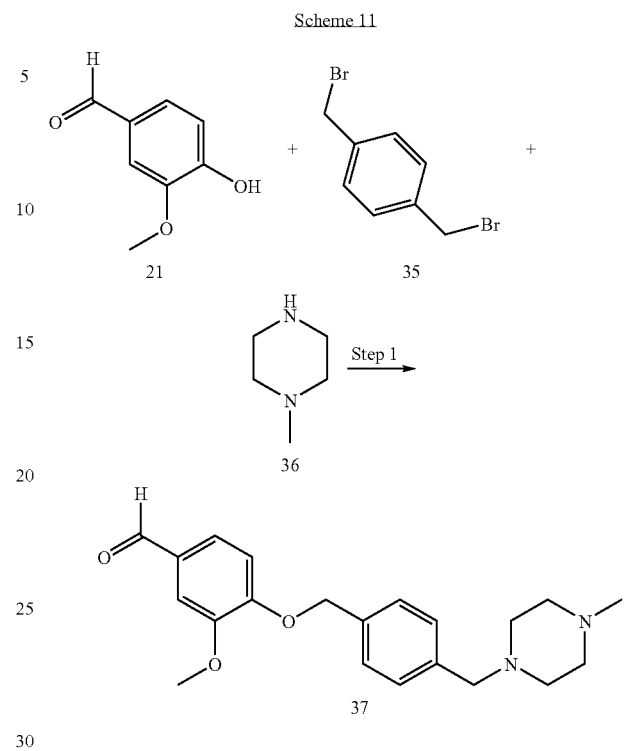

Step 1—Synthesis of 3-methoxy-4-[4-(4-methyl-piperazin-1-ylmethyl)-benzyloxy]-benzaldehyde (37)

To 4-hydroxy-3-methoxybenzaldehyde (21, 2.1 g, 0.014 mol) in N,N-dimethylformamide (40.0 mL) were added 1,4-bis(bromomethyl)-benzene (35, 4.00 g, 0.0152 mol) and potassium carbonate (5.0 g, 0.036 mol) under an atmosphere of nitrogen. After 12 hours 1-methyl-piperazine (36, 3.8 mL, 0.034 mol) was added to the reaction. After 2 hours, the reaction was poured into water and extracted with ethyl acetate. The organic layer was dried over anhydrous sodium sulfate and filtered. The filtrate was concentrated and purified by silica gel column chromatography eluting with 20% methanol in dichloromethane to give the compound (37, 1.2 g, 25.0%). MS (ESI) [M+H$^+$]$^+$=355.3.

2-Fluoro-4-hydroxy-5-methoxy-benzaldehyde 39 was synthesized in one step from 2-fluoro-4,5-dimethoxy-benzaldehyde 38 as shown in Scheme 12.

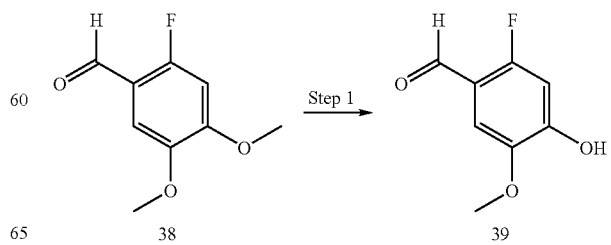

Step 1—Synthesis of 2-fluoro-4-hydroxy-5-methoxy-benzaldehyde (39)

To 2-fluoro-4,5-dimethoxy-benzaldehyde (38, 1.00 g, 5.43 mol) in dichloromethane (50.0 mL) was added aluminum trichloride (4.34 g, 32.6 mm 1) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and washed with ethyl acetate and hexane to give a white solid (39, 0.70 g, 76.0%).

2,5-Difluoro-4-hydroxy-benzaldehyde 43 was synthesized in three steps from 2,5-difluorophenol 40 as shown in Scheme 13.

under an atmosphere of nitrogen at −78° C., n-butyllithium (3.90 mL, 2.50 M in hexane) was added slowly. After 30 minutes, N,N-dimethylformamide (0.825 mL, 0.0106 mol) was added to the reaction. One hour later, the reaction was allowed to come to room temperature. The reaction was poured into water and 1 N HCl, then extracted with ethyl acetate. The organic layer was dried over anhydrous sodium sulfate and filtered. The filtrate was concentrated and purified by silica gel column chromatography eluting with 10% to 100% ethyl acetate in hexane to give the compound as an off-white solid (43, 0.86 g, 59.0%).

4-(4-Chloro-benzyloxy)-3-fluoro-benzaldehyde 46 was synthesized in one step from 3-fluoro-4-hydroxy-benzaldehyde 44 as shown in Scheme 14.

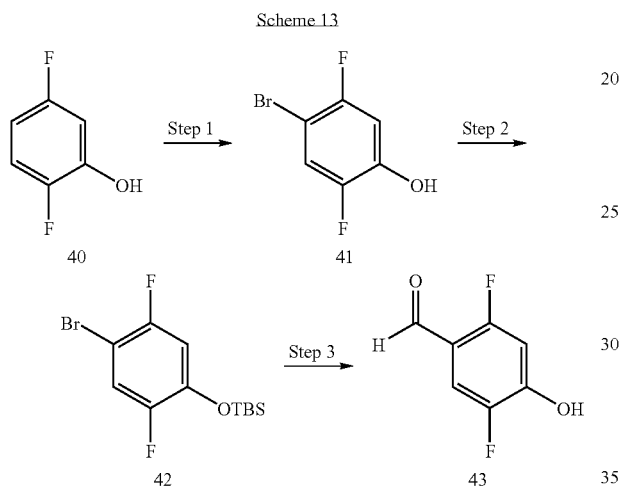

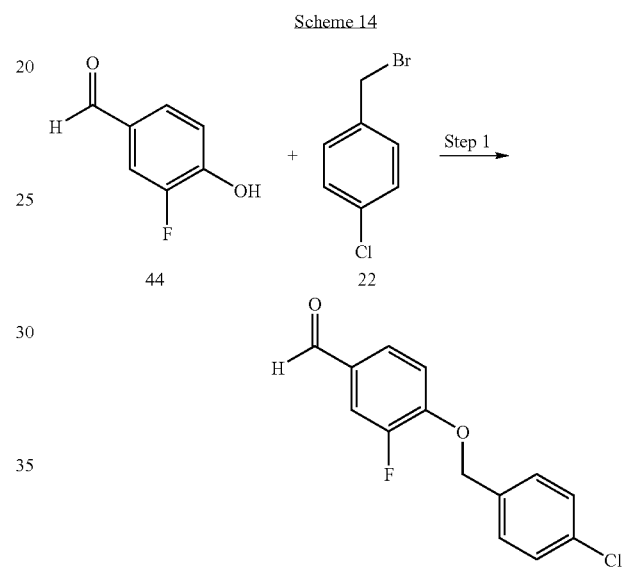

Step 1—Synthesis of 4-bromo-2,5-difluoro-phenol (41)

To 2,5-difluorophenol (40, 5.50 g, 0.0423 mol) in chloroform (110.0 mL), bromine (2.18 mL, 0.0423 mol) was added slowly. After 3 hours, the reaction was poured into a solution of sodium thiosulfate and extracted with ethyl acetate. The organic layer was dried over sodium sulfate, concentrated and purified with silica gel column chromatography eluting with 20% ethyl acetate in hexane to give a colorless oil (41, 6.20 g, 70.2%).

Step 2—(4-Bromo-2,5-difluoro-phenoxy)-tert-butyl-dimethyl-silane (42)

To 4-bromo-2,5-difluoro-phenol (41, 3.50 g, 0.0167 mol) in N,N-dimethylformamide (50.0 mL) were added tert-butyldimethylsilyl chloride (3.83 g, 0.0254 mol) and 1H-imidazole (6.00 g, 0.0529 mmol). The reaction was stirred at room temperature overnight, then poured into water and extracted with ethyl acetate. The organic layer was dried over anhydrous sodium sulfate and filtered. The filtrate was concentrated and purified by silica gel column chromatography eluting with 4% to 20% ethyl acetate in hexane to give the compound (42, 3.0 g, 55.4%).

Step 3—2,5-Difluoro-4-hydroxy-benzaldehyde (43)

To (4-bromo-2,5-difluoro-phenoxy)-tert-butyl-dimethyl-silane (42, 3.00 g, 9.28 mmol) in tetrahydrofuran (37.5 mL),

Step 1—Synthesis of 4-(4-chloro-benzyloxy)-3-fluoro-benzaldehyde (46)

To 3-fluoro-4-hydroxy-benzaldehyde (44, 0.800 g, 5.71 mmol) in N,N-dimethylformamide (50.0 mL) was added sodium hydride (260.0 mg, 60% in mineral oil, 6.50 mmol). After 15 minutes, 4-chlorobenzyl bromide (22, 1.29 g, 6.28 mmol) was added to the reaction mixture. The reaction was stirred at 80° C. for 5 hours. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give the compound (46, 1.3 g, 86.0%).

Additional aldehydes were prepared using the protocol of Scheme 14, replacing either 4-chlorobenzyl bromide 22 with a suitable alkylating agent, and/or 3-fluoro-4-hydroxy-benzaldehyde 44 with a suitable aldehyde. The following table indicates the alkylating agent (column 1) and the starting aldehyde (column 2) used to afford the aldehyde (column 3) synthesized following this protocol.

| Alkylating agent | Aldehyde | Compound |
|---|---|---|

-continued

| Alkylating agent | Aldehyde | Compound |
|---|---|---|

| Alkylating agent | Aldehyde | Compound |
|---|---|---|
| -continued | | |

Example 16

Synthesis of [4-(4-chloro-benzyloxy)-3-fluoro-phenyl]-(1H-pyrrolo[2,3-b]pyridin-3-yl)-methanone P-1897 and related compounds Compound P-1897 was synthesized in two steps from 4-(4-chloro-benzyloxy)-3-fluoro-benzaldehyde 46 as shown in Scheme 15.

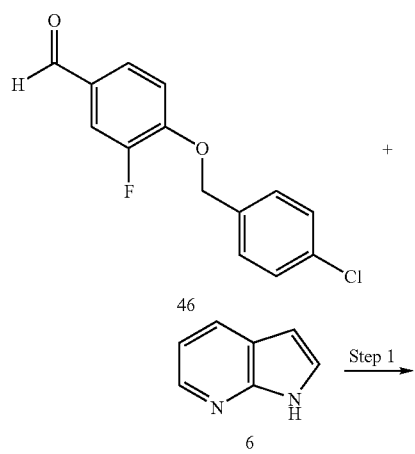

Scheme 15

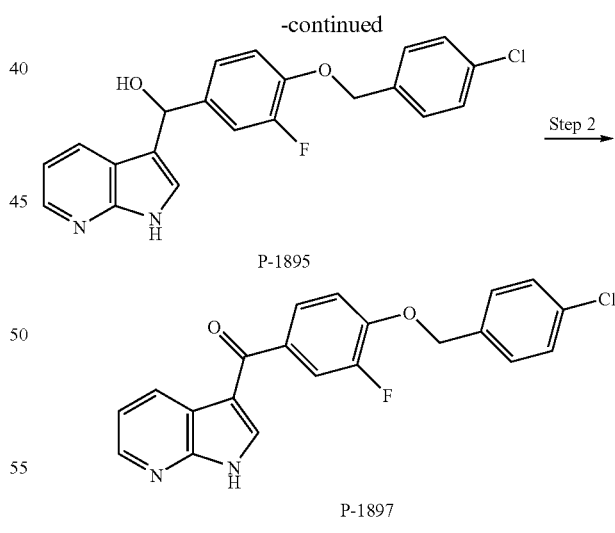

Step 1—Synthesis of [4-(4-chloro-benzyloxy)-3-fluoro-phenyl]-(1H-pyrrolo[2,3-b]pyridin-3-yl)-methanol (P-1895)

To 1H-Pyrrolo[2,3-b]pyridine (6, 100.0 mg, 0.85 mmol) in methanol (50.0 mL) were added 4-(4-chloro-benzyloxy)-3-fluoro-benzaldehyde (46, 250.0 mg, 0.94 mmol, prepared as described in Example 15) and potassium hydroxide (1.00 g, 17.82 mmol) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give the compound (P-1895, 55 mg, 17.0%). MS (ESI) $[M+H^+]^+$=383.3.

Step 2—Synthesis of [4-(4-chloro-benzyloxy-fluoro-phenyl]-(1H-pyrrolo[2,3-b]pyridin-3-yl)-methanone (P-1897)

To [4-(4-chloro-benzyloxy)-3-fluoro-phenyl]-(1H-pyrrolo[2,3-b]pyridin-3-yl)-methanol (P-1895, 17.7 mg, 0.046 mmol) in tetrahydrofuran (10.0 mL) was added Dess-Martin periodinane (23.5 mg, 0.056 mmol). The reaction was stirred at room temperature for 15 minutes. The reaction was concentrated, then purified with silica gel column chromatography eluting with 50% ethyl acetate in hexane to give a white solid (P-1897, 6.4 mg, 36.3%). MS (ESI) $[M+H^+]^+$=381.3.

Additional compounds were prepared using the protocol of Scheme 15, replacing 4-4-(4-chloro-benzyloxy)-3-fluoro-benzaldehyde 46 with a suitable aldehyde (prepared as described in Examples 15 or 34), and optionally replacing 1H-Pyrrolo[2,3-b]pyridine 6 with an appropriate substituted 7-azaindole (5-chloro-7-azaindole per Example 4,5-methoxy-7-azaindole per Example 8, or 5-(1-methyl-1H-pyrazol-4-yl)-7-azaindole per Example 35) in Step 1. The following compounds were made following this procedure:

[4-(4-Chloro-benzyloxy)-2-fluoro-5-methoxy-phenyl]-(1H-pyrrolo[2,3-b]pyridin-3-yl)-methanone (P-1845),
[4-(4-Chloro-3-trifluoromethyl-benzyloxy)-3-methoxy-phenyl]-(1H-pyrrolo[2,3-b]pyridin-3-yl)-methanone (P-1850),
[4-(1H-Benzoimidazol-2-ylmethoxy)-3-fluoro-phenyl]-(1H-pyrrolo[2,3-b]pyridin-3-yl)-methanone (P-1900),
(4-Benzyloxy-2,5-difluoro-phenyl)-(1H-pyrrolo[2,3-b]pyridin-3-yl)-methanone (P-1903),
[4-(1H-Benzoimidazol-2-ylmethoxy)-2-fluoro-5-methoxy-phenyl]-(5-methoxy-1H-pyrrolo[2,3-b]pyridin-3-yl)-methanone (P-1979),
[4-(1H-Benzoimidazol-2-ylmethoxy)-2-fluoro-5-methoxy-phenyl]-(1H-pyrrolo[2,3-b]pyridin-3-yl)-methanone (P-1982),
[4-(1H-Benzoimidazol-2-ylmethoxy)-2,5-difluoro-phenyl]-(1H-pyrrolo[2,3-b]pyridin-3-yl)-methanone (P-1987),
{4-[2-(2-Bromo-ethoxy)-ethoxy]-2-fluoro-5-methoxy-phenyl}-(5-chloro-1H-pyrrolo[2,3-b]pyridin-3-yl)-methanone (P-1988),
(5-Chloro-1H-pyrrolo[2,3-b]pyridin-3-yl)-[2,5-difluoro-4-(2-methoxy-ethoxy)-phenyl]-methanone (P-1989),
(5-Chloro-1H-pyrrolo[2,3-b]pyridin-3-yl)-[2-fluoro-5-methoxy-4-(2-methoxy-ethoxy)-phenyl]-methanone (P-1991),
2-[2-Chloro-5-fluoro-4-(5-methoxy-1H-pyrrolo[2,3-b]pyridin-3-ylmethyl)-phenoxymethyl]-1H-benzoimidazole (P-2116),
2-{2-Chloro-5-fluoro-4-[5-(1-methyl-1H-pyrazol-4-yl)-1H-pyrrolo[2,3-b]pyridin-3-ylmethyl]-phenoxymethyl}-1H-benzoimidazole (P-2117),
2-[2,5-Difluoro-4-(5-methanesulfonyl-1H-pyrrolo[2,3-b]pyridin-3-ylmethyl)-phenoxymethyl]-1H-benzoimidazole (P-2170),
3-[4-(1H-Benzoimidazol-2-ylmethoxy)-2-fluoro-5-methoxy-benzyl]-1H-pyrrolo[2,3-b]pyridine-5-carbonitrile (P-2171),
3-[4-(1H-Benzoimidazol-2-ylmethoxy)-2-fluoro-5-methoxy-benzyl]-1H-pyrrolo[2,3-b]pyridine-5-carboxylic acid methyl ester (P-2174),
2-{2,5-Difluoro-4-[5-(2-methoxy-ethoxy)-1H-pyrrolo[2,3-b]pyridin-3-ylmethyl]-phenoxymethyl}-1H-benzoimidazole (P-2176),
2-[4-(5-Bromo-1H-pyrrolo[2,3-b]pyridin-3-ylmethyl)-5-fluoro-2-methoxy-phenoxymethyl]-1H-benzoimidazole (P-2181),
3-[4-(1H-Benzoimidazol-2-ylmethoxy)-2,5-difluoro-benzyl]-1H-pyrrolo[2,3-b]pyridine-5-carbonitrile (P-2185), and
2-[5-Fluoro-4-(5-methanesulfonyl-1H-pyrrolo[2,3-b]pyridin-3-ylmethyl)-2-methoxy-phenoxymethyl]-1H-benzoimidazole (P-2186).

The following table indicates the aldehyde (column 2) and the azaindole (column 3) used to afford the target compound (column 4). Column 1 indicates the compound number and column 5 the observed mass.

| | Aldehyde | Azaindole |
|---|---|---|
| P-1845 | | |

-continued
P-1850 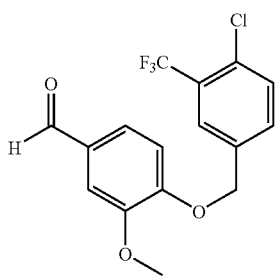 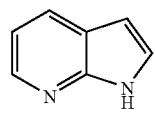
P-1900 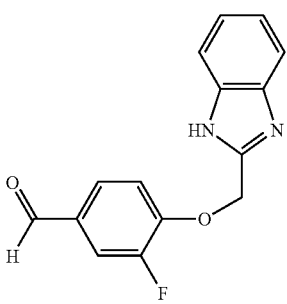 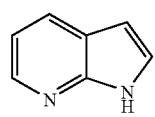
P-1903 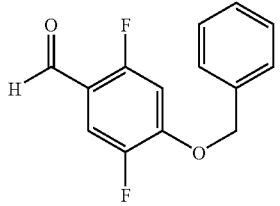 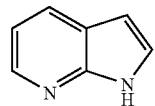
P-1979 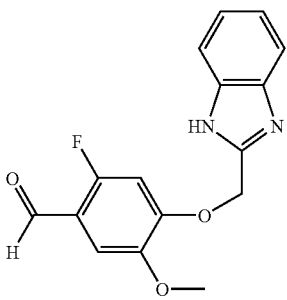 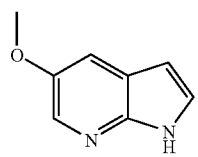
P-1982 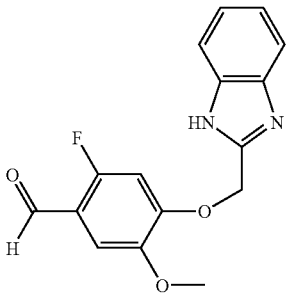 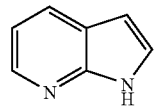

-continued
P-1987 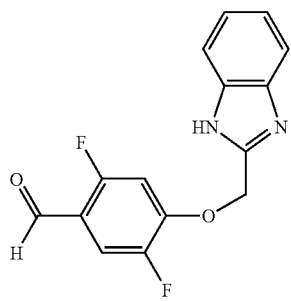 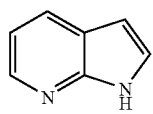
P-1988 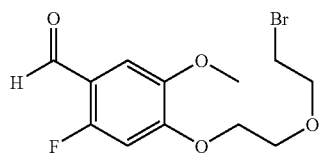 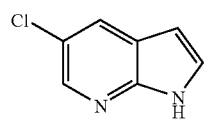
P-1989 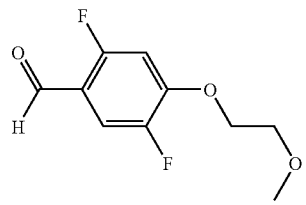 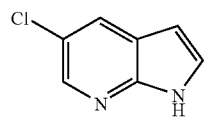
P-1991 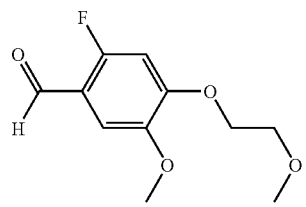 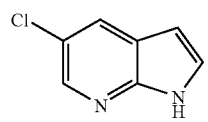
P-2116 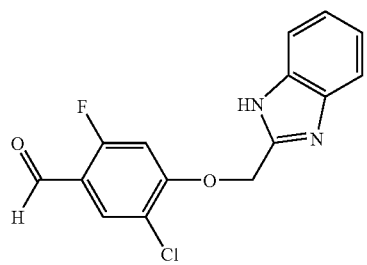 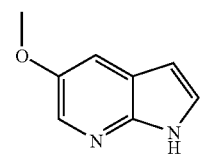
P-2117 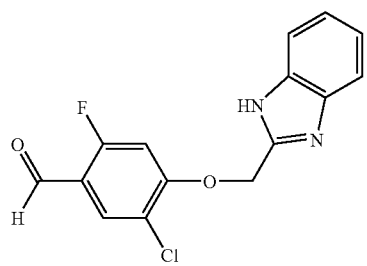 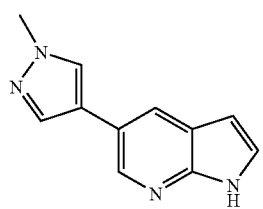

-continued
P-2170 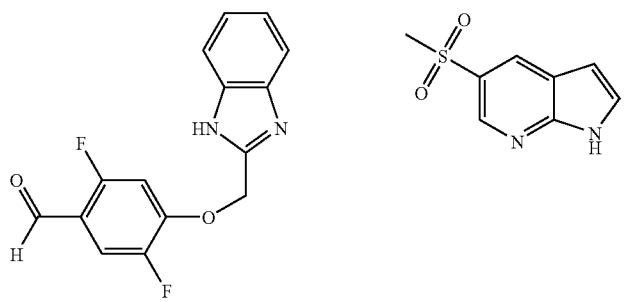
P-2171 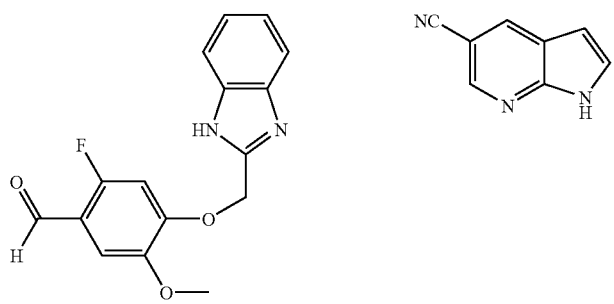
P-2174 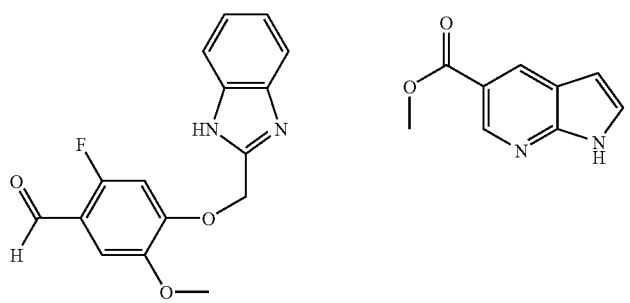
P-2176 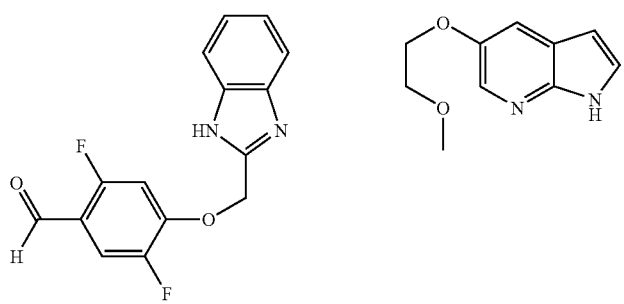
P-2181 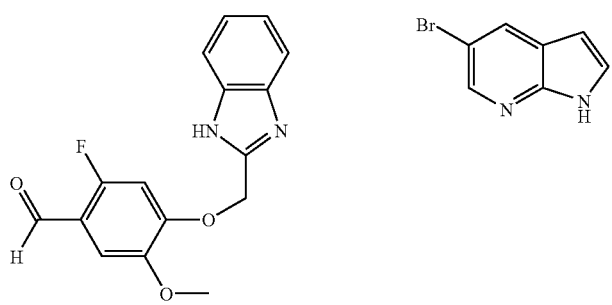

-continued
| | | |
|---|---|---|
| P-2185 | 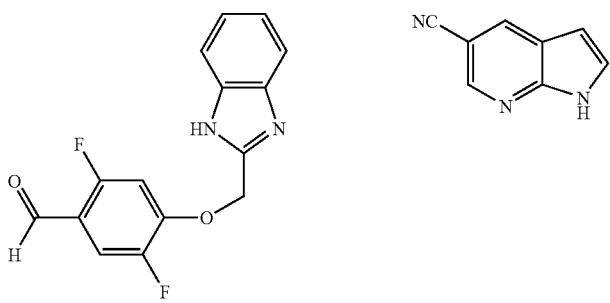 | |
| P-2186 | 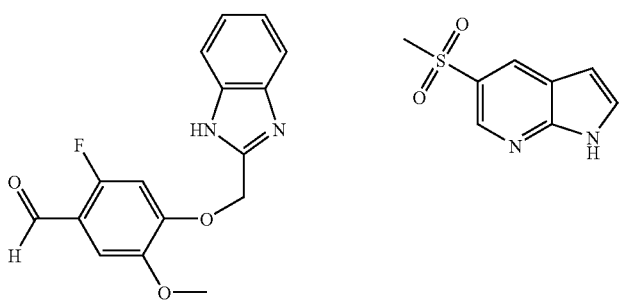 | |
| | Compound | MS (ESI) [M + H+]+ observed |
|---|---|---|
| P-1845 | 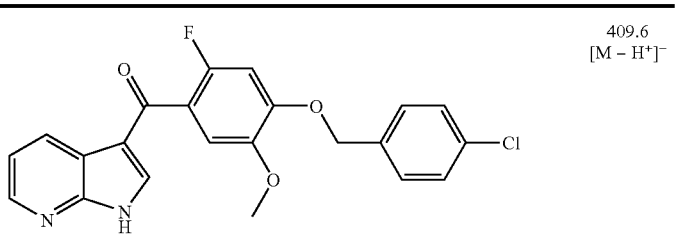 | 409.6 [M − H+]− |
| P-1850 | 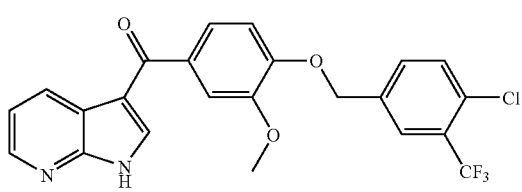 | |
| P-1900 | 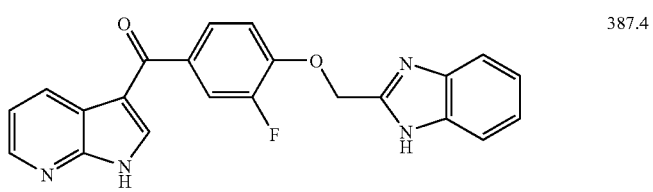 | 387.4 |
| P-1903 | 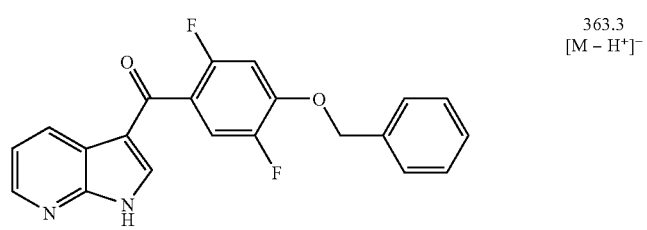 | 363.3 [M − H+]− |

-continued
| | | |
|---|---|---|
| P-1979 | 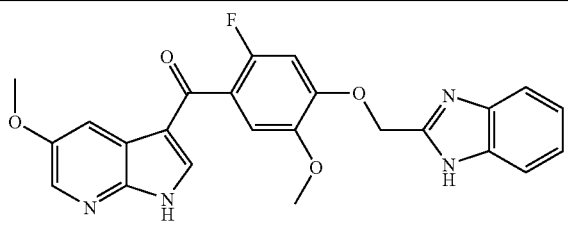 | 447.4 |
| P-1982 | 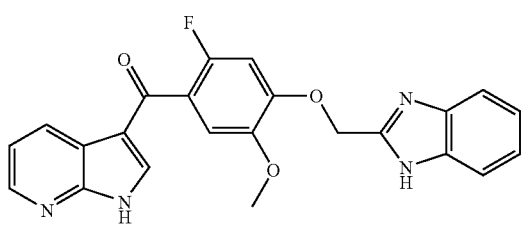 | 417.3 |
| P-1987 | 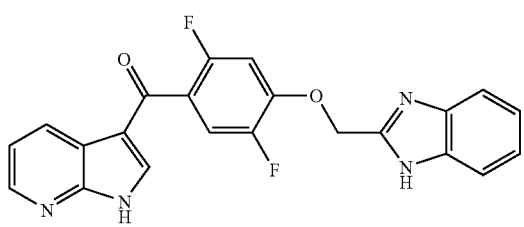 | 405.3 |
| P-1988 | 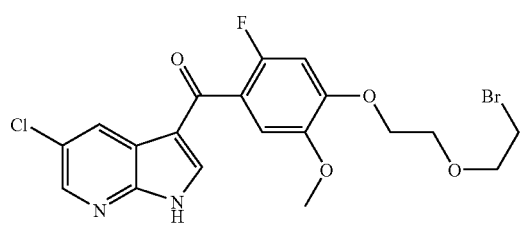 | 471.2<br>473.2 |
| P-1989 | 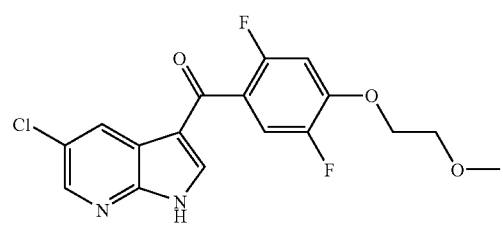 | 365.2<br>[M − H$^+$]$^-$ |
| P-1991 | 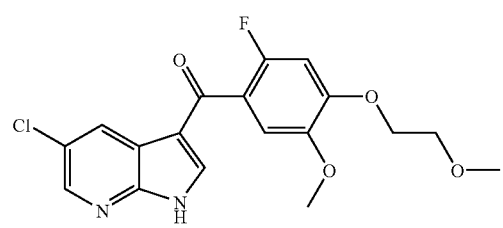 | 377.2<br>[M − H$^+$]$^-$ |
| P-2116 | 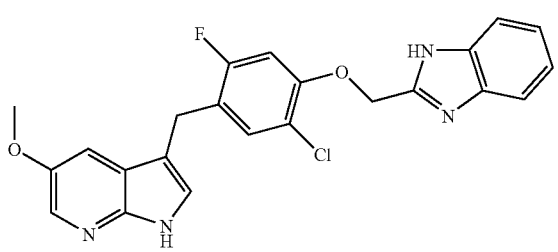 | |

-continued
P-2117 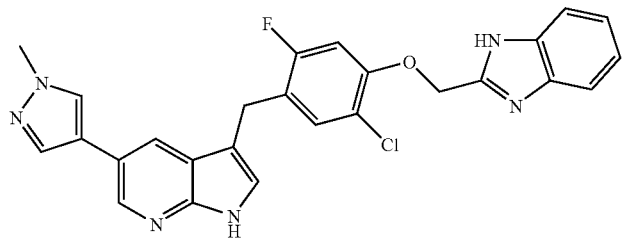
P-2170 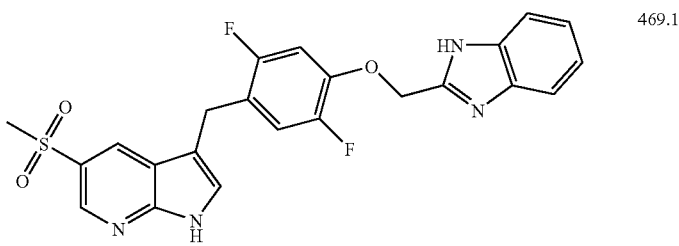 469.1
P-2171 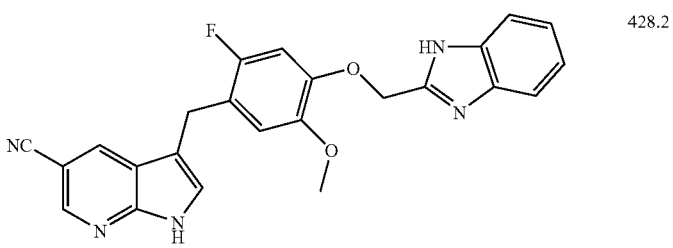 428.2
P-2174 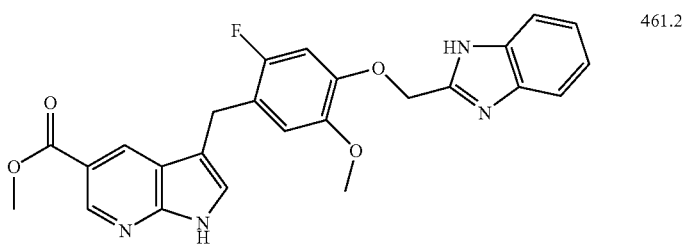 461.2
P-2176 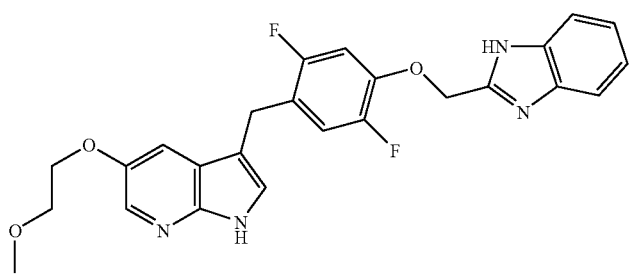 464.9
P-2181 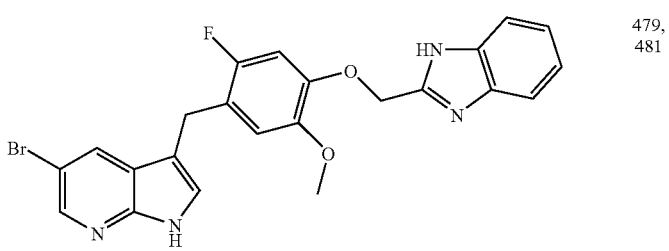 479, 481

P-2185

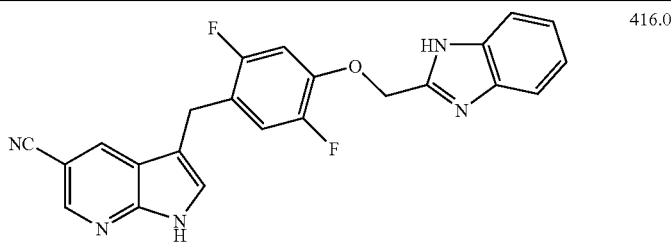

416.0

P-2186

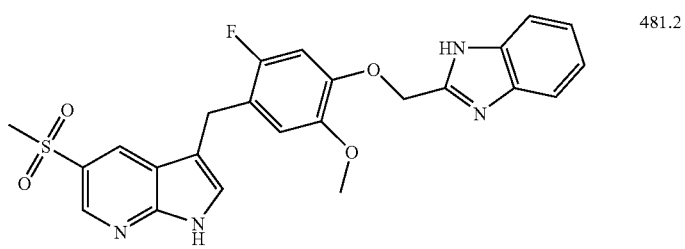

481.2

Example 17

Synthesis of 3-(4-Benzyloxy-2,5-difluoro-benzyl)-1H-pyrrolo[2,3-b]pyridine P-1901

Compound P-1901 was synthesized in four steps from 4-bromo-2,5-difluoro-phenol 41 as shown in Scheme 16.

Scheme 16

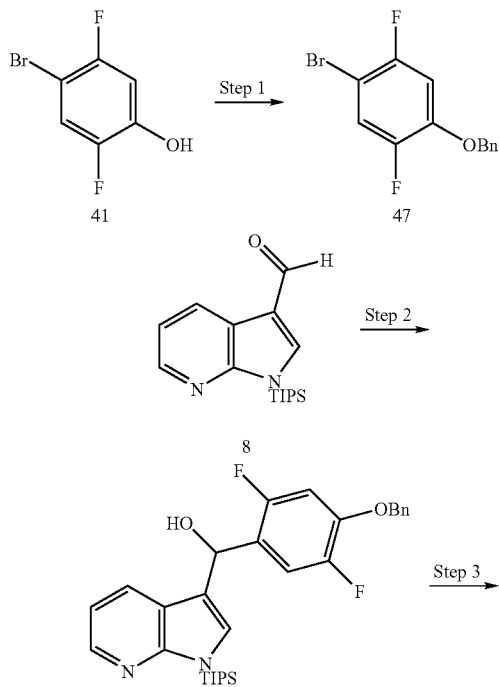

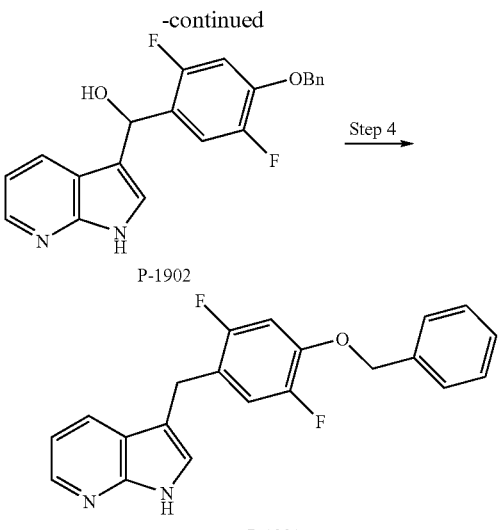

Step 1—Synthesis of 1-Benzyloxy-4-bromo-2,5-difluoro-benzene (47)

To 4-bromo-2,5-difluoro-phenol (41, 0.90 g, 0.0043 mol, prepared as described in Example 15, Scheme 3) in N,N-dimethylformamide (30.0 mL) were added sodium hydride (0.21 g, 60% in mineral oil, 0.0052 mol) and benzyl bromide (0.563 mL, 0.00474 mol). The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 5% ethyl acetate in hexane to give a white solid (47, 0.84 g, 65.0%).

Step 2—(4-Benzyloxy-2,5-difluoro-phenyl)-(1-tri-isopropylsilanyl-1H-pyrrolo[2,3-b]pyridin-3-yl)-methanol (48)

To 1-Benzyloxy-4-bromo-2,5-difluoro-benzene (47, 0.84 g, 2.80 mmol) in tetrahydrofuran (15.0 mL) and ether (15.0 mL), under an atmosphere of nitrogen at −78° C., n-butyl-lithium (1.20 mL, 2.50 M in hexane) was added slowly. After 20 minutes, 1-Triisopropylsilanyl-1H-pyrrolo[2,3-b]pyridine-3-carbaldehyde (8, 0.82 g, 0.0027 mol, prepared as described in Example 5) was added to the reaction. After 20 minutes, the reaction was allowed to warm to room temperature for 10 minutes, then poured into water and extracted with ethyl acetate. The organic layer was dried over anhydrous sodium sulfate and filtered. The filtrate was concentrated and purified with silica gel column chromatography eluting with 20% ethyl acetate in hexane to a white solid (48, 10 g, 70.0%).
MS (ESI) [M+H$^+$]$^+$=523.4.

Step 3—Synthesis of (4-Benzyloxy-2,5-trifluoro-phenyl)-(1H-pyrrolo[2,3-b]pyridin-3-yl)-methanol (P-1902)

To (4-Benzyloxy-2,5-difluoro-phenyl)-(1-triisopropylsilanyl-1H-pyrrolo[2,3-b]pyridin-3-yl)-methanol (48, 1.00 g, 1.91 mmol) in tetrahydrofuran (15.0 mL) was added tetrabutylammonium fluoride, trihydrate (0.63 g, 2.04 mmol). The reaction was stirred at room temperature for 10 minutes. The reaction was roto-evaporated and purified with silica gel column chromatography eluting with 50% ethyl acetate in hexane to give the compound as a white solid (P-1902, 0.59 g, 84.0%). MS (ESI) [M+H$^+$]$^+$=367.4.

Step 4—Synthesis of 3-(4-Benzyloxy-2,5-difluoro-benzyl)-1H-pyrrolo[2,3-b]pyridine (P-1901)

To (4-Benzyloxy-2,5-difluoro-phenyl)-(1H-pyrrolo[2,3-b]pyridin-3-yl)-methanol (P-1902, 500.0 mg, 1.37 mmol) in acetonitrile (25.0 mL) were added triethylsilane (2.00 mL, 0.0125 mol) and trifluoroacetic acid (1.00 mL, 0.0130 mol). The reaction was heated to reflux for 2 hours. The reaction was concentrated and purified with silica gel column chromatography eluting with 50% ethyl acetate in hexane to give a white solid (P-1901, 60.0 mg, 94.1%). MS (ESI) [M+H$^+$]$^+$ 351.4.

3-[3-Trifluoromethyl-4-(4-trifluoromethyl-benzyloxy)-benzyl]-1H-pyrrolo[2,3-b]pyridine P-1797

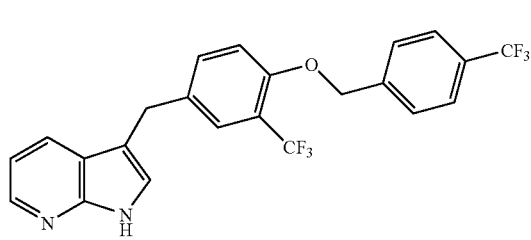

was prepared using the protocol of Scheme 16, substituting 4-bromo-2,5-difluoro-phenol 41 with 4-bromo-2-trifluoromethyl-phenol (prepared as described in Example 15, Scheme 13, Step 1, substituting 2,5-difluoro-phenol 40 with 2-trifluoromethyl-phenol) and benzyl bromide with 1-bromomethyl-4-trifluoromethyl-benzene in Step 1. MS (ESI) [M+H$^+$]$^+$= 451.

Example 18

Synthesis of 3-[4-(4-chloro-benzyloxy)-2,5-difluoro-benzyl]-1H-pyrrolo[2,3-b]pyridine P-1974

Compound P-1974 was synthesized in four steps from 3-(4-benzyloxy-2,5-difluoro-benzyl)-1H-pyrrolo[2,3-b]pyridine P-1901 as shown in Scheme 17.

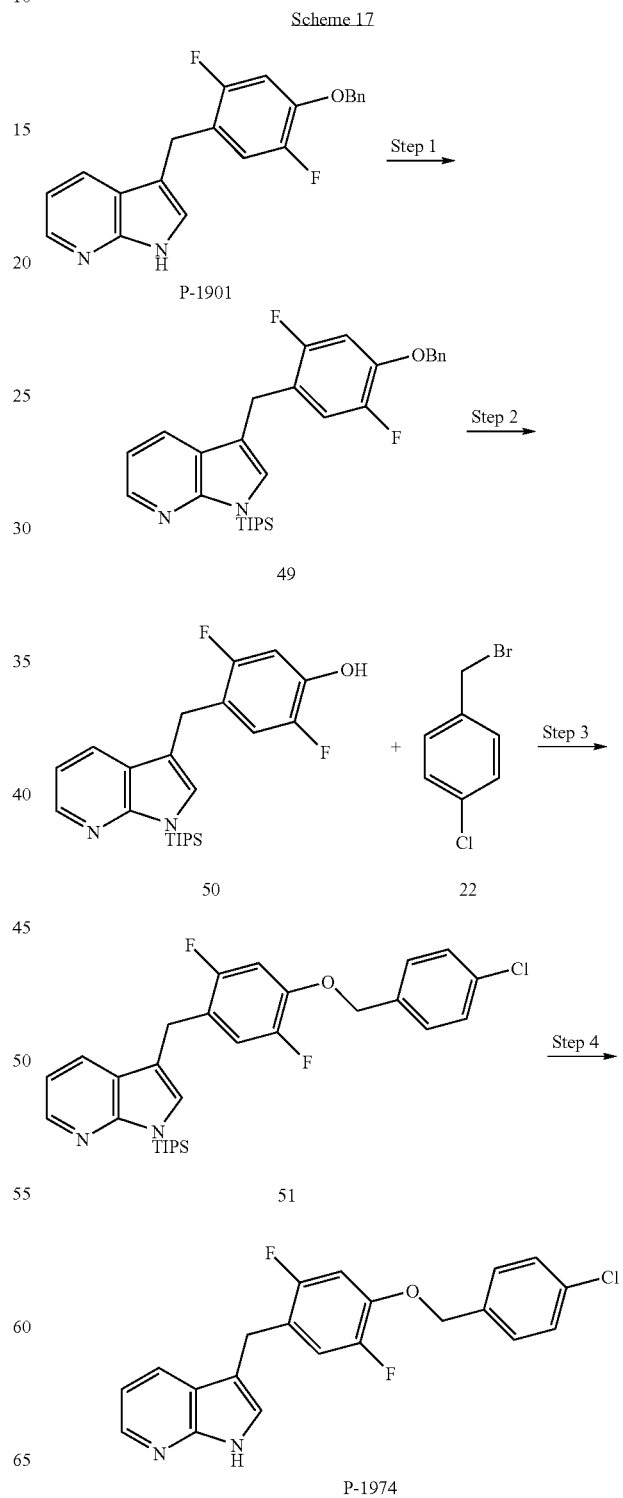

Step 1—Synthesis of 3-(4-benzyloxy-2,5-difluoro-benzyl)-1-triisopropylsilanyl-1H-pyrrolo[2,3-b]pyridine (49)

To 3-(4-benzyloxy-2,5-difluoro-benzyl)-1H-pyrrolo[2,3-b]pyridine (P-1901, 560.0 mg, 1.60 mmol, prepared as described in Example 17) in tetrahydrofuran (28.0 mL) was added sodium hydride (100.0 mg, 60% in mineral oil, 2.50 mmol). After 10 minutes, triisopropylsilyl chloride (0.500 mL, 2.36 mmol) was added to the reaction. After 4 hours, the reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give the compound (49, 0.70 g, 86.1%).

Step 2—Synthesis of 2,5-difluoro-4-(1-triisopropyl-silanyl-1H-pyrrolo[2,3-b]pyridin-3-ylmethyl)-phenol (50)

To 3-(4-Benzyloxy-2,5-difluoro-benzyl)-1-triisopropylsilanyl-1 yl-pyrrolo[2,3-b]pyridine (49, 0.70 g, 0.0014 mol) in methanol (30.0 mL) was added 50% palladium hydroxide on carbon (0.1 g) under an atmosphere of hydrogen. The reaction was stirred at room temperature overnight. The reaction was filtered and concentrated to give a colorless oil (50, 0.47 g, 82.0%).

Step 3—3-[4-(4-Chloro-benzyloxy)-2,5-difluoro-benzyl]-1-triisopropylsilanyl-1-1H-pyrrolo[2,3-b]pyridine (51)

To 2,5-difluoro-4-(1-triisopropylsilanyl-1H-pyrrolo[2,3-b]pyridin-3-ylmethyl)-phenol (50, 120.0 mg, 0.29 mmol) in N,N-dimethylformamide (15.0 mL) was added sodium hydride (18.0 mg, 60% in mineral oil, 0.45 mol) under an atmosphere of nitrogen. After 10 minutes, 4-chlorobenzyl bromide (22, 65.1 mg, 0.32 mol) was added to the reaction. The reaction was stirred at 40° C. overnight. The reaction was poured into water and extracted with ethyl acetate. The organic layer was dried over anhydrous sodium sulfate, and filtered. The filtrate was concentrated to give the crude compound (51, 0.15 g) that was used directly in the next step.

Step 4—Synthesis of 3-[4-(4-chloro-benzyloxy)-2,5-difluoro-benzyl]-1H-pyrrolo[2,3-b]pyridine (P-1974)

To 3-[4-(4-chloro-benzyloxy)-2,5-difluoro-benzyl]-1-triisopropylsilanyl-1H-pyrrolo[2,3-b]pyridine (51, 0.150 g, 0.28 mmol) in tetrahydrofuran (10.0 mL) was added tetra-n-butylammonium fluoride (80.0 mg, 0.31 mmol). After 10 minutes, the reaction was concentrated and purified by silica gel column chromatography eluting with 50% ethyl acetate in hexane to give the compound as a white solid (P-1974, 30.8 mg, 28.9%). MS (ESI) [M+H$^+$]$^+$=385.3.

2-[2,5-Difluoro-4-(1H-pyrrolo[2,3-b]pyridin-3-ylmethyl)-phenoxymethyl]-1H-benzoimidazole P-1975

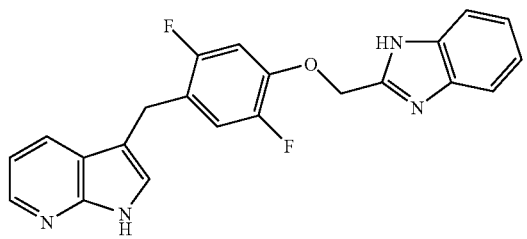

was prepared using the protocol of Scheme 17, substituting 4-chlorobenzyl bromide 22 with 2-chloromethyl-1H-benzoimidazole in step 3. MS (ESI) [M+H$^+$]$^+$=391.3.

Example 19

Synthesis of 3-(3-Benzyloxy-2-chloro-6-fluoro-benzyl)-1H-pyrrolo[2,3-b]pyridine P-1852, (3-Benzyloxy-2-chloro-6-fluoro-phenyl)-(1H-pyrrolo[2,3-b]pyridin-3-yl)-methanone P-1853 and Related Compounds Compounds P-1852 and P-1853 were synthesized in four steps from 2-chloro-4-fluorophenol 52 and 1H-pyrrolo[2,3-b]pyridine 6 as shown in Scheme 18.

Scheme 18

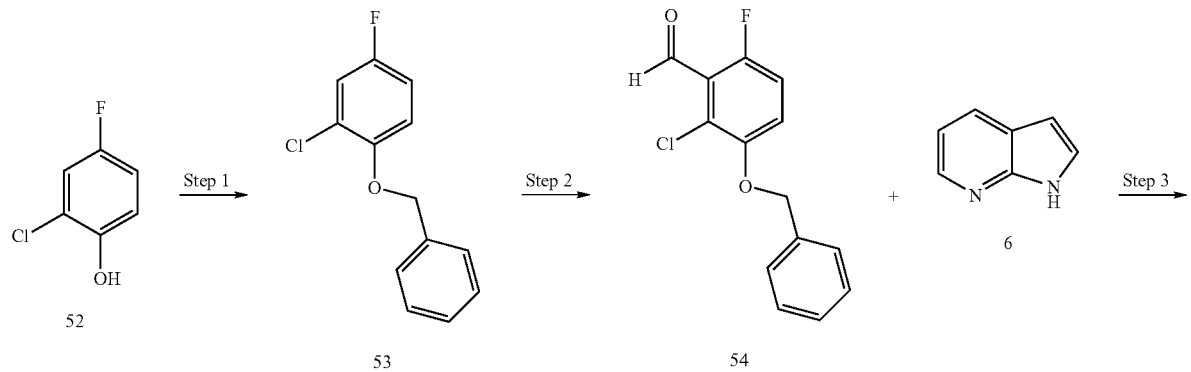

-continued

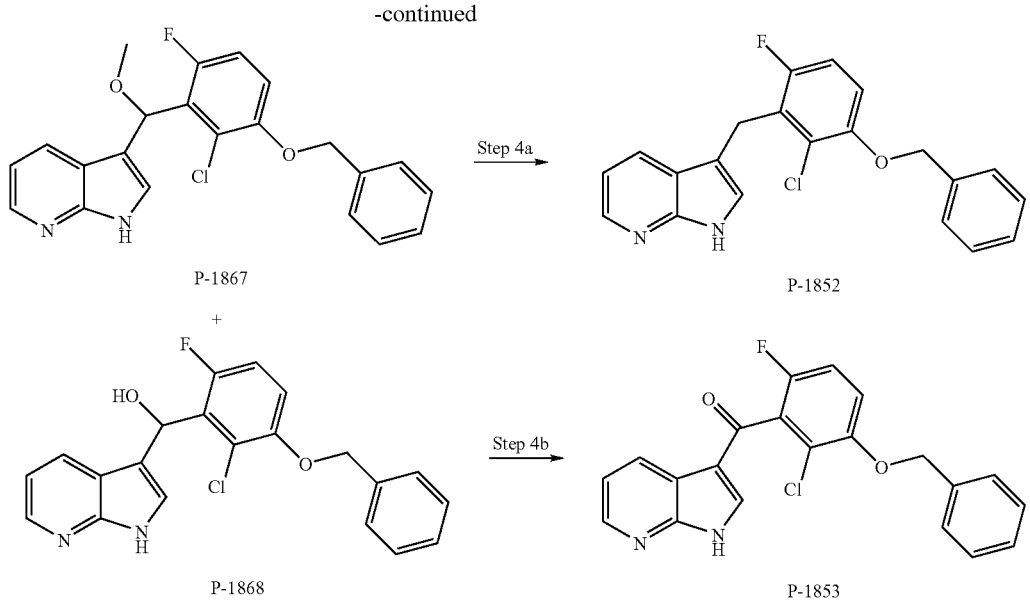

Step 1—Preparation of 1-Benzyloxy-2-chloro-4-fluoro-benzene (53)

To a solution of 2-chloro-4-fluorophenol (52, 7 g, 0.05 mol) in tetrahydrofuran (100 mL) was added sodium hydride (1.8 g, 95% dry powder, 0.071 mol) at room temperature over 15 minutes under an atmosphere of nitrogen. The reaction mixture was stirred at room temperature for 30 minutes. Benzyl bromide (10 g, 0.060 mol) was added slowly to the reaction mixture, then stirred at room temperature overnight. The reaction mixture was poured into ice water, extracted with ethyl acetate, washed with hydrochloric acid (10%), water, brine, and dried over magnesium sulfate. After removal of solvent, the residue was purified by silica gel column chromatography eluting with ethyl acetate in hexane to provide compound as a white solid (53, 7.6 g, 60%).

Step 2—Preparation of 3-Benzyloxy-2-chloro-6-fluoro-benzaldehyde (54)

To a solution of 1-benzyloxy-2-chloro-4-fluoro-benzene (53, 5.8 g, 0.024 mol) in tetrahydrofuran (100 mL) was added 2.50 M of n-butyllithium (2.7 mL, 2.50 M in hexane, 0.029 mol) slowly at −78° C. over 15 minutes under nitrogen. The reaction mixture was stirred at −78° C. for 30 minutes. To the reaction mixture was then added N,N-dimethylformamide (4.2 mL, 0.054 mol). The reaction was allowed to warm to room temperature and was continued at room temperature overnight. The reaction mixture was poured into ice water, extracted with ethyl acetate, washed with hydrochloric acid (10%), water, brine, and dried over magnesium sulfate. After removal of solvent, the residue was purified by silica gel column chromatography eluting with ethyl acetate in hexane to provide the compound as a white solid (54, 2.1 g, 32%). MS (ESI) [M+H$^+$]$^+$=265.08.

Step 3—Preparation of 3-[(3-Benzyloxy-2-chloro-6-fluoro-phenyl)-methoxy-methyl]-1H-pyrrolo[2,3-b]pyridine (P-1867) and (3-Benzyloxy-2-chloro-6-fluoro-phenyl)-(1H-pyrrolo[2,3-b]pyridin-3-yl)-methanol (P-1868)

A mixture of 1H-pyrrolo[2,3-b]pyridine (6, 0.5 g, 4 mmol), 3-benzyloxy-2-chloro-6-fluoro-benzaldehyde (54, 1.3 g, 4.9 mmol), and potassium hydroxide (0.99 g, 18 mmol) in methanol (30 mL) was stirred at room temperature overnight. The reaction mixture was concentrated and the residue was dissolved in ethyl acetate and water. The organic layer was collected and washed with brine. After removal of solvent, the residue was purified by silica gel column chromatography eluting with ethyl acetate in hexane to provide compound P-1867 as a white solid (1.3 g, 70%. MS (ESI) [M+H$^+$]$^+$= 397.16), and compound P-1868 as an off-white solid (0.2 g, 10, MS (ESI) [M+H$^+$]$^+$=383.14).

Step 4a—Preparation of 3-(3-benzyloxy-2-chloro-6-fluoro-benzyl)-1H-pyrrolo[2,3-b]pyridine (P-1852)

A mixture of 3-[(3-benzyloxy-2-chloro-6-fluoro-phenyl)-methoxy-methyl]-1H-pyrrolo[2,3-b]pyridine (P-1867, 0.1 g, 0.2 mmol), trifluoroacetic acid (0.6 mL, 8 mmol), and triethylsilane (0.3 mL, 2 mmol) in acetonitrile (10 mL) was refluxed for 2 hours. The mixture was concentrated and the residue was dissolved in ethyl acetate. The solution was washed with saturated sodium bicarbonate, brine, and dried over sodium sulfate. After removal of solvent, the residue was purified by silica gel column chromatography eluting with methanol in dichloromethane to provide compound as an off-white solid (P-1852, 62 mg, 70%). MS (ESI) [M+H$^+$]$^+$= 367.16.

Step 4b—Preparation of (3-benzyloxy-2-chloro-6-fluoro-phenyl)-(1H-pyrrolo[2,3-b]pyridin-3-yl)-methanone (P-1853)

To a solution of (3-benzyloxy-2-chloro-6-fluoro-phenyl)-(1-pyrrolo[2,3-b]pyridin-3-yl)-methanol (P-1868, 65 mg, 0.17 mmol) in tetrahydrofuran (10 mL) was added Dess-Martin periodinane (79 mg, 0.19 mmol) at 0° C. The reaction mixture was stirred at room temperature for 2 hours. The reaction was quenched with a saturated solution of sodium thiosulfate, extracted with ethyl acetate, washed with sodium bicarbonate, brine, and dried over magnesium sulfate. After removal of solvent, the residue was purified by silica gel column chromatography eluting with methanol in dichloromethane to provide the compound as a light yellow solid (P-1853, 32 mg, 50%). MS (ESI) [M+H$^+$]$^+$=381.13.

Additional compounds were prepared following the protocol of Scheme 18, optionally replacing 2-chloro-4-fluorophenol 52 with 2,6-difluorophenol or 2,6-dichlorophenol, optionally replacing benzyl bromide with an appropriate substituted benzyl bromide, and optionally replacing 1H-pyrrolo[2,3-b]pyridine 6 with an appropriate substituted 1H-pyrrolo[2,3-b]pyridine (5-chloro-7-azaindole per Example 4 or 5-methoxy-7-azaindole per Example 8). The following compounds were made following this procedure:

3-[2,6-Dichloro-3-(4-chloro-benzyloxy)-benzyl]-1H-pyrrolo[2,3-h]pyridine (P-1768),

[2,6-Dichloro-3-(4-chloro-benzyloxy)-phenyl]-(1-pyrrolo[2,3-b]pyridin-3-yl)methanone (P-1769), (3-Benzyloxy-2,6-difluoro-phenyl)-(1H-pyrrolo[2,3-b]pyridin-3-yl)-methanone (P-1802), 3-(3-Benzyloxy-2,6-difluoro-benzyl)-1H-pyrrolo[2,3-b]pyridine (P-1803), 3-(3-Benzyloxy-2,6-difluoro-benzyl)-5-methoxy-1H-pyrrolo[2,3-b]pyridine (P-1804), 3-(3-Benzyloxy-2,6-difluoro-benzyl)-5-chloro-1H-pyrrolo[2,3-b]pyridine (P-1824), (3-Benzyloxy-2,6-difluoro-phenyl)-(5-chloro-1H-pyrrolo[2,3-b]pyridin-3-yl)-methanone (P-1825),

[2-Chloro-3-(3-chloro-benzyloxy)-6-fluoro-phenyl]-(1H-pyrrolo[2,3-b]pyridin-3-yl)-methanone (P-1869).

[2-Chloro-3-(4-chloro-benzyloxy)-6-fluoro-phenyl]-(1H-pyrrolo[2,3-b]pyridin-3-yl)-methanone (P-1874), 3-[2,6-Difluoro-3-(pyridin-4-ylmethoxy)-benzyl]-1H-pyrrolo[2,3-b]pyridine (P-1993), and 3-[3-(4-Chloro-2-fluoro-benzyloxy)-2,6-difluoro-benzyl]-1H-pyrrolo[2,3-b]pyridine (P-1992).

The phenol, benzyl bromide and azaindole used in Steps 1, 2, and 3, respectively, are indicated in columns 2, 3, and 4 of the following table, respectively, to afford the target compound (column 5). The compound number is provided in column 1, and the observed mass is given in column 6.

| | Phenol | Benzyl bromide | Azaindole | Compound | MS (ESI) [M + H$^+$]$^+$ observed |
|---|---|---|---|---|---|
| P-1768 | | | | | 417.14 |
| P-1769 | | | | | 431.09 |
| P-1802 | | | | | 365.23 |

-continued

| | Phenol | Benzyl bromide | Azaindole | Compound | MS (ESI) [M + H⁺]⁺ observed |
|---|---|---|---|---|---|
| P-1803 | 2,4-difluorophenol | benzyl bromide | 7-azaindole | | 351.23 |
| P-1804 | 2,4-difluorophenol | benzyl bromide | 5-methoxy-7-azaindole | | 381.26 |
| P-1824 | 2,4-difluorophenol | benzyl bromide | 5-chloro-7-azaindole | | 385.22 |
| P-1825 | 2,4-difluorophenol | benzyl bromide | 5-chloro-7-azaindole | | 399.21 |
| P-1869 | 2-chloro-4-fluorophenol | 3-chlorobenzyl bromide | 7-azaindole | | 415.24 |
| P-1874 | 2-chloro-4-fluorophenol | 4-chlorobenzyl bromide | 7-azaindole | | 415.23 |

-continued

| | Phenol | Benzyl bromide | Azaindole | Compound | MS (ESI) [M + H+]+ observed |
|---|---|---|---|---|---|
| P-1993 | 2,4-difluorophenol | 4-(bromomethyl)pyridine | 7-azaindole | | 352.39 |
| P-1992 | 2,4-difluorophenol | 4-chloro-2-fluorobenzyl bromide | 7-azaindole | | 403.32 |

Example 20

Synthesis of (3-Benzyloxy-2-methyl-phenyl)-(1H-1-pyrrolo[2,3-b]pyridin-3-yl)-methanone P-1848 and 3-(3-Benzyloxy-2-methyl-benzyl)-1H-pyrrolo[2,3-b]pyridine P-1857

Compounds P-1848 and P-1857 were synthesized in five steps from compounds 55 and 1H-pyrrolo[2,3-b]pyridine 6 as shown in Scheme 19.

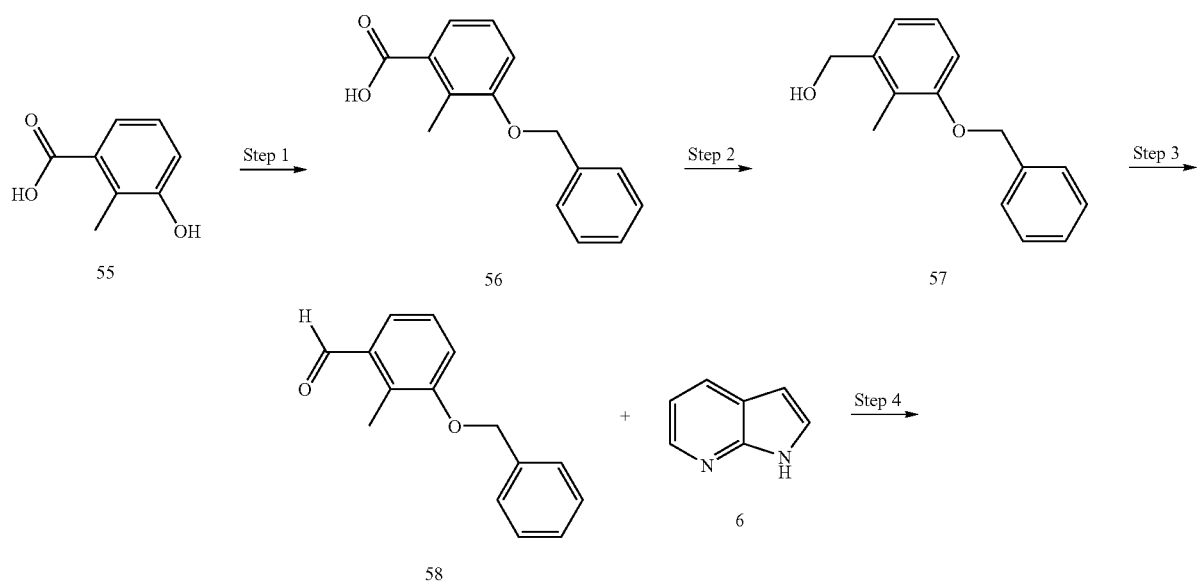

Scheme 19

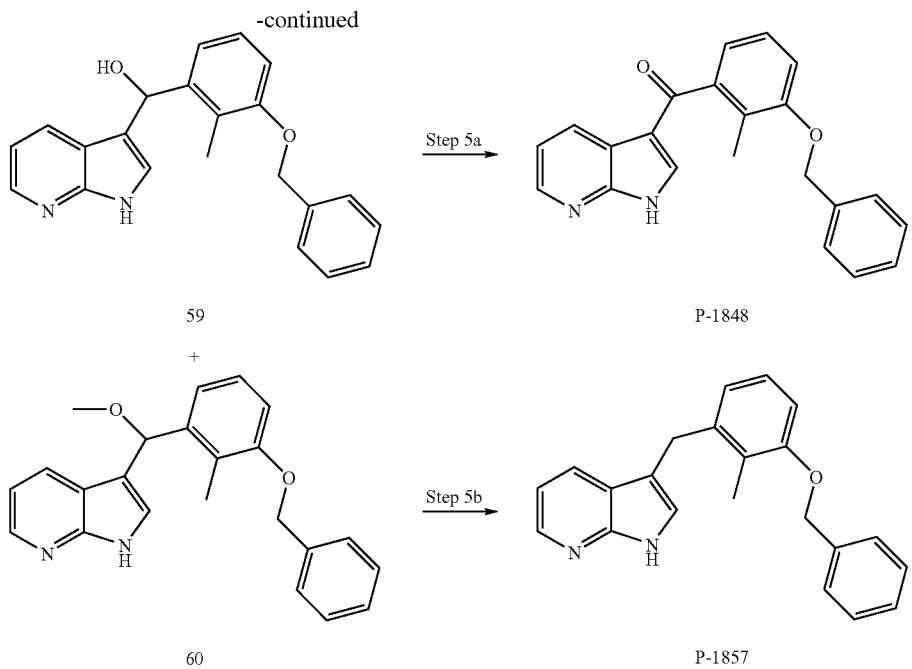

Step 1—Preparation of 3-Benzyloxy-2-methyl-benzoic acid (56)

To a solution of 3-hydroxy-2-methyl-benzoic acid (55, 5.0 g, 0.033 mol) in tetrahydrofuran (100 mL) and N,N-dimethylformamide (50 mL), sodium hydride (4.4 g as 60% dispersion in mineral oil, 0.11 mol) was added slowly over 30 minutes and the reaction was stirred at 0° C. under an atmosphere of nitrogen. The reaction mixture was allowed to warm to room temperature, then stirred at room temperature for 1 hour. Benzyl bromide (9.0 mL, 0.076 mol) was added slowly into the reaction mixture, and the reaction mixture was stirred at room temperature overnight. The reaction mixture was poured into water, extracted with ethyl acetate, washed with a solution of ammonium chloride and ammonium hydroxide (4:1), brine, and dried over magnesium sulfate. After removal of solvent, the residue was purified by silica gel column chromatography eluting with ethyl acetate in hexane to provide the compound as a white solid (56, 5.8 g, 73%).

Step 2—Preparation of (3-Benzyloxy-2-methyl-phenyl)-methanol (57)

To a solution of 3-benzyloxy-2-methyl-benzoic acid (56, 3.0 g, 0.012 mol) in tetrahydrofuran (100 mL), lithium aluminum hydride (25 mL, 1M solution in tetrahydrofuran, 0.025 mol) was added dropwise at 0° C. for 5 minutes. The reaction mixture was then stirred at room temperature overnight under an atmosphere of nitrogen. After sodium sulfate decahydrate (20.0 g, 0.062 mol) was added, the reaction mixture was stirred at room temperature for 10 minutes. A white solid was collected by filtration. The solid compound was further washed with a mixture of hexane and dichloromethane (9:1) and dried under high-vacuum (57, 2.8 g, 91%).

Step 3—Preparation of 3-Benzyloxy-2-methyl-benzaldehyde (58)

To a solution of (3-benzyloxy-2-methyl-phenyl)-methanol (57, 627 mg, 2.75 mmol) in tetrahydrofuran (60 mL) was added Dess-Martin periodinane (2.9 g, 6.87 mmol) at 0° C. The resulting mixture was stirred at 0° C. for 50 minutes. The reaction mixture was quenched with a solution of saturated sodium thiosulfate, extracted with ethyl acetate, washed with sodium bicarbonate, brine, and dried over magnesium sulfate. After removal of solvent, the residue was purified by silica gel column chromatography eluting with ethyl acetate in hexane to provide the compound as a white solid (58, 0.55 g, 84%).

Step 4—Preparation of (3-Benzyloxy-2-methyl-phenyl)-(1H-pyrrolo[2,3-b]pyridin-3-yl)-methanol (59) and 3-[(3-Benzyloxy-2-methyl-phenyl)-methoxymethyl]-1H-pyrrolo[2,3-b]pyridine (60)

A mixture of 1H-pyrrolo[2,3-b]pyridine (6, 0.33 g, 2.8 mmol), 3-benzyloxy-2-methyl-benzaldehyde (58, 0.55 g, 2.4 mmol), and potassium hydroxide (0.39 g, 6.1 mmol) in methanol (40 mL) was stirred at room temperature for 17 hours. The reaction mixture was poured into water and then extracted with ethyl acetate. The organic layer was collected, washed with brine, and dried over sodium sulfate. After removal of solvent, the residue was purified by silica gel column chromatography eluting with ethyl acetate in hexane to provide compound 59 as an off-white solid (330 mg, 39%, MS (ESI) $[M+H^+]^+$=345.29, and compound 60 as a white solid (24 mg, 3%, MS (ESI) $[M+H^+]^+$=359.30).

Step 5a—Preparation of (3-Benzyloxy-2-methyl-phenyl)-(1H-pyrrolo[2,3-b]pyridin-3-yl)-methanone (P-1848)

To a solution of (3-Benzyloxy-2-methyl-phenyl)-(1H-pyrrolo[2,3-b]pyridin-3-yl)-methanol (59, 0.12 g, 0.35 mmol) in tetrahydrofuran (15 mL) was added Dess-Martin periodinane (0.37 g, 0.89 mmol) at 0° C. The reaction mixture was stirred at 0° C. for 50 minutes, then quenched with a saturated solution of sodium thiosulfate, extracted with ethyl acetate, washed with sodium bicarbonate, brine, and dried over magnesium sulfate. After removal of solvent, the residue was washed with a mixture of ethyl ether and hexanes (1:1) to provide the compound as a yellow solid (P-1848, 108 mg, 90%). MS (ESI) [M+H$^+$]$^+$=343.22.

Step 5b—Preparation of 3-(3-Benzyloxy-2-methyl-benzyl)-1H-pyrrolo[2,3-b]pyridine (P-1857)

A mixture of 3-[(3-benzyloxy-2-methyl-phenyl)-methoxy-methyl]-1H-pyrrolo[2,3-b]pyridine (60, 24 mg, 0.067 mmol), trifluoroacetic acid (1 mL, 13 mmol), and triethylsilane (2 ml, 12.5 mmol) in acetonitrile (10 mL) was refluxed for 4 hours. The mixture was concentrated and the residue was dissolved in ethyl acetate. The solution was washed with saturated sodium bicarbonate, brine, and dried over sodium sulfate. After removal of solvent, the residue was washed with a mixture of ethyl ether and hexanes (1:1) to provide the compound as a yellow solid (P-1857, 17 mg, 75%). MS (ESI) [M+H$^+$]$^+$=329.24.

Example 21

Synthesis of [3-(4-chloro-benzyloxy)-2-ethoxy-phenyl]-(1H-pyrrolo[2,3-h]pyridin-3-yl)-methanone P-1892 and 3-[3-(4-chloro-benzyloxy)-2-ethoxy-benzyl]-1H-pyrrolo[2,3-h]pyridine P-1893

Compounds P-1892 and P-1893 were synthesized in five steps from compounds 61, 22 and 1H-pyrrolo[2,3-b]pyridine 6 as shown in Scheme 20.

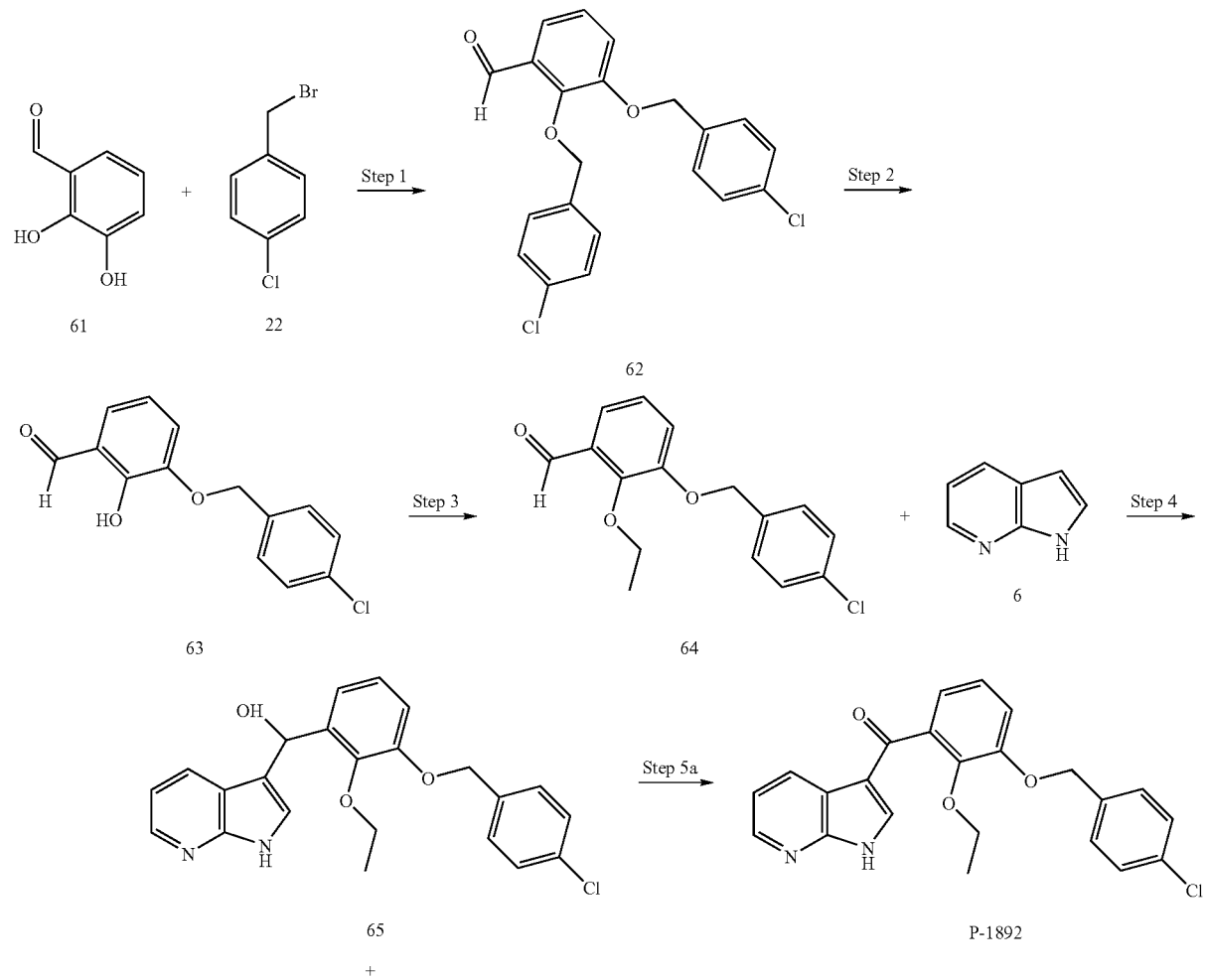

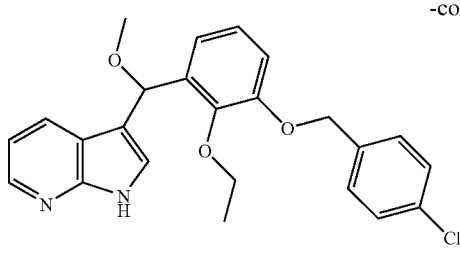

66

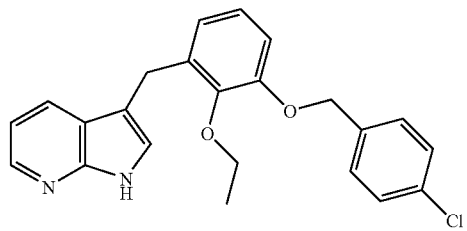

P-1893

Step 1—Preparation of 2,3-Bis-(4-chloro-benzyloxy)-benzaldehyde (62)

To a solution of 2,3-dihydroxybenzaldehyde (61, 2.0 g, 14.5 mmol) in tetrahydrofuran (100 mL) was added sodium hydride (0.52 g, 13.0 mmol) at 0° C. under an atmosphere of nitrogen. The reaction mixture was allowed to warm to room temperature and was stirred at room temperature for 30 minutes. To the reaction mixture was then added 4-chlorobenzyl bromide (22, 2.7 g, 13.0 mmol). The reaction mixture was stirred at room temperature under an atmosphere of nitrogen overnight. N,N-dimethylformamide (50 mL) was added into the reaction mixture and it was stirred at room temperature for 24 hours. The reaction mixture was poured into ice water and extracted with ethyl acetate. The organic layer was collected, washed with brine, and dried over magnesium sulfate. After removal of solvent, the residue was purified by silica gel column chromatography eluting with ethyl acetate in hexane to provide the compound as an off-white solid (62, 2.3 gm, 46%).

Step 2—Preparation of 3-(4-chloro-benzyloxy)-2-hydroxy-benzaldehyde (63)

To magnesium (0.098 g, turnings, 4.0 mmol) in a mixture of anhydrous ether (20 mL) and benzene (20 mL) at 0° C., bromine (0.10 mL, 2.0 mmol) was added dropwise. When the reaction had started, stirring was commenced and the addition of bromine continued until complete. The ice bath was removed and the reaction mixture was heated until the solution was almost colorless. After cooling down, the reaction mixture was slowly added to a solution of 2,3-bis-(4-chloro-benzyloxy)-benzaldehyde (62, 0.78 g, 2.0 mmol) in benzene (60 mL) at room temperature while stirring vigorously. Upon completion of the addition, the reaction mixture was stirred at room temperature overnight, then refluxed for 36 hours. After the reaction mixture was cooled down to room temperature, a solid was collected by filtration and washed with benzene, then boiled in hydrochloric acid (100 mL, 1.0 M) for 30 minutes. After cool down, the solution was extracted with dichloromethane. The organic layer was washed with brine and dried over magnesium sulfate. An off-white solid was obtained after removal of the solvent (63, 0.32 mg, 60%). MS (ESI) $[M-H^+]^-=261.25$.

Step 3—Preparation of 3-(4-chloro-benzyloxy)-2-ethoxy-benzaldehyde (64)

To a mixture of 3-(4-chloro-benzyloxy)-2-hydroxy-benzaldehyde (63, 110 mg, 0.42 mmol), potassium carbonate (150 mg, 1.1 mmol) in acetonitrile (8 mL) was added iodoethane (0.2 mL, 2.5 mmol) at room temperature. The mixture was stirred at 98° C. for 18 hours. The reaction mixture was poured into a solution of saturated ammonium chloride and was extracted with ethyl acetate. The organic layer was collected, washed with brine, and dried over magnesium sulfate. After removal of solvent, a light yellow solid was obtained (64, 116 mg, 95%).

Step 4—Preparation of [3-(4-chloro-benzyloxy)-2-ethoxy-phenyl]-(1H-pyrrolo[2,3-b]pyridin-3-yl)-methanol (65) and 3-{[3-(4-chloro-benzyloxy)-2-ethoxy-phenyl]-methoxy-methyl}-1H-pyrrolo[2,3-b]pyridine (66)

A mixture of 1H-Pyrrolo[2,3-b]pyridine (6, 26 mg, 0.22 mmol), 3-(4-chloro-benzyloxy)-2-ethoxy-benzaldehyde (64, 54 mg, 0.19 mmol), and potassium hydroxide (30 mg, 0.4.6 mmol) in methanol (5 mL) was stirred at room temperature for 4 days. The reaction mixture was poured into water and extracted with ethyl acetate. The organic layer was collected, washed with brine, and dried over sodium sulfate. After removal of solvent, the residue was purified by silica gel column chromatography eluting with ethyl acetate in hexane to provide compound 65 as an off-white solid (20 mg, 26%, MS (ESI) $[M+H^+]^+=409.32$) and compound 66 as an off-white solid (44 mg, 56%, MS (ESI) $[M+H^+]^+=423.33$.

Step 5a—Preparation of [3-(4-chloro-benzyloxy)-2-ethoxy-phenyl]-(1H-pyrrolo[2,3-b]pyridin-3-yl)-methanone (P-1892)

To a solution of [3-(4-chloro-benzyloxy)-2-ethoxy-phenyl]-(1H-pyrrolo[2,3-b]pyridin-3-yl)-methanol (65, 20 mg, 0.05 mmol) in tetrahydrofuran (8 mL) was added Dess-Martin periodinane (52 mg, 0.12 mmol) at 0° C. The reaction mixture was stirred at 0° C. for 50 minutes. The reaction was quenched with a saturated solution of sodium thiosulfate, extracted with ethyl acetate, washed with sodium bicarbonate, brine, and dried over magnesium sulfate. After removal of solvent, the residue was washed with a mixture of ethyl ether and hexanes (1:1) to provide the compound as a yellow solid (P-1892, 15 mg, 75%). MS (ESI) $[M+H^+]^+=407.38$.

Step 5b—Preparation of 3-[3-(4-chloro-benzyloxy)-2-ethoxy-benzyl]-1H-pyrrolo[2,3-b]pyridine (P-1893)

A mixture of 3-{[3-(4-chloro-benzyloxy)-2-ethoxy-phenyl]-methoxy-methyl}-1H-pyrrolo[2,3-b]pyridine (66, 44 mg, 0.1 mmol), trifluoroacetic acid (1 mL, 13 mmol), and triethylsilane (2 mL, 12.5 mmol) in acetonitrile (10 mL) was refluxed for 4 hours. The mixture was concentrated and the residue was dissolved in ethyl acetate. The solution was washed with saturated sodium bicarbonate, brine, and dried over sodium sulfate. After removal of solvent, the residue was washed with a mixture of ethyl ether and hexanes (1:1) to provide the compound as a yellow solid (P-1893, 40 mg, 98%). MS (ESI) [M+H⁺]⁺=393.39.

[3-(4-Chloro-benzyloxy)-2-methoxy-phenyl]-(1H-pyrrolo[2,3-b]pyridin-3-yl)-methanone (P-1891), [3-(4-Chloro-benzyloxy)-2-(2,2,2-trifluoroethoxy)-phenyl]-(1H-pyrrolo[2,3-b]pyridin-3-yl)-methanone (P-2076), [3-(4-chloro-2-fluoro-benzyloxy)-2-ethoxy-phenyl]-(5-methoxy-1H-pyrrolo[2,3-b]pyridin-3-yl)-methanone (P-2016), and 3-(4-Chloro-benzyloxy)-2-(2-fluoro-ethoxy)-phenyl]-(1H-pyrrolo[2,3-b]pyridin-3-yl)-methanone (P-2118)

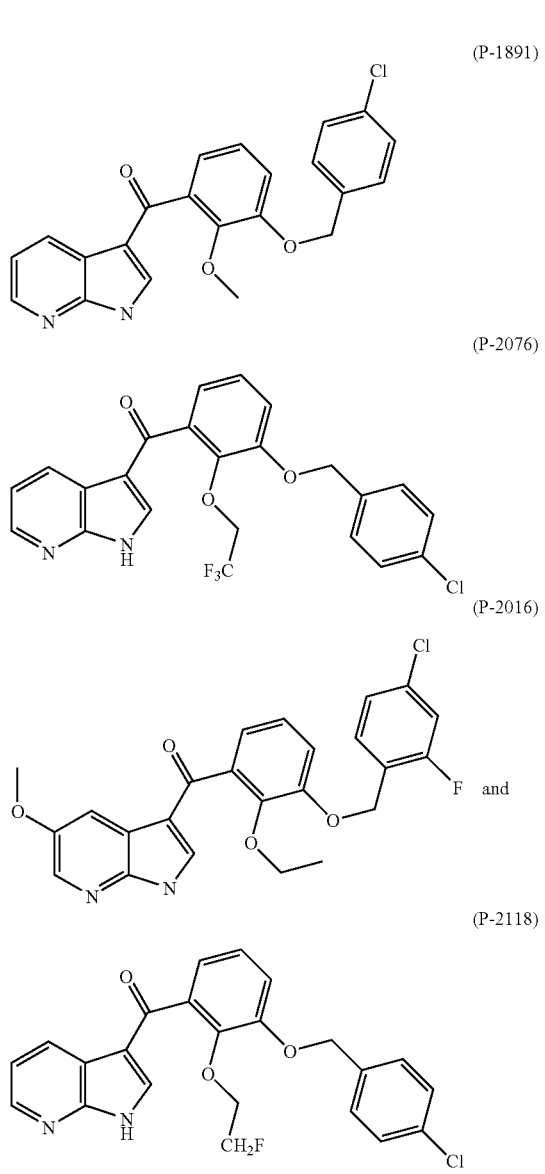

were prepared following the protocol of Scheme 20, substituting iodoethane with iodomethane in Step 3 to provide P-1891, or substituting iodoethane with 2-iodo-1,1,1-trifluoroethane in Step 3 to provide P-2076, or substituting iodoethane with 2-iodo-1-fluoroethane in Step 3 to provide P-2118, or substituting 4-chlorobenzyl bromide 22 with 4-chloro-2-fluoro-benzyl bromide in Step 1 and 7-azaindole 6 with 5-methoxy-7-azaindole in Step 4 to provide P-2016. MS (ESI) [M+H⁺]⁺=393.4 (P-1891), 461.08 (P-2076), 455.2 (P-2016), and 425.17 (P-2118).

Example 22

Synthesis of 3-Iodo-1-triisopropylsilanyl-1H-pyrrolo[2,3-b]pyridine 68

3-Iodo-1-triisopropylsilanyl-1H-pyrrolo[2,3-b]pyridine 68 was synthesized in one step from 3-Iodo-1H-pyrrolo[2,3-b]pyridine 67 as shown in Scheme 21.

Scheme 21

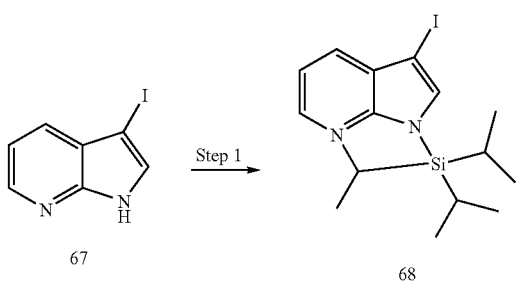

Step 1—Preparation of 3-Iodo-1-triisopropylsilanyl-1H-pyrrolo[2,3-b]pyridine (68)

3-Iodo-1H-pyrrolo[2,3-b]pyridine 67 (2.00 g, 8.20 mmol) was dissolved in N,N-dimethylformamide (50 mL). Sodium hydride (60% dispersion in mineral oil, 390 mg, 9.8 mmol) was added. After 20 minutes, triisopropylsilyl chloride (1.74 mL, 8.20 mmol) was added dropwise. After 1.5 hours, the reaction was poured into water and extracted with ethyl acetate, washed with saturated sodium bicarbonate and brine. The organic portions were dried over anhydrous sodium sulfate and concentrated. Purification by silica gel chromatography, 0-25% gradient ethyl acetate/hexane gave compound 68 as a white solid (3.224 g, 98.2%). ¹H-NMR was consistent with the desired compound.

Example 23

Synthesis of 1-(tert-Butyl-dimethyl-silanyl)-3-iodo-1H-pyrrolo[2,3-b]pyridine 69

1-(tert-Butyl-dimethyl-silanyl)-3-iodo-1H-pyrrolo[2,3-b]pyridine 69 was synthesized in one step from 3-Iodo-1H-pyrrolo[2,3-b]pyridine 67 as shown in Scheme 22.

Scheme 22

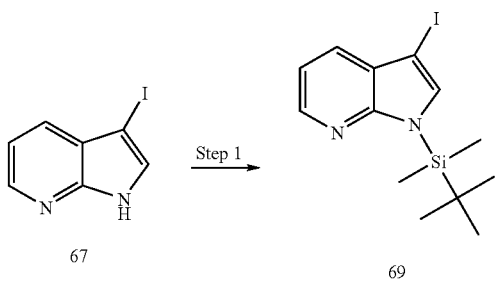

Step 1—Preparation a 1-(tert-Butyl-dimethyl-silanyl)-3-iodo-1H-pyrrolo[2,3-b]pyridine (69)

3-Iodo-1H-pyrrolo[2,3-b]pyridine 67 (1.11 g, 4.6 mmol) was dissolved in tetrahydrofuran (120 mL). Sodium hydride (60% dispersion in mineral oil, 0.13 g, 5.5 mmol) was added, followed by tert-butyldimethylsilyl chloride (0.85 g, 5.5 mmol). The reaction was stirred at room temperature overnight. The reaction was poured into water and extracted with ethyl acetate. The organic portion was washed with brine, dried over anhydrous sodium sulfate and filtered. The filtrate was concentrated and purified with silica gel column chromatography eluting with 30% ethyl acetate in hexane to give the compound as a white solid (69, 100 mg, 15%).

Example 24

Synthesis of [5-(4-chloro-benzyloxy)-4-methoxy-pyridin-2-yl]-(1H-pyrrolo[2,3-b]pyridin-3-yl)-methanone P-2024

[5-(4-Chloro-benzyloxy)-4-methoxy-pyridin-2-yl]-(1H-pyrrolo[2,3-b]pyridin-3-yl)-methanone P-2024 was synthesized in six steps from Kojic acid 70 and 3-iodo-1-triisopropylsilanyl-1H-pyrrolo[2,3-b]pyridine 68 as shown in Scheme 23.

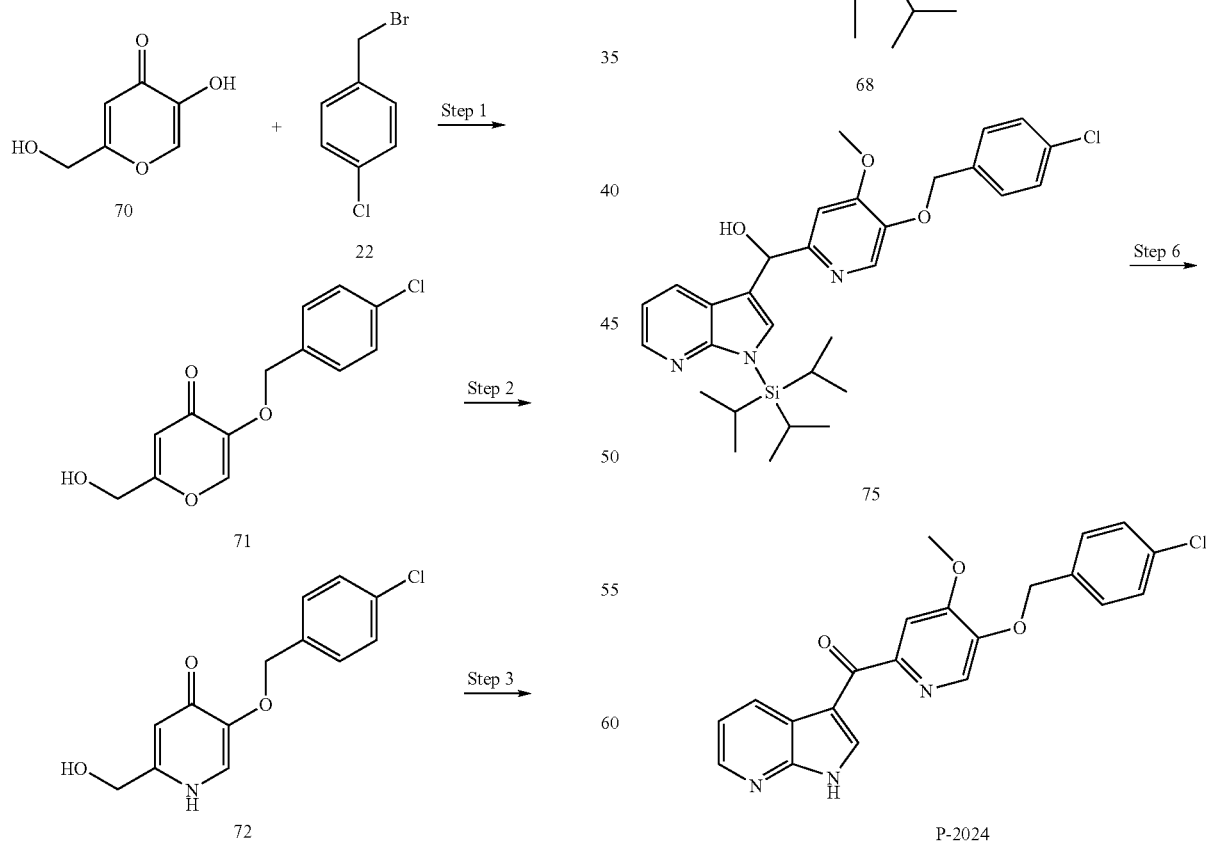

Step 1—Preparation of 5-(4-chloro-benzyloxy)-2-hydroxymethyl-pyran-4-one (71)

Kojic acid (70, 5.00 g, 35.2 mmol) and 4-chlorobenzyl bromide (22, 7.95 g, 38.7 mmol) were suspended in methanol (40 mL) in an 80 mL sealed tube. Sodium hydroxide in water (12 M, 2.93 ml) was added, The reaction was heated at 80° C. overnight. The resulting suspension was concentrated. Water was added and the mixture was filtered and washed with water to provide a brown solid. Washing with minimal methanol on the filter removed the brown color. A white solid (71, 7.58 g, 80%) was isolated. $^1$H-NMR was consistent with the desired compound.

Step 2—Preparation of 5-(4-chloro-benzyloxy)-2-hydroxymethyl-1H-pyridin-4-one (72)

5-(4-Chloro-benzyloxy)-2-hydroxymethyl-pyran-4-one (71, 8.00 g, 3.00 mmol) was suspended in ammonium hydroxide (200 mL) in an 80 mL sealed tube. The reaction was heated at 90° C. overnight. Upon cooling, the reaction was lowered to pH 10 with 6N HCl to provide a beige solid that was collected by filtration (72, 7.8 g, 98%).

Step 3—Preparation of [5-(4-(chloro-benzyloxy)-4-methoxy-pyridin-2-yl]-methanol (73)

5-(4-Chloro-benzyloxy)-2-hydroxymethyl-1H-pyridin-4-one (72, 1.06 g, 3.99 mmol) was dissolved in methanol (8.5 mL) and N,N-dimethylformamide (46 mL). Trimethylsilyldiazomethane in hexane (2.00 M, 3.99 mL) was added. The reaction was stirred at room temperature overnight, then additional trimethylsilyldiazomethane in hexane (2.00 M, 3.99 mL) was added. The reaction was stirred at room temperature for 2 days. The mixture was adsorbed onto silica and purified by silica gel chromatography, methanol:dichloromethane to provide the compound (73, 798 mg, 72%). MS (ESI) [M+H$^+$]$^+$=280.4, 282.4.

Step 4—Preparation of 5-(4-chloro-benzyloxy)-4-methoxy-pyridine-2-carbaldehyde (74)

[5-(4-Chloro-benzyloxy)-4-methoxy-pyridin-2-yl]-methanol (73, 480 mg, 1.7 mmol) was dissolved in dimethyl sulfoxide (26 mL) and Dess-Martin periodinane (909 mg, 2.1 mmol) was added. The reaction was allowed to stir at room temperature for 2 hours. The reaction was concentrated under high vacuum and then poured into a solution of NaHCO$_3$ and Na$_2$S$_2$O$_3$. The mixture was extracted with ethyl acetate. The organic portions were dried with anhydrous sodium sulfate and filtered. The filtrate was adsorbed onto silica and purified by silica gel chromatography, ethyl acetate:hexanes, to provide the desired compound as a white powder (74, 343 mg, 72%).

Step 5—Preparation of [5-(4-chloro-benzyloxy)-4-methoxy-pyridin-2-yl]-(1-triisopropylsilanyl-1H-pyrrolo[2,3-b]pyridin-3-yl)-methanol (75)

3-Iodo-1-triisopropylsilanyl-1H-pyrrolo[2,3-b]pyridine (68, 180 mg, 0.450 mmol, prepared as described in Example 22) was dissolved in tetrahydrofuran (2.5 mL) and the reaction was cooled to −20° C. under an atmosphere of nitrogen. Isopropylmagnesium chloride in tetrahydrofuran (2.00 M, 0.243 mL) was added. The reaction was stirred for 1 hour, during which the temperature rose to 0° C. The reaction was cooled to −20° C. and 5-(4-chloro-benzyloxy)-4-methoxy-pyridine-2-carbaldehyde (74, 80.0 mg, 0.288 mmol) in tetrahydrofuran (0.75 mL) was added. The reaction was allowed to warm to room temperature and stirred overnight. The reaction was quenched with methanol and adsorbed onto silica, then purified by silica gel chromatography, methanol:dichloromethane, to provide the desired compound (75, 94 mg, 59%). $^1$H-NMR was consistent with the desired compound. MS (ESI) [M+H$^+$]$^+$=552.4, 554.4, 555.4.

Step 6—Preparation of [5-(4-chloro-benzyloxy)-4-methoxy-pyridin-2-yl]-(1H-pyrrolo[2,3-b]pyridin-3-yl)-methanone (P-2024)

[5-(4-Chloro-benzyloxy)-4-methoxy-pyridin-2-yl]-(1-triisopropylsilanyl-1H-pyrrolo[2,3-b]pyridin-3-yl)-methanol (75, 60.0 mg, 0.11 mmol) was dissolved in tetrahydrofuran (2.00 mL). Dess-Martin periodinane (55.3 mg, 0.13 mmol) was added to the reaction and it was stirred at room temperature overnight. The mixture was extracted with ethyl acetate and saturated sodium bicarbonate. The organic portions were dried with anhydrous sodium sulfate, filtered and the filtrate was adsorbed onto silica and purified by silica gel chromatography, methanol:dichloromethane, to provide the desired compound (P-2024, 10.7 mg, 25%). $^1$H-NMR was consistent with the desired compound. MS (ESI) [M+H$^+$]$^+$=394.1, 396.1.

Example 25

Synthesis of 3-4-[1-(4-chloro-phenyl)-ethoxy]-3-methoxy-benzyl-1H-pyrrolo[2,3-b]pyridine P-2000

3-4-[1-(4-Chloro-phenyl)-ethoxy]-3-methoxy-benzyl-1H-pyrrolo[2,3-b]pyridine P-2000 was synthesized in three steps from vanillin 21, 4-chlorophenylmethylcarbinol 76, and 1-(tert-butyl-dimethyl-silanyl)-3-iodo-1H-pyrrolo[2,3-b]pyridine 69, as shown in Scheme 24.

Scheme 24

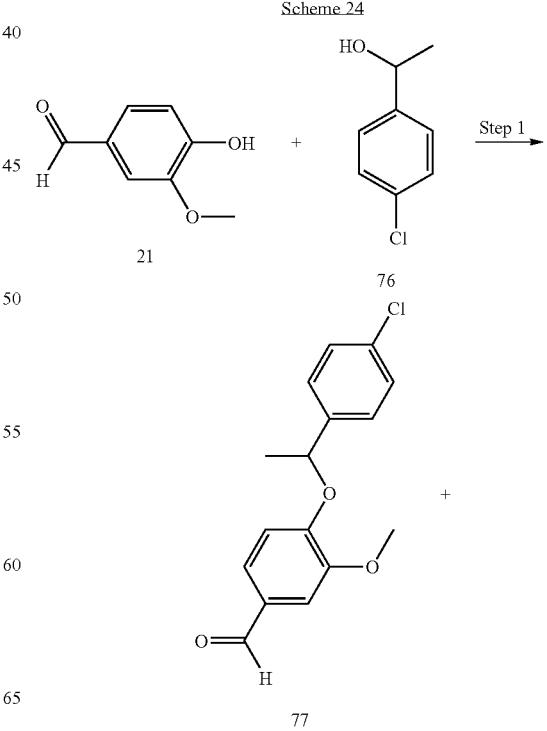

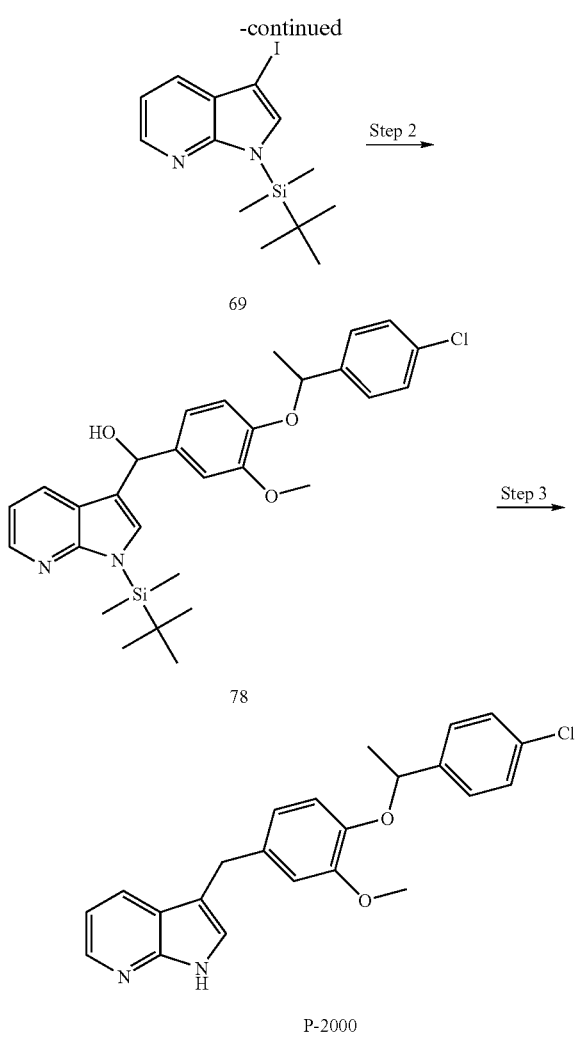

Step 1—Preparation of 4-[1-(4-chloro-phenyl)-ethoxy]-3-methoxy-benzaldehyde (77)

4-Chlorophenylmethylcarbinol (76, 0.668 mL, 6.57 mmol) was dissolved in tetrahydrofuran (60.0 mL) at 0° C. under an atmosphere of nitrogen. 4-Hydroxy-3-methoxybenzaldehyde (21, 1.00 g, 6.57 mmol) and triphenylphosphine (2.07 g, 7.89 mmol) were added to the reaction, followed by diisopropyl azodicarboxylate (1.55 mL, 7.89 mmol) over 10 minutes. The reaction was stirred for 2 hours. The mixture was adsorbed onto silica and purified by silica gel chromatography, ethyl acetate:hexanes, to provide the desired compound, (77, 1.14 g, 60%). $^1$H-NMR was consistent with the desired compound.

Step 2—Preparation of [1-(tert-Butyl-dimethyl-silanyl)-1H-pyrrolo[2,3-b]pyridin-3-yl]-4-[1-(4-chloro-phenyl)-ethoxy]-3-methoxy-phenyl-methanol (78)

1-(tert-Butyl-dimethyl-silanyl)-3-iodo-1H-pyrrolo[2,3-b]pyridine (69, 647.0 mg, 1.81 mmol, prepared as described in Example 23) was dissolved in tetrahydrofuran (10.0 mL) at −20° C. under an atmosphere of nitrogen. Isopropylmagnesium chloride in tetrahydrofuran (2.0 M, 0.98 mL) was added to the reaction. The reaction was stirred for 1 hour, during which the temperature rose to 0° C. The reaction was cooled to −20° C. and 4-[1-(4-chloro-phenyl)-ethoxy]-3-methoxy-benzaldehyde (77, 420 mg, 1.4 mmol) in tetrahydrofuran (3.00 mL) was added. The reaction was stirred for 2 hours during which time the temperature rose to 10° C. The reaction was quenched with methanol and adsorbed onto silica, then purified by silica gel chromatography, ethyl acetate:hexanes, to provide the desired compound, (78, 463 mg, 61%). $^1$H-NMR was consistent with the desired compound.

Step 2—Preparation of 3-4-[1-(4-chloro-phenyl)-ethoxy]-3-methoxy-benzyl-1H-pyrrolo[2,3-b]pyridine (P-2000)

[1-(tert-Butyl-dimethyl-silanyl)-1H-pyrrolo[2,3-b]pyridin-3-yl]-4-[1-(4-chloro-phenyl)-ethoxy]-3-methoxy-phenyl-methanol (78, 0.200 g, 0.382 mmol) was dissolved in acetonitrile (5.00 mL). Trifluoroacetic acid (0.138 mL) was added and the reaction was stirred for five minutes. Triethylsilane (0.285 mL) was added and the reaction was heated at 80° C. for 2 hours. The reaction was concentrated, then redissolved in ethyl acetate and adsorbed onto silica and purified by silica gel chromatography, ethyl acetate:hexanes, to provide the desired compound (P-2000, 57 mg, 38%). $^1$H-NMR was consistent with the desired compound. MS (ESI): $[M+H^+]^+$=393.3, 395.3.

Example 26

Synthesis of 5-[4-(2-methoxyethoxy)-phenyl]-1H-pyrrolo[2,3-b]pyridine 81

5-[4-(2-Methoxyethoxy)-phenyl]-1H-pyrrolo[2,3-b]pyridine 81 was synthesized in two steps from 4-bromophenol 79 as shown in Scheme 25.

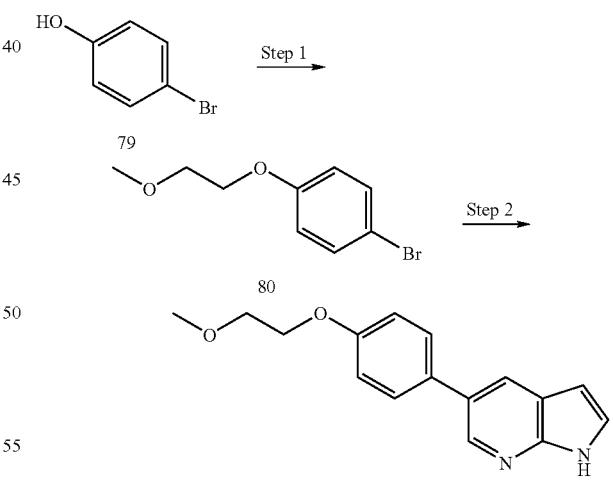

Scheme 25

Step 1—Preparation 1-Bromo-4-(2-methoxy-ethoxy)-benzene (80)

To a solution of 4-bromophenol (79, 5.0 g, 28.9 mmol) in dimethylformamide (15 mL) were added potassium carbonate (4.40 g, 31.8 mmol) and 1-bromo-2-methoxyethane (5.00 g, 36.0 mmol) under an atmosphere of nitrogen. The reaction mixture was stirred at ambient temperature overnight and concentrated under reduced pressure. The residue was slurried in ethyl acetate (50 mL) and filtered. The filtrate was washed with saturated sodium bicarbonate solution, dried over magnesium sulfate and filtered. Silica gel column chromatography (0-10% ethyl acetate in hexanes) gave the desired compound as a colorless oil (80, 3.2 g, 48%).

Step 2—Preparation of 5-[4-(2-Methoxy-ethoxy)-phenyl]-1H-pyrrolo[2,3-b]pyridine (81)

To a solution of 5-(4,4,5,5,-tetramethyl-[1,3,2]dioxaborolan-2-yl)-1H-pyrrolo[2,3-b]pyridine (1.1 g, 4.3 mmol) in tetrahydro ran (40 mL) was added 1-bromo-4-(2-methoxy-ethoxy)-benzene (80, 1.50 g, 6.49 mmol) and tetrakis(triphenylphosphine)palladium (0) (0.25 g, 0.21 mmol). The reaction mixture was stirred with potassium carbonate solution (10 mL, 1.0 M) and warmed to reflux overnight. The biphasic reaction mixture was diluted with ethyl acetate (50 mL) and saturated sodium carbonate solution (20 mL). The organic layer was separated, washed with brine, dried over magnesium sulfate and purified by silica gel column chromatography (50-100% ethyl acetate in hexanes) to give the desired compound as a colorless solid (81, 782 mg, 67%). MS (ESI) [M+H$^+$]$^+$=267.4.

Example 27

Synthesis of 5-fluoro-2-methoxy-4-(1-triisopropylsilanyl-1H-pyrrolo[2,3-b]pyridin-3-ylmethyl)-phenol 87

5-Fluoro-2-methoxy-4-(1-triisopropylsilanyl-1H-pyrrolo[2,3-b]pyridin-3-ylmethyl)-phenol 87 was synthesized in five steps from 2-fluoro-4-hydroxy-5-methoxy-benzaldehyde 39 and benzyl bromide as shown in Scheme 26.

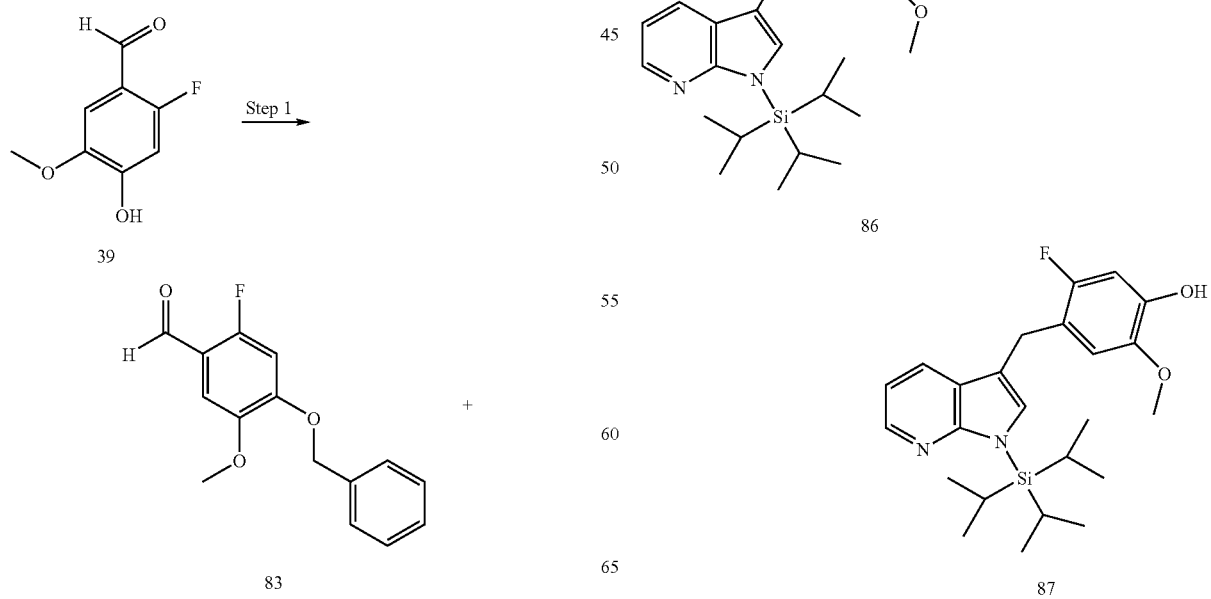

Step 1—Preparation of 4-Benzyloxy-2-fluoro-5-methoxy-benzaldehyde (83)

2-Fluoro-4-hydroxy-5-methoxy-benzaldehyde (39, 1.62 g, 9.52 mmol, prepared as described in Scheme 12 of Example 15) was dissolved in N,N-dimethylformamide (50 mL) and sodium hydride (60% dispersion in mineral oil, 530 mg, 13 mmol) was added. After 20 minutes, benzyl bromide (1.5 mL, 12 mmol) was added to the reaction mixture. The reaction was stirred at room temperature under an atmosphere of nitrogen for 5.5 hours. The reaction was poured into water and extracted with ethyl acetate. The organic layer was dried over anhydrous sodium sulfate, and filtered. The filtrate was concentrated and purified by silica gel column chromatography eluting with 0-50% ethyl acetate in hexane to provide compound as a white solid, consistent with the desired structure by $^1$H-NMR (83, 2.0 g, 81%).

Step 2—Preparation of (4-Benzyloxy-2-fluoro-5-methoxy-phenyl)-(1-triisopropylsilanyl-1H-pyrrolo[2,3-b]pyridin-3-yl)-methanol (84)

3-Iodo-1-triisopropylsilanyl-1H-pyrrolo[2,3-b]pyridine (68, 620 mg, 1.5 mmol, prepared as described in Example 22) was dissolved in tetrahydrofuran (15 mL) at −20° C. under an atmosphere of nitrogen. Isopropylmagnesium chloride (2.0 M in tetrahydrofuran, 840 µL) was added to the reaction. The reaction was stirred for 1.5 hours, during which the temperature rose to 5° C. The reaction was cooled to −20° C. 4-Benzyloxy-2-fluoro-5-methoxy-benzaldehyde (83, 250 mg, 0.9606 mmol) in tetrahydrofuran (5.0 mL) was added to the reaction. The reaction was stirred for 2.5 hours during which time the temperature rose to 5° C. The reaction was poured into water. The mixture was extracted with ethyl acetate. The organic layer was dried over an hydrous sodium sulfate, and filtered. The filtrate was concentrated and purified by silica gel column chromatography eluting with 2-25% ethyl acetate in hexane to provide compound as a white solid (84, 501 mg, 63%). MS (ESI) [M+H$^+$]$^+$=535.4.

Step 3—Preparation of 3-(4-Benzyloxy-2-fluoro-5-methoxy-benzyl)-1H-pyrrolo[2,3-b]pyridine (85)

(4-Benzyloxy-2-fluoro-5-methoxy-phenyl)-(1-triisopropylsilanyl-1H-pyrrolo[2,3-b]pyridin-3-yl)-methanol (84, 1.49 g, 2.79 mmol) was dissolved in acetonitrile (50 mL) and trifluoroacetic Acid (1.1 mL) was added. The reaction was stirred for 5 minutes. Triethylsilane (2.2 mL) was added to the reaction. The reaction was heated at 80° C. for 6 hours. The reaction was concentrated and the crude material was dissolved into ethyl acetate and washed with 1 N HCl, saturated sodium bicarbonate, and brine. The organic portion was dried over anhydrous sodium sulfate and concentrated. The solid obtained was used in the next reaction without further purification (85, 833 mg, 83%). MS (ESI) [M+H$^+$]$^+$=363.4.

Step 4—Preparation of 3-(4-Benzyloxy-2-fluoro-5-methoxy-benzyl)-1-triisopropylsilanyl-1H-pyrrolo[2,3-b]pyridine (86)

3-(4-Benzyloxy-2-fluoro-5-methoxy-benzyl)-1H-pyrrolo[2,3-b]pyridine (85, 0.877 g, 2.42 mmol) was dissolved in N,N-dimethylformamide (30 mL). Sodium hydride (60% dispersion in mineral oil, 140 mg, 3.6 mmol) was added at room temperature. After 20 minutes, triisopropylsilyl chloride (513 µL, 2.42 mmol) was added dropwise. The reaction was stirred for four hours. The reaction was poured into water and extracted with ethyl acetate. The organic portion was washed with saturated sodium bicarbonate and brine. The organic portion was dried over anhydrous sodium sulfate and filtered. The filtrate was adsorbed onto silica gel and purified by silica gel chromatography using 70-80% ethyl acetate/hexane. The resulting material was purified a second time with 5-30% gradient ethyl acetate/hexane to provide the desired compound (86, 831 mg, 66%). MS (ESI) [M+H$^+$]$^+$=519.4.

Step 5—Preparation of 5-Fluoro-2-methoxy-4-(1-triisopropylsilanyl-1H-pyrrolo[2,3-b]pyridin-3-ylmethyl)-phenol (87)

3-(4-Benzyloxy-2-fluoro-5-methoxy-benzyl)-1-triisopropylsilanyl-1H-pyrrolo[2,3-b]pyridine (86, 0.831 g, 1.60 mmol) was dissolved in methanol (40 mL) and tetrahydrofuran (40 mL). 10% Palladium on carbon (3.41 g) was added. The reaction was shaken at 50 psi for 1 hour. The reaction was filtered through Celite and washed with methanol. The organic portion was passed through celite several times until a clear solution was obtained. The organic portion was concentrated under reduced pressure to provide the desired compound as an off-white solid (87, 587 mg, 86%).

MS (ESI) [M+H$^+$]$^+$=429.5.

Example 28

Synthesis of 3-[2-fluoro-5-methoxy-4-(pyridin-4-ylmethoxy)-benzyl]-1H-pyrrolo[2,3-b]pyridine P-2040 and related compounds Compound P-2040 was synthesized in one step from 5-fluoro-2-methoxy-4-(1-triisopropylsilanyl-1H-pyrrolo[2,3-b]pyridin-3-ylmethyl)-phenol 87 and pyridin-4-yl-methanol 88 as shown in Scheme 27.

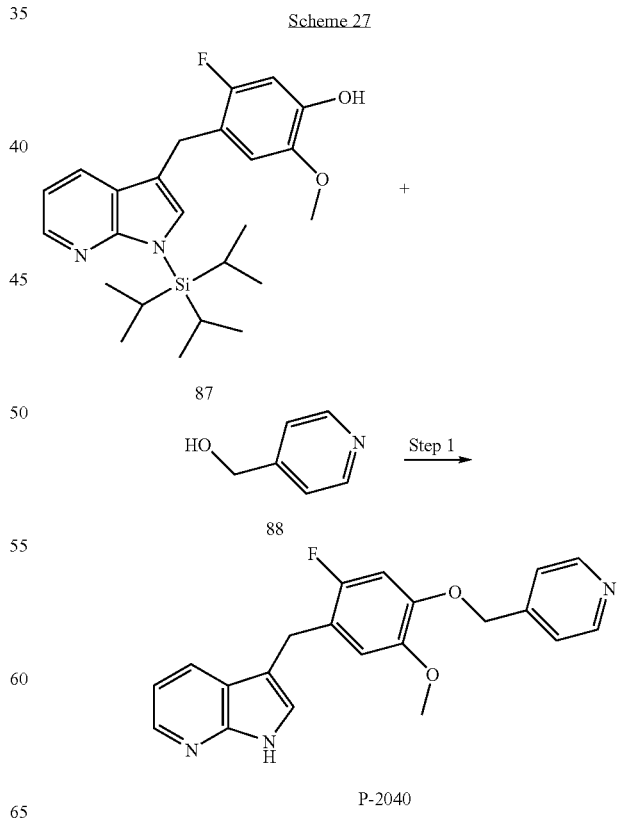

Step 1—Preparation of 3-[2-fluoro-5-methoxy-4-(pyridin-4-ylmethoxy)-benzyl]-1H-pyrrolo[2,3-b]pyridine (P-2040)

5-Fluoro-2-methoxy-4-(1-triisopropylsilanyl-1H-pyrrolo[2,3-b]pyridine-3-ylmethyl)-phenol (87, 10 mg, 0.024 mmol, prepared as described in Example 27) was combined with pyridin-4-yl-methanol (88, 32 mg, 0.029 mmol) in a 4 mL vial and dissolved in dry tetrahydrofuran (2001). Triphenylphosphine (7.7 mg) was added and the solution was shaken until homogenous. The mixture was cooled to below 0° C. in a liquid nitrogen bath and diisopropyl azodicarboxylate solution (50 µl of 20 mg/50 µl in THF) was added. The reaction mixture was allowed to warm to room temperature. After 2 hours, the solvent was removed under reduced atmosphere. The crude material was dissolved in dimethyl sulfoxide (300 µl) and potassium fluoride (10 mg, 0.18 mmol) was added. The mixture was heated gently and allowed to react overnight at room temperature. The vial was centrifuged and the DMSO solution was purified by reverse phase HPLC using a YMC-Pack ODS-A C-18 column (50 mm×10 mm ID), and eluting with water with 0.1% TFA and a gradient of 15%-80% acetonitrile with 0.1% TFA over 8 minutes and a flow rate of 6 mL/minute to provide the compound (P-2040, 4.4 mg, 50%). MS (ESI) [M+H$^+$]$^+$=364.3.

Additional compounds were prepared following the protocol of Scheme 27, replacing pyridin-4-yl-methanol 88 with an appropriate alcohol. The following compounds were made following this procedure:

3-[2-Fluoro-5-methoxy-4-(2-morpholin-4-yl-ethoxy)-benzyl]-1H-pyrrolo[2,3-b]pyridine (P-2037),
3-[2-Fluoro-5-methoxy-4-(pyridin-3-ylmethoxy)-benzyl]-1H-pyrrolo[2,3-b]pyridine (P-2038),
3-[2-Fluoro-5-methoxy-4-(6-methyl-pyridin-2-ylmethoxy)-benzyl]-1H-pyrrolo[2,3-b]pyridine (P-2039),
3-[2-Fluoro-5-methoxy-4-(pyridin-2-ylmethoxy)-benzyl]-1H-pyrrolo[2,3-b]pyridine (P-2041),
3-[2-Fluoro-4-(2-fluoro-4-trifluoromethyl-benzyloxy)-5-methoxy-benzyl]-1H-pyrrolo[2,3-b]pyridine (P-2042),
3-[4-(4-Chloro-2-fluoro-benzyloxy)-2-fluoro-5-methoxy-benzyl]-1H-pyrrolo[2,3-b]pyridine (P-1973),
3-[4-(2,4-Dimethyl-thiazol-5-ylmethoxy)-2-fluoro-5-methoxy-benzyl]-1H-pyrrolo[2,3-b]pyridine (P-2043),
3-[4-(2,5-Dimethyl-2H-pyrazol-3-ylmethoxy)-2-fluoro-5-methoxy-benzyl]-1H-pyrrolo[2,3-b]pyridine (P-2044),
3-[2-Fluoro-5-methoxy-4-(3-morpholin-4-yl-propoxy)-benzyl]-1H-pyrrolo[2,3-b]pyridine (P-2045),
1-{2-[5-Fluoro-2-methoxy-4-(1H-pyrrolo[2,3-b]pyridin-3-ylmethyl)-phenoxy]-ethyl}-pyrrolidin-2-one (P-2046),
3-[2-Fluoro-4-(2-fluoro-benzyloxy)-5-methoxy-benzyl]-1H-pyrrolo[2,3-b]pyridine (P-2047),
3-[2-Fluoro-5-methoxy-4-(3-methyl-pyridin-4-ylmethoxy)-benzyl]-1H-pyrrolo[2,3-b]pyridine (P-2048),
3-[2-Fluoro-5-methoxy-4-(6-trifluoromethyl-pyridin-3-ylmethoxy)-benzyl]-1H-pyrrolo[2,3-b]pyridine (P-2049),
3-[4-(2,4-Dichloro-benzyloxy)-2-fluoro-5-methoxy-benzyl]-1H-pyrrolo[2,3-b]pyridine (P-2050),
3-[2-Fluoro-4-(4-imidazol-1-yl-benzyloxy)-5-methoxy-benzyl]-1H-pyrrolo[2,3-b]pyridine (P-2051),
3-[4-(2,4-Difluoro-benzyloxy)-2-fluoro-5-methoxy-benzyl]-1H-pyrrolo[2,3-b]pyridine (P-2052),
3-{2-Fluoro-4-[1-(2-fluoro-phenyl)-ethoxy]-5-methoxy-benzyl}-1H-pyrrolo[2,3-b]pyridine (P-2053),
3-[4-(3-Cyclopentyl-propoxy)-2-fluoro-5-methoxy-benzyl]-1H-pyrrolo[2,3-b]pyridine (P-2054),
3-[4-(1,5-Dimethyl-1H-pyrazol-3-ylmethoxy)-2-fluoro-5-methoxy-benzyl]-1H-pyrrolo[2,3-b]pyridine (P-2055), and
3-[4-(2-Cyclopentyl-ethoxy)-2-fluoro-5-methoxy-benzyl]-1H-pyrrolo[2,3-b]pyridine (P-2056)

The following table indicates the alcohol (column 2) used in Scheme 78 to provide the compounds (column 4). Column 1 provides the compound number and column 4 the observed mass.

| | Alcohol | Compound | MS (ESI) [M + H$^+$]$^+$ observed |
|---|---|---|---|
| P-2037 | | | 386.3 |
| P-2038 | | | 364.3 |

-continued
| Alcohol | Compound | MS (ESI) [M + H+]+ observed |
|---|---|---|
| P-2039  | 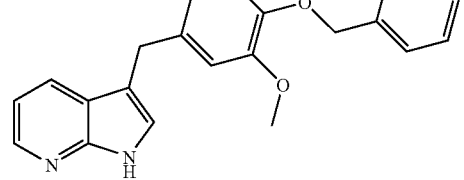 | 378.3 |
| P-2041 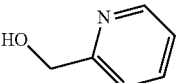 | 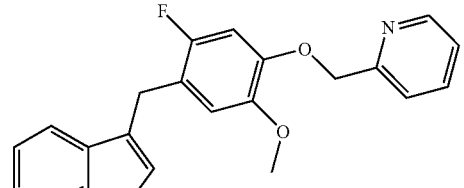 | 364.3 |
| P-2042 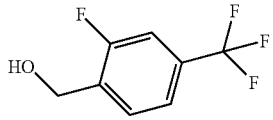 | 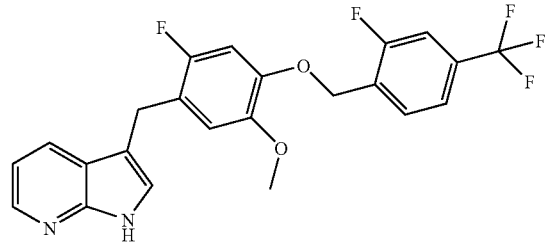 | 448.7 |
| P-1973 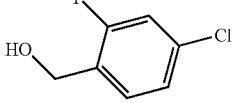 | 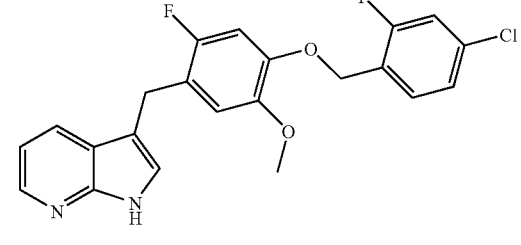 | 415.1 |
| P-2043 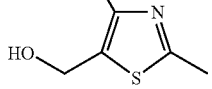 | 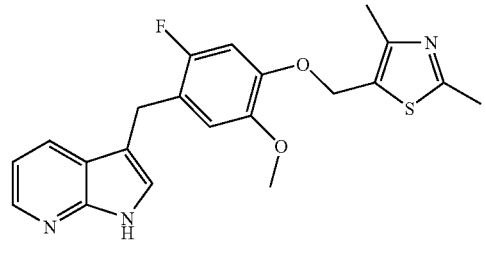 | 397.9 |
| P-2044 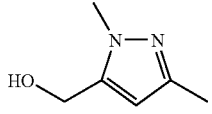 | 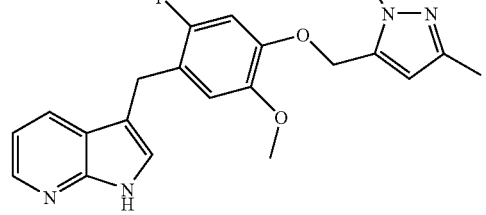 | 381.1 |

-continued
| | Alcohol | Compound | MS (ESI) [M + H+]+ observed |
|---|---|---|---|
| P-2045 | 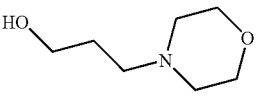 | 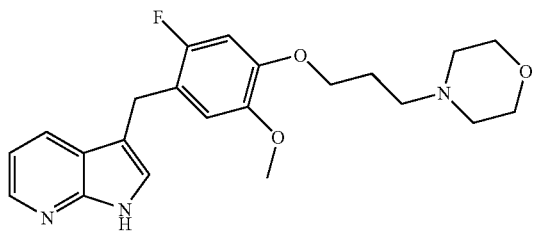 | 400.3 |
| P-2046 | 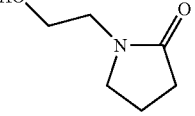 | 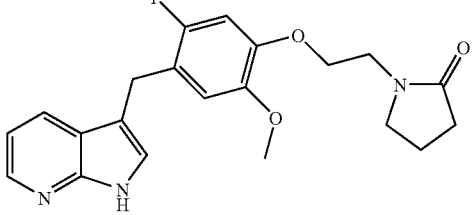 | 384.3 |
| P-2047 | 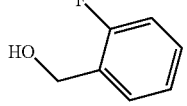 | 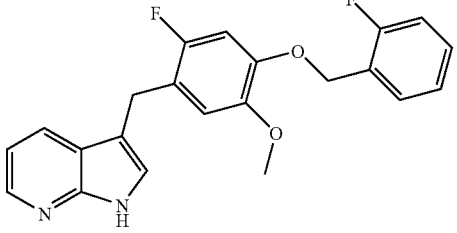 | 381.1 |
| P-2048 | 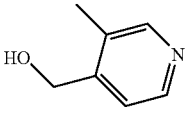 | 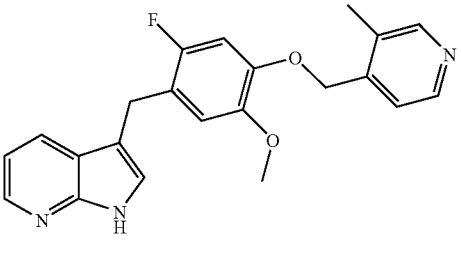 | 378.3 |
| P-2049 | 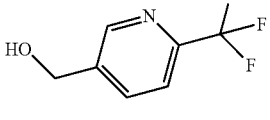 | 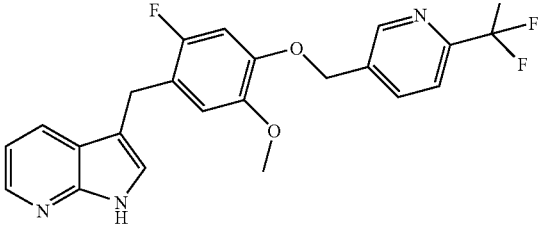 | 432.3 |
| P-2050 | 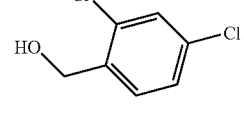 | 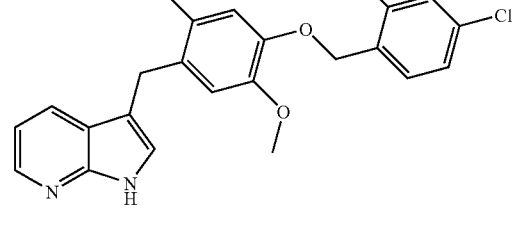 | 431.1 |

-continued

| | Alcohol | Compound | MS (ESI) [M + H+]+ observed |
|---|---|---|---|
| P-2051 | | | 429.1 |
| P-2052 | | | 399.1 |
| P-2053 | | | 395.1 |
| P-2054 | | | 383.1 |
| P-2055 | | | 381.1 |
| P-2056 | | | 369.1 |

Example 29

Synthesis of [2,6-difluoro-3-(pyridin-3-ylmethoxy)-phenyl]-(1H-pyrrolo[2,3-b]pyridin-3-yl)-methanone P-2058 and related compounds Compound P-2058 was synthesized in 1 step from (2,6-Difluoro-3-hydroxy-phenyl)-(1H-pyrrolo[2,3-b]pyridin-3-yl)-methanone 89 and Pyridin-3-yl-methanol 90 as shown in Scheme 28.

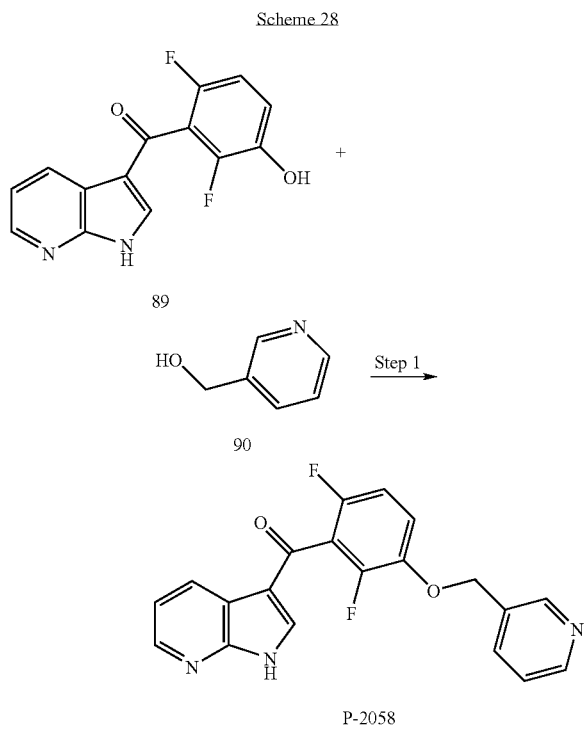

Scheme 28

Step 1—Preparation of [2,6-Difluoro-3-(pyridin-3-ylmethoxy)-phenyl]-(1H-pyrrolo[2,3-b]pyridin-3-yl)-methanone (P-2058)

In a 4 mL vial, (2,6-Difluoro-3-hydroxy-phenyl)-(1H-pyrrolo[2,3-b]pyridine-3-yl)-methanone (89, 10 mg, 0.037 mmol, prepared as described in Example 11) was combined with pyridin-3-yl-methanol (90, 4.9 mg 0.044 mmol). The solids were dissolved in dry tetrahydrofuran (200 µl) and triphenylphosphine (11.5 mg, 0.044 mmol) was added. Once the solution was homogenous, the mixture was cooled to below 0° C. in liquid nitrogen bath and diisopropyl azodicarboxylate solution (50 µl of 20 mg/50 µl THF) was added. The reaction mixture was allowed to warm to room temperature and the reaction was continued for 2 hours. The solvents were removed under reduced atmosphere. The resultant residue was diluted with 200 µl DMSO and the mixture purified by reverse phase HPLC using a YMC-Pack ODS-A C-18 column (50 mm×10 mm ID), and eluting with water with 0.1% TFA and a gradient of 15%-80% acetonitrile with 0.1% TFA over 8 minutes and a flow rate of 6 mL/minute to provide P-2058 (5.9 mg, 44%). MS (ESI) [M+H$^+$]$^+$=365.9.

Additional compounds were prepared following the protocol of Scheme 28, replacing pyridin-3-yl-methanol 90 with an appropriate alcohol and optionally replacing (2,6-difluoro-3-hydroxy-phenyl)-(1H-pyrrolo[2,3-b]pyridine-3-yl)-methanone 89 with (2,6-difluoro-3-hydroxy-phenyl)-(5-chloro-1H-pyrrolo[2,3-b]pyridine-3-yl)-methanone (prepared as described in Example 11, 3 and 4 of Scheme 8, replacing pyridin-3-yl-1H-pyrrolo[2,3-b]pyridine 20 with 5-chloro-1H-pyrrolo[2,3-b]pyridine 4 (see Example 4) in Step 3). The following compounds were made following this procedure:

[2,6-Difluoro-3-(1-methyl-1H-imidazol-2-ylmethoxy)-phenyl]-(1H-pyrrolo[2,3-b]pyridin-3-yl)-methanone (P-2033),

[2,6-Difluoro-3-(6-morpholin-4-yl-pyridin-3-ylmethoxy)-phenyl]-(1H-pyrrolo[2,3-b]pyridin-3-yl)-methanone (P-2034), {2,6-Difluoro-3-[4-(5-methyl-[1,2,4]oxadiazol-3-yl)-benzyloxy]-phenyl}-(1H-pyrrolo[2,3-b]pyridin-3-yl)-methanone (P-2035),

[3-(6-Diethylamino-pyridin-3-ylmethoxy)-2,6-difluoro-phenyl]-(H-pyrrolo[2,3-b]pyridin-3-yl)-methanone (P-2036),

[3-(2-Chloro-4-fluoro-benzyloxy)-2,6-difluoro-phenyl]-(1H-pyrrolo[2,3-b]pyridin-3-yl)-methanone (P-2057),

[2,6-Difluoro-3-(6-methyl-pyridin-2-ylmethoxy)-phenyl]-(1H-pyrrolo[2,3-b]pyridin-3-yl)-methanone (P-2059),

[2,6-Difluoro-3-(pyridin-4-ylmethoxy)-phenyl]-(1H-pyrrolo[2,3-b]pyridin-3-yl)-methanone (P-2060),

[3-(4-Chloro-2-fluoro-benzyloxy)-2,6-difluoro-phenyl]-(1H-pyrrolo[2,3-h]pyridin-3-yl)-methanone (P-2061),

[3-(2,4-Dimethyl-thiazol-5-ylmethoxy)-2,6-difluoro-phenyl]-(1H-pyrrolo[2,3-b]pyridin-3-yl)-methanone (P-2062),

[3-(2,5-Dimethyl-2H-pyrazol-3-ylmethoxy)-2,6-difluoro-phenyl]-(1H-pyrrolo[2,3-b]pyridin-3-yl)-methanone (P-2063),

[2,6-Difluoro-3-(3-morpholin-4-yl-propoxy)-phenyl]-(1H-pyrrolo[2,3-b]pyridin-3-yl)-methanone (P-2064), (5-Chloro-1H-pyrrolo[2,3-b]pyridin-3-yl)-[3-(2,4-dimethyl-thiazol-5-ylmethoxy)-2,6-difluoro-phenyl]-methanone (P-2162), (5-Chloro-1H-pyrrolo[2,3-b]pyridin-3-yl)-[2,6-difluoro-3-(6-trifluoromethyl-pyridin-3-ylmethoxy)-phenyl]-methanone (P-2163), (5-Chloro-1H-pyrrolo[2,3-b]pyridin-3-yl)-[3-(2,5-dimethyl-oxazol-4-ylmethoxy)-2,6-difluoro-phenyl]-methanone (P-2164), and (5-Chloro-1H-pyrrolo[2,3-b]pyridin-3-yl)-[2,6-difluoro-3-(1-methyl-1H-imidazol-2-ylmethoxy)-phenyl]-methanone (P2165).

The following table indicates the alcohol (column 2) used to afford the compound (column 3). P-2162, P-2163. P-2164 and P-2165 were made starting with (2,6-difluoro-3-hydroxy-phenyl)-(5-chloro-1H-pyrrolo[2,3-b]pyridine-3-yl)-methanone (not shown in table). Column 1 provides the compound number and column 4 the observed mass.

| | Alcohol | Compound | MS (ESI) [M + H⁺]⁺ observed |
|---|---|---|---|
| P-2033 | 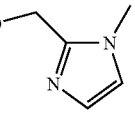 | 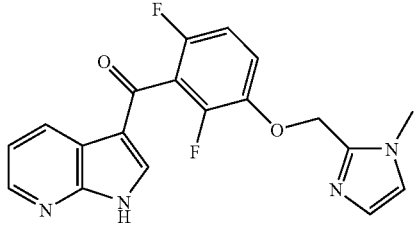 | 369.1 |
| P-2034 | 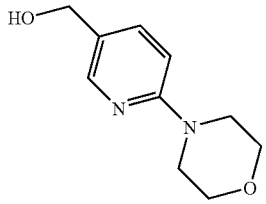 | 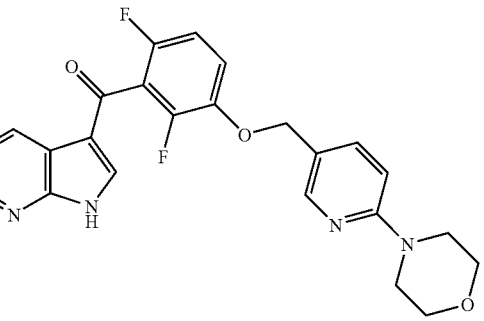 | 451.1 |
| P-2035 | 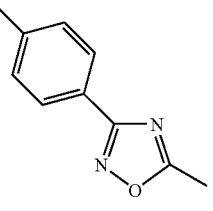 | 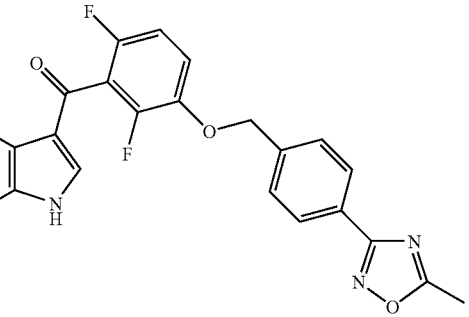 | 447.1 |
| P-2036 | 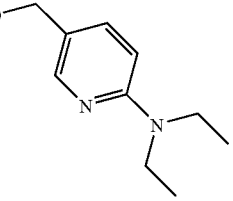 | 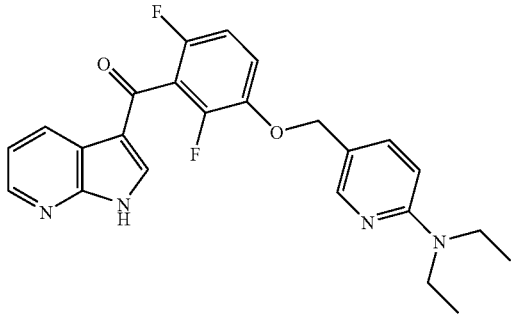 | 437.1 |
| P-2057 | 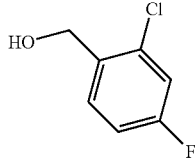 | 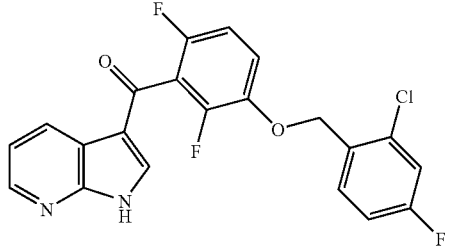 | 417.1 |

-continued
| | Alcohol | Compound | MS (ESI) [M + H+]+ observed |
|---|---|---|---|
| P-2059 | 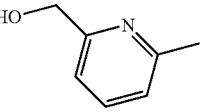 | 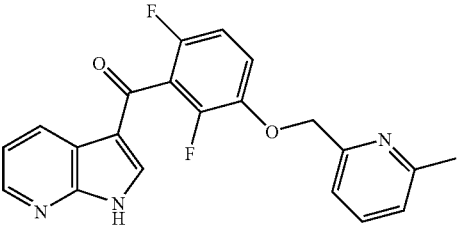 | 380.3 |
| P-2060 | 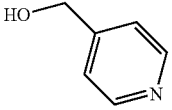 | 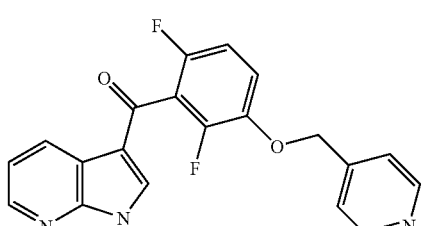 | 365.9 |
| P-2061 | 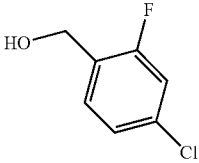 | 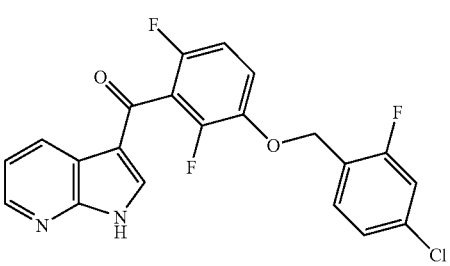 | 417.1 |
| P-2062 | 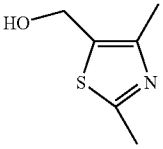 | 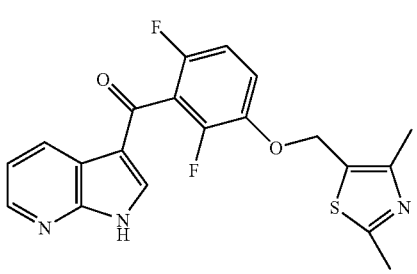 | 399.9 |
| P-2063 | 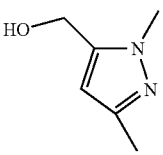 | 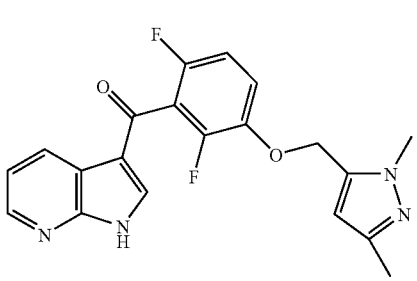 | 383.1 |
| P-2064 | 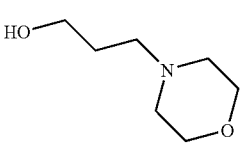 | 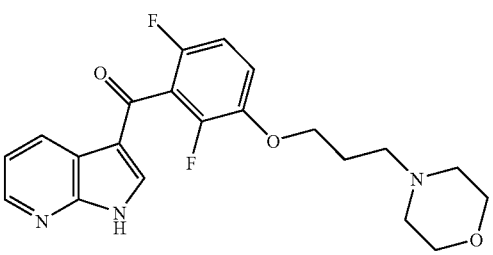 | 402.3 |

| | Alcohol | Compound | MS (ESI) [M + H+]+ observed |
|---|---|---|---|
| P-2162 | HO-CH2-(2,4-dimethylthiazol-5-yl) | 5-chloro-3-[2,6-difluoro-3-(2,4-dimethylthiazol-5-ylmethoxy)benzoyl]-7-azaindole | 432.06 [M − H+]− |
| P-2163 | HO-CH2-(6-trifluoromethylpyridin-3-yl) | 5-chloro-3-[2,6-difluoro-3-(6-trifluoromethylpyridin-3-ylmethoxy)benzoyl]-7-azaindole | 466.06 [M − H+]− |
| P-2164 | HO-CH2-(2,5-dimethyloxazol-4-yl) | 5-chloro-3-[2,6-difluoro-3-(2,5-dimethyloxazol-4-ylmethoxy)benzoyl]-7-azaindole | 416.0 [M − H+]− |
| P-2165 | HO-CH2-(1-methylimidazol-2-yl) | 5-chloro-3-[2,6-difluoro-3-(1-methylimidazol-2-ylmethoxy)benzoyl]-7-azaindole | 403.18 |

Example 30

Synthesis of 4-chloro-7-azaindole 92

4-chloro-7-azaindole 92 was synthesized in two steps from 7-azaindole according to the protocol of Scheme 29.

Scheme 29

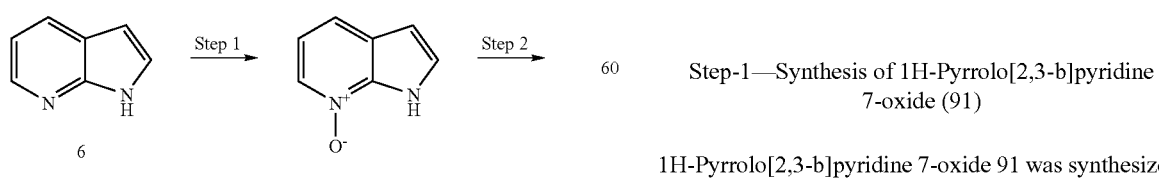

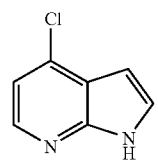

92

Step-1—Synthesis of 1H-Pyrrolo[2,3-b]pyridine 7-oxide (91)

1H-Pyrrolo[2,3-b]pyridine 7-oxide 91 was synthesized by reacting 7-azaindole 6 with an oxidizing agent (e.g. m-CPBA) in a non-reactive solvent (e.g. dimethoxyethane) as described by Schneller, S. W.; Luo, Jiann-Kuan. J. Org.

Chem. 1980, 45:4045-4048. The compound was isolated by filtration of the resulting solid that forms upon standing at 5° C. for typically 1-3 h.

Step-2—Synthesis of 4-chloro-7-azaindole (92)

4-chloro-7-azaindole 92 was synthesized by reacting 1H-Pyrrolo[2,3-b]pyridine 7-oxide 91 with a chlorinating agent (e.g. POCl$_3$) neat as described by Schneller, S. W.; Luo, Jiann-Kuan. J. Org. Chem. 1980, 45:4045-4048. The resulting solution after heating for 3-5 h at elevated temperatures (100-150° C.) was neutralized with a base (e.g. NH$_4$OH) until a solid precipitated. The solid was isolated by filtration.

Example 31

Synthesis of [3-(4-Chloro-2-fluoro-benzyloxy)-2-(2-fluoro-ethoxy)-phenyl]-(1H-pyrrolo[2,3-b]pyridin-3-yl)-methanone P-2086 and 3-[3-(4-Chloro-2-fluoro-benzyloxy)-2-(2-fluoro-ethoxy)-benzyl]-1H-pyrrolo[2,3-b]pyridine P-2085

Compounds P-2086 and P-2085 were synthesized in three steps from compounds 93 and 1H-pyrrolo[2,3-b]pyridine 6 as show in Scheme 30.

Step 1—Preparation of 3-(4-Chloro-2-fluoro-benzyloxy)-2-(2-fluoro-ethoxy)-benzaldehyde (94)

To a solution of 3-(4-chloro-2-fluoro-benzyloxy)-2-hydroxy-benzaldehyde (93, yyyy140 mg, 0.5 mmol, prepared by protocol of Example 21, Steps 1 and 2 of Scheme 20, using 4-chloro-2-fluoro-benzyl bromide in place of 4-chloro-benzyl bromide in Step 1) in tetrahydrofuran (8 mL) was added dropwise a mixture of 2-fluoro-ethanol (64 mg, 1.0 mmol), triphenylphosphine (180 mg, 0.7 mmol), and diisopropyl azodicarboxylate (120 mg, 0.6 mol) in tetrahydrofuran (5 ml) at 0° C. The reaction mixture was stirred at 0° C. for 10 minutes and then at 40° C. for 3 days. The reaction mixture was dissolved in water and ethyl acetate. The organic layers were collected, washed with brine, and dried over magnesium sulfate. After removal of solvent, the residue was purified by silica gel column chromatography eluting with ethyl acetate in hexanes to provide the compound as a white solid (94, 88 mg, 54%). MS (ESI) [M+H$^+$]$^+$=327.12.

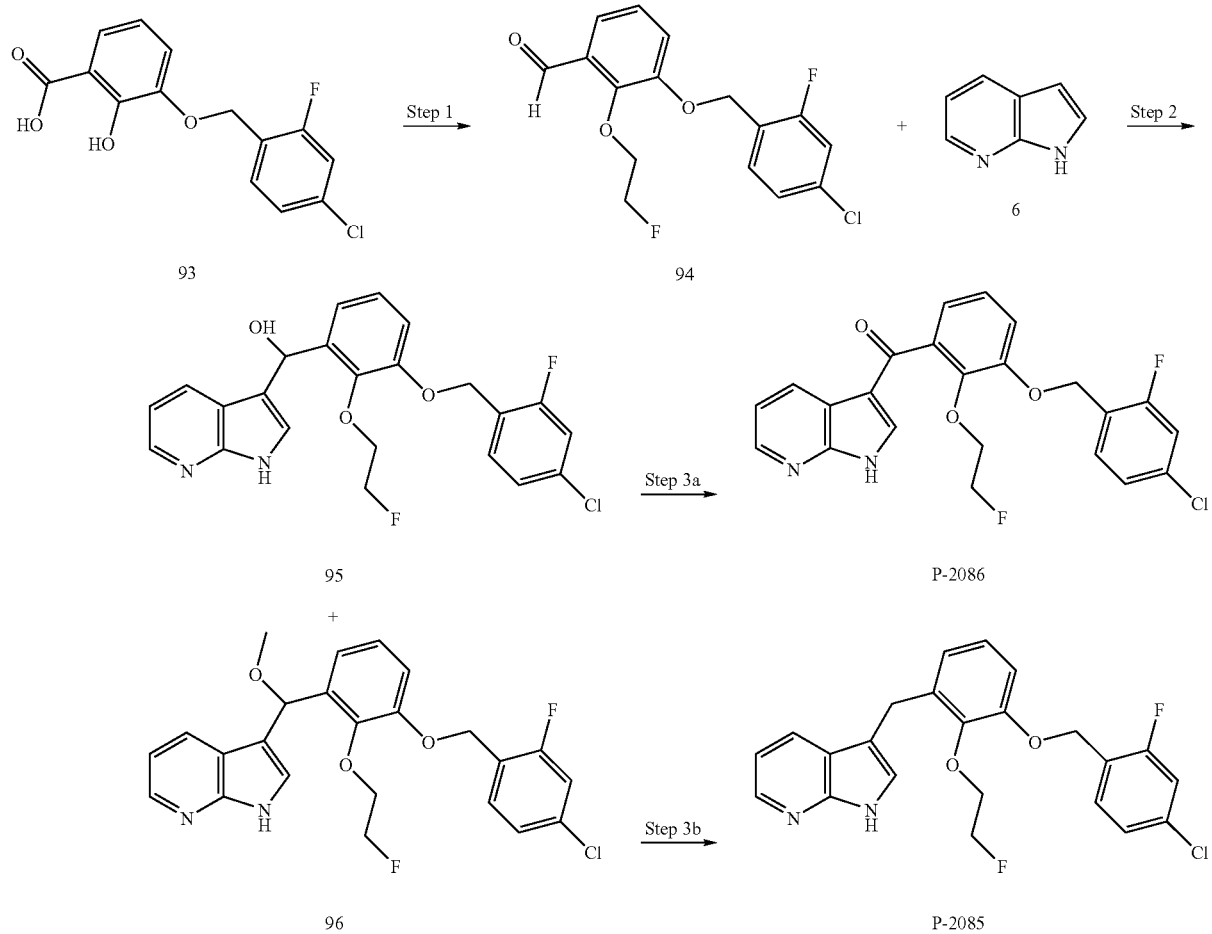

Scheme 30

Step 2—Preparation of [3-(4-Chloro-2-fluoro-benzy-loxy)-2-(2-fluoro-ethoxy)-phenyl]-(1H-pyrrolo[2,3-b]pyridin-3-yl)-methanol (95) and 3-{[3-(4-Chloro-2-fluoro-benzyloxy)-2-(2-fluoro-ethoxy)-phenyl]-methoxy-methyl}-1H-pyrrolo[2,3-b]pyridine (96)

A solution of 3-(4-chloro-2-fluoro-benzyloxy)-2-(2-fluoro-ethoxy)-benzaldehyde (94, 88 mg, 0.27 mmol), 1H-pyrrolo[2,3-b]pyridine (6, 38 mg, 0.32 mmol), and potassium hydroxide (45 mg, 0.81 mmol) in methanol (5 mL) was stirred at room temperature for 24 hours. The reaction mixture was poured into water and extracted with ethyl acetate. The organic layer was collected, washed with brine, and dried over sodium sulfate. After removal of solvent, the residue was purified by silica gel column chromatography eluting with ethyl acetate in hexane to provide compound 95 as a white solid (67 mg, 56%), MS (ESI) [M+H$^+$]$^+$=445.13 and compound 96 as a white solid (36 mg, 29%), MS (ESI) [M+H$^+$]$^+$=459.15.

Step 3a—Preparation of [3-(4-Chloro-2-fluoro-benzyloxy)-2-(2-fluoro-ethoxy)-phenyl]-(1H-pyrrolo[2,3-b]pyridin-3-yl)-methanone (P-2086)

To a solution of [3-(4-chloro-2-fluoro-benzyloxy)-2-(2-fluoro-ethoxy)-phenyl]-(1H-pyrrolo[2,3-b]pyridin-3-yl)-methanol (95, 60 mg, 0.1 mmol) in tetrahydrofuran (10 mL) was added Dess-Martin periodinane (69 mg, 0.16 mmol) at 0° C. The reaction mixture was stirred at room temperature for 3 hours. The reaction was quenched with a saturated solution of sodium thiosulfate, extracted with ethyl acetate, washed with sodium bicarbonate, brine, and dried over magnesium sulfate. After removal of solvent, the residue was purified by silica gel column chromatography eluting with ethyl acetate in hexanes to provide the compound as a white solid (P-2086, 15 mg, 20%). MS (ESI) [M+H$^+$]$^+$=441.06.

Step 3b—Preparation of 3-[3-(4-Chloro-2-fluoro-benzyloxy)-2-(2-fluoro-ethoxy)-benzyl]-1H-pyrrolo[2,3-b]pyridine (P-2085)

A mixture of 3-{[3-(4-chloro-2-fluoro-benzyloxy)-2-(2-fluoro-ethoxy)-phenyl]-methoxy-methyl}-1H-pyrrolo[2,3-b]pyridine (96, 36 mg, 0.078 mmol), triethylsilane (0.5 mL, 3 mmol), and trifluoroacetic acid (0.2 mL, 2 mmol) in acetonitrile (20 mL) was stirred at 80° C. for 2 hours. The mixture was concentrated and the residue was dissolved in ethyl acetate. The solution was washed with saturated sodium bicarbonate, brine, and dried over sodium sulfate. After removal of solvent, the residue was purified by silica gel column chromatography eluting with ethyl acetate in hexanes to provide the compound as a yellow solid (P-2085, 24 mg, 71%). MS (ESI) [M+H$^+$]$^+$=429.15.

3-(4-Chloro-benzyloxy)-2-(2,2-difluoro-ethoxy)-phenyl]-(1H-pyrrolo[2,3-b]pyridin-3-yl)-methanone (P-2075)

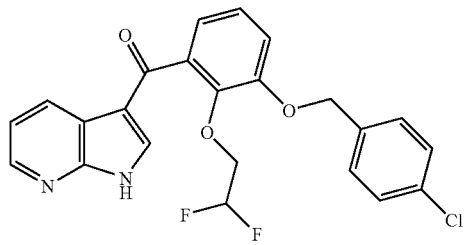

(P-2075)

was prepared following the protocol of Scheme 30, substituting 2-fluoro-ethanol with 2,2-difluoro-ethanol and substituting 3-(4-chloro-2-fluoro-benzyloxy)-2-hydroxy-benzaldehyde 93 with 3-(4-chloro-benzyloxy)-2-hydroxy-benzaldehyde (63 of Example 21) in Step 1 to provide P-2075.

MS (ESI) [M+H$^+$]$^+$=443.1.

[3-(4-Chloro-2-fluoro-benzyloxy)-2-(2,2-difluoro-ethoxy)-phenyl]-(1H-pyrrolo[2,3-b]pyridin-3-yl)-methanone (P-2119), [3-(4-Chloro-2-fluoro-benzyloxy)-2-cyclopropylmethoxy-phenyl]-(1H-pyrrolo[2,3-b]pyridin-3-yl)-methanone (P-2120), and [3-(4-Chloro-2-fluoro-benzyloxy)-2-(2,2,2-trifluoro-ethoxy)-phenyl]-(1H-pyrrolo[2,3-b]pyridin-3-yl)-methanone (P-2139)

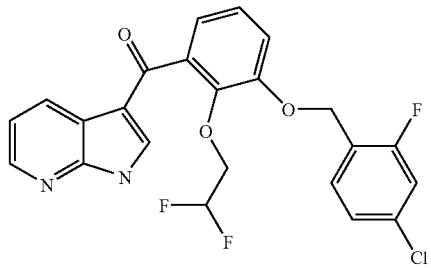

(P-2119)

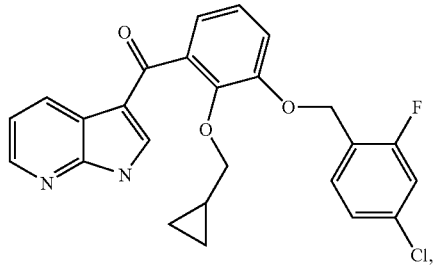

(P-2120)

and

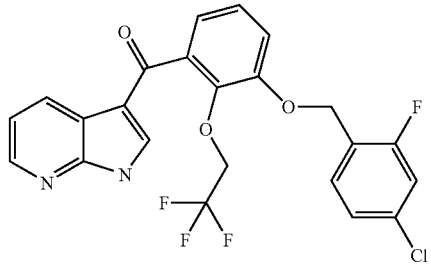

(P-2139)

were prepared following the protocol of Scheme 30, substituting 2-fluoro-ethanol with 2,2-difluoro-ethanol in Step 1 to provide P-2119 (MS (ESI) [M+H$^+$]$^+$=461.15), or substituting 2-fluoro-ethanol with cyclopropyl-methanol in Step 1 to provide P-2120 (MS (ESI) [M+H$^+$]$^+$=451.18), or substituting 2-fluoro-ethanol with 2,2,2-trifluoro-ethanol in Step 1 to provide P2139 (MS (ESI) [M+H$^+$]$^+$=479.11).

Example 32

Synthesis of [3-(2-chloro-4-methanesulfonyl-benzyloxy)-2-ethoxy-phenyl]-(1H-pyrrolo[2,3-b]pyridin-3-yl)-methanone P-2094

Compound P-2094 was synthesized in four steps from compounds 68 and 97 as shown in Scheme 31.

Scheme 31

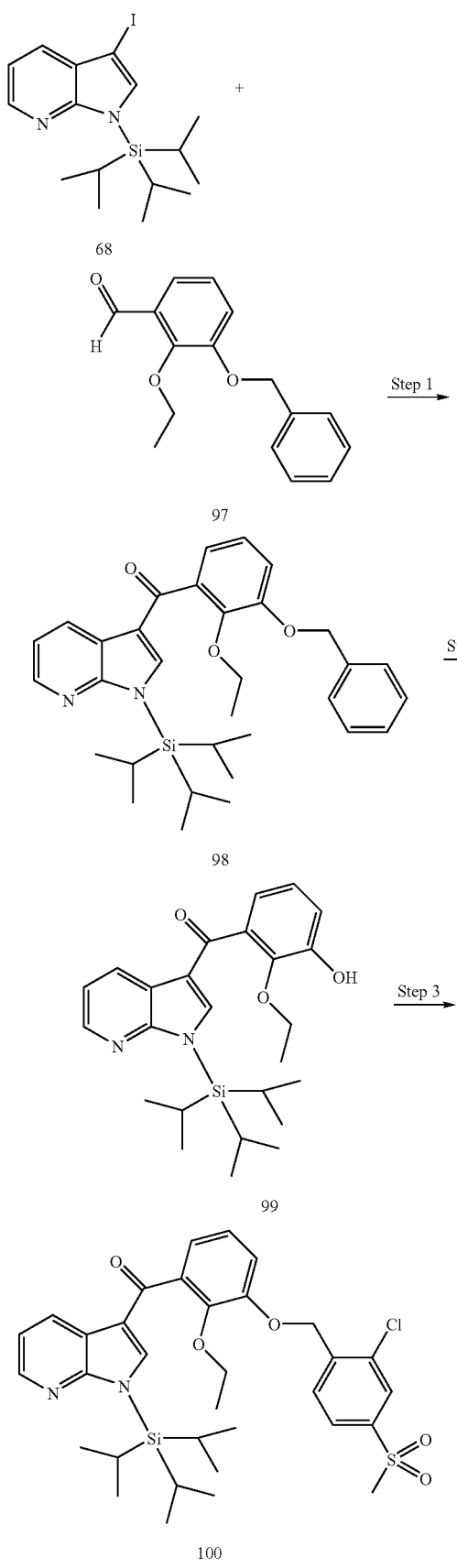

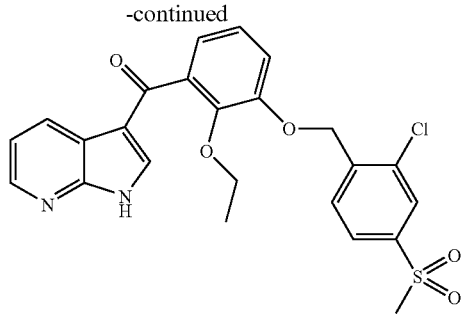

P-2094

Step 1—Preparation of (3-Benzyloxy-2-ethoxy-phenyl)-(1-triisopropylsilanyl-1H-pyrrolo[2,3-b]pyridin-3-yl)-methanol (98)

To a solution of 3-iodo-1-triisopropylsilanyl-1H-pyrrolo[2,3-b]pyridine (68, 1.306 g, 3.26 mmol, prepared as described in Example 22) in tetrahydrofuran (42 mL) at −20° C. under nitrogen was added isopropylmagnesium chloride (1.70 mL, 2.0 M solution in tetrahydrofuran, 3.40 mmol). The reaction mixture was stirred at −20° C. for 1.5 hours. It was allowed to warm to 5° C. and then kept at 5° C. for 1 hour. The reaction mixture was then cooled down to −20° C. To this solution was slowly added a solution of 2-ethoxy-3-benzyloxybenzaldehyde (97, 0.698 g, 2.72 mmol, prepared by protocol of Example 21, Steps 1-3 of Scheme 20, using benzyl bromide in place of 4-chloro-benzyl bromide in Step 1) in tetrahydrofuran (42 mL). The reaction mixture was stirred at −20° C. for 2.5 hrs, and was allowed to warm to 5° C. for 2.5 hours. The reaction mixture was poured into iced water, extracted with ethyl acetate, washed with saturated ammonium chloride and brine, and dried over magnesium sulfate. After removal of solvent, the residue was purified by silica gel column chromatography eluting with ethyl acetate in hexane to provide the compound as light-yellow oil (98, 200 mg, 13.9%).

Step 2—Preparation of (2-ethoxy-3-hydroxy-phenyl)-(1-triisopropylsilanyl-1H-pyrrolo[2,3-h]pyridin-3-yl)-methanone (99)

To a solution of (3-benzyloxy-2-ethoxy-phenyl)-(1-triisopropylsilanyl-1H-pyrrolo[2,3-b]pyridin-3-yl)-methanol (98, 195 mg, 0.37 mmol) in a mixture of methanol (20 mL) and tetrahydrofuran (50 mL) was added palladium on carbon (50 mg, 10% wt., 0.2 mmol). The mixture was stirred under hydrogenation for seventeen hours. After removal of solvent, the residue was washed with a mixture of ethyl ether and hexanes to provide the compound as a white solid (99, 63 mg, 95%). MS (ESI) [M+H$^+$]$^+$=439.37.

Step 3—Preparation of [3-(2-Chloro-4-methanesulfonyl-benzyloxy)-2-ethoxy-phenyl]-(1-triisopropylsilanyl-1H-pyrrolo[2,3-b]pyridin-3-yl)-methanone (100)

To a solution of (2-ethoxy-3-hydroxy-phenyl)-(1-triisopropylsilanyl-1H-pyrrolo[2,3-b]pyridin-3-yl)-methanone (99, 40 mg, 0.064 mmol) in tetrahydrofuran (15 mL) was added sodium hydride (3.32 mg, 0.083 mmol) at room temperature under an atmosphere of nitrogen. The mixture was stirred at room temperature for 40 minutes, then 1-bromomethyl-2-chloro-4-methanesulfonyl-benzene (21.72 mg, 0.077 mmol) was added to the reaction mixture. It was stirred at room temperature overnight. The mixture was then poured into water and was extracted with ethyl acetate. The organic layer was collected and washed with brine, dried over magnesium sulfate. After removal of the solvent, a crude compound as light yellow oil was obtained (100, 84 mg).

Step 4—Preparation of [3-(2-Chloro-4-methanesulfonyl-benzyloxy)-2-ethoxy-phenyl]-(1H-pyrrolo[2,3-b]pyridin-3-yl)-methanone (P-2094)

To a solution of (2-ethoxy-3-hydroxy-phenyl)-(1-triisopropylsilanyl-1H-pyrrolo[2,3-b]pyridin-3-yl)-methanone (100, 84 mg, 0.054 mmol) in methanol (10 mL) was added potassium hydroxide (6 N solution) until pH of the solution turned to over 10. Potassium fluoride (30 mg, 0.5 mmol) was then added to the reaction mixture and the mixture was stirred at room temperature for 6 hours. The reaction mixture was then poured into saturated sodium carbonate and was extracted with ethyl acetate. The organic layer was collected and washed with brine, dried over magnesium sulfate. After removal of the solvent, the residue was purified by preparative HPLC to provide as a white solid (P-2094, 5 mg, 19%). MS (ESI) [M+H$^+$]$^+$=485.17.

Example 33

Synthesis of 4-(3-diethylamino-propoxy)-2-fluoro-5-methoxy-benzaldehyde 102

4-(3-Diethylamino-propoxy)-2-fluoro-5-methoxy-benzaldehyde 102 was synthesized in one step from 2-fluoro-4-hydroxy-5-methoxy-benzaldehyde 39 as shown in Scheme 32.

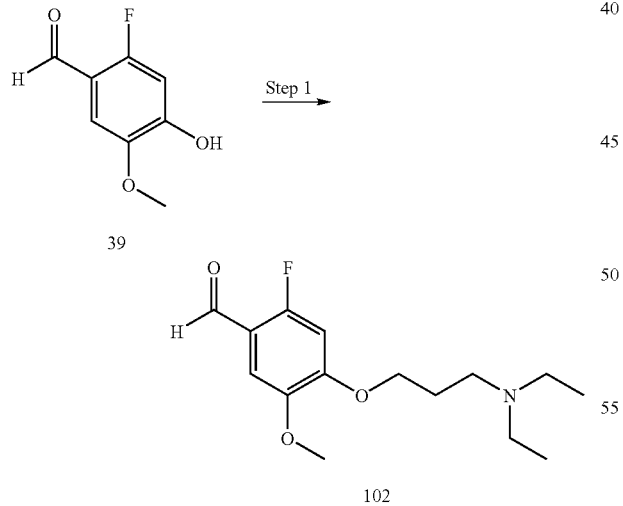

Step 1—Synthesis of 4-(3-diethylamino-propoxy)-2-fluoro-5-methoxy-benzaldehyde (102)

To 2-fluoro-4-hydroxy-5-methoxy-benzaldehyde (39, 1.20 g, 7.05 mmol, prepared as described in Scheme 12 of Example 15) in tetrahydrofuran (60.0 mL) were added triphenylphosphine (1.93 g, 7.35 mmol) and 3-(diethylamino)-propan-1-ol, (0.96 g, 7.30 mmol). The reaction was cooled to 0° C., followed by slow addition of diethyl azodicarboxylate (1.28 g, 7.35 mmol). The reaction was allowed to warm to room temperature overnight. The reaction was poured into water and extracted with ethyl acetate. The organic layer was dried over anhydrous sodium sulfate and filtered. The filtrate was concentrated and purified by silica gel column chromatography eluting with 10% methanol in dichloromethane to give a colorless oil (102, 0.90 g, 45.0%).

Example 34

Synthesis of 4-(1H-benzoimidazol-2-ylmethoxy)-5-chloro-2-fluoro-benzaldehyde 106

4-(1H-benzoimidazol-2-ylmethoxy)-5-chloro-2-fluoro-benzaldehyde 106 was synthesized in three steps from 2-chloro-5-fluoro-phenol 103 as shown in Scheme 33.

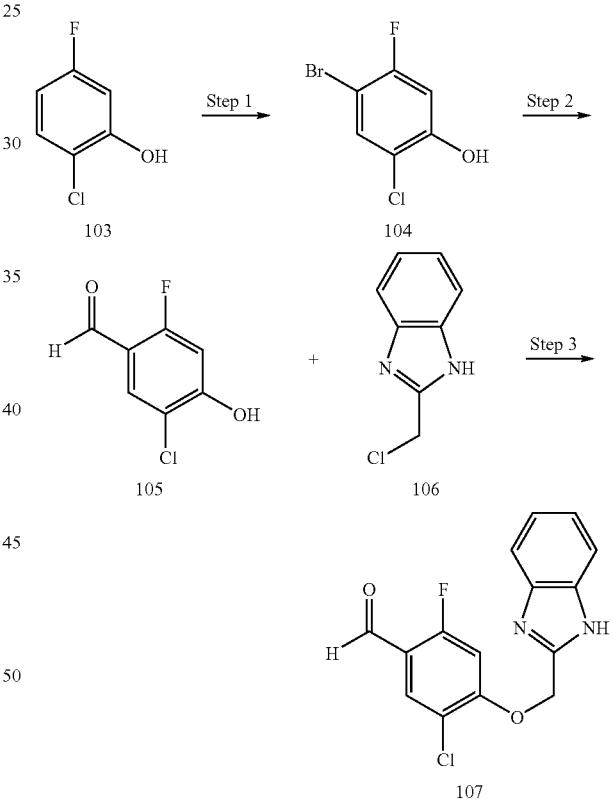

Step 1—Preparation of 4-bromo-2-chloro-5-fluoro-phenol (104)

To 2-chloro-5-fluoro-phenol (103, 6.20 g, 0.0423 mol) in chloroform (110.0 mL) bromine (2.18 mL, 0.0423 mol) was added slowly. The reaction was stirred at room temperature for 3 hours. The reaction was poured into a solution of sodium thiosulfate and extracted with ethyl acetate. The organic layer was dried over sodium sulfate, concentrated and purified with silica gel column chromatography eluting with 20% ethyl acetate in hexane to give the desired compound as a colorless oil (104, 4.50 g, 47.2%).

Step 2—Preparation of 5-chloro-2-fluoro-4-hydroxy-benzaldehyde (105)

To 4-bromo-2-chloro-5-fluoro-phenol (104, 2.25 g, 9.98 mmol) in tetrahydrofuran (50 mL), cooled to −78° C. under an atmosphere of nitrogen, was added n-butyllithium (2.50 M in hexane, 4.21 mL) and 1,2-bis-(chloro-dimethyl-silanyl)-ethane (1.08 g, 5.01 mmol). The reaction was stirred at room temperature for 2 hours. The reaction was cooled to −78° C., followed by adding tert-butyllithium (1.70 M in hexane, 12.4 mL). After 30 minutes, N,N-dimethylformamide (0.97 mL, 0.0125 mol) was added to the reaction. After 30 minutes, the reaction was warmed to room temperature for 10 minutes. 5N HCl (20 mL) was added to the reaction. After 30 minutes, the reaction was poured into water and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (105, 0.50 g, 28.7). $^1$H NMR consistent with structure.

Step 3—Preparation of 4-(1H-benzoimidazol-2-yl-methoxy)-5-chloro-2-fluoro-benzaldehyde (107)

To 5-chloro-2-fluoro-4-hydroxy-benzaldehyde (105, 0.500 g, 2.86 mmol) in N,N-dimethylformamide (30.0 mL, 0.387 mol) was added sodium hydride (130.0 mg, 3.25 mmol, 60% in mineral oil). After 20 minutes, 2-chloromethyl-1H-benzoimidazole (106, 436.0 mg, 2.62 mmol) was added to the reaction. The reaction was stirred at 30° C. for 15 hours. The reaction was poured into water and extracted with ethyl acetate. The organic layer was dried over anhydrous sodium sulfate and filtered. The filtrate was concentrated and purified by silica gel column chromatography eluting with 20% to 100% ethyl acetate in hexane to give a white solid (107, 0.35 g, 43.9%). MS (ESI) [M+H$^+$]$^+$=305.1.

Example 35

Synthesis of 5-(1-methyl-1H-pyrazol-4-yl)-1-pyrrolo[2,3-b]pyridine 109

5-(1-Methyl-1H-pyrazol-4-yl)-1H-pyrrolo[2,3-b]pyridine 109 was synthesized in 1 step from 5-bromo-1H-pyrrolo[2,3-b]pyridine 1 as shown in Scheme 34.

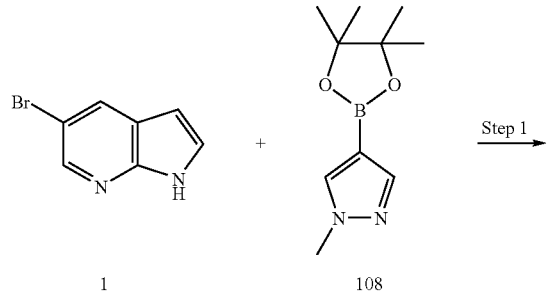

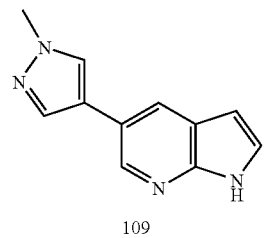

Step 1—Preparation of 5-(1-Methyl-1H-pyrazol-4-yl)-1H-pyrrolo[2,3-b]pyridine (109)

To 5-bromo-7-azaindole (1, 1.04 g, 5.28 mmol) in 1.00 M potassium carbonate in water (15.8 mL) and tetrahydrofuran (50.0 mL) were added 1-methyl-4-(4,4,5,5-tetramethyl-[1,3,2]dioxaborolan-2-yl)-1H-pyrazole (108, 1.65 g, 7.92 mmol), Tetrakis(triphenylphosphine)-palladium(0) (0.305 mg, 0.26 mmol) and tetra-n-butylammonium iodide (0.20 g, 0.53 mmol). The reaction mixture was stirred at 70° C. overnight. The reaction mixture was poured into water and the organic layer was washed with brine, dried over sodium sulfate, and concentrated. The residue was purified with silica gel column chromatography eluting with 25% ethyl acetate in hexane to provide a light yellow solid (109, 670 mg, 64.0%). MS (ESI) [M+H$^+$]$^+$=199.4.

Example 36

Synthesis of [2,6-dichloro-3-(2,2,2-trifluoro-ethoxy)-phenyl]-[5-(1-methyl-1H-pyrazol-4-yl)-1H-pyrrolo[2,3-b]pyridin-3-yl]-methanone P-2151

[2,6-Dichloro-3-(2,2,2-trifluoro-ethoxy)-phenyl]-[5-(1-methyl-1H-pyrazol-4-yl)-1H-pyrrolo[2,3-b]pyridin-3-yl]-methanone P-2151 was synthesized in five steps as shown in Scheme 35.

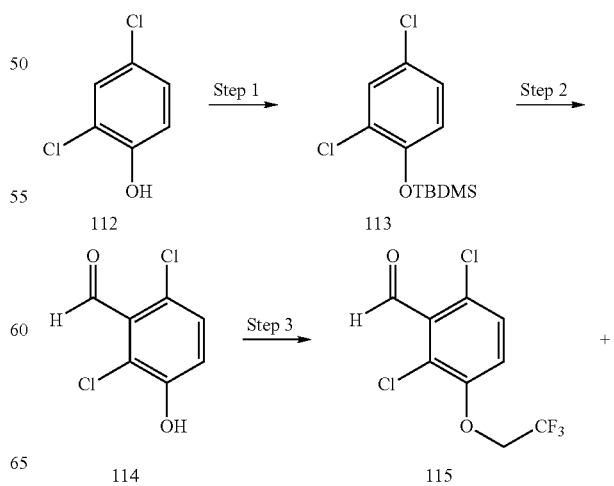

221

-continued

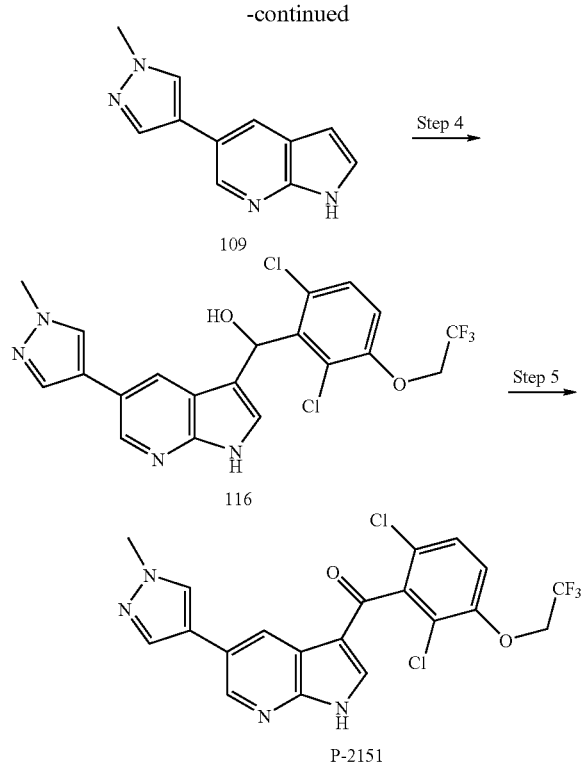

Step 1—Preparation of
tert-butyl-(2,4-dichloro-phenoxy)-dimethyl-silane
(113)

To 2,4-dichloro-phenol, (112, 4.80 g, 0.0294 mol) in N,N-dimethylformamide (100.0 mL) were added 1H-imidazole (5.21 g, 0.0766 mol) and tert-butyldimethylsilyl chloride (5.33 g, 0.0353 mol). The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 15% to 50% ethyl acetate in hexane to give a colorless oil (113, 7.10 g, 87.0%).

Step 2—Preparation of
2,6-dichloro-3-hydroxy-benzaldehyde (114)

To tert-butyl-(2,4-dichloro-phenoxy)-dimethyl-silane (113, 4.00 g, 0.0144 mol) in tetrahydrofuran (50.0 mL), under an atmosphere of nitrogen at −78° C., n-butyllithium (2.50 M in hexane, 6.06 mL) was added slowly. After 30 minutes, N,N-dimethylformamide (1.34 mL, 0.0173 mol) was added to the reaction. After 1 hour, the reaction was allowed to warm to room temperature. 1N HCl (40 mL) was added to the reaction. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give a yellow solid (114, 2.0 g, 72.6%).

Step 3—Preparation of 2,6-dichloro-3-(2,2,2-trifluoro-ethoxy)-benzaldehyde (115)

To 2,6-dichloro-3-hydroxy-benzaldehyde (114, 2.06 g, 0.0108 mol) in N-methylpyrrolidinone (25.0 mL) were added

222 cesium carbonate (7.02 g, 0.0215 mol) and trifluoro-methanesulfonic acid 2,2,2-trifluoro-ethyl ester (2.50 g, 0.0108 mol) under an atmosphere of nitrogen. The reaction was stirred at room temperature for 90 hours. The reaction was poured into water and extracted with ethyl acetate. The organic layer was dried over anhydrous sodium sulfate and filtered. The filtrate was concentrated and purified by silica gel column chromatography eluting with 15% to 100% ethyl acetate in hexane to give a colorless oil (115, 1.00 g, 34.0%).

Step 4—Preparation of [2,6-dichloro-3-(2,2,2-trifluoro-ethoxy)-phenyl]-[5-(1-methyl-1H-pyrazol-4-yl)-1H-pyrrolo[2,3-b]pyridin-3-yl]-methanol (116)

To 5-(1-methyl-1H-pyrazol-4-yl)-1H-pyrrolo[2,3-b]pyridine (109, 100.0 mg, 0.51 mmol, prepared as described in Example 35) in methanol (30 mL) were added 2,6-dichloro-3-(2,2,2-trifluoro-ethoxy)-benzaldehyde (115, 154 mg, 0.56 mmol) and potassium hydroxide (596.0 mg, 10.62 mmol) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 2% to 25% methanol in dichloromethane to give the desired compound (116, 0.18 g, 75.7%).

Step 5—Preparation of [2,6-dichloro-3-(2,2,2-trifluoro-ethoxy)-phenyl]-[5-(1-methyl-1H-pyrazol-4-yl)-1H-pyrrolo-[2,3-b]pyridin-3-yl]-methanone (P-2151)

To [2,6-dichloro-3-(2,2,2-trifluoro-ethoxy)-phenyl]-[5-(1-methyl-1H-pyrazol-4-yl)-1H-pyrrolo[2,3-b]pyridin-3-yl]-methanol (116, 100.0 mg, 0.21 mmol) in dichloromethane (10.0 mL), Dess-Martin periodinane (108 mg, 0.26 mmol) was added. The reaction was stirred at room temperature for 10 minutes. The reaction mixture was poured into aqueous potassium carbonate and extracted with ethyl acetate. The organic layer was dried over anhydrous sodium sulfate and filtered. The filtrate was concentrated and purified by silica gel column chromatography eluting with 20% to 100% ethyl acetate in hexane to give a white solid (P-2151, 19.4 mg, 19.5%). MS (ESI) $[M+H^+]^+=469.1$.

2,6-Difluoro-4-hydroxy-benzaldehyde 117

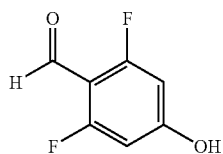

was prepared following the protocol of Scheme 35, steps 1 and 2, substituting 2,4-dichloro-phenol with 3,5-difluoro-phenol in step 1.

Example 37

Synthesis of 2-chloro-5-fluoro-4-[2-(2-methoxy-ethoxy)-ethoxy]-benzaldehyde 121

2-Chloro-5-fluoro-4-[2-(2-methoxy-ethoxy)-ethoxy]-benzaldehyde 121 was synthesized in 4 steps as shown in Scheme 36.

Scheme 36

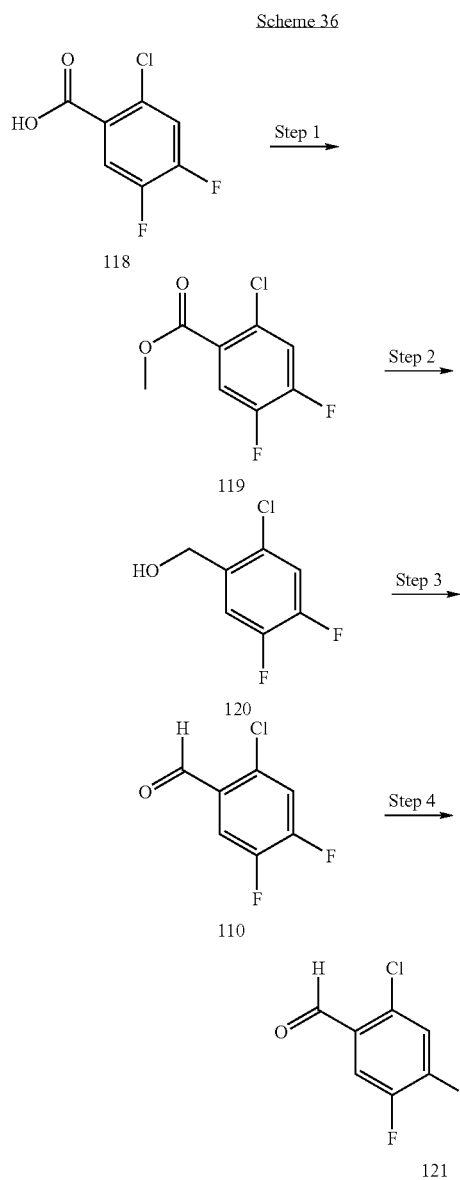

Step 1—Preparation of 2-chloro-4,5-difluoro-benzoic acid methyl ester (119)

To 2-chloro-4,5-difluoro-benzoic acid (118, 14.0 g, 0.0727 mol) in methanol (100 mL) was added sulfuric acid (concentrated, 98%, 2.00 mL, 0.0375 mol). The reaction was stirred at 60° C. for 48 hours. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give a colorless oil (119, 13.0 g, 86.6%).

Step 2—Preparation of (2-chloro-4,5-difluoro-phenyl)-methanol (120)

To 2-chloro-4,5-difluoro-benzoic acid methyl ester (119, 5.70 g, 0.0276 mol) in tetrahydrofuran (120.0 mL), 1.00 M of lithium tetrahydroaluminate in tetrahydrofuran (30.0 mL) was added slowly under an atmosphere of nitrogen. The reaction was stirred at room temperature for 4 hours, followed by adding sodium sulfate decahydrate. After 30 minutes, the reaction mixture was filtered, concentrated and purified with silica gel column chromatography eluting with 8% methanol in dichloromethane to give a white solid (120, 4.20 g, 85.2%).

Step 3—Preparation of 2-chloro-4,5-difluoro-benzaldehyde (110)

To (2-chloro-4,5-difluoro-phenyl)-methanol (120, 2.40 g, 0.0134 mol) in dichloromethane (40.0 mL) was added Dess-Martin periodinane (6.84 g, 0.0161 mol). The reaction was stirred at room temperature for 10 minutes. The reaction was poured into aqueous potassium carbonate and extracted with ethyl acetate. The organic layer was dried over anhydrous sodium sulfate and filtered. The filtrate was concentrated and purified by silica gel column chromatography eluting with 30% ethyl acetate in hexane to give a white solid (110, 1.7 g, 71.6%).

Step 4—Preparation of 2-chloro-5-fluoro-4-[2-(2-methoxy-ethoxy)-ethoxy]-benzaldehyde (121)

To 2-chloro-4,5-difluoro-benzaldehyde (110, 0.40 g, 0.0023 mol) in N,N-dimethylformamide (10.0 mL), 2-(2-methoxyethoxy)-ethanol (0.327 g, 2.72 mmol) and cesium carbonate (0.886 g, 2.72 mmol) were added. The reaction was stirred at 90° C. overnight. The reaction was poured into water, acidified to pH around 5, and extracted with ethyl acetate. The organic layer was dried over an hydrous sodium sulfate and filtered. The filtrate was concentrated and purified by silica gel column chromatography eluting with 30% ethyl acetate in hexane to give a white solid (121, 0.15 g, 24.0%).

Example 38

Synthesis of 2-chloro-5-fluoro-4-hydroxy-benzaldehyde 111

2-Chloro-5-fluoro-4-hydroxy-benzaldehyde 111 was synthesized in one step from 2-chloro-4,5-difluoro-benzaldehyde 110 as shown in Scheme 37.

Scheme 37

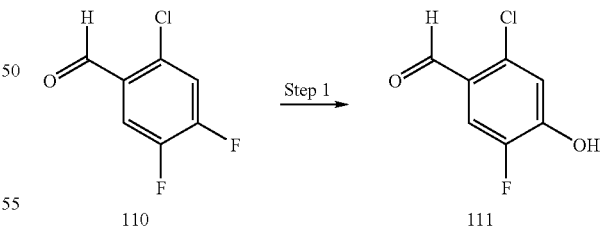

Step 1—Preparation of 2-chloro-5-fluoro-4-hydroxy-benzaldehyde (111)

To 2-chloro-4,5-difluoro-benzaldehyde (110, 0.40 g, 2.30 mmol, prepared as described in Example 37) in N,N-dimethylformamide (10.0 mL) were added 2-(2-methoxyethoxy)-ethanol, (0.327 g, 2.72 mmol) and cesium carbonate (0.886 g, 2.72 mmol). The reaction was stirred at 90° C. overnight. The reaction was poured into water, acidified to pH around 5, and extracted with ethyl acetate. The organic layer was dried over anhydrous sodium sulfate and filtered. The filtrate was concentrated and purified by silica gel column chromatography eluting with 30% ethyl acetate in hexane to give a white solid (111, 0.24 g, 61.0%). MS (ESI) [M+H$^+$]$^+$=173.1.

Example 39

Synthesis of 2-chloro-6-fluoro-3-(2-methoxy-ethoxy)-benzaldehyde 123

2-Chloro-6-fluoro-3-(2-methoxy-ethoxy)-benzaldehyde 123 was synthesized in 2 steps from 2-chloro-4-fluorophenol 52 as shown in Scheme 38.

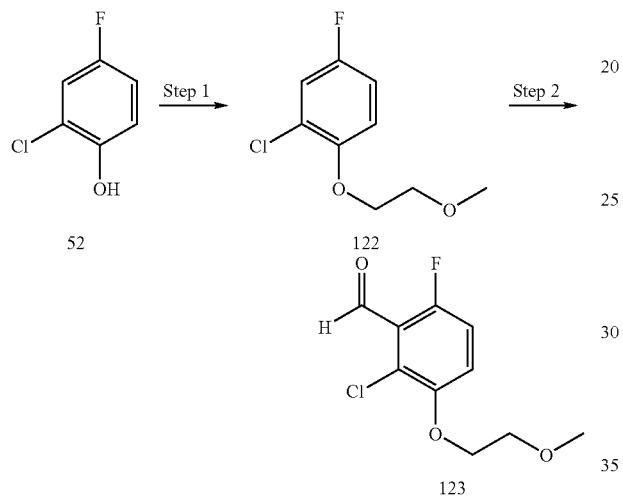

Step 1—Preparation of 2-chloro-4-fluoro-1-(2-methoxy-ethoxy)-benzene (122)

To 2-chloro-4-fluorophenol (52, 2.40 mL, 0.0213 mol) in N,N-dimethylformamide (30.0 mL), 1-bromo-2-methoxy-ethane (2.00 mL, 0.0213 mol) and potassium carbonate (3.00 g, 0.0217 mol) were added under an atmosphere of nitrogen. The reaction was stirred at 80° C. for 2 hours. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give a colorless oil (122, 1.50 g, 34.4%).

Step 2—Preparation of 2-chloro-6-fluoro-3-(2-methoxy-ethoxy)-benzaldehyde (123)

To 2-chloro-4-fluoro-1-(2-methoxy-ethoxy)-benzene (122, 1.50 g, 7.33 mmol) in tetrahydrofuran (44.0 mL), under an atmosphere of nitrogen at −78° C., n-butyllithium (2.50 M in hexane, 3.08 mL) was added slowly. After 15 minutes, N,N-dimethylformamide (0.681 mL, 8.80 mmol) was added to the reaction. After 30 minutes, the reaction was allowed to warm to room temperature. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give a light yellow solid (123, 1.20 g, 70.4%).

Example 40

Synthesis of 2-chloro-6-fluoro-3-(2,2,2-trifluoro-ethoxy)-benzaldehyde 125

2-Chloro-6-fluoro-3-(2,2,2-trifluoro-ethoxy)-benzaldehyde 125 was synthesized in 2 steps from 2-chloro-4-fluorophenol 52 as shown in Scheme 39.

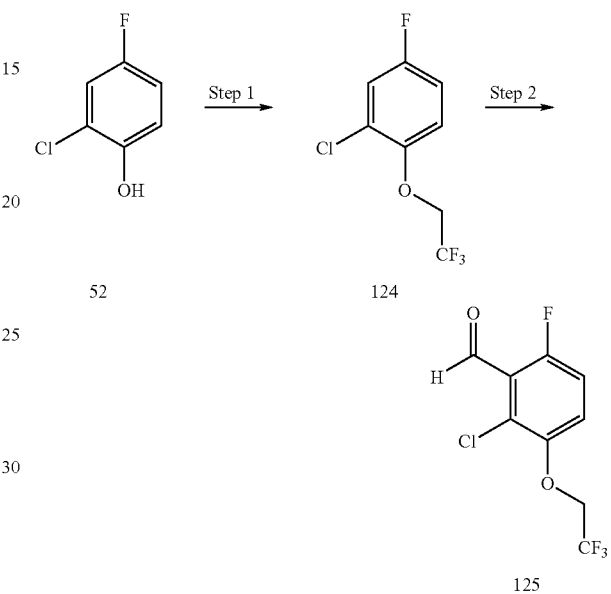

Step 1—Preparation of 2-chloro-4-fluoro-1-(2,2,2-trifluoro-ethoxy)-benzene (124)

To 2-chloro-4-fluorophenol (52, 1.58 g, 0.0108 mol) in N-methylpyrrolidinone (25.0 mL), cesium carbonate (7.02 g, 0.0215 mol) and trifluoro-methanesulfonic acid 2,2,2-trifluoro-ethyl ester (2.50 g, 0.0108 mmol) were added under an atmosphere of nitrogen. The reaction was stirred at room temperature for 90 hours. The reaction was poured into water and extracted with ethyl acetate. The organic layer was dried over anhydrous sodium sulfate and filtered. The filtrate was concentrated and purified by silica gel column chromatography eluting with 15% to 100% ethyl acetate in hexane to give a colorless oil (124, 2.10 g, 85.3%).

Step 2—Preparation of 2-chloro-6-fluoro-3-(2,2,2-trifluoro-ethoxy)-benzaldehyde (125)

To 2-chloro-4-fluoro-1-(2,2,2-trifluoro-ethoxy)-benzene (124, 2.10 g, 9.19 mmol), under an atmosphere of nitrogen at −78° C., n-butyllithium (2.50 M in hexane, 3.86 mL) was added slowly. After 60 minutes, N,N-dimethylformamide (0.782 mL, 0.0101 mol) was added to the reaction. After 30 minutes, the reaction was allowed to warm to room temperature for 10 minutes. The reaction was poured into water and extracted with ethyl acetate. The organic layer was dried over anhydrous sodium sulfate, and filtered. The filtrate was concentrated and purified by silica gel column chromatography eluting with 20% ethyl acetate in hexane to give the desired compound (125, 450 mg, 19.0%).

Example 41

Synthesis of 5-chloro-3-2-chloro-5-fluoro-4-[2-(2-methoxy-ethoxy)-ethoxy]-benzyl-1H-pyrrolo[2,3-b] pyridine P-2155

5-Chloro-3-2-chloro-5-fluoro-4-[2-(2-methoxy-ethoxy)-ethoxy]-benzyl-1H-pyrrolo[2,3-b]pyridine P-2155 was synthesized in 2 steps from 5-Chloro-1H-pyrrolo[2,3-b]pyridine 4 as shown in Scheme 40.

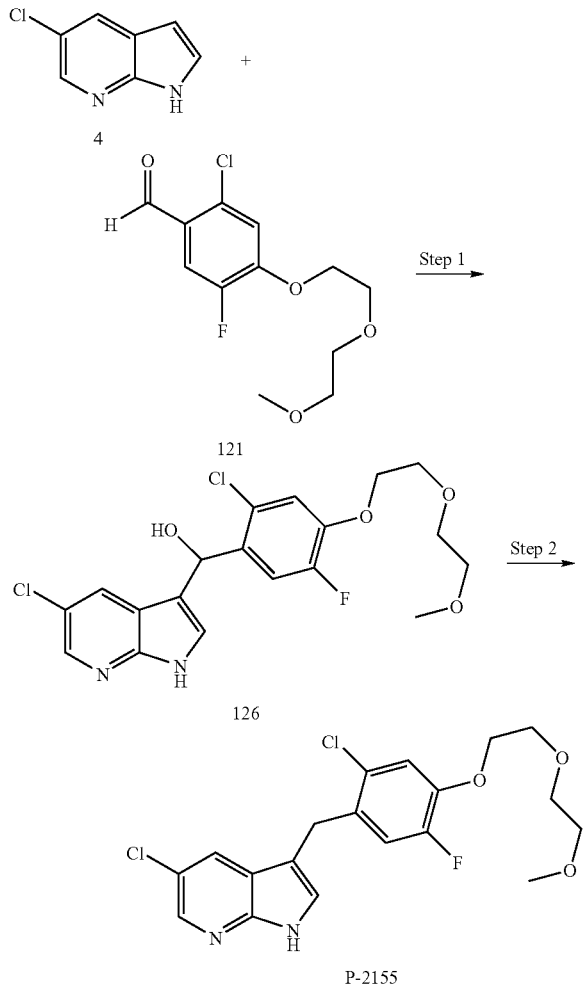

Step 1—Preparation of 2-chloro-5-fluoro-4-[2-methoxy-ethoxy)-ethoxy]-phenyl-(5-chloro-1H-pyrrolo[2, 3-b]pyridin-3-yl)-methanol (126)

To 5-chloro-1H-pyrrolo[2,3-b]pyridine (4, 74.1 mg, 0.49 mmol, prepared as described in Example 4) in methanol (30.0 mL), 2-chloro-5-fluoro-4-[2-(2-methoxy-ethoxy)-ethoxy]-benzaldehyde (121, 150.0 mg, 0.54 mmol, prepared as described in Example 37) and potassium hydroxide (574.0 mg, 10.23 mmol) were added under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the desired compound (126, 0.11 g, 52.7%).

Step 2—Preparation of 5-chloro-3-2-chloro-5-fluoro-4-[2-(2-methoxy-ethoxy)-ethoxy]-benzyl-1H-pyrrolo[2,3-b]pyridine (P-2155)

To 2-chloro-5-fluoro-4-[2-(2-methoxy-ethoxy)-ethoxy]-phenyl-(5-chloro-1-pyrrolo[2,3-b]pyridin-3-yl)-methanol (126, 65.0 mg, 0.15 mmol) in acetonitrile (10.0 mL), triethylsilane (1.00 mL, 6.26 mmol) and trifluoroacetic acid (0.50 mL, 6.50 mmol) were added. The reaction was heated to reflux for 2 hours. The reaction was poured into aqueous potassium carbonate and extracted with ethyl acetate. The organic layer was dried over anhydrous sodium sulfate and filtered. The filtrate was concentrated and washed with ethyl acetate in hexane to give a white solid (P-2155, 21.3 mg, 34.0%). MS (ESI) [M+H$^+$]$^+$=413.2.

Additional compounds were prepared using the protocol of Scheme 40, substituting 2-chloro-5-fluoro-4-[2-(2-methoxy-ethoxy)-ethoxy]-benzaldehyde 121 with a suitable aldehyde (prepared as described in Examples 15, 36, 39, or 40), and optionally replacing 5-chloro-1H-pyrrolo[2,3-b]pyridine 4 with an appropriate substituted 7-azaindole (5-methoxy-7-azaindole per Example 8, 5-(1-methyl-1H-pyrazol-4-yl)-7-azaindole per Example 35) in Step 1. The following compounds were made following this procedure:

5-Chloro-3-[2-chloro-5-fluoro-4-(pyridin-3-ylmethoxy)-benzyl]-1H-pyrrolo[2,3-b]pyridine (P-2156),
2-[5-Chloro-4-(5-chloro-1-pyrrolo[2,3-b]pyridin-3-ylmethyl)-2-fluoro-phenoxymethyl]-1H-benzoimidazole (P-2099),
2-[4-(5-Chloro-1H-pyrrolo[2,3-b]pyridin-3-ylmethyl)-2,5-difluoro-phenoxymethyl]-1H-benzoimidazole (P-2100),
2-[2,5-Difluoro-4-(5-methoxy-1H-pyrrolo[2,3-b]pyridin-3-ylmethyl)-phenoxymethyl]-1H-benzoimidazole (P-2101),
2-[3,5-Difluoro-4-(1H-pyrrolo[2,3-b]pyridin-3-ylmethyl)-phenoxymethyl]-1H-benzoimidazole (P-2102),
2-[4-(5-Chloro-1H-pyrrolo[2,3-b]pyridin-3-ylmethyl)-3,5-difluoro-phenoxymethyl]-1H-benzoimidazole (P-2105),
2-[4-(5-Bromo-1H-pyrrolo[2,3-b]pyridin-3-ylmethyl)-2,5-difluoro-phenoxymethyl]-1H-benzoimidazole (P-2107),
2-{2,5-Difluoro-4-[5-(1-methyl-1H-pyrazol-4-yl)-1H-pyrrolo[2,3-b]pyridin-3-ylmethyl]-phenoxymethyl}-1H-benzoimidazole (P-2108),
2-{5-Chloro-2-fluoro-4-[5-(1-methyl-1H-pyrazol-4-yl)-1H-pyrrolo[2,3-b]pyridin-3-ylmethyl]-phenoxymethyl}-1H-benzoimidazole (P-2109),
5-Chloro-3-[2-chloro-6-fluoro-3-(2-methoxy-ethoxy)-benzyl]-1H-pyrrolo[2,3-b]pyridine (P-2157)
3-[2-Chloro-6-fluoro-3-(2-methoxy-ethoxy)-benzyl]-1H-pyrrolo[2,3-b]pyridine (P-2158),
3-[2-Chloro-6-fluoro-3-(2,2,2-trifluoro-ethoxy)-benzyl]-5-(1-methyl-1H-pyrazol-4-yl)-1H-pyrrolo[2,3-b]pyridine (P-2146),
3-[2-Chloro-6-fluoro-3-(2,2,2-trifluoro-ethoxy)-benzyl]-5-methoxy-1H-pyrrolo[2,3-b]pyridine (P-2147),
2-[5-Chloro-2-fluoro-4-(5-methoxy-1H-pyrrolo[2,3-b]pyridin-3-ylmethyl)-phenoxymethyl]-1H-benzoimidazole (P-2114),
3-[2-Chloro-6-fluoro-3-(2,2,2-trifluoro-ethoxy)-benzyl]-1H-pyrrolo[2,3-b]pyridine (P-2148), 3-[2,6-Dichloro-3-(2,2,2-trifluoro-ethoxy)-benzyl]-5-(1-methyl-1H-pyrazol-4-yl)-1H-pyrrolo[2,3-b]pyridine (P-2152), and
3-[2,6-Dichloro-3-(2,2,2-trifluoro-ethoxy)-benzyl]-5-methoxy-1H-pyrrolo[2,3-b]pyridine (P-2153).

The following table indicates the aldehyde (column 2) and the azaindole (column 3) used to afford the target compound (column 4). Column 1 indicates the compound number and column 5 the observed mass.

| | Aldehyde | Azaindole |
|---|---|---|
| P-2156 | | |
| P-2099 | | |
| P-2100 | | |
| P-2101 | | |
| P-2102 | | |
| P-2105 | | |

-continued
P-2107 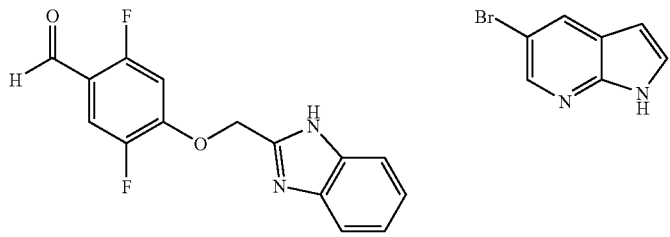 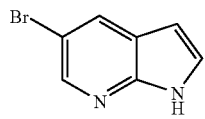
P-2108 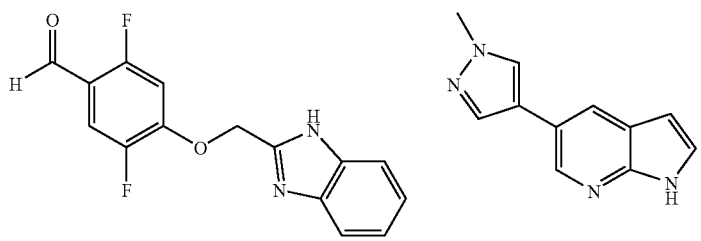 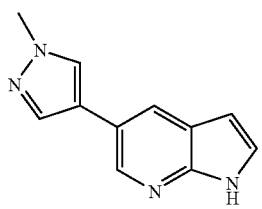
P-2109 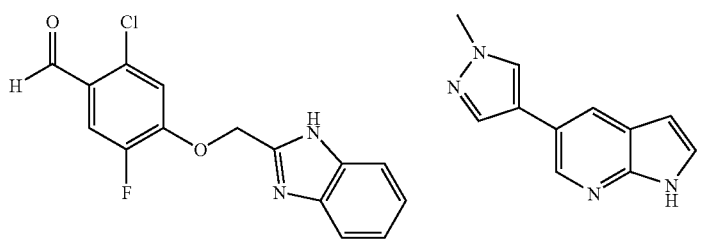 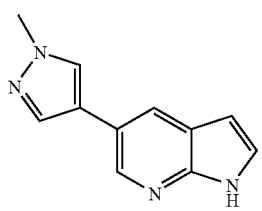
P-2157 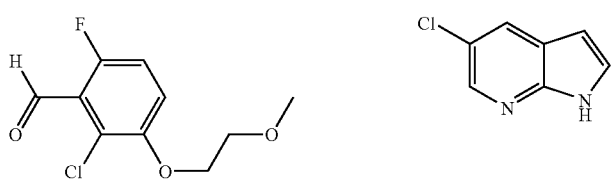 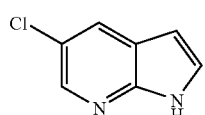
P-2158 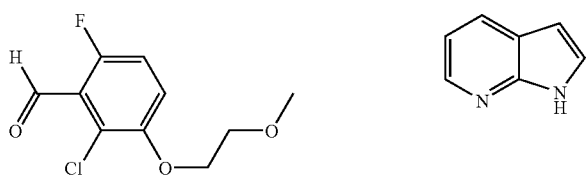 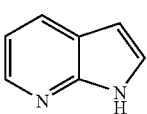
P-2146 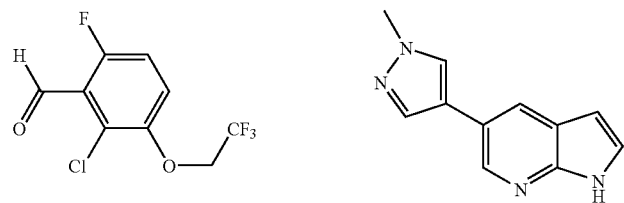 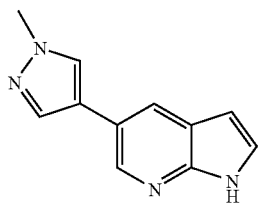
P-2147 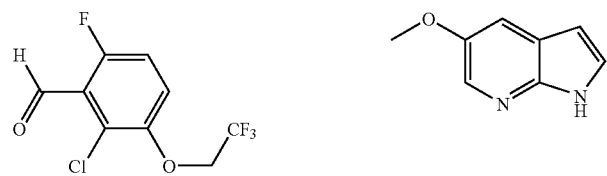 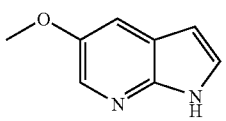

-continued
| | | |
|---|---|---|
| P-2114 | 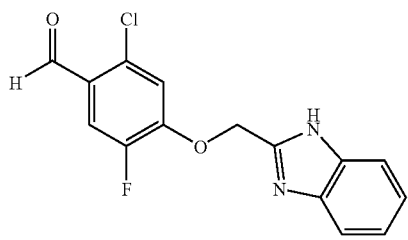 | 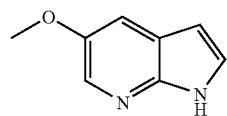 |
| P-2148 | 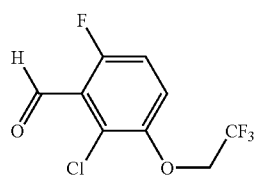 | 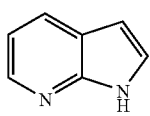 |
| P-2152 | 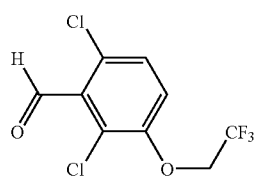 | 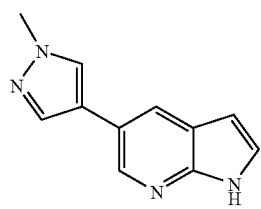 |
| P-2153 | 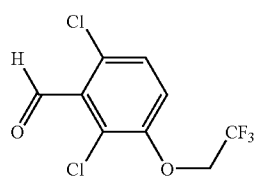 | 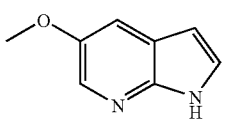 |
| | Compound | MS (ESI) [M + H+]+ observed |
|---|---|---|
| P-2156 | 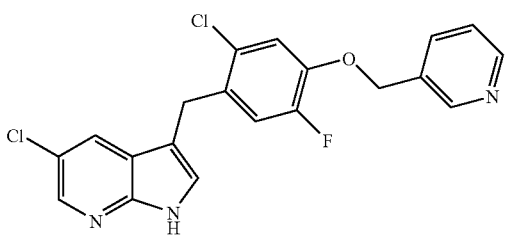 | 402.1 |
| P-2099 | 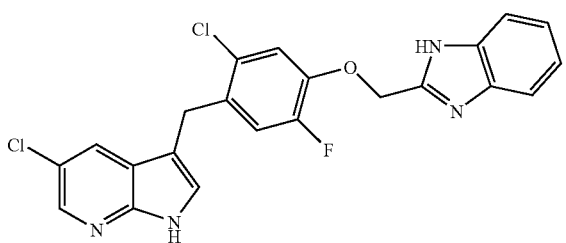 | 441.2 |

-continued
| | | |
|---|---|---|
| P-2100 | 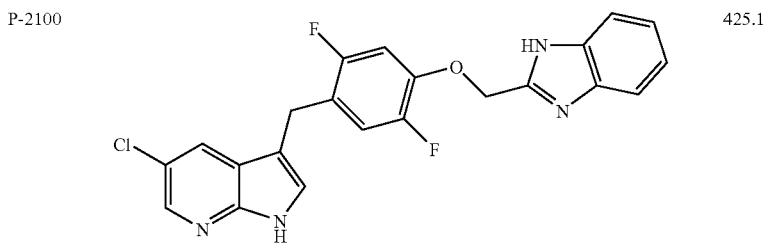 | 425.1 |
| P-2101 | 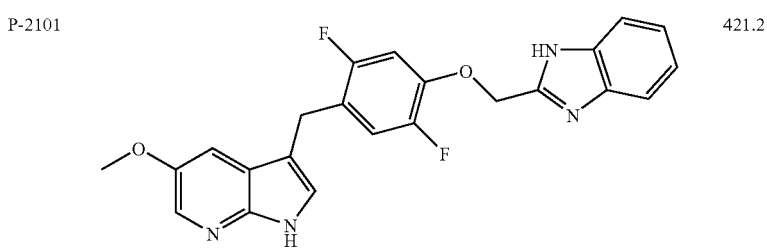 | 421.2 |
| P-2102 | 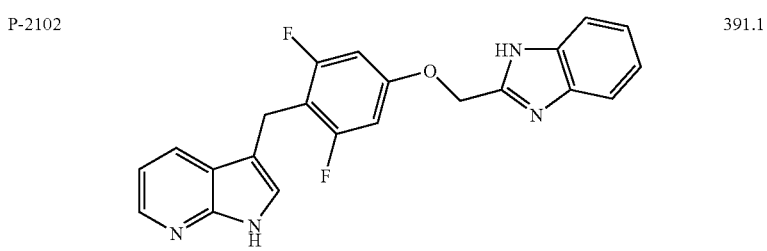 | 391.1 |
| P-2105 | 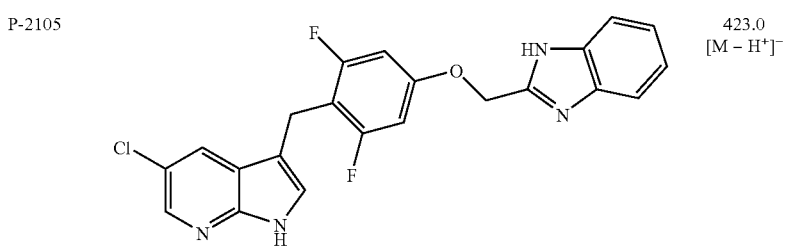 | 423.0 [M − H⁺]⁻ |
| P-2107 | 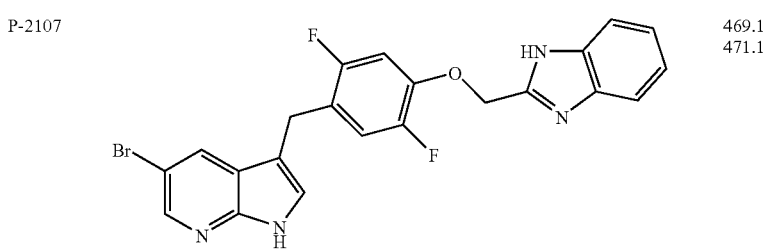 | 469.1 471.1 |
| P-2108 | 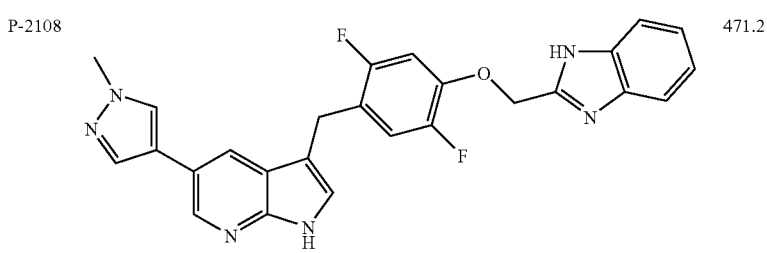 | 471.2 |

-continued
| | | |
|---|---|---|
| P-2109 | 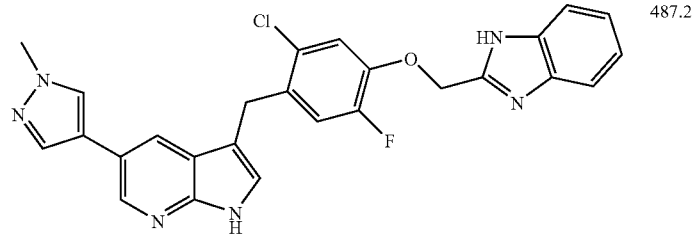 | 487.2 |
| P-2157 | 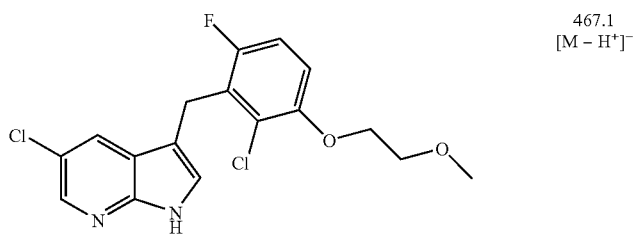 | 467.1 [M − H⁺]⁻ |
| P-2158 | 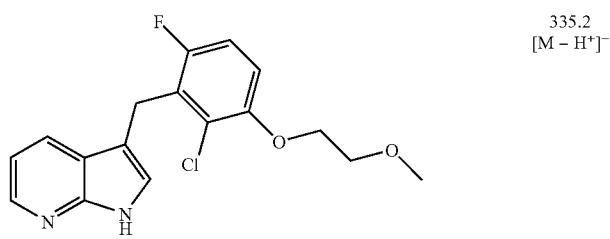 | 335.2 [M − H⁺]⁻ |
| P-2146 | 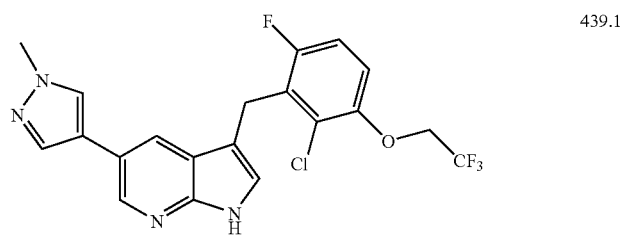 | 439.1 |
| P-2147 | 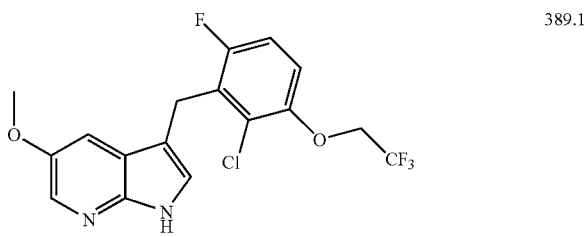 | 389.1 |
| P-2114 | 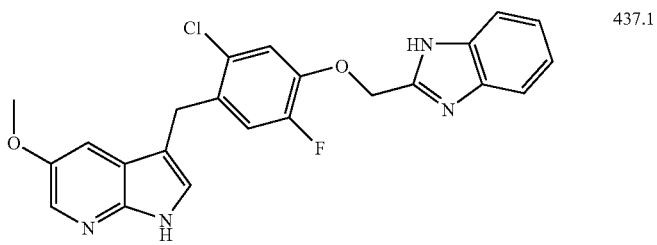 | 437.1 |

-continued

| | | |
|---|---|---|
| P-2148 | 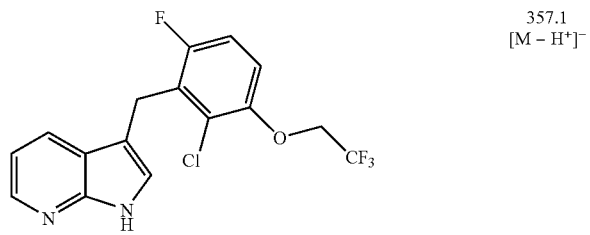 | 357.1 [M − H⁺]⁻ |
| P-2152 | 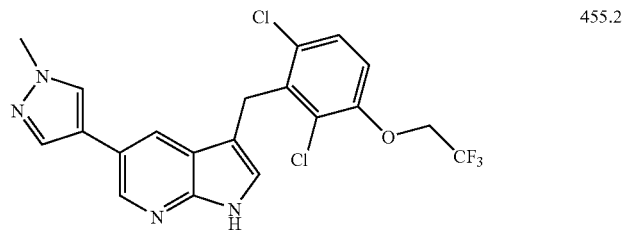 | 455.2 |
| P-2153 | 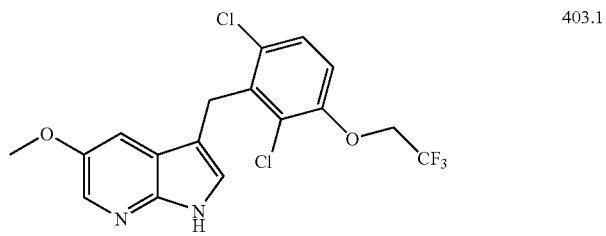 | 403.1 |

Example 42

Synthesis of [2-chloro-6-fluoro-3-(2-methoxy-ethoxy)-phenyl]-(5-chloro-1H-pyrrolo[2,3-b]pyridin-3-yl)-methanone P-2159

[2-Chloro-6-fluoro-3-(2-methoxy-ethoxy)-phenyl]-(5-chloro-1H-pyrrolo[2,3-b]pyridin-3-yl)-methanone P-2159 was synthesized in 2 steps from 5-Chloro-1H-pyrrolo[2,3-b]pyridine 4 as shown in Scheme 41.

Scheme 41

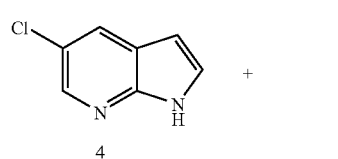

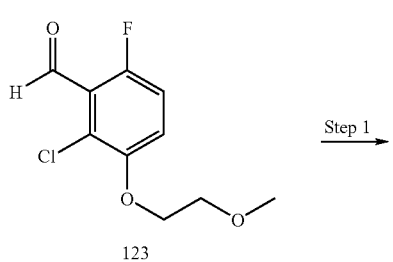

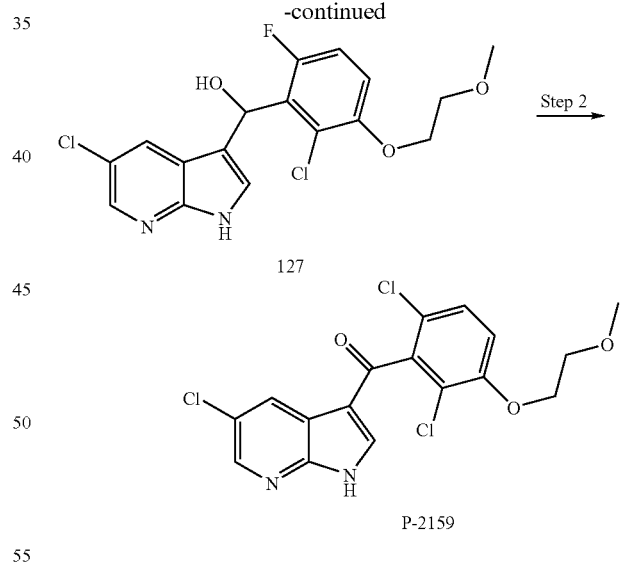

Step 1—Preparation of [2-chloro-6-fluoro-3-(2-methoxy-ethoxy-phenyl]-(5-chloro-1H-pyrrolo[2,3-b]pyridin-3-yl)-methanol (127)

To 5-chloro-1H-pyrrolo[2,3-b]pyridine (4, 270.0 mg, 1.77 mmol, prepared as described in Example 4) in methanol (15.0 mL), 2-chloro-6-fluoro-3-(2-methoxy-ethoxy)-benzaldehyde (123, 474.0 mg, 2.04 mmol, prepared as described in Example 39) and potassium hydroxide (1.20 g, 0.0214 mol) were added under an atmosphere of nitrogen. The reaction was stirred at room temperature for 4 hours. The reaction was poured into water and extracted with ethyl acetate. The organic layer was dried over anhydrous sodium sulfate and filtered. The filtrate was concentrated and purified by silica gel column chromatography eluting with 40% ethyl acetate in hexane to give a colorless oil (127, 0.26 g, 38.1%). MS (ESI) [M+H$^+$]$^+$=383.1.

Step 2—Preparation of [2-chloro-6-fluoro-3-(2-methoxy-ethoxy)-phenyl]-(5-chloro-1H-pyrrolo[2,3-b]pyridin-3-yl)-methanone (P-2159)

To [2-chloro-6-fluoro-3-(2-methoxy-ethoxy)-phenyl]-(5-chloro-1H-pyrrolo[2,3-b]pyridin-3-yl)-methanol (127, 210.0 mg, 0.5.45 mmol) in tetrahydrofuran (20.0 mL) was added Dess-Martin periodinane (277 mg, 0.65 mmol). The reaction was stirred at room temperature for 10 minutes. The reaction was poured into aqueous potassium carbonate and extracted with ethyl acetate. The organic layer was dried with anhydrous sodium sulfate. The filtrate was concentrated and purified silica gel column chromatography eluting with 50% ethyl acetate in hexane to give a white solid (P-2159, 88.1 mg, 42.2%). MS (ESI) [M−H$^+$]$^+$=381.1.

Additional compounds were prepared using the protocol of Scheme 41, optionally substituting 2-chloro-6-fluoro-3-(2-methoxy-ethoxy)-benzaldehyde 123 with a suitable aldehyde (prepared as described in Examples 36, 39 or 40), and/or optionally replacing 5-chloro-1H-pyrrolo[2,3-b]pyridine 4 with an appropriate substituted 7-azaindole (5-methoxy-7-azaindole per Example 8, 5-(1-methyl-1H-pyrazol-4-yl)-7-azaindole per Example 35) in Step 1. The following compounds were made following this procedure:

[2-Chloro-6-fluoro-3-(2-methoxy-ethoxy)-phenyl]-(1H-pyrrolo[2,3-b]pyridin-3-yl)-meth one (P-2160),
[2-Chloro-6-fluoro-3-(2,2,2-trifluoro-ethoxy)-phenyl]-[5-(1-methyl-1H-pyrazol-4-yl)-1H-pyrrolo[2,3-b]pyridin-3-yl]-methanone (P-2145),
[2-Chloro-6-fluoro-3-(2,2,2-trifluoro-ethoxy)-phenyl]-(5-methoxy-1H-pyrrolo[2,3-b]pyridin-3-yl)-methanone (P-2149),
[2-Chloro-6-fluoro-3-(2,2,2-trifluoro-ethoxy)-phenyl]-(1H-pyrrolo[2,3-b]pyridin-3-yl)-methanone (P-2150),
[2,6-Dichloro-3-(2,2,2-trifluoro-ethoxy)-phenyl]-[5-(1-methyl-1H-pyrazol-4-yl)-1H-pyrrolo[2,3-b]pyridin-3-yl]-methanone (P-2151), and
[2,6-Dichloro-3-(2,2,2-trifluoro-ethoxy)-phenyl]-(5-methoxy-1H-pyrrolo[2,3-b]pyridin-3-yl)-methanone (P-2154).

The following table indicates the aldehyde (column 2) and the azaindole (column 3) used to afford the target compound (column 4). Column 1 indicates the compound number and column 5 the observed mass.

| | Aldehyde | Azaindole | Compound | MS (ESI) [M + H$^+$]$^+$ observed |
|---|---|---|---|---|
| P-2160 | | | | 347.1 [M − H$^+$]$^-$ |
| P-2145 | | | | 453.1 |
| P-2149 | | | | 403.0 |

-continued

| | Aldehyde | Azaindole | Compound | MS (ESI) [M + H⁺]⁺ observed |
|---|---|---|---|---|
| P-2150 | | | | 373.0 |
| P-2151 | | | | 469.1 |
| P-2154 | | | | 417.1 [M − H⁺]⁻ |

Example 43

Synthesis of 2,5-Difluoro-4-[5-(1-methyl-1H-pyrazol-4-yl)-1H-pyrrolo[2,3-b]pyridin-3-ylmethyl]-phenol P-2161

2,5-Difluoro-4-[5-(1-methyl-1H-pyrazol-4-yl)-1H-pyrrolo[2,3-b]pyridin-3-ylmethyl]-phenol P-2161 was synthesized in 1 step from 2-[4-(5-bromo-1-pyrrolo[2,3-b]pyridin-3-ylmethyl)-2,5-difluoro-phenoxymethyl]-1H-benzoimidazole P-2107 as shown in Scheme 42.

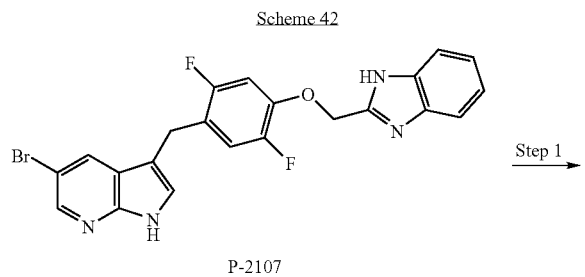

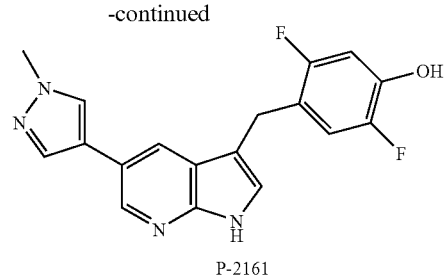

Step 1—Preparation of 2,5-difluoro-4-[5-(1-methyl-1H-pyrazol-4-yl)-1H-pyrrolo[2,3-b]pyridin-3-ylmethyl]-phenol (P-2161)

To 2-[4-(5-bromo-1H-pyrrolo[2,3-b]pyridin-3-ylmethyl)-2,5-difluoro-phenoxymethyl]-1H-benzoimidazole (P-2107, 25.0 mg, 0.053 mmol, prepared as described in Example 41) in acetonitrile (4.00 mL) and 1M potassium carbonate in water (2.00 mL), 1-methyl-4-(4,4,5,5-tetramethyl-[1,3,2]dioxaborolan-2-yl)-1H-pyrazole (13.3 mg, 0.064 mmol) and tetrakis(triphenylphosphine)-palladium(0) (10.0 mg, 8.65E-3 mmol) were added. The reaction was heated to 160°

C. for 20 minutes in a CEM Discover microwave instrument. The reaction was poured into water and extracted with ethyl acetate. The organic layer was dried over anhydrous sodium sulfate and filtered. The filtrate was concentrated and purified by silica gel column chromatography eluting with 20% to 100% ethyl acetate in hexane to give a white solid (P-2161, 5.4 mg, 29.8%). MS (ESI) [M+H⁺]⁺=341.2.

Example 44

Synthesis of (5-chloro-1H-pyrrolo[2,3-b]pyridin-3-yl)-[2-cyclopropylmethoxy-3-(2,4,6-trifluoro-benzyloxy)-phenyl]-methanone P-2141

(5-Chloro-1H-pyrrolo[2,3-b]pyridin-3-yl)-[2-cyclopropylmethoxy-3-(2,4,6-trifluoro-benzyloxy)-phenyl]-methanone P-2141 was synthesized in 7 steps as shown in Scheme 43.

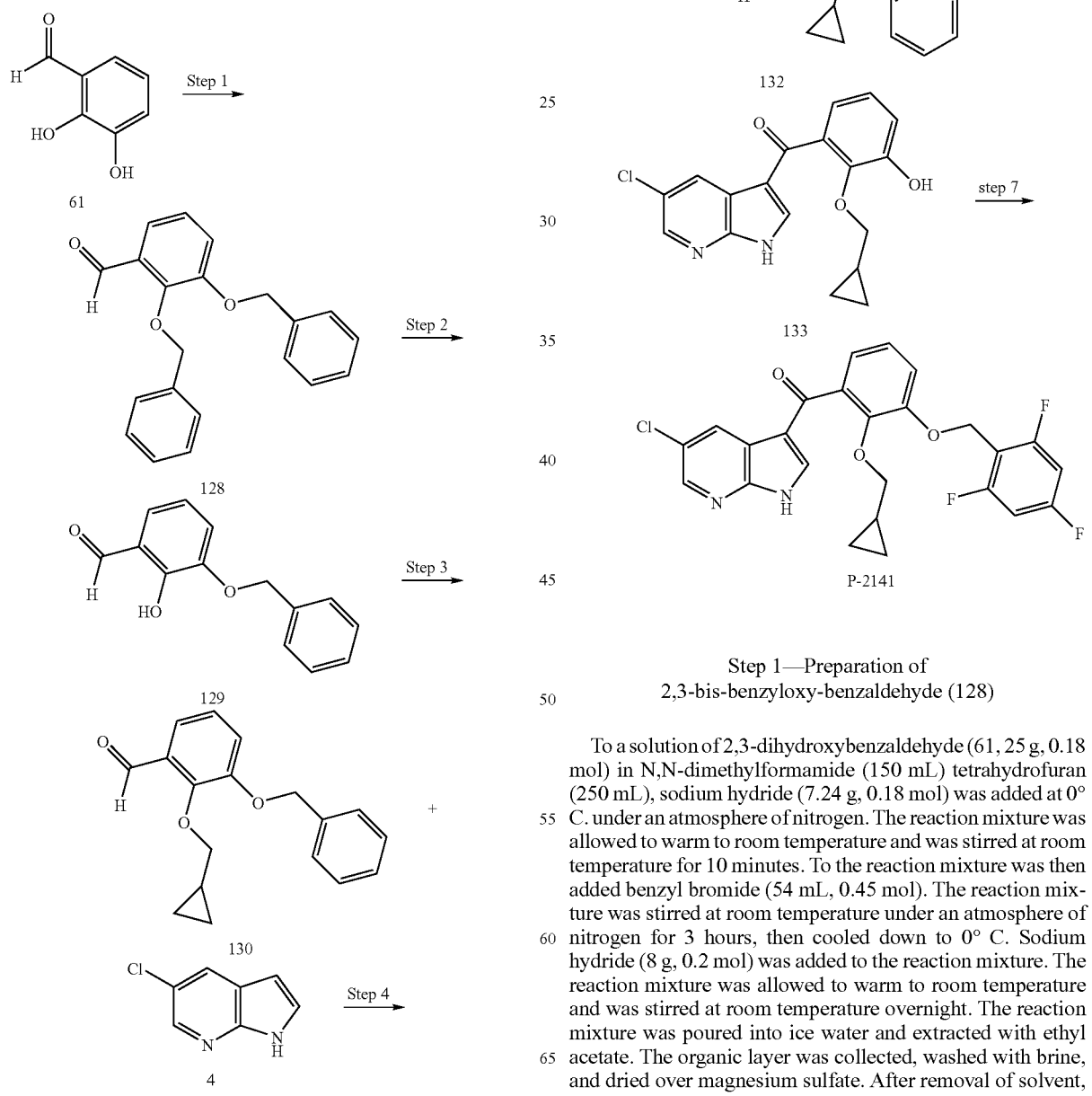

Step 1—Preparation of 2,3-bis-benzyloxy-benzaldehyde (128)

To a solution of 2,3-dihydroxybenzaldehyde (61, 25 g, 0.18 mol) in N,N-dimethylformamide (150 mL) tetrahydrofuran (250 mL), sodium hydride (7.24 g, 0.18 mol) was added at 0° C. under an atmosphere of nitrogen. The reaction mixture was allowed to warm to room temperature and was stirred at room temperature for 10 minutes. To the reaction mixture was then added benzyl bromide (54 mL, 0.45 mol). The reaction mixture was stirred at room temperature under an atmosphere of nitrogen for 3 hours, then cooled down to 0° C. Sodium hydride (8 g, 0.2 mol) was added to the reaction mixture. The reaction mixture was allowed to warm to room temperature and was stirred at room temperature overnight. The reaction mixture was poured into ice water and extracted with ethyl acetate. The organic layer was collected, washed with brine, and dried over magnesium sulfate. After removal of solvent, the residue was purified by silica gel column chromatography eluting with ethyl acetate in hexane to provide the compound as an off-white solid (128, 46.2 gm, 80%).

Step 2—Preparation of 3-benzyloxy-2-hydroxy-benzaldehyde (129)

To magnesium (2.9 g, turnings, 0.12 mol) in a mixture of anhydrous ether (85 mL) and benzene (85 mL) at 0° C., bromine (3.4 mL, 0.066 mol) was added dropwise. When the reaction had started, stirring was commenced and the addition of bromine continued until complete. The ice bath was removed and the reaction mixture was heated until the solution was almost colorless. After cooling down, the reaction mixture was slowly added to a solution of 2,3-bis-benzyloxy-benzaldehyde (128, 20 g, 0.063 mol) in benzene (415 mL) at room temperature while stirring vigorously. Upon completion of the addition, the reaction mixture was stirred at room temperature overnight, and then refluxed for 36 hours. After the reaction mixture was cooled down to room temperature, a solid was collected by filtration and washed with benzene, then boiled in hydrochloric acid (100 mL, 1.0 M) for 30 minutes. After cool down, the solution was extracted with dichloromethane. The organic layer was washed with brine and dried over magnesium sulfate. A light tan solid was obtained after removal of the solvent (129, 12.5 g, 87%).

Step 3—Preparation of 3-benzyloxy-2-cyclopropylmethoxy-benzaldehyde (130)

To a mixture of 3-benzyloxy-2-hydroxy-benzaldehyde (129, 1.0 g, 4.38 mmol) and cesium carbonate (2.14 g, 6.57 mmol) in N,N-dimethylformamide (50 mL), cyclopropylmethyl bromide (1.77 g, 13.1 mmol) was added at room temperature. The mixture was stirred at 40° C. for 3 days. The reaction mixture was poured into a solution of saturated ammonium chloride and was extracted with ethyl acetate. The organic layer was collected, washed with brine, and dried over magnesium sulfate. After removal of solvent, a viscous liquid was obtained (130, 1.21 g, 98%).

Step 4—Preparation of [3-benzyloxy-2-cyclopropyl-methoxy-phenyl]-(5-chloro-1H-pyrrolo[2,3-b]pyridin-3-yl)-methanol (131)

A mixture of 5-chloro-1H-Pyrrolo[2,3-b]pyridine (4, 0.68 g, 4.46 mmol, prepared as described in Example 4), 3-benzyloxy-2-cyclopropylmethoxy-benzaldehyde (130, 1.2 g, 4.25 mmol), and potassium hydroxide (0.68 g, 11 mmol) in methanol (50 mL) was stirred at room temperature for 4 days. The reaction mixture was poured into water and extracted with ethyl acetate. The organic layer was collected, washed with brine, and dried over sodium sulfate. After removal of solvent, the residue was purified by silica gel column chromatography eluting with ethyl acetate in hexane to provide compound as a white solid (131, 0.99 g, 54%). MS (ESI) [M+H$^+$]$^+$=435.21.

Step 5—Preparation of [3-benzyloxy-2-cyclopropyl-methoxy-phenyl]-(5-chloro-1H-pyrrolo[2,3-b]pyridin-3-yl)-methanone (132)

To a solution of [3-benzyloxy-2-cyclopropylmethoxy-phenyl]-(5-chloro-1H-pyrrolo[2,3-b]pyridin-3-yl)-methanol (131, 0.99 g, 2.28 mmol) in tetrahydrofuran (120 mL), Dess-Martin periodinane (2.4 g, 5.69 mmol) was added at 0° C. The reaction mixture was stirred at 0° C. for 50 minutes. The reaction was quenched with a saturated solution of sodium thiosulfate, extracted with ethyl acetate, washed with sodium bicarbonate, brine, and dried over magnesium sulfate. After removal of solvent, the residue was dried over vacuum to provide the compound as a yellow solid (132, 0.92 g, 93%).

Step 6—Preparation of (5-chloro-1H-pyrrolo[2,3-b]pyridin-3-yl)-(2-cyclopropylmethoxy-3-hydroxy-phenyl)-methanone (133)

A mixture of [3-benzyloxy-2-cyclopropylmethoxy-phenyl]-(5-chloro-1H-pyrrolo[2,3-b]pyridin-3-yl)-methanone (132, 0.92 g, 2.13 mmol) and palladium on carbon (100 mg, 10%, 0.5 mmol) in methanol (60 mL) and tetrahydrofuran (60 mL) was stirred under an atmosphere of hydrogen overnight. After filtering off of catalyst and removal of solvent, the residue was purified by silica gel column chromatography eluting with ethyl acetate in hexane to provide the compound as a white solid (133, 236 mg, 32%).

Step 7—Preparation of (5-chloro-1H-pyrrolo[2,3-b]pyridin-3-yl)-[2-cyclopropylmethoxy-3-(2,4,6-trifluoro-benzyloxy)-phenyl]-methanone (P-2141)

To a solution of (5-chloro-1H-pyrrolo[2,3-b]pyridin-3-yl)-(2-cyclopropylmethoxy-3-hydroxy-phenyl)-methanone (133, 50 mg, 0.15 mmol) in tetrahydrofuran (3.0 mL), a mixture of (2,4,6-trifluoro-phenyl)-methanol (47.3 mg, 0.29 mmol), triphenylphosphine (53.6 mg, 0.20 mmol), and diisopropyl azodicarboxylate (35.4 mg, 0.18 mmol) in tetrahydrofuran (2.0 mL) was added at 0° C. The reaction mixture was stirred at 65° C. overnight. The reaction mixture was poured into ice water and extracted with ethyl acetate. The organic layer was collected, washed with brine, and dried over magnesium sulfate. After removal of solvent, the residue was purified by silica gel column chromatography eluting with ethyl acetate in hexane to provide the compound as a white solid (P-2141, 19.3 mg, 27%). MS (ESI) [M+H$^+$]$^+$=487.22.

[(5-Chloro-1H-pyrrolo[2,3-b]pyridin-3-yl)-[2-cyclopropylmethoxy-3-(6-trifluoromethyl-pyridin-3-ylmethoxy)-phenyl]-methanone (P-2142) and (5-chloro-1H-pyrrolo[2,3-b]pyridin-3-yl)-[2-cyclopropylmethoxy-3-(2,4-dimethyl-thiazol-5-ylmethoxy)-phenyl]-methanone (P-2140)

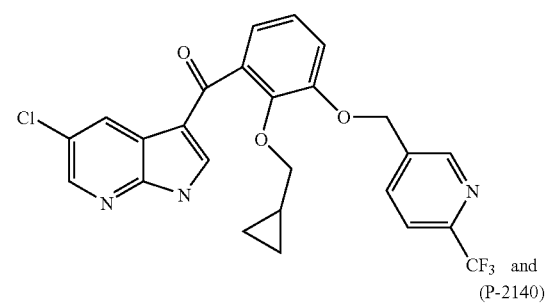
(P-2142)

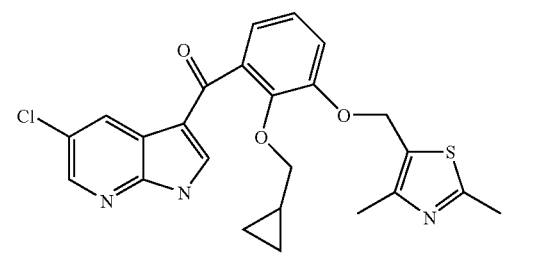
(P-2140)

were prepared following the protocol of Scheme 43, substituting (2,4,6-trifluoro-phenyl)-methanol with (6-trifluoromethyl-pyridin-3-yl)-methanol in Step 7 to provide P-2142 (MS (ESI) [M+H⁺]⁺=502.23), or substituting (2,4,6-trifluoro-phenyl)-methanol with (2,4-dimethyl-thiazol-5-yl)-methanol in Step 7 to provide P-2140. (MS (ESI) [M+H⁺]⁺= 468.19).

Example 45

Synthesis of [2-ethoxy-3-(2-fluoro-benzyloxy)-phenyl]-(1H-pyrrolo[2,3-b]pyridin-3-yl)-methanone P-2127 and related compounds

[2-Ethoxy-3-(2-fluoro-benzyloxy)-phenyl]-(1H-pyrrolo[2,3-b]pyridin-3-yl)-methanone P-2127 was synthesized in one step from (2-ethoxy-3-hydroxy-phenyl)-(1-triisopropyl-silanyl-1H-pyrrolo[2,3-b]pyridin-3-yl)-methanone 99 as shown in Scheme 44.

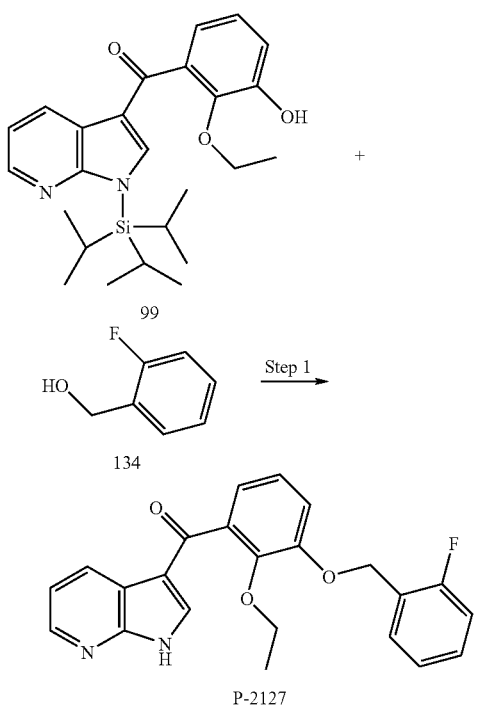

Step 1—Preparation [2-ethoxy-3-(2-fluoro-benzyloxy)-(phenyl]-(1H-pyrrolo[2,3-b]pyridin-3-yl)-methanone (P-2127)

In a 4 mL vial, (2-ethoxy-3-hydroxy-phenyl)-(1-triisopropylsilanyl-1H-pyrrolo[2,3-b]pyridin-3-yl)-methanone (99, 10 mg, 0.022 mmol, isolated after step 2 of Scheme 31, Example 32) was combined with (2-fluoro-phenyl)-methanol (134, 3.5 mg 0.027 mmol). The solids were dissolved in dry tetrahydrofuran (200 μl) and triphenylphosphine (7.0 mg, 0.022 mmol) was added. Once the solution was homogeneous, the mixture was cooled to below 0° C. in a liquid nitrogen bath and diisopropyl azodicarboxylate solution (20 mg in 100 μl tetrahydrofuran) was added. The reaction mixture was allowed to warm to room temperature and the reaction was continued for 2 hours. The solvents were removed under reduced atmosphere. The resultant residue was diluted with 200 μl dimethyl sulfoxide and potassium fluoride (10 mg) was added. The solution was allowed to react overnight to remove the TiPS group. The supernatant was purified by reverse phase HPLC using a Phenomenex C-18 column (50 mm×10 mm ID), and eluting with water with 0.1% trifluoroacetic acid and a gradient of 20%-100% acetonitrile with 0.1% trifluoroacetic acid over 16 minutes and a flow rate of 6 mL/minute to provide P-2127 (1.2 mg, 14%). MS (ESI) [M+H⁺]⁺=391.1.

Additional compounds were prepared following the protocol of Scheme 44, replacing (2-fluoro-phenyl)-methanol 134 with an appropriate alcohol. The following compounds were made following this procedure:

[2-Ethoxy-3-(2-pyrrolidin-1-yl-ethoxy)-phenyl]-(1H-pyrrolo[2,3-b]pyridin-3-yl)-methanone (P-2121),

[2-Ethoxy-3-(6-methyl-pyridin-2-ylmethoxy)-phenyl]-(1H-pyrrolo[2,3-b]pyridin-3-yl)-methanone (P-2122),

[3-(4-Chloro-2-fluoro-benzyloxy)-2-ethoxy-phenyl]-(1H-pyrrolo[2,3-b]pyridin-3-yl)-methanone (P-2123)

[3-(2,4-Dimethyl-thiazol-5-ylmethoxy)-2-ethoxy-phenyl]-(1H-pyrrolo[2,3-b]pyridin-3-yl)-methanone (P-2124),

[3-(2,5-Dimethyl-2H-pyrazol-3-ylmethoxy)-2-ethoxy-phenyl]-(1H-pyrrolo[2,3-b]pyridin-3-yl)-methanone (P-2125),

[2-Ethoxy-3-(3-morpholin-4-yl-propoxy)-phenyl]-(1H-pyrrolo[2,3-b]pyridin-3-yl)-methanone (P-2126),

[2-Ethoxy-3-(6-morpholin-4-yl-pyridin-3-ylmethoxy)-phenyl]-(1H-pyrrolo[2,3-b]pyridin-3-yl)-methanone (P-2128),

[2-Ethoxy-3-(6-trifluoromethyl-pyridin-3-ylmethoxy)-phenyl]-(1H-pyrrolo[2,3-b]pyridin-3-yl)-methanone (P-2129),

[3-(2,4-Dichloro-benzyloxy)-2-ethoxy-phenyl]-(1H-pyrrolo[2,3-b]pyridin-3-yl)-methanone (P-2130),

[2-Ethoxy-3-(4-imidazol-1-yl-benzyloxy)-phenyl]-(1H-pyrrolo[2,3-b]pyridin-3-yl)-methanone (P-2131),

[3-(2,4-Difluoro-benzyloxy)-2-ethoxy-phenyl]-(1H-pyrrolo[2,3-b]pyridin-3-yl)-methanone (P-2132), {2-Ethoxy-3-[1-(2-fluoro-phenyl)-ethoxy]-phenyl}-(1H-pyrrolo[2,3-b]pyridin-3-yl)-methanone (P-2133),

[3-(1,5-Dimethyl-1H-pyrazol-3-ylmethoxy)-2-ethoxy-phenyl]-(1H-pyrrolo[2,3-b]pyridin-3-yl)-methanone (P-2134),

[2-Ethoxy-3-(1-pyridin-4-yl-ethoxy)-phenyl]-(1H-pyrrolo[2,3-b]pyridin-3-yl)-methanone (P-2135),

[2-Ethoxy-3-((R)-1-pyridin-4-yl-ethoxy)-phenyl]-(1H-pyrrolo[2,3-b]pyridin-3-yl)-methanone (P-2136),

[2-Ethoxy-3-(2,4,6-trifluoro-benzyloxy)-phenyl]-(1H-pyrrolo[2,3-b]pyridin-3-yl)-methanone (P-2137), {3-[1-(2,4-Dichloro-phenyl)-ethoxy]-2-ethoxy-phenyl}-(1H-pyrrolo[2,3-b]pyridin-3-yl)-methanone (P-2138),

[3-(6-Diethylamino-pyridin-3-ylmethoxy)-2-ethoxy-phenyl]-(1H-pyrrolo[2,3-b]pyridin-3-yl)-methanone (P-2143), and

[2-Ethoxy-3-(6-pyrrolidin-1-yl-pyridin-3-ylmethoxy)-phenyl]-(H-pyrrolo[2,3-b]pyridin-3-yl)-methanone (P-2144).

The following table indicates the alcohol used in Column 2 to provide the compounds shown by structure in Column 3. Column 1 provides the compound number and Column 4 the mass spectrometry result.

| Alcohol | Compound | MS (ESI) [M + H⁺]⁺ observed |
|---|---|---|
| P-2121 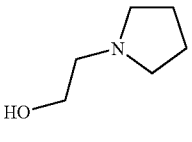 | 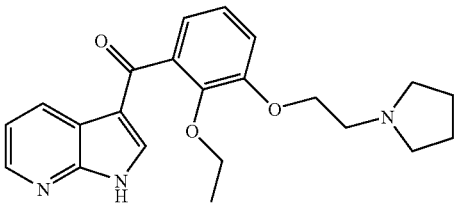 | 380.3 |
| P-2122 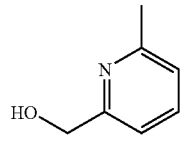 | 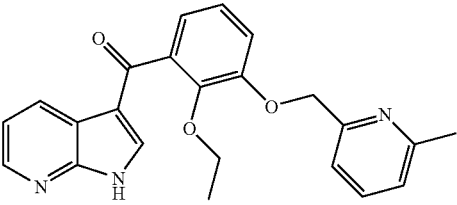 | 388.3 |
| P-2123 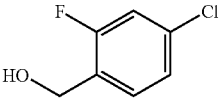 | 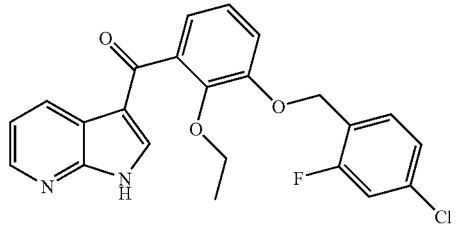 | 425.1 |
| P-2124 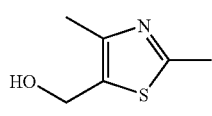 | 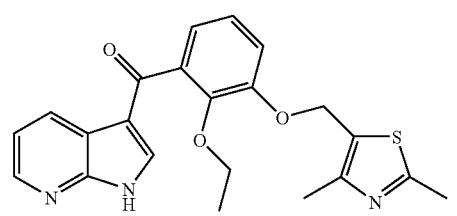 | 408.3 |
| P-2125 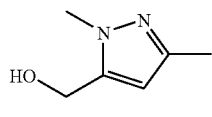 | 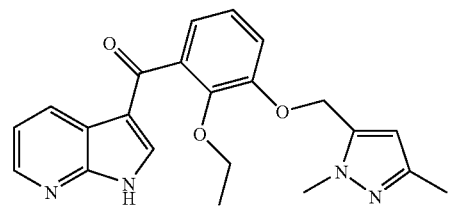 | 391.1 |
| P-2126 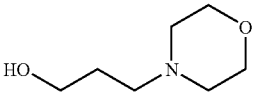 | 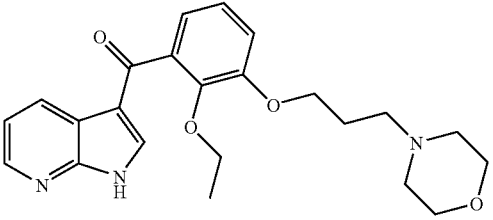 | 410.3 |
| P-2128 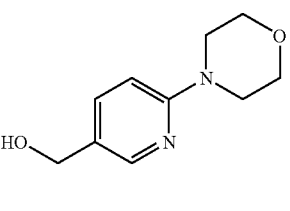 | 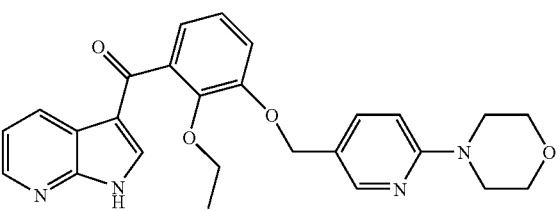 | 459.1 |

| | Alcohol | Compound | MS (ESI) [M + H⁺]⁺ observed |
|---|---|---|---|
| P-2129 | 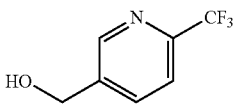 | 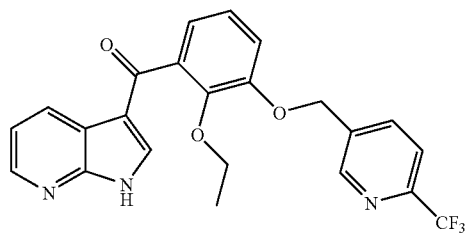 | 442.3 |
| P-2130 | 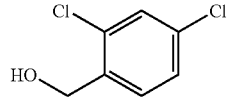 | 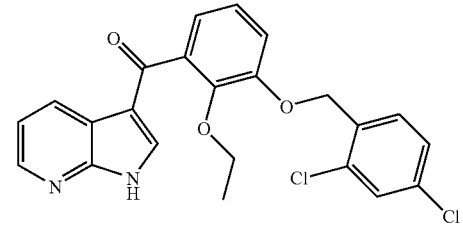 | 441.1 |
| P-2131 | 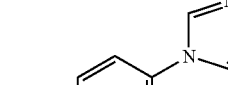 | 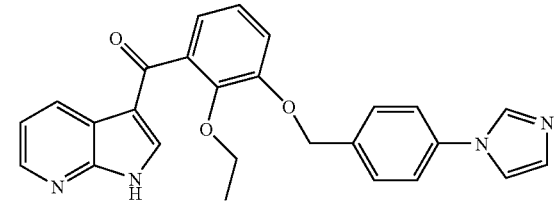 | 439.1 |
| P-2132 | 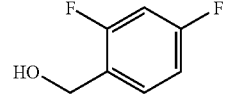 | 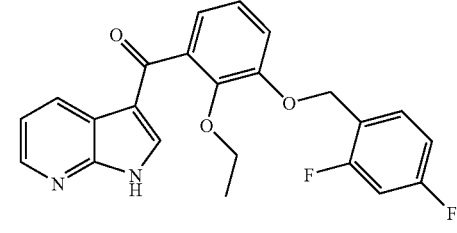 | 409.1 |
| P-2133 | 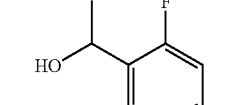 | 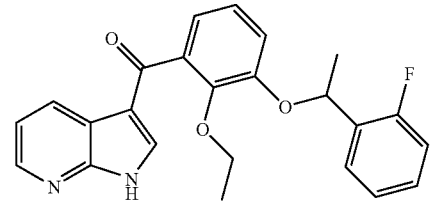 | 405.1 |
| P-2134 | 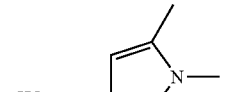 | 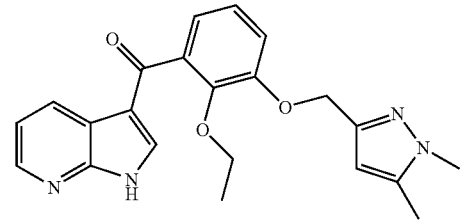 | 391.1 |

| | Alcohol | Compound | MS (ESI) [M + H⁺]⁺ observed |
|---|---|---|---|
| P-2135 | 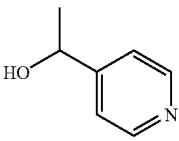 | 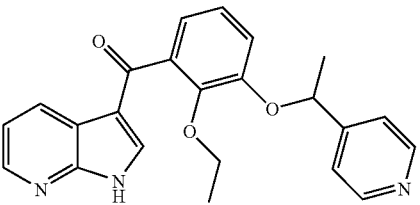 | 388.3 |
| P-2136 | 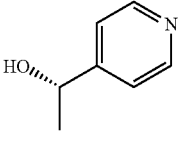 | 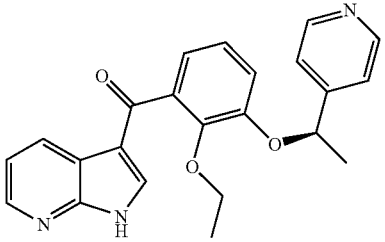 | 388.3 |
| P-2137 |  | 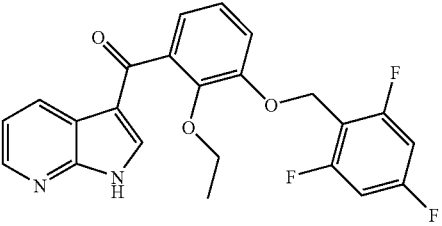 | 427.1 |
| P-2138 | 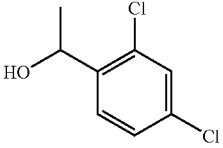 | 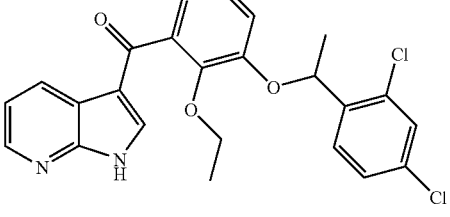 | 455.1 |
| P-2143 | 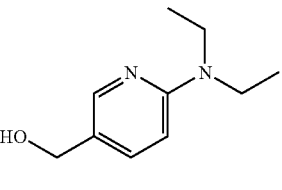 | 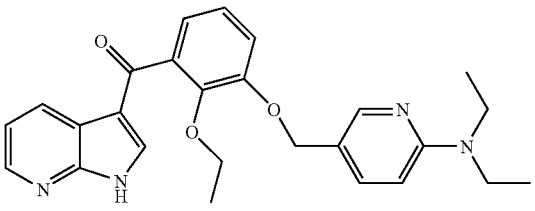 | 445.1 |
| P-2144 | 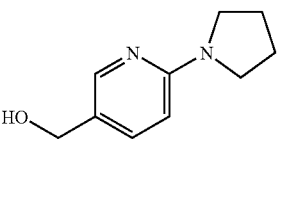 | 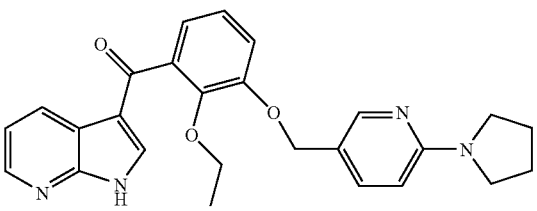 | 443.1 |

Example 46

Synthesis of 2-[5-chloro-4-(5-chloro-1H-pyrrolo[2,3-b]pyridin-3-ylmethyl)-2-methoxy-phenoxymethyl]-1H-benzoimidazole P-2104

2-[5-Chloro-4-(5-chloro-1H-pyrrolo[2,3-b]pyridin-3-ylmethyl)-2-methoxy-phenoxymethyl]-1H-benzoimidazole P-2104 was synthesized in four steps from 2-chloro-4,5-dimethoxy-benzaldehyde 135 as shown in Scheme 45.

Scheme 45

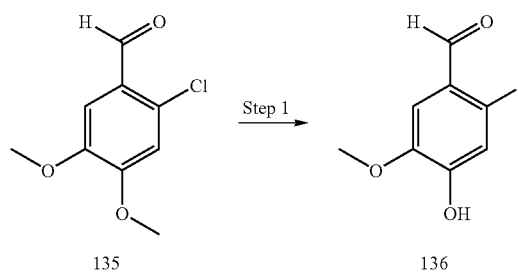

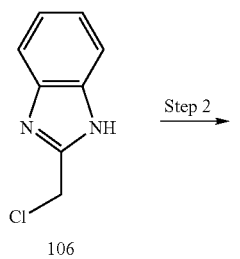

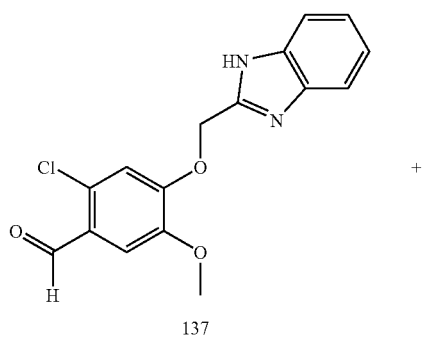

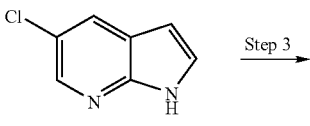

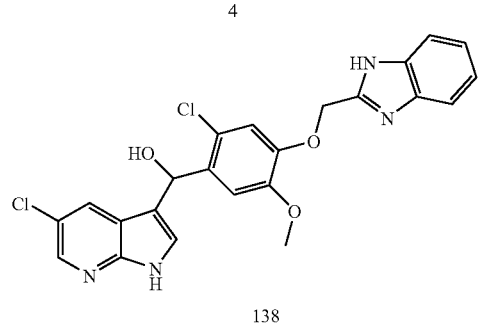

-continued

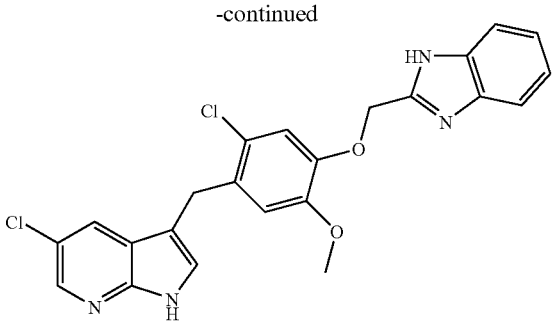

P2104

Step 1—Preparation of 2-chloro-4-hydroxy-5-methoxy-benzaldehyde (136)

2-Chloro-4,5-dimethoxy-benzaldehyde (135, 2.00 g, 0.00997 mol), dichloromethane (73.44 mL) and aluminum trichloride (2.50 g, 0.0187 mol) were combined under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and washed with 5% ethyl acetate in hexane to provide an off-white solid (136, 757 mg, 41%). MS (ESI) $[M-H^+]^-=185.0, 187.0$.

Step 2—Preparation of 4-(1H-benzoimidazol-2-ylmethoxy)-2-chloro-5-methoxy-benzaldehyde (137)

2-Chloro-4-hydroxy-5-methoxy-benzaldehyde (136, 2.30 g, 0.0123 mol) was dissolved in N,N-dimethylformamide (89.5 mL, 1.16 mol) and sodium hydride (60% dispersion in mineral oil, 541 mg, 0.0135 mol) was added. After 20 minutes, 2-chloromethyl-1H-benzoimidazole (106, 2.05 g, 0.0123 mol) was added to the reaction. The reaction was stirred at 80° C. overnight. The reaction was concentrated in vacuo to an oil. Ethyl acetate was added and washed with saturated sodium bicarbonate and brine. The organic layer was dried over anhydrous sodium sulfate and filtered. The filtrate was concentrated and purified by silica gel column chromatography eluting with 30-70% ethyl acetate in hexane over 30 minutes to provide a white solid (137, 1.79 g, 46%). MS (ESI) $[M+H^+]^+=317.1, 319.1$.

Step 3—Preparation of [4-(1H-benzoimidazol-2-ylmethoxy)-2-chloro-5-methoxy-phenyl]-(5-chloro-1H-pyrrolo[2,3-b]pyridin-3-yl)-methanol (138)

5-Chloro-1H-pyrrolo[2,3-b]pyridine (4, 783.9 mg, 0.005138 mol, prepared as described in Example 4) and 4-(H-benzoimidazol-2-ylmethoxy)-2-chloro-5-methoxy-benzaldehyde (137, 1.79 g, 0.00565 mmol) were combined in methanol (100 mL, 2 mol) and potassium hydroxide (2.88 g, 0.0514 mol) was added. The reaction was stirred at room temperature overnight. The reaction was adsorbed onto silica and purified by silica gel column chromatography, eluting with 1-15% methanol:dichloromethane to provide the desired compound as a yellow oil, which was redissolved in 200 mL of 25% ethyl acetate:hexanes and concentrated to provide a yellow solid (138, 1.2 g, 50%). MS (ESI) $[M+H^+]^+=469.1, 471.1$.

Step 4—Preparation of 2-[5-chloro-4-(5-chloro-1H-pyrrolo-[2,3-b]pyridin-3-ylmethyl)-2-methoxy-phenoxymethyl]-1H-benzoimidazole (P-2104)

[4-(1H-Benzoimidazol-2-ylmethoxy)-2-chloro-5-methoxy-phenyl]-(5-chloro-1H-pyrrolo[2,3-b]pyridin-3-yl)-methanol (138, 1.25 g, 0.00266 mol) was dissolved in acetonitrile (100 mL, 2 mol) and trifluoroacetic acid (5.65 mL, 0.0734 mol) and triethylsilane (11.3 mL, 0.0708 mol) were added. The reaction was heated at 70° C. for 2.5 hours. The reaction was concentrated and ethyl acetate and 1M aqueous potassium carbonate were added. The organic layer was washed with brine, dried over anhydrous sodium sulfate, and filtered. The filtrate was adsorbed onto silica and purified with silica gel column chromatography, eluting with 0-8% methanol:dichloromethane to provide the desired compound as a solid, which was washed with a minimum of ethyl acetate and hexanes and filtered. The collected solid was dried to provide P-2104 (232 mg, 19%). MS (ESI) [M+H$^+$]$^+$=453.1, 455.1.

2-[5-Chloro-2-methoxy-4-(1H-pyrrolo[2,3-b]pyridin-3-ylmethyl)-phenoxymethyl]-1H-benzoimidazole P-2103

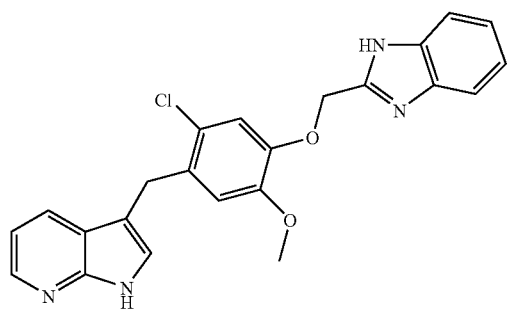

was prepared following the protocol of Scheme 45, replacing 5-chloro-1H-pyrrolo[2,3-b]pyridine 4 with 1H-pyrrolo[2,3-b]pyridine in Step 3. MS (ESI) [M+H$^+$]$^+$=419.2, 421.2.

Example 47

Synthesis of 3-[2-chloro-4-(4-chloro-2-fluoro-benzyloxy)-5-methoxy-benzyl]-1H-pyrrolo[2,3-b]pyridine P-2166

3-[2-Chloro-4-(4-chloro-2-fluoro-benzyloxy)-5-methoxy-benzyl]-1H-pyrrolo[2,3-b]pyridine P-2166 was synthesized in three steps from 2-chloro-4-hydroxy-5-methoxy-benzaldehyde 136 as shown in Scheme 46.

Scheme 46

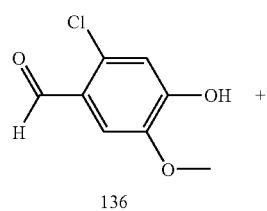

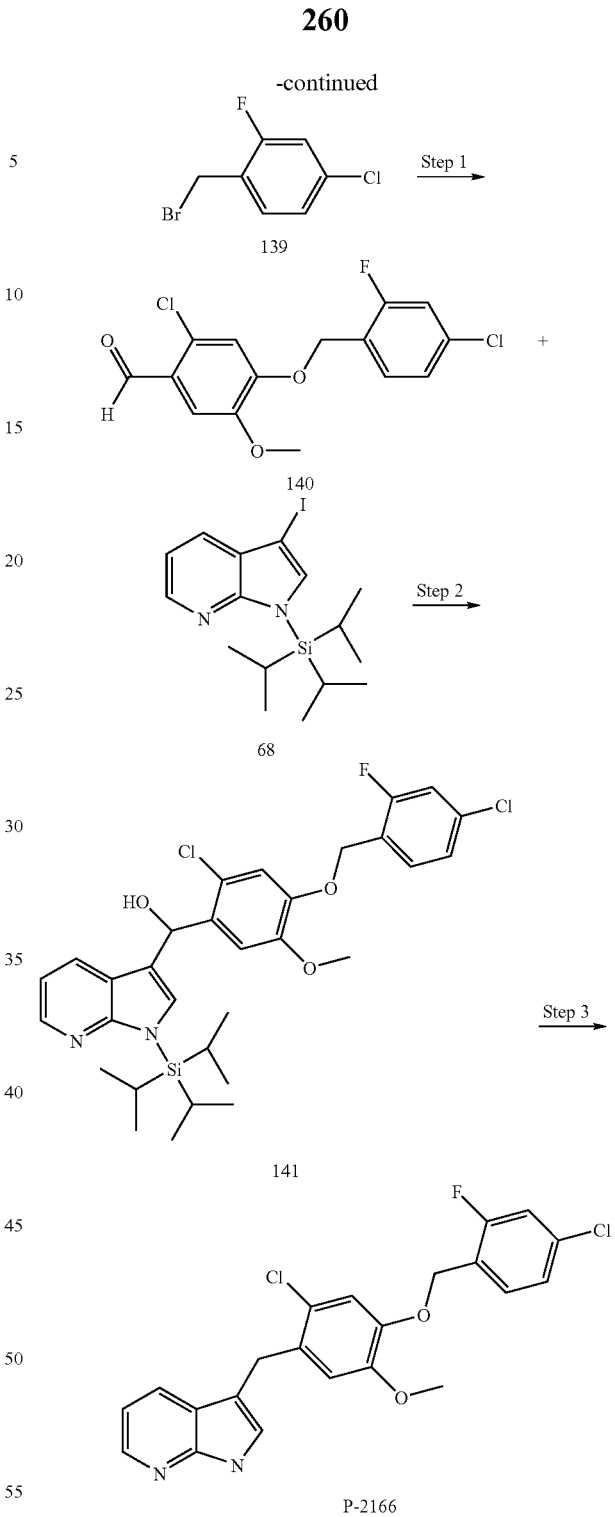

Step 1—Preparation of 2-chloro-4-(4-chloro-2-fluoro-benzyloxy)-5-methoxy-benzaldehyde (14)

2-Chloro-4-hydroxy-5-methoxy-benzaldehyde (136, 0.548 g, 2.94 mmol, prepared as described in Example 46, Scheme 45, step 1) was dissolved in N,N-dimethylformamide (40 mL) and sodium hydride (60% dispersion in mineral oil, 0.200 g, 5.00 mmol) was added. After 20 minutes, 1-bromomethyl-4-chloro-2-fluoro-benzene (139, 685 μL, 5.00 mmol)

was added to the reaction mixture. The reaction was stirred at room temperature under an atmosphere of nitrogen for 5.5 hours. The reaction was concentrated to dryness in vacuo. The reaction was resuspended in water/saturated sodium bicarbonate and extracted with ethyl acetate. The organic layer was dried over anhydrous sodium sulfate and filtered. The filtrate was concentrated and purified by silica gel column chromatography, eluting with 5-35% ethyl acetate in hexane give a white solid (140, 0.942 g, 97%), consistent with the desired compound by $^1$H-NMR.

Step 2—Preparation of [2-chloro-4-(4-chloro-2-fluoro-benzyloxy)-5-methoxy-phenyl]-(1-triisopropylsilanyl-1H-pyrrolo[2,3-b]pyridin-3-yl)-methanol (141)

3-iodo-1-triisopropylsilanyl-1H-pyrrolo[2,3-b]pyridine (68, 582.0 mg, 1.45 mmol, prepared as described in Example 22) was dissolved in tetrahydrofuran (10.0 mL) at −20° C. under an atmosphere of nitrogen. Isopropylmagnesium chloride in tetrahydrofuran (2.0 M, 0.79 mL) was added to the reaction. The reaction was stirred for 1 hour, during which the temperature rose to 0° C. The reaction was cooled to −20° C. and 2-chloro-4-(4-chloro-2-fluoro-benzyloxy)-5-methoxy-benzaldehyde (140, 200 mg, 0.61 mmol) in tetrahydrofuran (7.0 mL) was added. The reaction was stirred for 1.5 hours during which time the temperature rose to 0° C. The reaction was quenched with methanol and adsorbed onto silica, then purified by silica gel chromatography, eluting with 0-20% ethyl acetate:hexanes, to provide the desired compound (141, 318 mg, 87%). MS (ESI): [M+H$^+$]$^+$=603.3, 605.3.

Step 3—Preparation of 3-4-[1-(4-chloro-phenyl)-ethoxy]-3-methoxy-benzyl-1H-pyrrolo[2,3-b]pyridine (P-2166)

[2-Chloro-4-(4-chloro-2-fluoro-benzyloxy)-5-methoxy-phenyl]-(1-triisopropylsilanyl-1H-pyrrolo[2,3-b]pyridin-3-yl)-methanol (141, 0.160 g, 0.27 mmol) was dissolved in acetonitrile (10.0 mL). Trifluoroacetic acid (0.150 mL) and triethylsilane (0.250 mL) were added and the reaction was heated at 80° C. for 1.5 hours. The reaction was adsorbed onto silica and purified by silica gel chromatography, eluting with 20-65% ethyl acetate:hexanes, to provide the desired compound (P-2166, 83.4 mg, 74%). MS (ESI): [M+H$^+$]$^+$=431.2, 433.2.

5-Chloro-3-[2-chloro-4-(4-chloro-2-fluoro-benzyloxy)-5-methoxy-benzyl]-1H-pyrrolo[2,3-b]pyridine P-2167

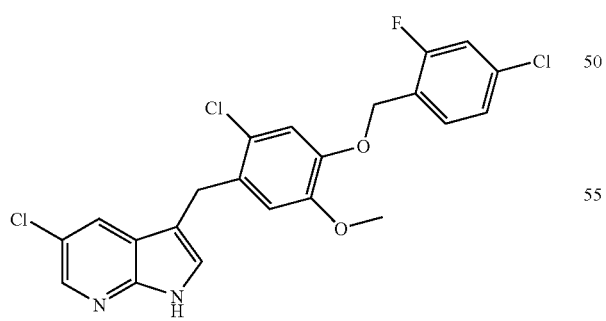

was prepared following the protocol of Scheme 46, replacing 3-iodo-1-triisopropylsilanyl-1H-pyrrolo[2,3-b]pyridine 68 with 5-chloro-3-iodo-1-triisopropylsilanyl-1H-pyrrolo[2,3-b]pyridine (prepared as described in Example 49) in Step 2 and eluting with 30-95% ethyl acetate in hexanes in Step 3. MS (ESI) [M+H$^+$]$^+$=465.1, 467.1.

Example 48

Synthesis of 2-[4-(5-Chloro-1H-pyrrolo[2,3-b]pyridin-3-ylmethyl)-5-fluoro-2-methoxy-phenoxymethyl]-1-methyl-1H-benzimidazole P-2106

2-[4-(5-Chloro-1H-pyrrolo[2,3-b]pyridin-3-ylmethyl)-5-fluoro-2-methoxy-phenoxymethyl]-1-methyl-1-benzimidazole P-2106 was synthesized in four steps from 2-Fluoro-4-hydroxy-5-methoxy-benzaldehyde 39 as shown in Scheme 47.

Scheme 47

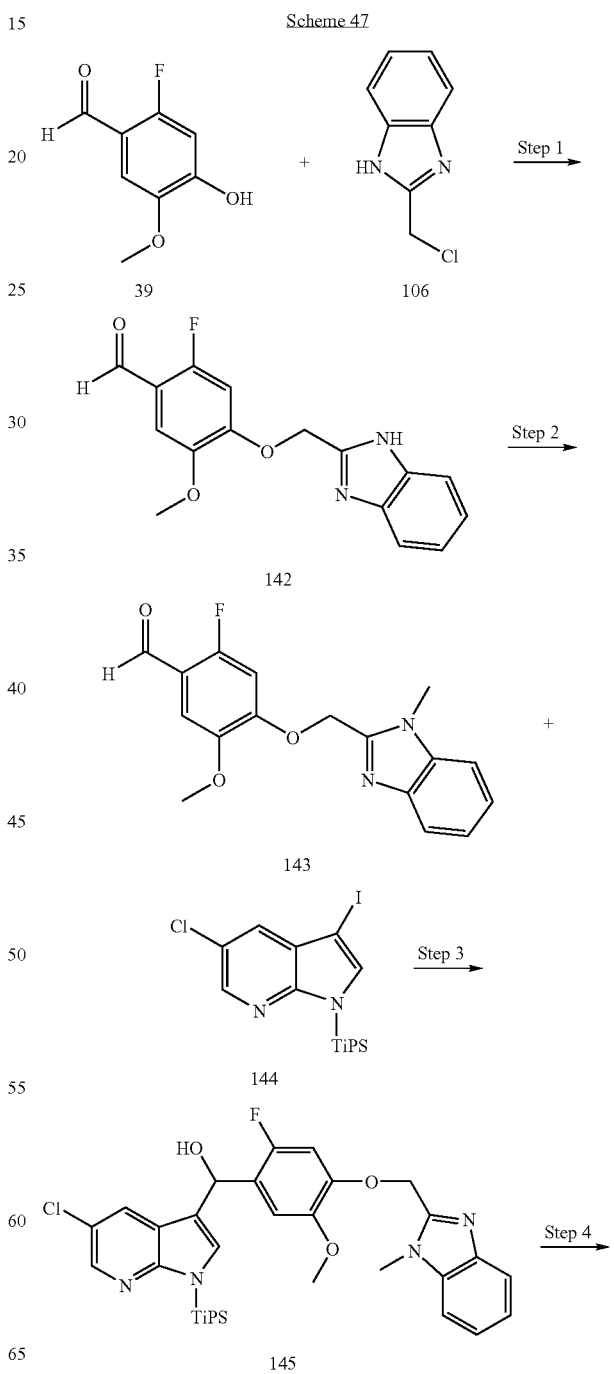

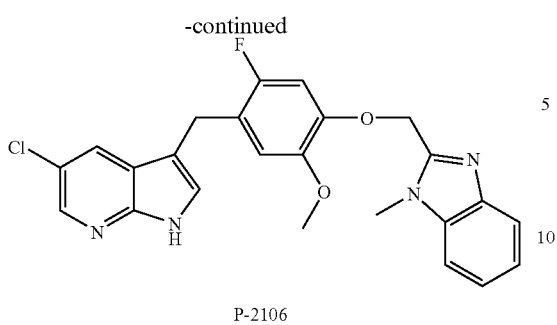

P-2106

Step 1—Preparation of 4-(1H-benzimidazol-2-yl-methoxy)-2-fluoro-5-methoxy-benzaldehyde (142)

2-Fluoro-4-hydroxy-5-methoxy-benzaldehyde (39, 0.290 g, 1.7 mmol, prepared as described in Scheme 12 of Example 15) was dissolved in N,N-dimethylformamide (20 mL, 200 mmol). Sodium hydride (60% dispersion in oil, 0.852 g, 2.13 mmol) was added to the solution and after the mixture was stirred for 20 minutes at room temperature, 2-chloromethyl-1H-benzoimidazole (106, 0.28 g, 1.7 mmol) was added to the reaction. The obtained mixture was heated to 80° C. and stirred overnight. After cooling to room temperature, the reaction was poured into water and extracted with ethyl acetate. The organic portion was dried over anhydrous sodium sulfate and filtered. The filtrate was concentrated and purified by silica gel column chromatography eluting with a gradient of ethyl acetate (40 to 100%) in hexane to give the desired compound (142, 0.233 g, 45%).

Step 2—Preparation of 2-fluoro-5-methoxy-4-(1-methyl-1H-benzimidazol-2-ylmethoxy)-benzaldehyde (143)

4-(1H-Benzimidazol-2-ylmethoxy)-2-fluoro-5-methoxy-benzaldehyde (142) (0.600 g, 2.0 mmol) was dissolved in N,N-dimethylformamide (15 mL, 190 mmol). After the addition of sodium hydride (60% dispersion in oil, 0.072 g, 3.0 mmol) the reaction was stirred for 15 minutes at room temperature. Methyl iodide (140 µL, 2.2 mmol) was added dropwise to the mixture. The reaction was stirred overnight at room temperature under an atmosphere of nitrogen. The solvent was evaporated to dryness under reduced pressure. Ethyl acetate was added and the organic portion was washed with water, dried over anhydrous sodium sulfate and concentrated. Purification with silica gel flash chromatography with a gradient of ethyl acetate in hexanes gave the desired compound as a white powder (143, 0.345 g, 55%). MS (ESI) [M+H$^+$]$^+$= 315.2.

Step 3—Preparation (5-Chloro-1-triisopropylsilanyl-1H-pyrrolo[2,3-b]pyridin-3-yl)-[2-fluoro-5-methoxy-4-(1-methyl-1H-benzoimidazol-2-ylmethoxy)-phenyl]-methanol (145)

5-Chloro-3-iodo-1-triisopropylsilanyl-1H-pyrrolo[2,3-b]pyridine (144, 0.235 g, 0.541 mmol, prepared as described in Example 49) was dissolved in tetrahydrofuran (5 mL, 60 mmol). The solution was cooled to −25° C. After the addition of 2 M of isopropylmagnesium chloride in tetrahydrofuran (400 µL) the reaction was warmed to −10° C. with stirring. The reaction was cooled to −30° C. and 2-fluoro-5-methoxy-4-(1-methyl-1H-benzimidazol-2-ylmethoxy)-benzaldehyde (143, 0.170 g, 0.541 mmol) in 4 mL of tetrahydrofuran was added at once to the mixture. The reaction warmed to −10° C. and then evaporated to dryness. Ethyl acetate was added and the organic portion was washed with saturated sodium bicarbonate solution and brine, dried over anhydrous sodium sulfate and concentrated. Purification with silica gel flash chromatography with a gradient of ethyl acetate (5 to 80%) in hexanes gave the desired compound 145.

Step 4—Preparation 2-[4-(5-Chloro-1H-pyrrolo[2,3-b]pyridin-3-ylmethyl)-5-fluoro-2-methoxy-phenoxymethyl]-1-methyl-1H-benzimidazole (P-2106)

(5-Chloro-1-triisopropylsilanyl-1H-pyrrolo[2,3-b]pyridin-3-yl)-[2-fluoro-5-methoxy-4-(1-methyl-1H-benzimidazol-2-ylmethoxy)-phenyl]-methanol (145) (0.140 g, 0.225 mmol) was suspended in acetonitrile (5 ml, 100 mmol). Triethylsilane (1.0 mL, 6.3 mmol) was added followed by trifluoroacetic acid (0.500 mL, 6.4 mmol). After the reaction was stirred at 60-80° C. for 1.5 hours the solvent was evaporated to dryness. Ethyl acetate was added and the organic portion was washed with saturated sodium bicarbonate solution and brine, dried over anhydrous sodium sulfate and concentrated. Purification with silica gel flash chromatography eluting with a gradient of ethyl acetate (20 to 100%) in hexanes gave the desired compound as a white powder (P-2106, 0.034 g, 34%). MS (ESI) [M+H$^+$]$^+$=451.2.

2-(1-Chloro-ethyl)-1H-benzoimidazole 147 was prepared in one step from 1-(1H-benzoimidazol-2-yl)-ethanol 146 as shown in Scheme 48.

Scheme 48

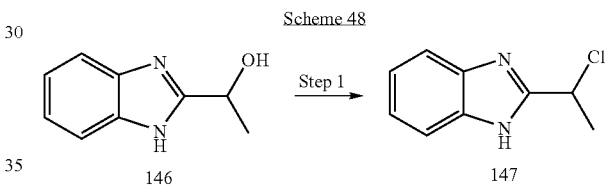

146 147

Step I—Preparation of 2-(1-Chloro-ethyl)-1H-benzimidazole (147)

1-(1H-Benzimidazol-2-yl)-ethanol (146) (1.00 g, 6.16 mmol) was suspended in dichloro ethane (50 mL, 800 mmol). Thionyl chloride (4.00 mL, 54.8 mmol) was added dropwise and the reaction was stirred at room temperature and then heated to 60° C. for 6 hours. After cooling to room temperature the reaction was evaporated to dryness under reduced pressure. The obtained solid was washed with ethyl acetate. The powder was suspended in ethyl acetate and washed with saturated sodium bicarbonate solution and brine. The organic portion was dried over anhydrous sodium sulfate and concentrated. The obtained off-white solid was used without further purification (147, 0.864 g, 76%). MS (ESI) [M+H$^+$]$^+$=181.2.

2-1-[4-(5-Chloro-1H-pyrrolo[2,3-b]pyridin-3-ylmethyl)-5-fluoro-2-methoxy-phenoxy]-ethyl-1H-benzimidazole P-2110

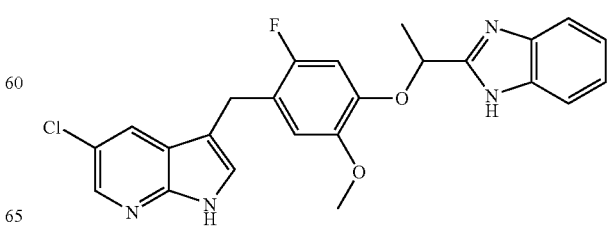

was prepared following the protocol of Scheme 47, replacing 2-chloromethyl-1H-benzimidazole 106 with 2-(1-chloroethyl)-1H-benzimidazole 147. MS (ESI) [M+H$^+$]$^+$=451.2, 453.2.

5-Chloro-2-chloromethyl-1H-benzoimidazole 148 and 2-Chloromethyl-5-methoxy-1H-benzoimidazole 149

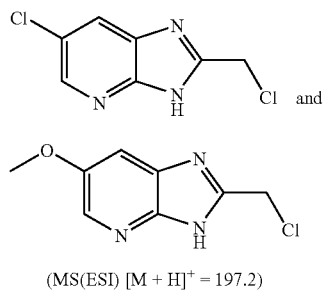

(MS(ESI) [M + H]$^+$ = 197.2)

were prepared following the protocol of Scheme 48 replacing 1-(1H-benzimidazol-2-yl)-ethanol 146 with (5-chloro-1H-benzoimidazol-2-yl)-methanol and (5-methoxy-1H-benzoimidazol-2-yl)-methanol, respectively.

Example 49

Synthesis of 5-chloro-3-iodo-1-triisopropylsilanyl-1H-pyrrolo[2,3-b]pyridine 144

5-Chloro-3-iodo-1-triisopropylsilanyl-1H-pyrrolo[2,3-b]pyridine 144 was synthesized in one step from 5-Chloro-3-iodo-1H-pyrrolo[2,3-b]pyridine 150 as shown in Scheme 49.

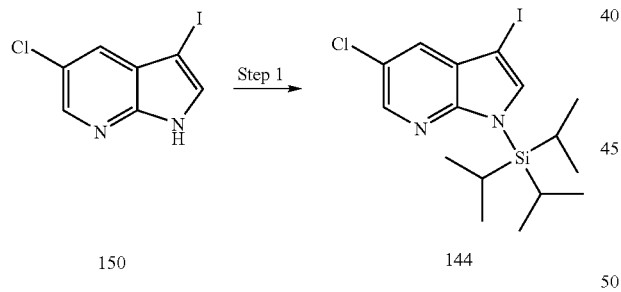

Step 1—Preparation of 5-Chloro-3-iodo-1-triisopropylsilanyl-1H-pyrrolo[2,3-b]pyridine (144)

5-Chloro-3-iodo-1H-pyrrolo[2,3-b]pyridine (150, 31.2 g, 0.112 mol) was dissolved in N-methylpyrrolidinone (800 mL) and NaH (60% dispersion, 4.93 g, 0.123 mol) was added at room temperature. The resulting mixture was stirred for 30 minutes. To this mixture was then added triisopropylsilylchloride (24.0 mL, 0.112 mol) and the resulting mixture was stirred for 2 hours. The reaction was quenched with water and extracted with ethyl acetate three times, washed by brine, dried, filtered, and concentrated in vacuo. The residue was subjected to silica gel flash chromatography (eluted by heptane to 5% ethyl acetate/heptane) to afford the desired compound (43 g 88%) as a pale-yellow solid.

Example 50

Synthesis of 6-chloro-2-[5-fluoro-2-methoxy-4-(1H-pyrrolo[2,3-b]pyridin-3-ylmethyl)-phenoxymethyl]-1H-benzimidazole P-2112

6-chloro-2-[5-fluoro-2-methoxy-4-(1H-pyrrolo[2,3-b]pyridin-3-ylmethyl)-phenoxymethyl]-1H-benzimidazole P-2112 was synthesized in four steps from 2-Fluoro-4-hydroxy-5-methoxy-benzaldehyde 39 as shown in Scheme 50.

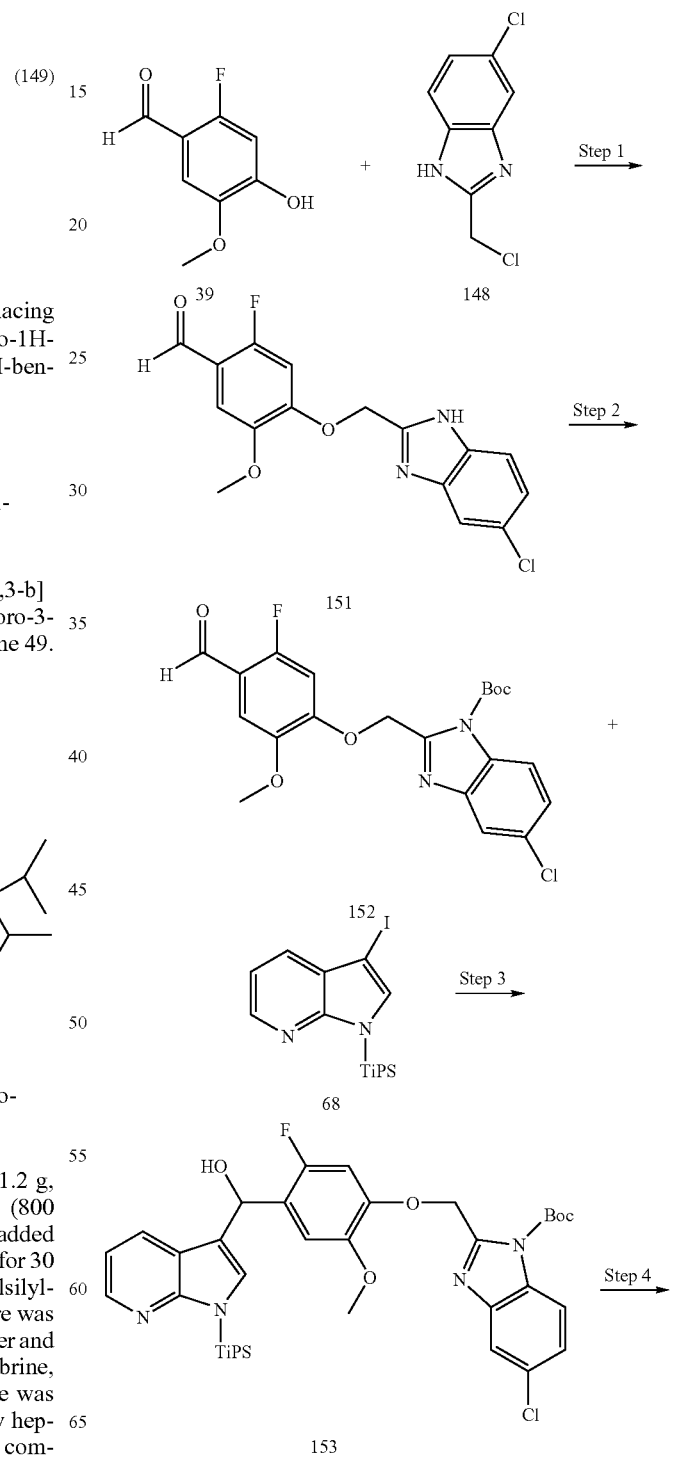

-continued

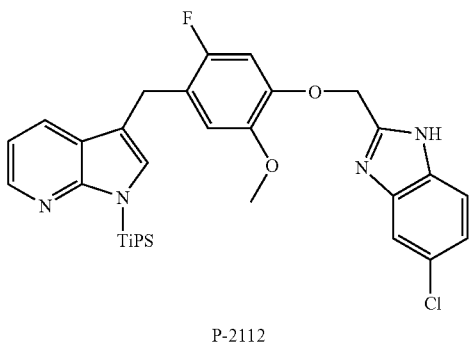

P-2112

Step 1—Preparation of 4-(6-chloro-1H-benzimidazol-2-ylmethoxy)-2-fluoro-5-ethoxy-benzaldehyde (151)

4-(6-Chloro-1H-benzimidazol-2-ylmethoxy)-2-fluoro-5-methoxy-benzaldehyde (151) was prepared using the same protocol as described in Scheme 47 substituting 2-chloromethyl-1H-benzoimidazole 106 with 5-Chloro-2-chloromethyl-H-benzoimidazole 148 (prepared as described in Example 48) in Step 1. Purification through silica gel column chromatography eluting with a gradient of ethyl acetate (10 to 100%) in hexane gave the desired compound 151.

Step 2—Preparation of 6-chloro-2-(5-fluoro-4-formyl-2-methoxy-phenoxymethyl)-benzimidazole-1-carboxylic acid tert-butyl ester (152)

To a solution of 4-(5-chloro-1H-benzoimidazol-2-ylmethoxy)-2-fluoro-5-methoxy-benzaldehyde (151) (0.330 g, 0.98 mmol) in tetrahydrofuran (10 ml) at room temperature was added N,N-diisopropylethylamine (0.40 mL, 2.3 mmol) followed by the addition of 4-dimethylaminopyridine (0.01 g, 0.1 mmol) polymer bound. To the stirring mixture a solution of di-tert-butyldicarbonate (0.24 g, 1.1 mmol) in tetrahydrofuran (5 mL) was added. After the reaction mixture was stirred at room temperature overnight the solvent was removed under reduced pressure. The resulting solid was dissolved in ethyl acetate and the organic portion was washed with water, dried over anhydrous sodium sulfate and evaporated to dryness. The desired compound 152 was used without further purification.

Step 3—Preparation of (5-Chloro-2-{5-fluoro-4-[hydroxy-(1-triisopropylsilanyl-1H-pyrrolo[2,3-b]pyridin-3-yl)-methyl]-2-methoxy-phenoxymethyl}-benzimidazole-1-carboxylic acid tert-butyl ester (153)

3-Iodo-1-triisopropylsilanyl-1H-pyrrolo[2,3-b]pyridine (68, 0.200 g, 0.5 mmol, prepared as described in Example 22) was dissolved in tetrahydrofuran (3 mL, 40 mmol). After the reaction reached the temperature of −20° C., a solution of 2M of isopropylmagnesium chloride in tetrahydrofuran (300 µL) was added dropwise. The resulted mixture was stirred to −5° C. After cooling the reaction to −20° C., a solution of 6-chloro-2-(5-fluoro-4-formyl-2-methoxy-phenoxymethyl)-benzoimidazole-1-carboxylic acid tert-butyl ester (152, 0.2 g, 0.46 mmol) in tetrahydrofuran (4 mL) was added at once to the mixture. The reaction warmed to −5° C. and was then evaporated to dryness under reduced pressure. Ethyl acetate was added. The organic portion was washed with saturated sodium bicarbonate solution, brine, dried over anhydrous sodium sulfate and concentrated. Purification with silica gel flash chromatography eluting with a gradient of ethyl acetate (5 to 80%) in hexanes gave the desired compound (153, 0.142 g, 44%). MS (ESI) [M+H$^+$]$^+$=709.4.

Step 4—Preparation of 6-Chloro-2-[5-fluoro-2-methoxy-4-(1H-pyrrolo[2,3-b]pyridin-3-ylmethyl)-phenoxymethyl]-1H-benzimidazole (P-2112)

6-Chloro-2-[5-fluoro-2-methoxy-4-(1H-pyrrolo[2,3-b]pyridin-3-ylmethyl)-phenoxymethyl]-1H-benzimidazole (P-2112) was prepared using the same protocol as described in Scheme 47, step 4, substituting (5-chloro-1-triisopropylsilanyl-1H-pyrrolo[2,3-b]pyridin-3-yl)-[2-fluoro-5-methoxy-4-(1-methyl-1H-benzoimidazol-2-ylmethoxy)-phenyl]-methanol 145 with (5-chloro-2-{5-fluoro-4-[hydroxy-(1-triisopropylsilanyl-1H-pyrrolo[2,3-b]pyridin-3-yl)-methyl]-2-methoxy-phenoxymethyl}-benzoimidazole-1-carboxylic acid tert-butyl ester 153. Purification with silica gel flash chromatography eluting with a gradient of methanol (2 to 25%) in dichloromethane gave the desired compound (P-2112, 0.052 g, 59%). MS (ESI) [M+H$^+$]$^+$=437.1, 439.1.

Additional compounds were prepared following the protocol of Scheme 50, substituting 5-chloro-2-chloromethyl-1H-benzoimidazole 148 with the appropriate benzoimidazole in Step 1, and 3-iodo-1-triisopropylsilanyl-1H-pyrrolo[2,3-b]pyridine 68 with the appropriate substituted 7-azaindole in Step 3. Compound P-1976 (see Example 10) was prepared by this procedure and isolated with silica gel flash chromatography eluting with a gradient of ethyl acetate (60 to 100%) in hexanes followed by additional washes with acetonitrile over the final solid. Compound P-2113 was further purified with silica gel flash chromatography eluting with a gradient of ethyl acetate (20 to 100%) in hexanes. The following compounds were also made following this procedure:

5-Chloro-2-[4-(5-chloro-1H-pyrrolo[2,3-b]pyridin-3-ylmethyl)-5-fluoro-2-methoxy-phenoxymethyl]-1H-benzimidazole (P-2111), 2-[5-Fluoro-2-methoxy-4-(1H-pyrrolo[2,3-b]pyridin-3-ylmethyl)-phenoxymethyl]-5-methoxy-1H-benzimidazole (P-2113), 2-[5-Fluoro-4-(5-fluoro-1H-pyrrolo[2,3-b]pyridin-3-ylmethyl)-2-methoxy-phenoxymethyl]-1H-benzimidazole (P-2115)

The following table indicates the benzoimidazole used in Column 2 and the 7-azaindole used in Column 3 to provide the compounds shown by structure in Column 4. Column 1 provides the compound number and Column 5 the mass spectrometry result.

| | Benzoimidazole | 7-Azaindole |
|---|---|---|
| P-2111 | 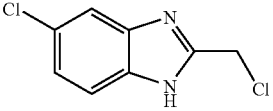 | 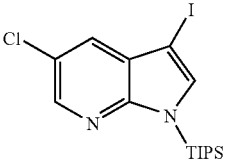 |
| P-2113 | 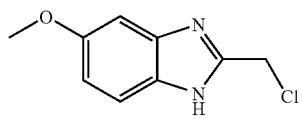 | 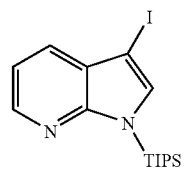 |
| P-2115 | 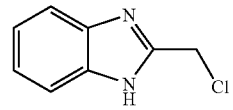 | 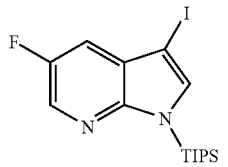 |
| | Compound | MS (ESI) [M + H$^+$]$^+$ observed |
|---|---|---|
| P-2111 | 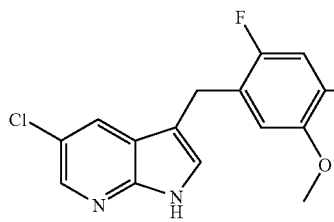 | 471.1 473.1 |
| P-2113 | 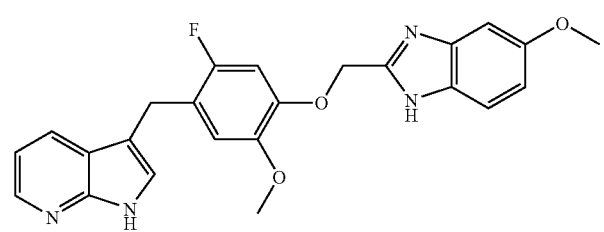 | 433.2 |
| P-2115 | 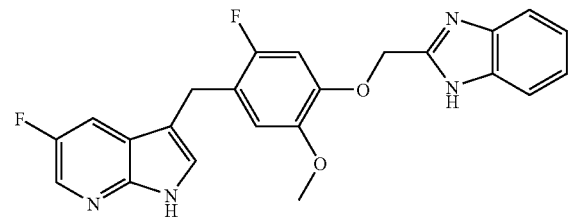 | 421.2 |

Example 51

Synthesis of N-phenyl-1H-pyrrolo[2,3-b]pyridin-6-amine 158 and Related Compounds N-phenyl-1H-pyrrolo[2,3-b]pyridin-6-amine 158 was synthesized in five steps from 1H-pyrrolo[2,3-b]pyridine 6 as shown in Scheme 51.

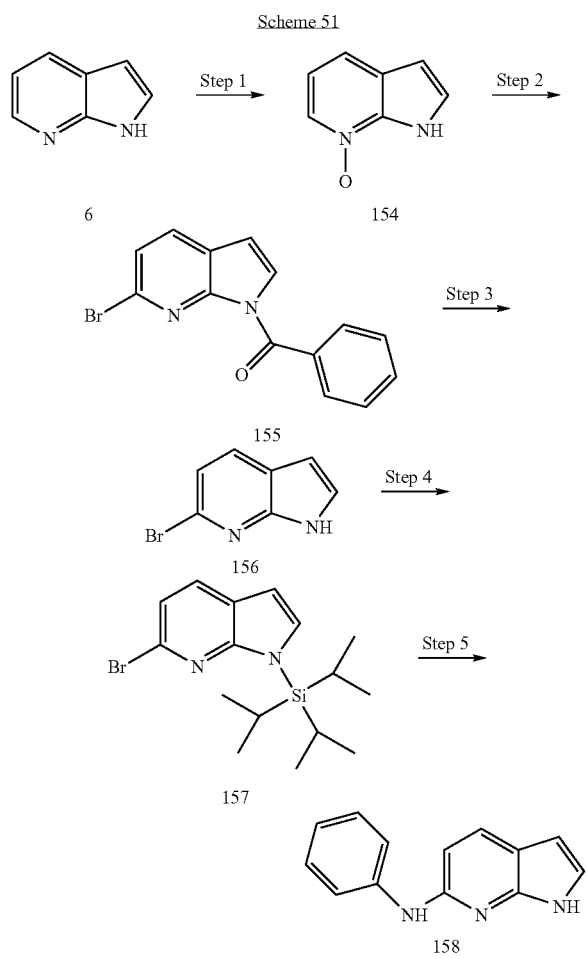

Step 1—Preparation of 1H-pyrrolo[2,3-b]pyridine-N-oxide (154)

To 1H-pyrrolo[2,3-b]pyridine (6, 3.0 g, 25.3 mmol) dissolved in 175 mL of diethyl ether was added m-CPBA (1.5 equiv) in portions over 30 minutes with vigorous stirring. The solution turned yellow, and precipitates formed. After two hours the solid was collected, washed with 2×50 mL of ether, and recrystallized from acetone:ether. Yield was approximately 125% due to contaminating acid. This crude material was carried through to the next step.

Step 2—(6-bromo-1H-pyrrolo[2,3-b]pyridin-1-yl)(phenyl)methanone (155)

1H-pyrrolo[2,3-b]pyridine-N-oxide (154, 500 mg, 3.72 mmol) was dissolved in 40 mL of dry benzene. In a separate dry flask, benzoyl bromide (2.5 equiv) and 1,1,1,3,3,3-hexamethyldisilazane (1.0 equiv) were combined in 20 mL of dry benzene. The bromide solution was added in 5 mL aliquots over 30 minutes to the reaction flask. The reaction was stirred at ambient temperature for two hours. It was then washed with 3×30 ml, NaHCO$_3$ (aq., satd.) and 1×30 mL brine. The organic layer was dried over sodium sulfate and evaporated. The crude material was taken directly to the next step without further purification.

Step 3—Preparation of 6-bromo-1H-pyrrolo[2,3-b]pyridine (156)

(6-bromo-1H-pyrrolo[2,3-b]pyridin-1-yl)(phenyl)methanone 155 was dissolved in 20 mL of dioxane and 20 mL of 2M KOH (aq). This was stirred at ambient temperature until analysis indicated all of the starting material had been consumed (2 to 4 hours). The reaction was diluted with 50 mL of ethyl acetate and washed with 2×25 mL of NaHCO$_3$ (aq. satd.) and 25 mL of brine. The organic layer was dried with sodium sulfate, evaporated and purified by column chromatography. Combined steps 2 and 3 gave approximately 65% overall yield.

Step 4—Preparation of 6-bromo-1H-(triisopropylsilyl)-1H-pyrrolo[2,3-b]pyridine (157)

6-bromo-1H-pyrrolo[2,3-b]pyridine (156, 275 mg, 1.39 mmol) was dissolved in 4 mL of dry dioxane. DIEA (3 equiv) and TIPS-OTf (2.5 equiv) were added and the reaction was stirred at 50° C. overnight. The reaction was then diluted with 20 mL of ethyl acetate and washed 2 times with 10 mL NaHCO$_3$ (aq., 5%) and once with 10 mL brine. The organic fraction was dried over MgSO$_4$, evaporated and diluted with 5.5 mL of dry toluene (~10 mg bromide per 0.2 mL of solution) to use directly in the next reaction step.

Step 5—Preparation of <N-phenyl-1H-pyrrolo[2,3-b]pyridin-6-amine (158)

A 1 dram vial was charged with aniline (2-3 equiv), and 0.200 mL of the 157 stock solution of bromide in toluene was added. A catalyst stock solution containing 3 mmol Pd(OAc), 3 mmol biphenyl-2-yl-di-tert-butyl-phosphane and 15 mL of toluene was prepared and 0.050 mL of the catalyst solution was added to the reaction. An excess of NaOtBu was added as a solid to the reaction. The vial was placed in an 80° C. oven for 60 minutes (shaken several times over the hour). After cooling, the reaction was neutralized with 0.1 on mL of TFA. After 30 minutes the sample was evaporated and resolvated in 0.300 mL of DMSO. The desired compound was isolated by preparative HPLC/MS. MS (ESI) [M+H$^+$]$^+$=210.4.

The following compounds were prepared following the protocol of scheme 51, substituting aniline with a suitable amine is Step 5:

Cyclohexyl-(1H-pyrrolo[2,3-b]pyridin-6-yl)-amine (159),
Benzyl-(1H-pyrrolo[2,3-b]pyridin-6-yl)-amine (160),
Cyclopropylmethyl-(1H-pyrrolo[2,3-b]pyridin-6-yl)-amine (161),
(3-Methoxy-benzyl)-(1H-pyrrolo[2,3-b]pyridin-6-yl)-amine (162),
(1H-Pyrrolo[2,3-b]pyridin-6-yl)-(3-trifluoromethyl-benzyl)-amine (163),
(1H-Pyrrolo[2,3-b]pyridin-6-yl)-(2-trifluoromethyl-benzyl)-amine (164),
Cyclohexylmethyl-(1H-pyrrolo[2,3-b]pyridin-6-yl)-amine (165), (1H-Pyrrolo[2,3-b]pyridin-6-yl)-(4-trifluoromethoxy-benzyl)-amine (166),
(1H-Pyrrolo[2,3-b]pyridin-6-yl)-(3-trifluoromethoxy-benzyl)-amine (167),
(1H-Pyrrolo[2,3-b]pyridin-6-yl)-(2-trifluoromethoxy-benzyl)-amine (168),
Pyridin-2-ylmethyl-(1H-pyrrolo[2,3-b]pyridin-6-yl)-amine (169),
(4-Methanesulfonyl-benzyl)-(1H-pyrrolo[2,3-b]pyridin-6-yl)-amine (170),
(4-Methoxy-benzyl)-(1H-pyrrolo[2,3-b]pyridin-6-yl)-amine (171),
Ethyl-(1H-pyrrolo[2,3-b]pyridin-6-yl)-amine (172),
(3-Chloro-benzyl)-(1H-pyrrolo[2,3-b]pyridin-6-yl)-amine (173),
(4-Methyl-benzyl)-(1H-pyrrolo[2,3-b]pyridin-6-yl)-amine (174),
(1-Methyl-piperidin-4-yl)-(1H-pyrrolo[2,3-b]pyridin-6-yl)-amine (175),
Pyridin-3-ylmethyl-(1H-pyrrolo[2,3-b]pyridin-6-yl)-amine (176),
[4-(Morpholine-4-sulfonyl)-phenyl]-(1H-pyrrolo[2,3-b]pyridin-6-yl)-amine (177),
(4-Methanesulfonyl-phenyl)-(1H-pyrrolo[2,3-b]pyridin-6-yl)-amine (178),
(2-Chloro-benzyl)-(1H-pyrrolo[2,3-b]pyridin-6-yl)-amine (179),
(1H-Pyrrolo[2,3-b]pyridin-6-yl)-(tetrahydro-pyran-4-yl)-amine (180),
(4-Chloro-benzyl)-(1H-pyrrolo[2,3-b]pyridin-6-yl)-amine (181),
(3-Methyl-benzyl)-(1H-pyrrolo[2,3-b]pyridin-6-yl)-amine (182),
[3-(Morpholine-4-sulfonyl)-phenyl]-(1H-pyrrolo[2,3-b]pyridin-6-yl)-amine (183),
(3-Methanesulfonyl-phenyl)-(1H-pyrrolo[2,3-b]pyridin-6-yl)-amine (184),
Pyridin-3-yl-(H-pyrrolo[2,3-b]pyridin-6-yl)-amine (185),
(2-Methoxy-phenyl)-(1H-pyrrolo[2,3-b]pyridin-6-yl)-amine (186),
(1H-Pyrrolo[2,3-b]pyridin-6-yl)-(3-trifluoromethyl-phenyl)-amine (187),
(1H-Pyrrolo[2,3-b]pyridin-6-yl)-(4-trifluoromethoxy-phenyl)-amine (188),
(4-Methoxy-phenyl)-(1H-pyrrolo[2,3-b]pyridin-6-yl)-amine (189),
N,N-Dimethyl-N'-(1H-pyrrolo[2,3-b]pyridin-6-yl)-benzene-1,4-diamine (190),
(3-Methoxy-phenyl)-(1H-pyrrolo[2,3-b]pyridin-6-yl)-amine (191),
(4-Morpholin-4-yl-phenyl)-(1H-pyrrolo[2,3-b]pyridin-6-yl)-amine (192),
(4-Piperidin-1-yl-phenyl)-(1H-pyrrolo[2,3-b]pyridin-6-yl)-amine (193),
(1H-Pyrrolo[2,3-b]pyridin-6-yl)-(3-trifluoromethoxy-phenyl)-amine (194),
(1H-Pyrrolo[2,3-b]pyridin-6-yl)-p-tolyl-amine (195),
(3-tert-Butyl-phenyl)-(1H-pyrrolo[2,3-b]pyridin-6-yl)-amine (196),
(3-Dimethylamino-benzyl)-(1H-pyrrolo[2,3-b]pyridin-6-yl)-amine (197),
(3,5-Dichloro-phenyl)-(1H-pyrrolo[2,3-b]pyridin-6-yl)-amine (198),
(1H-Pyrrolo[2,3-b]pyridin-6-yl)-(4-trifluoromethyl-benzyl)-amine (199),
N,N-Dimethyl-N'-(1H-pyrrolo[2,3-b]pyridin-6-yl)-benzene-1,3-diamine (200),
(3-Chloro-phenyl)-(1H-pyrrolo[2,3-b]pyridin-6-yl)-amine (201),
(4-Chloro-phenyl)-(1H-pyrrolo[2,3-b]pyridin-6-yl)-amine (202),
(2-Chloro-phenyl)-(1H-pyrrolo[2,3-b]pyridin-6-yl)-amine (203),
(5-Methyl-isoxazol-3-yl)-(1H-pyrrolo[2,3-b]pyridin-6-yl)-amine (204),
(2-Morpholin-4-yl-phenyl)-(1H-pyrrolo[2,3-b]pyridin-6-yl)-amine (205), and
(2-Methanesulfonyl-phenyl)-(1H-pyrrolo[2,3-b]pyridin-6-yl)-amine (206).

The following table indicates the amine (Column 2) that is substituted in place of the aniline in Step 5 to afford the compound (Column 3). Column 1 provides the compound number and Column 4 the observed mass.

| Compound number | Amine | Compound structure | MS (ESI) $[M + H^+]^+$ observed |
|---|---|---|---|
| 159 | cyclohexylamine | cyclohexyl-NH-pyrrolopyridine | 216.3 |
| 160 | benzylamine | benzyl-NH-pyrrolopyridine | 224.3 |
| 161 | cyclopropylmethylamine | cyclopropylmethyl-NH-pyrrolopyridine | 188.2 |

-continued

| Compound number | Amine | Compound structure | MS (ESI) [M + H⁺]⁺ observed |
|---|---|---|---|
| 162 | 3-methoxybenzylamine | 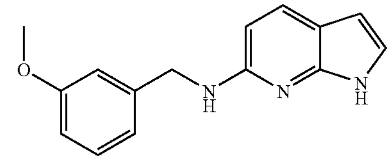 | 254.3 |
| 163 | 3-(trifluoromethyl)benzylamine | 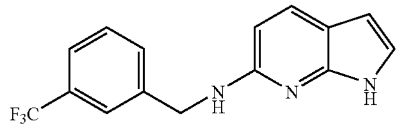 | 291.9 |
| 164 | 2-(trifluoromethyl)benzylamine | 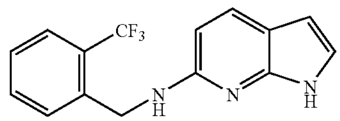 | 291.9 |
| 165 | cyclohexylmethylamine | 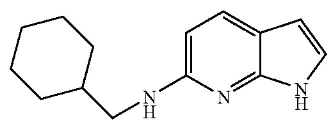 | 230.3 |
| 166 | 4-(trifluoromethoxy)benzylamine | 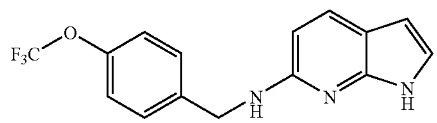 | 308.3 |
| 167 | 3-(trifluoromethoxy)benzylamine | 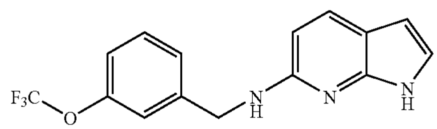 | 308.3 |
| 168 | 2-(trifluoromethoxy)benzylamine | 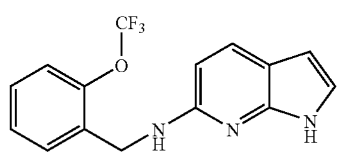 | 308.3 |
| 169 | 2-picolylamine | 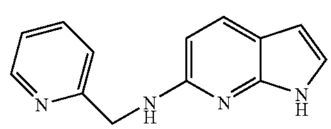 | 225.1 |
| 170 | 4-(methylsulfonyl)benzylamine | 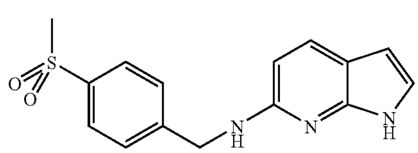 | 302.3 |
| 171 | 4-methoxybenzylamine | 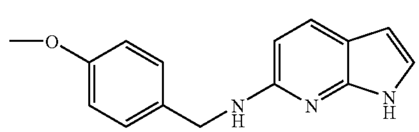 | 254.3 |

-continued

| Compound number | Amine | Compound structure | MS (ESI) [M + H+]+ observed |
|---|---|---|---|
| 172 | ethylamine | N-ethyl-7-azaindol-6-amine | 162.2 |
| 173 | 3-chlorobenzylamine | N-(3-chlorobenzyl)-7-azaindol-6-amine | 258.3 |
| 174 | 4-methylbenzylamine | N-(4-methylbenzyl)-7-azaindol-6-amine | 238.3 |
| 175 | 1-methylpiperidin-4-amine | N-(1-methylpiperidin-4-yl)-7-azaindol-6-amine | 231.1 |
| 176 | 3-(aminomethyl)pyridine | N-(pyridin-3-ylmethyl)-7-azaindol-6-amine | 225.1 |
| 177 | 4-(morpholinosulfonyl)aniline | N-(4-(morpholinosulfonyl)phenyl)-7-azaindol-6-amine | 359.1 |
| 178 | 4-(methylsulfonyl)aniline | N-(4-(methylsulfonyl)phenyl)-7-azaindol-6-amine | 287.9 |
| 179 | 2-chlorobenzylamine | N-(2-chlorobenzyl)-7-azaindol-6-amine | 258.3 |
| 180 | tetrahydro-2H-pyran-4-amine | N-(tetrahydro-2H-pyran-4-yl)-7-azaindol-6-amine | 218.3 |
| 181 | 4-chlorobenzylamine | N-(4-chlorobenzyl)-7-azaindol-6-amine | 258.3 |
| 182 | 3-methylbenzylamine | N-(3-methylbenzyl)-7-azaindol-6-amine | 238.3 |

| Compound number | Amine | Compound structure | MS (ESI) [M + H⁺]⁺ observed |
|---|---|---|---|
| 183 | | 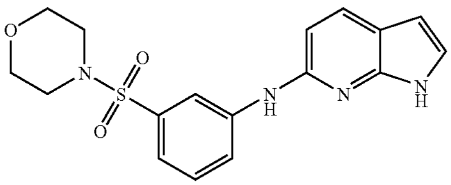 | 359.1 |
| 184 | | 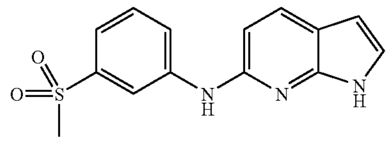 | 287.9 |
| 185 | | 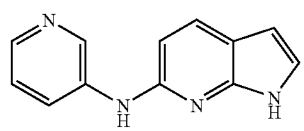 | 211.0 |
| 186 | | 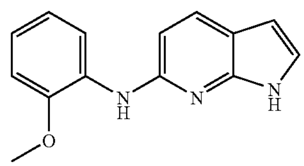 | 240.3 |
| 187 | | 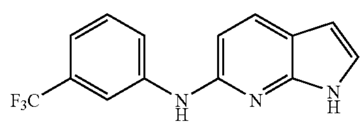 | 278.3 |
| 188 | | 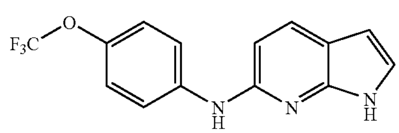 | 293.9 |
| 189 | | 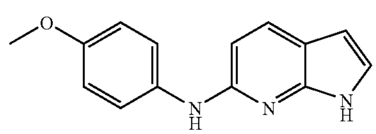 | 240.3 |
| 190 | | 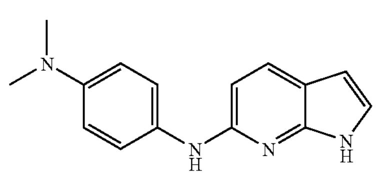 | 253.1 |
| 191 | | 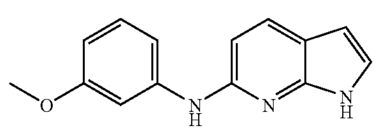 | 240.3 |

-continued
| Compound number | Amine | Compound structure | MS (ESI) [M + H⁺]⁺ observed |
|---|---|---|---|
| 192 | 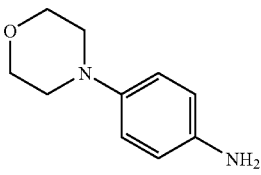 | 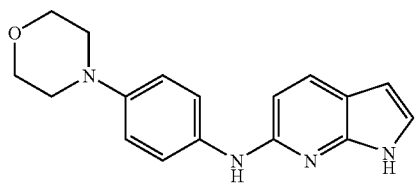 | 295.1 |
| 193 | 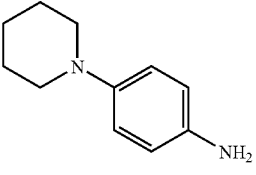 | 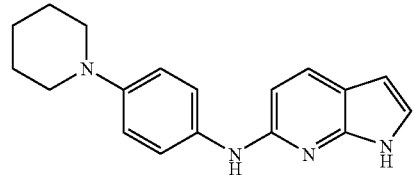 | 293.1 |
| 194 | 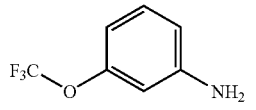 | 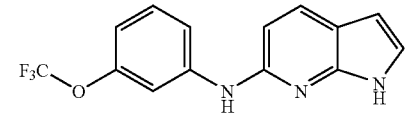 | 293.9 |
| 195 | 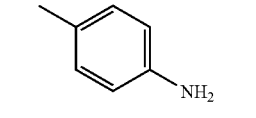 | 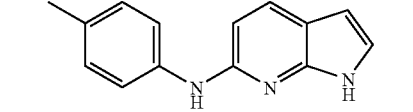 | 224.3 |
| 196 | 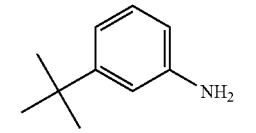 | 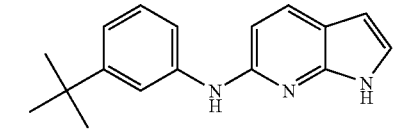 | 266.3 |
| 197 | 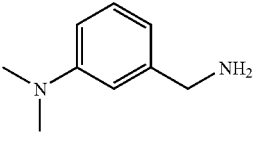 | 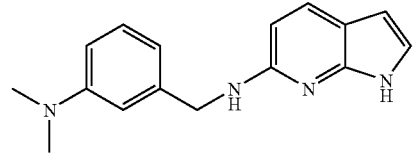 | 267.1 |
| 198 | 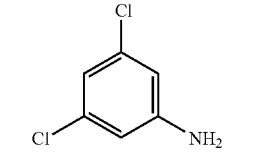 | 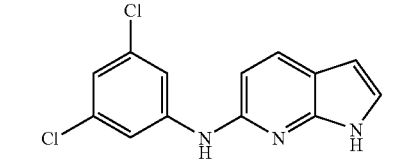 | 278.3 |
| 199 | 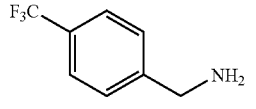 | 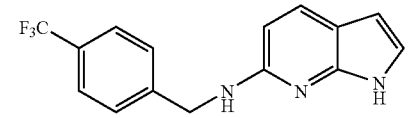 | 291.9 |
| 200 | 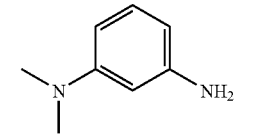 | 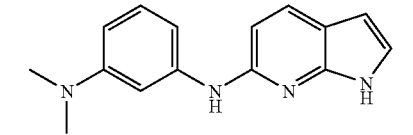 | 253.1 |

-continued

| Compound number | Amine | Compound structure | MS (ESI) [M + H⁺]⁺ observed |
|---|---|---|---|
| 201 | | 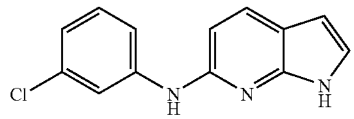 | 244.3 |
| 202 | | 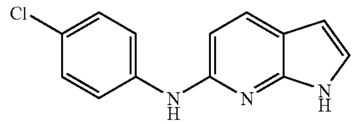 | 244.3 |
| 203 | | 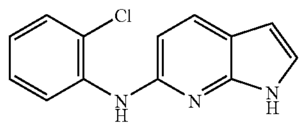 | 244.3 |
| 204 | | 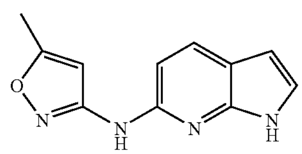 | 215.0 |
| 205 | | 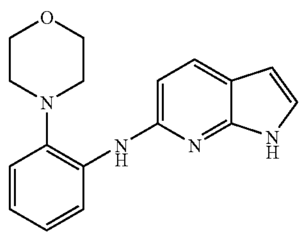 | 295.1 |
| 206 | | 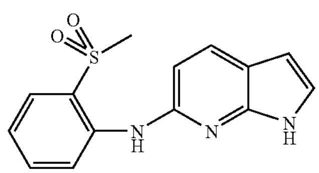 | 287.9 |

Example 52

Synthesis of 5-methanesulfonyl-1H-pyrrolo[2,3-b]pyridine 207

5-Methanesulfonyl-1-pyrrolo[2,3-b]pyridine 207 was synthesized in one step from 5-bromo-7-azaindole 1 as shown in Scheme 52.

Scheme 52

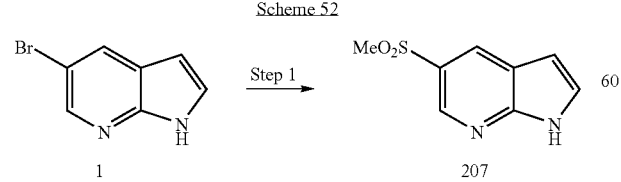

To 5-bromo-7-azaindole (1, 1.00 g, 5.08 mmol) in dimethyl sulfoxide (15.0 mL) were added sodium methanesulfinate (0.622 g, 6.09 mmol), L-proline (0.117 g, 1.02 mmol), copper (I) iodide (0.200 g, 1.05 mmol), and sodium hydroxide (0.0406 g, 1.02 mmol). The reaction was stirred at 120° C. overnight. The reaction was poured into aqueous ammonia, and extracted with ethyl acetate. The organic layer was dried over anhydrous sodium sulfate, and filtered. The filtrate was concentrated and purified by silica gel column chromatography eluting with 20% to 100% ethyl acetate in hexane to give the desired compound as a white solid (207, 0.50 g, 50.2%). MS (ESI) [M−H⁺]⁻=195.1.

Example 53

Synthesis of 3-[4-(1H-Benzoimidazol-2-ylmethoxy)-2-fluoro-5-methoxy-benzyl]-1H-pyrrolo[2,3-b]pyridine-5-carboxylic acid P-2175

3-[4-(1-Benzoimidazol-2-ylmethoxy)-2-fluoro-5-methoxy-benzyl]-1H-pyrrolo[2,3-b]pyridine-5-carboxylic acid P-2175 was synthesized in one step from 3-[4-(1H-benzoimidazol-2-ylmethoxy)-2-fluoro-5-methoxy-benzyl]-1H-pyrrolo[2,3-b]pyridine-5-carboxylic acid methyl ester P-2174 as shown in Scheme 53.

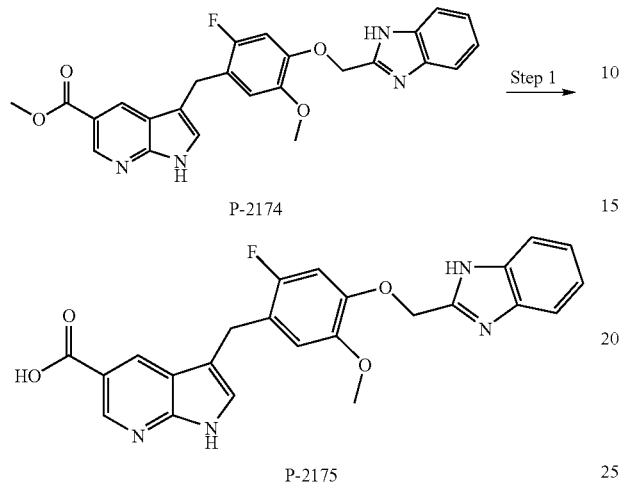

To 3-[4-(1H-benzoimidazol-2-ylmethoxy)-2-fluoro-5-methoxy-benzyl]-1H-pyrrolo[2,3-b]pyridine-5-carboxylic acid methyl ester (P-2174, 0.030 g, 0.065 mmol, prepared as described in Example 16) in tetrahydrofuran (9.0 mL) were added water (3.0 mL) and lithium hydroxide (20.0 mg, 0.84 mmol). The reaction was stirred at room temperature overnight. The reaction was poured into water, and extracted with ethyl acetate. The organic layer was discarded. The aqueous layer was acidified with 5 N HCl to pH around 3, and then extracted with ethyl acetate. The organic layer was dried over anhydrous sodium sulfate, and filtered. The filtrate was concentrated, and washed with ethyl acetate and hexane to give a white solid (P-2175, 21.3 mg, 73%). MS (ESI) [M+H$^+$]$^+$= 447.0.

Example 54

Synthesis of 5,6-Dichloro-2-[4-(5-chloro-1H-pyrrolo[2,3-b]pyridin-3-ylmethyl)-5-fluoro-2-methoxy-phenoxymethyl]-1H-benzoimidazole P-2172

5,6-Dichloro-2-[4-(5-chloro-1H-pyrrolo[2,3-b]pyridin-3-ylmethyl)-5-fluoro-2-methoxy-phenoxymethyl]-1H-benzoimidazole P-2172 was synthesized in 3 steps from 2-fluoro-4-hydroxy-5-methoxy-benzaldehyde 38 as shown in Scheme 54.

Scheme 54

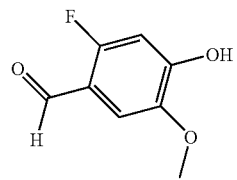

38

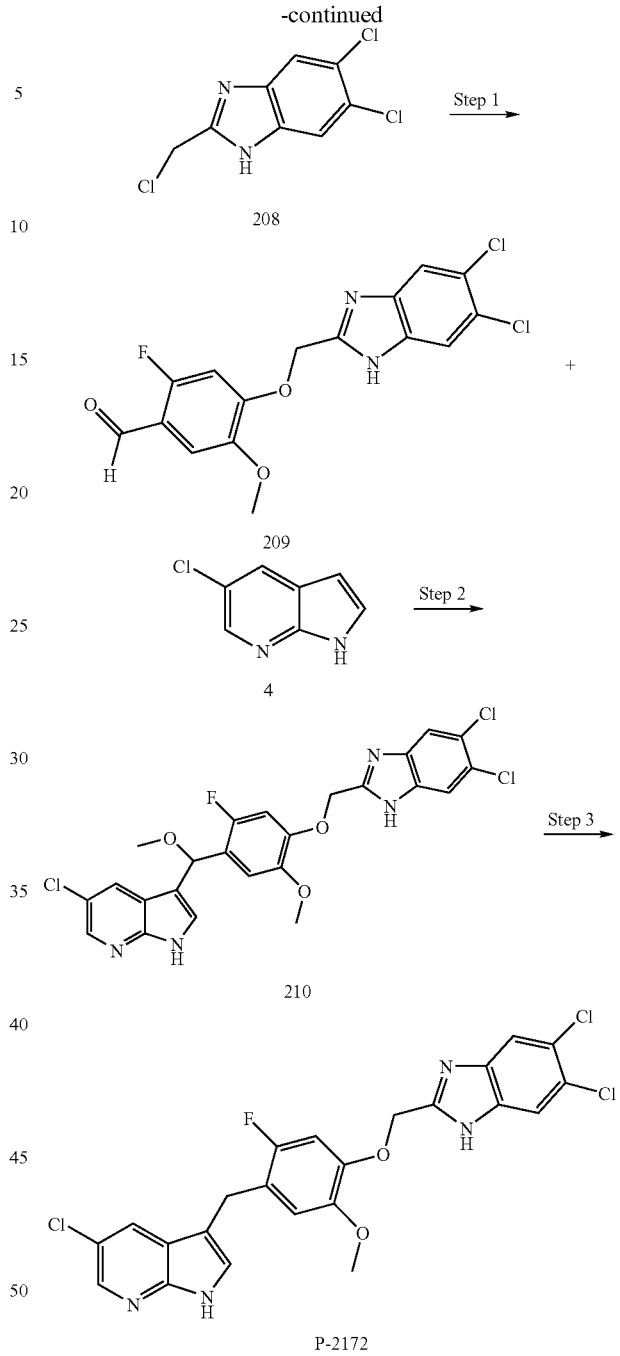

Step 1—Preparation of 4-(5,6-dichloro-1-benzoimidazol-2-ylmethoxy)-2-fluoro-5-methoxy-benzaldehyde (209)

2-Fluoro-4-hydroxy-5-methoxy-benzaldehyde (38, 0.364 g, 2.14 mmol) was dissolved in N,N-dimethylformamide (10.0 mL) and sodium hydride (60% dispersion in mineral oil, 100 mg, 2.50 mmol) was added. After 20 minutes, 5,6-dichloro-2-chloromethyl-1H-benzoimidazole (208, 0.420 g, 1.78 mmol) was added. The reaction was stirred at 80° C. overnight. The reaction was concentrated, then washed with ethyl acetate and saturated sodium bicarbonate. The organic portions were dried with anhydrous sodium sulfate, filtered and the filtrate was adsorbed onto silica. The mixture was purified by silica gel chromatography, eluting with methanol/dichloromethane, to provide the desired compound, consistent by $^1$H-NMR (209, 140 mg, 21%).

Step 2—Preparation of 5,6-dichloro-2-4-[(5-chloro-1H-pyrrolo[2,3-b]pyridin-3-yl)-methoxy-methyl]-5-fluoro-2-ethoxy-phenoxymethyl-1H-benzoimidazole (210)

5-Chloro-1H-pyrrolo[2,3-b]pyridine (4, 52.6 mg, 0.345 mmol) and 4-(5,6-dichloro-1H-benzoimidazol-2-yl-methoxy)-2-fluoro-5-methoxy-benzaldehyde (209, 0.140 g, 0.379 mmol) were dissolved in methanol (7 mL) and potassium hydroxide (0.193 g, 3.45 mmol) was added. The reaction was stirred at room temperature for 72 hours. The reaction was adsorbed onto silica and purified by silica gel chromatography, eluting with methanol/dichloromethane to provide the desired compound, consistent by $^1$H-NMR and MS (ESI) [M+H$^+$]$^+$=535.1 (210, 60 mg, 33%).

Step 3—Preparation of 5,6-Dichloro-2-[4-(5-chloro-1H-pyrrolo[2,3-b]pyridin-3-ylmethyl)-5-fluoro-2-methoxy-phenoxymethyl]-1H-benzoimidazole (P-2172)

5,6-Dichloro-2-4-[(5-chloro-1H-pyrrolo[2,3-b]pyridin-3-yl)-methoxy-methyl]-5-fluoro-2-methoxy-phenoxymethyl-1H-benzoimidazole (210, 0.041 g, 0.077 mmol) was dissolved in acetonitrile (10 mL) and trifluoroacetic acid (0.3 mL, 4.0 mmol) and triethylsilane (0.6 mL, 4.0 mmol) were added. The reaction was heated to reflux for 2 hours. The mixture was adsorbed onto silica gel and purified by silica gel chromatography, eluting with methanol/dichloromethane, to provide the desired compound, consistent by $^1$H-NMR and MS (ESI): [M+H$^+$]$^+$=505.0, 507.0 (P-2172, 8.1 mg, 21%).

2-[4-(5-Chloro-1H-pyrrolo[2,3-b]pyridin-3-ylmethyl)-5-fluoro-2-methoxy-phenoxymethyl]-5-trifluoromethyl-1H-benzoimidazole P-2178 and 2-[4-(5-chloro-1H-pyrrolo[2,3-b]pyridin-3-ylmethyl)-5-fluoro-2-methoxy-phenoxymethyl]-5-fluoro-1H-benzoimidazole P-2179, were prepared following the protocol of Scheme 54, replacing 5,6-dichloro-2-chloromethyl-1H-benzoimidazole 208 with 2-chloromethyl-5-trifluoromethyl-1H-benzoimidazole or 2-chloromethyl-5-fluoro-1H-benzoimidazole, respectively, in Step 1. MS (ESI): [M+H$^+$]$^+$=505.1, 507.1 (P-2178) and 455.0, 456.5 (P-2179).

Example 55

Synthesis of 2-[4-(5-chloro-1H-pyrrolo[2,3-b]pyridin-3-ylmethyl)-5-fluoro-2-methoxy-phenoxymethyl]-1-methyl-1H-benzoimidazole P-2106

2-[4-(5-Chloro-1H-pyrrolo[2,3-b]pyridin-3-ylmethyl)-5-fluoro-2-methoxy-phenoxymethyl]-1-methyl-1H-benzoimidazole P-2106 was synthesized in 4 steps from N-methyl-phenylenediamine 211 as shown in Scheme 55.

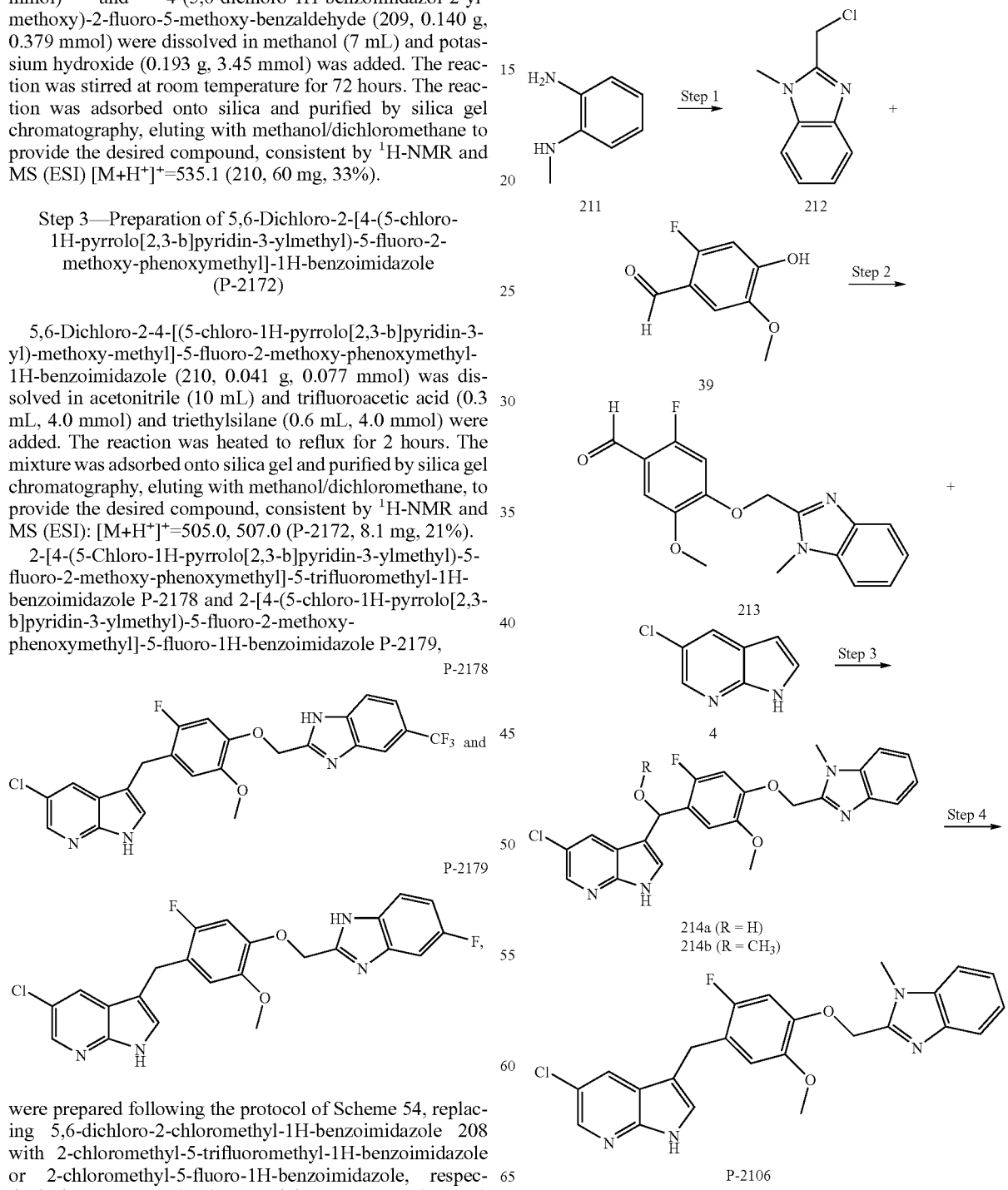

Step 1—Preparation of 2-chloromethyl-1-methyl-1H-benzoimidazole (212)

N-methyl-phenylenediamine (1 g, 8.2 mmol) and chloroacetic acid (0.9 g, 9.4 mol) were dissolved in 5 N aqueous hydrochloric acid (10 mL) and stirred at 55° C. overnight. The reaction mixture was then diluted with water and basified with solid sodium bicarbonate to give a precipitate which was filtered, washed with water and dried to provide the desired compound (1.3 g, 87%).

Step 2—Preparation of 2-fluoro-5-methoxy-4-(1-methyl-1H-benzoimidazol-2-ylmethoxy)-benzaldehyde (213)

To a solution of 2-fluoro-4-hydroxy-5-methoxy-benzaldehyde (39, 3.0 g, 5 mmol) in N,N-dimethylacetamide (120 mL) was added sodium hydride (60% dispersion in mineral oil, 0.8 g, 19 mmol) portion wise. After the addition was complete, the reaction was stirred for 30 minutes after which 2-chloromethyl-1-methyl-1H-benzoimidazole (212, 2.9 g, 16 mmol) was added and then heated at 80° C. overnight. The reaction mixture was then poured into water (1 L) with stirring and the precipitated solid was filtered, washed with water and dried to give the desired compound (213, 4.2 g, 84% yield).

Step 3—Preparation of (5-chloro-1H-pyrrolo[2,3-b]pyridin-3-yl)-[2-fluoro-5-methoxy-4-(1-methyl-1H-benzoimidazol-2-ylmethoxy)-phenyl]-methanol (214a) and 2-{4-[(5-chloro-1H-pyrrolo[2,3-b]pyridin-3-yl)-methoxy-methyl]-5-fluoro-2-methoxy-phenoxymethyl}-1-methyl-1H-benzoimidazole (214b)

To a solution of 2-fluoro-5-methoxy-4-(1-methyl-1H-benzoimidazol-2-ylmethoxy)-benzaldehyde (213, 4 g, 13 mmol) and 5-chloro-1H-pyrrolo[2,3-b]pyridine (4, 2 g, 13 mmol) in methanol (140 mL) and tetrahydrofuran (140 mL) was added potassium hydroxide (5 g, 89 mmol). The reaction was stirred for 5 days at room temperature. The solution was diluted with water and extracted with ethyl acetate. The layers were separated and the aqueous layer was back-extracted with ethyl acetate. The combined organic layers were dried over sodium sulfate and evaporated in vacuo to give crude compound as a yellow semi-solid which was used directly in the next step.

Step 4—Preparation of 2-[4-(5-Chloro-1H-pyrrolo[2,3-b]pyridin-3-ylmethyl)-5-fluoro-2-methoxy-phenoxymethyl]-1-methyl-1H-benzoimidazole (P-2106)

To a solution of above crude mixture of aldol compounds 214a and 214b (13 mmol, theoretical yield) in acetonitrile (300 mL) was added trifluoroacetic acid (5.7 mL, 77 mmol) and triethylsilane (54 mL, 339 mmol). The resulting mixture was stirred for 2 hours at reflux. The solvent was removed in vacuo and the residue taken up in ethyl acetate (1 L) and then washed with saturated aqueous potassium carbonate. The layers were separated and the aqueous layer was back-extracted with ethyl acetate (1 L). The combined organic layers were dried over sodium sulfate and evaporated in vacuo to give a crude oily solid that was subjected to Boc protection (20 volumes of tetrahydrofuran, 2.0 equiv. of Boc-anhydride, 0.10 equiv. of DMAP) followed by silica gel chromatography (ethyl acetate/hexanes). The isolated material was then deprotected using 20% trifluoroacetic acid in dichloromethane (10 volumes) and neutralized to the free base using saturated aqueous potassium carbonate. The dichloromethane was removed it vacuo and the resulting product was filtered, washed with water and the solid was slurried with ethyl acetate, filtered, and dried to give P-2106 (1.3 g, 23% over 2 steps) MS (ESI): [M+H$^+$]$^+$=451.2, 453.0.

2-[4-(5-Chloro-1H-pyrrolo[2,3-b]pyridin-3-ylmethyl)-5-fluoro-2-methoxy-phenoxymethyl]-1-ethyl-1H-benzoimidazole P-2177

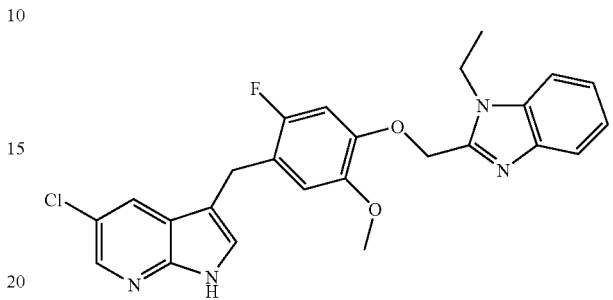

was prepared following the protocol of Scheme 55, steps 3 and 4, substituting 2-fluoro-5-methoxy-4-(1-methyl-1H-benzoimidazol-2-ylmethoxy)-benzaldehyde 213 with 4-(1-ethyl-1-benzoimidazol-2-ylmethoxy)-2-fluoro-5-methoxy-benzaldehyde 216 (see Example 56) in step 3. MS (ESI): [M+H$^+$]$^+$=465.3, 467.1.

Example 56

Synthesis of 4-(1-ethyl-1H-benzoimidazol-2-ylmethoxy)-2-fluoro-5-methoxy-benzaldehyde 216

4-(1-Ethyl-1H-benzoimidazol-2-ylmethoxy)-2-fluoro-5-methoxy-benzaldehyde 216 was synthesized in 1 step from 4-(1H-Benzoimidazol-2-ylmethoxy)-2-fluoro-5-methoxy-benzaldehyde 215 as shown in Scheme 56.

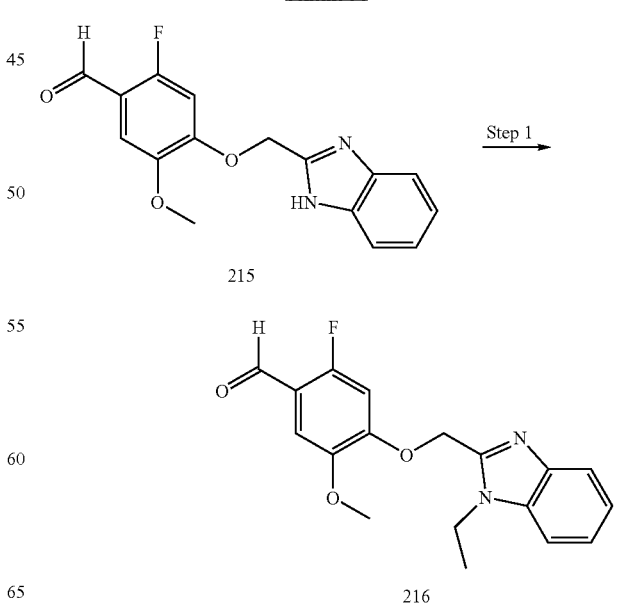

Step 1—Preparation of 4-(1-Ethyl-1H-benzoimidazol-2-ylmethoxy)-2-fluoro-5-methoxy-benzaldehyde (22)

To a solution of 4-(1H-benzoimidazol-2-ylmethoxy)-2-fluoro-5-methoxy-benzaldehyde (215, 4.0 g, 13 mmol) in N,N-dimethylacetamide (80 mL) was added sodium hydride (60% dispersion in mineral oil, 0.65 g, 16 mmol) portion wise. After the addition was complete, the reaction was stirred for 30 minutes after which bromoethane (1.2 mL, 16 mmol) was added and then allowed to stir for several hours. The reaction mixture was then poured into water (1 L) with stirring and the precipitated solid was filtered, washed with water and dried to give the desired compound (216, 3.8 g, 87% yield).

Example 57

Synthesis of 2-[4-(5-chloro-1H-pyrrolo[2,3-b]pyridin-3-ylmethyl)-5-fluoro-2-methoxy-phenoxymethyl]-1H-benzoimidazole-5-sulfonic acid dimethylamide P-2173

2-[4-(5-Chloro-1H-pyrrolo[2,3-b]pyridin-3-ylmethyl)-5-fluoro-2-methoxy-phenoxymethyl]-1H-benzoimidazole-5-sulfonic acid dimethylamide P-2173 was synthesized in 4 steps from 2-fluoro-4-hydroxy-5-methoxy-benzaldehyde 39 as shown in Scheme 57.

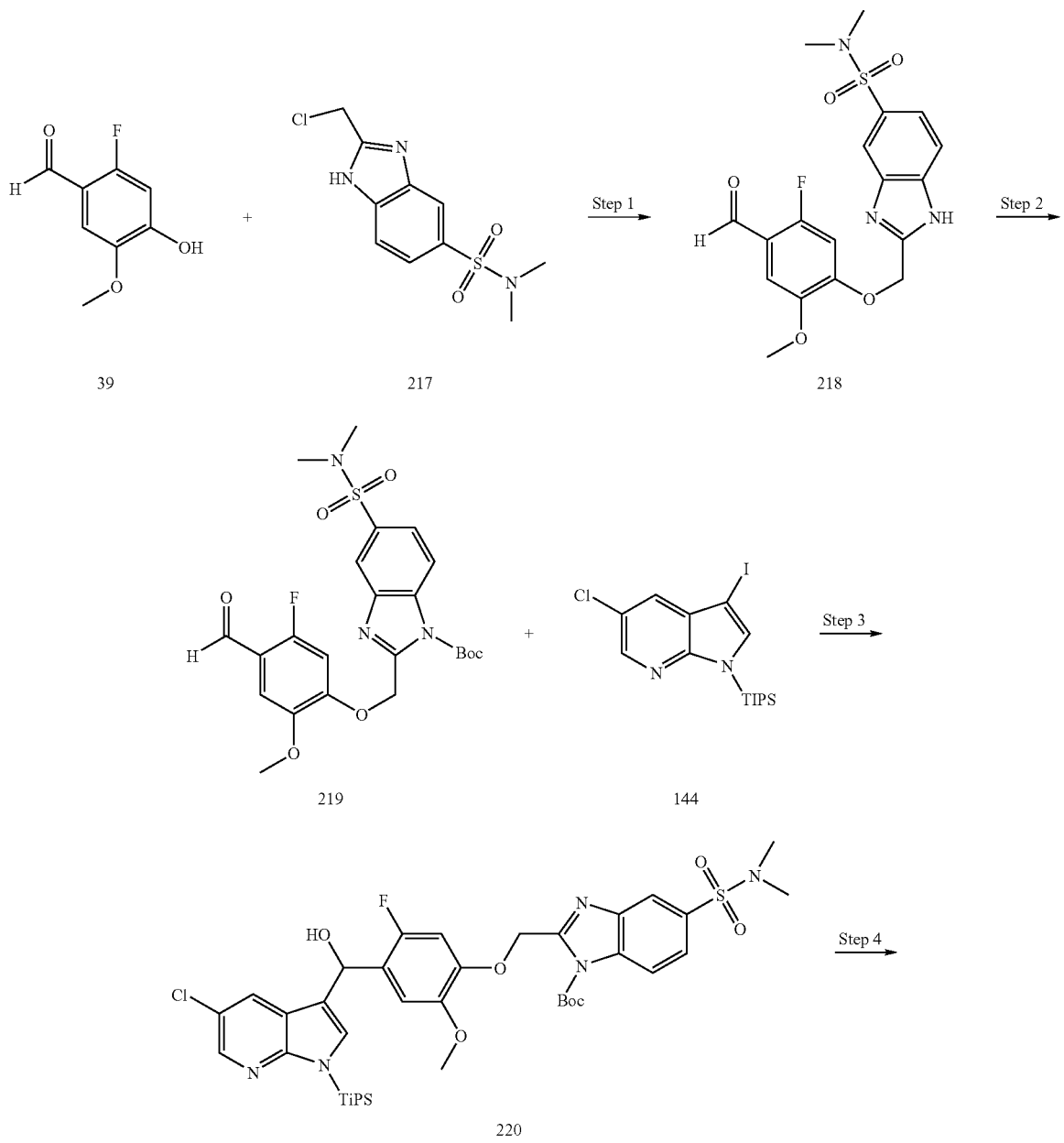

Scheme 57

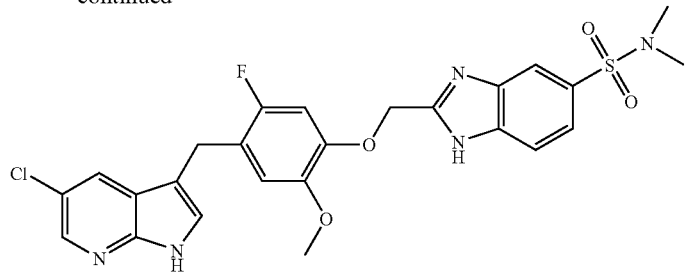

P-2173

Step 1—Preparation of 2-(5-fluoro-4-formyl-2-methoxy-phenoxymethyl)-1H-benzoimidazole-5-sulfonic acid dimethylamide (218)

2-Fluoro-4-hydroxy-5-methoxy-benzaldehyde (39, 0.38 g, 2.2 mmol) was dissolved in N,N-dimethylformamide (30 mL) and sodium hydride 60% dispersion in mineral oil (120 mg) was added. After 20 minutes, 2-chloromethyl-1H-benzoimidazole-5-sulfonic acid dimethylamide hydrochloride salt (217, 0.559 g, 1.80 mmol) was added to the mixture. The reaction was stirred at 60° C. overnight. The solvent was removed under reduced pressure. Ethyl acetate was added and the organic layer was washed with water, dried over anhydrous sodium sulfate, and filtered. The filtrate was concentrated and purified by silica gel column chromatography eluting with a gradient of ethyl acetate (20-100%) in hexane to provide the desired compound (218, 0.122 g, 17%).

Step 2—Preparation of 5-dimethylsulfamoyl-2-(5-fluoro-4-formyl-2-methoxy-phenoxymethyl)-benzimidazole-1-carboxylic acid tert-butyl ester (219)

2-(5-Fluoro-4-formyl-2-methoxy-phenoxyethyl)-1-benzoimidazole-5-sulfonic acid dimethylamide (218, 0.122 g, 0.299 mmol) was dissolved in tetrahydrofuran (5 mL). N,N-Diisopropylethylamine (0.10 mL, 0.60 mmol) and 4-dimethyl aminopyridine polymer bound (0.007 g, 0.06 mol) were added followed by di-tert-butyldicarbonate (0.072 g, 0.33 mmol). The reaction was stirred at room temperature overnight. The solvent was removed under reduced pressure. Ethyl acetate was added and washed with water, dried over anhydrous sodium sulfate, and concentrated. The resulting compound was used without further purification (219, 0.133 g, 87%).

Step 3—Preparation of 2-4-[(5-chloro-1-triisopropylsilanyl-1H-pyrrolo[2,3-b]pyridin-3-yl)-hydroxymethyl]-5-fluoro-2-methoxy-phenoxymethyl-5-dimethylsulfamoyl-benzoimidazole-1-carboxylic acid tert-butyl ester (220)

5-Chloro-3-iodo-1-triisopropylsilanyl-1H-pyrrolo[2,3-b]pyridine (144, 0.17 g, 0.39 mmol) was dissolved in tetrahydrofuran (2 mL). The reaction was cooled to −20° C.

2 M isopropylmagnesium chloride in tetrahydrofuran (0.2 mL) was added drop wise to the mixture. The reaction was stirred to −5° C. 5-Dimethylsulfamoyl-2-(5-fluoro-4-formyl-2-methoxy-phenoxymethyl)-benzimidazole-1-carboxylic acid tert-butyl ester (219, 0.133 g, 0.262 mmol) in tetrahydrofuran (3 mL) was added at once to the mixture at −20° C.

The reaction was stirred to −5° C. and concentrated. Ethyl acetate was added and washed with sodium bicarbonate saturated solution and brine, dried over anhydrous sodium sulfate and concentrated. Purification with silica gel column chromatography, eluting with a gradient of ethyl acetate (5-80%) in hexanes, gave the isolation of the desired compound (220, 0.083 g, 39%).

Step 4—Preparation of 2-[4-(5-chloro-1H-pyrrolo[2,3-b]pyridin-3-ylmethyl)-5-fluoro-2-methoxy-phenoxymethyl]-1H-benzoimidazole-5-sulfonic acid dimethylamide (P-2173)

2-4-[(5-Chloro-1-triisopropylsilanyl-1H-pyrrolo[2,3-b]pyridin-3-yl)-hydroxy-methyl]-5-fluoro-2-methoxy-phenoxymethyl-5-dimethylsulfamoyl-benzoimidazole-1-carboxylic acid tert-butyl ester (220, 0.083 g, 0.10 mmol) was combined with acetonitrile (4 mL). Triethylsilane (0.6 mL) was added followed by trifluoroacetic acid (0.3 mL). The reaction was stirred at 60° C. for one hour. The solvent was removed under reduced pressure. Ethyl acetate was added and washed with sodium bicarbonate saturated solution and brine. After the organic layer was dried over anhydrous sodium sulfate the solvent was evaporated to dryness. Purification by trituration with t mixture of ethyl acetate in hexanes allowed obtaining the desired compound. The remaining material was further purified with silica gel column chromatography, eluting with a gradient of methanol (5-35%) in dichloromethane, to provide the desired compound (P-2173, 0.022 g, 41%). MS (ESI) [M+H$^+$]$^+$=544.1, [M−H$^+$]$^-$=542.1.

2-[4-(5-Chloro-1H-pyrrolo[2,3-b]pyridin-3-ylmethyl)-5-fluoro-2-methoxy-phenoxymethyl]-5-methoxy-1H-benzoimidazole P-2182

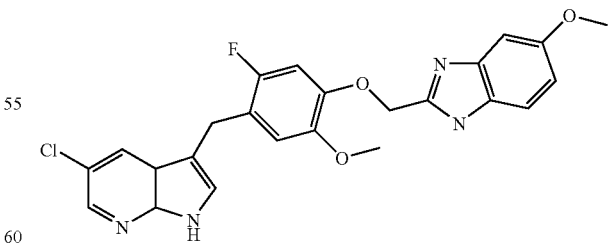

was prepared following the protocol of Scheme 57, replacing 2-chloromethyl-1H-benzoimidazole-5-sulfonic acid dimethylamide hydrochloride salt 217 with 2-Chloromethyl-5-methoxy-1H-benzoimidazole 222 (see Example 58) in step 1. MS (ESI) [M+H$^+$]$^+$=467.2.

Example 58

Synthesis of 2-chloromethyl-5-methoxy-1H-benzoimidazole 222

2-Chloromethyl-5-methoxy-1H-benzoimidazole 222 was synthesized in 1 step from (5-Methoxy-1H-benzoimidazol-2-yl)-methanol 221 as shown in Scheme 58.

Scheme 58

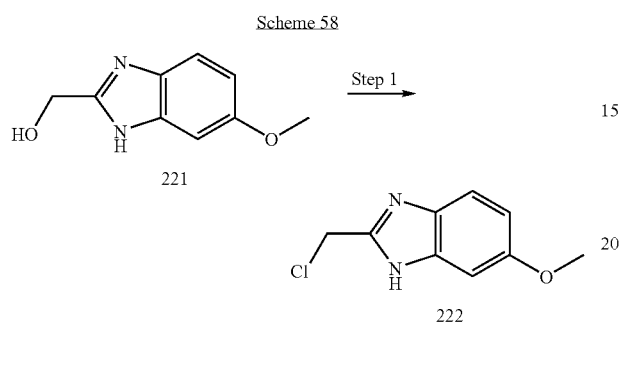

Step 1—Preparation of 2-chloromethyl-5-methoxy-1H-benzoimidazole (222)

(5-Methoxy-1H-benzoimidazol-2-yl)-methanol (221, 0.5 g, 3 mmol) was combined with 30 mL dichloromethane. Thionyl chloride (0.51 mL, 7 mmol) was added and the reaction was stirred at room temperature for 2 hours. The reaction was concentrated. Ethyl acetate was added and washed with sodium bicarbonate saturated solution and brine. The organic portion was dried over anhydrous sodium sulfate, filtered through Celite and evaporated to dryness. The resulting desired compound was used without further purification. MS (ESI) $[M+H^+]^+=197.2$.

Example 59

Synthesis of 2-2-[4-(5-chloro-1H-pyrrolo[2,3-b]pyridin-3-ylmethyl)-5-fluoro-2-methoxy-phenoxy]-ethyl-1H-benzimidazole P-2180

2-2-[4-(5-Chloro-1H-pyrrolo[2,3-b]pyridin-3-ylmethyl)-5-fluoro-2-methoxy-phenoxy]-ethyl-1H-benzimidazole P-2180 was synthesized in 4 steps from 4-Benzyloxy-2-fluoro-5-methoxy-benzaldehyde 83 as shown in Scheme 59.

Scheme 59

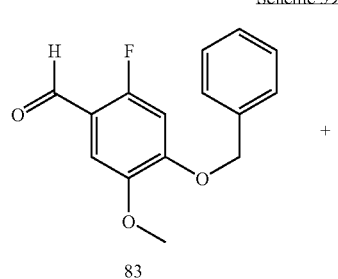

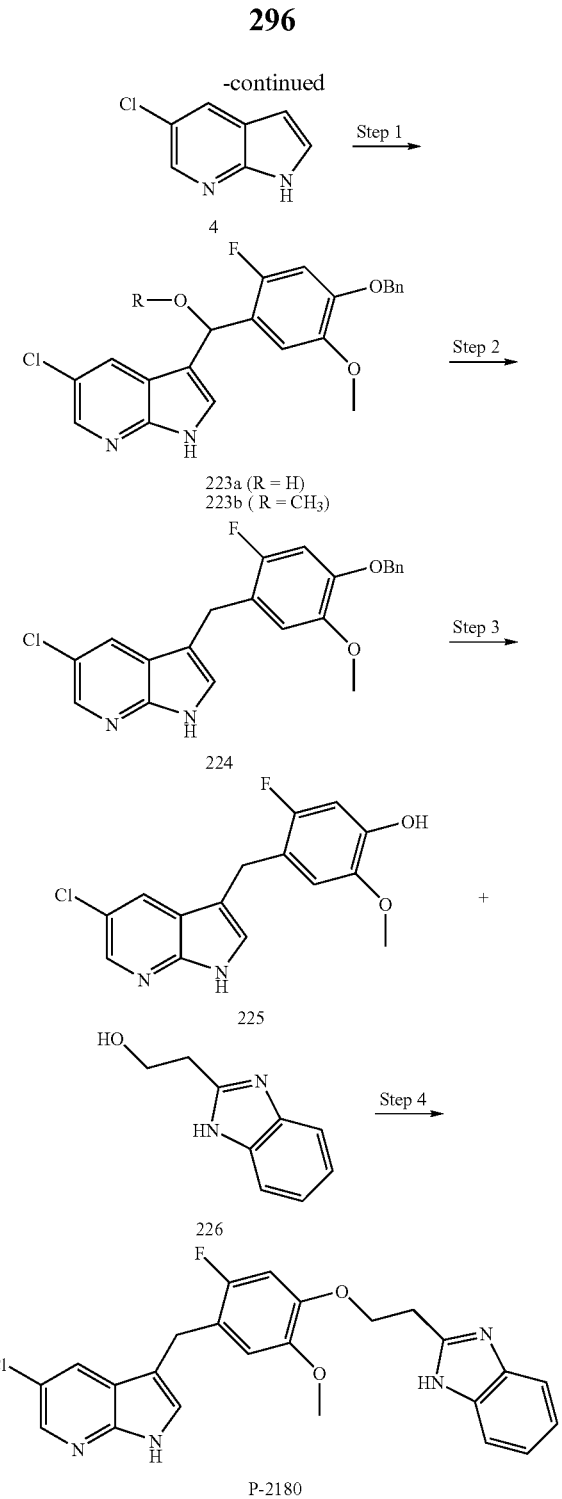

Step 1—Preparation of (4-Benzyloxy-2-fluoro-5-methoxy-phenyl)-(5-chloro-1H-pyrrolo[2,3-b]pyridin-3-yl)-methanol (223a) and 3-[(4-Benzyloxy-2-fluoro-5-methoxy-phenyl)-methoxy-methyl]-5-chloro-1H-pyrrolo[2,3-b]pyridine (223b)

4-Benzyloxy-2-fluoro-5-methoxy-benzaldehyde (83, 12.4 g, 48 mmol) was combined with 5-chloro-1H-pyrrolo[2,3-b]pyridine (4, 7.3 g, 48 mmol), methanol (500 mL) and potassium hydroxide (22 g, 335 mmol). The reaction was stirred overnight at room temperature. The solution was diluted with water and extracted with ethyl acetate. The organic portion was dried over anhydrous sodium sulfate and evaporated under reduced pressure to give the desired compounds 223a and 223b that were used without further purification.

Step 2—Preparation of 3-(4-benzyloxy-2-fluoro-5-methoxy-benzyl)-5-chloro-1H-pyrrolo[2,3-b]pyridine (224)

(4-Benzyloxy-2-fluoro-5-methoxy-phenyl)-(5-chloro-1H-pyrrolo[2,3-b]pyridin-3-yl)-methanol 223a and 3-[(4-benzyloxy-2-fluoro-5-methoxy-phenyl)-methoxy-methyl]-5-chloro-1H-pyrrolo[2,3-b]pyridine 223b (48 mmol) were combined with acetonitrile (1.4 L), trifluoroacetic acid (21 mL, 288 mmol) and triethylsilane (31 mL, 192 mmol). The resulting mixture was stirred for two hours at reflux. The solvent was removed under reduced pressure. Ethyl acetate (6 L) was added and the organic layer was washed with aqueous potassium carbonate saturated solution. The layers were separated and the aqueous layer was back-extracted with ethyl acetate (2 L). The combined organic portions were dried over anhydrous sodium sulfate and evaporated under reduced pressure to give the desired compound 224 which was used without further purification.

Step 3—Preparation of 4-(5-chloro-1H-pyrrolo[2,3-b]pyridin-3-ylmethyl)-5-fluoro-2-methoxy-phenol (225)

3-(4-Benzyloxy-2-fluoro-5-methoxy-benzyl)-5-chloro-1H-pyrrolo[2,3-b]pyridine (224, 48 mmol) was dissolved in tetrahydrofuran (300 mL) and 20% palladium on carbon (50% water wet, 2.3 g) was added. The mixture was stirred under an atmosphere of hydrogen at 50 psi in the presence of acetic acid (100 mL). The reaction mixture was filtered through Celite and evaporated to dryness to give the desired compound 225. MS (ESI) [M+H$^+$]$^+$=307.1.

Step 4—Preparation of 2-2-[4-(5-Chloro-1H-pyrrolo[2,3-b]pyridin-3-ylmethyl)-5-fluoro-2-methoxy-phenoxy]-ethyl-1H-benzimidazole (P-2180)

4-(5-Chloro-1H-pyrrolo[2,3-b]pyridin-3-ylmethyl)-5-fluoro-2-methoxy-phenol (225, 0.200 g, 0.652 mmol) was dissolved in tetrahydrofuran (5 mL). Triphenylphosphine (0.190 g, 0.72 mmol) and 2-(1H-benzoimidazol-2-yl)-ethanol (226, 0.110 g, 0.68 mmol) were added followed by diisopropyl azodicarboxylate (0.140 mL, 0.72 mmol). The reaction was stirred at room temperature overnight. The mixture was placed into water and extracted with ethyl acetate. The organic portion was dried over anhydrous sodium sulfate, and concentrated. Purification with silica gel column chromatography, eluting with a gradient of ethyl acetate (20-100%) in hexanes, gave the isolation of the desired compound (P-2180, 0.0189 g, 6%). MS (ESI): [M+H$^+$]$^+$=451.0, [M–H$^+$]$^-$=449.1

Example 60

Synthesis of 5-chloro-2-[5-fluoro-2-methoxy-4-(5-methyl-1H-pyrrolo[2,3-b]pyridin-3-ylmethyl)-phenoxymethyl]h-benzoimidazole P-2184

5-Chloro-2-[5-fluoro-2-methoxy-4-(5-methyl-1H-pyrrolo[2,3-b]pyridin-3-ylmethyl)-phenoxymethyl]-1H-benzoimidazole P-2184 was synthesized in 2 steps from 4-(1H-Benzoimidazol-2-ylmethoxy)-2-fluoro-5-methoxy-benzaldehyde 227 as shown in Scheme 60.

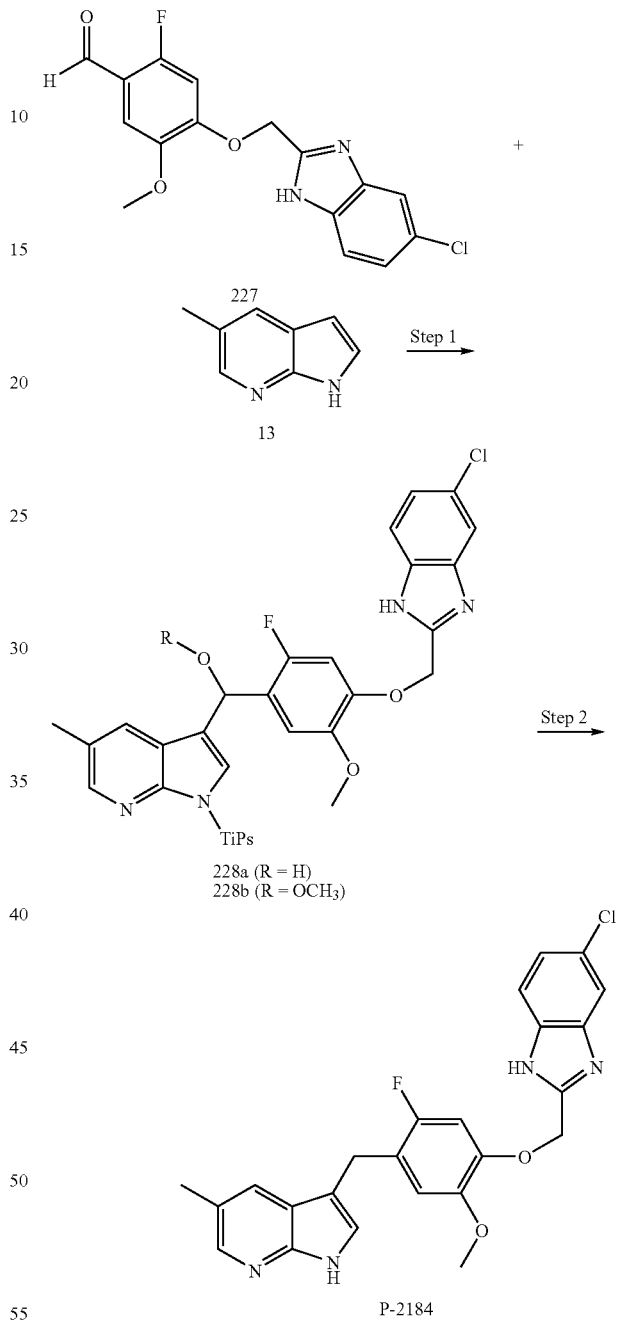

Step 1—Preparation of [4-(5-chloro-1H-benzoimidazol-2-ylmethoxy)-2-fluoro-5-methoxy-phenyl]-(5-methyl-1H-pyrrolo[2,3-b]pyridin-3-yl)-methanol (228a) and 5-chloro-2-{5-fluoro-2-methoxy-4-[methoxy-(5-methyl-1H-pyrrolo[2,3-b]pyridin-3-yl)-methyl]-phenoxymethyl}-1H-benzoimidazole (228b)

5-Methyl-1H-pyrrolo[2,3-b]pyridine (13) was combined with methanol and potassium hydroxide. After the mixture was stirred for 45 minutes 4-(5-chloro-1H-benzoimidazol-2- ylmethoxy)-2-fluoro-5-methoxy-benzaldehyde (227, per step 1 of Example 57 substituting 2-chloromethyl-1H-benzoimidazole-5-sulfonic acid dimethylamide 217 with 5-chloro-2-chloromethyl-1H-benzoimidazole) was added and the reaction was stirred at room temperature overnight. The solvent was removed under reduced pressure. Ethyl acetate was added and washed with sodium bicarbonate saturated solution and brine, dried over anhydrous sodium sulfate and concentrated. Purification with silica gel chromatography, eluting with a gradient of ethyl acetate (10-100%) in hexanes, gave the desired compounds 228a and 228b as a mixture.

Step 2—Preparation of 5-chloro-2-[5-fluoro-2-methoxy-4-(5-methyl-1H-pyrrolo[2,3-b]pyridin-3-ylmethyl)-phenoxymethyl]-1H-benzoimidazole (P-2184)

[4-(5-chloro-1H-benzoimidazol-2-ylmethoxy)-2-fluoro-5-methoxy-phenyl]-(5-methyl-1H-pyrrolo[2,3-b]pyridin-3-yl)-methanol (228a) and 5-chloro-2-{5-fluoro-2-methoxy-4-[methoxy-(5-methyl-1H-pyrrolo[2,3-b]pyridin-3-yl)-methyl]-phenoxymethyl}-1H-benzoimidazole (228b) were dissolved in acetonitrile. Triethylsilane was added followed by trifluoroacetic acid. The reaction was stirred for one hour at 60° C. The solvent was removed under reduced pressure, Ethyl acetate was added and the organic layer was washed with sodium bicarbonate saturated solution and brine, then dried over anhydrous sodium sulfate and concentrated. Purification with silica gel column chromatography, eluting with a gradient of methanol (2-25%) in dichloromethane, provided the desired compound P-2184. MS (ESI): $[M+H^+]^+=451.0$, $[M-H^+]^-=449.1$.

Example 61

Synthesis of Benzoimidazole Compounds of Formula XXX

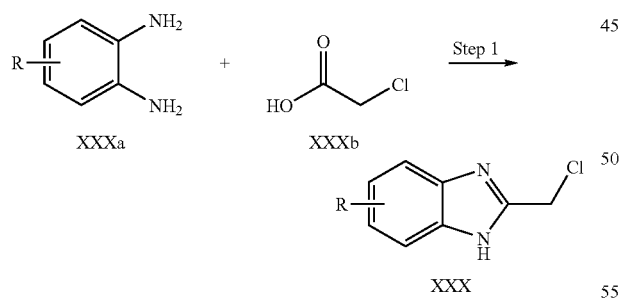

Step 1—Preparation of Compounds of Formula XXXb

A phenyldiamine compound of Formula XXXa (R is an optional substituent of benzoimidazole) and chloroacetic acid are typically refluxed in 4N hydrochloric acid for one to several hours and then cooled and neutralized. Isolation by conventional means (e.g. extraction, washing and filtering) affords a mixture containing compound of Formula XXXb, which may be isolated by silica gel chromatography if desired. Bloom and Day, *J. Org. Chem.* 1939, 14, 17.

Example 62

Synthesis of Compounds of Formula XXX

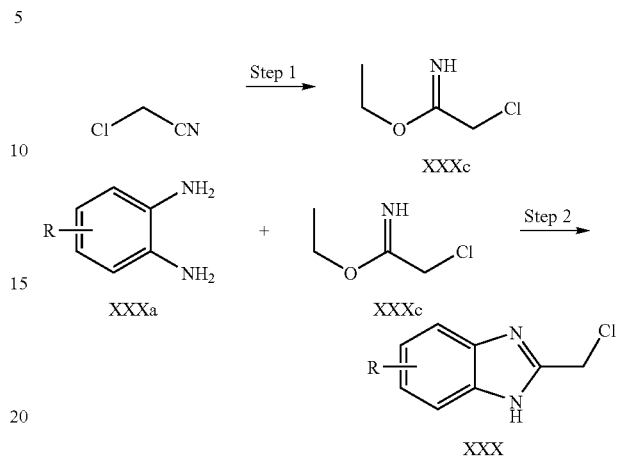

Step 1—Preparation of 2-Chloro-acetimidic Acid Ethyl Ester

2-Chloro-acetimidic acid ethyl ester may be prepared by dissolving chloroacetonitrile in an appropriated solvent (e.g. ether, THI) with ethanol and bubbling hydrogen chloride gas with cooling. The hydrogen chloride solution is stirred in a closed system for one to several hours and warmed to room temperature. Isolation by conventional means (e.g. extraction, distillation, washing and filtering) affords a mixture containing compound of Formula XXXc, which may be isolated by silica gel chromatography if desired.

Step 2—Preparation of Compounds of Formula XXX

A phenyldiamine compound of Formula XXXa (see Example 52) and 2-chloro-acetimidic acid ethyl ester XXXc are typically stirred together in an appropriate solvent (e.g. ethanol) for one to several hours at room temperature. Isolation by conventional means (e.g. extraction, washing and filtering) affords a mixture containing compound of Formula X, which may be isolated by silica gel chromatography if desired. Komoyira, et. al., *Bioorg. Med. Chem.* 2004, 12, 2099.

Example 63

Cell-Based Assays of c-fms Kinase Activity or c-kit Kinase Activity

M-CSF dependent RAW264.7 cells were seeded on a 12 well plate, $2.5\times10^5$ cells/well and the cells were allowed to attach overnight at 37° C., 5% $CO_2$. The cells were then starved in serum-free medium overnight at 37° C., 5% $CO_2$. The cells were treated with compound for 1 hour in serum-free media (1% DMSO final concentration); and then stimulated with 20 ng/ml M-CSF for 5 minutes. After stimulation, the cells were lysed on ice, and the lysates were centrifuged at 13,000 rpm for 1 minute. The amount of protein in the sample was quantitated, sample buffer was added, and the samples were boiled at 95° C. for 10 minutes. The samples were then centrifuged at 13,000 rpm for 1 minute. The samples (15-20 μg/lane) were loaded and run on 4-12% tris-glycine gel at 75V, and then transferred onto a PVDF membrane. The membrane was blocked for 1 hour with 5% BSA in PBS/1% Tween-20 (PBST); or 5% milk, depending on the primary antibody used. Then the blots were incubated with primary antibody overnight at 4 degrees with gentle shaking. After incubation with the capture antibody, the membranes were washed 3×10 minutes with PBST; then incubated with detection antibody Goat Anti-Rabbit-HRP for 1 hour, with gentle shaking. The membranes were washed again 3×10 minutes with PBST. ECL Plus substrate was then added to the blots, the image captured with chemiluminescence camera, and the bands quantitated for pFMS and FMS levels.

The Fms inhibitors may also be assessed using M-NFS-60 mouse myelogenous leukemia cell line (ATCC catalog #CRL-1838). This cell line proliferation is stimulated by M-CSF, which binds and activates the fms tyrosine kinase receptor. Inhibitors of fms kinase activity reduce or eliminate the M-CSF stimulated kinase activity, resulting in reduced cell proliferation. This inhibition is measured as a function of compound concentration to assess $IC_{50}$ values. M-NFS-60 cells were seeded at $5 \times 10^4$ cells per well of a 96 well cell culture plate in 50 µl of cell culture medium of RPMI 1640 (CellGro Mediatech catalog #10-040-CV) supplemented with 10% FBS (HyClone catalog #SH30071.03). Compounds were dissolved in DMSO at a concentration of 1 mM and were serially diluted 1:3 for a total of eight points and added to the cells to final concentrations of 10, 3.3, 1.1, 0.37, 0.12, 0.041, 0.014 and 0.0046 µM in 100 µl cell culture medium (final concentration 0.2% DMSO). Cells were also treated with staurosporine as a positive control. The cells were stimulated by adding 20 µl of 372 ng/ml M-CSF to a final concentration of 62 ng/ml (R&D Systems catalog #216-MC). The cells were incubated at 37° C., 5% $CO_2$ for three days. CellTiter-Glo Buffer (Promega Cell Viability Assay catalog #G7573) and substrate were equilibrated to room temperature, and enzyme/substrate Recombinant Firefly Luciferase/Beetle Luciferin was reconstituted. The cell plates were equilibrated to room temperature for 30 minutes, then lysed by addition of an equivalent volume of the Celltiter-Glo Reagent. The plate was mixed for 2 minutes on a plate shaker to lyse the cells, then incubated for 10 minutes at room temperature. The plates were read on a Victor Wallac II using Luminescence protocol modified to read 0.1 s per well. The luminescence reading assesses the ATP content, which correlates directly with cell number such that the reading as a function of compound concentration was used to determine the $IC_{50}$ value.

The c-Kit inhibitors were assessed using M-07e cell line (DSMZ catalog #ACC 104). The M-07e proliferation is stimulated by SCF (Stem Cell Factor), which binds and activates c-Kit tyrosine kinase receptor. Inhibitors of c-Kit kinase reduce or eliminate the SCF mediated kinase activation, resulting in reduced cell proliferation of SCF stimulated cells. This inhibition is measured by the effect of compound concentration on cell growth to assess $IC_{50}$ values. M-07e cells were seeded at $5 \times 10^4$ cells per well of a 96 well cell culture plate in 50 µl of cell culture medium of Iscove's Medium 1× (MOD, CellGro Mediatech catalog #15-016-CV) supplemented with 10% FBS (HyClone catalog #SH30071.03). Compounds were dissolved in DMSO at a concentration of 0.1 mM and were serially diluted 1:3 for a total of eight points and added to the cells to final concentrations of 1, 0.33, 0.11, 0.037, 0.012, 0.0041, 0.0014 and 0.00046 µM in 100 µl cell culture medium (final concentration 0.2% DMSO). Cells were also treated with staurosporine as a positive control. Cells were stimulated by adding 20 µl of 600 ng/ml SCF to a final concentration of 100 ng/ml (Biosource International SCF kit ligand catalog #PHC2115) in cell culture medium. The cells were incubated at 37° C., 5% $CO_2$ for three days. CellTiter-Glo Buffer (Promega Cell Viability Assay catalog #G7573) and substrate were equilibrated to room temperature, and enzyme/substrate Recombinant Firefly Luciferase/Beetle Luciferin was reconstituted. The cell plates were equilibrated to room temperature for 30 minutes, then lysed by addition of an equivalent volume of the Celltiter-Glo Reagent. The plate was mixed for 2 minutes on a plate shaker to lyse the cells, then incubated for 10 minutes at room temperature. The plates were read on a Victor Wallac II using Luminescence protocol modified to read 0.1 s per well. The luminescence reading assesses the ATP content, which correlates directly with cell number such that the reading as a function of compound concentration is used to determine the $IC_{50}$ value.

This cell based assay was also used to assess phosphorylation. Samples were prepared with compounds as described for the growth inhibition assay only M-07e cells were seeded at $2 \times 10^5$ cells per well in a 96 well filter plate. Cells were incubated for 1 hour at 37° C. with the compounds as described above, and then stimulated by adding SCF to a final concentration of 50 ng/ml and incubated for 10 minutes at 37° C. The culture medium was removed by centrifugation and the cells were lysed by addition of 30 µl lysis buffer (25 mM Tris HCl pH 7.5, 150 mM NaCl, 5 mM EDTA, 1% Triton X100, 5 mM NaF, 1 mM Na Vanadate, 10 mM Beta-glycerophosphate, no EDTA (Boehringer-Roche catalog #1873580) and placed on ice for 30 minutes. A 15 µl aliquot of the lysate was taken and assayed according to Biosource Immunoassay Kit: Human c-Kit [pY823] (Catalog #KHO0401) by diluting the aliquot with 85 µl dilution buffer in the assay plate, incubating for 2 hours at room temperature and washing the plate 4 times with wash buffer. Detection antibody (100 µl) was added to the plate and samples incubated for 1 hour at room temperature, then washed 4 times with wash buffer. HP anti-rabbit antibody (100 µl) was added and samples incubated for 30 minutes at room temperature, then washed 4 times with wash buffer. Stabilized chromogen (100 µl) was added and samples incubated for 15-25 minutes at room temperature, then washed 4 times with wash buffer. Stop solution (100 µl) was added and the samples read on a Wallac Victor reader at 450 nm. The absorbance was plotted against the compound concentration and the $IC_{50}$ concentration was determined.

Additional cell based assays can be correlated to the Fms activity of compounds of the invention. For example, the ability of osteoclast precursor cells (commercially available from Lonza) to differentiate into mature osteoclasts, due to stimulation by M-CSF and RANKL, in the presence of compounds, can be measured using a method analogous to that previously reported (Hudson et al., Journal of Urology, 1947, 58:89-92), where the amount of acid phosphatase in the supernatant (i.e. TRAP5b excreted by mature osteoclasts) is proportional to the number of mature osteoclasts present. In another example, the ability of M-CSF-dependent murine macrophage cells (BAC1.2F5) to proliferate in the presence of compounds can be measured by culturing cells as previously described (Morgan et al., Journal of Cellular Physiology, 1987, 130:420-427) and determining cell viability by analysis of ATP levels in the cell culture (Crouch et al., Journal of Immunological Methods, 1993, 160:81-8).

Example 64

Kinase Activity Assays

The effect of potential modulators of kinase activity of c-kit and other kinases can be measured in a variety of different assays known in the art, e.g., biochemical assays, cell-based assays, and in vivo testing (e.g. model system testing). Such in vitro and/or in viva assays and tests can be used in the present invention. As an exemplary kinase assay, the kinase activity of c-kit or Fms is measured in AlphaScreening (Packard BioScience). Assays for the activity of various kinases are described, for example, in U.S. patent application Ser. No. 11/473,347 (see also, PCT publication WO2007002433), the disclosure of which is hereby incorporated by reference.

Exemplary c-kit Biochemical Assay

The c-kit (or kinase domain thereof) is an active kinase in AlphaScreen. $IC_{50}$ values are determined with respect to inhibition of c-Kit kinase activity, where inhibition of phosphorylation of a peptide substrate is measured as a function of compound concentration. Compounds to be tested were dissolved in DMSO to a concentration of 20 mM. These were diluted 30 µl into 120 µl of DMSO (4 mM) and 1 µl was added to an assay plate. These were then serially diluted 1:3 (50 µl to 100 µl DMSO) for a total of 8 points. Plates were prepared such that each kinase reaction is 20 µl in 1× kinase buffer (50 mM HEPES, pH 7.2, 5 mM $MgCl_2$, 5 mM $MnCl_2$, 0.01% NP-40, 0.2% BSA), 5% DMSO and 10 µM ATP. Substrate was 100 nM biotin-$(E4Y)_3$ (Open Source Biotech, Inc.). C-kit kinase was at 0.1 ng per sample. After incubation of the kinase reaction for 1 hour at room temperature, 5 µl of donor beads (Streptavidin coated beads (Perkin Elmer Life Science) final concentration 1 µg/ml) in stop buffer (500 mM EDTA in 1× kinase buffer) was added, the sample was mixed and incubated for 20 minutes at room temperature before adding 5 µl of acceptor beads (PY20 coated beads (Perkin Elmer Life Science) final concentration 1 µg/ml) in stop buffer. The samples were incubated for 60 minutes at room temperature and the signal per well was read on AlphaQuest reader. Phosphorylated substrate results in binding of the PY20 antibody and association of the donor and acceptor beads such that signal correlates with kinase activity. The signal vs. compound concentration was used to determine the $IC_{50}$.

Compounds were also tested using a similar assay with a 10-fold higher ATP concentration. For these samples, compounds to be tested were dissolved in DMSO to a concentration of 20 mM. These were diluted 30 µl into 120 µl of DMSO (4 mM) and 1 µl was added to an assay plate. These were then serially diluted 1:3 (50 µl to 100 µl DMSO) for a total of 8 points. Plates were prepared such that each kinase reaction is 20 µl in 1× kinase buffer (25 mM HEPES, pH 7.5, 2 mM $MgCl_2$, 2 mM $MnCl_2$, 0.01% Tween-20, 1 mM DTT, and 0.001% BSA), 5% DMSO and 100 µM ATP. Substrate was 30 nM biotin-(E4Y)10 (Upstate Biotech, Cat# 12-440). C-kit kinase was at 1 ng per sample. After incubation of the kinase reaction for 1 hour at room temperature, 5 µl of donor beads (Streptavidin coated beads (Perkin Elmer Life Science) final concentration 10 µg/ml) in stop buffer (25 mM HEPES pH 7.5, 100 mM EDTA, 0.3% BSA) was added, the sample was mixed and incubated for 20 minutes at room temperature before adding 5 µl of acceptor beads (PY20 coated beads (Perkin Elmer Life Science) final concentration 10 µg/ml) in stop buffer. The samples were incubated for 60 minutes at room temperature and the signal per well was read on AlphaQuest or Envision reader (Perkin Elmer Life Science). Phosphorylated substrate results in binding of the PY20 antibody and association of the donor and acceptor beads such that signal correlates with kinase activity. The signal vs. compound concentration was used to determine the $IC_{50}$.

The c-kit enzyme used in the above assay was either obtained from Cell Signaling Technology (Cat. #7754) or was prepared as follows: A plasmid encoding kit (DNA and encoded protein sequences shown below) was engineered using common polymerase chain reaction (PCR) methods. Complementary DNA cloned from various human tissues were purchased from Invitrogen, and these were used as substrates in the PCR reactions. Specific custom synthetic oligonucleotide primers were designed to initiate the PCR product, and also to provide the appropriate restriction enzyme cleavage sites for ligation with the plasmids. The entire sequence encoding the enzyme was made through a gene synthesis procedure, using custom synthetic oligonucleotides covering the entire coding sequence (Invitrogen, see below).

The plasmid used for ligation with the kinase-encoding inserts was derivative of pET (Novagen) for expression using *E. coli*. The Kit kinase was engineered to include a Histidine tag for purification using metal affinity chromatography. The kinase-encoding plasmid was engineered as bicistronic mRNA to co-express a second protein that modifies the kinase protein during its expression in the host cell. Protein tyrosine phosphatase 1B (PTP), was co-expressed for dephosphorylation of the phospho-Tyrosines.

For protein expression, the plasmid containing the Kit gene was transformed into *E. coli* strains BL21(DE3)RIL and transform ants selected for growth on LB agar plates containing appropriate antibiotics. Single colonies were grown overnight at 37° C. in 200 ml TB (Terrific broth) media. 16×1 L of fresh TB media in 2.8 L flasks were inoculated with 10 ml of overnight culture and grown with constant shaking at 37° C. Once cultures reached an absorbance of 1.0 at 600 nm, IPTG was added and cultures were allowed to grow for a further 12 to 18 hrs at temperatures ranging from 12-30° C. Cells were harvested by centrifugation and pellets frozen at –80° C. until ready for lysis.

For protein Purification; frozen *E. coli* cell pellets were resuspended in lysis buffer and lysed using standard mechanical methods. Protein was purified via poly-Histidine tags using immobilized metal affinity purification IMAC. The Kit kinase was purified using a 3 step purification process utilizing; IMAC, size exclusion chromatography and ion exchange chromatography. The poly-Histidine tag was removed using Thrombin (Calbiochem).

Compounds were assayed using a similar assay to that described above, using in a final reaction volume of 25 µl: c-Kit (h) (5-10 mU) in 8 mM MOPS pH 7.0, 0.2 mM EDTA, 10 mM $MnCl_2$, 0.1 mg/ml poly (Glu, Tyr) 4:1, 10 mM MgAcetate and $\gamma$-$^{33}$P-ATP (approximately 500 cpm/pmol), with appropriate concentrations of compound. Incubated for 40 minutes at room temperature and stopped by addition of 5 µl of 3% phosphoric acid. Spotted 10 µl of each sample onto Filtermat A and washed 3× with 75 mM phosphoric acid, once with methanol, dried and measured on scintillation counter (performed at Upstate USA, Charlottesville, Va.).

| | PCR primers | | |
|---|---|---|---|
| KIT 8K1A | ATGTACGAAGTTCAGTGGAAAGTTGTTGAAGAAATCAACGG (SEQ ID NO:__) | 1776 |
| 8K1B | GGTCGATGTAAACGTAGTTGTTACCGTTGATTTCTTCAACAACTTT (SEQ ID NO:__) | 1777 |
| 8K2A | AACAACTACGTTTACATCGACCCGACCCAGCTGCCGTACGAC (SEQ ID NO:__) | 1779 |

-continued

| PCR primers | | |
|---|---|---|
| 8K2B | GTTACGCGGGAACTCCCATTTGTGGTCGTACGGCAGCTGGGTC (SEQ ID NO:__) | 1781 |
| 8K3A | AAATGGGAGTTCCCGCGTAACCGTCTGTCTTTCGGTAAAACCC (SEQ ID NO:__) | 1782 |
| 8K3B | ACCGAACGCACCCGCACCCAGGGTTTTACCGAAAGACAGAC (SEQ ID NO:__) | 1783 |
| 8K4A | GGTGCGGGTGCGTTCGGTAAAGTTGTTGAAGCGACCGCGTACG (SEQ ID NO:__) | 1784 |
| 8K4B | GCCGCGTCAGATTTGATCAGACCGTACGCGGTCGCTTCAAC (SEQ ID NO:__) | 1785 |
| 8K5A | CTGATCAAATCTGACGCGGCGATGACCGTTGCGGTTAAAATGC (SEQ ID NO:__) | 1786 |
| 8K5B | GTCAGGTGCGCAGACGGTTTCAGCATTTTAACCGCAACGGTCA (SEQ ID NO:__) | 1787 |
| 8K6A | AAACCGTCTGCGCACCTGACCGAACGTGAAGCGCTGATGTCTG (SEQ ID NO:__) | 1788 |
| 8K6B | CCAGGTAAGACAGAACTTTCAGTTCAGACATCAGCGCTTCACGT (SEQ ID NO:__) | 1789 |
| 8K7A | CTGAAAGTTCTGTCTTACCTGGGTAACCACATGAACATCGTTAA (SEQ ID NO:__) | 1791 |
| 8K7B | GGTGCACGCACCCAGCAGGTTAACGATGTTCATGTCGTTAC (SEQ ID NO:__) | 1792 |
| 8K8A | CTGCTGGGTGCGTGCACCATCGGTGGTCCGACCCTGGTTATCA (SEQ ID NO:__) | 1793 |
| 8K8B | GTCACCGTAGCAGCAGTATTCGGTGATAACCAGGGTCGGACCA (SEQ ID NO:__) | 1794 |
| 8K9A | GAATACTGCTGCTACGGTGACCTGCTGAACTTCCTGCGTCGTA (SEQ ID NO:__) | 1795 |
| 8K9B | AGAGCAGATGAAAGAGTCACGTTTACGACGCAGGAAGTTCAGC (SEQ ID NO:__) | 1796 |
| 8K10A | CGTGACTCTTTCATCTGCTCTAAACAGGAAGACCACGCGGAAG (SEQ ID NO:__) | 1797 |
| 8K10B | CAGCAGGTTTTTGTACAGCGCCGCTTCCGCGTGGTCTTCCTGT (SEQ ID NO:__) | 1798 |
| 8K11A | GCGCTGTACAAAAACCTGCTGCACTCTAAAGAATCTTCTTGCTC (SEQ ID NO:__) | 1799 |
| 8K11B | CCATGTATTCGTTGGTAGAGTCAGAGCAAGAAGATTCTTTAGAGT (SEQ ID NO:__) | 1811 |
| 8K11A | GACTCTACCAACGAATACATGGACATGAAACCGGGTGTTTCTTA (SEQ ID NO:__) | 1812 |
| 8K11B | TCCGCTTTGGTCGGAACAAGCTAAGAAACACCCGGTTTCATGT (SEQ ID NO:__) | 1813 |
| 8K12A | GTTGTTCCGACCAAAGCGGACAAACGTCCTTCTGTTCGTATCG (SEQ ID NO:__) | 1814 |
| 8K12B | TAACGTCACGTTCGATGTAAGAACCGATACGAACAGAACGACGTTT (SEQ ID NO:__) | 1815 |
| 8K13A | TCTTACATCGAACCTGACGTTACCCCGGCGATCATGGAAGACC (SEQ ID NO:__) | 1816 |
| 8K13B | CCAGGTCCAGCGCCAGTTCGTCGTCTTCCATGATCGCCGC (SEQ ID NO:__) | 1817 |

-continued

| | PCR primers | |
|---|---|---|
| 8K14A | GAACTGGCGCTGGACCTGGAAGACCTGCTGTCTTTCTCTTACC (SEQ ID NO:__) | 1818 |
| 8K14B | GAACGCCATACCTTTCGCAACCTGGTAAGAGAAAGACAGCAGGT (SEQ ID NO:__) | 1819 |
| 8K15A | GTTGCGAAAGGTATGGCGTTCCTGGCGTCTAAAAACTGCATCCA (SEQ ID NO:__) | 1821 |
| 8K15B | CGCGCCGCCAGGTCACGGTGGATGCAGTTTTTAGACGCC (SEQ ID NO:__) | 1822 |
| 8K16A | CGTGACCTGGCGGCGCGTAACATCCTGCTGACCCACGGTCG (SEQ ID NO:__) | 1823 |
| 8K16B | ACCGAAGTCGCAGATTTTGGTGATACGACCGTGGGTCAGCAGG (SEQ ID NO:__) | 1824 |
| 8K17A | ACCAAAATCTGCGACTTCGGTCTGGCGCGTGACATCAAAAACG (SEQ ID NO:__) | 1825 |
| 8K17B | GTTACCTTTAACAACGTAGTTAGAGTCGTTTTTGATGTCACGCGCC (SEQ ID NO:__) | 1826 |
| 8K18A | TCTAACTACGTTGTTAAAGGTAACGCGCGTCTGCCGGTTAAATG (SEQ ID NO:__) | 1827 |
| 8K18B | GAAGATAGATTCCGGCGCCATCCATTTAACCGGCAGACGCGC (SEQ ID NO:__) | 1829 |
| 8K19A | ATGGCGCCGGAATCTATCTTCAACTGCGTTTACACCTTCGAATC (SEQ ID NO:__) | 1831 |
| 8K19B | GATACCGTAAGACCAAACGTCAGATTCGAAGGTGTAAACGCAG (SEQ ID NO:__) | 1832 |
| 8K20A | GACGTTTGGTCTTACGGTATCTTCCTGTGGGAACTGTTCTCTC (SEQ ID NO:__) | 1833 |
| 8K20B | CCTGTGGGAACTGTTCTCTCTGGGTTCTTCTCCGTACCCGG (SEQ ID NO:__) | 1834 |
| 8K21A | GGTTCTTCTCCGTACCCGGGTATGCCGGTTGACTCTAAATTCTAT (SEQ ID NO:__) | 1835 |
| 8K21B | CGGAAACCTTCTTTGATCATTTTGTAGAATTTAGAGTCAACCGGC (SEQ ID NO:__) | 1836 |
| 8K22A | AAAATGATCAAAGAAGGTTTCCGTATGCTGTCTCCGGAACACG (SEQ ID NO:__) | 1837 |
| 8K22B | ATGTCGTACATTTCCGCCGGCGCGTGTTCCGGAGACAGCATA (SEQ ID NO:__) | 1838 |
| 8K23A | CCGGCGGAAATGTACGACATCATGAAAACCTGCTGGGACGCG (SEQ ID NO:__) | 1839 |
| 8K23B | AAGGTCGGACGTTTCAGCGGGTCCGCGTCCCAGCAGGTTTTC (SEQ ID NO:__) | 1841 |
| 8K24A | CCGCTGAAACGTCCGACCTTCAAACAGATCGTTCAGCTGATCG (SEQ ID NO:__) | 1842 |
| 8K24B | TTGGTAGATTCAGAGATCTGTTTTTCGATCAGCTGAACGATCTGTT (SEQ ID NO:__) | 1843 |
| 8K25A | AAACAGATCTCTGAATCTACCAACCACATCTACTCTAACCTGGC (SEQ ID NO:__) | 1844 |
| 8K25B | TGACGGTTCGGAGAGCAGTTCGCCAGGTTAGAGTAGATGTGG (SEQ ID NO:__) | 1845 |
| 8K26A | AACTGCTCTCCGAACCGTCAGAAACCGGTTGTTGACCACTCTG (SEQ ID NO:__) | 1846 |

PCR primers

| | | |
|---|---|---|
| 8K26B | GTAGAACCAACAGAGTTGATACGAACAGTGGTCAACAACCGGT (SEQ ID NO:__) | 1847 |
| 8K27A | CGTATCAACTCTGTTGGTTCTACCGCGTCTTCTTCTCAGCCG (SEQ ID NO:__) | 1848 |
| 8K27B | AACGTCGTCGTGAACCAGCAGCGGCTGAGAAGAAGACGCG (SEQ ID NO:__) | 1849 |
| 8K-F | GTTGTTTCATATGTACGAAGTTCAGTGGAAAG (SEQ ID NO:__) | 1851 |
| 8K-R | GTTGTTTGTCGACTAAACGTCGTCGTGAACCAGCAG (SEQ ID NO:__) | 1852 |
| KIT COD-K948X | GTTCTTGTCGACTAtttctgacggttcggagagc | 3411 |

```
P1332.N6 BI PTP KIT M552-K948-X COD
(Nucleic Acid SEQ ID NO:__) (Protein SEQ ID NO:__)
taatacgactcactatagggggaattgtgagcggataacaattcccctcta gaaataattttgtttaactttaagaaggagatataccatgggtcaccac
                                         M  G  H  H atcaccatcatatgtacgaagttcagtggaaagttgttgaagaaatcaac
 H  H  H  H  M  Y  E  V  Q  W  K  V  V  E  E  I  N ggtaacaactacgtttacatcgacccgacccagctgccgtacgaccacaa
 G  N  N  Y  V  Y  I  D  P  T  Q  L  P  Y  D  H  K atgggagttcccgcgtaaccgtctgtctttcggtaaaaccctgggtgcgg
 W  E  F  P  R  N  R  L  S  F  G  K  T  L  G  A  G gtgcgttcggtaaagttgttgaagcgaccgcgtacggtctgatcaaatct
  A  F  G  K  V  V  E  A  T  A  Y  G  L  I  K  S gacgcggcgatgaccgttgcggttaaaatgctgaaaccgtctgcgcacct
 D  A  A  M  T  V  A  V  K  M  L  K  P  S  A  H  L gaccgaacgtgaagcgctgatgtctgaactgaaagttctgtcttacctgg
  T  H  R  E  A  L  M  S  E  L  K  V  L  S  Y  L  G gtaaccacatgaacatcgttaacctgctgggtgcgtgcaccatcggtggt
  N  H  M  N  I  V  N  L  L  G  A  C  T  I  G  G ccgaccctggttatcaccgaatactgctgctacggtgacctgctgaactt
 P  T  L  V  I  T  E  Y  C  C  Y  G  D  L  L  N  F cctgcgtcgtaaacgtgactcttttcatctgctctaaacaggaagaccacg
 L  R  R  K  R  D  S  F  I  C  S  K  Q  E  D  H  A cggaagcggcgctgtacaaaaacctgctgcactctaaagaatcttcttgc
  E  A  A  L  Y  K  N  L  L  H  S  K  E  S  S  C tctgactctaccaacgaatacatggacatgaaaccgggtgtttcttacgt
 S  D  S  T  N  E  Y  M  D  M  K  P  G  V  S  Y  V tgttccgaccaaagcggacaaacgtcgttctgttcgtatcggttcttaca
  V  P  T  K  A  D  K  R  R  S  V  R  I  G  S  Y  I tcgaacgtgacgttaccccggcgatcatggaagacgacgaactggcgctg
 E  R  D  V  T  P  A  I  M  E  D  D  E  L  A  L gacctggaagacctgctgtctttctcttaccaggttgcgaaaggtatggc
 D  L  E  D  L  L  S  F  S  Y  Q  V  A  K  G  M  A gttcctggcgtctaaaaactgcatccaccgtgacctggcggcgcgtaaca
 F  L  A  S  K  N  C  I  H  R  D  L  A  A  R  N  I tcctgctgacccacggtcgtatcaccaaaatctgcgacttcggtctggcg
 L  L  T  H  G  R  I  T  K  I  C  D  F  G  L  A cgtgacatcaaaaacgactctaactacgttgttaaaggtaacgcgcgtct
 R  D  I  K  N  D  S  N  Y  V  V  K  G  N  A  R  L gccggttaaatggatggcgccggaatctatcttcaactgcgtttacacct
 P  V  K  W  M  A  P  E  S  I  F  N  C  V  Y  T  F tcgaatctgacgtttggtcttacggtatcttcctgtgggaactgttctct
  E  S  D  V  W  S  Y  G  I  F  L  W  E  L  F  S ctgggttcttctccgtacccgggtatgccggttgactctaaattctacaa
 L  G  S  S  P  Y  P  G  M  P  V  D  S  K  F  Y  K aatgatcaaagaaggtttccgtatgctgtctccggaacacgcgccggcgg
  M  I  K  E  G  F  R  M  L  S  P  E  H  A  P  A  E aaatgtacgacatcatgaaaacctgctgggacgcggacccgctgaaacgt
  M  Y  D  I  M  K  T  C  W  D  A  D  P  L  K  R ccgaccttcaaacagatcgttcagctgatcgaaaaacagatctctgaatc
 P  T  F  K  Q  I  V  Q  L  I  E  K  Q  I  S  E  S taccaaccacatctactctaacctggcgaactctctccgaaccgtcagaa
  T  N  H  I  Y  S  N  L  A  N  C  S  P  N  R  Q  K atagtcgactgaaaaagga
-
agagt
```

Additional Biochemical and Cell-Based Assays

In general, any protein kinase assay can be adapted for use with c-kit. For example, assays (e.g. biochemical and cell-based assays) as described in Lipson et al., U.S. Patent Publ. 20040002534 (incorporated herein by reference in its entirety) can be used in the present invention.

In Vivo Model System Testing

For in vivo testing, a suitable animal model system can be selected for use. For example, for multiple sclerosis, the rodent experimental allergic encephalomyelitis (EAE) is commonly used. This system is well-known, and is described, for example, in Steinman, 1996, Cell 85:299-302 and Secor et al., 2000, J. Exp. Med 5:813-821, which are incorporated herein by reference in their entireties. Similarly, other model systems can be selected and used in assessing compounds of the present invention.

Exemplary Fms Biochemical Assay $IC_{50}$ values were determined with respect to inhibition of Fms kinase activity, where inhibition of phosphorylation of a peptide substrate is measured as a function of compound concentration. Compounds to be tested, dissolved in DMSO (1 µL), were added to a white 384-well plate (Costar #3705). Working stocks of Fms kinase (Upstate Biotech, #14-551), biotin-(E4Y)$_{10}$ substrate (Upstate Biotech, Cat# 12-440), and ATP (Sigma, Cat#A-3377) were prepared in 8 mM MOPS pH 7.4, 2 M MgCl$_2$, 8 mM MnCl$_2$, 2 mM DTT, and 0.01% Tween-20. All components were added to the 384-well plate for a final concentration of 0.5 ng/well Fms, 30 nM biotin-(E4Y)$_{10}$ (Upstate Biotechnology) and 10 µM ATP in a volume of 20 µL. Each sample was at 5% DMSO. The plate was then incubated for 60 minutes at room temperature. Just before use, working stocks of donor and acceptor beads from the AlphaScreen PY20 Detection Kit (PerkinElmer, Cat#4676601M) were prepared in 8 mM MOPS, pH 7.4, 100 mM EDTA, 0.3% BSA. To stop the reaction, the plate was uncovered in the dark and 5 µl of Donor Beads solution (Streptavidin beads) was added to each well. The plate was incubated at room temperature for 20 minutes. Five microliters of Acceptor Beads solution (PY20 coated beads) were then added to each well. The final concentration of each bead was 20 µg/mL. The plates were incubated at room temperature for 60 minutes. Fluorescence signal was recorded on the Fusion Alpha reader or AlphaQuest reader. Phosphorylated substrate results in binding of the PY20 antibody and association of the donor and acceptor beads such that signal correlates with kinase activity. The signal vs. compound concentration was used to determine the IC$_{50}$.

Compounds were also tested using a similar assay with a 10-fold higher ATP concentration. Compounds to be tested, dissolved in DMSO (1 µL), were added to a white 384-well plate (Costar #3705). Working stocks of Fms kinase (Upstate Biotech, #14-551), biotin-(E4Y)$_{10}$ substrate (Upstate Biotech, Cat#12-440), and ATP (Sigma, Cat#A-3377) were prepared in 25 mM HEPES pH 7.5, 0.5 mM MgCl$_2$, 2 mM MnCl$_2$, 2 mM DTT, 0.01% BSA, and 0.01% Tween-20. All components were added to the 384-well plate for a final concentration of 0.5 ng/well Fms, 30 nM biotin-(E4Y)$_{10}$ (Upstate Biotechnology) and 100 µM ATP in a volume of 20 µL. Each sample was at 5% DMSO. The plate was then incubated for 30 minutes at room temperature. Just before use, working stocks of donor and acceptor beads from the AlphaScreen PY20 Detection Kit (PerkinElmer, Cat#676601M) were prepared in 25 mM HEPES pH 7.5, 100 mM EDTA, 0.01% BSA. To stop the reaction, the plate was uncovered in the dark and 5 µl of Donor Beads solution (Streptavidin beads) was added to each well. The plate was incubated at room temperature for 20 minutes. Five microliters of Acceptor Beads solution (PY20 coated beads) were then added to each well. The final concentration of each bead was 10 µg/mL. The plates were incubated at room temperature for 60 minutes. Fluorescence signal was recorded on the AlphaQuest or Envision reader. Phosphorylated substrate results in binding of the PY20 antibody and association of the donor and acceptor beads such that signal correlates with kinase activity. The signal vs. compound concentration was used to determine the IC$_{50}$.

Compounds were assayed using a similar assay to that described above, using in a final reaction volume of 25 µl: Fms (h) (5-10 mU) in 8 mM MOPS pH 7.0, 0.2 mM EDTA, 250 mM KKKSPGEYVNIEFG (SEQ ID NO:62), 10 mM Mg Acetate and γ-$^{33}$P-ATP (approximately 500 cpm/pmol), with appropriate concentrations of compound. Samples were incubated for 40 minutes at room temperature and stopped by addition of 5 µl of 3% phosphoric acid. 10 µl of each sample is spotted onto a P30 filtermat and washed 3× with 75 mM phosphoric acid, once with methanol, dried and measured on scintillation counter (Upstate USA, Charlottesville, Va.).

Exemplary TrkA Biochemical Assay

Compounds were similarly assayed to determine IC$_{50}$ values with respect to inhibition of TrkA kinase activity, where inhibition of phosphorylation of a peptide substrate was measured as a function of compound concentration. Compounds tested were dissolved in DMSO (1 µL) and added to a white 384-well plate (Costar #3705). Working stocks of TrkA kinase (Upstate Biotech, #14-571), biotin-(E4Y)$_{10}$ substrate (Upstate Biotech, Cat# 12-440), and ATP (Sigma, Cat#A-3377) were prepared in 25 mM Hepes pH 7.5, 10 mM MnCl$_2$ 1 mM DTT, and 0.01% Tween-20. All components were added to the 384-well plate for a final concentration of 1 ng/well TrkA, 30 nM biotin-(E4Y)$_{10}$ (Upstate Biotechnology) and 100 mM ATP in a volume of 20 µL. Each sample was at 5% DMSO. The plate was then incubated for 40 minutes at room temperature. Just before use, working stocks of donor and acceptor beads from the AlphaScreen PY20 Detection Kit (PerkinElmer, Cat#676601M) were prepared in 25 mM Hepes pH 7.5, 100 mM EDTA, 0.3% BSA. To stop the reaction, the plate was uncovered in the dark and 5 µl of Donor Beads solution (Streptavidin beads) was added to each well. The plate was incubated at room temperature for 20 minutes. Five microliters of Acceptor Beads solution (PY20 coated beads) were then added to each well. The final concentration of each bead was 10 µg/mL. The plates were incubated at room temperature for 60 minutes. Fluorescence signal was recorded on the AlphaQuest or Envision reader. Phosphorylated substrate results in binding of the PY20 antibody and association of the donor and acceptor beads such that signal correlates with kinase activity. The signal vs. compound concentration was used to determine the IC$_{50}$.

Exemplary HGK Biochemical Assay

The MAP4K4 (or kinase domain thereof is an active kinase in AlphaScreen. IC$_{50}$ values are determined with respect to inhibition of MAP4K4 kinase activity, where inhibition of phosphorylation of a peptide substrate is measured as a function of compound concentration. Compounds to be tested were dissolved in DMSO to a concentration of 20 mM. These were diluted 30 µl into 120 µl of DMSO (4 mM) and 1 µl was added to an assay plate. These were then serially diluted 1:3 (50 µl to 100 µl DMSO) for a total of 8 points. Plates were prepared such that each kinase reaction is 20 µl in 1× kinase buffer (20 mM Tris, pH 7.4, 10 mM MgCl$_2$, 1 mM DTT, 0.011% Tween-20), 5% DMSO and 10 µM ATP. Substrate was 10 nM biotin-ERM (T567/T564/T558, Cell Signaling, Inc., cat#1344). MAP4K4 kinase was at 0.5 ng per sample. After incubation of the kinase reaction for 40 min at room temperature, 5 µl of donor beads and protein A acceptor beads (Perkin Elmer Life Science, cat#67606017) at final concentration 1 µg/ml in stop buffer (20 mM Tris, pH 7.4, 200 mM Nacl, 100 mM EDTA, 0.03% BSA) was added, along with Phospho-ERM Antibody (T567/T564/T558, Cell Signaling, Inc., cat#3141) at 1:1000 dilution. The samples were incubated for 2 hours at room temperature and the signal per well was read on AlphaQuest reader. Phosphorylated substrate results in binding of the antibody which binds to protein A acceptor bead and association of the donor and acceptor beads is such that the signal correlates with kinase activity. The signal vs. compound concentration was used to determine the IC$_{50}$.

Representative compounds screened by at least one of the methods described above, or as described in U.S. patent application Ser. No. 11/473,347 (PCT publication WO2007002433), or by similar methods, having IC$_{50}$ of less than 10 µM under the test conditions employed are shown in tables 2a (B-Raf), 2b (B-Raf V600E), 2c (B-Raf V600E/T5291), 2d (Btk), 2e (c-Raf-1), 2f (Fak), 2g (FGFR1), 2h (Flt1), 2i (Fms), 2j (Jnk1), 2k (Kdh), 2l (Kit), 2m (Met), 2n (p38), 2o (Src), 2p (TrkA), and 2q (HGK).

TABLE 2a

Compounds with activity toward kinase B-Raf with $IC_{50} \leq 10\ \mu M$ under the test conditions employed.

| | |
|---|---|
| B-Raf | P-1247, P-1453, P-1454, P-1455, P-1467, P-1532, P-1544, P-1568, P-1569, P-1584, P-1597, P-1613, P-1616, P-1721, P-1768, P-1769, P-1802, P-1825, P-2100, P-2144, P-2145, P-2151, P-2164, P-2165, P-2170, P-2173, P-2185, P-2186 |

TABLE 2b

Compounds with activity toward kinase B-Raf V600E with $IC_{50} \leq 10\ \mu M$ under the test conditions employed.

| | |
|---|---|
| B-Raf V600E | P-1247, P-1449, P-1450, P-1453, P-1454, P-1455, P-1462, P-1466, P-1467, P-1470, P-1471, P-1531, P-1532, P-1544, P-1568, P-1569, P-1578, P-1579, P-1584, P-1597, P-1613, P-1698, P-1721, P-1768, P-1769, P-1797, P-1802, P-2100, P-2164, P-2165, P-2185, P-2186 |

TABLE 2c

Compounds with activity toward kinase B-Raf V600E/T529I with $IC_{50} \leq 10\ \mu M$ under the test conditions employed.

| | |
|---|---|
| B-Raf V600E/ T529I | P-2151, P-2152, P-2154, P-2156, P-2166 |

TABLE 2d

Compounds with activity toward kinase Btk with $IC_{50} \leq 10\ \mu M$ under the test conditions employed.

| | |
|---|---|
| Btk: | P-2140, P-2143, P-2144, P-2145, P-2161, P-2162, P-2163, P-2164 |

TABLE 2e

Compounds with activity toward kinase c-Raf-1 with $IC_{50} \leq 10\ \mu M$ under the test conditions employed.

| | |
|---|---|
| c-Raf-1: | P-1247, P-1453, P-1454, P-1455, P-2107, P-2143, P-2155, P-2185 |

TABLE 2f

Compounds with activity toward kinase Fak with $IC_{50} \leq 10\ \mu M$ under the test conditions employed.

| | |
|---|---|
| Fak: | P-1247, P-1449, P-1450, P-1453, P-1455, P-2181 |

TABLE 2g

Compounds with activity toward kinase FGFR with $IC_{50} \leq 10\ \mu M$ under the test conditions employed.

| | |
|---|---|
| FGFR: | P-1249, P-1453, P-1454, P-1455, P-1467, P-1584, P-1597, P-2155, P-2157, P-2159, P-2160 |

TABLE 2h

Compounds with activity toward kinase Flt1 with $IC_{50} \leq 10\ \mu M$ under the test conditions employed.

| | |
|---|---|
| Flt1: | P-1247, P-1462, P-1467, P-1531, P-1532, P-1544, P-1569, P-1584, P-1597, P-1613, P-2101, P-2107, P-2108, P-2109, P-2117, P-2145, P-2146, P-2149, P-2151, P-2154, P-2161, P-2164, P-2165, P-2170, P-2185 |

TABLE 2i

Compounds with activity toward kinase Fms with $IC_{50} \leq 10\ \mu M$ under the test conditions employed.

| | |
|---|---|
| Fms: | P-1247, P-1449, P-1450, P-1453, P-1454, P-1455, P-1462, P-1466, P-1467, P-1470, P-1471, P-1532, P-1544, P-1568, P-1569, P-1597, P-1613, P-1616, P-1721, P-1768, P-1769, P-1802, P-1803, P-1821, P-2099, P-2100, P-2101, P-2102, P-2103, P-2104, P-2105, P-2106, P-2107, P-2108, P-2109, P-2110, P-2111, P-2112, P-2113, P-2114, P-2115, P-2116, P-2117, P-2118, P-2119, P-2120, P-2122, P-2123, P-2124, P-2125, P-2126, P-2127, P-2128, P-2129, P-2130, P-2131, P-2132, P-2133, P-2134, P-2135, P-2137, P-2138, P-2139, P-2140, P-2141, P-2143, P-2144, P-2145, P-2146, P-2147, P-2148, P-2149, P-2150, P-2151, P-2152, P-2153, P-2154, P-2155, P-2156, P-2157, P-2158, P-2159, P-2160, P-2161, P-2162, P-2163, P-2164, P-2165, P-2166, P-2167, P-2170, P-2171, P-2172, P-2173, P-2174, P-2175, P-2176, P-2178, P-2179, P-2180, P-2181, P-2182, P-2184, P-2185, P-2186 |

TABLE 2j

Compounds with activity toward kinase Jnk1 with $IC_{50} \leq 10\ \mu M$ under the test conditions employed.

| | |
|---|---|
| Jnk1: | P-1896, P-1897 |

TABLE 2k

Compounds with activity toward kinase Kdr with $IC_{50} \leq 10\ \mu M$ under the test conditions employed.

| | |
|---|---|
| Kdr: | P-2100, P-2101, P-2105, P-2107, P-2108, P-2109, P-2114, P-2117, P-2145, P-2146, P-2147, P-2149, P-2150, P-2151, P-2152, P-2153, P-2154, P-2155, P-2156, P-2157, P-2158, P-2159, P-2160, P-2161, P-2162, P-2163, P-2164, P-2165, P-2166, P-2167, P-2176, P-2185 |

TABLE 2l

Compounds with activity toward kinase Kit with $IC_{50} \leq 10\ \mu M$ under the test conditions employed.

| | |
|---|---|
| Kit: | P-1247, P-1449, P-1450, P-1453, P-1454, P-1455, P-1462, P-1466, P-1467, P-1470, P-1471, P-1531, P-1532, P-1544, P-1568, P-1569, P-1578, P-2100, P-2101, P-2105, P-2106, P-2107, P-2108, P-2109, P-2110, P-2111, P-2112, P-2114, P-2117, P-2120, P-2130, P-2137, P-2139, P-2140, P-2145, P-2146, P-2148, P-2149, P-2151, P-2156, P-2157, P-2158, P-2159, P-2160, P-2161, P-2162, P-2163, P-2164, P-2165, P-2167, P-2172, P-2173, P-2174, P-2176, P-2178, P-2180, P-2184, P-2185 |

TABLE 2m

Compounds with activity toward kinase Met with $IC_{50} \leq 10$ μM under the test conditions employed.

| Met: | P-2157 |
|---|---|

TABLE 2n

Compounds with activity toward kinase p38 with $IC_{50} \leq 10$ μM under the test conditions employed.

| p38: | P-2167 |
|---|---|

TABLE 2o

Compounds with activity toward kinase Src with $IC_{50} \leq 10$ μM under the test conditions employed.

| Src: | P-1247, P-2108, P-2109, P-2117, P-2145, P-2151 |
|---|---|

TABLE 2p

Compounds with activity toward kinase TrkA with $IC_{50} \leq 10$ μM under the test conditions employed.

| TrkA: | P-1844, P-1885, P-1976, P-1978, P-2038, P-2099, P-2100, P-2101, P-2103, P-2104, P-2106, P-2107, P-2108, P-2109, P-2110, P-2111, P-2112, P-2114, P-2115, P-2116, P-2117, P-2145, P-2146, P-2170, P-2171, P-2172, P-2173, P-2174, P-2175, P-2176, P-2178, P-2179, P-2180, P-2181, P-2182, P-2185, P-2186 |
|---|---|

TABLE 2q

Compounds with activity toward kinase HGK with $IC_{50} \leq 10$ μM under the test conditions employed.

| HGK: | P-2099, P-2100, P-2101, P-2102, P-2103, P-2104, P-2105, P-2106, P-2107, P-2109, P-2110, P-2111, P-2112, P-2113, P-2114, P-2115, P-2116, P-2146, P-2149, P-2170, P-2171, P-2172, P-2173, P-2174, P-2175, P-2176, P-2178, P-2180, P-2181, P-2182, P-2184, P-2185, P-2186 |
|---|---|

Example 55

Efficacy of Compounds in Combination with Standard-of-Care Chemotherapeutic Agents in Four Human Cancer Cell Lines Compounds of the invention, such as compounds of Formula I, Formula II, Formula III, or Formula IV, in combination with a standard chemotherapeutic agent, such as 5-fluorouracil, carboplatin, dacarbazine, gefitinib, oxaliplatin, paclitaxel, SN-38, temozolomide, or vinblastine, can be assessed for their effectiveness in killing human tumor cells. Human tumor cell lines, such as A-375 (malignant melanoma), SK-MEL-2 (malignant melanoma, skin metastasis), COLO 205 (colorectal adenocarcinoma, ascites metastasis) or SW-620 (colorectal adenocarcinoma, lymph node metastasis) can be treated with a compound of Formula I, Formula II, Formula III, or Formula IV, alone, or in combination with one of the above-mentioned chemotherapeutic agents.

Tumor cells are grown as a monolayer at 37° C. in a humidified atmosphere (5% $CO_2$, 95% air). Cells are grown in a suitable culture medium, e.g. RPMI 1640 (Ref BE12-702F, Cambrex, Verviers, Belgium) containing 2 mM L-glutamine and supplemented with 10% fetal bovine serum (RefDE14-801E, Cambrex). For experimental use, the tumor cells are detached from the culture flask by a 5-minute treatment with trypsin-versene (Ref 02-007E, Cambrex), diluted in Hanks' medium without calcium or magnesium (Ref BE10-543F, Cambrex). Trypsin treatment is neutralized by culture medium addition. The cells are counted in a hemocytometer and their viability assessed by 0.25% trypan blue exclusion.

The cell lines are checked for mycoplasma contamination with the Mycotect assay kit (Ref 15672-017, Invitrogen, Cergy-Pontoise, France) in accordance with the manufacturer's instructions. The mycoplasma test is assayed from the culture supernatants of the cell lines and compared to negative and positive controls.

The tumor cells (10,000 per well) are plated in 96-well flat-bottom microtitration plates (Ref 055260, Nunc, Dutscher, Brumath, France) and incubated at 37° C. for 24 hours before treatment in 100 μl of drug-free culture medium supplemented with 10% FBS. In order to assess the $IC_{50}$ of each compound to be used for each cell line, the tumor cells are incubated in a 200 μl final volume of RPMI 1640 supplemented with 10% FBS and containing either a compound of Formula I, Formula II, Formula III, or Formula IV, or one of 5-fluorouracil, carboplatin, dacarbazine, gefitinib, oxaliplatin, paclitaxel, SN-38, temozolomide, or vinblastine. The compounds are tested in a suitable concentration range, such as $10^{-8}$ to $10^{-3}$ M for a compound of Formula I, Formula II, Formula III, or Formula IV, 5-fluorouracil, dacarbazine or gefitinib, $10^{-9}$ to $10^{-4}$ M for carboplatin, oxaliplatin, or temozolomide, $10^{-10}$ to $10^{-6}$ M for paclitaxel or SN-3, and $10^{-15}$ to $10^{-10}$ M for vinblastine. Compounds of Formula I, Formula II, Formula III, or Formula IV, are dissolved in DMSO and diluted with culture medium to the desired concentrations. 5-fluorouracil (50 mg/ml, Dakota Pharm, LePlessis Robinson, France), carboplatin (10 mg/ml, Aguettant, Lyon, France), and paclitaxel (6 mg/ml, Bristol-Myers Squibb SpA, Rueil Malmaison, France), are diluted with culture medium to the desired concentrations. Dacarbazine (Sigma, Saint Quentin Fallavier, France) and vinblastine (Lilly France S.A., Saint Cloud, France) are dissolved in NaCl 0.9% and diluted with culture medium to the desired concentrations. Gefitinib is dissolved in a mixed solution of RPMI 1640 and DMSO and diluted with culture medium to the desired concentrations (maximum final DMSO of 0.1% v/v). SN-38 (LKT Laboratories, Inc., St. Paul, Minn.) is dissolved in DMSO and diluted with culture medium to the desired concentrations (maximum final DMSO of 0.1% v/v). Temozolomide (LKT Laboratories, Inc., St. Paul, Minn.) is dissolved in water for injection and diluted with culture medium to the desired concentrations. Cells are incubated for 96 hours in the presence of test substances at 37° C. under 5% $CO_2$. At the end of treatments, the cytotoxic activity is evaluated by an MTT assay.

For the MTT assay, at the end of the cells treatment, 20 μl of a 5 mg/ml solution 0.22 μm filtered tetrazolium reagent (MTT, Ref M2128, Sigma) in Phosphate Buffered Saline (PBS, Ref BE17-517Q, Cambrex), is added in each well. Culture plates are incubated for 2 h at 37° C. The resulting supernatant is removed and formazan crystals dissolved with 200 μl of DMSO per well. Absorbency (OD) is measured at 570 nm in each well using VICTOR³™ 1420 multilabeled counter (Wallac, PerkinElmer, Courtaboeuf, France).

The $IC_{50}$ for each compound on each cell line is determined from the OD measurements of each sample. The dose response inhibition of cell proliferation is expressed as:

$$IC = (OD \text{ of drug exposed cells}/OD \text{ of drug free wells}) \times 100.$$

The mean of multiple measurements for each concentration is plotted vs. the drug concentration. The dose-response curves are plotted using XLFit 3 (IDBS, United Kingdom). The $IC_{50}$ (drug concentration to obtain 50% inhibition of cell proliferation) determination values are calculated using the XLFit 3 from semi-log curves. The $IC_{50}$ value determined for each compound in each cell line is used to determine the concentration of a compound of Formula I, Formula II, Formula III, or Formula IV, and of the standard chemotherapeutic to be used in combination.

The cells are treated with a combination of five concentrations of a compound of Formula I, Formula II, Formula III, or Formula IV, and five concentrations of one of 5-fluorouracil, carboplatin, dacarbazine, gefitinib, oxaliplatin, paclitaxel, SN-38, temozolomide, or vinblastine, based on the $IC_{50}$ results. The compounds and cells are treated per the IC50 determination described above and assayed by the MTT assay.

The results are assessed to determine whether the combination is synergistic or antagonistic. The compound interactions are calculated by multiple drug effect analysis and are performed by the median equation principle according to the methodology described by Chou and Talalay (Adv. Enzyme Regul. 1984, 22: 27-55).

The combination index (CI) will be calculated by the Chou et al. equation (Adv. Enzyme Regul. 1984, 22: 27-55; Encyclopaedia of human biology, Academic Press, 1991, 2: 371-9; Synergism and Antagonism in Chemotherapy, Academic Press, 1991, 61-102) which takes into account both the potency ($D_m$ or $IC_{50}$) and the shape of the dose-effect curve (the m value). The general equation for the CI of the two compounds is given by:

$$CI = \frac{(D)_1}{(D_x)_1} + \frac{(D)_2}{(D_x)_2} + \frac{(D)_1(D)_2}{(D_x)_1(D_x)_2}$$

where:

$(D_x)_1$ and $(D_x)_2$ in the denominators are the doses (or concentrations) for compound 1 and compound 2 alone which demonstrate x % of inhibition, whereas $(D)_1$ and $(D)_2$ in the numerators are doses of both compounds (1 and 2) in combination that also inhibit x % (iso-effective). CI<1, =1, and >1 indicate synergism, additive effect and antagonism, respectively.

The $(D_x)_1$ and $(D_x)_2$ can be calculated from the median-effect equation of Chou et al. (J. Natl. Cancer Inst. 1994, 86: 1517-24):

$$D_x = D_m \left( \frac{f_a}{(1-f_a)} \right)^{1/m}$$

where:

$D_m$ is the median-effect dose that is obtained from the anti-log of x-intercept of the median-effect plot, $x = \log(D)$ versus $y = \log\{f_a/(1-f_a)\}$, or $D_m = 10^{-(y\text{-}intercept)/m}$; and m is the slope of the median-effect plot and $f_a$ is the fraction of cells affected by the treatment.

Each CI will be calculated with CalcuSyn software (Biosoft, UK) from the mean affected fraction at each drug ratio concentration.

Additional examples of certain methods contemplated by the present invention may be found in the following applications: U.S. Patent Publ. No. 2006/058339, application Ser. No. 11/154,287; U.S. Patent Publ. No. 2006/058340, application Ser. No. 11/154,988; U.S. Prov. App. No. 60/682,076, filed May 17, 2005; U.S. Prov. App. No. 60/682,058, filed May 17, 2005; U.S. Prov. App. No. 60/682,063, filed May 17, 2005; U.S. Prov. App. No. 60/682,051, filed May 17, 2005; U.S. Prov. App. No. 60/682,042, filed May 17, 2005; U.S. Prov. App. No. 60/692,750, filed Jun. 22, 2005; and U.S. Prov. App. No. 60/692,960, filed Jun. 22, 2005; U.S. Prov. App. No. 60/731,528, filed Oct. 28, 2005, U.S. patent application Ser. No. 11/435,381, filed May 16, 2006, and U.S. patent application Ser. No. 11/473,347, filed Jun. 21, 2006, each of which are hereby incorporated by reference herein in their entireties including all specifications, figures, and tables, and for all purposes.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having the chemical structure of Formula II,

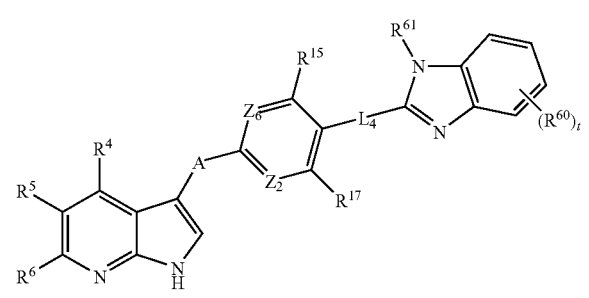

all salts, tautomers, and isomers thereof, wherein:

$t$ is 0, 1, 2, or 3;

$Z_2$ is N or $CR^{12}$;

$Z_6$ is N or $CR^{16}$;

$L_4$ is selected from the group consisting of $-(CR^{10}R^{11})_p-NR^{25}-(CR^{10}R^{11})_q-$, $-(CR^{10}R^{11})_p-X-(CR^{10}R^{11})_q-$, $-(CR^{10}R^{11})_p-C(X)-(CR^{10}R^{11})_q-$, $-(CR^{10}R^{11})_p-S(O)-(CR^{10}R^{11})_q-$, $-(CR^{10}R^{11})_p-S(O)_2-(CR^{10}R^{11})_q-$, $-(CR^{10}R^{11})_p-C(X)NR^{25}-(CR^{10}R^{11})_q-$, $-(CR^{10}R^{11})_p-S(O)_2NR^{25}-(CR^{10}R^{11})_q-$, $-(CR^{10}R^{11})_p-NR^{25}C(X)-(CR^{10}R^{11})_q-$, $-(CR^{10}R^{11})_p-NR^{25}S(O)_2-(CR^{10}R^{11})_q-$, $-(CR^{10}R^{11})_p-NR^{25}C(X)NR^{25}-(CR^{10}R^{11})_q-$, and $-(CR^{10}R^{11})_p-NR^{25}S(O)_2NR^{25}-(CR^{10}R^{11})_q-$;

p and q are independently 0, 1, or 2 provided, however, that at least one of p and q is 0;

$R^{60}$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —CR$^a$R$^b$R$^{26}$, and -LR$^{26}$;

$R^{61}$ is hydrogen, lower alkyl, or fluoro substituted lower alkyl;

A is selected from the group consisting of —O—, —S—, —CR$^a$R$^b$—, —NR$^1$—, —C(O)—, —C(S)—, —S(O)—, and —S(O)$_2$—;

$R^a$ and $R^b$ at each occurrence are independently selected from the group consisting of hydrogen, fluoro, —OH, —NH$_2$, lower alkyl, lower alkoxy, lower alkylthio, mono-alkylamino, di-alkylamino, and —NR$^8$R$^9$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro; or $R^a$ and $R^b$ combine to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^1$ is selected from the group consisting of hydrogen, lower alkyl, cycloalkyl, heterocycloalkyl, aryl, heteroaryl, —C(O)R$^7$, —C(S)R$^7$, —S(O)$_2$R$^7$, —C(O)NHR$^7$, —C(S)NHR$^7$, and —S(O)$_2$NHR$^7$, wherein lower alkyl is optionally substituted with one or more substituents selected from the group consisting of fluoro, —OH, —NH$_2$, lower alkoxy, lower alkylthio, mono-alkylamino, di-alkylamino, and —NR$^8$R$^9$, wherein the alkyl chain(s) of lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, further provided that when $R^1$ is lower alkyl, any substitution on the lower alkyl carbon bound to the N of —NR$^1$— is fluoro, and wherein cycloalkyl, heterocycloalkyl, aryl or heteroaryl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^7$ is selected from the group consisting of lower alkyl, cycloalkyl, heterocycloalkyl, aryl, and heteroaryl, wherein lower alkyl is optionally substituted with one or more substituents selected from the group consisting of fluoro, —OH, —NH$_2$, lower alkoxy, lower alkylthio, mono-alkylamino, di-alkylamino, and —NR$^8$R$^9$, provided, however, that any substitution of the alkyl carbon bound to the N of —C(O)NHR$^7$, —C(S)NHR$^7$ or —S(O)$_2$NHR$^7$ is fluoro, wherein the alkyl chain(s) of lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro, and wherein cycloalkyl, heterocycloalkyl, aryl and heteroaryl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

each of $R^4$, $R^5$, $R^6$, $R^{12}$, $R^{15}$, and $R^{16}$, are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —CR$^a$R$^b$R$^{26}$, and -LR$^{26}$;

L at each occurrence is independently selected from the group consisting of -(alk)$_a$-X-(alk)$_b$-, -(alk)$_a$-NR$^{25}$-(alk)$_b$-, -(alk)$_a$-C(X)-(alk)$_b$-, -(alk)$_a$-S(O)-(alk)$_b$-, -(alk)$_a$-S(O)$_2$-(alk)$_b$-, -(alk)$_a$-OC(X)-(alk)$_b$-, -(alk)$_a$-C(X)O-(alk)$_b$-, -(alk)$_a$-C(X)NR$^{25}$—(alk)$_b$-, -(alk)$_a$-S(O)$_2$NR$^{25}$-(alk)$_b$-, -(alk)$_a$-NR$^{25}$C(X)-(alk)$_b$-, -(alk)$_a$-NR$^{25}$S(O)$_2$-(alk)$_b$-, -(alk)$_a$-NR$^{25}$C(X)O-(alk)$_b$-, -(alk)$_a$-OC(X)NR$^{25}$-(alk)$_b$-, -(alk)$_a$-NR$^{25}$C(X)NR$^{25}$-(alk)$_b$-, and -(alk)$_a$-NR$^{25}$S(O)$_2$NR$^{25}$-(alk)$_b$-;

a and b are independently 0 or 1;

alk at each occurrence is independently C$_{1-3}$ alkylene or C$_{1-3}$ alkylene substituted with one or more substituents selected from the group consisting of fluoro, —OH, —NH$_2$, lower alkyl, lower alkoxy, lower alkylthio, mono-alkylamino, di-alkylamino, and —NR$^8$R$^9$, wherein lower alkyl or the alkyl chain(s) of lower alkoxy, lower alkylthio, mono-alkylamino or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution of the alkyl chain carbon bound to O of alkoxy, S of thioalkyl or N of mono- or di-alkylamino is fluoro;

X at each occurrence is independently O or S;

$R^{25}$ at each occurrence is independently selected from the group consisting of hydrogen, optionally substituted lower alkyl, optionally substituted cycloalkyl, optionally substituted heterocycloalkyl, optionally substituted aryl, and optionally substituted heteroaryl;

$R^{26}$ at each occurrence is independently selected from the group consisting of hydrogen, provided, however, that hydrogen is not bound to any of S(O), S(O)$_2$, C(O) or C(S) of L, optionally substituted lower alkyl, optionally substituted lower alkenyl, provided, however, that when $R^{26}$ is optionally substituted lower alkenyl, no alkene carbon thereof is bound to N, S, O, S(O), S(O)$_2$, C(O) or C(S) of L, optionally substituted lower alkynyl, provided, however, that when $R^{26}$ is optionally substituted lower alkynyl, no alkyne carbon thereof is bound to N, S, O, S(O), S(O)$_2$, C(O) or C(S) of L, optionally substituted cycloalkyl, optionally substituted heterocycloalkyl, optionally substituted aryl, and optionally substituted heteroaryl;

$R^{10}$ and $R^{11}$ at each occurrence are independently selected from the group consisting of hydrogen, fluoro, lower alkyl, and lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino; or any two of $R^{10}$ and $R^{11}$ on the same or adjacent carbon atoms combine to form a 3-7 membered monocyclic cycloalkyl or 5-7 membered monocyclic heterocycloalkyl, and any others of $R^{10}$ and $R^{11}$ are independently selected from the group consisting of hydrogen, fluoro, lower alkyl, and lower alkyl optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein the monocyclic cycloalkyl or monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^8$ and $R^9$ combine with the nitrogen to which they are attached to form a 5-7 membered heterocycloalkyl optionally substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio;

$R^{17}$ is selected from the group consisting of hydrogen, halogen, optionally substituted lower alkyl and —OR$^{18}$; and $R^{18}$ is hydrogen or optionally substituted lower alkyl, provided, however, that the compound is not

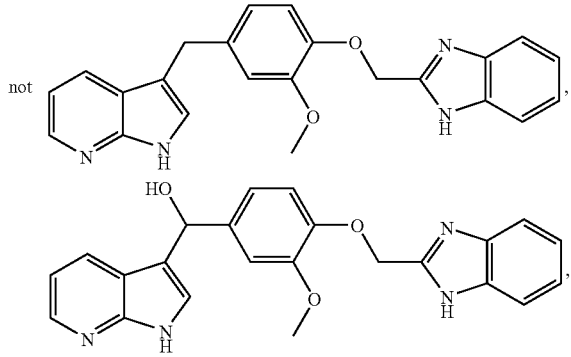

-continued

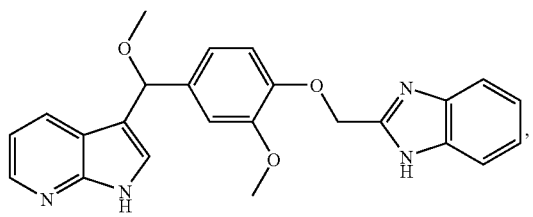

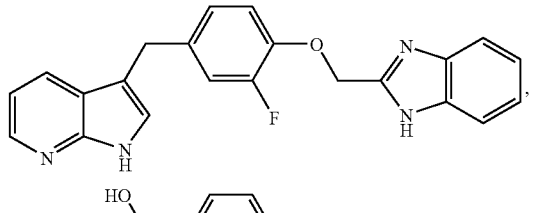

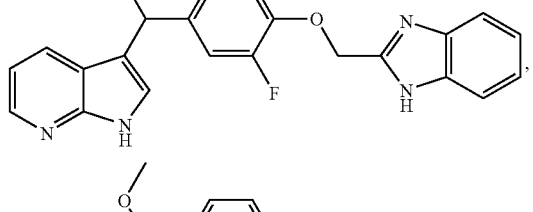

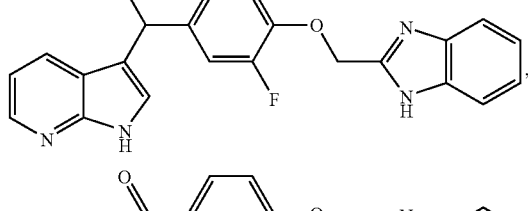

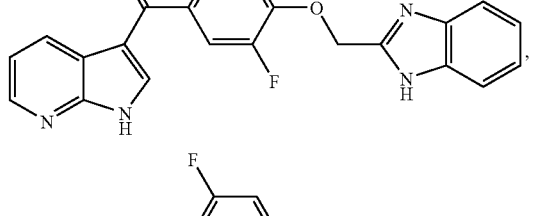

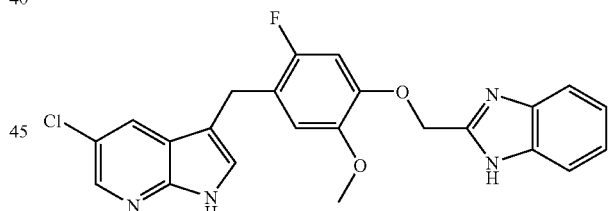

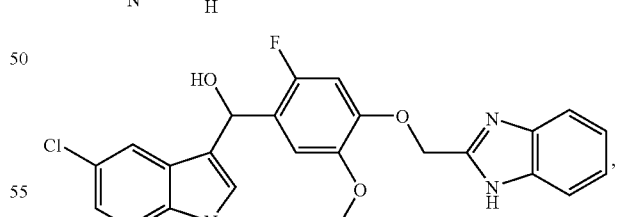

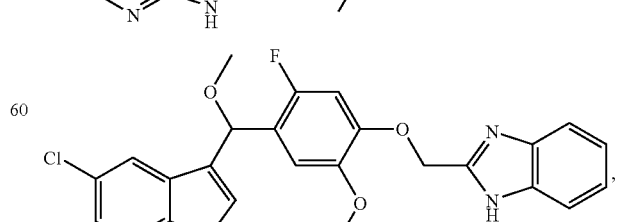

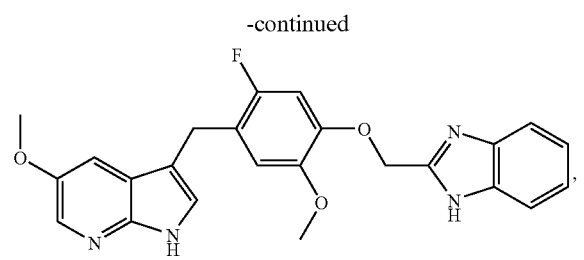
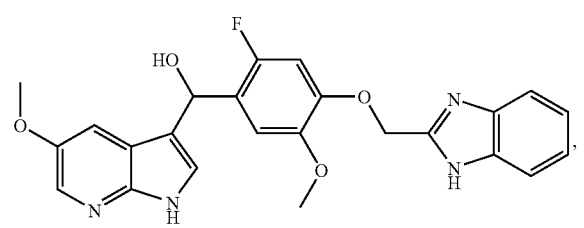
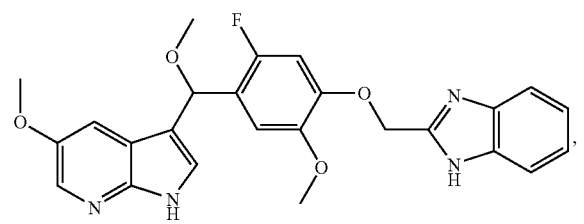
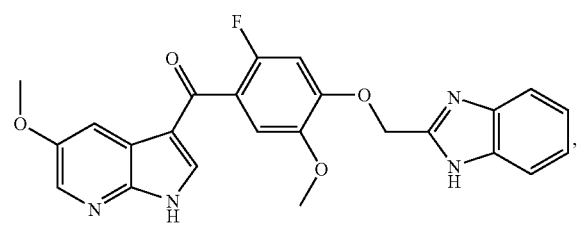
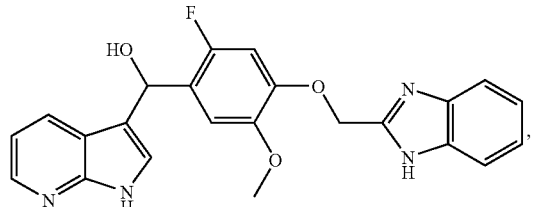
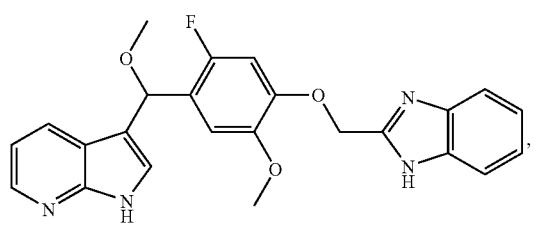
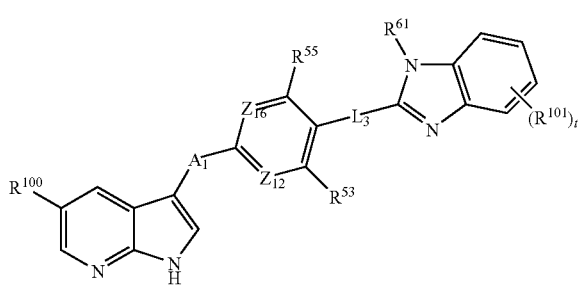
2. The compound of claim 1, having the chemical structure of Formula IIa,
all salts, tautomers, and isomers thereof,
wherein:
 $A_1$ is —O—, —CR$^{40}$R$^{41}$—, —C(O)— or —NR$^{48}$—;
 $Z_{12}$ is N or CR$^{52}$;

$Z_{16}$ is N or $CR^{56}$;

$L_3$ is selected from the group consisting of $-NR^{48}-$, $-S-$, $-O-$, $-NR^{48}CH(R^{49})-$, $-SCH(R^{49})-$, $-OCH(R^{49})-$, $-C(O)NR^{48}$, $-S(O)_2NR^{48}-$, $-CH(R^{49})NR^{48}-$, $-CH(R^{49})O-$, $-CH(R^{49})S-$, $-NR^{48}C(O)-$, and $-NR^{48}S(O)_2-$;

$R^{40}$ and $R^{41}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or $R^{40}$ and $R^{41}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^{61}$ is hydrogen, lower alkyl, or fluoro substituted lower alkyl;

$R^{100}$ is selected from the group consisting of hydrogen, $-OH$, $-NH_2$, $-CN$, $-NO_2$, $-C(O)OH$, $-S(O)_2NH_2$, $-C(O)NH_2$, $-OR^{57}$, $-SR^{57}$, $-NR^{48}R^{57}$, $-NR^{48}C(O)R^{57}$, $-NR^{48}S(O)_2R^{57}$, $-S(O)R^{57}$, $-S(O)_2R^{57}$, $-C(O)R^{57}$, $-C(O)OR^{57}$, $-C(O)NR^{48}R^{57}$, $-S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, $-OH$, $-NH_2$, $C(O)OH$, $-C(O)NH_2$, $-OR^{57}$, $-SR^{57}$, $-NR^{48}R^{57}$, $-C(O)OR^{57}$, $-C(O)NR^{48}R^{57}$, cycloalkyl, heterocycloalkyl, aryl, and heteroaryl, and wherein cycloalkyl, heterocycloalkyl, aryl, and heteroaryl as $R^{100}$, or as substituents of lower alkyl, are optionally substituted with one or more independent substituents $R^{101}$;

$R^{101}$ at each occurrence is independently selected from the group consisting of $-OH$, $-NH_2$, $-CN$, $-NO_2$, $-C(O)OH$, $-S(O)_2NH_2$, $-C(O)NH_2$, $-OR^{57}$, $-SR^{57}$, $-NR^{48}R^{57}$, $NR^{48}R^{57}$, $-NR^{48}C(O)R^{57}$, $-NR^{48}S(O)_2R^{57}$, $-S(O)R^{57}$, $-S(O)_2R^{57}$, $-C(O)R^{57}$, $-C(O)OR^{57}$, $-C(O)NR^{48}R^{57}$, $-S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, $-OH$, $-NH_2$, $C(O)OH$, $-C(O)NH_2$, $-OR^{57}$, $-SR^{57}$, $-NR^{48}R^{57}$, $-C(O)OR^{57}$, $-C(O)NR^{48}R^{57}$, cycloalkyl, heterocycloalkyl, aryl, and heteroaryl, and wherein cycloalkyl, heterocycloalkyl, aryl, and heteroaryl as $R^{101}$, or as substituents of lower alkyl, are optionally substituted with one or more substituents selected from the group consisting of $-OH$, $-NH_2$, $-CN$, $-NO_2$, $-C(O)OH$, $-S(O)_2NH_2$, $-C(O)NH_2$, $-OR^{58}$, $-SR^{58}$, $-NR^{48}R^{58}$, $-NR^{48}C(O)R^{58}$, $-NR^{48}S(O)_2R^{58}$, $-S(O)R^{58}$, $-S(O)_2R^{58}$, $-C(O)R^{58}$, $-C(O)OR^{58}$, $-C(O)NR^{48}R^{58}$, $-S(O)_2NR^{48}R^{58}$, halogen, lower alkyl, fluoro substituted lower alkyl, and cycloalkylamino;

$R^{53}$ and $R^{55}$ are independently selected from the group consisting of hydrogen, halogen, lower alkyl and lower alkoxy, wherein the alkyl chain of lower alkyl or lower alkoxy is optionally substituted with fluoro, $-OH$, $-NH_2$, lower alkoxy, fluoro substituted lower alkoxy, lower alkylthio, fluoro substituted lower alkylthio, mono-alkylamino, di-alkylamino or cycloalkylamino, provided, however, that any substitution on the alkyl carbon bound to the $-O-$ of lower alkoxy is fluoro;

$R^{52}$ and $R^{56}$ are independently selected from the group consisting of hydrogen, halogen, lower alkyl, fluoro substituted lower alkyl, lower alkoxy, and fluoro substituted lower alkoxy;

$R^{57}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of $-OR^{57}$, $-SR^{57}$, $-NR^{48}R^{57}$, $-C(O)OR^{57}$, $-C(O)NR^{48}R^{57}$, or $-S(O)_2NR^{48}R^{57}$ is fluoro, cycloalkyl, heterocycloalkyl, aryl or heteroaryl, and wherein cycloalkyl, heterocycloalkyl, aryl, and heteroaryl as $R^{57}$ or as substituents of lower alkyl are optionally substituted with one or more substituents selected from the group consisting of $-OH$, $-NH_2$, $-CN$, $-NO_2$, $-C(O)OH$, $-S(O)_2NH_2$, $-C(O)NH_2$, $-OR^{58}$, $-SR^{58}$, $-NR^{48}R^{58}$, $-NR^{48}C(O)R^{58}$, $-NR^{48}S(O)_2R^{58}$, $-S(O)_2R^{58}$, $-C(O)R^{58}$, $-C(O)OR^{58}$, $-C(O)NR^{48}R^{58}$, $-S(O)_2NR^{48}R^{58}$, halogen, lower alkyl, fluoro substituted lower alkyl, and cycloalkylamino;

$R^{58}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of $-OR^{58}$, $-SR^{58}$, $-NR^{48}R^{58}$, $-C(O)OR^{58}$, $-C(O)NR^{48}R^{58}$ or $-S(O)_2NR^{48}R^{58}$ is fluoro, and wherein heterocycloalkyl and heteroaryl are optionally substituted with one or more substituents selected from the group consisting of halogen, $-CN$, lower alkyl, fluoro substituted lower alkyl, lower alkoxy and fluoro substituted lower alkoxy;

$R^{48}$ at each occurrence is independently hydrogen or lower alkyl;

$R^{49}$ is selected from the group consisting of hydrogen, lower alkyl, and fluoro substituted lower alkyl; and t is 0, 1, 2, or 3.

3. The compound of claim 2 wherein $A_1$ is $-CR^{40}R^{41}-$ or $-C(O)-$.

4. The compound of claim 3 wherein $L_3$ is $-NR^{48}CH(R^{49})-$, $-SCH(R^{49})-$, or $-OCH(R^{49})-$.

5. The compound of claim 4 wherein $R^{53}$ and $R^{55}$ are independently selected from the group consisting of hydrogen, halogen, lower alkyl, fluoro substituted lower alkyl, lower alkoxy, and fluoro substituted lower alkoxy.

6. The compound of claim 5, wherein:

$R^{100}$ is selected from the group consisting of hydrogen, $-OH$, $-NH_2$, $-CN$, $-NO_2$, $-C(O)OH$, $-S(O)_2NH_2$, $-C(O)NH_2$, $-OR^{57}$, $-SR^{57}$, $-NR^{48}R^{57}$, $-NR^{48}C(O)R^{57}$, $-NR^{48}S(O)_2R^{57}$, $-S(O)R^{57}$, $-S(O)_2R^{57}$, $-C(O)R^{57}$, $-C(O)OR^{57}$, $-C(O)NR^{48}R^{57}$, $-S(O)_2NR^{48}R^{57}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{100}$ or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{58}$, —$SR^{58}$, —$NHR^{58}$, —$NR^{48}R^{58}$, —$NR^{48}C(O)R^{58}$, —$NR^{48}S(O)_2R^{58}$, —$S(O)_2R^{58}$, —$S(O)_2NR^{48}R^{58}$, —$C(O)R^{58}$, —$C(O)NR^{48}R^{58}$, halogen, lower alkyl, fluoro substituted lower alkyl, and cycloalkylamino.

7. The compound of claim 6 wherein $A_1$ is —$CH_2$—.

8. The compound of claim 7 wherein $L_3$ is —$OCH(R^{49})$—.

9. The compound of claim 8 wherein:
$Z_{12}$ is $CR^{52}$;
$Z_{16}$ is $CR^{56}$;
$R^{100}$ is selected from the group consisting of hydrogen, —CN, —C(O)OH, —$C(O)OR^{57}$, —$NR^{48}R^{57}$, —$OR^{57}$, —$S(O)_2R^{57}$, fluoro, chloro, bromo, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —$NR^{48}R^{58}$, —$OR^{58}$ and —$S(O)_2R^{58}$; and
$R^{101}$ is selected from the group consisting of —OH, —$NH_2$, —CN, —$NO_2$, —C(O)OH, —$C(O)NH_2$, —$S(O)_2NH_2$—, $C(O)OR^{57}$, —$NR^{48}R^{57}$, —$OR^{57}$, —$S(O)_2R^{57}$, —$C(O)NR^{48}R^{57}$, —$S(O)_2NR^{48}R^{57}$, halogen, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —$NR^{48}R^{58}$, —$OR^{58}$ and —$S(O)_2R^{58}$.

10. The compound of claim 9, wherein the compound is selected from the group consisting of:

2-[5-Chloro-4-(5-chloro-1H-pyrrolo[2,3-b]pyridin-3-ylmethyl)-2-fluoro-phenoxymethyl]-1H-benzoimidazole, 2-[4-(5-Chloro-1H-pyrrolo[2,3-b]pyridin-3-ylmethyl)-2,5-difluoro-phenoxymethyl]-1H-benzoimidazole, 2-[2,5-Difluoro-4-(5-methoxy-1H-pyrrolo[2,3-b]pyridin-3-ylmethyl)-phenoxymethyl]-1H-benzoimidazole, 2-[3,5-Difluoro-4-(1H-pyrrolo[2,3-b]pyridin-3-ylmethyl)-phenoxymethyl]-1H-benzoimidazole, 2-[5-Chloro-2-methoxy-4-(1H-pyrrolo[2,3-b]pyridin-3-ylmethyl)-phenoxymethyl]-1H-benzoimidazole, 2-[5-Chloro-4-(5-chloro-1H-pyrrolo[2,3-b]pyridin-3-ylmethyl)-2-methoxy-phenoxymethyl]-1H-benzoimidazole, 2-[4-(5-Chloro-1H-pyrrolo[2,3-b]pyridin-3-ylmethyl)-3,5-difluoro-phenoxymethyl]-1H-benzoimidazole, 2-[4-(5-Chloro-1H-pyrrolo[2,3-b]pyridin-3-ylmethyl)-5-fluoro-2-methoxy-phenoxymethyl]-1-methyl-1H-benzoimidazole, 2-[4-(5-Bromo-1H-pyrrolo[2,3-b]pyridin-3-ylmethyl)-2,5-difluoro-phenoxymethyl]-1H-benzoimidazole, 2-{2,5-Difluoro-4-[5-(1-methyl-1H-pyrazol-4-yl)-1H-pyrrolo[2,3-b]pyridin-3-ylmethyl]-phenoxymethyl}-1H-benzoimidazole, 2-{5-Chloro-2-fluoro-4-[5-(1-methyl-1H-pyrazol-4-yl)-1H-pyrrolo[2,3-b]pyridin-3-ylmethyl]-phenoxymethyl}-1H-benzoimidazole, 2-{1-[4-(5-Chloro-1H-pyrrolo[2,3-b]pyridin-3-ylmethyl)-5-fluoro-2-methoxy-phenoxy]-ethyl}-1H-benzoimidazole, 6-Chloro-2-[4-(5-chloro-1H-pyrrolo[2,3-b]pyridin-3-ylmethyl)-5-fluoro-2-methoxy-phenoxymethyl]-1H-benzoimidazole, 6-Chloro-2-[5-fluoro-2-methoxy-4-(1H-pyrrolo[2,3-b]pyridin-3-ylmethyl)-phenoxymethyl]-1H-benzoimidazole, 2-[5-Fluoro-2-methoxy-4-(1H-pyrrolo[2,3-b]pyridin-3-ylmethyl)-phenoxymethyl]-6-methoxy-1H-benzoimidazole, 2-[5-Chloro-2-fluoro-4-(5-methoxy-1H-pyrrolo[2,3-b]pyridin-3-ylmethyl)-phenoxymethyl]-1H-benzoimidazole, 2-[5-Fluoro-4-(5-fluoro-1H-pyrrolo[2,3-b]pyridin-3-ylmethyl)-2-methoxy-phenoxymethyl]-1H-benzoimidazole, 2-[2-Chloro-5-fluoro-4-(5-methoxy-1H-pyrrolo[2,3-b]pyridin-3-ylmethyl)-phenoxymethyl]-1H-benzoimidazole, 2-{2-Chloro-5-fluoro-4-[5-(1-methyl-1H-pyrazol-4-yl)-1H-pyrrolo[2,3-b]pyridin-3-ylmethyl]-phenoxymethyl}-1H-benzoimidazole, 2-{4-[(5-Chloro-1H-pyrrolo[2,3-b]pyridin-3-yl)-methoxy-methyl]-5-fluoro-2-methoxy-phenoxymethyl}-1H-benzoimidazole,

[4-(1H-Benzoimidazol-2-ylmethoxy)-2-fluoro-5-methoxy-phenyl]-(5-chloro-1H-pyrrolo[2,3-b]pyridin-3-yl)-methanone, 2-[2,5-Difluoro-4-(5-methanesulfonyl-1H-pyrrolo[2,3-b]pyridin-3-ylmethyl)-phenoxymethyl]-1H-benzoimidazole, 3-[4-(1H-Benzoimidazol-2-ylmethoxy)-2-fluoro-5-methoxy-benzyl]-1H-pyrrolo[2,3-b]pyridine-5-carbonitrile, 5,6-Dichloro-2-[4-(5-chloro-1H-pyrrolo[2,3-b]pyridin-3-ylmethyl)-5-fluoro-2-methoxy-phenoxymethyl]-1H-benzoimidazole, 2-[4-(5-Chloro-1H-pyrrolo[2,3-b]pyridin-3-ylmethyl)-5-fluoro-2-methoxy-phenoxymethyl]-1H-benzoimidazole-5-sulfonic acid dimethylamide, 3-[4-(1H-Benzoimidazol-2-ylmethoxy)-2-fluoro-5-methoxy-benzyl]-1H-pyrrolo[2,3-b]pyridine-5-carboxylic acid methyl ester, 3-[4-(1H-Benzoimidazol-2-ylmethoxy)-2-fluoro-5-methoxy-benzyl]-1H-pyrrolo[2,3-b]pyridine-5-carboxylic acid, 2-{2,5-Difluoro-4-[5-(2-methoxy-ethoxy)-1H-pyrrolo[2,3-b]pyridin-3-ylmethyl]-phenoxymethyl}-1H-benzoimidazole, 2-[4-(5-Chloro-1H-pyrrolo[2,3-b]pyridin-3-ylmethyl)-5-fluoro-2-methoxy-phenoxymethyl]-1-ethyl-1H-benzoimidazole, 2-[4-(5-Chloro-1H-pyrrolo[2,3-b]pyridin-3-ylmethyl)-5-fluoro-2-methoxy-phenoxymethyl]-5-trifluoromethyl-1H-benzoimidazole, 2-[4-(5-Chloro-1H-pyrrolo[2,3-b]pyridin-3-ylmethyl)-5-fluoro-2-methoxy-phenoxymethyl]-5-fluoro-1H-benzoimidazole, 2-{2-[4-(5-Chloro-1H-pyrrolo[2,3-b]pyridin-3-ylmethyl)-5-fluoro-2-methoxy-phenoxy]-ethyl}-1H-benzoimidazole, 2-[4-(5-Bromo-1H-pyrrolo[2,3-b]pyridin-3-ylmethyl)-5-fluoro-2-methoxy-phenoxymethyl]-1H-benzoimidazole, 2-[4-(5-Chloro-1H-pyrrolo[2,3-b]pyridin-3-ylmethyl)-5-fluoro-2-methoxy-phenoxymethyl]-5-methoxy-1H-benzoimidazole, 5-Chloro-2-[5-fluoro-2-methoxy-4-(5-methyl-1H-pyrrolo[2,3-b]pyridin-3-ylmethyl)-phenoxymethyl]-1-benzoimidazole, 3-[4-(1H-Benzoimidazol-2-ylmethoxy)-2,5-difluoro-benzyl]-1H-pyrrolo[2,3-b]pyridine-5-carbonitrile, 2-[5-Fluoro-4-(5-methanesulfonyl-1H-pyrrolo[2,3-b]pyridin-3-ylmethyl)-2-methoxy-phenoxymethyl]-1H-benzoimidazole, and all salts, tautomers, and isomers thereof.

11. A composition comprising:
    a pharmaceutically acceptable carrier; and
    a compound according to claim 1.

12. A kit comprising a compound according to claim 1.

* * * * *

UNITED STATES PATENT AND TRADEMARK OFFICE
CERTIFICATE OF CORRECTION

PATENT NO. : 7,872,018 B2  
APPLICATION NO. : 11/962044  
DATED : January 18, 2011  
INVENTOR(S) : Prabha N. Ibrahim et al.

Page 1 of 1

It is certified that error appears in the above-identified patent and that said Letters Patent is hereby corrected as shown below:

Title page, item "(73) Assignee: Plexxikon, Inc., Berkeley, CA (US)" should read as follows:

Item -- (73) Assignee: Plexxikon Inc., Berkeley, CA (US) --

Signed and Sealed this
Fifth Day of June, 2012

David J. Kappos
*Director of the United States Patent and Trademark Office*

```
                          SEQUENCE LISTING

<160> NUMBER OF SEQ ID NOS: 62

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgtacgaag ttcagtggaa agttgttgaa gaaatcaacg g                              41

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtcgatgta aacgtagttg ttaccgttga tttcttcaac aacttt                         46

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aacaactacg tttacatcga cccgacccag ctgccgtacg ac                             42

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gttacgcggg aactcccatt tgtggtcgta cggcagctgg gtc                            43

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaatgggagt tcccgcgtaa ccgtctgtct ttcggtaaaa ccc                            43

<210> SEQ ID NO 6
<211> LENGTH: 41
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
accgaacgca cccgcaccca gggttttacc gaaagacaga c                          41

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtgcgggtg cgttcggtaa agttgttgaa gcgaccgcgt acg                        43

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccgcgtcag atttgatcag accgtacgcg gtcgcttcaa c                          41

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgatcaaat ctgacgcggc gatgaccgtt gcggttaaaa tgc                        43

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtcaggtgcg cagacggttt cagcatttta accgcaacgg tca                       43

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaaccgtctg cgcacctgac cgaacgtgaa gcgctgatgt ctg                       43

<210> SEQ ID NO 12
<211> LENGTH: 44
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 12
ccaggtaaga cagaactttc agttcagaca tcagcgcttc acgt                          44

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgaaagttc tgtcttacct gggtaaccac atgaacatcg ttaa                          44

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtgcacgca cccagcaggt taacgatgtt catgtggtta c                             41

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctgctgggtg cgtgcaccat cggtggtccg accctggtta tca                           43

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtcaccgtag cagcagtatt cggtgataac cagggtcgga cca                           43

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaatactgct gctacggtga cctgctgaac ttcctgcgtc gta                           43

<210> SEQ ID NO 18
<211> LENGTH: 43
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 18
agagcagatg aaagagtcac gtttacgacg caggaagttc agc                    43

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgtgactctt tcatctgctc taaacaggaa gaccacgcgg aag                    43

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagcaggttt ttgtacagcg ccgcttccgc gtggtcttcc tgt                    43

<210> SEQ ID NO 21
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcgctgtaca aaaacctgct gcactctaaa gaatcttctt gctc                   44

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccatgtattc gttggtagag tcagagcaag aagattcttt agagt                  45

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gactctacca acgaatacat ggacatgaaa ccgggtgttt ctta                   44

<210> SEQ ID NO 24
<211> LENGTH: 43
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 24
tccgctttgg tcggaacaac gtaagaaaca cccggtttca tgt                         43

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gttgttccga ccaaagcgga caaacgtcgt tctgttcgta tcg                         43

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
taacgtcacg ttcgatgtaa gaaccgatac gaacagaacg acgttt                      46

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tcttacatcg aacgtgacgt taccccggcg atcatggaag acg                         43

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccaggtccag cgccagttcg tcgtcttcca tgatcgccgg                             40

<210> SEQ ID NO 29
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaactggcgc tggacctgga agacctgctg tctttctctt acc                         43

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gaacgccata cctttcgcaa cctggtaaga gaaagacagc aggt    44

<210> SEQ ID NO 31
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gttgcgaaag gtatggcgtt cctggcgtct aaaaactgca tcca    44

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgcgccgcca ggtcacggtg gatgcagttt ttagacgcc    39

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgtgacctgg cggcgcgtaa catcctgctg acccacggtc g    41

<210> SEQ ID NO 34
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
accgaagtcg cagattttgg tgatacgacc gtgggtcagc agg    43

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
accaaaatct gcgacttcgg tctggcgcgt gacatcaaaa acg    43

<210> SEQ ID NO 36
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 36 gttacccttta acaacgtagt tagagtcgtt tttgatgtca cgcgcc                    46

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tctaactacg ttgttaaagg taacgcgcgt ctgccggtta aatg                       44

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaagatagat tccggcgcca tccatttaac cggcagacgc gc                         42

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atggcgccgg aatctatctt caactgcgtt tacaccttcg aatc                       44

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gataccgtaa gaccaaacgt cagattcgaa ggtgtaaacg cag                        43

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gacgtttggt cttacggtat cttcctgtgg gaactgttct ctc                        43

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 42
cctgtgggaa ctgttctctc tgggttcttc tccgtacccg g                41

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggttcttctc cgtacccggg tatgccggtt gactctaaat tctat            45

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cggaaacctt ctttgatcat tttgtagaat ttagagtcaa ccggc            45

<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aaaatgatca agaaggtttt ccgtatgctg tctccggaac acg              43

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atgtcgtaca tttccgccgg cgcgtgttcc ggagacagca ta               42

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccggcggaaa tgtacgacat catgaaaacc tgctgggacg cg               42

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aaggtcggac gtttcagcgg gtccgcgtcc cagcaggttt tc                42

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccgctgaaac gtccgacctt caaacagatc gttcagctga tcg               43

<210> SEQ ID NO 50
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttggtagatt cagagatctg tttttcgatc agctgaacga tctgtt            46

<210> SEQ ID NO 51
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aaacagatct ctgaatctac caaccacatc tactctaacc tggc              44

<210> SEQ ID NO 52
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgacggttcg gagagcagtt cgccaggtta gagtagatgt gg                42

<210> SEQ ID NO 53
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aactgctctc cgaaccgtca gaaaccggtt gttgaccact ctg               43

<210> SEQ ID NO 54
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtagaaccaa cagagttgat acgaacagag tggtcaacaa ccggt       45

<210> SEQ ID NO 55
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cgtatcaact ctgttggttc taccgcgtct tcttctcagc cg       42

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aacgtcgtcg tgaaccagca gcggctgaga agaagacgcg       40

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gttgtttcat atgtacgaag ttcagtggaa ag       32

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gttgtttgtc gactaaacgt cgtcgtgaac cagcag       36

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gttcttgtcg actatttctg acggttcgga gagc       34

<210> SEQ ID NO 60
<211> LENGTH: 1325
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (88)..(1302)

<400> SEQUENCE: 60

```
taatacgact cactataggg gaattgtgag cggataacaa ttcccctcta gaaataattt      60
tgtttaactt taagaaggag atatacc atg ggt cac cac cat cac cat cat atg     114
                                Met Gly His His His His His His Met
                                 1               5
```

| tac | gaa | gtt | cag | tgg | aaa | gtt | gtt | gaa | gaa | atc | aac | ggt | aac | aac | tac | 162 |
|-----|-----|-----|-----|-----|-----|-----|-----|-----|-----|-----|-----|-----|-----|-----|-----|-----|
| Tyr | Glu | Val | Gln | Trp | Lys | Val | Val | Glu | Glu | Ile | Asn | Gly | Asn | Asn | Tyr |     |
| 10  |     |     |     | 15  |     |     |     |     | 20  |     |     |     |     | 25  |     |     |

| gtt | tac | atc | gac | ccg | acc | cag | ctg | ccg | tac | gac | cac | aaa | tgg | gag | ttc | 210 |
|-----|-----|-----|-----|-----|-----|-----|-----|-----|-----|-----|-----|-----|-----|-----|-----|-----|
| Val | Tyr | Ile | Asp | Pro | Thr | Gln | Leu | Pro | Tyr | Asp | His | Lys | Trp | Glu | Phe |     |
|     |     |     | 30  |     |     |     |     | 35  |     |     |     |     | 40  |     |     |     |

| ccg | cgt | aac | cgt | ctg | tct | ttc | ggt | aaa | acc | ctg | ggt | gcg | ggt | gcg | ttc | 258 |
|-----|-----|-----|-----|-----|-----|-----|-----|-----|-----|-----|-----|-----|-----|-----|-----|-----|
| Pro | Arg | Asn | Arg | Leu | Ser | Phe | Gly | Lys | Thr | Leu | Gly | Ala | Gly | Ala | Phe |     |
|     |     | 45  |     |     |     |     | 50  |     |     |     |     | 55  |     |     |     |     |

| ggt | aaa | gtt | gtt | gaa | gcg | acc | gcg | tac | ggt | ctg | atc | aaa | tct | gac | gcg | 306 |
|-----|-----|-----|-----|-----|-----|-----|-----|-----|-----|-----|-----|-----|-----|-----|-----|-----|
| Gly | Lys | Val | Val | Glu | Ala | Thr | Ala | Tyr | Gly | Leu | Ile | Lys | Ser | Asp | Ala |     |
|     |     | 60  |     |     |     |     | 65  |     |     |     |     | 70  |     |     |     |     |

| gcg | atg | acc | gtt | gcg | gtt | aaa | atg | ctg | aaa | ccg | tct | gcg | cac | ctg | acc | 354 |
|-----|-----|-----|-----|-----|-----|-----|-----|-----|-----|-----|-----|-----|-----|-----|-----|-----|
| Ala | Met | Thr | Val | Ala | Val | Lys | Met | Leu | Lys | Pro | Ser | Ala | His | Leu | Thr |     |
| 75  |     |     |     |     | 80  |     |     |     |     | 85  |     |     |     |     |     |     |

| gaa | cgt | gaa | gcg | ctg | atg | tct | gaa | ctg | aaa | gtt | ctg | tct | tac | ctg | ggt | 402 |
|-----|-----|-----|-----|-----|-----|-----|-----|-----|-----|-----|-----|-----|-----|-----|-----|-----|
| Glu | Arg | Glu | Ala | Leu | Met | Ser | Glu | Leu | Lys | Val | Leu | Ser | Tyr | Leu | Gly |     |
| 90  |     |     |     |     | 95  |     |     |     |     | 100 |     |     |     |     | 105 |     |

| aac | cac | atg | aac | atc | gtt | aac | ctg | ctg | ggt | gcg | tgc | acc | atc | ggt | ggt | 450 |
|-----|-----|-----|-----|-----|-----|-----|-----|-----|-----|-----|-----|-----|-----|-----|-----|-----|
| Asn | His | Met | Asn | Ile | Val | Asn | Leu | Leu | Gly | Ala | Cys | Thr | Ile | Gly | Gly |     |
|     |     |     | 110 |     |     |     |     | 115 |     |     |     |     | 120 |     |     |     |

| ccg | acc | ctg | gtt | atc | acc | gaa | tac | tgc | tgc | tac | ggt | gac | ctg | ctg | aac | 498 |
|-----|-----|-----|-----|-----|-----|-----|-----|-----|-----|-----|-----|-----|-----|-----|-----|-----|
| Pro | Thr | Leu | Val | Ile | Thr | Glu | Tyr | Cys | Cys | Tyr | Gly | Asp | Leu | Leu | Asn |     |
|     |     |     |     | 125 |     |     |     |     | 130 |     |     |     |     | 135 |     |     |

| ttc | ctg | cgt | cgt | aaa | cgt | gac | tct | ttc | atc | tgc | tct | aaa | cag | gaa | gac | 546 |
|-----|-----|-----|-----|-----|-----|-----|-----|-----|-----|-----|-----|-----|-----|-----|-----|-----|
| Phe | Leu | Arg | Arg | Lys | Arg | Asp | Ser | Phe | Ile | Cys | Ser | Lys | Gln | Glu | Asp |     |
|     |     | 140 |     |     |     |     | 145 |     |     |     |     | 150 |     |     |     |     |

| cac | gcg | gaa | gcg | gcg | ctg | tac | aaa | aac | ctg | ctg | cac | tct | aaa | gaa | tct | 594 |
|-----|-----|-----|-----|-----|-----|-----|-----|-----|-----|-----|-----|-----|-----|-----|-----|-----|
| His | Ala | Glu | Ala | Ala | Leu | Tyr | Lys | Asn | Leu | Leu | His | Ser | Lys | Glu | Ser |     |
|     | 155 |     |     |     |     | 160 |     |     |     |     | 165 |     |     |     |     |     |

| tct | tgc | tct | gac | tct | acc | aac | gaa | tac | atg | gac | atg | aaa | ccg | ggt | gtt | 642 |
|-----|-----|-----|-----|-----|-----|-----|-----|-----|-----|-----|-----|-----|-----|-----|-----|-----|
| Ser | Cys | Ser | Asp | Ser | Thr | Asn | Glu | Tyr | Met | Asp | Met | Lys | Pro | Gly | Val |     |
| 170 |     |     |     |     | 175 |     |     |     |     | 180 |     |     |     |     | 185 |     |

| tct | tac | gtt | gtt | ccg | acc | aaa | gcg | gac | aaa | cgt | cgt | tct | gtt | cgt | atc | 690 |
|-----|-----|-----|-----|-----|-----|-----|-----|-----|-----|-----|-----|-----|-----|-----|-----|-----|
| Ser | Tyr | Val | Val | Pro | Thr | Lys | Ala | Asp | Lys | Arg | Arg | Ser | Val | Arg | Ile |     |
|     |     |     |     | 190 |     |     |     |     | 195 |     |     |     |     | 200 |     |     |

| ggt | tct | tac | atc | gaa | cgt | gac | gtt | acc | ccg | gcg | atc | atg | gaa | gac | gac | 738 |
|-----|-----|-----|-----|-----|-----|-----|-----|-----|-----|-----|-----|-----|-----|-----|-----|-----|
| Gly | Ser | Tyr | Ile | Glu | Arg | Asp | Val | Thr | Pro | Ala | Ile | Met | Glu | Asp | Asp |     |
|     |     |     | 205 |     |     |     |     | 210 |     |     |     |     | 215 |     |     |     |

| gaa | ctg | gcg | ctg | gac | ctg | gaa | gac | ctg | ctg | tct | ttc | tct | tac | cag | gtt | 786 |
|-----|-----|-----|-----|-----|-----|-----|-----|-----|-----|-----|-----|-----|-----|-----|-----|-----|
| Glu | Leu | Ala | Leu | Asp | Leu | Glu | Asp | Leu | Leu | Ser | Phe | Ser | Tyr | Gln | Val |     |
|     |     | 220 |     |     |     |     | 225 |     |     |     |     | 230 |     |     |     |     |

| gcg | aaa | ggt | atg | gcg | ttc | ctg | gcg | tct | aaa | aac | tgc | atc | cac | cgt | gac | 834 |
|-----|-----|-----|-----|-----|-----|-----|-----|-----|-----|-----|-----|-----|-----|-----|-----|-----|
| Ala | Lys | Gly | Met | Ala | Phe | Leu | Ala | Ser | Lys | Asn | Cys | Ile | His | Arg | Asp |     |
|     | 235 |     |     |     |     | 240 |     |     |     |     | 245 |     |     |     |     |     |

| ctg | gcg | gcg | cgt | aac | atc | ctg | ctg | acc | cac | ggt | cgt | atc | acc | aaa | atc | 882 |
|-----|-----|-----|-----|-----|-----|-----|-----|-----|-----|-----|-----|-----|-----|-----|-----|-----|
| Leu | Ala | Ala | Arg | Asn | Ile | Leu | Leu | Thr | His | Gly | Arg | Ile | Thr | Lys | Ile |     |
| 250 |     |     |     |     | 255 |     |     |     |     | 260 |     |     |     |     | 265 |     |

| tgc | gac | ttc | ggt | ctg | gcg | cgt | gac | atc | aaa | aac | gac | tct | aac | tac | gtt | 930 |
|-----|-----|-----|-----|-----|-----|-----|-----|-----|-----|-----|-----|-----|-----|-----|-----|-----|
| Cys | Asp | Phe | Gly | Leu | Ala | Arg | Asp | Ile | Lys | Asn | Asp | Ser | Asn | Tyr | Val |     |
|     |     |     | 270 |     |     |     |     | 275 |     |     |     |     | 280 |     |     |     |

| gtt | aaa | ggt | aac | gcg | cgt | ctg | ccg | gtt | aaa | tgg | atg | gcg | ccg | gaa | tct | 978 |
|-----|-----|-----|-----|-----|-----|-----|-----|-----|-----|-----|-----|-----|-----|-----|-----|-----|
| Val | Lys | Gly | Asn | Ala | Arg | Leu | Pro | Val | Lys | Trp | Met | Ala | Pro | Glu | Ser |     |
|     | 285 |     |     |     |     | 290 |     |     |     |     | 295 |     |     |     |     |     |

```
atc ttc aac tgc gtt tac acc ttc gaa tct gac gtt tgg tct tac ggt    1026
Ile Phe Asn Cys Val Tyr Thr Phe Glu Ser Asp Val Trp Ser Tyr Gly
            300                 305                 310 atc ttc ctg tgg gaa ctg ttc tct ctg ggt tct tct ccg tac ccg ggt    1074
Ile Phe Leu Trp Glu Leu Phe Ser Leu Gly Ser Ser Pro Tyr Pro Gly
            315                 320                 325 atg ccg gtt gac tct aaa ttc tac aaa atg atc aaa gaa ggt ttc cgt    1122
Met Pro Val Asp Ser Lys Phe Tyr Lys Met Ile Lys Glu Gly Phe Arg
330                 335                 340                 345 atg ctg tct ccg gaa cac gcg ccg gcg gaa atg tac gac atc atg aaa    1170
Met Leu Ser Pro Glu His Ala Pro Ala Glu Met Tyr Asp Ile Met Lys
                350                 355                 360 acc tgc tgg gac gcg gac ccg ctg aaa cgt ccg acc ttc aaa cag atc    1218
Thr Cys Trp Asp Ala Asp Pro Leu Lys Arg Pro Thr Phe Lys Gln Ile
            365                 370                 375 gtt cag ctg atc gaa aaa cag atc tct gaa tct acc aac cac atc tac    1266
Val Gln Leu Ile Glu Lys Gln Ile Ser Glu Ser Thr Asn His Ile Tyr
        380                 385                 390 tct aac ctg gcg aac tgc tct ccg aac cgt cag aaa tagtcgactg         1312
Ser Asn Leu Ala Asn Cys Ser Pro Asn Arg Gln Lys
395                 400                 405 aaaaaggaag agt                                                     1325

<210> SEQ ID NO 61
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Gly His His His His His His Met Tyr Glu Val Gln Trp Lys Val
1               5                   10                  15

Val Glu Glu Ile Asn Gly Asn Asn Tyr Val Tyr Ile Asp Pro Thr Gln
            20                  25                  30

Leu Pro Tyr Asp His Lys Trp Glu Phe Pro Arg Asn Arg Leu Ser Phe
        35                  40                  45

Gly Lys Thr Leu Gly Ala Gly Ala Phe Gly Lys Val Val Glu Ala Thr
    50                  55                  60

Ala Tyr Gly Leu Ile Lys Ser Asp Ala Ala Met Thr Val Ala Val Lys
65                  70                  75                  80

Met Leu Lys Pro Ser Ala His Leu Thr Glu Arg Glu Ala Leu Met Ser
                85                  90                  95

Glu Leu Lys Val Leu Ser Tyr Leu Gly Asn His Met Asn Ile Val Asn
            100                 105                 110

Leu Leu Gly Ala Cys Thr Ile Gly Gly Pro Thr Leu Val Ile Thr Glu
        115                 120                 125

Tyr Cys Cys Tyr Gly Asp Leu Leu Asn Phe Leu Arg Arg Lys Arg Asp
    130                 135                 140

Ser Phe Ile Cys Ser Lys Gln Glu Asp His Ala Glu Ala Ala Leu Tyr
145                 150                 155                 160

Lys Asn Leu Leu His Ser Lys Glu Ser Ser Cys Ser Asp Ser Thr Asn
                165                 170                 175

Glu Tyr Met Asp Met Lys Pro Gly Val Ser Tyr Val Val Pro Thr Lys
            180                 185                 190

Ala Asp Lys Arg Arg Ser Val Arg Ile Gly Ser Tyr Ile Glu Arg Asp
```

```
                    195                 200                 205
Val Thr Pro Ala Ile Met Glu Asp Asp Glu Leu Ala Leu Asp Leu Glu
    210                 215                 220

Asp Leu Leu Ser Phe Ser Tyr Gln Val Ala Lys Gly Met Ala Phe Leu
225                 230                 235                 240

Ala Ser Lys Asn Cys Ile His Arg Asp Leu Ala Ala Arg Asn Ile Leu
                245                 250                 255

Leu Thr His Gly Arg Ile Thr Lys Ile Cys Asp Phe Gly Leu Ala Arg
                260                 265                 270

Asp Ile Lys Asn Asp Ser Asn Tyr Val Val Lys Gly Asn Ala Arg Leu
            275                 280                 285

Pro Val Lys Trp Met Ala Pro Glu Ser Ile Phe Asn Cys Val Tyr Thr
        290                 295                 300

Phe Glu Ser Asp Val Trp Ser Tyr Gly Ile Phe Leu Trp Glu Leu Phe
305                 310                 315                 320

Ser Leu Gly Ser Ser Pro Tyr Pro Gly Met Pro Val Asp Ser Lys Phe
                325                 330                 335

Tyr Lys Met Ile Lys Glu Gly Phe Arg Met Leu Ser Pro Glu His Ala
                340                 345                 350

Pro Ala Glu Met Tyr Asp Ile Met Lys Thr Cys Trp Asp Ala Asp Pro
            355                 360                 365

Leu Lys Arg Pro Thr Phe Lys Gln Ile Val Gln Leu Ile Glu Lys Gln
    370                 375                 380

Ile Ser Glu Ser Thr Asn His Ile Tyr Ser Asn Leu Ala Asn Cys Ser
385                 390                 395                 400

Pro Asn Arg Gln Lys
                405

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Lys Lys Ser Pro Gly Glu Tyr Val Asn Ile Glu Phe Gly
1               5                   10
```